(12) United States Patent
Smith et al.

(10) Patent No.: US 9,115,092 B2
(45) Date of Patent: *Aug. 25, 2015

(54) SUBSTITUTED QUINAZOLINE AND PYRIDO-PYRIMIDINE DERIVATIVES

(71) Applicant: Asana Biosciences, LLC, Bridgewater, NJ (US)

(72) Inventors: Roger Astbury Smith, Chester Springs, PA (US); Scott Kevin Thompson, Phoenixville, PA (US); Subramanya Hosahalli, Bangalore (IN); Mallesham Bejugam, Parbhani (IN); Srinivas Nanduri, Hyderabad (IN); Sunil Kumar Panigrahi, Kantamal (IN); Natarajan Mahalingam, Ariyalur (IN)

(73) Assignee: Asana Biosciences, LLC, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/474,697

(22) Filed: Sep. 2, 2014

(65) Prior Publication Data

US 2015/0011547 A1  Jan. 8, 2015

Related U.S. Application Data

(63) Continuation of application No. 14/076,765, filed on Nov. 11, 2013, now abandoned, which is a continuation of application No. 13/787,946, filed on Mar. 7, 2013, now abandoned, which is a continuation of application No. 13/285,227, filed on Oct. 31, 2011, now Pat. No. 8,440,662.

(60) Provisional application No. 61/501,901, filed on Jun. 28, 2011, provisional application No. 61/408,620, filed on Oct. 31, 2010.

(51) Int. Cl.
| | | |
|---|---|---|
| *A61K 31/535* | (2006.01) |
| *C07D 413/14* | (2006.01) |
| *C07D 413/04* | (2006.01) |
| *C07D 239/72* | (2006.01) |
| *C07D 239/42* | (2006.01) |
| *C07D 401/04* | (2006.01) |
| *C07D 401/12* | (2006.01) |
| *C07D 401/14* | (2006.01) |
| *C07D 403/04* | (2006.01) |
| *C07D 405/04* | (2006.01) |
| *C07D 405/14* | (2006.01) |
| *C07D 471/04* | (2006.01) |
| *C07D 295/155* | (2006.01) |
| *C07D 409/04* | (2006.01) |

(52) U.S. Cl.
CPC ............ *C07D 239/72* (2013.01); *A61K 31/535* (2013.01); *C07D 239/42* (2013.01); *C07D 295/155* (2013.01); *C07D 401/04* (2013.01); *C07D 401/12* (2013.01); *C07D 401/14* (2013.01); *C07D 403/04* (2013.01); *C07D 405/04* (2013.01); *C07D 405/14* (2013.01); *C07D 409/04* (2013.01); *C07D 413/04* (2013.01); *C07D 413/14* (2013.01); *C07D 471/04* (2013.01)

(58) Field of Classification Search
CPC ... A61K 31/535; C07D 413/14; C07D 413/04
USPC .......................................... 514/234.5; 544/115
See application file for complete search history.

(56) References Cited

U.S. PATENT DOCUMENTS

| 6,613,772 B1 | 9/2003 | Schindler et al. |
| 7,173,029 B2 | 2/2007 | Hayakawa et al. |
| 7,557,112 B2 | 7/2009 | Yonetoku et al. |
| 7,691,851 B2 | 4/2010 | Gege et al. |
| 8,440,662 B2 | 5/2013 | Smith et al. |

(Continued)

FOREIGN PATENT DOCUMENTS

| EP | 1277738 A1 | 1/2003 |
| GB | 2431156 A | 4/2007 |

(Continued)

OTHER PUBLICATIONS

Venkatesan, "Bis(morpholino-1,3,5-triazine) Derivatives: Potent Adenosine 5'-Triphosphate Competitive Phosphatidylinositol-3-kinase/MammalianTarget of Rapamycin Inhibitors: Discovery of Compound 26 (PKI-587), a Highly Efficacious Dual Inhibitor", Journal of Medicinal Chemistry, 53:2636-2643 (Mar. 2010; e-publication: Feb. 18, 2010).

(Continued)

*Primary Examiner* — Rebecca Anderson
(74) *Attorney, Agent, or Firm* — Lerner, David, Littenberg, Krumholz & Mentlik, LLP

(57) ABSTRACT

The present application provides novel substituted quinazoline and pyrido-pyrimidine compounds and pharmaceutically acceptable salts thereof. Also provided are methods for preparing these compounds. These compounds are useful in co-regulating PI3K and/or mTOR activity by administering a therapeutically effective amount of one or more of the compounds to a patient. By doing so, these compounds are effective in treating conditions associated with the dysregulation of the PI3K/AKT/mTOR pathway. Advantageously, these compounds perform as dual PI3K/mTOR inhibitors. A variety of conditions can be treated using these compounds and include diseases which are characterized by inflammation or abnormal cellular proliferation. In one embodiment, the disease is cancer.

12 Claims, No Drawings

(56) References Cited

U.S. PATENT DOCUMENTS

| | | |
|---|---|---|
| 2004/0067938 A1 | 4/2004 | Zhang et al. |
| 2005/0176760 A1 | 8/2005 | Cezanne et al. |
| 2006/0217377 A1 | 9/2006 | Gonzalez et al. |
| 2008/0009477 A1 | 1/2008 | Hutchison et al. |
| 2008/0171743 A1 | 7/2008 | Finlay et al. |
| 2008/0221093 A1 | 9/2008 | Gege et al. |
| 2009/0018134 A1 | 1/2009 | Pike et al. |
| 2009/0163489 A1 | 6/2009 | Booker et al. |
| 2009/0209536 A1 | 8/2009 | Gahman et al. |
| 2009/0285782 A1 | 11/2009 | Gao et al. |

FOREIGN PATENT DOCUMENTS

| | | |
|---|---|---|
| WO | 2004048365 A1 | 6/2004 |
| WO | 2008152387 A1 | 12/2008 |
| WO | 2009111547 A1 | 9/2009 |
| WO | 2010120994 A2 | 10/2010 |

OTHER PUBLICATIONS

Combined International Search Report and Written Opinion of the International Searching Authority dated Jan. 5, 2012 issued in counterpart International Patent Application No. PCT/US2011/058584.

Marone et al., "Targeting phosphoinositide 3-kinase: moving towards therapy", Biochimica et Biophysica Acta, 1784: 159-185 (2008; e-publication: Oct. 12, 2007).

Hayakawa et al., "Synthesis and biological evaluation of 4-morpholino-2-phenylquinazolines and related derivatives as novel PI3 kinase p110.alpha. inhibitors", Bioorganic & Medicinal Chemistry 14: 6847-6858 (2006; e-publication: Jul. 11, 2006).

Zhang et al., "Targeting cancer with small molecule kinase inhibitors", Nature Reviews Cancer, 9(1): 28-39 (Jan. 2009).

Dehnhardt et al., "Beyond temsirolimus: Discovery of PKI-587 a highly efficacious dual PI3K/mTOR inhibitor", In: Proceedings of the 101st Annual Meeting of the American Association for Cancer Research; Washington, DC. Philadelphia (PA): AACR (Apr. 17-21, 2010).

Richard et al., "Incorporation of water-solubilizing groups in pyrazolopyrimidine mTOR inhibitors: discovery of highly potent and selective analogs with improved human microsomal stability", Bioorganic & Medicinal Chemistry Letters 19:6830-6835(2009; e-publication: Oct. 25, 2009).

Richard et al., "Triazines incorporating (R)-3-methylmorpholine are potent inhibitors of the mammalian target of rapamycin (mTOR) with selectivity over PI3K.alpha." Bioorganic & Medicinal Chemistry Letters 20: 2654-2657 (2010; e-publication: Feb. 11, 2010).

Dehnhardt et al., "Lead Optimization of N-3-Substituted 7-Morpholinotriazolopyrimidines as Dual Phosphoinositide 3-Kinase/Mammalian Target of Rapamycin Inhibitors: Discovery of PKI-402" J. Med. Chem., 53(2): 798-810 (Jan. 29, 2010; e-publication:Dec. 7, 2009).

SUBSTITUTED QUINAZOLINE AND PYRIDO-PYRIMIDINE DERIVATIVES

CROSS-REFERENCE TO RELATED APPLICATIONS

This application is a continuation of U.S. application Ser. No. 14/076,765, filed on Nov. 11, 2013, now abandoned, which is a continuation of U.S. application Ser. No. 13/285,227, filed on Oct. 31, 2011 (now issued U.S. Pat. No. 8,440,662), which claims benefit of U.S. Provisional Application No. 61/408,620, filed on Oct. 31, 2010, and U.S. Provisional Application No. 61/501,901, filed on Jun. 28, 2011, all of which are incorporated herein by reference.

BACKGROUND

With the onset of cancers which are refractory to most conventional treatments, there is a need for new and effective chemotherapeutics. As details emerge about the molecular etiology of various cancers, new chemotherapeutics can be designed which affect one or more vulnerable targets associated with a given cancer at a sub-cellular level.

Certain cancers (and indeed other diseases of abnormal cellular growth) include those which are due to the dysregulation of one particular molecular signaling pathway in the body. Restoring regulation of that particular pathway to normal or near-normal levels can have a positive impact in treating the patient, including a reduction in tumor size or even putting the patient into remission.

For example, perturbations of the phosphoinositide 3-kinase (PI3K)/AKT/mammalian target of rapamycin (mTOR) signaling pathway are closely associated with the etiology of most solid tumors. The PI3K/AKT/mTOR pathway can be overactivated by a number of molecular effectors, including chemokines, the loss of INPP4B or PTEN expression, or by mutations in PI3K itself. Overactivation of this pathway can manifest in a number of molecular and morphological changes which are characteristic of tumorigenesis, including increased cell proliferation, survival and motility, and altered cell cycle entry. mTOR is a central regulator of cell growth which acts by controlling cellular protein translation. Several small molecules have been described as being mTOR inhibitors which are useful for treating cancers. PI3K is a heterodimeric enzyme that generates lipid second messengers, such as phosphatidylinositol-3,4,5-triphosphate (PIP3), that mediate signal transduction. PI3K enzymes regulate key signal transduction pathways controlling vital cell processes that are implicated in carcinogenesis, and include four isoforms; i.e., p110α, p110β, p110δ and p110γ. Specific mutations in p110α have been identified in various cancers. Several small molecules have been described as inhibitors of PI3K. Further, there are a number of compounds, including wortmannins and rapamycins, which have been shown to be highly potent and specific inhibitors of PI3K and mTOR, respectively.

Indeed, several recent compounds have been described as being useful in regulating the PI3K/mTOR pathway. For example, GDC-0941, PX-866, XL-147, BKM-120, and BAY 80-6946 are inhibitors of PI3K, whereas rapamycin, temsirolimus (CCI-779), everolimus (RAD001), ridaforolimus (deforolimus, AP23573, MK-8669), OSI-027 and AZD8055 are inhibitors of mTOR. However, intervention at a single point in a the PI3K/AKT/mTOR signaling pathway may not be as effective in treating solid tumors as targeting multiple pathway members. Administering multiple drugs to a cancer patient, each of which inhibit a certain target in the PI3K or mTOR pathway, carries its own risks in terms of increased drug load, potential toxicity, drug-drug interactions and the like. What remains in the art, therefore, is the need for single compounds which regulate the PI3K/AKT/mTOR pathway by targeting both PI3K and mTOR. Certain compounds recently described in the art, including BEZ-235, XL-765, GDC-0980, GSK-2126458, PKI-587, and PF-04691502, have been reported to target both PI3K and mTOR. However, the need remains for compounds with this type of dual activity profile to be developed and approved for clinical use.

SUMMARY OF THE INVENTION

In one aspect, the present invention provides a compound of formula (I), wherein $R^1$-$R^6$, A, X, Y, Z, and M are defined herein, or a pharmaceutically acceptable salt or solvate thereof.

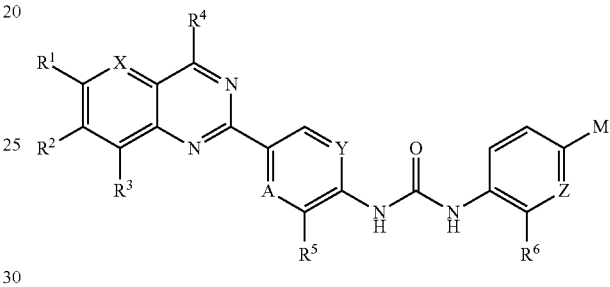

In another aspect, the present invention provides a compound of formula (IA), wherein $R^1$-$R^8$, A, X, Y, and Z are defined herein, or a pharmaceutically acceptable salt or solvate thereof.

(IA)

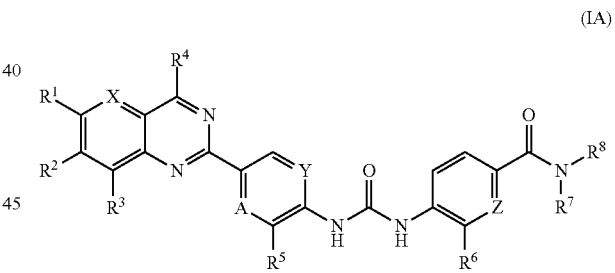

In a further aspect, the present invention provides a compound of formula (IB), wherein $R^1$-$R^6$, $R^9$, $R^{10}$, A, X, Y, and Z are defined herein, or a pharmaceutically acceptable salt or solvate thereof.

(IB)

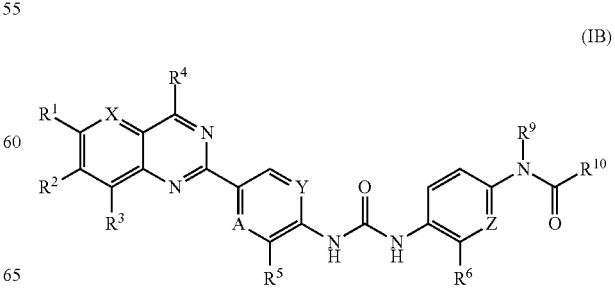

In still another aspect, compounds of formulae (II)-(XVIII) are provided, wherein $R^1$-$R^3$, $R^5$-$R^8$, M are defined herein.
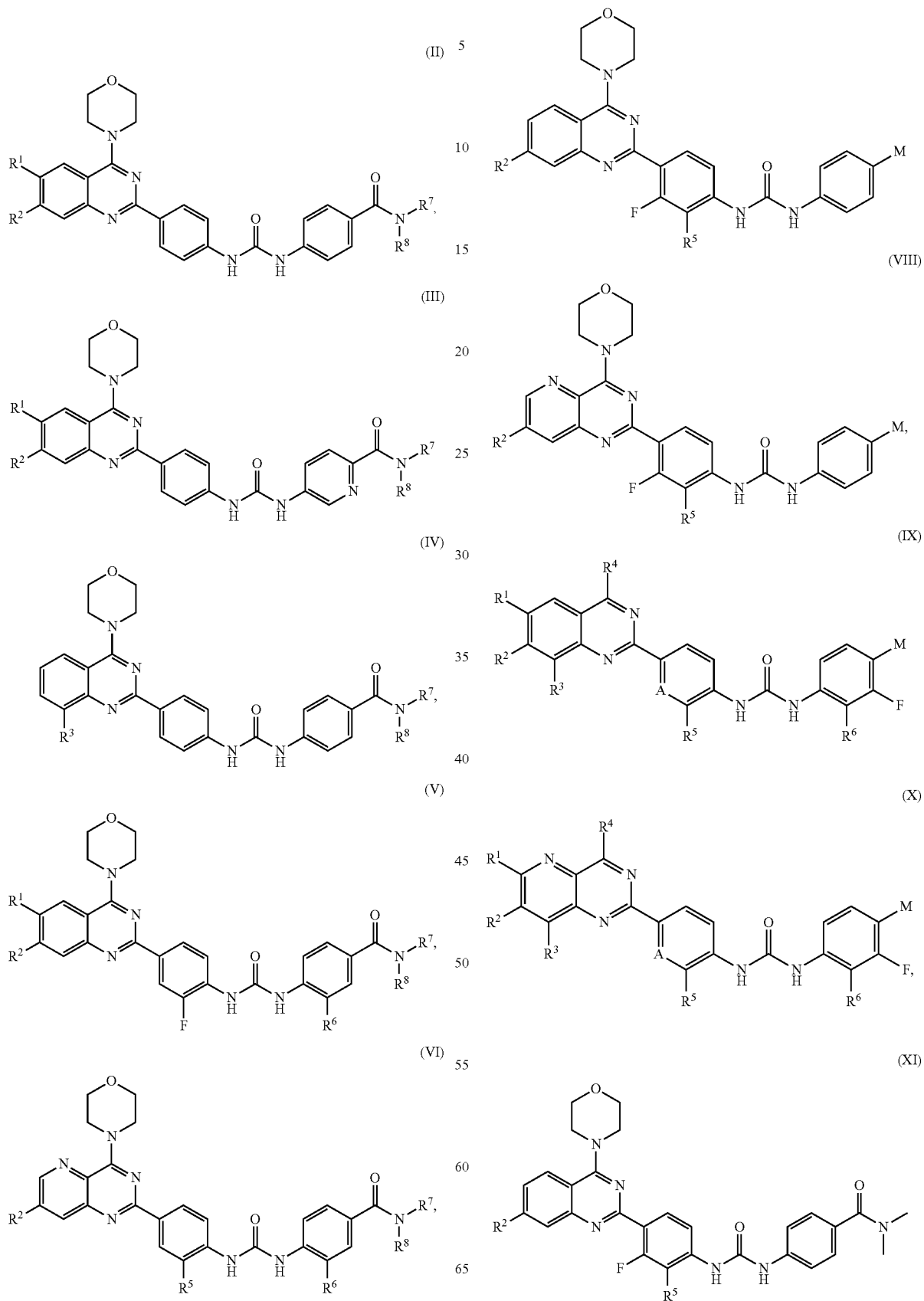

(XII)

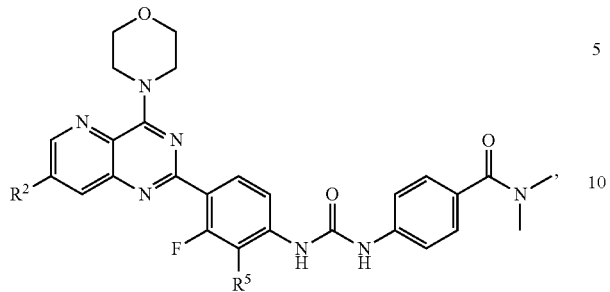

(XIII)

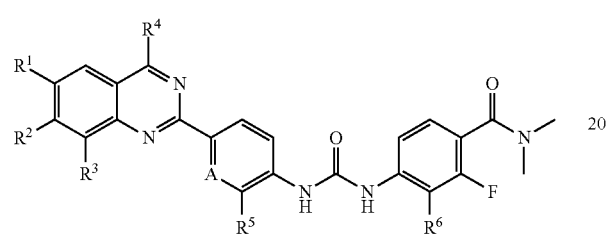

(XIV)

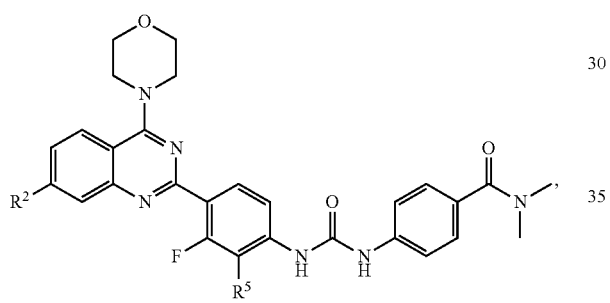

(XV)

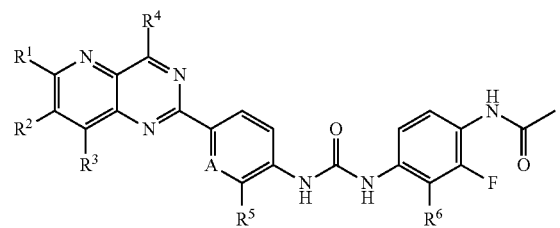

(XVI)

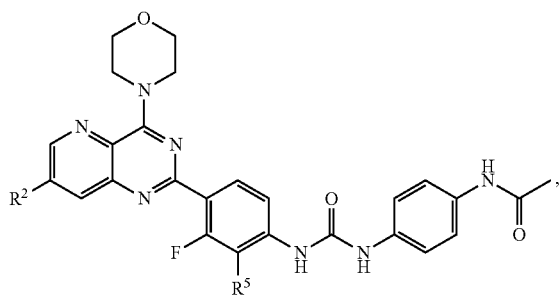

(XVII)

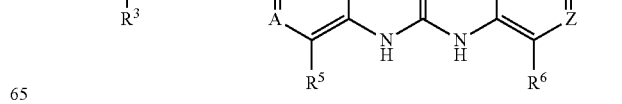

(XVIII)

In yet another aspect, the invention provides a pharmaceutical composition comprising a compound of any of formula (I) to (XVIII), or a pharmaceutically acceptable salt or solvate thereof, and a pharmaceutically acceptable carrier.

In another aspect, methods for co-regulating PI3K and mTOR are provided and include administering a therapeutically effective amount of a compound described herein to a patient in need thereof. Desirably, co-regulation includes inhibition of the PI3K/AKT/mTOR pathway.

In still a further aspect, methods for treating a disease characterized by abnormal cellular growth resulting from a dysregulated PI3K/AKT/mTOR pathway are provided. These methods include administering a therapeutically effective amount of a compound described herein to a patient in need thereof. In one embodiment, the disease is cancer. In another embodiment, the disease is characterized by the presence of at least one solid tumor. In yet another embodiment, the disease is characterized by inflammation.

Other aspects and advantages of the invention will be readily apparent from the following detailed description of the invention.

DETAILED DESCRIPTION OF THE INVENTION

The present invention provides novel compounds which have capabilities in modulating two (2) members of the PI3K/AKT/mTOR pathway, i.e., PI3K and mTOR. These compounds are can be used to treat disease affected by a dysregulation of the PI3K/AKT/mTOR pathway.

In the present invention, the compound is of formula (I), or a pharmaceutically acceptable salt or solvate thereof.

(I)

In this structure, $R^1$ is H, F, Cl, or $OCH_3$.

$R^2$ is H, optionally substituted aryl, optionally substituted heterocycle, optionally substituted heteroaryl, optionally substituted alkyl, optionally substituted alkenyl, optionally substituted alkynyl, optionally substituted alkylamino, optionally substituted dialkylamino, optionally substituted arylamino, optionally substituted heteroarylamino, optionally substituted heterocycle-amino, optionally substituted alkylcarbonylamino, optionally substituted alkylsulfonylamino, optionally substituted alkylthio, optionally substituted alkylsulfonyl, optionally substituted alkoxy, optionally substituted hydroxyalkyl, optionally substituted aryloxy, optionally substituted heteroaryloxy, optionally substituted heterocycle-oxy, optionally substituted alkylaminocarbonyl, optionally substituted arylaminocarbonyl, optionally substituted heteroarylaminocarbonyl, optionally substituted heterocycle-aminocarbonyl, or C(O)-(optionally substituted heterocycle) and $R^3$ is H, halogen, CN, OH, $NH_2$, $NHCH_3$, or $OCH_3$. Alternatively, $R^2$ is H, halogen, CN, OH, $NH_2$, $NHCH_3$, or $OCH_3$ and $R^3$ is H, optionally substituted aryl, optionally substituted heterocycle, optionally substituted heteroaryl, optionally substituted alkyl, optionally substituted alkenyl, optionally substituted alkynyl, optionally substituted alkylamino, optionally substituted dialkylamino, optionally substituted arylamino, optionally substituted heteroarylamino, optionally substituted heterocycle-amino, optionally substituted alkylcarbonylamino, optionally substituted alkylsulfonylamino, optionally substituted alkylthio, optionally substituted alkylsulfonyl, optionally substituted alkoxy, optionally substituted hydroxyalkyl, optionally substituted aryloxy, optionally substituted heteroaryloxy, optionally substituted heterocycle-oxy, optionally substituted alkylaminocarbonyl, optionally substituted arylaminocarbonyl, optionally substituted heteroarylaminocarbonyl, optionally substituted heterocycle-aminocarbonyl, or C(O)-(optionally substituted heterocycle).

In one embodiment, $R^2$ or $R^3$ is an optionally substituted phenyl group of the following structure. In this structure, n is 1 to 5 and each $R^{10}$ is independently selected from among OH, halogen, alkoxy, $CF_3$, $OCF_3$, CN, alkylamino, dialkylamino, hydroxyalkyl, alkylsulfonyl, alkylthio, aminoalkyl, alkylaminoalkyl, dialkylaminoalkyl, alkylcarbonylamino, alkylsulfonylamino, alkylsulfonylalkyl, alkylaminocarbonyl, alkylaminosulfonyl, or cyanoalkyl. The phenyl ring may be attached through any carbon atom of the ring and may be substituted with 1-5 groups. In one example, the $R^2$ or $R^3$ phenyl ring contains a substituent at the 3-position. In another example, the $R^2$ or $R^3$ phenyl ring contains a substituent at the 4-position. In another example, the $R^2$ or $R^3$ phenyl ring is substituted with OH, $CH_2OH$, $CH_2CH_2OH$, F, Cl, CN, $N(CH_3)_2$, $CH_2N(CH_3)_2$, $CH_2CH_2N(CH_3)_2$, $CONHCH_3$, $NHCOCH_3$, $NHSO_2CH_3$, $CH_2CN$, $CH(CH_3)CN$, $C(CH_3)_2CN$, $OCH_3$, $OCF_3$, or $SO_2CH_3$.

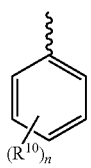

In another embodiment, $R^2$ or $R^3$ is optionally substituted heterocycle or heteroaryl. When the heterocycle or heteroaryl $R^2$ or $R^3$ group contains substituents, the same may be selected from among 1 to 3 $R^{11}$ groups independently selected from among OH, halogen, alkoxy, $CF_3$, $OCF_3$, CN, alkylamino, dialkylamino, hydroxyalkyl, alkylsulfonyl, alkylthio, aminoalkyl, alkylaminoalkyl, dialkylaminoalkyl, alkylcarbonylamino, alkylsulfonylamino, alkylsulfonylalkyl, alkylaminocarbonyl, alkylaminosulfonyl, and cyanoalkyl.

In a further embodiment, $R^2$ or $R^3$ is a heteroaryl of the following formula, $Z^1$ is O, S, or $NR^{12}$; $Z^2$ is CH or N; $R^{12}$ is absent, H or alkyl; p is 0 to 2; and each $R^{11}$ is, independently, selected from among OH, halogen, alkoxy, $CF_3$, $OCF_3$, CN, alkylamino, dialkylamino, hydroxyalkyl, alkylsulfonyl, alkylthio, aminoalkyl, alkylaminoalkyl, dialkylaminoalkyl, alkylcarbonylamino, alkylsulfonylamino, alkylsulfonylalkyl, alkylaminocarbonyl, alkylaminosulfonyl, and cyanoalkyl. In another example, $R^2$ or $R^3$ is selected from among pyrazole, imidazole, pyrrole, thiophene and furan. In a further example, $R^2$ or $R^3$ is selected from among pyrazole and imidazole. In still a further example, the $R^2$ or $R^3$ heteroaryl or heterocycle is substituted with $CH_2OH$, $CH_2CH_2OH$, F, Cl, CN, $N(CH_3)_2$, $CH_2N(CH_3)_2$, $CH_2CH_2N(CH_3)_2$, $CONHCH_3$, $NHCOCH_3$, $NHSO_2CH_3$, $CH_2CN$, $CH(CH_3)CN$, $C(CH_3)_2CN$, $OCH_3$, $OCF_3$, or $SO_2CH_3$.

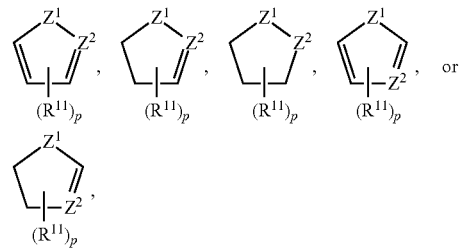

In still another embodiment, $R^2$ or $R^3$ is a heteroaryl selected from among the following, m is 0 to 4, q is 0 to 3, each $R^{14}$ is, independently, selected from among OH, halogen, alkoxy, $CF_3$, $OCF_3$, CN, alkylamino, dialkylamino, hydroxyalkyl, alkylsulfonyl, alkylthio, aminoalkyl, alkylaminoalkyl, dialkylaminoalkyl, alkylcarbonylamino, alkylsulfonylamino, alkylsulfonylalkyl, alkylaminocarbonyl, alkylaminosulfonyl, and cyanoalkyl. In one example, $R^2$ or $R^3$ is selected from among pyridine, pyrimidine, and pyridazine. In another example, $R^2$ or $R^3$ is substituted with $CH_2OH$, $CH_2CH_2OH$, F, Cl, CN, $N(CH_3)_2$, $CH_2N(CH_3)_2$, $CH_2CH_2N(CH_3)_2$, $CONHCH_3$, $NHCOCH_3$, $NHSO_2CH_3$, $CH_2CN$, $CH(CH_3)CN$, $C(CH_3)_2CN$, $OCH_3$, $OCF_3$, or $SO_2CH_3$.

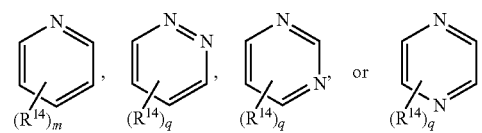

$R^4$ in formula (I) is optionally substituted morpholine or thiomorpholine. In one embodiment, $R^4$ is morpholine. In another embodiment, $R^4$ is morpholine substituted by one or more methyl. In a further embodiment, $R^4$ is

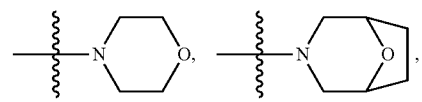

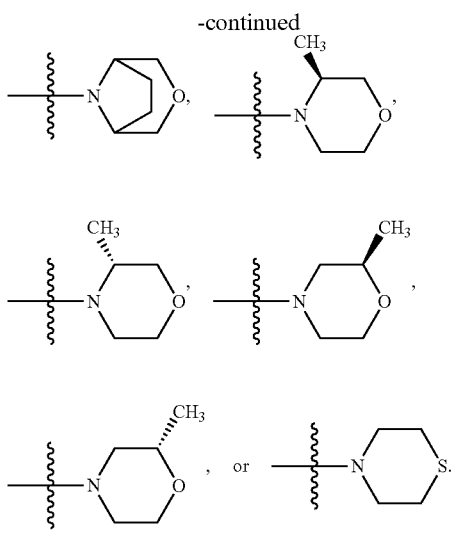

$R^5$ in formula (I) is H, F or Cl. $R^6$ is H, F or Cl. In one embodiment, $R^5$ and $R^6$ are both H.

X is N, CH, C—F or C—Cl. Y is N, CH, C—F or C—Cl. Z is N, CH, C—F, or C—Cl. A is CH or C—F.

M is selected from among

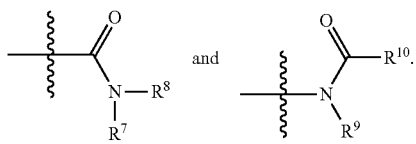

In one embodiment, M is

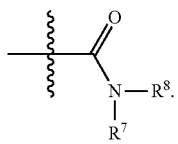

In another embodiment, M is

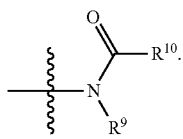

$R^7$ and $R^8$ as included in formula I are, independently, H or optionally substituted alkyl.

Alternatively, $R^7$ and $R^8$ are joined to form an optionally-substituted heterocycle containing 1 or 2 nitrogen atoms, 0 or 1 oxygen atom, 0 or 1 sulfur atom, 0 or 1 S(O) fragment, 0 or 1 S(O)$_2$ fragment, and 3 to 6 carbon atoms. In one embodiment, $R^7$ and $R^8$ are joined to form an optionally substituted ring containing 1 nitrogen atom. In another embodiment, $R^7$ and $R^8$ are joined to form optionally substituted piperidinyl, pyrrolidinyl, azepanyl, piperazinyl, homopiperazinyl, morpholinyl, or thiomorpholinyl. In a further embodiment, $R^7$ and $R^8$ are, independently, H or alkyl optionally substituted with OH, halogen, alkoxy, $CF_3$, $OCF_3$, CN, alkylamino, dialkylamino, amino, alkylsulfonyl, alkylthio, alkylcarbonylamino, alkylsulfonylamino, alkylaminocarbonyl, or alkylaminosulfonyl. In yet another embodiment, $R^7$ and $R^8$ are, independently, H or alkyl optionally substituted with $CH_2OH$, $CH_2CH_2OH$, F, Cl, CN, $NH_2$, $NH(CH_3)$, $N(CH_3)_2$, $CONHCH_3$, $NHCOCH_3$, $NHSO_2CH_3$, $OCH_3$, $OCF_3$, or $SO_2CH_3$. In still a further embodiment, $R^7$ and $R^8$ are joined to form a heterocycle optionally substituted with 0 to 3 groups independently selected from among OH, halogen, alkoxy, $CF_3$, $OCF_3$, CN, alkylamino, dialkylamino, amino, hydroxyalkyl, alkylsulfonyl, alkylthio, aminoalkyl, alkylaminoalkyl, dialkylaminoalkyl, alkylcarbonylamino, alkylsulfonylamino, alkylsulfonylalkyl, alkylaminocarbonyl, alkylaminosulfonyl, and cyanoalkyl. In another embodiment, $R^7$ and $R^8$ are joined to form a heterocycle substituted with 0 to 3 groups independently selected from among OH, $CH_2OH$, $CH_2CH_2OH$, F, Cl, CN, $NH_2$, $NH(CH_3)$, $N(CH_3)_2$, $CH_2N(CH_3)_2$, $CH_2CH_2N(CH_3)_2$, $CONHCH_3$, $NHCOCH_3$, $NHSO_2CH_3$, $CH_2CN$, $CH(CH_3)CN$, $C(CH_3)_2CN$, $OCH_3$, $OCF_3$, and $SO_2CH_3$. In still a further embodiment, $R^7$ and $R^8$ are both $CH_3$.

$R^9$ is H or alkyl and $R^{10}$ is H or alkyl optionally substituted with OH, $NH_2$, $NHCH_3$, $N(CH_3)_2$, halogen, alkoxy, $CF_3$, $OCF_3$, or CN.

Alternatively, $R^9$ and $R^{10}$ are joined to form an optionally-substituted heterocycle wherein the fragment —$R^9$-$R^{10}$— is optionally substituted —$CH_2CH_2CH_2$—, —$CH_2CH_2CH_2CH_2$—, or —$CH_2CH_2$ $CH_2$ $CH_2CH_2$—.

In one embodiment, the compound is of formula (IA) or a pharmaceutically salt or solvate thereof, wherein $R^1$-$R^8$, A, X, Y, and Z are defined above (IA)

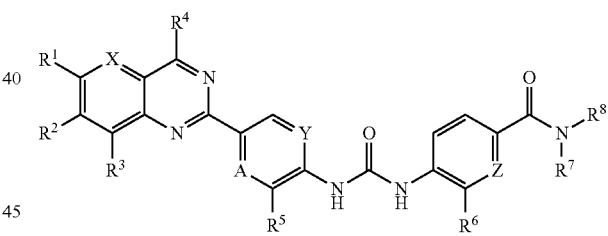

In a further embodiment, the compound is of formula (IB) or a pharmaceutically salt or solvate thereof, wherein $R^1$-$R^6$, $R^9$, $R^{10}$, A, X, Y and Z are defined above.

(IB)

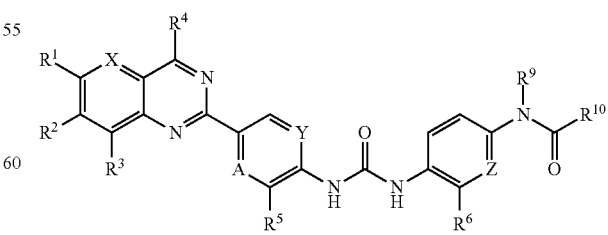

In yet a further embodiment, the compound is of formula (II) or a pharmaceutically salt or solvate thereof, wherein $R^1$ is H or F.

(II)

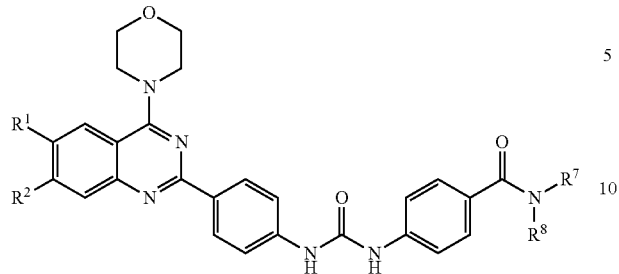

In another embodiment, the compound is of formula (III) of a pharmaceutically acceptable salt or solvate thereof, wherein $R^1$ is H or F.

(III)

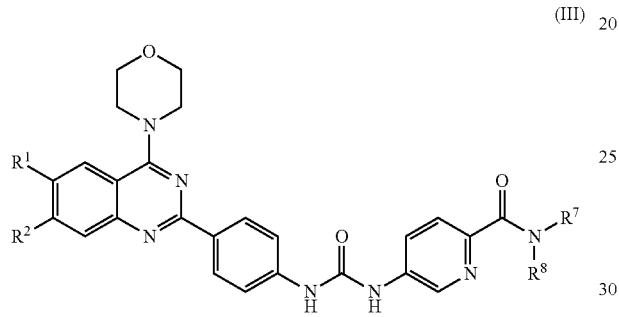

In a further embodiment, the compound is of formula (IV), or a pharmaceutically acceptable salt or solvate thereof.

(IV)

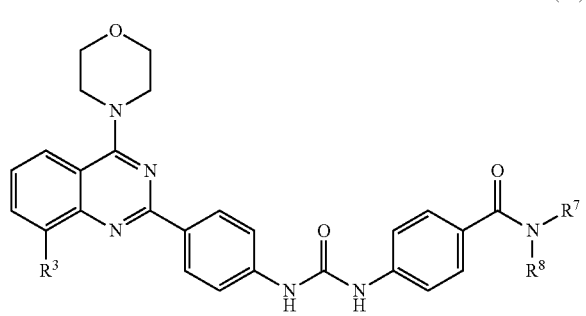

In still another embodiment, the compound is of formula (V) or a pharmaceutically acceptable salt or solvate thereof, wherein $R^1$ and $R^6$ are independently H or F.

(V)

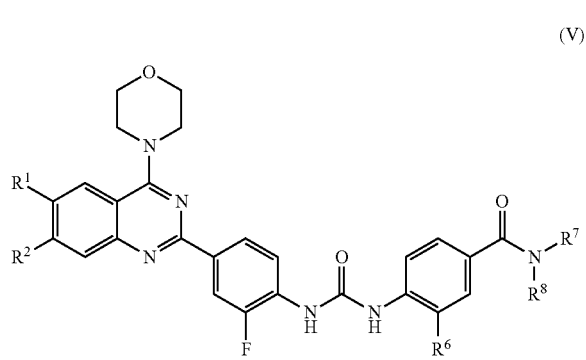

In yet a further embodiment, the compound is of formula (VI) or a pharmaceutically acceptable salt or solvate thereof, wherein one of $R^5$ or $R^6$ is F.

(VI)

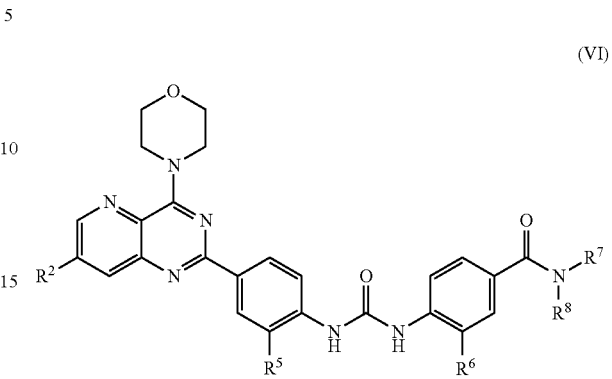

In another embodiment, the compound is of formula (VII) or a pharmaceutically acceptable salt or solvate thereof, wherein $R^2$, $R^5$, and M are defined herein.

(VII)

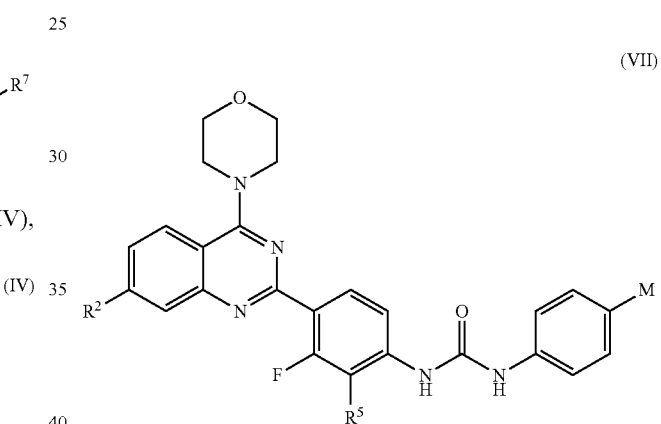

In a further embodiment, the compound is of formula (VIII) or a pharmaceutically acceptable salt or solvate thereof, wherein $R^2$, $R^5$, and M are defined herein.

(VIII)

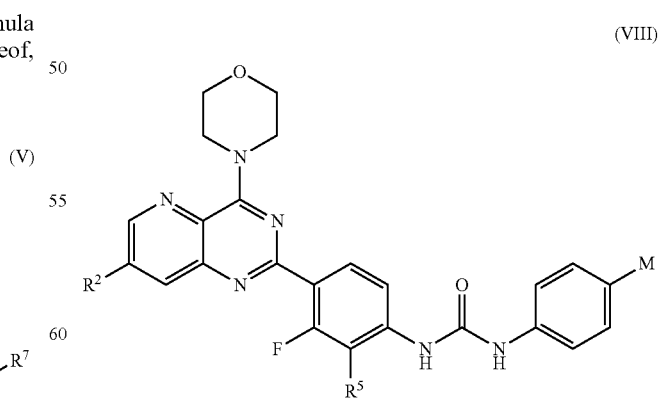

In yet another embodiment, the compound is of formula (b) or a pharmaceutically acceptable salt or solvate thereof, wherein $R^1$-$R^6$ and M are defined herein.

(IX)

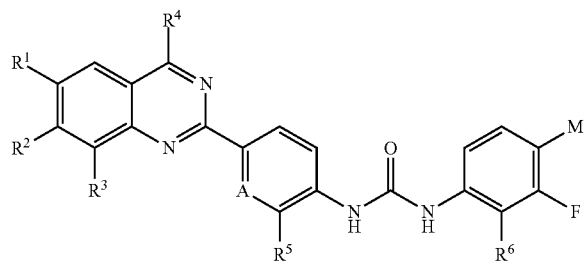

In still a further embodiment, the compound is of formula (X) or a pharmaceutically acceptable salt or solvate thereof, wherein $R^1$-$R^6$, A, and M are defined herein.

(X)

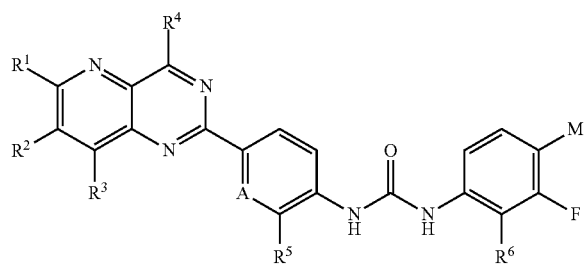

In yet another embodiment, the compound is of formula (XI) or a pharmaceutically acceptable salt or solvate thereof, wherein $R^2$ and $R^5$ are defined herein.

(XI)

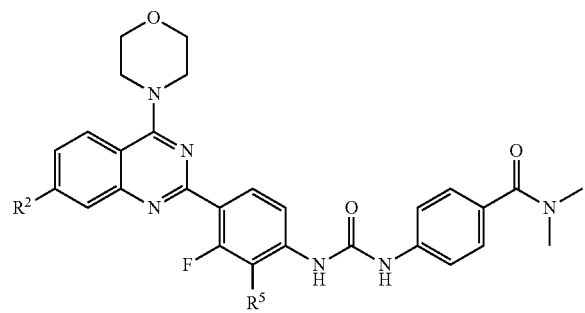

In a further embodiment, the compound is of formula (XII) or a pharmaceutically acceptable salt or solvate thereof, wherein $R^2$ and $R^5$ are defined herein.

(XII)

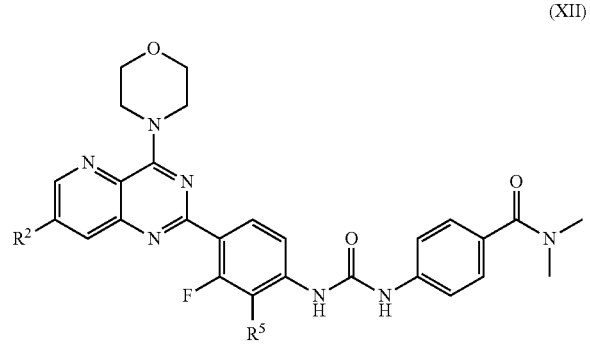

In still another embodiment, the compound is of formula (XIII) or a pharmaceutically acceptable salt or solvate thereof, wherein $R^1$-$R^6$ and A are defined herein.

(XIII)

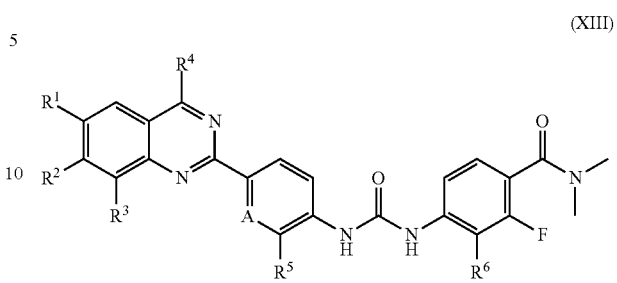

In a further embodiment, the compound is of formula (XIV) or a pharmaceutically acceptable salt or solvate thereof, wherein $R^2$ and $R^5$ are defined herein.

(XIV)

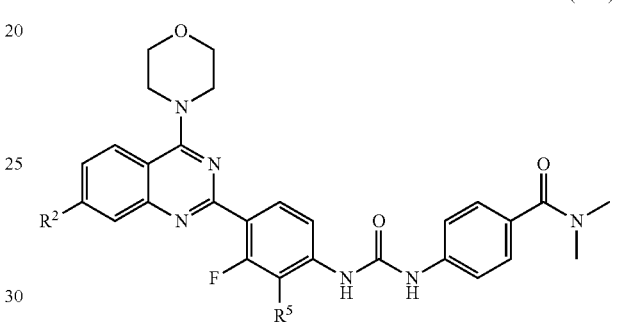

In yet another embodiment, the compound is of formula (XIV) or a pharmaceutically acceptable salt or solvate thereof, wherein $R^1$-$R^6$ and A are defined herein.

(XV)

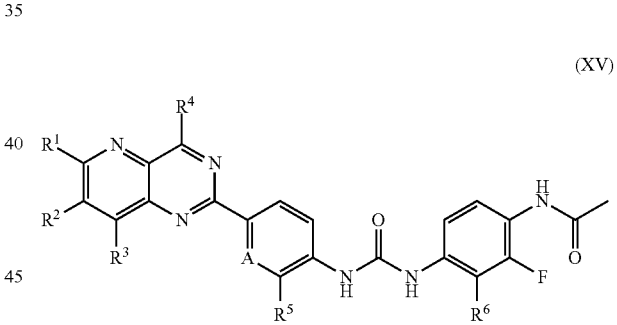

In still a further embodiment, the compound is of formula (XVI) or a pharmaceutically acceptable salt or solvate thereof, wherein $R^2$ and $R^5$ are defined herein.

(XVI)

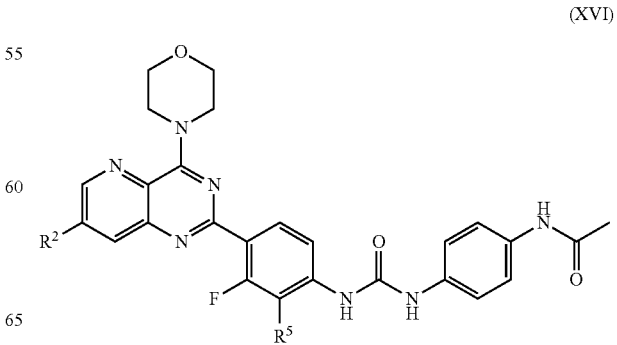

In another embodiment, the compound is of formula (XVII) or a pharmaceutically acceptable salt or solvate thereof, wherein $R^1$-$R^6$ and A are defined herein.

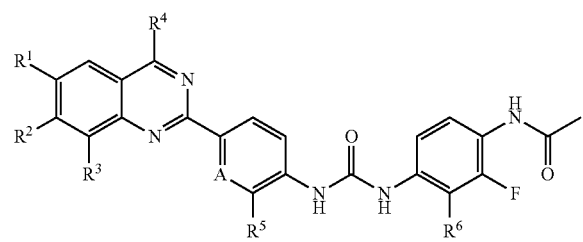

(XVII)

In a further embodiment, the compound is of formula (XVIII) or a pharmaceutically acceptable salt or solvate thereof, wherein $R^1$-$R^6$ and A are defined herein.

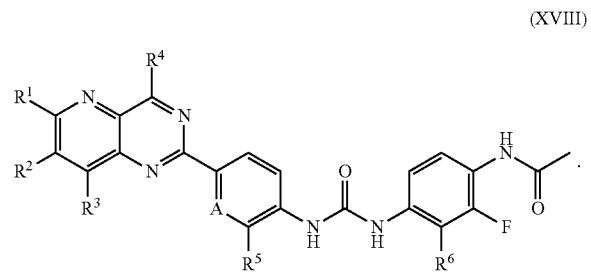

(XVIII)

Representative "pharmaceutically acceptable salts" include but are not limited to water-soluble and water-insoluble salts. In one embodiment, the salt is of a base. In another embodiment, the salt is of an acid. The salt can be of an acid selected from, e.g., among acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, trifluoroacetic, and camphorsulfonic. Optionally, a composition of the invention may contain both a pharmaceutically acceptable salt and the free base form of a compound of the invention.

In a further embodiment, a compound of the invention may be a solvate. As used herein, a solvate does not significantly alter the physiological activity or toxicity of the compounds, and as such may function as pharmacological equivalents to non-solvate compounds of the invention. The term "solvate" as used herein is a combination, physical association and/or solvation of a compound of the present invention with a solvent molecule. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates.

Some compounds within the present invention possess one or more chiral centers, and the present invention includes each separate enantiomer of such compounds as well as mixtures of the enantiomers. Where multiple chiral centers exist in compounds of the present invention, the invention includes each possible combination of chiral centers within a compound, as well as all possible enantiomeric mixtures thereof. All chiral, diastereomeric, and racemic forms of a structure are intended, unless the specific stereochemistry or isomeric form is specifically indicated. It is well known in the art how to prepare optically active forms, such as by resolution of racemic forms or by synthesis from optically active starting materials.

The following definitions are used in connection with the compounds described herein. In general, the number of carbon atoms present in a given group is designated "$C_x$ to $C_y$", where x and y are the lower and upper limits, respectively. The carbon number as used in the definitions herein refers to carbon backbone and carbon branching, but does not include carbon atoms of the substituents, such as alkoxy substitutions and the like. Unless indicated otherwise, the nomenclature of substituents that are not explicitly defined herein are determined by naming from left to right the terminal portion of the functionality followed by the adjacent functionality toward the point of attachment. As used herein, "optionally substituted" means that at least 1 hydrogen atom of the optionally substituted group has been replaced.

"Alkyl" refers to a hydrocarbon chain that may be straight or branched, or to a hydrocarbon group that consists of or contains a cyclic alkyl radical. In one embodiment, an alkyl contains 1 to 8 (inclusive) carbon atoms or integers or ranges there between (2, 3, 4, 5, 6, or 7). In another embodiment, an alkyl contains 1 to 7 (inclusive) carbon atoms or ranges there between. In a further embodiment, an alkyl contains 1 to 6 (inclusive) carbon atoms. In yet another embodiment, an alkyl contains 1 to 5 (inclusive) carbon atoms. In still a further embodiment, an alkyl contains 1 to 4 (inclusive) carbon atoms. Examples of alkyl groups that are hydrocarbon chains include, but are not limited to, methyl, ethyl, propyl, butyl, pentyl, hexyl, and heptyl, where all isomers of these examples are contemplated. Examples of alkyl groups that consist of or contain a cyclic alkyl radical include, but are not limited to, cyclopropyl, cyclobutyl, cyclopentyl, 3,3-dimethylcyclobutyl, (cyclopropyl)methyl, and (cyclopentyl)methyl. An alkyl can be unsubstituted or substituted with one or more groups including, without limitation, halogen, OH, $NH_2$, $N(C_1$ to $C_3$ alkyl)$C(O)(C_1$ to $C_6$ alkyl), $NHC(O)(C_1$ to $C_6$ alkyl), $NHC(O)H$, $C(O)NH_2$, $C(O)NH(C_1$ to $C_6$ alkyl), $C(O)N(C_1$ to $C_6$ alkyl)($C_1$ to $C_6$ alkyl), CN, $C_1$ to $C_6$ alkoxy, $C(O)OH$, $C(O)O(C_1$ to $C_6$ alkyl), $C(O)(C_1$ to $C_6$ alkyl), aryl, heteroaryl, $NH(C_1$ to $C_6$ alkyl), $N(C_1$ to $C_6$ alkyl)($C_1$ to $C_6$ alkyl), $OC(O)(C_1$ to $C_6$ alkyl), optionally substituted heterocycle, and $NO_2$. In one embodiment, the substituted alkyl is $CH_2OH$.

"Alkenyl" refers to hydrocarbon chain which is straight or branched and contains at least one degree of unsaturation (i.e., with one or more carbon-carbon double bonds), or to a hydrocarbon group that consists of or contains a cyclic alkenyl radical. Each alkenyl double bond may exist in the E or Z conformation. In one embodiment, an alkenyl contains 2 to about 8 (inclusive) carbon atoms or integers or ranges there between (3, 4, 5, 6, or 7). In another embodiment, an alkenyl contains 2 to 7 (inclusive) carbon atoms. In a further embodiment, an alkenyl contains 2 to 6 (inclusive) carbon atoms. In yet another embodiment, an alkenyl contains 2 to 5 (inclusive) carbon atoms. In still a further embodiment, an alkenyl contains 2 to 4 (inclusive) carbon atoms. An alkenyl contains at least 1 double bond. In one embodiment, the alkenyl may contain 1, 2, 3, or 4 double bonds. Examples of alkenyl hydrocarbon chain include, but are not limited to, ethene, propene, butene, pentene, hexene, heptene, and octene. Examples of alkenyl that consist of or contain a cyclic alkenyl radical include, but are not limited to, cyclopentene, and cyclohexene. An alkenyl can be unsubstituted or substituted with one or more groups including, without limitation, halogen, OH, $NH_2$, $N(C_1$ to $C_3$ alkyl)$C(O)(C_1$ to $C_6$ alkyl), NHC (O)($C_1$ to $C_6$ alkyl), NHC(O)H, C(O)$NH_2$, C(O)NH($C_1$ to $C_6$ alkyl), C(O)N($C_1$ to $C_6$ alkyl)($C_1$ to $C_6$ alkyl), CN, $C_1$ to $C_6$ alkoxy, C(O)OH, C(O)O($C_1$ to $C_6$ alkyl), C(O)($C_1$ to $C_6$ alkyl), aryl, heteroaryl, NH($C_1$ to $C_6$ alkyl), N($C_1$ to $C_6$ alkyl)($C_1$ to $C_6$ alkyl), OC(O)($C_1$ to $C_6$ alkyl), and $NO_2$.

"Alkynyl" refers to a hydrocarbon chain which is straight or branched chain and contains at least one degree of unsaturation, i.e., with one or more carbon-carbon triple bond. In one embodiment, an alkynyl contains 2 to about 8 (inclusive) carbon atoms or integers or ranges there between (3, 4, 5, 6, or 7). In another embodiment, an alkynyl contains 2 to 7 (inclusive) carbon atoms. In a further embodiment, an alkynyl contains 2 to 6 (inclusive) carbon atoms. In yet another embodiment, an alkynyl contains 2 to 5 (inclusive) carbon atoms. In still a further embodiment, an alkynyl contains 2 to 4 (inclusive) carbon atoms. An alkynyl contains at least 1 triple bond. In one embodiment, the alkynyl may contain 1, 2, 3, or 4 triple bonds. Examples of alkynyl include, but are not limited to, ethyne, propyne, butyne, pentyne, hexyne, heptyne, and octyne. An alkynyl can be unsubstituted or substituted with one or more groups including, without limitation, halogen, OH, $NH_2$, N($C_1$ to $C_3$ alkyl)C(O)($C_1$ to $C_6$ alkyl), NHC(O)($C_1$ to $C_6$ alkyl), NHC(O)H, C(O)$NH_2$, C(O)NH($C_1$ to $C_6$ alkyl), C(O)N($C_1$ to $C_6$ alkyl)($C_1$ to $C_6$ alkyl), CN, $C_1$ to $C_6$ alkoxy, C(O)OH, C(O)O($C_1$ to $C_6$ alkyl), C(O)($C_1$ to $C_6$ alkyl), aryl, heteroaryl, NH($C_1$ to $C_6$ alkyl), N($C_1$ to $C_6$ alkyl)($C_1$ to $C_6$ alkyl), OC(O)($C_1$ to $C_6$ alkyl), and $NO_2$.

"Alkoxy" refers to (alkyl)O, where the alkyl is optionally substituted and is defined above. In one embodiment, an alkoxy contains 1 to 8 (inclusive) carbon atoms or integers or ranges there between (2, 3, 4, 5, 6, or 7). In another embodiment, an alkoxy contains 1 to 7 (inclusive) carbon atoms or ranges there between. In a further embodiment, an alkoxy contains 1 to 6 (inclusive) carbon atoms. In yet another embodiment, an alkoxy contains 1 to 5 (inclusive) carbon atoms. In still a further embodiment, an alkoxy contains 1 to 4 (inclusive) carbon atoms. Examples of alkoxy include, but are not limited to, methoxy, ethoxy, propoxy, and butoxy. The alkyl radical of an alkoxy group can be unsubstituted or substituted as defined above for "alkyl".

"Hydroxyalkyl" refers to (alkyl)OH, where the alkyl is optionally substituted and is defined above. The OH moiety of the hydroxyalkyl may be bound to any carbon atom, for example, any one of the internal carbon atoms or the terminal carbon atom of a hydrocarbon alkyl chain. In one embodiment, a hydroxyalkyl contains 1 to 8 (inclusive) carbon atoms or integers or ranges there between (2, 3, 4, 5, 6, or 7). In another embodiment, a hydroxyalkyl contains 1 to 7 (inclusive) carbon atoms or ranges there between. In a further embodiment, a hydroxyalkyl contains 1 to 6 (inclusive) carbon atoms. In yet another embodiment, a hydroxyalkyl contains 1 to 5 (inclusive) carbon atoms. In still a further embodiment, a hydroxyalkyl contains 1 to 4 (inclusive) carbon atoms. Examples of a hydroxyalkyl include, but are not limited to, $CH_2OH$, $CH_2CH_2OH$, $CH(OH)CH_3$, $CH_2CH_2CH_2OH$, $CH_2CH(OH)CH_3$, $CH(OH)CH_2CH_3$, $C(OH)(CH_3)_2$, (2-hydroxy)-cyclopentyl, (3-hydroxy)-cyclobutyl, and the like.

"Cyanoalkyl" refers to (alkyl)CN, where the alkyl is optionally substituted and is defined above. The CN moiety of the cyanoalkyl may be bound to any carbon atom; for example, any one of the internal carbon atoms or the terminal carbon atom of a hydrocarbon alkyl chain. In one embodiment, a cyanoalkyl contains 1 to 8 (inclusive) carbon atoms or integers or ranges there between (2, 3, 4, 5, 6, or 7). In another embodiment, a cyanoalkyl contains 1 to 7 (inclusive) carbon atoms or ranges there between. In a further embodiment, a cyanoalkyl contains 1 to 6 (inclusive) carbon atoms. In yet another embodiment, a cyanoalkyl contains 1 to 5 (inclusive) carbon atoms. In still a further embodiment, a cyanoalkyl contains 1 to 4 (inclusive) carbon atoms. Examples of cyanoalkyl include, but are not limited to, $CH_2CN$, $CH_2CH_2CN$, $CH(CN)CH_3$, $CH_2CH_2CH_2CN$, $CH_2CH(CN)CH_3$, $CH(CN)CH_2CH_3$, $C(CN)(CH_3)_2$, (2-cyano)-cyclopentyl, (3-cyano)-cyclobutyl, and the like.

"Aryl" refers to an aromatic hydrocarbon group containing carbon atoms. In one embodiment, the aryl contains 6, 7 or 8 carbon atoms, and is phenyl or is an aromatic or partly aromatic bicyclic group. In a further embodiment, the aryl is a phenyl group. In another embodiment, the aryl is naphthyl (such as α-naphthyl or β-naphthyl), 1,2,3,4-tetrahydronaphthyl, or indanyl. An aryl group can be unsubstituted or substituted with one or more groups including, without limitation, halogen, OH, $NH_2$, N($C_1$ to $C_3$ alkyl)C(O)($C_1$ to $C_6$ alkyl), NHC(O)($C_1$ to $C_6$ alkyl), NHC(O)H, C(O)$NH_2$, C(O)NH($C_1$ to $C_6$ alkyl), C(O)N($C_1$ to $C_6$ alkyl)($C_1$ to $C_6$ alkyl), $C_1$ to $C_6$ alkyl, CN, $C_1$ to $C_6$ alkoxy, C(O)OH, C(O)O($C_1$ to $C_6$ alkyl), C(O)($C_1$ to $C_6$ alkyl), aryl, heteroaryl, NH($C_1$ to $C_6$ alkyl), N($C_1$ to $C_6$ alkyl)($C_1$ to $C_6$ alkyl), OC(O)($C_1$ to $C_6$ alkyl), and $NO_2$. In one embodiment, an aryl is substituted with one or more halogen, OH, CN, $NH_2$, $C_1$ to $C_6$ alkylamino, $C_1$ to $C_6$ alkyl substituted with OH, $C_1$ to $C_6$ alkoxy, $C_1$ to $C_6$ haloalkyl, $OCF_3$, $SO_2$($C_1$ to $C_6$ alkyl), or $NHSO_2$($C_1$ to $C_6$ alkyl). In another embodiment, an aryl is substituted with one halogen, OH, CN, $NH_2$, $C_1$ to $C_6$ alkylamino, $C_1$ to $C_6$ alkyl substituted with OH, $C_1$ to $C_6$ alkoxy, $CF_3$, $OCF_3$, $SO_2CH_3$, $NHCOCH_3$, or $NHSO_2CH_3$. In a further embodiment, an aryl is substituted with one halogen, OH, CN, $N(CH_3)_2$, $CH_2OH$, $OCH_3$, $OCF_3$, $CF_3$, $SO_2CH_3$, $NHCOCH_3$, or $NHSO_2CH_3$.

"Halogen" refers to F, Cl, Br and I.

The term "heteroatom" refers to a sulfur, nitrogen, or oxygen atom.

"Heteroaryl" refers to a monocyclic aromatic 5- or 6-membered ring containing at least one ring heteroatom. In one embodiment, the heteroaryl contains 1 to 5 carbon atoms (inclusive) or integers or ranges there between (2, 3, or 4). In a further embodiment, the heteroaryl contains 2 to 5 carbon atoms (inclusive). In another embodiment, the heteroaryl contains 3 to 5 carbon atoms (inclusive). In still a further embodiment, the heteroaryl contains 4 or 5 carbon atoms. "Heteroaryl" also refers to bicyclic aromatic ring systems wherein a heteroaryl group as just described is fused to at least one other cyclic moiety. In one embodiment, a phenyl radical is fused to a 5- or 6-membered monocyclic heteroaryl to form the bicyclic heteroaryl. In another embodiment, a cyclic alkyl is fused to a monocyclic heteroaryl to form the bicyclic heteroaryl. In yet a further embodiment, the bicyclic heteroaryl is a pyridine fused to a 5- or 6-membered monocyclic heteroaryl. In another embodiment, the bicyclic heteroaryl is a pyrimidine fused to a 5- or 6-membered monocyclic heteroaryl. In yet a further embodiment, the bicyclic heteroaryl is a pyridazine fused to a 5- or 6-membered monocyclic heteroaryl. In still another embodiment, the heteroaryl ring has 1 or 2 nitrogen atoms in the ring. In a further embodiment, the heteroaryl ring has 1 nitrogen atom and 1 oxygen atom. In yet another embodiment, the heteroaryl ring has 1 nitrogen atom and 1 sulfur atom. Examples of heteroaryl groups include, without limitation, furan, thiophene, indole, azaindole, oxazole, thiazole, isoxazole, isothiazole, imidazole, pyridine, pyrimidine, pyrazine, pyridazine, pyrrole, pyrazole, 1,3,4-oxadiazole, 1,2,4-triazole, tetrazole, benzoxazole, benzothiazole, benzofuran, benzisoxazole, benzimidazole, azabenzimidazole, indazole, quinazoline, quinoline, and isoquinoline. A heteroaryl may be unsubstituted or substituted with one or more groups including, without limitation, halogen, $C_1$ to $C_6$ alkyl, OH, $C_1$ to $C_6$ hydroxyalkyl, $NH_2$, $N(C_1$ to $C_3$ alkyl)$C(O)(C_1$ to $C_6$ alkyl), $NHC(O)(C_1$ to $C_6$ alkyl), NHC(O)H, $C(O)NH_2$, $C(O)NH(C_1$ to $C_6$ alkyl), $C(O)N(C_1$ to $C_6$ alkyl)($C_1$ to $C_6$ alkyl), CN, $C_1$ to $C_6$ alkoxy, C(O)OH, $C(O)O(C_1$ to $C_6$ alkyl), $C(O)(C_1$ to $C_6$ alkyl), aryl, heteroaryl, $NH(C_1$ to $C_6$ alkyl), $N(C_1$ to $C_6$ alkyl)($C_1$ to $C_6$ alkyl), $OC(O)(C_1$ to $C_6$ alkyl), $NH(C_1$ to $C_6$ hydroxyalkyl), $N(C_1$ to $C_6$ hydroxyalkyl)$_2$, $C(O)NH[—(C_1$ to $C_6$ alkyl)-$N(C_1$ to $C_6$ alkyl)$_2$], $C(O)NH[—(C_1$ to $C_6$ alkyl)-$NH(C_1$ to $C_6$ alkyl)], $C(O)N(C_1$ to $C_6$ alkyl)[—($C_1$ to $C_6$ alkyl)-$N(C_1$ to $C_6$ alkyl)$_2$] and $NO_2$. In one embodiment, a heteroaryl is substituted with one or more halogen, OH, CN, $NH_2$, $C_1$ to $C_6$ alkylamino, $C_1$ to $C_6$ alkyl substituted with OH, $C_1$ to $C_6$ alkoxy, $C_1$ to $C_6$ haloalkyl, $OCF_3$, $SO_2(C_1$ to $C_6$ alkyl), $NHCOCH_3$, or $NHSO_2(C_1$ to $C_6$ alkyl). In another embodiment, a heteroaryl is substituted with one halogen, OH, CN, $N(CH_3)_2$, $CH_2OH$, $OCH_3$, $OCF_3$, $CF_3$, $SO_2CH_3$, $NHCOCH_3$, or $NHSO_2CH_3$.

"Heterocycle" refers to a monocyclic or bicyclic group in which at least 1 ring atom is a heteroatom. A heterocycle may be saturated or partially saturated. In one embodiment, the heterocycle contains 3 to 7 carbon atoms (inclusive) or integers or ranges there between (4, 5, or 6). In a further embodiment, the heterocycle contains 4 to 7 carbon atoms (inclusive). In another embodiment, the heterocycle contains 4 to 6 carbon atoms (inclusive). In still a further embodiment, the heterocycle contains 5 or 6 carbon atoms (inclusive). Examples of heterocycles include, but are not limited, to aziridine, oxirane, thiirane, morpholine, thiomorpholine, pyrroline, pyrrolidine, azepane, dihydrofuran, THF, dihydrothiophene, tetrahydrothiophene, dithiolane, piperidine, 1,2,3,6-tetrahydropyridine-1-yl, tetrahydropyran, pyran, thiane, thiine, piperazine, homopiperazine, oxazine, azecane, tetrahydroquinoline, perhydroisoquinoline, 5,6-dihydro-4H-1,3-oxazin-2-yl, 2,5-diazabicyclo[2.2.1]heptane, 2,5-diazabicyclo[2.2.2]octane, 3,6-diazabicyclo[3.1.1]heptane, 3,8-diazabicyclo[3.2.1]octane, 6-oxa-3,8-diazabicyclo[3.2.1]octane, 7-oxa-2,5-diazabicyclo[2.2.2]octane, 2,7-dioxa-5-azabicyclo[2.2.2]octane, 2-oxa-5-azabicyclo[2.2.1]heptane-5-yl, 2-oxa-5-azabicyclo[2.2.2]octane, 3,6-dioxa-8-azabicyclo[3.2.1]octane, 3-oxa-6-azabicyclo[3.1.1]heptane, 3-oxa-8-azabicyclo[3.2.1]octan-8-yl, 5,7-dioxa-2-azabicyclo[2.2.2]octane, 6,8-dioxa-3-azabicyclo[3.2.1]octane, 6-oxa-3-azabicyclo[3.1.1]heptane, 8-oxa-3-azabicyclo[3.2.1]octan-3-yl, 2,5-diazabicyclo[2.2.1]heptane-5-yl, 6-azabicyclo[3.2.1]oct-6-yl, 8-azabicyclo[3.2.1]octan-8-yl, 3-oxa-7,9-diazabicyclo[3.3.1]nonan-9-yl, 9-oxa-3-azabicyclo[3.3.1]nonan-3-yl, 3-oxa-9-azabicyclo[3.3.1]nonan-9-yl, 3,7-dioxa-9-azabicyclo[3.3.1]nonan-9-yl, 3,4-dihydro-2H-1,4-benzoxazin-7-yl, thiazine, dithiane, and dioxane. In another embodiment, the heterocycle contains 1 or 2 nitrogen atoms. In a further embodiment, the heterocycle contains 1 or 2 nitrogen atoms and 3 to 6 carbon atoms. In yet another embodiment, the heterocycle contains 1 or 2 nitrogen atoms, 3 to 6 carbon atoms, and 1 oxygen atom. In still a further embodiment, the heterocycle is morpholine. In one embodiment, the heterocycle is morpholine and is substituted with one or more $C_1$ to $C_3$ alkyl. In another embodiment, the heterocycle is morpholine and 2 carbons of the heterocycle are joined to form a 4- or 5-membered ring. A heterocycle may be unsubstituted or substituted with one or more groups including, without limitation, halogen, $C_1$ to $C_6$ alkyl, OH, $NH_2$, $N(C_1$ to $C_3$ alkyl)$C(O)(C_1$ to $C_6$ alkyl), $NHC(O)(C_1$ to $C_6$ alkyl), NHC(O)H, $C(O)NH_2$, $C(O)NH(C_1$ to $C_6$ alkyl), $C(O)N(C_1$ to $C_6$ alkyl)($C_1$ to $C_6$ alkyl), CN, $C_1$ to $C_6$ alkoxy, C(O)OH, $C(O)O(C_1$ to $C_6$ alkyl), $C(O)(C_1$ to $C_6$ alkyl), aryl, heteroaryl, $NH(C_1$ to $C_6$ alkyl), $N(C_1$ to $C_6$ alkyl)($C_1$ to $C_6$ alkyl), $OC(O)(C_1$ to $C_6$ alkyl), $NH(C_1$ to $C_{6\ hydroxyalkyl}), N(C_1$ to $C_6$ hydroxyalkyl)$_2$, $C(O)NH[—(C_1$ to $C_6$ alkyl)-$N(C_1$ to $C_6$ alkyl)$_2$], $C(O)NH[—(C_1$ to $C_6$ alkyl)-$NH(C_1$ to $C_6$ alkyl)], $C(O)N(C_1$ to $C_6$ alkyl)[—($C_1$ to $C_6$ alkyl)-$N(C_1$ to $C_6$ alkyl)$_2$] and $NO_2$. In one embodiment, a heterocycle is substituted with one or more halogen, OH, CN, $NH_2$, $C_1$ to $C_6$ alkylamino, $C_1$ to $C_6$ alkyl substituted with OH, $C_1$ to $C_6$ alkoxy, $C_1$ to $C_6$ haloalkyl, $OCF_3$, $SO_2(C_1$ to $C_6$ alkyl), $NHCOCH_3$, or $NHSO_2(C_1$ to $C_6$ alkyl). In another embodiment, a heterocycle is substituted with one F, OH, CN, $NH_2$, $N(CH_3)_2$, $CH_2OH$, $OCH_3$, $OCF_3$, $CF_3$, $SO_2CH_3$, $NHCOCH_3$, or $NHSO_2CH_3$.

"Optionally-substituted —$CH_2CH_2CH_2$—, —$CH_2CH_2CH_2CH_2$—, or —$CH_2CH_2CH_2CH_2CH_2$-" refers to —$CH_2CH_2CH_2$—, —$CH_2CH_2CH_2CH_2$—, or —$CH_2CH_2CH_2CH_2CH_2$— wherein 1 or 2 of the hydrogen atoms are replaced with OH, $NH_2$, $NHCH_3$, $N(CH_3)_2$, halogen, alkoxy, $CF_3$, $OCF_3$, or CN.

"$C_1$ to $C_6$ haloalkyl" refers to a $C_1$ to $C_6$ alkyl group, as defined above, wherein one or more of the $C_1$ to $C_6$ alkyl group's hydrogen atoms has been replaced with F, Cl, Br, or I. Each substitution can be independently selected from F, Cl, Br, or I. Representative examples of an $C_1$ to $C_6$ haloalkyl group include, but are not limited to, $CH_2F$, $CF_3$, $CH_2CF_3$, and the like.

"Alkylthio" refers to (alkyl)S$\sim$, where the alkyl is optionally substituted and is defined above. In one embodiment, an alkylthio contains 1 to 8 (inclusive) carbon atoms or integers or ranges there between (2, 3, 4, 5, 6, or 7). Examples of alkylthio include, but are not limited to, $SCH_3$, $SCH_2CH_3$, $SCH_2CH_2CH_3$, and $SCH_2CH_2CH_2CH_3$.

"Aryloxy" refers to (aryl)O$\sim$, where the aryl is defined above and is optionally substituted as described above. An aryloxy group is attached through the oxygen atom moiety. Examples of aryloxy include, but are not limited to, phenoxy and pentafluorophenoxy.

"Heteroaryloxy" refers to (heteroaryl)O$\sim$, where the heteroaryl is optionally substituted and is defined above. The heteroaryloxy moiety is bound through the oxygen atom moiety. Examples of heteroaryloxy include, but are not limited to, (3-pyridyl)oxy and (4-pyridyl)oxy.

"Heterocycle-oxy" refers to (heterocycle)O$\sim$, where the heterocycle is optionally substituted and is defined above. The heterocycle-oxy moiety is bound through the oxygen atom. Examples of heterocycleoxy include, but are not limited to, (4-piperidinyl)oxy.

"Alkylsulfonyl" refers to an (alkyl)$SO_2$$\sim$ group, which is bound through the $SO_2$ moiety. The alkyl group is defined and optionally substituted as described above. Examples of alkylsulfonyl include, but are not limited to, $CH_3SO_2$, $CH_3CH_2CH_2SO_2$, $CH_3CH(CH_3)SO_2$, $CH_3CH_2CH_2CH_2SO_2$, $CH_3CH(CH_3)CH_2SO_2$, $(CH_3)_3CSO_2$, and the like.

"Alkylsulfonylalkyl" refers to an (alkyl)$SO_2$(alkyl) group, which is bound through one of the alkyl groups. The alkyl group is defined and optionally substituted as described above. The alkyl groups may be the same or different. Examples of alkylsulfonylalkyl include, but are not limited to, 3-(methylsulfonyl)propyl and 3-(methylsulfonyl)cyclopentyl.

"Alkylamino" refers to an NH or N group, the nitrogen atom of said group being attached to 1 or 2 alkyl substituents, respectively, where alkyl is as defined above. The alkylamino is bound through the nitrogen atom of the group. In one embodiment, alkylamino refers to a (alkyl)NH$\sim$ group. In another embodiment, alkylamino refers to a (alkyl)(alkyl)N$\sim$ group, i.e., a "dialkylamino". When the nitrogen atom is bound to 2 alkyls, each alkyl group may be independently selected. In another embodiment, two alkyl groups on the nitrogen atom may be taken together with the nitrogen to which they are attached to form a 3- to 7-membered nitrogen-containing heterocycle wherein up to two of the carbon atoms of the heterocycle can be replaced with N(H), N($C_1$ to $C_6$ alkyl), N(aryl), N(heteroaryl), O, S, S(O), or S(O)$_2$. Examples of alkylamino include, but are not limited to CH$_3$NH, CH$_3$CH$_2$NH, CH$_3$CH$_2$CH$_2$NH, CH$_3$CH$_2$CH$_2$CH$_2$NH, (CH$_3$)$_2$CHNH, (CH$_3$)$_2$CHCH$_2$NH, CH$_3$CH$_2$CH(CH$_3$)NH, (CH$_3$)$_3$CNH, N(CH$_3$)$_2$, N(CH$_2$CH$_3$)(CH$_3$), N(CH$_2$CH$_3$)$_2$, N(CH$_2$CH$_2$CH$_3$)$_2$, N(CH$_2$CH$_2$CH$_2$CH$_3$)$_2$, N(CH(CH$_3$)$_2$)(CH$_3$), and the like.

"Aminoalkyl" refers to an alkyl group having an NH$_2$ substituent. The aminoalkyl is bound through one carbon atom of the group. That is, alkylamino refers to a NH$_2$(alkyl)〰 group. Examples of aminoalkyl include, but are not limited to CH$_2$NH$_2$, CH$_2$CH$_2$NH$_2$, CH$_2$CH$_2$CH$_2$NH$_2$, CH$_2$CH$_2$CH$_2$CH$_2$NH$_2$, C(CH$_3$)$_2$NH$_2$, C(CH$_3$)$_2$CH$_2$NH$_2$, and the like.

"Alkylaminoalkyl" refers to an (alkyl)NH(alkyl)〰 group, the nitrogen atom of being attached to 2 alkyl substituents, respectively, as defined above, and where the group is bound through one of the alkyl groups. Each of the alkyl groups may be independently selected and substituted as described above. In another embodiment, the alkyl groups may be taken together with the nitrogen to which they are attached to form a 3- to 7-membered nitrogen containing heterocycle wherein up to two of the carbon atoms of the heterocycle can be replaced with N(H), N($C_1$ to $C_6$ alkyl), N(aryl), N(heteroaryl), O, S, S(O), or S(O)$_2$. Examples of alkylaminoalkyl include, but are not limited to CH$_3$NHCH$_2$, CH$_3$NHCH$_2$CH$_2$, CH$_3$NHCH(CH$_3$), CH$_3$CH$_2$NHCH$_2$, CH$_3$CH$_2$NHCH$_2$CH$_2$, CH$_3$CH$_2$NHCH(CH$_3$), and the like.

"Dialkylaminoalkyl" refers to an (alkyl)$_2$N(alkyl)〰 group, the nitrogen atom of being attached to 3 alkyl substituents, respectively, as defined above, and where the group is bound through one of the alkyl groups. Each of the alkyl groups may be independently selected and substituted as described above. In another embodiment, two of the alkyl groups may be taken together with the nitrogen to which they are attached to form a 3- to 7-membered nitrogen containing heterocycle wherein up to two of the carbon atoms of the heterocycle can be replaced with N(H), N($C_1$ to $C_6$ alkyl), N(aryl), N(heteroaryl), O, S, S(O), or S(O)$_2$. Examples of dialkylaminoalkyl include, but are not limited to (CH$_3$)$_2$NCH$_2$, (CH$_3$)$_2$NCH$_2$CH$_2$, (CH$_3$)$_2$NCH(CH$_3$), (CH$_3$CH$_2$)$_2$NCH$_2$, (CH$_3$CH$_2$)$_2$NCH$_2$CH$_2$, (CH$_3$CH$_2$)$_2$NCH(CH$_3$), (CH$_3$)(CH$_3$CH$_2$)NCH$_2$, and the like.

"Arylamino" refers to an (aryl)NH$^w$ group, where aryl is optionally substituted and defined as above. The arylamino is bound through the nitrogen atom. Examples of arylamino include, but are not limited to, phenyl-amino.

"Heteroarylamino" refers to a (heteroaryl)NH〰 group, where heteroaryl is optionally substituted and defined as above. The heteroarylamino is bound through the amino nitrogen atom. Examples of heteroarylamino include, but are not limited to (pyridin-2-yl)amino and (pyrimidin-2-yl)amino.

"Heterocycle-amino" refers to a (heterocycle)NH〰 group, where heterocycle is optionally substituted and defined as above. Examples of heterocycle-amino include, but are not limited to (piperidin-4-yl)amino.

"Alkylcarbonylamino" refers to an (alkyl)C(O)NH〰 group, which is bound through the nitrogen atom. The alkyl group is defined and optionally substituted as described above. Examples of alkylcarbonylamino include, but are not limited to, CH$_3$CONH, CH$_3$CH$_2$CONH, CH$_3$CH$_2$CH$_2$CONH, CH$_3$CH(CH$_3$)CONH, and the like.

"Alkylsulfonylamino" refers to an (alkyl)SO$_2$NH〰 group which is bound through the nitrogen atom. The alkyl group is defined and optionally substituted as described above. Examples of alkylsulfonylamino include, but are not limited to CH$_3$SO$_2$NH, CH$_3$CH$_2$SO$_2$NH, CH$_3$CH$_2$CH$_2$SO$_2$NH, CH$_3$CH(CH$_3$)SO$_2$NH, and the like.

"Alkylaminocarbonyl" refers to an (alkyl)NHC(O)〰 group, which is bound through the carbonyl moiety. The alkyl group is defined and optionally substituted as described above. Examples of alkylaminocarbonyl include, but are not limited to, CH$_3$NHCO, CH$_3$CH$_2$NHCO, CH$_3$CH$_2$CH$_2$NHCO, CH$_3$CH(CH$_3$)NHCO, and the like.

"Alkylaminosulfonyl" refers to an (alkyl)NHSO$_2$〰 group, which is bound through the sulfur atom. The alkyl group is defined and optionally substituted as described above. Examples of alkylaminosulfonyl include, but are not limited to, CH$_3$NHSO$_2$, CH$_3$CH$_2$NHSO$_2$, CH$_3$CH$_2$CH$_2$NHSO$_2$, CH$_3$CH(CH$_3$)NHSO$_2$, and the like.

"Arylaminocarbonyl" refers to an (aryl)NHC(O)〰 group, which is bound through the carbon atom of the carbonyl moiety. The aryl group is defined and optionally substituted as described above. Examples of arylaminocarbonyl include, but are not limited to phenyl-NHC(O)—.

"Heteroarylaminocarbonyl" refers to an (heteroaryl)NHC(O)〰 group, which is bound through the carbon atom of the carbonyl moiety. The heteroaryl group is defined and optionally substituted as described above. Examples of heteroarylaminocarbonyl include, but are not limited to (pyridine-4-yl)NHC(O).

"Heterocycleaminocarbonyl" refers to an (heterocycle)NHC(O)〰 group, which is bound through the carbonyl moiety. The heterocycle group is defined and optionally substituted as described above. Examples of heterocycleaminocarbonyl include, but are not limited to (tetrahydro-2H-pyran-4-yl)NHC(O).

A "patient" or "subject" is a mammal, e.g., a human or a veterinary patient or subject, e.g., mouse, rat, guinea pig, dog, cat, horse, cow, pig, or non-human primate, such as a monkey, chimpanzee, baboon or gorilla.

The term "treating" or "treatment" is meant to encompass administering to a subject a compound of the present invention for the purposes of amelioration of one or more symptoms of a disease or disorder, including palliative care. A "therapeutically effective amount" refers to the minimum amount of the active compound which effects treatment.

The following abbreviations are used herein and have the indicated definitions:
ACN is acetonitrile; BCA is bicinchoninic acid; bid po means twice daily by mouth; conc is concentrated; DMSO is dimethylsulfoxide; DCC is dicyclohexylcarbodiimide; DCM is dichloromethane; DIPEA is diisopropylethylamine; DMF is N,N-dimethylformamide; dppf is 1,1'-bis(diphenylphosphino)ferrocene; DTT is dithiothreitol; EDCI.HCl is 1-(3-dimethylaminopropyl)-3-ethylcarbodiimide hydrochloride; EDTA is ethylenediamine tetraacetic acid; EGTA is ethylene glycol tetraacetic acid; ELISA is enzyme-linked immunosorbent assay; EtOH is ethanol; ESI is electrospray ionization; EI is electron impact ionization; HATU is 2-(1H-7-azabenzotriazol-1-yl)-1,1,3,3-tetramethyl uronium hexafluorophosphate methanaminium; HEPES is (4-(2-hydroxyethyl)-1-piperazineethanesulfonic acid; HPCD is hydroxypropyl-β-cyclodextrin; HPLC is high performance liquid chromatography; Hz is hertz; HOAt is 1-hydroxy-7-azabenzotriazole; HOBt is 1-hydroxy benzotriazole; KOAc is potassium acetate; LC is liquid chromatography; MS is mass spectroscopy; MeOH is MeOH; MHz is megahertz; mM is millimolar; mL is milliliter; min is minutes; mol is moles; M$^+$ is molecular ion; [M+H]+ is protonated molecular ion; N is normality; NMR is nuclear magnetic resonance; PIP2 is 5-bisphosphate; PBS is phosphate buffered saline; PH is pleckstrin homology; PMSF is phenylmethanesulfonyl fluoride; PPh$_3$ is triphenylphosphine; psi is pound per square inch; PPM is parts per million; qd po means daily by mouth; rt is room temperature; RT is retention time; TLC is thin layer chromatography; TFA is trifluoroacetic acid; TEA is triethylamine; THF is tetrahydrofuran; TMS is tetramethylsilane; and XTT is sodium 2,3,-bis(2-methoxy-4-nitro-5-sulfophenyl)-5-[(phenylamino)-carbonyl]-2H-tetrazolium inner salt.

The words "comprise", "comprises", and "comprising" are to be interpreted inclusively rather than exclusively. The works "consist", "consisting", and its variants, are to be interpreted exclusively, rather than inclusively.

As used herein, the term "about" means a variability of 10% from the reference given, unless otherwise specified.

Methods useful for making the compounds of formula (I) are set forth in the Examples below and generalized in Schemes 1-15. One of skill in the art will recognize that Schemes 1-15 can be adapted to produce the other compounds of formula (I) and pharmaceutically acceptable salts of compounds of formula (I) according to the present invention.

The following methods outline the synthesis of the compounds of formula (I). The following examples are presented to illustrate certain embodiments of the present invention, but should not be construed as limiting the scope of this invention.

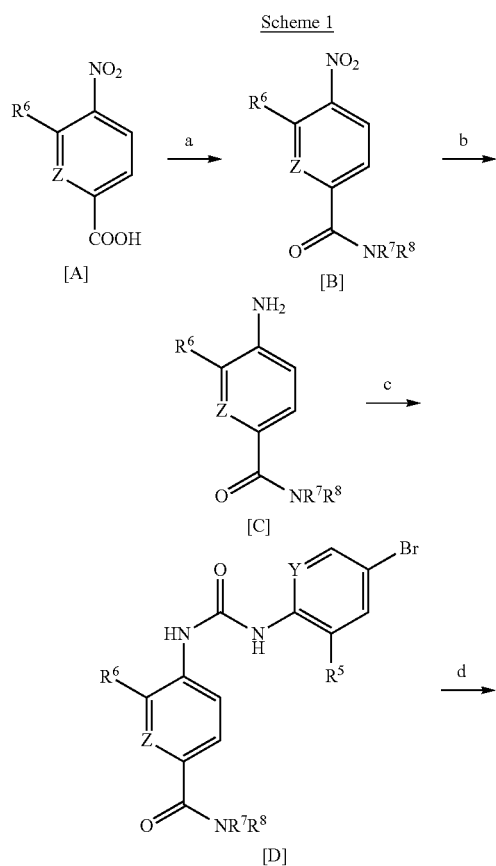

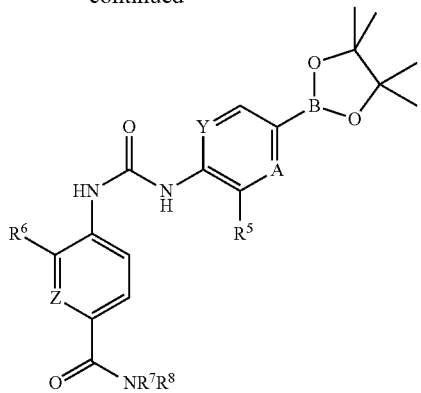

[1]

Scheme 1 depicts a first synthesis of the boronic acid pinacol ester intermediate compound [1]. Specifically, a 4-nitrobenzoic acid [A] is converted to the corresponding amide [B] using an amine such as R$^7$R$^8$NH, a coupling agent such as EDCI.HCl, DCC, HBTU, or HATU, an additive such as HOBt or HOAt, a base such as TEA or DIPEA and solvent such as DMF, THF, or DCM. In one embodiment, the amine may be NH$_3$, NH$_2$CH$_3$, NH(CH$_3$)$_2$, morpholine, piperidine, 1-methyl-piperazine and N(CH$_3$)$_2$CH$_2$CH$_2$N(CH$_3$)$_2$, among others. Typically, this is performed at rt such as about 25 to about 30° C. for about 10 to about 15 h such as about 10 h. The 4-nitro amide [B] is then reduced to the corresponding amine [C] using H$_2$ and a catalyst such as Pd/C 10%, PtO$_2$, or Pd(OH)$_2$. Typically, the reduction is performed under pressures such as 60 psi, in a solvent such as MeOH, dioxane, or ethylacetate, for about 3 to about 5 h such as about 3 h. Amine [C] is then converted to urea [D] using an appropriately substituted isocyanate such as 4-bromophenyl isocyanate. This reaction is typically performed in the presence of a base such as TEA or DIPEA and solvent such as CH$_2$Cl$_2$, CHCl$_3$, or THF at about rt such as about 25 to about 30° C. for about 5 to about 15 h such as about 12 h. As one alternative method, amine [C] can be converted to the corresponding 2,2,2-trichloroethyl carbamate and then reacted with an appropriately substituted aniline or pyridinyl amine, to produce the desired urea [D]. For example, amine [C] would typically be treated with 2,2,2-trichloroethyl chloroformate in the presence of a base such as triethylamine or DIPEA, in a solvent such as CH$_2$Cl$_2$, CHCl$_3$, or THF, at temperatures such as 0° C. to about 30° C. for about 30 minutes to 5 hours, to produce the 2,2,2-trichloroethyl carbamate intermediate. Then the 2,2,2-trichloroethyl carbamate intermediate is typically reacted with the aniline or pyridinyl amine in the presence of a base such as triethylamine or DIPEA, in a solvent such as toluene, 1,4-dioxane or THF, at about room temperature up to elevated temperatures such as about 110° C. for about 1 to 16 hours. This alternative two-step procedure provides the urea [D]. Intermediate boronic acid pinacal ester [1] is then formed by reacting urea [D] with bis(pinacolato)diboron. This reaction may be performed in the presence of a weak base such as KOAc, palladium catalyst such as Pd(dppf)Cl$_2$.DCM or Pd(dppf)Cl$_2$, in a solvent such as 1,4-dioxane or DMF. Desirably, the reaction is performed at elevated temperatures such as the reflux temperatures of the solvent. In one embodiment, this reaction is performed at about 80 to about 120° C. for about 2 to about 15 h. In another embodiment, this reaction is performed at about 110° C. for about 10 h.

Scheme 1A

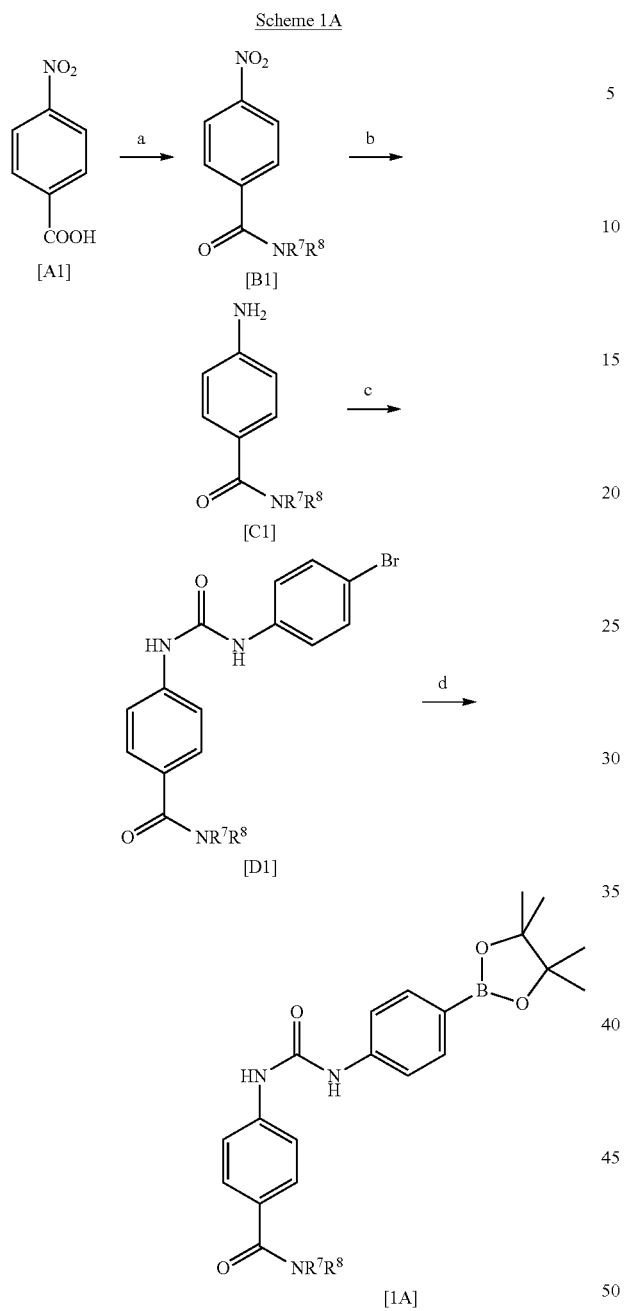

[1A]

Scheme 2

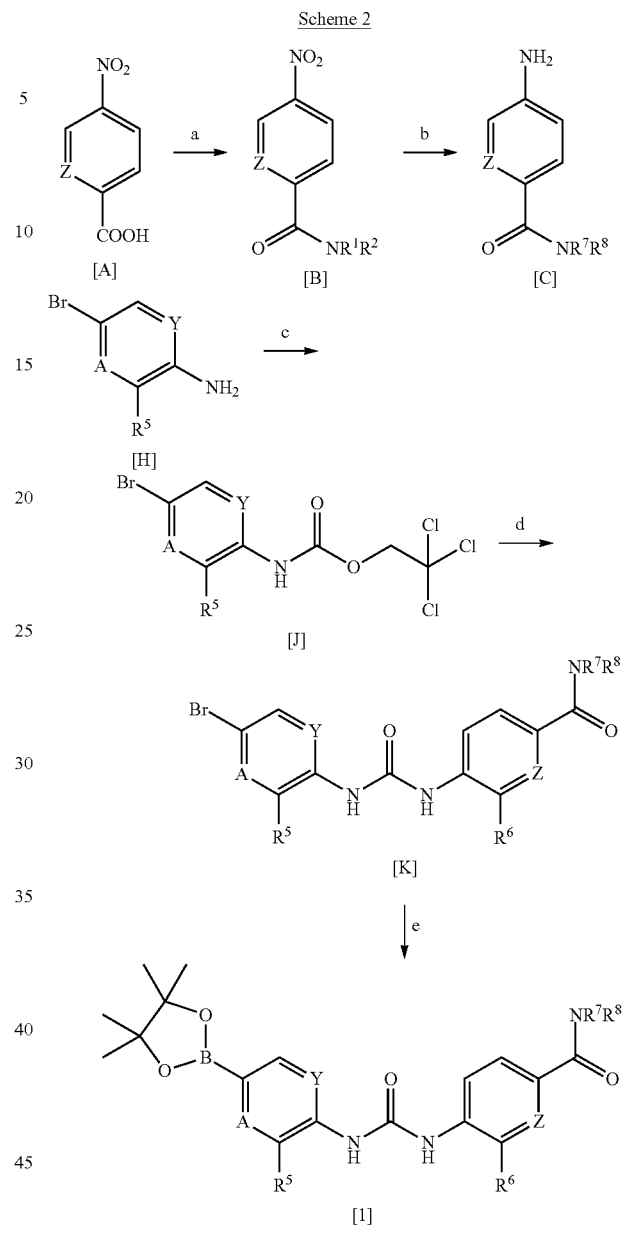

[I]

Scheme 1A depicts the synthesis of the boronic acid intermediate compound [1A]. In one embodiment, 4-nitrobenzoic acid [A1] is converted to the corresponding amide [B1] using $R^7R^8NH$ and 1-ethyl-3-(3-dimethylaminopropyl) carbodiimide hydrochloride (EDCI.HCl), HOBt and TEA in DMF at rt for about 10 h. The 4-nitro amide [B1] is then reduced to the corresponding amine [C1] using $H_2$ and Pd/C 10% at 60 psi, in MeOH for about 3 h. Amine [C1] is then converted to urea [D1] using 4-bromophenyl isocyanate in the presence of TEA in $CH_2Cl_2$ at about rt for about 12 h. Intermediate boronic acid pinacol ester [1A] is then formed by reacting urea [D1] with bis(pinacolato)diboron in the presence of KOAc, Pd(dppf) $Cl_2$.DCM, 1,4-dioxane at 110° C. for about 10 h.

Scheme 2 provides a second synthesis of the boronic acid pinacol ester intermediate [1]. Intermediate compound [C] is prepared as described in Scheme 1. In a separate reaction, an appropriately substituted aniline such as 4-bromo aniline [H] is converted to the corresponding carbamate [J] using 2,2,2-trichloroethyl chloroformate or trichloromethyl chloroformate and a base such as TEA or DIPEA. Typically, this conversion is performed in the presence of a solvent such as DCM, $CHCl_3$, or THF at reduced temperatures, i.e., about 0° C. to rt, for about 2 to about 4 hours, for example about 4 h. It will be recognized by those skilled in the art that in certain cases, when the desired aniline [H] is not commercially available, it can be prepared by methods known in the art. For example, 4-bromo-2,3-difluoroaniline is prepared by reaction of 2,3-difluoroaniline with tetrabutylammonium tribromide, as described in Int. Pat. Appl. WO2010091272 (2010). An amine such as intermediate compound [C] is then coupled with carbamate [J] in the presence of a base such as TEA or DIPEA and in a solvent such as 1,4-dioxane, toluene, or mixtures thereof to form urea [K]. Typically, the coupling is performed at elevated temperatures, i.e., about 90 to about 110° C. such as about 95° C., for about 10 to about 15 h, such as about 10 h. Reaction of urea [K] with bis(pinacolato) diboron in the presence of a catalyst such as Pd(dppf)Cl$_2$ DCM or Pd(dppf)Cl$_2$ provides intermediate [1]. Typically, this reaction is performed in the presence of a base such as KOAc, a solvent such as 1,4-dioxane or DMF, and at elevated temperatures such as about 80 to about 120° C., such as about 110° C., for about 2 to about 15 h, such as about 10 h.

Scheme 2A

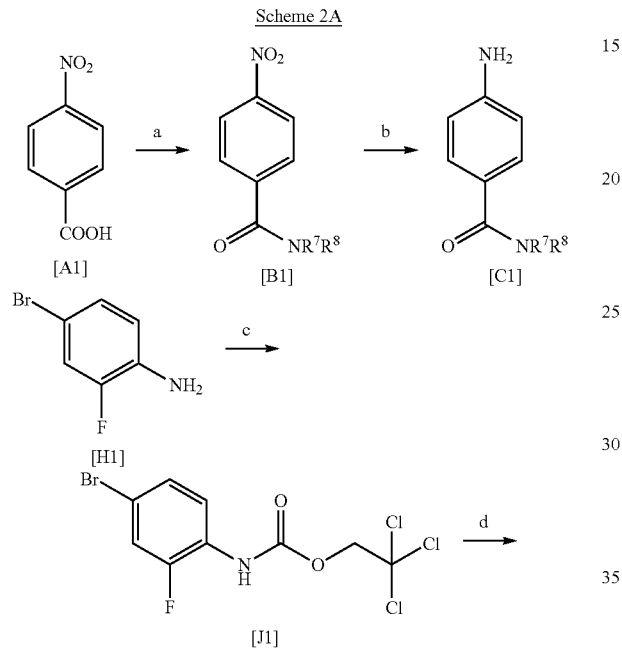

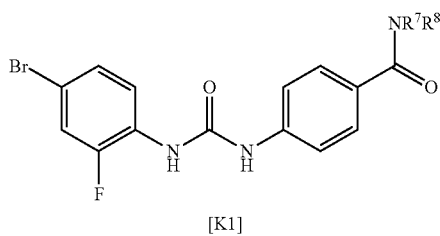

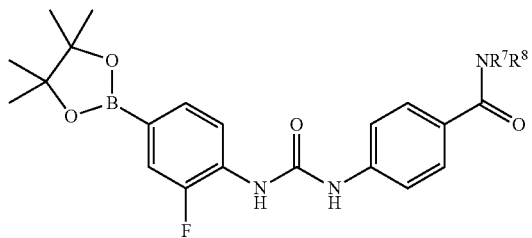

Scheme 2A provides a synthesis of boronic acid intermediate [1B]. Intermediate compound [C1] is prepared as described in Scheme 1A. In a separate reaction, 2-fluoro-4-bromo aniline [H] is converted to the corresponding carbamate [J1] using 2,2,2-trichloroethyl chloroformate and TEA in the presence of DCM at about 0° C. to rt for about 4 h. Intermediate compound [C1] is then coupled with carbamate [J1] in the presence of TEA and 1,4-dioxane at about 95° C., for about 10 h to form urea [K1]. Reaction of urea [K1] with bis(pinacolato)diboron in the presence of Pd(dppf)Cl$_2$ DCM, KOAc, and 1,4-dioxane at 110° C. for about 10 h provides intermediate [1B].

Scheme 3

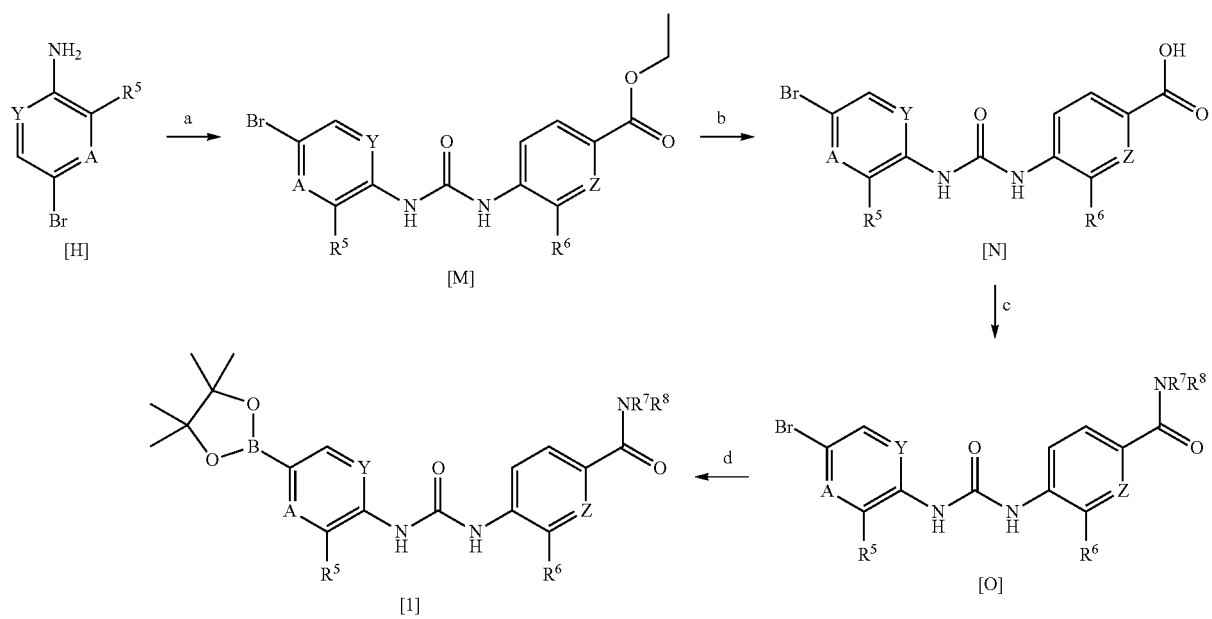

Scheme 3 provides a third route to intermediate [1]. In this route, an appropriately substituted aniline, such as 4-bromo aniline [H], is reacted with an appropriate isocyanate such as ethyl 4-isocyanatobenzoate to form the corresponding urea [M]. Typically, this reaction is performed in a solvent such as DCM or CHCl$_3$, base such as TEA or DIPEA, at about rt, such as about 25 to about 30° C., for about 3 to about 6 h, such as about 3 h. The ester moiety of urea [M] is then hydrolyzed to the corresponding benzoic acid [N] using a base such as LiOH.H$_2$O or NaOH in one or more solvents such as EtOH, THF, and/or water over a period of about 6 to about 12 h, such as about 6 h. Conversion of the benzoic acid [N] to benzamide [O] is performed using an amine such as R$^7$R$^8$NH, with coupling agents such as EDCI.HCl, DCC, HATU, or HBTU, and HOBt or HOAt. Typically, benzamide [O] is prepared using a base such as TEA or DIPEA, in solvent such as DMF, THF, or DCM, at rt, such as about 25 to about 30° C., over a period of about 10 to about 15 h, such as about 10 h. Conversion of benzamide [O] to intermediate [1] is performed using the reagents and conditions described in step e of Scheme 2.

Scheme 3A

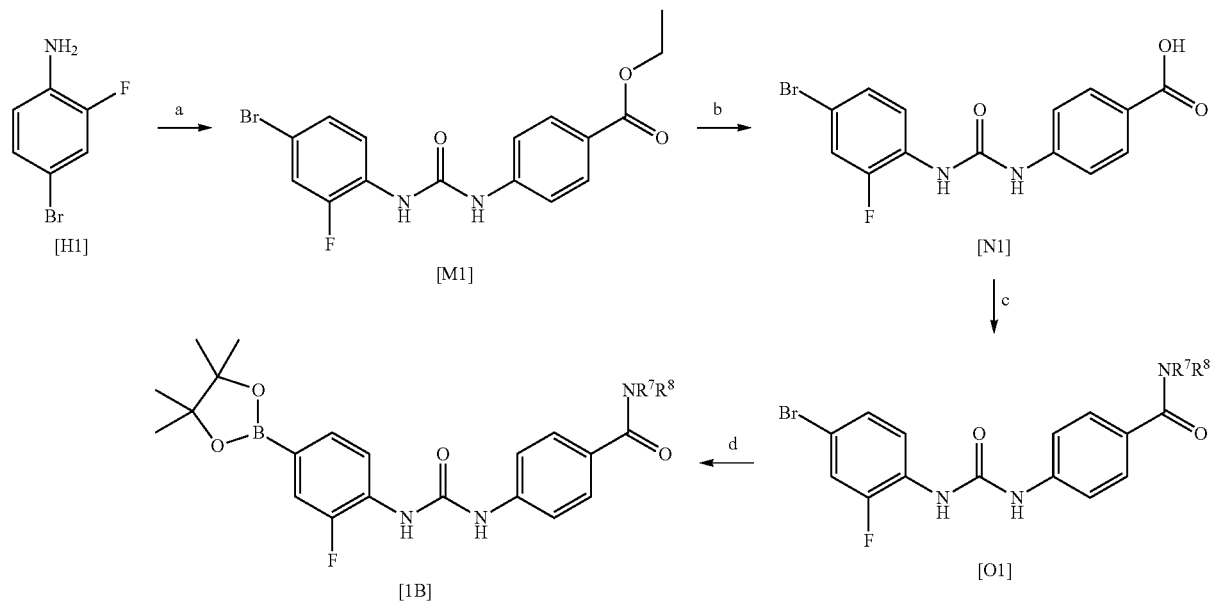

In one embodiment, Scheme 3A provides a third synthesis of intermediate [1B]. In this route, 2-fluoro-4-bromoaniline [H1] is reacted with ethyl 4-isocyanatobenzoate in DCM and TEA at about rt for about 3 h to form the corresponding urea [M1]. The ester moiety of urea [M] is then hydrolyzed to the corresponding benzoic acid [N1] using LiOH.H$_2$O, in EtOH, THF, and water over a period of about 6 h. Conversion of the benzoic acid [N1] to benzamide [O1] is performed using R$^7$R$^8$NH, EDCI.HCl and HOBt in the presence TEA and DMF at rt over a period of about 10 h. Conversion of benzamide [O1] to intermediate [1B] is performed using the reagents and conditions described in step e of Scheme 2A.

Scheme 4

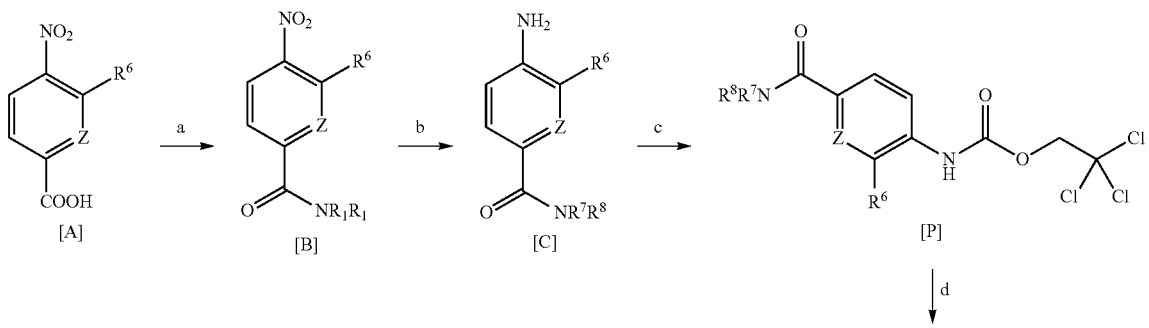

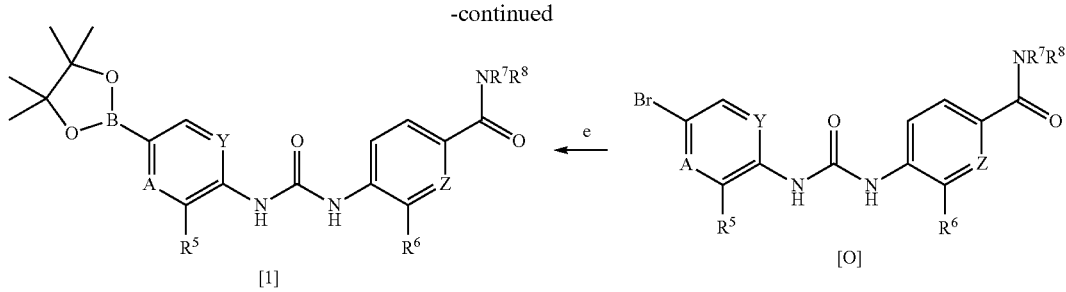

The fourth route to intermediate [1] is outlined in Scheme 4. Intermediate compound [C] is prepared as described in Scheme 2. 4-Amino benzamide [C] is then reacted with 2,2,2-trichloroethyl chloroformate or trichloromethyl chloroformate to form the corresponding carbamate [P]. Typically, this reaction is performed in the presence of a base such as TEA or DIPEA, solvent such as DCM, THF, or CHCl$_3$, at reduced temperatures, i.e., about 0° C. to about rt, for about 2 to about 12 h, such as about 4 h. Reaction of compound [P] with an appropriately substituted aniline affords urea intermediate [O]. Typically, this reaction is performed in the presence of a base such as TEA or DIPEA, a solvent such as 1,4-dioxane, toluene, or mixtures thereof, at elevated temperatures such as about 90 to about 120° C., i.e., about 95° C., and over a period of about 10 to about 15 h, such as about 10 h. The urea intermediate [O] is then reacted with bis(pinacolato)diboron in the presence of a catalyst such as Pd(dppf)Cl$_2$ DCM or Pd(dppf)Cl$_2$ to form intermediate [1]. Typically, this reaction is performed in the presence of a base such as KOAc, solvent such as 1,4-dioxane or DMF, at elevated temperatures such as about 80 to about 120° C., such as about 110° C., and over a period of about 3 to about 15 h, such as about 10 h.

In one embodiment, intermediate [1B] is prepared as described in outlined in Scheme 4A. Intermediate compound [C1] is prepared as described in Scheme 2A. 4-amino benzamide [C1] is then reacted with 2,2,2-trichloroethyl chloroformate in TEA and DCM at about 0° C. to about rt for about 4 h to form the corresponding carbamate [P1]. Reaction of compound [P1] with 4-bromo-2-fluoroaniline in TEA and 1,4-dioxane, at about 95° C. for about 10 h affords urea intermediate [O1]. The urea intermediate [O1] is then reacted with bis(pinacolato)diboron and Pd(dppf)Cl$_2$.DCM, KOAc and 1,4-dioxane at about 110° C. for about 10 h to form intermediate [1B].

Scheme 5

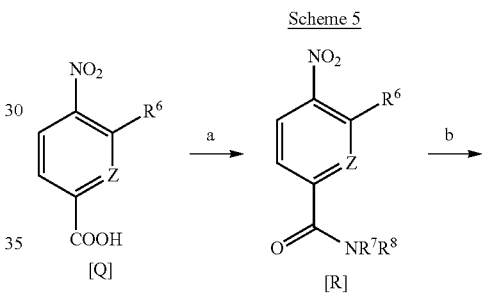

Scheme 4A

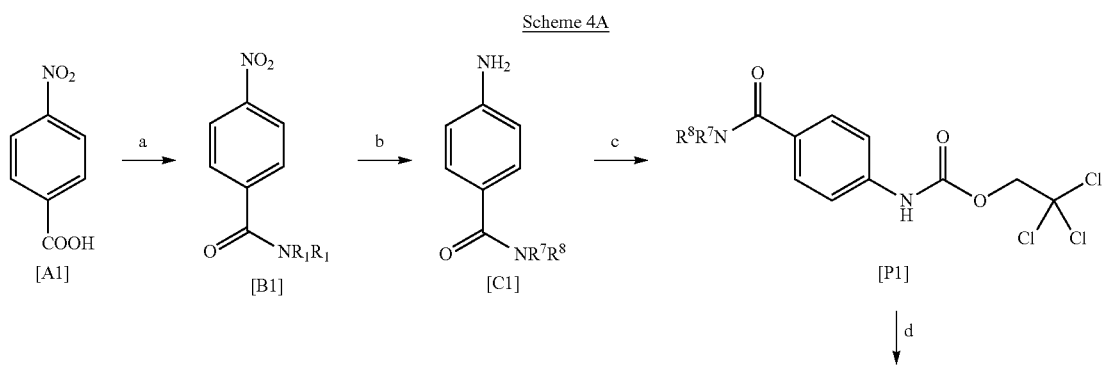

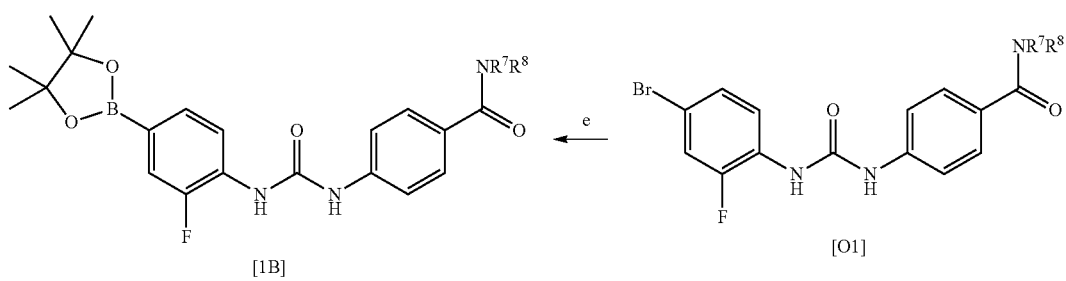

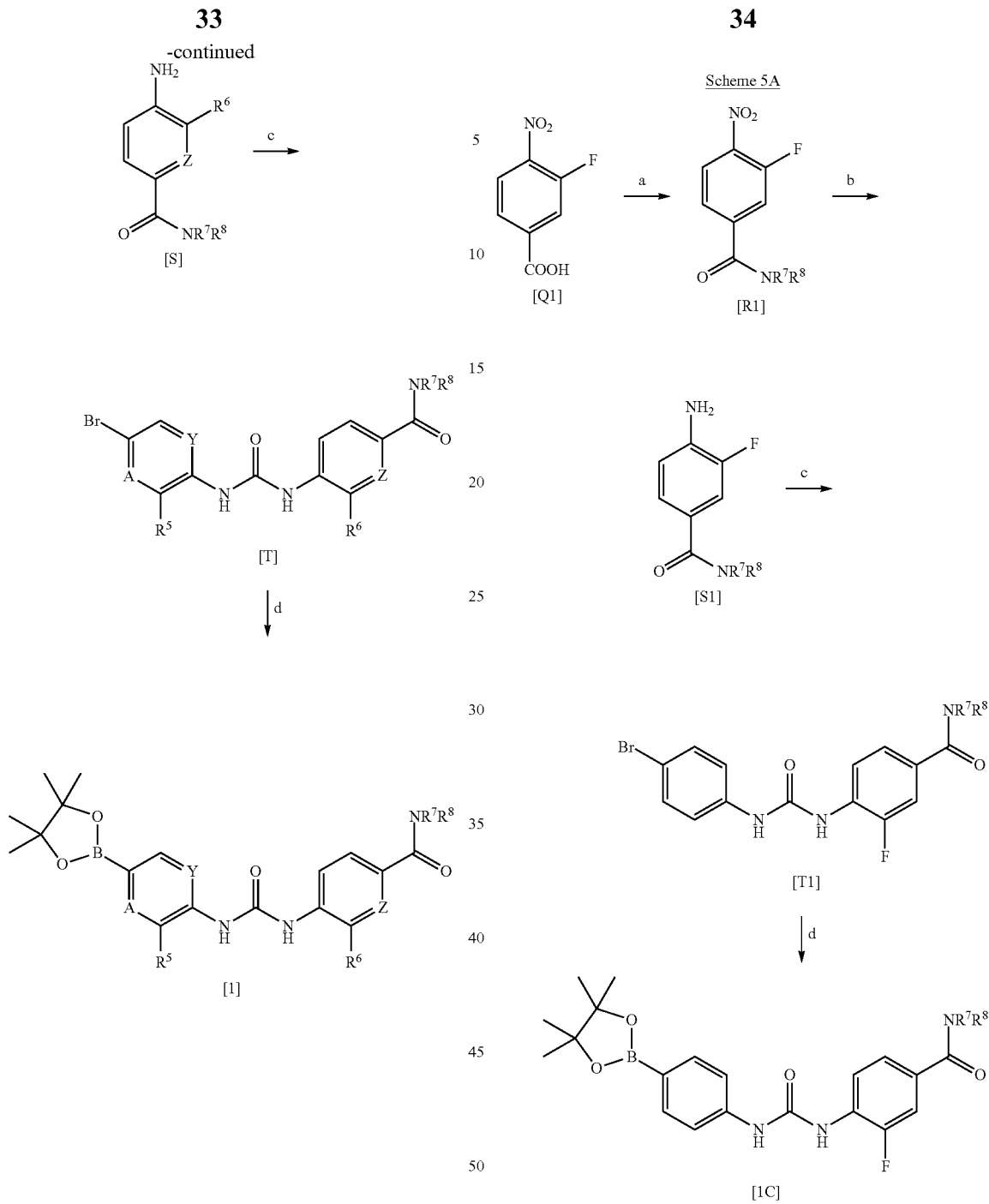

Scheme 5 provides an alternate synthesis of intermediate compound [1]. In this route, benzoic acid [Q] is converted to corresponding amide [R] using an amine such as R⁷R⁸NH, coupling agents such as EDCI.HCl, DCC, HATU, or HBTU, and HOBt or HOAt, a base such as TEA or DIPEA, and DMF, DCM, or THF. The nitro amide [R] is then reduced using tin chemistry to provide amino-substituted benzamide [S]. Benzamide [S] is then converted to urea [T] using an appropriately substituted isocyanate in the presence of a base and solvent. Conversion of urea [T] to intermediate [1] is accomplished using the same reagents and conditions as described in step e of Scheme 4, i.e., Pd(dppf)Cl₂.DCM or Pd(dppf)Cl₂, bis(pinacolato)diboron, KOAc, and 1,4-dioxane or DMF at elevated temperatures of about 80 to about 120° C. over a period of about 3 to about 15 h.

In one embodiment, intermediate [1C] is prepared according to Scheme 5A. In this route, 3-fluoro-4-nitro benzoic acid [Q1] is converted to corresponding amide [R1] using R⁷R⁸NH, EDCI.HCl, HOBt, TEA, and DMF at about rt for about 10 h. Amide [R¹] is then reduced using SnCl₂ in EtOH at reflux for about 3-4 h to provide benzamide [S1]. Benzamide [S1] is then converted to urea [T1] using 4-bromophenylisocyanate in the presence of TEA and DCM at about rt. Conversion of urea [T1] to intermediate [1C] is accomplished using Pd(dppf)Cl₂.DCM, bis(pinacolato)diboron, KOAc, and 1,4-dioxane, at about 110° C. for about 10 h.

Schemes 6-8 describe the preparation of compounds encompassed by generic formula (I).

Scheme 6

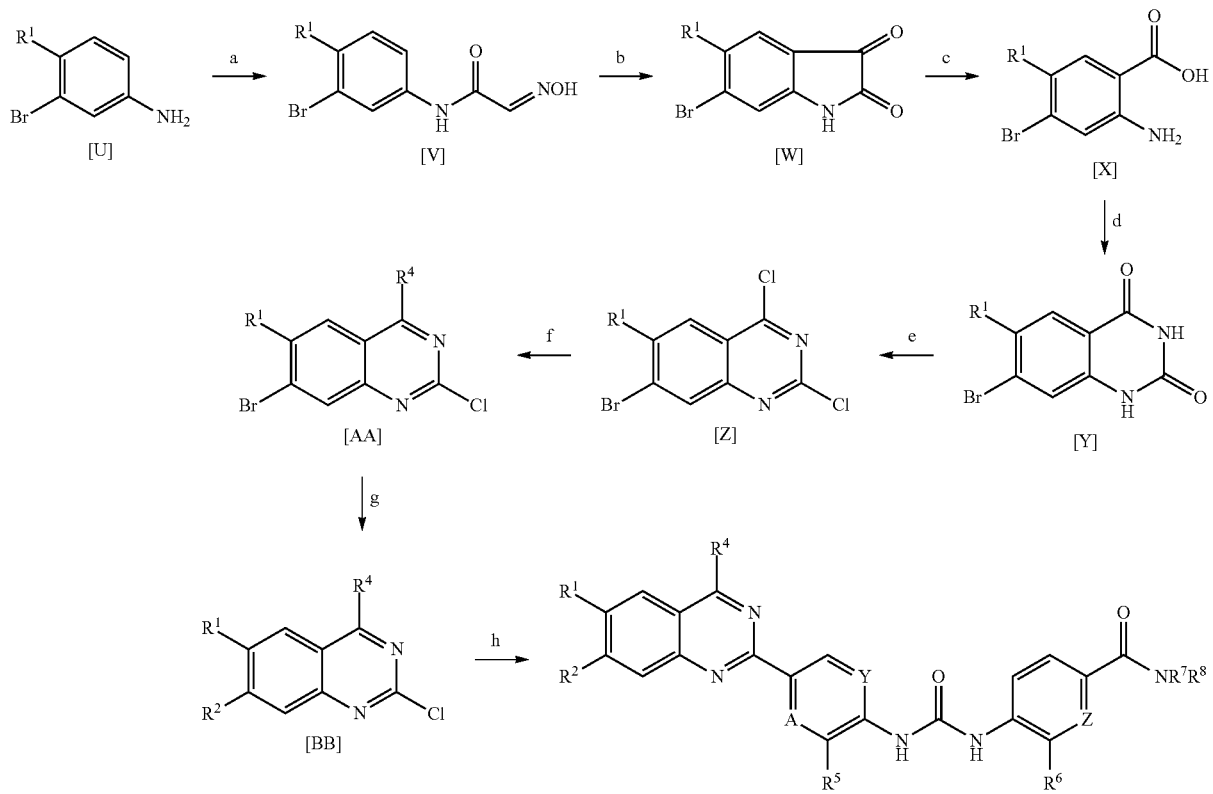

Scheme 6 provides the synthesis of compounds which are encompassed by the structure of formula (I) when X, Y, and Z are CH and $R^3$ is H. Specifically, a 3-bromoaniline [U] is converted to the corresponding hydroxylamine [V] using chloral hydrate and $NH_2OH \cdot HCl$. Reaction of compound [V] with a strong acid such as $H_2SO_4$ results in the preparation of cyclic isatin [W]. The isatin ring of [W] is then cleaved using $H_2O_2$. The resultant acid [X] is converted to quinazolinedione [Y] using urea. Quinazolinedione [Y] is then chlorinated at the 2- and 4-positions to form compound [Z] using chlorinating agents. The 4-position of quinazoline [Z] is then substituted by reaction with an optionally substituted morpholine or thiomorpholine to afford compound [AA]. The 7-position of quinazoline compound [AA] is then $R^2$-substituted by coupling with a reagent such as $R^2B(OR)_2$, $R^2SnBu_3$, $R^2MgCl$, or $R^2ZnCl$. Finally, intermediate [BB] is reacted with intermediate [1].

Scheme 6A

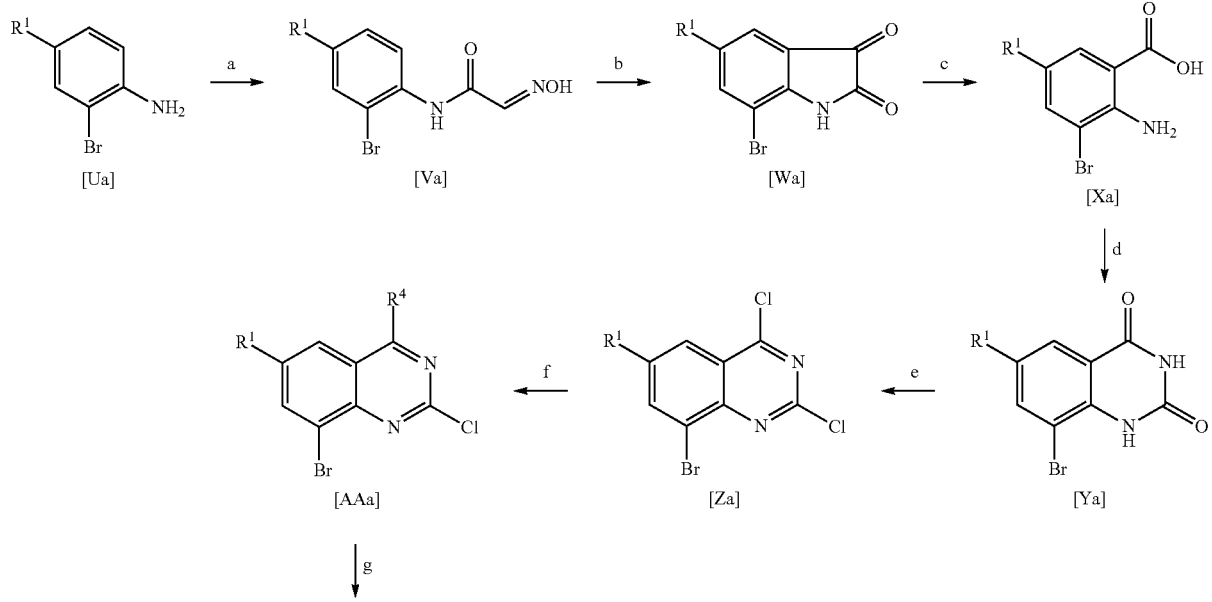

-continued

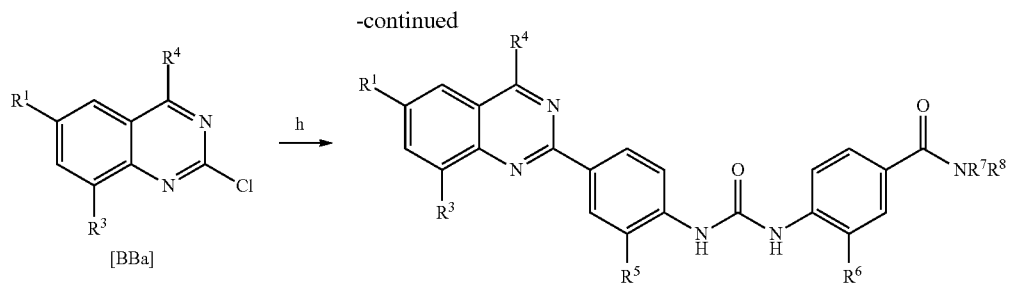

[BBa]

Scheme 6A provides the synthesis of compounds which are encompassed by the structure of formula (I) when X, Y, and Z are CH and $R^2$ is H. Specifically, a 2-bromoaniline [Ua] is converted to the corresponding hydroxylamine [Va] using chloral hydrate and $NH_2OH \cdot HCl$. Reaction of compound [Va] with a strong acid such as $H_2SO_4$ results in the preparation of cyclic isatin [Wa]. The isatin ring of [Wa] is then cleaved using $H_2O_2$. The resultant acid [Xa] is converted to quinazolinedione [Ya] using urea. Quinazolinedione [Ya] is then chlorinated at the 2- and 4-positions to form compound [Za] using chlorinating agents. The 4-position of quinazoline [Za] is then substituted by reaction with an optionally substituted morpholine or thiomorpholine ($R^4$) to afford compound [AAa]. The 8-position of quinazoline compound [AA] is then $R^3$-substituted by coupling with a reagent such as $R^3B(OR)_2$, $R^2SnBu_3$, $R^2MgCl$, or $R^2ZnCl$. Finally, intermediate [BB] is reacted with intermediate [1].

Scheme 6B provides one synthetic route to compounds which are encompassed by formula (I), where $R^4$ may be morpholine. In this route, 3-bromoaniline is converted to the corresponding hydroxylamine [V1] using chloral hydrate, $NH_2OH \cdot HCl$, $Na_2SO_4$, and hydrochloric acid in water at about 90° C. for about 2 h. Reaction of compound [V1] with $H_2SO_4$ at elevated temperatures results in the preparation of cyclic isatin [W1]. The isatin ring of [W1] is then cleaved using aqueous $H_2O_2$ and NaOH at 0° C. for 2 h. The resultant amino benzoic acid [X1] is converted to quinazolinedione [Y1] using urea (10 eq) at about 200° C. for about 3 h. Quinazolinedione [Y1] is then chlorinated using $POCl_3$ and DIPEA at about 130° C. for about 12 h to form compound [Z1]. The 4-position of quinazoline [Z1] is then substituted with morpholine by reaction with morpholine in a solvent such as DCM at reduced temperatures of about 0° C. for about 15 min to afford compound [AA1]. The 7-position of Scheme 6B

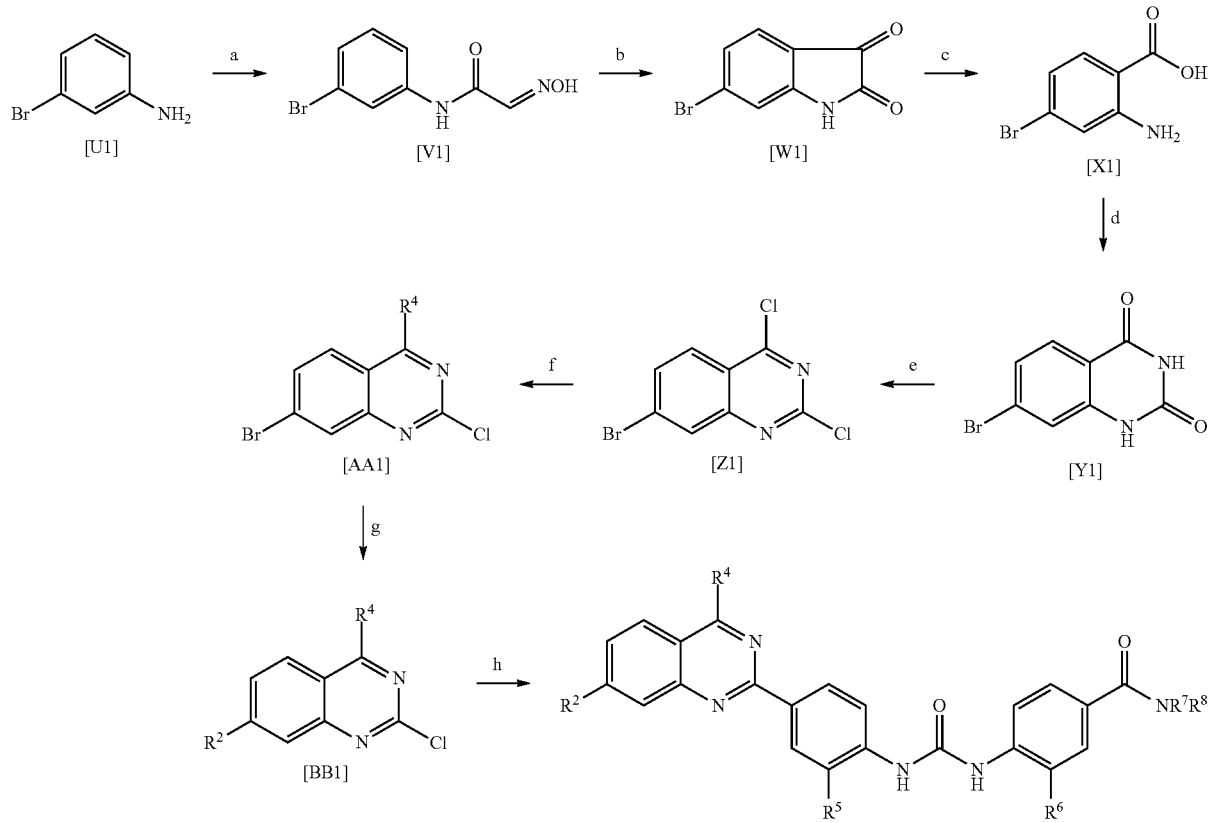

quinazoline compound [AA1] is then $R^2$-substituted using $R^2B(OR)_2$, $PdCl_2(PPh_3)_2$ (0.05 eq), $Na_2CO_3$ (1.5 eq), DMF, $H_2O$ at 90° C. for 2-3 h. Finally, compound (VIc) is prepared by reacting intermediate [BB1] with intermediate [1] using $PdCl_2(PPh_3)_2$ (0.05 eq) and $Cs_2CO_3$ (2 eq) at elevated temperatures of about 90° C. over a period of about 2-3 hours The reaction may occur in $DMF/H_2O$ or toluene/ethanol/$H_2O$, Scheme 6B may also be performed using compound [Ua] in place of compound [U1] to provide additional compounds encompassed by generic formula (I).

Scheme 6C

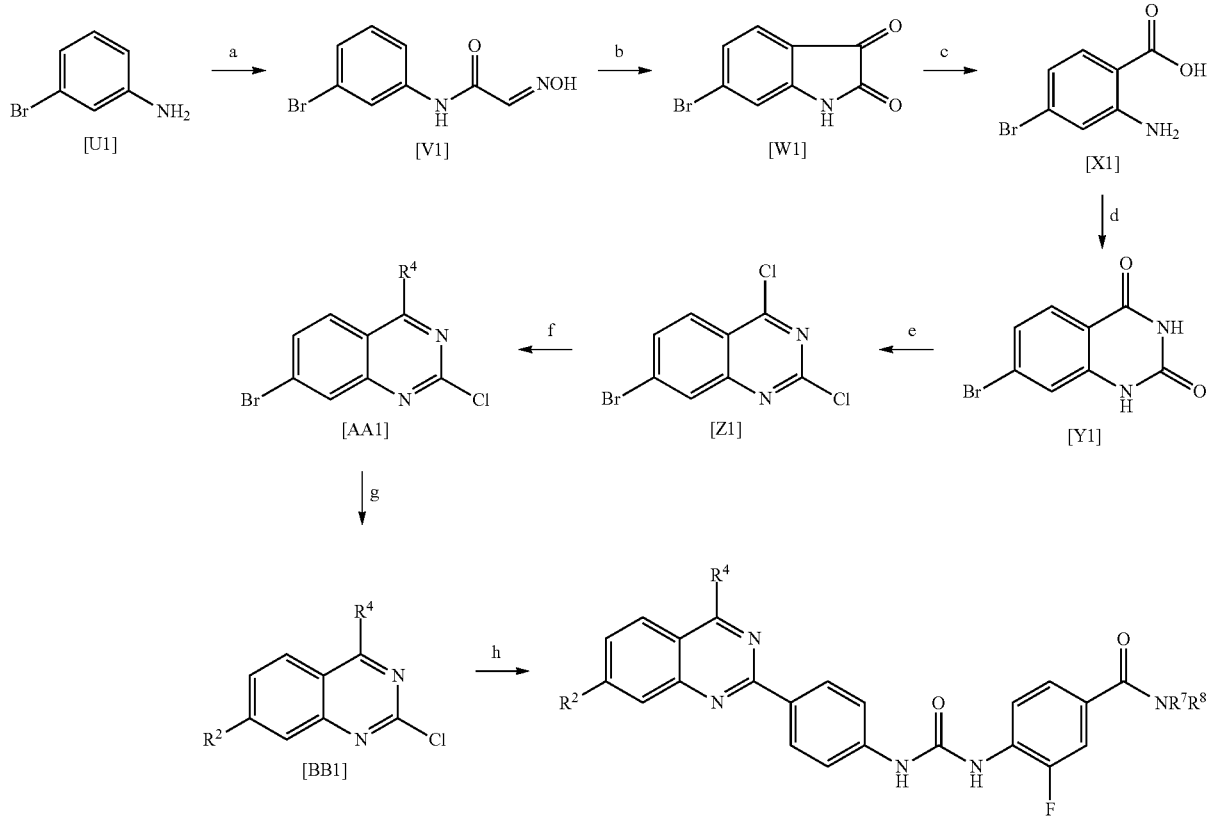

Scheme 6C provides the synthesis of 2,4,7-tri-substituted quinazoline compounds, which are encompassed by the compound of formula (I) when X—Z are CH, $R^1$ and $R^3$ are H, $R^4$ may be morpholine, $R^5$ is H, and $R^6$ is F. Specifically, steps a-g of this scheme are identical to steps a-g of Scheme 6 and thereby provide compound [BB1]. Reaction of intermediate [BB1] with intermediate [1] progresses using $PdCl_2(PPh_3)_2$ (0.05 eq) and $Cs_2CO_3$ (2 eq) at elevated temperatures of about 90° C. over a period of about 2-3 hours in $DMF/H_2O$ or toluene/ethanol/$H_2O$, Scheme 6C may also be performed using compound [Ua] in place of compound [U1] to provide additional compounds encompassed by generic formula (I).

Scheme 6D

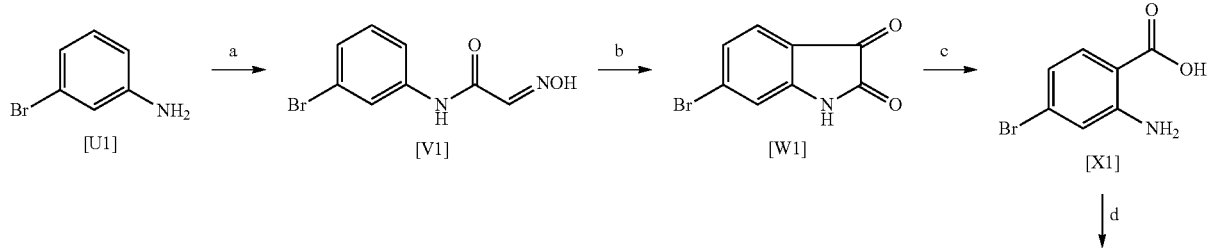

-continued

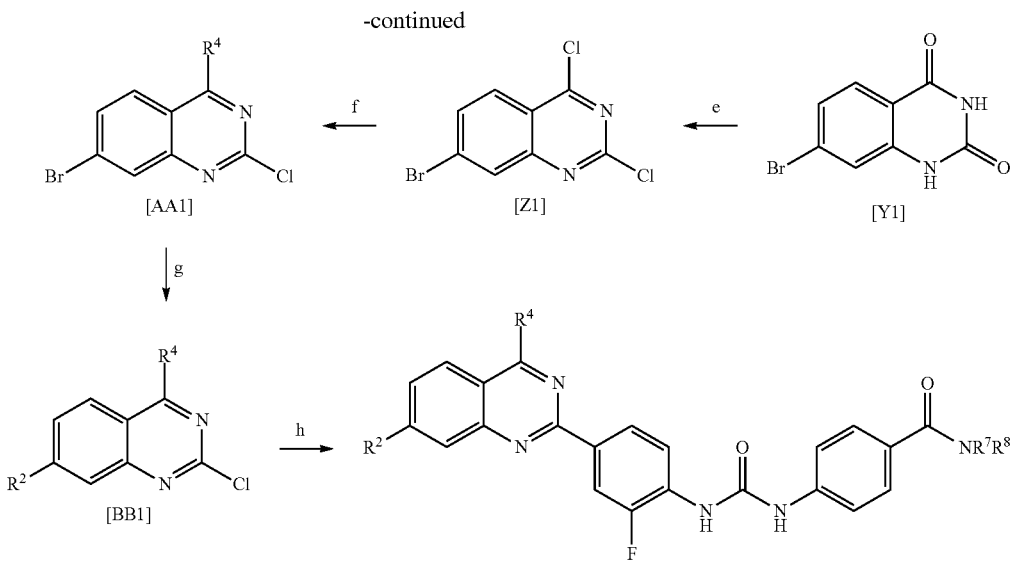

Scheme 6D provides a the synthesis of 2,4,7-tri-substituted quinazoline compounds which are encompassed by formula (I), where X—Z are CH, $R^1$, $R^3$, and $R^6$ are H, $R^4$ may be morpholine, and $R^5$ is F. Specifically, steps a-g of this scheme are identical to steps a-g of Schemes 6 and 6A and thereby provide compound [BB1]. Reaction of intermediate [BB1] with intermediate [2B] progresses using $PdCl_2(PPh_3)_2$ (0.05 eq) and $Cs_2CO_3$ (2 eq) at about 90° C. over a period of about 2-3 hours in $DMF/H_2O$ or toluene/ethanol/$H_2O$, Scheme 6D may also be performed using compound [Ua] in place of compound [U1] to provide additional compounds encompassed by generic formula (I).

Scheme 6E

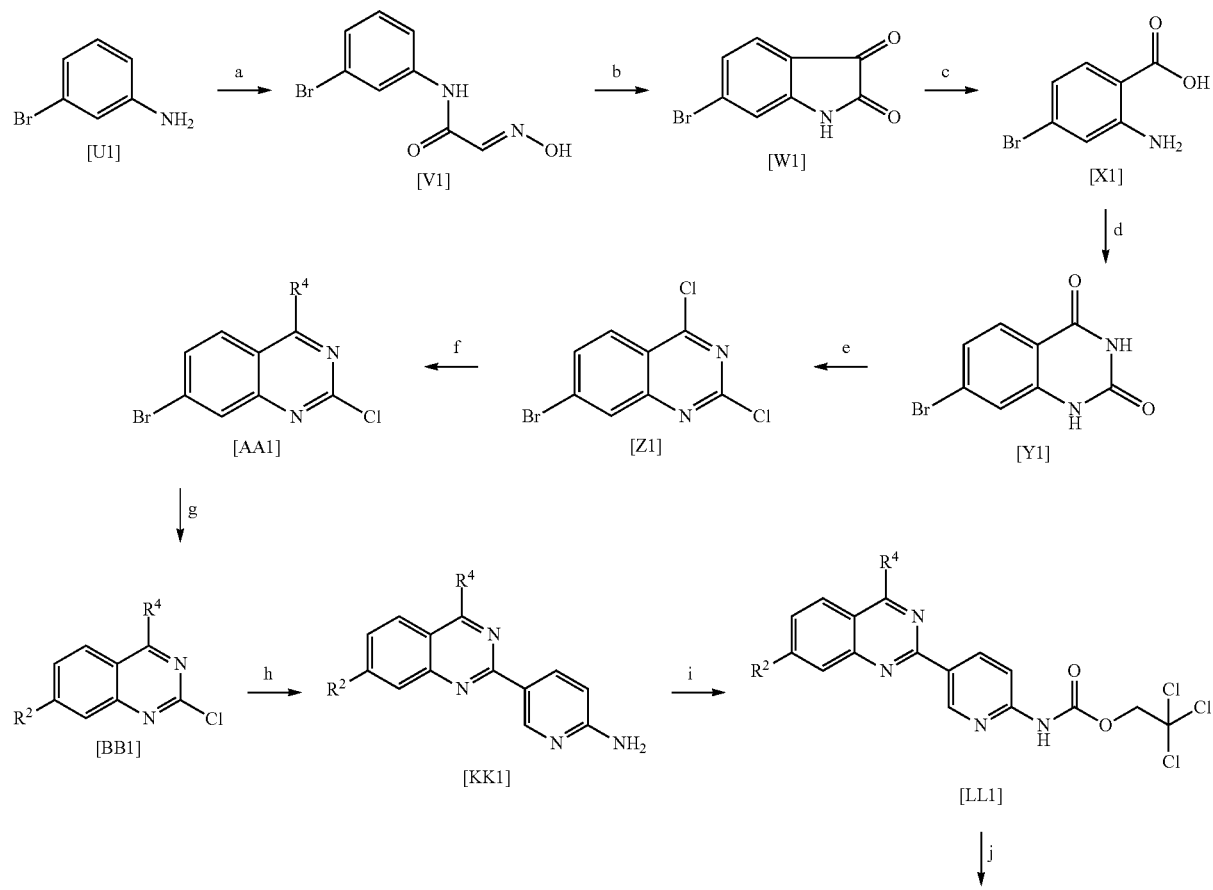

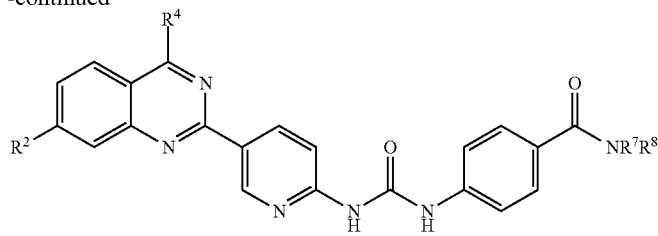

Scheme 6E provides the synthesis of 2,4,7-tri-substituted quinazoline compounds which are encompassed by formula (I), where X and Z are CH, Y is N, and $R^1$, $R^3$, $R^5$, and $R^6$ are H, and $R^4$ may be morpholine. Specifically, steps a-g to form compound [BB1] may be performed using the reagents and conditions outlined in Scheme 6. Compound [BB1] may then be converted to compound [KK1] using 2-aminopyridine-5-boronic acid pinacol ester, $PdCl_2(PPh_3)_2$, $Cs_2CO_3$, DMF, and $H_2O$ at 90° C. for about 2-3 h. Compound [LL1] may be prepared by reacting compound [KK1] with $Cl_3CCH_2OCOCl$, TEA, $CH_2Cl_2$ at 0° C. to rt for about 5 h. Compound [LL1] is then converted to the title compound using an appropriately substituted aniline such as 4-amino-N,N-dimethylbenzamide in a sealed tube in toluene at 110° C. for about 10 to about 15 h, such as about 10 h. Scheme 6E may also be performed using compound [Ua] in place of compound [Ua] to provide additional compounds encompassed by generic formula (I).

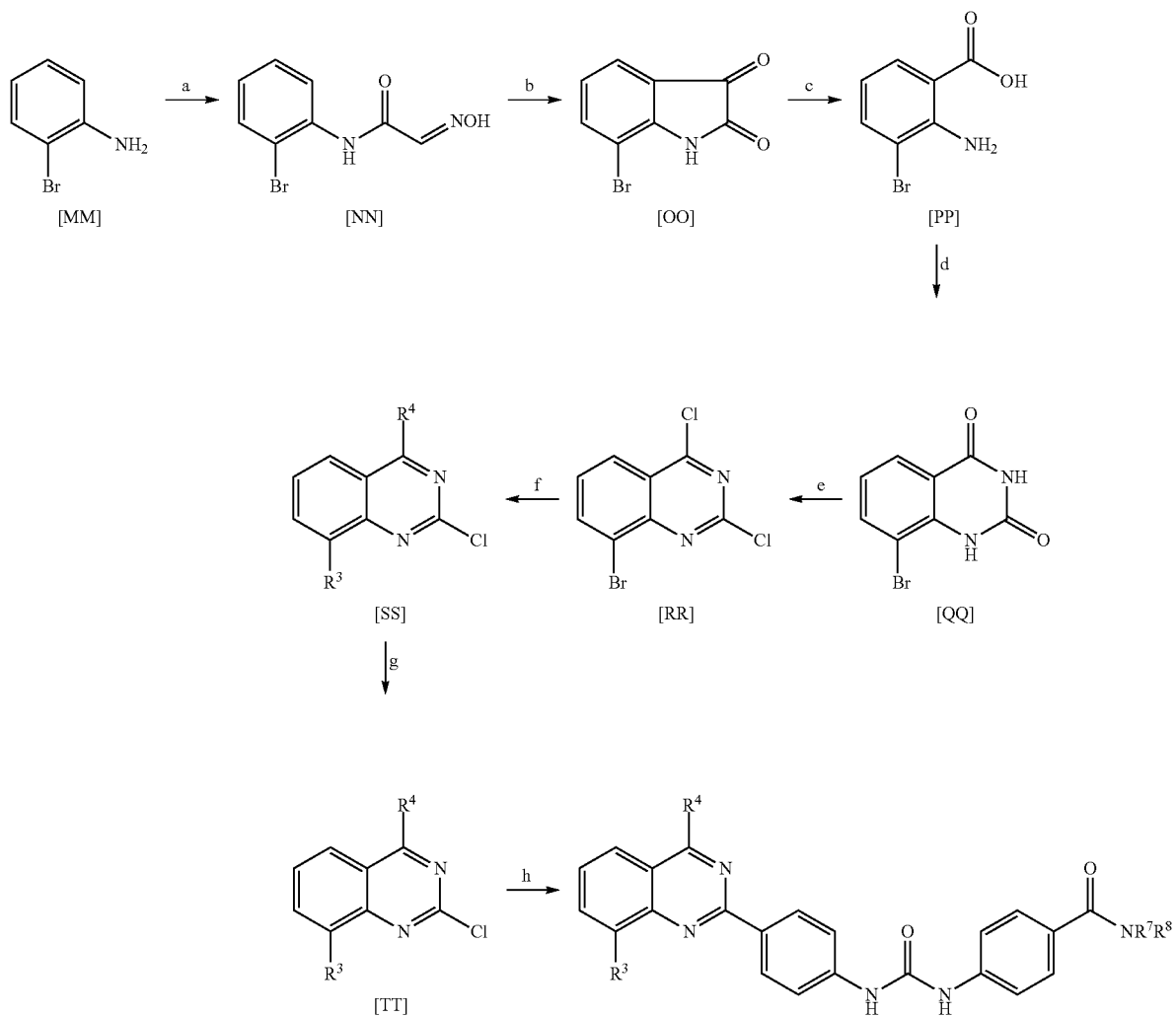

Scheme 6F

Scheme 6F provides the synthesis of 2,4,7-tri-substituted quinazoline compounds which are encompassed by formula (I), where $R^1$, $R^2$, $R^5$, and $R^6$ are H and $R^4$ may be morpholine. This scheme is performed according to the procedure of Scheme 6, but using compound [MM] instead of compound [U].

0° C. over about 2 h to form acid [XX]. Cyclization of acid [XX] to form quinazolinedione [YY] is performed using urea (10 eq) at about 200° C. for about 3 h. Chlorination of compound [YY] is performed using $POCl_3$ and DIPEA at about 130° C. for about 12 h to form intermediate [ZZ]. Substitution at the 4-position occurs using morpholine in $CH_2Cl_2$ at about

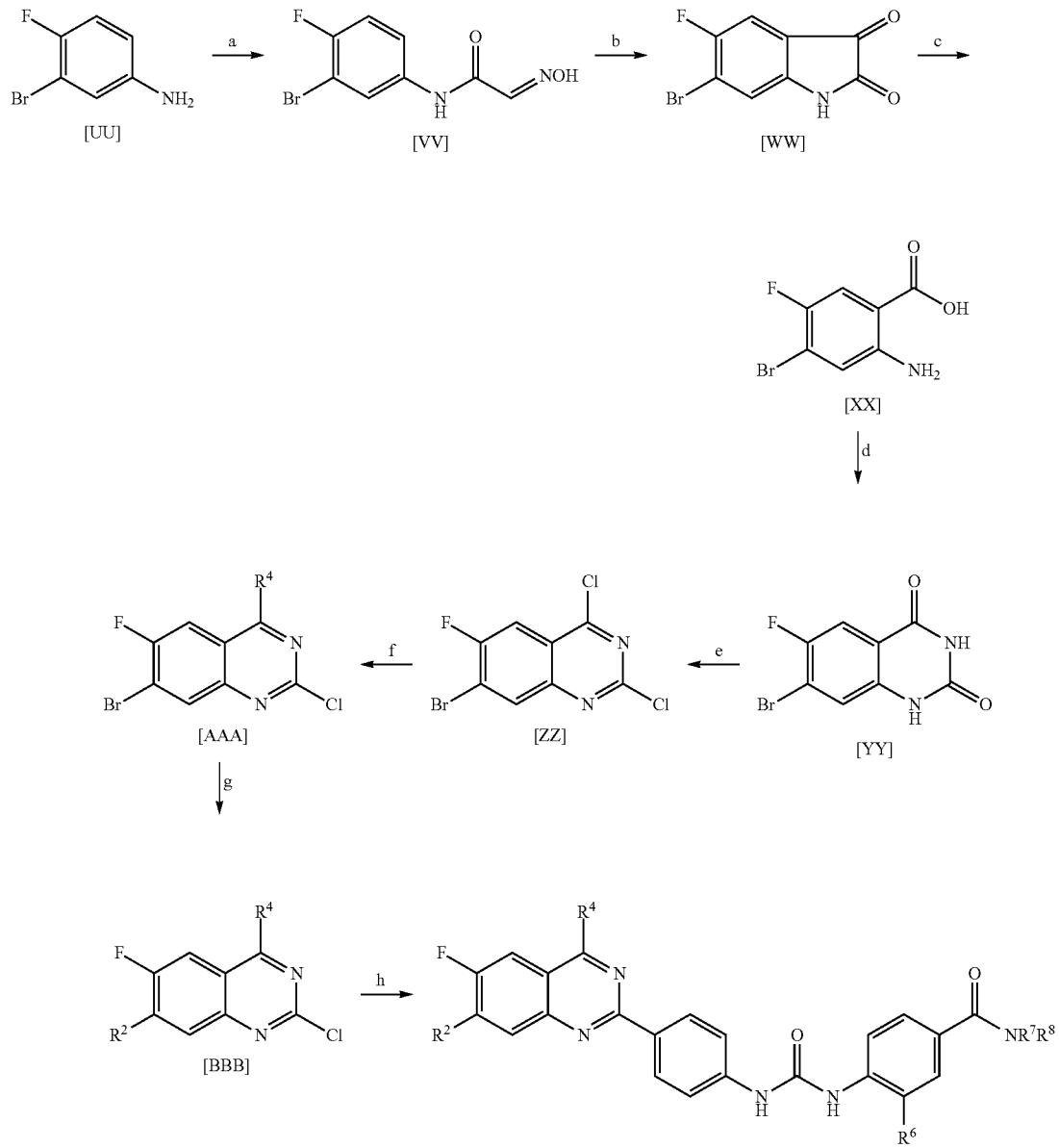

Scheme 6G provides the synthesis of 2,4,6,7-quinazoline compounds where $R^1$ is F, $R^3$ is H, and $R^4$ in formula (I) may be morpholine. Specifically, steps a-h are performed as described in Scheme 6, but using compound [UU] instead of compound [U]. In one embodiment, compound [UU] is reacted with chloral hydrate, $NH_2OH \cdot HCl$, $Na_2SO_4$, hydrochloric acid in water at about 90° C. for about 2 h to provide oxime [VV]. Addition of compound [VV] at 50° C. to $H_2SO_4$ at about 90° C. for about 2 h provided isatin [WW]. The isatin [WW] ring is opened using aqueous $H_2O_2$ and NaOH at about 0° C. for about 15 min to form compound [AAA]. Reaction of compound [AAA] with $R^2B(OR)_2$, $PdCl_2(PPh_3)_2$ (0.05 eq), $Na_2CO_3$ (1.5 eq), DMF, and $H_2O$ at about 90° C. for about 2-3 h provides compound [BBB]. Finally, compound [BBB] is reacted with compound [1], $PdCl_2(PPh_3)_2$ (0.05 eq), $Cs_2CO_3$ (2 eq), in $DMF/H_2O$ or toluene/ethanol/$H_2O$ at about 90° C. for about 2-3 h. Scheme 6G may be performed using 2-bromo-4-fluoroaniline in place of compound [UU] to provide additional compounds encompassed by generic formula (I).

Scheme 7

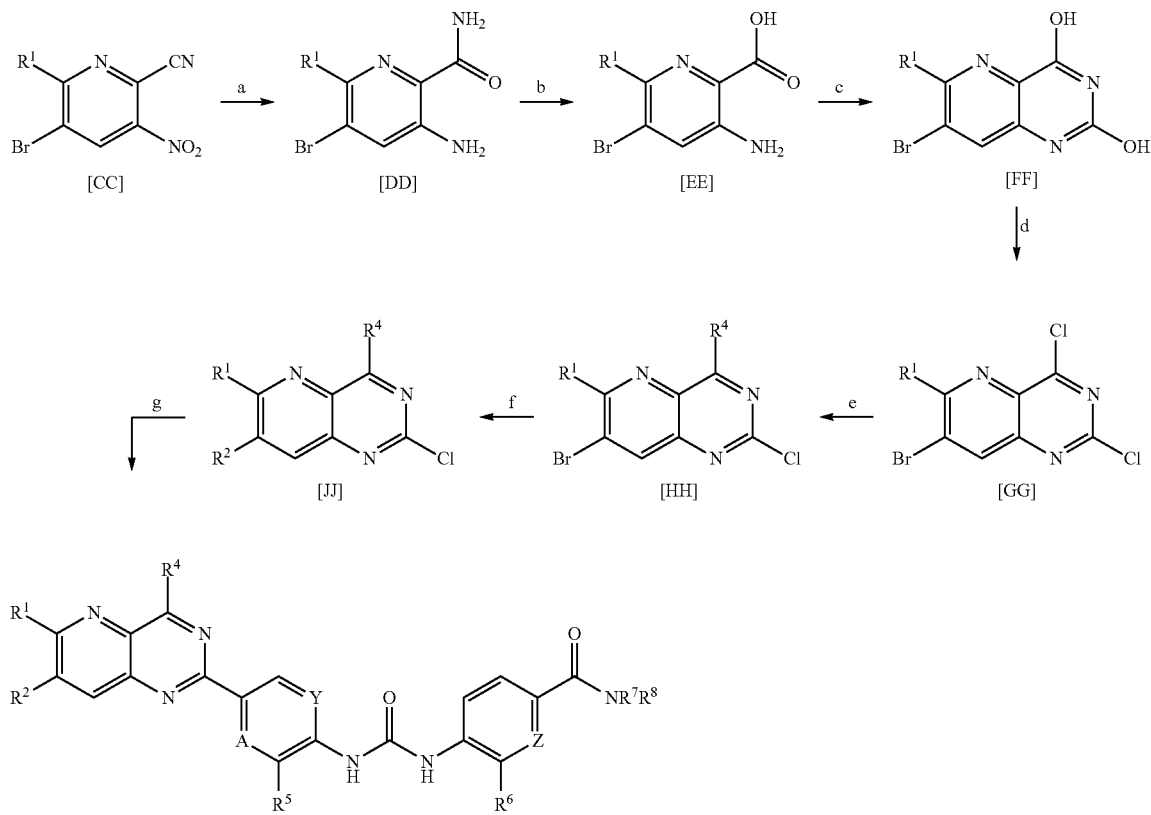

Scheme 7 provides the preparation of 2,4,7-pyrido-pyrimidine compounds which are encompassed by formula (I), where X is N, Y and Z are CH, and $R^1$ and $R^3$ are H. Specifically, 5-bromo-3-nitro-picolinonitrile [CC] is converted to the corresponding amide [DD] using Raney Nickel and $H_2$. Amide [DD] is then converted to the corresponding acid [EE] using a base. Reaction of compound [EE] with a reagent such as urea results in the formation of compound [FF]. Chlorination of compound [FF] may be formed using a chlorinating agent. Substitution at the 4-position may be performed using an optionally substituted morpholine or thiomorpholine to result in compound [HH]. Substitution of the 7-position of compound [HH] to form compound [JJ] may be accomplished by coupling with a reagent such as $R^2B(OR)_2$, $R^2SnBu_3$, $R^2MgCl$, or $R^2ZnCl$ and a catalyst. Finally, compound [JJ] is reacted with compound [1], $PdCl_2(PPh_3)_2$ (0.05 eq), $Cs_2CO_3$ (2 eq), in $DMF/H_2O$ or toluene/ethanol/$H_2O$ at about 90° C. for about 2-3 h to form the noted compound. Scheme 7 may be performed using 2-cyano-3-nitro-4-bromo-6-$R^1$-pyridine in place of compound [CC] to provide additional compounds encompassed by generic formula (I).

Scheme 7A

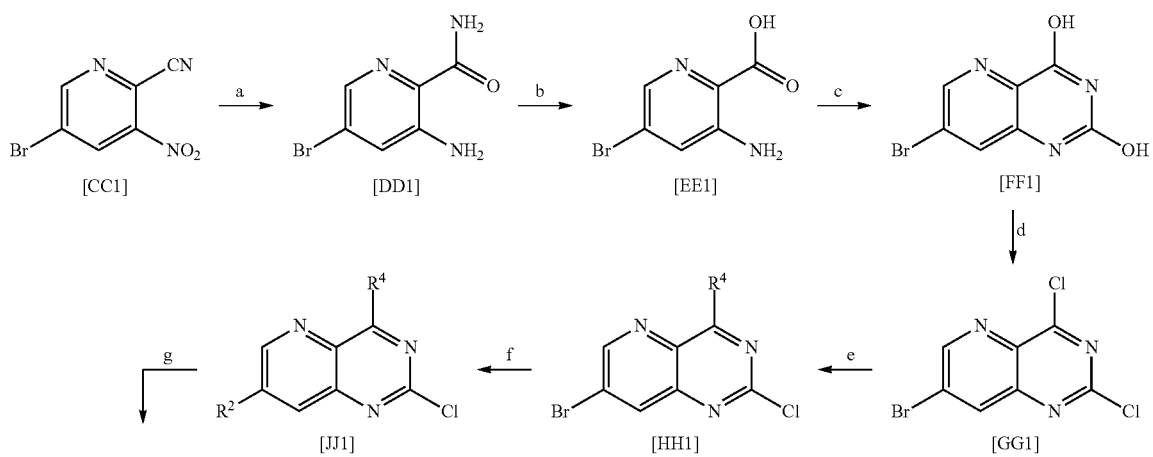

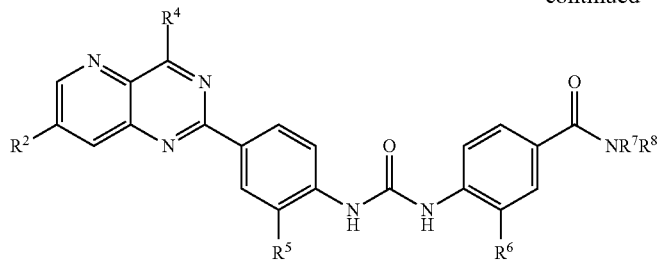

In one embodiment, Scheme 7A provides the preparation of compounds which are encompassed by formula (I). In this scheme, 5-bromo-3-nitro-picolinonitrile [CC1] is converted to the corresponding amide [DD1] using Raney Nickel and $H_2$ in ethanol for about 14-20 h. Amide [DD1] is then converted to the corresponding acid [EE1] using NaOH in $H_2O$ at about 110° C., followed up by work-up in dilute HCl. Reaction of compound [EE1] with urea at elevated temperatures results in the formation of compound [FF1]. Chlorination of compound [FF1] may be performed using $POCl_3$ at elevated temperatures. Substitution at the 4-position may be performed using morpholine to result in compound [HH1]. Substitution of the 7-position of compound [HH1] with $R^2$ to form compound [JJ1] may be accomplished using $R^2B(OR)_2$ and a catalyst such as $PdCl_2(PPh_3)_2$ in solvent systems such as DMF/$H_2O$ or toluene/ethanol/$H_2O$. Finally, compound [JJ1] is reacted with compound [1], $PdCl_2(PPh_3)_2$ (0.05 eq), $Cs_2CO_3$ (2 eq), in DMF/$H_2O$ or toluene/ethanol/$H_2O$ at about 90° C. for about 2-3 h to form the noted compound. Scheme 7A may be performed using 5-bromo-3-nitro-picolinonitrile in place of compound [CC1] to provide additional compounds encompassed by generic formula (I).

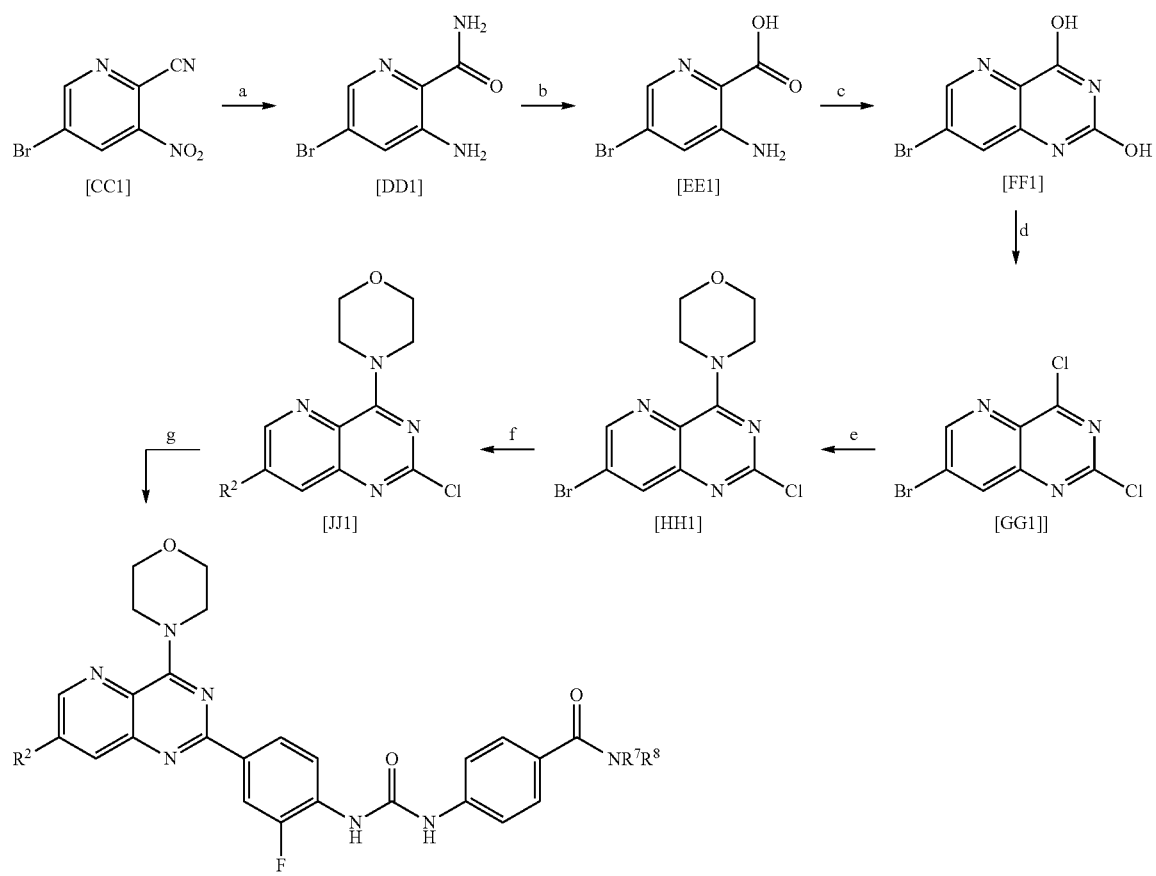

Scheme 7B

In another embodiment, Scheme 7B provides the preparation of 2,4,7-trisubstituted pyrido-pyrimidine compounds which are encompassed by formula (I), where X is N, Y and Z are CH, and $R^1$, $R^3$, and $R^6$ are H. Specifically, 2-cyano-3-nitro-5-bromopyridine [CC1] is converted to the corresponding amide [DD1] using Raney Nickel and $H_2$. Desirably, the reaction is performed in the presence of ethanol for about 14-20 h. Amide [DD1] is then converted to the corresponding acid [EE1] using NaOH (5 eq) and H₂O at about 110° C. for about 5 h, followed by work-up using dil. HCl. Acid [EE1] is cyclized using urea (10 eq) at about 200° C. for about 3 h to form pyrido-pyrimidine intermediate [FF1]. Intermediate [FF1] is reacted with POCl₃ and DIPEA at about 130° C. for about 10 h. The 4-position of the pyrido-pyrimidine is then substituted using morpholine in CH₂Cl₂ at a temperature of about 0° C. for about 30 min to form compound [HH1]. Compound [HH1] is then coupled with R² using R²B(OR)₂, PdCl₂(PPh₃)₂ (0.05 eq), Na₂CO₃ (1.5 eq), DMF, and H₂O at about 90° C. for about 2-3 h to form compound [JJ1]. The title compound is then formed by reacting compound [JJ1] with PdCl₂(PPh₃)₂ (0.05 eq), Cs₂CO₃ (2 eq), DMF, and H₂O at a temperature of about 90° C. for about 2-3 h. Alternatively, the title compound may be formed by reacting intermediate [JJ1] with PdCl₂(PPh₃)₂ (0.05 eq) and Cs₂CO₃ (2 eq) in toluene, ethanol, and H₂O at a temperature of about 90° C. for about 2-3 h.

Scheme 7C

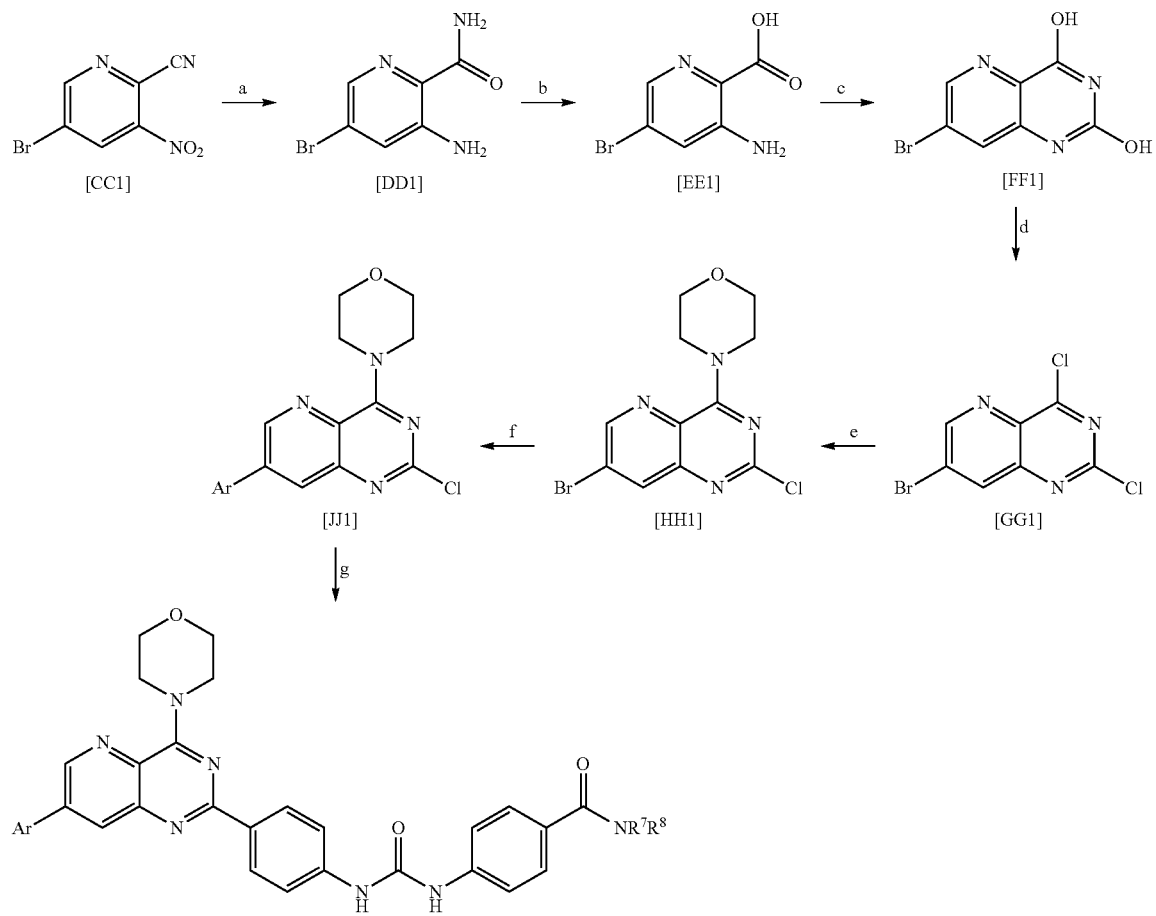

In a further embodiment, Scheme 7C provides the synthesis of 2,4,7-pyrido-pyrimidine compounds which are encompassed by formula (I), where X is N, Y and Z are CH, R² is aryl, and R¹, R³, R⁵, and R⁶ are H. This synthesis was performed according to the steps outlined in Scheme 7B, with the exception that ArB(OR)₂ was utilized in place of R²B(OR)₂. Scheme 7C may be performed using 2-cyano-3-nitro-4-bromopyridine in place of compound [CC1] to provide additional compounds encompassed by generic formula (I).

Scheme 8

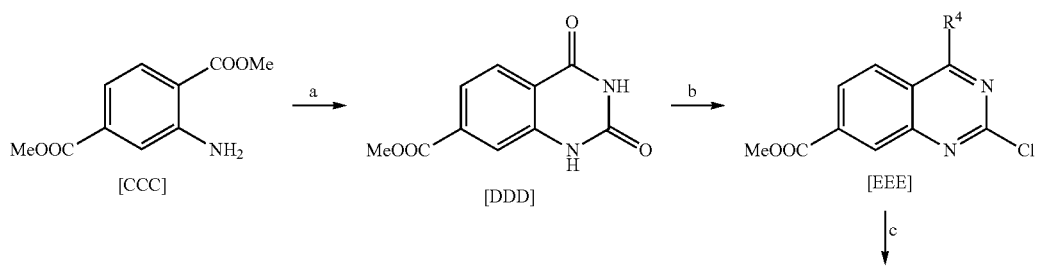

-continued

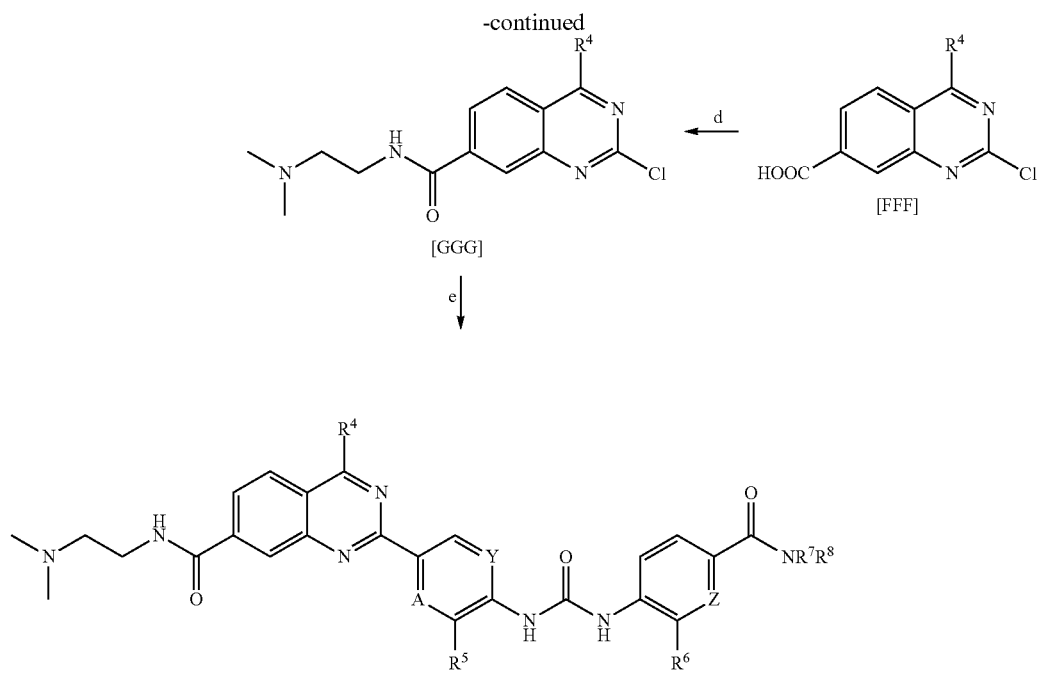

Scheme 8 provides another synthesis of 2,4,7-tri-substituted quinazolines. In this scheme, diester aniline [CCC] is reacted with urea to form isatin [DDD]. Chlorination of the 2-position, followed by substitution of the 4-position with an optionally substituted morpholine or thiomorpholine ($R^4$) affords compound [EEE]. Hydrolysis of the ester moiety of [EEE] affords acid [FFF]. The acid moiety of [FFF] is then reacted with an amine to provide amide [GGG]. Finally reaction of amide [GGG] with compound [1] provides the final compound.

In one embodiment, diester aniline [CCC] is reacted with urea at elevated temperatures such as about 200° C. for about 3 h to provide isatin [DDD]. Yields of about 80% of compound [DDD] may be obtained. Chlorination at the 2- and 4-position of compound [DDD] may be accomplished using $POCl_3$ and a base such as N,N-dimethyl aniline or DIPEA. In one embodiment, this reaction is performed at elevated temperatures such as about 120 to about 130° C., such as about 120° C., for about 5 to about 6 h, such as about 5 h. An optionally substituted morpholine or thiomorpholine is then added in a solvent such as DCM. In one embodiment, this reaction is performed at reduced temperatures such as about 0° C. for about 15 to about 30 min, such as about 30 min, to provide compound [EEE]. Yields of about 70% of compound [EEE] may be obtained. Hydrolysis of the ester moiety of compound [EEE] may be performed using a weak base such as LiOH or NaOH in a solvent such as $THF:MeOH:H_2O$ (1:1:1). In one embodiment, this hydrolysis is performed at about ambient temperature, such as about 25 to about 30° C., for about 1 to about 3 h, such as about 1 h. By doing so, yields of about 80% of compound [FFF] may be obtained. Reaction of the acid moiety of compound [FFF] may be performed using an amine such as N,N-dimethylethylenediamine in the presence of DIPEA and HATU. Desirably, the reaction is performed in a solvent such as DMF for an extended period of time, e.g., overnight, to provide amide [GGG]. Yields of about 70% of amide [GGG] may be obtained. Finally, reaction of amide [GGG] with intermediate compound [1] provides the final product. In one embodiment, amide [GGG] is reacted in the presence of a catalyst such as $PdCl_2(PPh_3)_2$ or $Pd(PPh_3)_4$, $Cs_2CO_3$, $Na_2CO_3$, or $K_2CO_3$, and a solvent system such as DMF/water or toluene/ethanol/water. Desirably, the reaction is performed at elevated temperatures of about 80 to about 110° C., such as about 95° C., for an extended period of time including about 5 to about 8 h, such as about 5 h. Yields of about 50% of the title compound may be obtained.

Scheme 8A

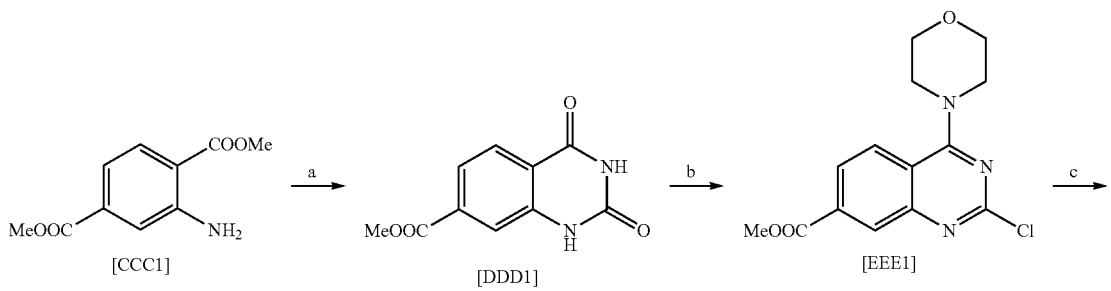

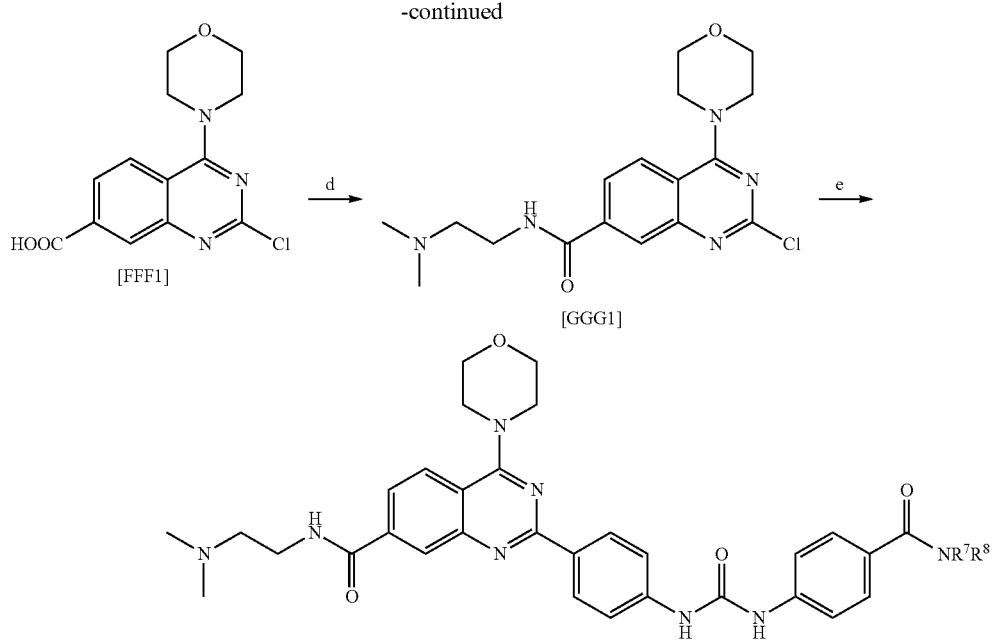

Scheme 8A provides the synthesis of compounds encompassed by formula (I). In this scheme, diester aniline [CCC1] is reacted with urea at about 200° C. for about 3 h to provide isatin [DDD1]. Chlorination at the 2- and 4-position of compound [DDD] may be accomplished using $POCl_3$ and N,N-dimethyl aniline at about 120° C. for about 5 h. Morpholine is then added in DCM at about 0° C. for about 30 min to provide compound [EEE1]. Hydrolysis of the ester moiety of compound [EEE1] may be performed using LiOH in THF: $MeOH:H_2O$ (1:1:1) at rt for about 1 h. Compound [FFF1] is reacted with N,N-dimethylethylenediamine, DIPEA, HATU, and DMF overnight to provide amide [GGG1]. Finally, reaction of amide [GGG1] with N,N-dimethyl-4-(4,4,5,5-tetramethyl-1,3,2-dioxaborolan-2-yl)phenyl)ureido)benzamide, $PdCl_2(PPh_3)_2$, and $Cs_2CO_3$, in DMF at about 95° C. for 5 h provides the final product.

Scheme 9

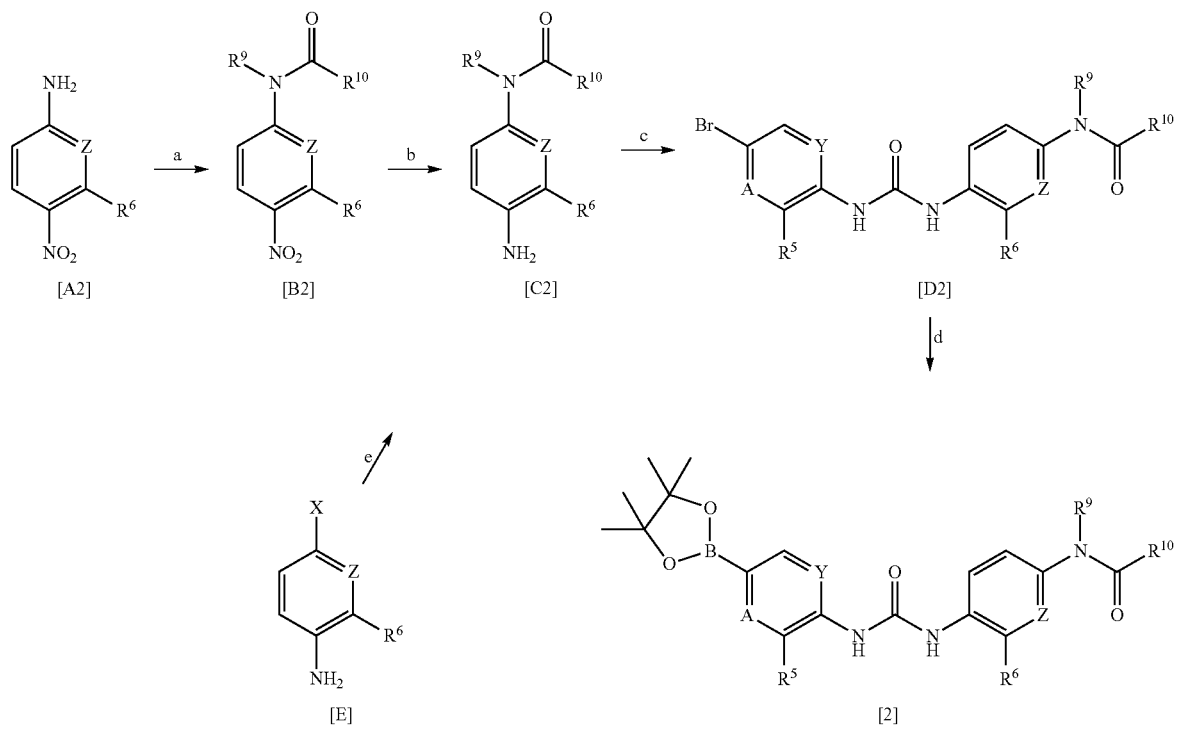

It will be apparent to those skilled in the art that compounds of formula (I), where M is amide group —N(R⁹)—C(O)R¹⁰, can be synthesized by methodology similar to those methods described above, wherein M is an amide group of type —C(O)NR⁷R⁸. For example, the boronic acid pinacol ester intermediate compounds where M is amide group —N(R⁹)—C(O)R¹⁰ can be prepared by methods similar to those described in Schemes 1, 2 and 5. For example, Scheme 9 depicts an example of the synthesis of boronic acid pinacol ester intermediate compound [2]. Specifically, a 4-nitrobenzoic acid [A2] is converted to the corresponding amide [B2] by reaction with an acyl chloride R¹⁰COCl, in the presence of a base such as TEA or DIPEA, and using a solvent such as DMF, THF, or DCM, typically at temperatures of 0 to 25° C., for about 30 minutes to 24 hours such as 12 hours. The nitro-phenyl intermediate [B2] that is formed (R⁹=H in this case) is then reduced to give the amino-phenyl intermediate [C2], for example by using hydrogen over catalytic 10% Pd/C, in a solvent such as methanol or ethanol, for about 1 hour to 24 hours such as 12 hours. The intermediate [C2] is then converted to the urea [D] by methods described in Schemes 1 to 5 above, and urea [D2] is then converted to the desired boronic acid pinacol ester compound [2] by methods described in Schemes 1, 2 and 5. Additional compounds [2] are prepared from other intermediates [C2] that can be synthesized by methods known to those skilled in the art, for example from halogen compounds [E]. As a specific example, 1-(4-aminophenyl)pyrrolidin-2-one is used for the preparation of compounds of formula (I) where M is an amide group of type —N(R⁹)—C(O)R¹⁰, wherein R⁹ and R¹⁰ are joined such that —R⁹-R¹⁰— is —CH₂CH₂— to form a 1-pyrrolidinyl group. The intermediate [C2] which is 1-(4-aminophenyl)pyrrolidin-2-one in this case, can be prepared by reaction of the compound [E] which is 4-iodoaniline in this case, with 2-pyrrolidinone, in the presence of N,N'-ethylenediamine, CuI, and dry K₂CO₃, using 1,4-dioxane as solvent at 110° C., based on the method described in International Patent Publication No. WO-2006/055951.

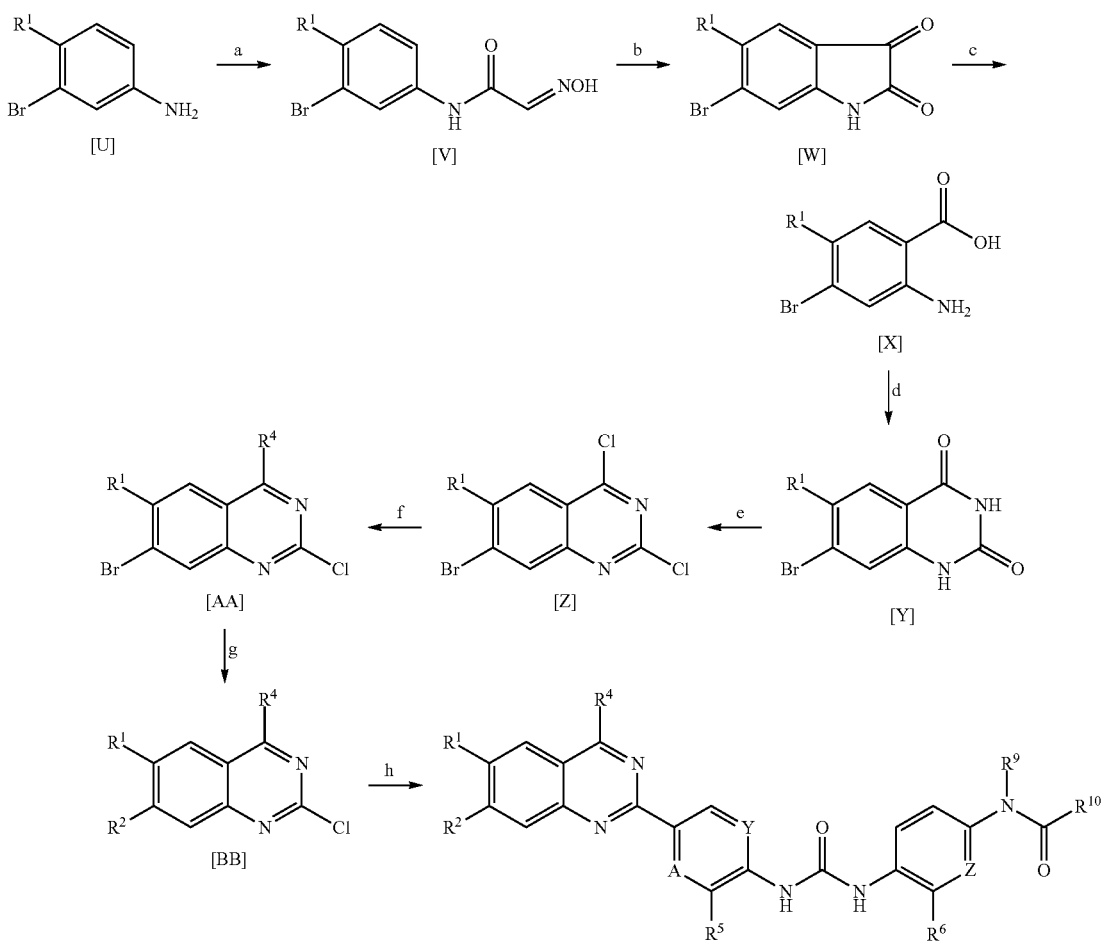

Scheme 10

The intermediate compounds [1] that are prepared by these various methods in Scheme 9 can be converted to compounds of formula (I), where M is an amide group of type —N(R⁹)—C(O)R¹⁰, by using the coupling reaction methods that are described for Schemes 6, 7 and 8. Scheme 10 depicts an example for the synthesis of compounds which are encompassed by the structure of formula (I), where R³ is H and M is an amide group of type —N(R⁹)—C(O)R¹⁰. The synthetic method is similar to that described in Scheme 6, except that the final coupling step uses a boronic acid pinacol ester intermediate compound that is prepared as described in Scheme 9.

It will be recognized by those skilled in the art that in certain cases the groups R², R³, R⁷ and R⁸, as well as substituents on the groups $R^2$, $R^3$, $R^7$ and $R^8$, can be modified to produce different groups $R^2$, $R^3$, $R^7$ and $R^8$. The reactions to effect these modifications can be conducted during the course of the synthetic sequences that are depicted in Schemes 1 to 8. Alternatively, in certain cases the groups $R^2$, $R^3$, $R^7$ and $R^8$, as well as substituents on the groups $R^2$, $R^3$, $R^7$ and $R^8$, can be modified after the preparation of compounds of the invention of formula I, to produce additional compounds of formula I. Likewise, some substituents can be converted into hydrogen, to afford the corresponding derivative that is unsubstituted at that atom position. Examples of such reactions to convert one substituent into a different substituent include, but are not limited to: the reduction of an aldehyde or ester substituent to a hydroxymethylene group; the conversion of an aldehyde to form a secondary alcohol fragment; the conversion of an aldehyde or ester group to form a dialkyl tertiary alcohol group; the conversion of an aldehyde group to a methyl group; the conversion of an aldehyde group to a methyl ester group and then (at a later step) to an amide or carboxylic acid group; the conversion of an aldehyde group to a dimethylamino-methylene fragment; the conversion of an aldehyde group to a cyano group; and the conversion of an aldehyde group to a methyl ketone fragment. Examples of these conversions and the reaction methods that can be used in these cases are depicted in Schemes 11 & 12.

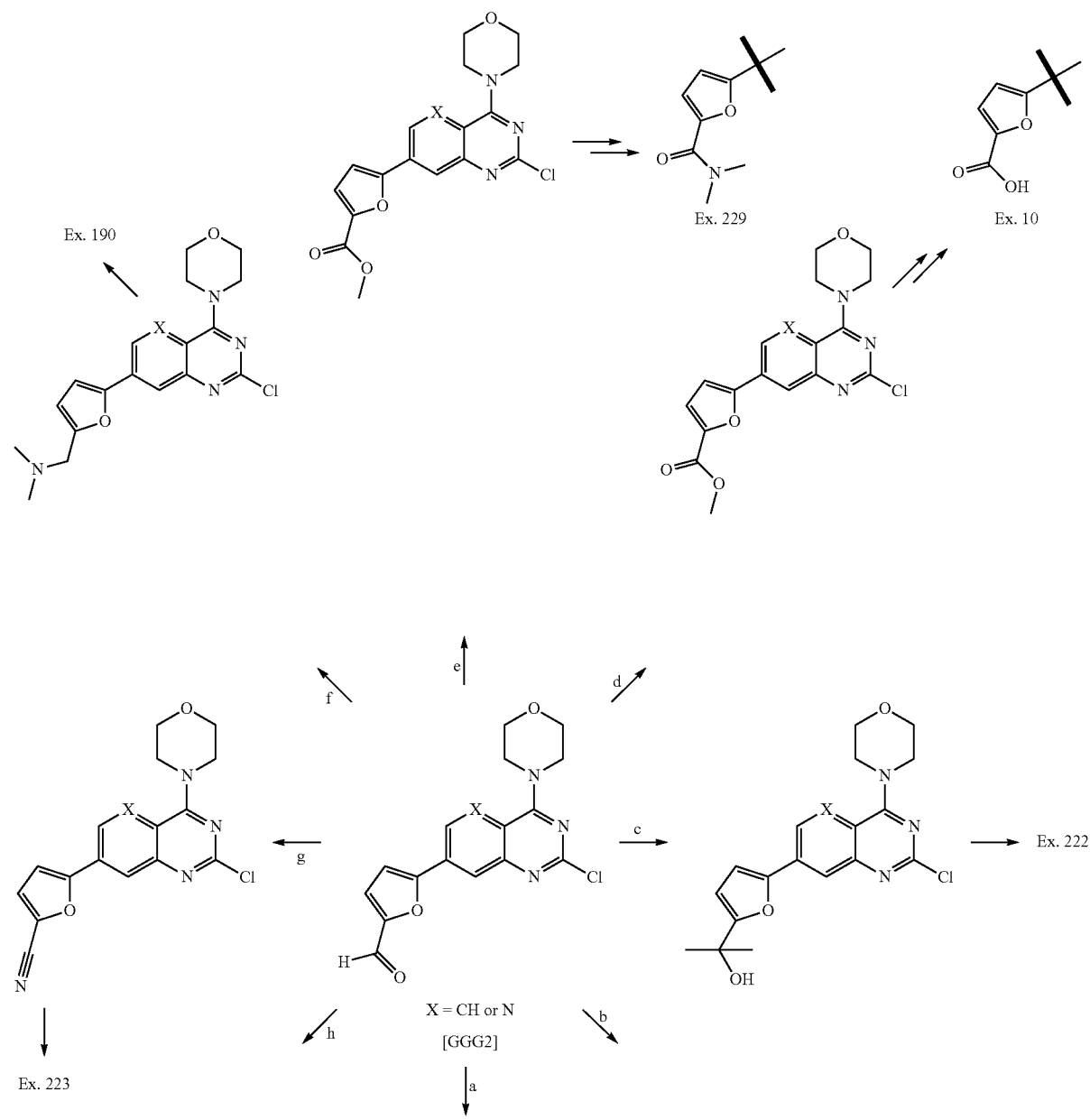

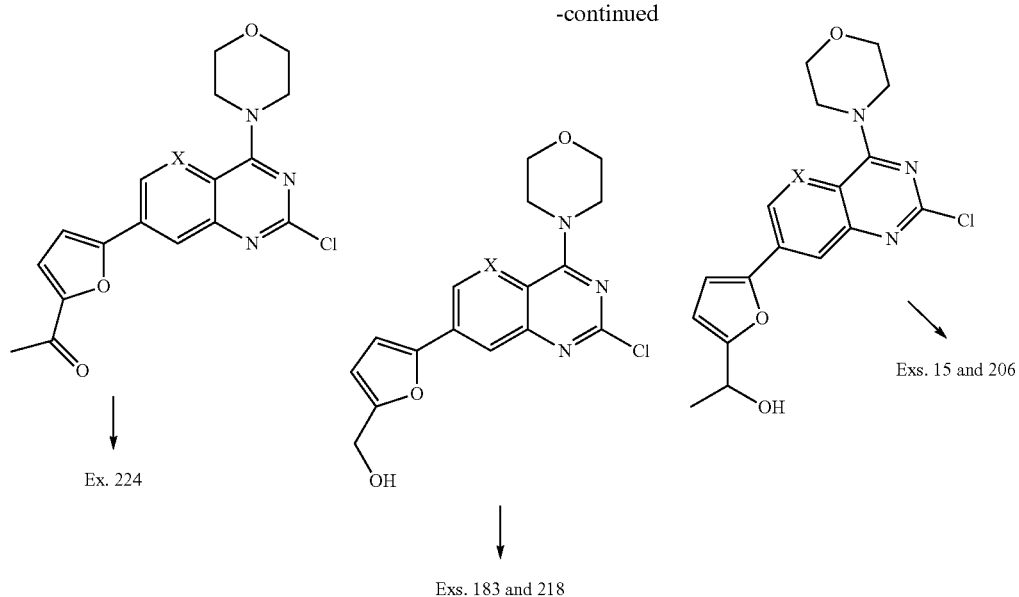

In Scheme 11, intermediate [GGG2] is prepared by using the methodology described in Schemes 6 and 7 (e.g., see Example 10, Step 1, in the Examples), and then methods a to h are applied to effect various modifications of the $R^2$ group. The resulting intermediates with these different $R^2$ groups are then converted to various compounds of the invention of formula (I) by methods that are well-known to those skilled in the art, and the methods described in Schemes 6 and 7. Examples of the reagents and conditions used for steps a to h in Scheme 11 are as follows: (a) NaBH$_4$, MeOH, rt, 1 h; (b) MeMgBr, THF, rt, 2 h; (c) i. NaCN, MnO$_2$, MeOH, 0° C.-rt, 3 h; ii. MeMgBr, THF, 0° C., 3 h; (d) i. NaCN, MnO$_2$, MeOH, 0° C.-rt, 3 h; (e) i. NaCN, MnO$_2$, MeOH, 0° C.-rt, 3 h; (f) NH(CH$_3$)$_2$.HCl, trimethyl orthoformate, NaCNBH$_3$, DCM, rt, 6 h; (g) NH$_3$(aq), I$_2$, acetonitrile, rt, 3 h; (h) i. MeMgBr, THF, rt, 2 h; ii. MnO$_2$, DCM, rt, 12 h.

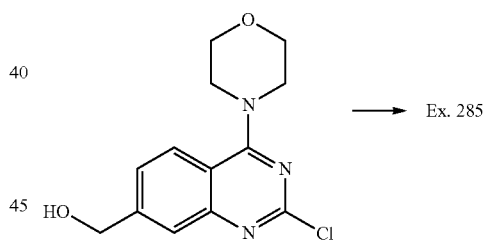

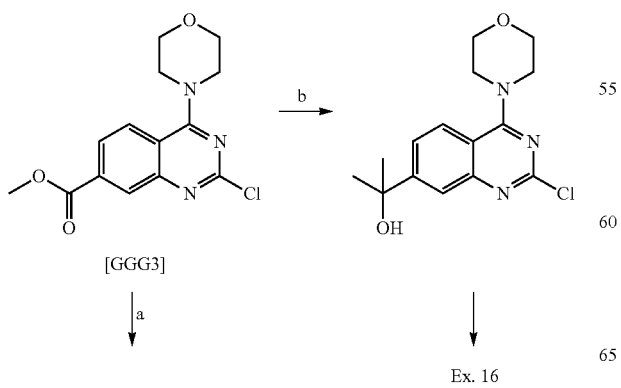

In Scheme 12, intermediate [GGG3] is prepared by using the methodology described in Scheme 8, and then methods a and b are applied to effect modifications of the $R^2$ group. The resulting intermediates with these different $R^2$ groups are then converted to compounds of formula (I) by methods described in Schemes 6. Examples of the reagents and conditions used for steps a and b in Scheme 12 are: (a) LiAlH$_4$, THF, 0° C.-rt, 5 h; (b) MeMgBr, THF, 0° C.-rt, 12 h.

Scheme 13

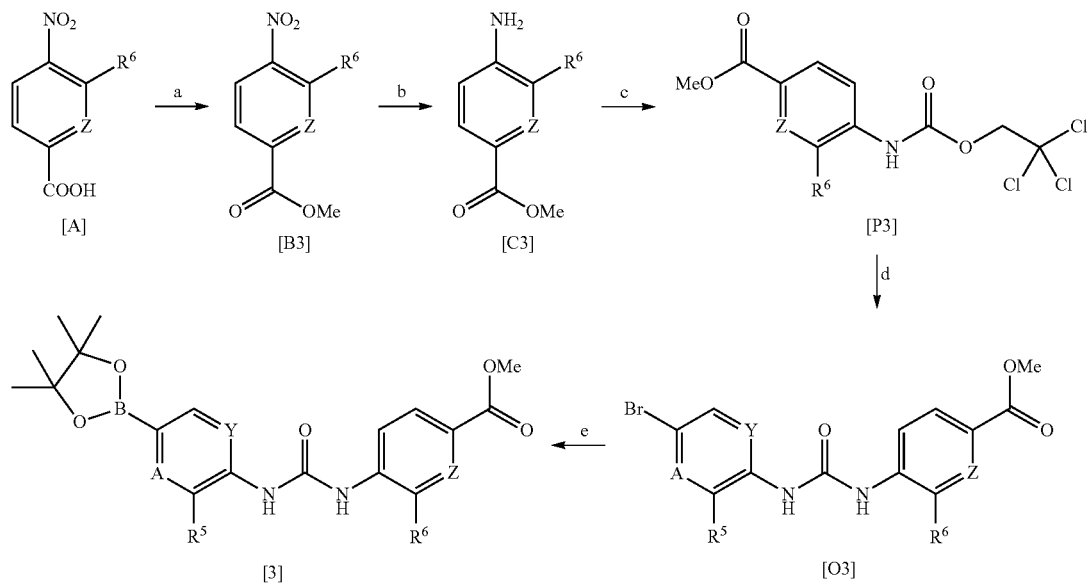

Scheme 13 depicts the preparation of boronic acid pinacol ester intermediate [3], in which the synthetic methodology is similar to that used as described in Scheme 4, after the initial formation of the ester [B3] from the carboxylic acid [A]. The ester [B3] can be prepared by various methods known to those skilled in the art, such as by reaction of the acid [A] with methyl iodide in the presence of potassium carbonate, for example in DMF at room temperature for 2 hours. Reduction of the nitro group in [B3] to give intermediate [C3] is followed by steps c and d to provide the urea intermediate [O3] via the trichloroethyl carbamate intermediate [P3]. Alternatively, in certain cases the intermediate [C3] can be converted in one step to the urea intermediate [O3], by treatment with the appropriate isocyanate, for example by the method as described in Scheme 5. Conversion of urea [O3] to intermediate [3] is accomplished by using the same reagents and conditions as described in step e of Scheme 4.

Scheme 14 compound [BBB]
compound [BB1] ⟶
compound [JJ1]
or
compound [EE1]

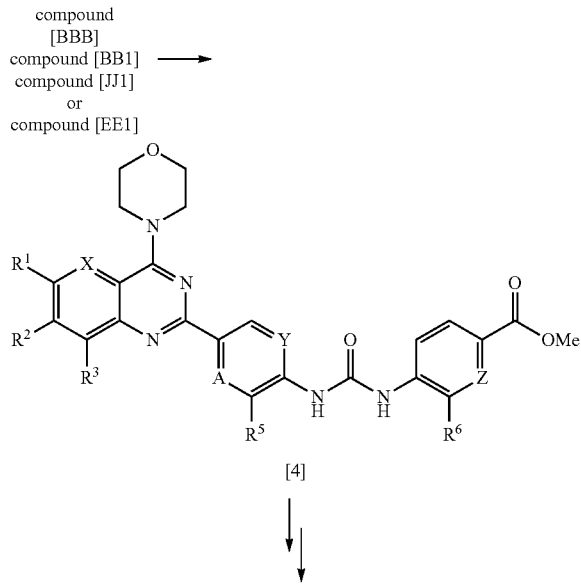

[4]

↓

-continued

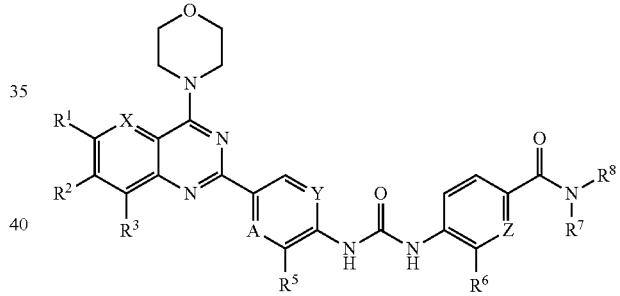

As depicted in Scheme 14, the intermediate [BB1] from Scheme 6B, [BBB] from Scheme 6G, [JJ1] from Scheme 7A or [EEE1] from Scheme 8A can be treated with compound [1] in Scheme 13 by using $PdCl_2(PPh_3)_2$, $Cs_2CO_3$, DMF, $H_2O$ at 90-95° C. for 2-3 h, or $PdCl_2(PPh_3)_2$, $Cs_2CO_3$, toluene, ethanol and $H_2O$ at 90-95° C., for 2-3 h. The obtained ester intermediate [4] is then hydrolysed, for example using lithium hydroxide in methanol, THF and $H_2O$, at rt for 5-12 h. The resulting acid intermediate is then subjected to amide coupling with the appropriate amine $R^7R^8NH$, using amide coupling conditions that are well known to those skilled in the art, such as HATU, with DIPEA or TEA, in DMF at rt for 12 h; or EDCI.HCl, with HOBt, and DIPEA or TEA, in DMF at rt for 12 h to obtain the desired compounds encompassed by formula (I).

Scheme 15

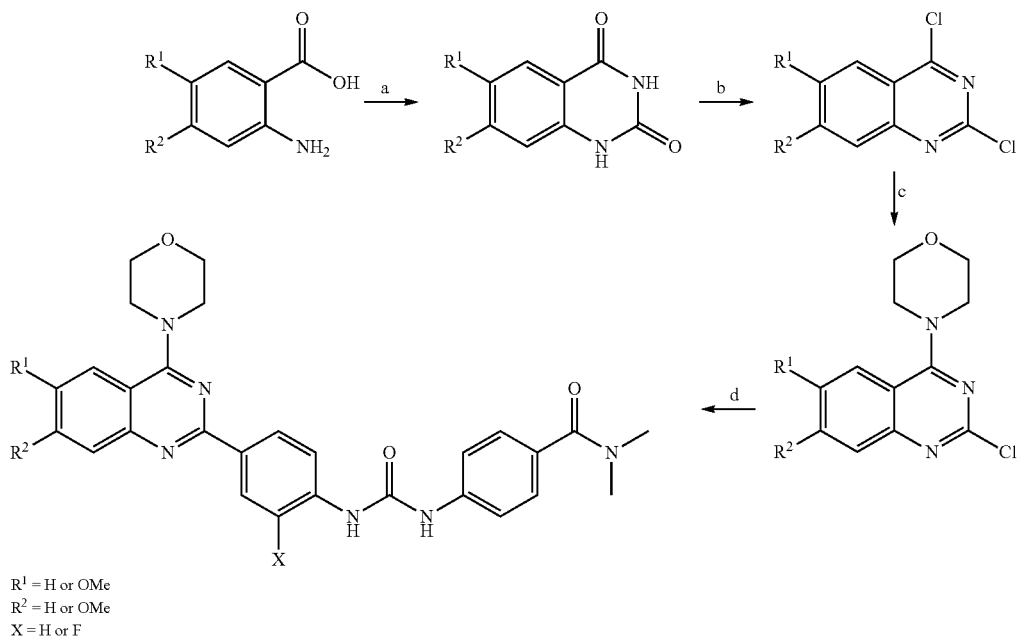

R¹ = H or OMe
R² = H or OMe
X = H or F

The method described in Scheme 15, which is similar to the methods depicted in Schemes 6 and 7, is used to prepare certain compounds of formula (I), where R¹ is H or methoxy, R² is H or methoxy, and X is H or F. Examples of the reagents and reaction conditions include, without limitation, (a) urea, 200° C., 2-3 h; (b) POCl₃, DIPEA, 130° C., 4-12 h; or POCl₃, DIPEA, toluene, 130° C., 4-12 h; (c) morpholine, DCM, 0° C., 15 min; or morpholine, DCM, 0° C. to rt, 15 min-4 h; (d) substituted urea boronic acid pinacol borate ester intermediate, PdCl₂(PPh₃)₂, Cs₂CO₃, DMF, H₂O, 90-95° C., 2-3 h; or substituted urea boronic acid pinacol borate ester, PdCl₂ (PPh₃)₂, Cs₂CO₃, toluene, ethanol, H₂O, 90-95° C., 2-3 h.

Pharmaceutical compositions useful herein contain a compound of formula (I) in a pharmaceutically acceptable carrier optionally with other pharmaceutically inert or inactive ingredients. In another embodiment, a compound of formula (I) is present in a single composition. In a further embodiment, a compound of formula (I) is combined with one or more excipients and/or other therapeutic agents as described below.

The pharmaceutical compositions of the invention comprise an amount of a compound of formula (I) or a pharmaceutically acceptable salt thereof that is effective for regulating the PI3K/AKT/mTOR pathway in a subject. Specifically, the dosage of the compound of formula (I) to achieve a therapeutic effect will depend on the formulation, age, weight and sex of the patient and route of delivery. It is also contemplated that the treatment and dosage of the compound of formula (I) may be administered in unit dosage form and that one skilled in the art would adjust the unit dosage form accordingly to reflect the relative level of activity. The decision as to the particular dosage to be employed (and the number of times to be administered per day) is within the discretion of the ordinarily-skilled physician, and may be varied by titration of the dosage to the particular circumstances to produce the desired therapeutic effect. In one embodiment, the therapeutically effective amount is about 0.01 mg/kg to 10 mg/kg body weight. In another embodiment, the therapeutically effective amount is less than about 5 g/kg, about 500 mg/kg, about 400 mg/kg, about 300 mg/kg, about 200 mg/kg, about 100 mg/kg, about 50 mg/kg, about 25 mg/kg, about 10 mg/kg, about 1 mg/kg, about 0.5 mg/kg, about 0.25 mg/kg, about 0.1 mg/kg, about 100 μg/kg, about 75 μg/kg, about 50 μg/kg, about 25 μg/kg, about 10 μg/kg, or about 1 μg/kg. However, the therapeutically effective amount of the compound of formula (I) can be determined by the attending physician and depends on the condition treated, the compound administered, the route of delivery, the age, weight, severity of the patient's symptoms and response pattern of the patient.

The therapeutically effective amounts may be provided on regular schedule, i.e., daily, weekly, monthly, or yearly basis or on an irregular schedule with varying administration days, weeks, months, etc. Alternatively, the therapeutically effective amount to be administered may vary. In one embodiment, the therapeutically effective amount for the first dose is higher than the therapeutically effective amount for one or more of the subsequent doses. In another embodiment, the therapeutically effective amount for the first dose is lower than the therapeutically effective amount for one or more of the subsequent doses. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the judgment of a health-care practitioner. The therapeutically effective amounts described herein refer to total amounts administered for a given time period; that is, if more than one compound of formula (I) or a pharmaceutically acceptable salt thereof is administered, the therapeutically effective amounts correspond to the total amount administered.

The pharmaceutical compositions containing a compound of formula (I) may be formulated neat or with one or more pharmaceutical carriers for administration. The amount of the pharmaceutical carrier(s) is determined by the solubility and chemical nature of the compound of formula (I), chosen route of administration and standard pharmacological practice. The pharmaceutical carrier(s) may be solid or liquid and may incorporate both solid and liquid carriers. A variety of suitable liquid carriers are known and may be readily selected by one of skill in the art. Such carriers may include, e.g., DMSO, saline, buffered saline, hydroxypropylcyclodextrin, and mixtures thereof. Similarly, a variety of solid carriers and excipients are known to those of skill in the art. The compounds of formula (I) may be administered by any route, taking into consideration the specific condition for which it has been selected. The compounds of formula (I) may, be delivered orally, by injection, inhalation (including orally, intranasally and intratracheally), ocularly, transdermally, intravascularly, subcutaneously, intramuscularly, sublingually, intracranially, epidurally, rectally, and vaginally, among others.

Although the compound of formula (I) may be administered alone, it may also be administered in the presence of one or more pharmaceutical carriers that are physiologically compatible. The carriers may be in dry or liquid form and must be pharmaceutically acceptable. Liquid pharmaceutical compositions are typically sterile solutions or suspensions. When liquid carriers are utilized for parenteral administration, they are desirably sterile liquids. Liquid carriers are typically utilized in preparing solutions, suspensions, emulsions, syrups and elixirs. In one embodiment, the compound of formula (I) is dissolved a liquid carrier. In another embodiment, the compound of formula (I) is suspended in a liquid carrier. One of skill in the art of formulations would be able to select a suitable liquid carrier, depending on the route of administration. The compound of formula (I) may alternatively be formulated in a solid carrier. In one embodiment, the composition may be compacted into a unit dose form, i.e., tablet or caplet. In another embodiment, the composition may be added to unit dose form, i.e., a capsule. In a further embodiment, the composition may be formulated for administration as a powder. The solid carrier may perform a variety of functions, i.e., may perform the functions of two or more of the excipients described below. For example, solid carrier may also act as a flavoring agent, lubricant, solubilizer, suspending agent, filler, glidant, compression aid, binder, disintegrant, or encapsulating material.

The composition may also be sub-divided to contain appropriate quantities of the compound of formula (I). For example, the unit dosage can be packaged compositions, e.g., packeted powders, vials, ampoules, prefilled syringes or sachets containing liquids.

Examples of excipients which may be combined with one or more compound of formula (I) include, without limitation, adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, suspending agents, syrups, thickening agents, or viscosity regulators. See, for example, the excipients described in the "Handbook of Pharmaceutical Excipients", $5^{th}$ Edition, Eds.: Rowe, Sheskey, and Owen, APhA Publications (Washington, D.C.), Dec. 14, 2005, which is incorporated herein by reference.

In one embodiment, the compositions may be utilized as inhalants. For this route of administration, compositions may be prepared as fluid unit doses using a compound of formula (I) and a vehicle for delivery by an atomizing spray pump or by dry powder for insufflation.

In another embodiment, the compositions may be utilized as aerosols, i.e., oral or intranasal. For this route of administration, the compositions are formulated for use in a pressurized aerosol container together with a gaseous or liquefied propellant, e.g., dichlorodifluoromethane, carbon dioxide, nitrogen, propane, and the like. Also provided is the delivery of a metered dose in one or more actuations.

In another embodiment, the compositions may be administered by a sustained delivery device. "Sustained delivery" as used herein refers to delivery of a compound of formula (I) which is delayed or otherwise controlled. Those of skill in the art know suitable sustained delivery devices. For use in such sustained delivery devices, the compound of formula (I) is formulated as described herein.

In addition to the components described above for use in the composition and the compound of formula (I), the compositions may contain one or more medications or therapeutic agents which are used to treat solid tumors. In one embodiment, the medication is a chemotherapeutic. Examples of chemotherapeutics include those recited in the "Physician's Desk Reference", $64^{th}$ Edition, Thomson Reuters, 2010, which is hereby incorporated by reference. Therapeutically effective amounts of the additional medication(s) or therapeutic agents are well known to those skilled in the art. However, it is well within the attending physician to determine the amount of other medication to be delivered.

The compounds of formula (I) and/or other medication(s) or therapeutic agent(s) may be administered in a single composition. However, the present invention is not so limited. In other embodiments, the compounds of formula (I) may be administered in one or more separate formulations from other compounds of formula (I), chemotherapeutic agents, or other agents as is desired.

Also provided herein are kits or packages of pharmaceutical formulations containing the compounds of formula (I) or compositions described herein. The kits may be organized to indicate a single formulation or combination of formulations to be taken at each desired time.

Suitably, the kit contains packaging or a container with the compound of formula (I) formulated for the desired delivery route. Suitably, the kit contains instructions on dosing and an insert regarding the active agent. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of a spray pump or other delivery device. Other suitable components to include in such kits will be readily apparent to one of skill in the art, taking into consideration the desired indication and the delivery route.

The compounds of formula (I) or compositions described herein can be a single dose or for continuous or periodic discontinuous administration. For continuous administration, a package or kit can include the compound of formula (I) in each dosage unit (e.g., solution, lotion, tablet, pill, or other unit described above or utilized in drug delivery), and optionally instructions for administering the doses daily, weekly, or monthly, for a predetermined length of time or as prescribed. When the compound of formula (I) is to be delivered periodically in a discontinuous fashion, a package or kit can include placebos during periods when the compound of formula (I) is not delivered. When varying concentrations of a composition, of the components of the composition, or the relative ratios of the compounds of formula (I) or agents within a composition over time is desired, a package or kit may contain a sequence of dosage units which provide the desired variability.

A number of packages or kits are known in the art for dispensing pharmaceutical agents for periodic oral use. In one embodiment, the package has indicators for each period. In another embodiment, the package is a labeled blister package, dial dispenser package, or bottle.

The packaging means of a kit may itself be geared for administration, such as an inhalant, syringe, pipette, eye dropper, or other such apparatus, from which the formulation may be applied to an affected area of the body, such as the lungs, injected into a subject, or even applied to and mixed with the other components of the kit.

The compositions of these kits also may be provided in dried or lyophilized forms. When reagents or components are provided as a dried form, reconstitution generally is by the addition of a suitable solvent. It is envisioned that the solvent also may be provided in another package.

The kits of the present invention also will typically include a means for containing the vials in close confinement for commercial sale such as, e.g., injection or blow-molded plastic containers into which the desired vials are retained. Irrespective of the number or type of packages and as discussed above, the kits also may include, or be packaged with a separate instrument for assisting with the injection/administration or placement of the composition within the body of an animal. Such an instrument may be an inhalant, syringe, pipette, forcep, measuring spoon, eye dropper or any such medically approved delivery means.

In one embodiment, a kit is provided and contains a compound of formula (I). The compound of formula (I) may be in the presence or absence of one or more of the carriers or excipients described above. The kit may optionally contain instructions for administering the medication and the compound of formula (I) to a subject having a disease characterized by the dysregulation of the PI3K/AKT/mTOR pathway.

In a further embodiment, a kit is provided and contains a compound of formula (I) in a second dosage unit, and one or more of the carriers or excipients described above in a third dosage unit. The kit may optionally contain instructions for administering the medication and the compound of formula (I) to a subject having a disease characterized by the dysregulation of the PI3K/AKT/mTOR pathway.

The compounds described herein are useful in regulating conditions which are associated with the PI3K/AKT/mTOR pathway. In one embodiment, such a disease is associated with abnormal cellular proliferation. The term "abnormal cellular proliferation" refers to the uncontrolled growth of cells which are naturally present in a mammalian body. In one embodiment, a disease which is characterized by abnormal cellular proliferation is cancer, including, without limitation, cancer of the prostate, head, neck, eye, mouth, throat, esophagus, bronchus, larynx, pharynx, chest, bone, lung, colon, rectum, stomach, bladder, uterus, cervix, breast, ovaries, vagina, testicles, skin, thyroid, blood, lymph nodes, kidney, liver, intestines, pancreas, brain, central nervous system, adrenal gland, or skin or a leukemia. In one embodiment, the disease characterized by abnormal cellular proliferation is cancer of the prostate.

The compounds of formula (I) regulate activity of mTOR and of PI3K. In a further embodiment, the compounds of formula (I) regulate PI3K activity. The tested compounds of formula (I) have the ability to inhibit all four isoforms of PI3K ($\alpha$, $\beta$, $\delta$, $\gamma$) with at least two of the compounds showing selectivity for the $\alpha$ PI3K isoform. These compounds associated with selective activity for the $\alpha$ isoform may be particularly well suited for treatment of conditions associated with the PI3K isoform, including, e.g., breast and gastric cancers, colorectal tumors, glioblastomas, and prostate cancer, and lung cancers.

In another embodiment, the compounds of formula (I) regulate the pathway of the PI3K-$\beta$ isoform. In still a further embodiment, the compounds of formula (I) regulate the pathway of the PI3K-$\delta$ isoform. In yet another embodiment, the compounds of formula (I) regulate the pathway of the PI3K-$\gamma$ isoform.

The ability of compounds to inhibit the PI3K delta and PI3K gamma isoforms has been described with the ability to treat acute and chronic inflammatory disorders. See, e.g., R C Camps et al, Nat Rev Immunol., 2007 Mar. 7(3): 191-201. Other inflammatory disorders have been associated more specifically with the PI3K delta isoform, including neutrophil-associated inflammation. Models for testing the ability of compounds to reduce inflammation in inflammatory arthritis are known, e.g., as described by Camps et al, Nature Med., 2005, 11, 936-943. Camps et al (2005) also describes models useful in assessing the ability of compounds to reduce inflammation in peritonitis. Models for testing the ability of compounds to reduce inflammation and/or improve healing after myocardial infarction are described by Siragusa et al, Circ. Res. (2010), 106, 757-768. A model for testing the ability of compounds to prevent bleomycin-induced pulmonary fibrosis is described by Wei et al, Biochem Biophys Res Comm. 2010, 397: 311-317 and Brent et al, Toxicology, 2000, 147: 1-13.

The term "regulation" or variations thereof as used herein refers to the ability of a compound of formula (I) to inhibit one or more components of a biological pathway. In one embodiment, "regulation" refers to inhibition of mTOR activity. In another embodiment, "regulation" refers to inhibition of PI3K activity. In a further embodiment, regulation refers to dual inhibition of mTOR and PI3K activity.

The utility of the compounds of formula (I) can be illustrated, for example, by their activity in the in vitro tumor cell proliferation assay described below. The compounds of formula (I) exhibit an mTOR and PI3K inhibitory activity, and therefore can be utilized in order to inhibit abnormal cell growth in which mTOR plays a role. Thus, the compounds of formula (I) are effective in the treatment of disorders with which abnormal cell growth actions of mTOR and/or PI3K dysregulation are associated, such as cancer.

In one embodiment, methods for regulating the PI3K and/or mTOR pathways are provided and include administering a therapeutically effective amount of a compound of formula (I) to a patient in need thereof.

In another desirable embodiment, methods for treating a disease characterized by an abnormal cellular growth resulting from a dysregulated PI3K/mTOR pathway are provided and include administering of a therapeutically effective amount of a compound of formula (I) to a patient in need thereof.

In a further desirable embodiment, methods for treating a condition treatable by inhibiting the PI3K/AKT/mTOR pathway are provided and include administering a therapeutically effective amount of a compound of formula (I) to a patient in need thereof.

As described herein, a therapeutically effective amount of a compound when used for the treatment of cancer is an amount which may reduce the number of cancer cells, reduce tumor size, inhibit metastasis, inhibit tumor growth and/or ameliorate one or more of the symptoms of the cancer. For cancer therapy, efficacy can be measured for example, by assessing the time to disease progression and/or determining the response rate.

As described herein, a therapeutically effective amount of a compound when used for the treatment of an inflammatory disorder is an amount which may delay the onset of or reduce the severity or duration of an inflammatory response, or which mitigates one or more symptoms of an inflammatory response. For treatment of an inflammatory disorder, efficacy can be measured, for example, by a reduction in physiologic signs of inflammation (e.g., redness, swelling, heat, loss of function) or by measuring changes in the levels of cells (e.g., monocytes, macrophages and other mononuclear cells) or molecules (e.g., pro-inflammatory cytokines) associated with inflammation.

The following examples are illustrative only and are not intended to limit the present invention.

EXAMPLES

Unless otherwise stated, all the raw materials are purchased from Sigma-Aldrich, Fluorochem, Apollo Scientific and Matrix Labs and solvents from Ranchem, S. D. Fine and Merck labs. ¹H NMR spectra were recorded on Varian 300 and 400 MHz instruments, using TMS as internal reference. The chemical shift values are quoted in δ (parts per million). Mass spectra of all the intermediates and final compounds were recorded using Agilent® LC/MSD/VL and API 2000 LC/MS instruments using a Synergi™ 2.5μ MAX-RP column (100 Å Mercury; 20×4.0 mm), a mobile phase of 0.1% formic acid in water and ACN, a flow rate of 2 mL/min, a temperature of 30° C., and a run time of 3.0 min. The purity of all the final compounds was detected using Agilent® HPLC 1100 & 1200 instruments and the following conditions:

- Condition 1: Column: AG/C18/25-008 (Zorbax® Eclipse XDB-C18 column, 4.6×250 mm, 5μ, mobile phase: A=0.01% TFA in water; B=ACN/MeOH (1:1); gradient: 95:05; flow: 1.0 mL/min; temperature: 40° C.; run time: 12 min
- Condition 2: Column: AG/C18/15-001 (Zorbax® Eclipse XDB-C18 column, 4.6×150 mm, 5μ), mobile phase: A=0.01% TFA in water; B=ACN/MeOH (1:1), isocratic: 40:60, flow: 1.0 mL/min, temperature: 25° C., run time: 12 min,
- Condition 3: Column: AG/C18/15-009 (Zorbax® Eclipse XDB-C18 column, 4.6×150 mm, 5μ), mobile phase: A=5 mM ammonium acetate in water; B: ACN, gradient: 95:05, flow: 1.0 mL/min, temperature: 40° C., run time: 12.0 min Preparation 1: N,N-Dimethyl-4-{3-[4-(4,4,5,5-tetramethyl-[1,3,2]dioxaborolan-2-yl)phenyl]-ureido}-benzamide

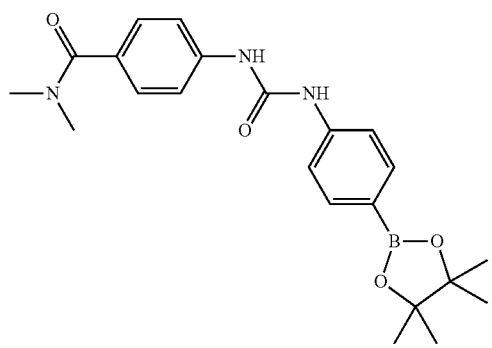

Step 1: N,N-dimethyl-4-nitro benzamide

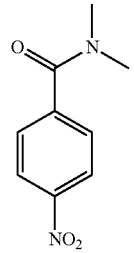

To a solution of 4-nitro-benzoic acid (20 g, 0.1196 mol) in DMF (300 mL) N, N-dimethylamine hydrochloride (11.7 g, 0.1436 mol), HOBt (20.9 g, 0.1554 mol), EDC.HCl (34.3 g, 0.1794 mol) and DIPEA (30.91 g, 0.2392 mol) were added. The reaction mixture was stirred at room temperature for 12 h. The reaction mixture was diluted with water and extracted with ethyl acetate (3×500 mL). The organic layer was washed with water, brine and dried over sodium sulfate. The solvent was evaporated under reduced pressure to afford the title compound [23.0 g, 99%]; LC-MS (ESI): Calculated mass: 194.1; Observed mass: 195.1 [M+H]⁺ (RT: 1.70 min).

Step 2: 4-Amino-N,N-dimethyl-benzamide

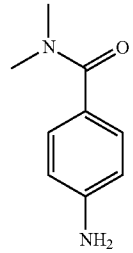

To a solution of N,N-dimethyl-4-nitro benzamide (23 g, 0.1185 mol) in MeOH (200 mL) was added Pd/C 10% (2.3 g) in portions and the Parr reaction vessel was purged with nitrogen for 10 min. The reaction vessel was fixed in Parr shaker at 60 psi pressure for 3 h. The reaction mixture was filtered through the Celite® pad and the filtrate was concentrated under reduced pressure to afford the title compound [18.0 g, 93%]; LC-MS (ESI): Calculated mass: 164.1; Observed mass: 165.2 [M+H]⁺ (RT: 0.17 min).

Step 3: 4-[3-(4-Bromo-phenyl)-ureido]-N,N-dimethyl-benzamide

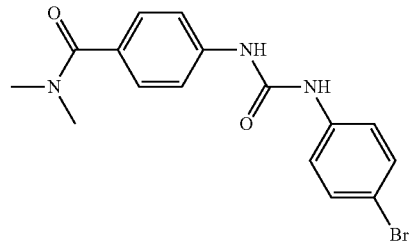 [SMILES: CN(C)C(=O)c1ccc(NC(=O)Nc2ccc(Br)cc2)cc1]

To a solution of 4-amino-N,N-dimethyl-benzamide (3.5 g, 0.0213 mol), TEA (2.15 g, 0.0213 mol) in DCM (50 mL) was added 4-bromophenyl isocyanate (5.07 g, 0.0256 mol). The reaction mixture was stirred at room temperature for 12 h. The white solid was obtained and was filtered and dried to afford the title compound [6.8 g, 88%]; LC-MS (ESI): Calculated mass: 361.0; Observed mass: 362.0 [M+H]$^+$ (RT: 0.17 min).

Step 4: N,N-Dimethyl-4-{3-[4-(4,4,5,5-tetramethyl-[1,3,2]dioxaborolan-2-yl)phenyl]-ureido}-benzamide

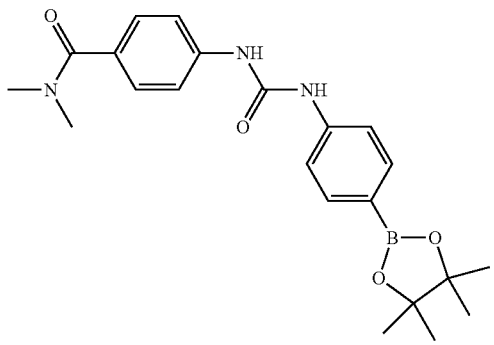

To a solution of 4-[3-(4-bromo-phenyl)-ureido]-N,N-dimethyl-benzamide (6.8 g, 0.0187 mol) in 1,4-dioxane (350 mL) were added bis(pinacolato)diboron (7.15 g, 0.0281 mol), KOAc (5.5 g, 0.0561 mol) and PdCl$_2$(dppf).DCM (1.0 g, 0.0013 mol). The reaction vessel was purged with nitrogen for 10 min. The reaction mixture was stirred at 105° C. for 12 h. The reaction mixture was diluted with water and extracted with ethyl acetate [3×100 mL]. The organic layer was washed with water, brine and dried over sodium sulfate. The solvent was removed under reduced pressure to afford the crude residue. The crude product was purified using column chromatography (60-120 silica gel, 5% MeOH in chloroform) to yield the desired title product. [3.7 g, 48%]; $^1$H NMR (300 MHz, DMSO-d$_6$): δ 8.91 (d, J=6.0 Hz, 2H), 7.43-7.61 (m, 6H), 2.95 (s, 6H), 1.25 (s, 12H); LC-MS (ESI): Calculated mass: 409.2; Observed mass: 410.1 [M+H]$^+$ (RT: 1.5 min).

Preparation 2: N-(2-Dimethylamino-ethyl)-N-methyl-4-{3-[4-(4,4,5,5-tetramethyl-[1,3,2]dioxaborolan-2-yl)-phenyl]-ureido}-benzamide

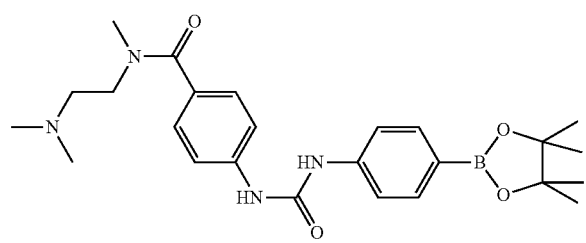

Step 1: N-(2-Dimethylamino-ethyl)-N-methyl-4-nitro benzamide

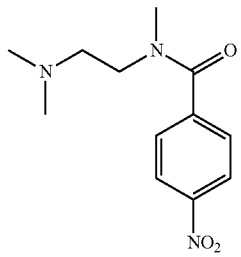

To a solution of 4-nitro-benzoic acid (3.0 g, 0.01795 mol) in DMF (40 mL), N,N,N'-trimethyl ethylenediamine (2.2 g, 0.02154 mol), HOBt (3.15 g, 0.02335 mol), EDC.HCl (5.16 g, 0.02692 mol) and DIPEA (4.64 g, 0.0359 mol) were added. The reaction mixture was stirred at ambient temperature for 12 h. The reaction mixture was diluted with water and extracted with ethyl acetate (3×100 mL). The organic layer was washed with water, brine and dried over sodium sulfate. The solvent was evaporated under reduced pressure to afford the title compound [4.5 g, 100%]; LC-MS (ESI): Calculated mass: 251.1; Observed mass: 251.9 [M+H]$^+$ (RT: 0.21 min).

Step 2: 4-Amino-N-(2-dimethylamino-ethyl)-N-methyl-benzamide

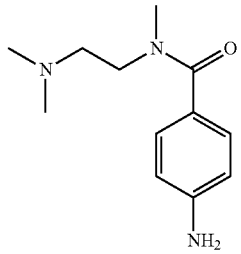 [SMILES: CN(C)CCN(C)C(=O)c1ccc(N)cc1]

To a solution of N-(2-dimethylamino-ethyl)-N-methyl-4-nitro benzamide (4.5 g, 0.0179 mol) in MeOH (100 mL) was added Pd/C 10% (0.5 g) in portions and the Parr reaction vessel was purged with nitrogen for 10 min. The reaction vessel was fixed in Parr shaker at 60 psi pressure for 3 h. The reaction mixture was filtered through the Celite® pad and the filtrate was concentrated under reduced pressure to afford the title compound [4.0 g, 100%]; LC-MS (ESI): Calculated mass: 221.2; Observed mass: 222.1 [M+H]$^+$ (RT: 0.17 min).

Step 3: 4-[3-(4-Bromo-phenyl)-ureido]-N-(2-dimethylamino-ethyl)-N-methyl-benzamide

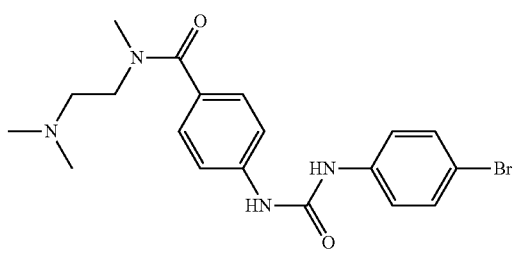 [SMILES: CN(C)CCN(C)C(=O)c1ccc(NC(=O)Nc2ccc(Br)cc2)cc1]

To a solution of 4-amino-N-(2-dimethylamino-ethyl)-N-methyl-benzamide (4.0 g, 0.01809 mol) and TEA (2.01 g, 0.01809 mol) in DCM (50 mL) was added 4-bromophenyl isocyanate (4.3 g, 0.0217 mol). The reaction mixture was stirred at room temperature for 12 h. The white solid was obtained and was filtered and dried to afford the title compound [5.0 g, 67%]; LC-MS (ESI): Calculated mass: 418.1; Observed mass: 421.1 [M+H]$^+$ (RT: 1.23 min).

Step 4: N-(2-Dimethylamino-ethyl)-N-methyl-4-{3-[4-(4,4,5,5-tetramethyl-[1,3,2]dioxaborolan-2-yl)-phenyl]-ureido}-benzamide

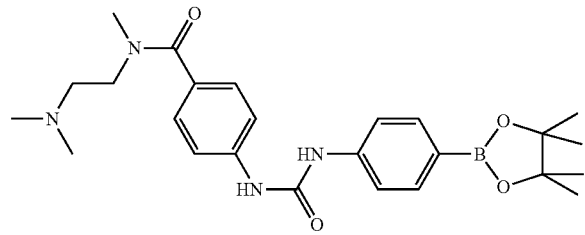

To a solution of 4-[3-(4-bromo-phenyl)-ureido]-N-(2-dimethylamino-ethyl)-N-methyl-benzamide (5.0 g, 0.0119 mol) in 1,4-dioxane (250 mL) were added bis(pinacolato)diboron (4.5 g, 0.01789 mol), KOAc (3.5 g, 0.0357 mol) and PdCl$_2$(dppf).DCM (0.681 g, 0.00083 mol). The reaction vessel was purged with nitrogen for 10 min. The reaction mixture was stirred at 105° C. for 12 h. The reaction mixture was diluted with water and extracted with ethyl acetate [3×100 mL]. The organic layer was washed with water, brine and dried over sodium sulfate. The solvent was removed under reduced pressure to afford the crude residue. The crude product was purified using column chromatography (60-120 silica gel, 40% MeOH in chloroform) to get the desired product [0.5 g, 9%]; $^1$H NMR (300 MHz, DMSO-d$_6$): δ 7.66-7.72 (m, 4H), 7.46-7.60 (m, 3H), 7.28-7.32 (m, 1H), 4.01 (d, J=6.6 Hz, 4H), 2.94 (s, 3H), 1.80-1.98 (m, 6H), 1.28 (s, 12H); LC-MS (ESI): Calculated mass: 466.3; Observed mass: 467.2 [M+H]$^+$ (RT: 0.62 min).

Preparation 3: 1-[4-(4-Methyl-piperazine-1-carbonyl)-phenyl]-3-[4-(4,4,5,5-tetramethyl-[1,3,2]dioxaborolan-2-yl)-phenyl]-urea

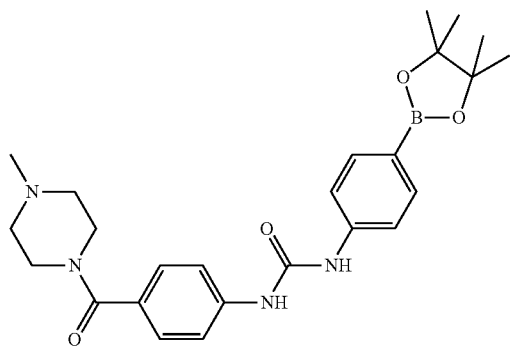 [SMILES: CN1CCN(C(=O)c2ccc(NC(=O)Nc3ccc(B4OC(C)(C)C(C)(C)O4)cc3)cc2)CC1]

Step 1: (4-Methyl-piperazin-1-yl)-(4-nitro-phenyl)-methanone

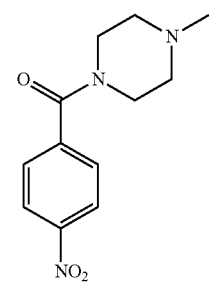

To a solution of 4-nitro-benzoic acid (10 g, 0.0598 mol) in DMF (300 mL) 1-methyl-piperazine (7.19 g, 0.0718 mol), HOBt (10.5 g, 0.0777 mol), EDC.HCl (17.12 g, 0.0897 mol) and TEA (12.1 g, 0.1196 mol) were added. The reaction mixture was stirred at room temperature for 12 h. The reaction mixture was diluted with water and extracted with ethyl acetate (3×200 mL). The organic layer was washed with water, brine and dried over sodium sulfate. The solvent was evaporated under reduced pressure to afford the title compound [14 g, 95%]; LC-MS (ESI): Calculated mass: 249.1; Observed mass: 250.0 [M+H]$^+$ (RT: 0.10 min).

Step 2: (4-Amino-phenyl)-(4-methyl-piperazine-1-yl)-methanone

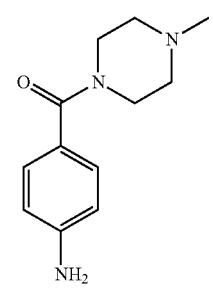 [SMILES: CN1CCN(C(=O)c2ccc([N+](=O)[O-])cc2)CC1]

To a solution of (4-Methyl-piperazin-1-yl)-(4-nitro-phenyl)-methanone (14 g, 0.05623 mol) in MeOH (100 mL) was added Pd/C 10% (1.4 g) in portions and the Parr reaction vessel was purged with nitrogen for 10 min. reaction vessel was fixed in Parr shaker at 60 psi pressure for 3 h. The reaction mixture was filtered through the Celite® pad and the filtrate was concentrated under reduced pressure to afford the title compound [11 g, 89%]; LC-MS (ESI): Calculated mass 219.1; Observed mass: 220.1 [M+H]$^+$ (RT: 0.16 min).

Step 3: 1-(4-Bromo-phenyl)-3-[4-(4-methyl-piperazine-1-carbonyl)-phenyl]-urea

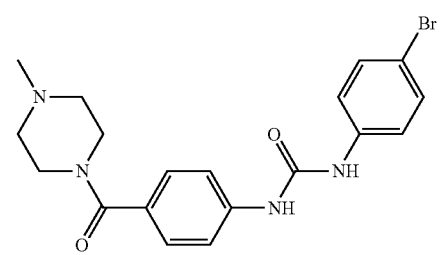 [SMILES: CN1CCN(C(=O)c2ccc(NC(=O)Nc3ccc(Br)cc3)cc2)CC1]

To a solution of (4-amino-phenyl)-(4-methyl-piperazine-1-yl)-methanone (10.0 g, 0.0456 mol) and TEA (4.7 g, 0.0456 mol) in DCM (150 mL) was added 4-bromophenyl isocyanate (10.9 g, 0.0547 mol). The reaction mixture was stirred at room temperature for 12 h. The white solid was obtained and was filtered and dried to afford the title compound [15.0 g, 79%]; LC-MS (ESI): Calculated mass: 416.1; Observed mass: 417.1 [M+H]$^+$ (RT: 0.23 min).

Step 4: 1-[4-(4-Methyl-piperazine-1-carbonyl)-phenyl]-3-[4-(4,4,5,5-tetramethyl-[1,3,2]dioxaborolan-2-yl)-phenyl]-urea

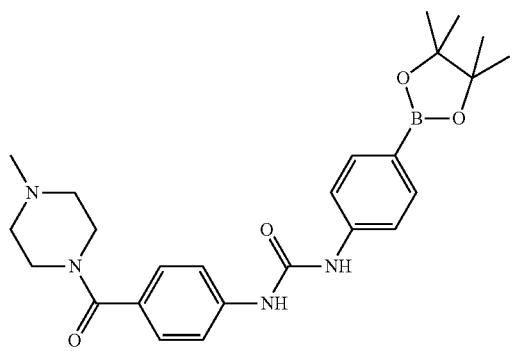 [SMILES: CN1CCN(C(=O)c2ccc(NC(=O)Nc3ccc(B4OC(C)(C)C(C)(C)O4)cc3)cc2)CC1]

To a solution of 1-(4-bromo-phenyl)-3-[4-(4-methyl-piperazine-1-carbonyl)-phenyl]-urea (2.5 g, 0.006 mol) in 1,4-dioxane (60 mL). were added bis(pinacolato)diboron (2.2 g, 0.0089 mol), KOAc (1.76 g, 0.01797 mol) and PdCl$_2$(dppf).DCM (0.34 g, 0.00041 mol). The reaction vessel was purged with nitrogen for 10 min. The reaction mixture was stirred at 105° C. for 12 h. The reaction mixture was diluted with water and extracted with ethyl acetate [3×100 mL]. The organic layer was washed with water, brine and dried over sodium sulfate. The solvent was removed under reduced pressure to afford the crude residue. The crude product was purified using column chromatography (60-120 silica gel, 15% MeOH in chloroform) to yield the desired title product [0.9 g, 32%]; $^1$H NMR (300 MHz, DMSO-d$_6$): δ 8.76 (s, 1H), 8.48 (s, 1H), 7.57 (d, J=8.1 Hz, 2H), 7.45 (d, J=8.7 Hz, 2H), 7.30 (d, J=8.7 Hz, 2H), 6.88 (d, J=9.0 Hz, 2H), 3.34-3.36 (m, 4H) 3.05-3.08 (m, 4H), 2.26 (s, 3H), 1.26 (s, 12H); LC-MS (ESI): Calculated mass: 464.3; Observed mass: 465.1 [M+H]$^+$ (RT: 0.61 min).

Preparation 4: 4-{3-[2-Fluoro-4-(4,4,5,5-tetramethyl-[1,3,2]dioxaborolan-2-yl)phenyl]-ureido}-N,N-dimethyl-benzamide

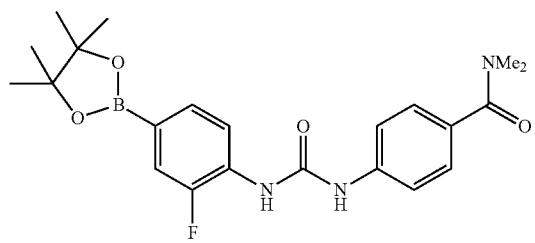 [SMILES: CN(C)C(=O)c1ccc(NC(=O)Nc2ccc(B3OC(C)(C)C(C)(C)O3)cc2F)cc1]

Step 1: 4-[3-(4-Bromo-2-fluoro-phenyl)-ureido]-benzoic acid ethyl ester

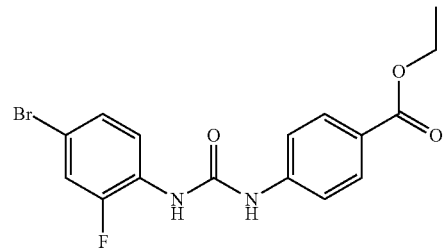 [SMILES: CCOC(=O)c1ccc(NC(=O)Nc2ccc(Br)cc2F)cc1]

To a solution of 4-bromo-2-fluoroaniline (0.5 g, 0.0026 mol) and TEA (0.38 mL, 0.0026 mol) in DCM (15 mL) was added ethyl 4-isocyanatobenzoate (0.503 g, 0.0026 mol). The reaction mixture was stirred at room temperature for 3 h. The white solid was obtained and was filtered and dried to afford the title compound [0.7 g, 70%]; LC-MS (ESI): Calculated mass: 380.0; Observed mass: 381.0 [M+H]$^+$ (RT: 1.78 min).

Step 2: 4-[3-(4-Bromo-2-fluoro-phenyl)-ureido]-benzoic acid

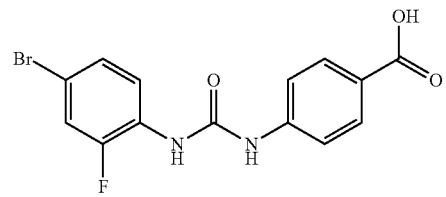 [SMILES: O=C(Nc1ccc(C(=O)O)cc1)Nc1ccc(Br)cc1F]

To a solution of 4-[3-(4-bromo-2-fluoro-phenyl)-ureido]-benzoic acid ethyl ester (0.7 g, 0.0018 mol) in EtOH (5 mL) and THF (4 mL), was added a solution of lithium hydroxide monohydrate in water (0.385 g, 0.009 mol, in 5 mL water) at room temperature. The reaction mass was stirred at room temperature for 5 h. The volatiles were evaporated under reduced pressure. The white solid was washed with diethyl ether. Subsequently, the reaction mixture was acidified with 2 N HCl [pH-6] at 0° C. to afford the solid compound. The solid material was collected by filtration and dried to obtain the title compound [0.55 g, 84%]; LC-MS (ESI): Calculated mass: 352.0; Observed mass: 352.9 [M+H]$^+$ (RT: 1.49 min).

Step 3: 4-[3-(4-Bromo-2-fluoro-phenyl)-ureido]-N,N-dimethyl-benzamide

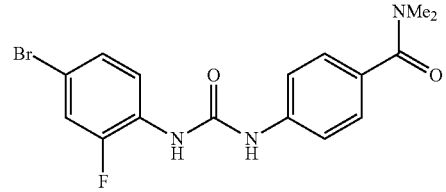 [SMILES: CN(C)C(=O)c1ccc(NC(=O)Nc2ccc(Br)cc2F)cc1]

To a solution of 4-[3-(4-bromo-2-fluoro-phenyl)-ureido]-benzoic acid (0.5 g, 0.014 mol) in DMF (5 mL) N,N-dimethylamine hydrochloride (0.14 g, 0.0017 mol), HOBt (0.25 g, 0.0.0018 mol), EDC.HCl (0.41 g, 0.0021 mol) and TEA (0.4 mL, 0.0028 mol) were added. The reaction mixture was stirred at room temperature for 10 h. The reaction mixture was diluted with water and extracted with ethyl acetate (3×15 mL). The organic layer was washed with water, brine and dried over sodium sulfate. The solvent was evaporated under reduced pressure to afford the title compound [0.33 g, 65%]; LC-MS (ESI): Calculated mass: 379.0; Observed mass: 382.0 [M+H]$^+$ (RT: 1.41 min).

Step 4: 4-{3-[2-Fluoro-4-(4,4,5,5-tetramethyl-[1,3,2]dioxaborolan-2-yl)phenyl]-ureido}-N,N-dimethyl-benzamide

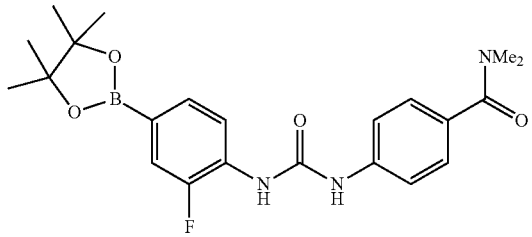 [SMILES: CN(C)C(=O)c1ccc(NC(=O)Nc2ccc(B3OC(C)(C)C(C)(C)O3)cc2F)cc1]

To a solution of 4-[3-(4-bromo-2-fluoro-phenyl)-ureido]-N,N-dimethyl-benzamide (0.25 g, 0.000658 mmol) in 1,4-dioxane (10 mL) were added bis(pinacolato)diboron (0.25 g, 0.000987 mol), KOAc (0.19 g, 0.00193 mol) and PdCl$_2$(dppf) .DCM (0.037 g, 0.000046 mol). The reaction vessel was purged with nitrogen for 10 min. The reaction mixture was stirred at 105° C. for 12 h. The reaction mixture was diluted with water and extracted with ethyl acetate [3×100 mL]. The organic layer was washed with water, brine and dried over sodium sulfate. The solvent was removed under reduced pressure to afford the crude residue. The crude product was purified using column chromatography (60-120 silica gel, 5% MeOH in chloroform) to yield the desired title product. [0.183 g, 65%]; $^1$H NMR (300 MHz, DMSO-d$_6$): δ 9.34 (s, 1H), 8.79 (s, 1H), 8.22-8.39 (m, 1H), 7.35-7.52 (m, 6H), 2.96 (s, 6H), 1.29 (s, 12H); LC-MS (ESI): Calculated mass: 427.2; Observed mass: 428.2 [M+H]$^+$ (RT: 1.59 min)

Preparation 5: Synthesis of 4-(3-(3-fluoro-4-(4,4,5,5-tetramethyl-1,3,2-dioxaborolan-2-yl)phenyl)ureido)-N,N-dimethyl-benzamide Step 1: 2,2,2-trichloroethyl(4-(dimethylcarbamoyl)phenyl)carbamate

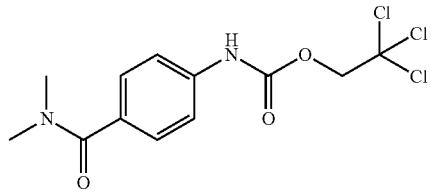 [SMILES: CN(C)C(=O)c1ccc(NC(=O)OCC(Cl)(Cl)Cl)cc1]

To a 250 mL round bottom flask, 4-amino-N,N-dimethyl-benzamide (20 g, 0.1219 mol; prepared as described in Preparation 1) and 2,2,2-trichloroethyl chloroformate (30 g, 0.1463 mol), TEA (34 mL, 0.2438 mol) and DCM (100 mL) was added. The reaction mixture was stirred at room temperature for 1 h. The reaction mass was diluted with DCM and washed with water. The organic layer was dried over anhydrous sodium sulfate and evaporated under reduced pressure to get the crude product. The crude product was washed with diethyl ether and dried under reduced pressure to afford the title compound [30 g, 73%]. LC-MS (ESI): Calculated mass: 338.0; Observed mass: 341.0 (RT: 1.38 min). The compound was directly taken to the next step.

Step 2: 4-(3-(4-bromo-3-fluorophenyl)ureido)-N,N-dimethyl-benzamide

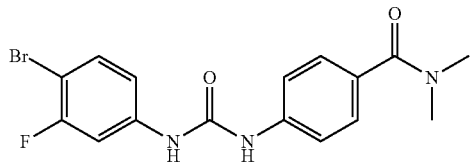 [SMILES: CN(C)C(=O)c1ccc(NC(=O)Nc2ccc(Br)c(F)c2)cc1]

To a 250 mL round bottom flask, 2,2,2-trichloroethyl(4-(dimethylcarbamoyl)phenyl)carbamate (30 g, 0.0885 mol), 4-bromo-3-fluoroaniline (20 g, 0.1062 mol), TEA (24.6 mL, 0.177 mol) and toluene (150 mL) was added. The reaction mixture was maintained at 110° C. for 12 h. The reaction mass was cooled to room temperature. The obtained precipitate was collected by filtration and dried under vacuum to get the desired product [15 g, 50%]. $^1$H NMR (300 MHz, DMSO-d$_6$): δ 9.09 (s, 1H), 8.99 (s, 1H), 7.65-7.53 (m, 2H), 7.49 (d, J=8.4 Hz, 2H), 7.35 (d, J=8.4 Hz, 2H), 7.14 (d, J=8.4 Hz, 1H), 2.93 (s, 6H); LC-MS (ESI): Calculated mass: 379.0; Observed mass: 382.1 (RT: 1.43 min).

Step 3: 4-(3-(3-fluoro-4-(4,4,5,5-tetramethyl-1,3,2-dioxaborolan-2-yl)phenyl)ureido)-N,N-dimethyl-benzamide

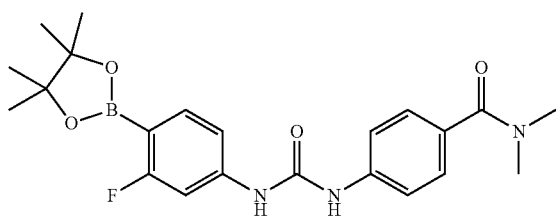

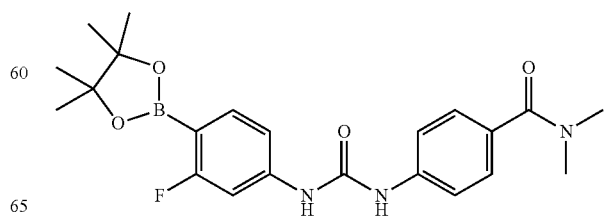

To a 500 mL round bottom flask, 4-(3-(4-bromo-3-fluorophenyl)ureido)-N,N-dimethyl-benzamide (15.0 g, 0.0395), bis(pinacolato)diboron (15.19 g, 0.0593 mol), KOAc (7.7 g, 0.0790 mol) and 1,4-dioxane (200 mL) was added. The reaction vessel was degassed with nitrogen for 5 min. To the flask was added Pd(dppf)Cl$_2$.DCM (2.2 g, 0.0027 mol) and again degassed with nitrogen for 5 min. The reaction mixture was maintained at 115° C. for 12 h. The cooled reaction mass was filtered through a pad of Celite® reagent. Water was then added to the filtrate and the product extracted with ethyl acetate. The ethyl acetate layer was dried over anhydrous sodium sulfate and evaporated under reduced pressure to obtain the crude product. The crude product was purified by column chromatography using 60-120 silica gel, 2-5% MeOH in chloroform to get the title compound [7 g, 43%]. $^1$H NMR (400 MHz, CDCl$_3$): δ 8.56 (s, 1H), 8.23 (s, 1H), 7.63 (t, J=7.6 Hz, 1H), 7.39 (dd, J'=1.6 Hz, J"=11.6 Hz, 1H), 7.21 (d, J=8.4 z, 2H), 7.07 (dd, J'=8.0 Hz, J'=1.6 Hz, 1H), 7.00 (d, J=8.8 Hz, 2H), 3.18 (s, 3H), 3.02 (s, 3H), 1.35 (s, 12H); LC-MS (ESI): Calculated mass: 427.2; Observed mass: 428.1 (RT: 1.54 min).

Preparation 6: 2-fluoro-N,N-dimethyl-4-(3-(4-(4,4,5,5-tetramethyl-1,3,2-dioxaborolan-2-yl)phenyl)ureido)-benzamide Step 1: 2-fluoro-N,N-dimethyl-4-nitro benzamide

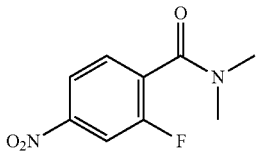

To a 50 mL round bottom flask, 2-fluoro-4-nitrobenzoic acid (3.0 g, 0.0162 mol) and DMF (10 mL) was added. To the same flask, TEA (4.6 mL, 0.0324 mol), dimethylamine hydrochloride (2.65 g, 0.0324 mol), HOBt (3.28 g, 0.0243 mol) and EDCI.HCl (4.62 g, 0.0243 mol) was added. The reaction mixture was stirred at room temperature for 12 h. The reaction mass was quenched with water and extracted with ethyl acetate. The organic layer was dried over anhydrous sodium sulfate and evaporated under reduced pressure to get the title compound [2.8 g, 81%]. $^1$H NMR (300 MHz, CDCl$_3$): δ 8.12 (d, J=8.4 Hz, 1H), 8.02 (d, J=8.7 Hz, 1H), 7.62 (dd, J'=8.1 Hz, J"=6.6 Hz, 1H), 3.16 (s, 3H), 2.93 (s, 3H); LC-MS (ESI): Calculated mass: 212.1; Observed mass: 213.1 (RT: 0.37 min).

Step 2: 4-amino-2-fluoro-N,N-dimethyl-benzamide

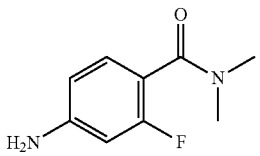

To a 50 mL round bottom flask was added 2-fluoro-N,N-dimethyl-4-nitro benzamide (2.8 g, 0.0132 mol) and EtOH (20 mL). To the same flask, SnCl$_2$.2H$_2$O (11.9 g, 0.0528 mol) was added and the reaction mixture was maintained at 85° C. for 2 h. The reaction mass was cooled to room temperature and the volatiles were evaporated under reduced pressure. The residue was dissolved in water and ethyl acetate. Aqueous saturated sodium bicarbonate was added to adjust to a pH of 7.0. The reaction mixture was filtered through a pad of Celite® reagent and washed with ethyl acetate. The organic layer was separated, dried over anhydrous sodium sulfate and evaporated under reduced pressure to obtain the title compound [2.5 g, 100%]. $^1$H NMR (300 MHz, CDCl$_3$): δ 7.21 (t, J=7.8 Hz, 1H), 6.46 (dd, J'=8.4 Hz, J"=2.4 Hz, 1H), 6.34 (d, J'=11.4 Hz, J"=1.8 Hz, 1H), 3.95 (brs, 2H), 3.08 (s, 3H), 2.95 (d, J=1.8 Hz, 3H); LC-MS (ESI): Calculated mass: 182.1; Observed mass: 183.1 (RT: 0.17 min).

Step 3: 4-(3-(4-bromophenyl)ureido)-2-fluoro-N,N-dimethyl-benzamide

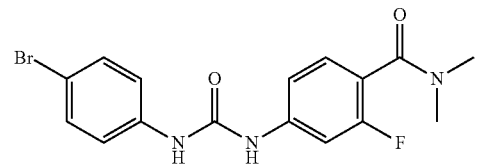 [SMILES: CN(C)C(=O)c1ccc(NC(=O)Nc2ccc(Br)cc2)cc1F]

To a 100 mL round bottom flask, 4-amino-2-fluoro-N,N-dimethyl-benzamide (2.5 g, 0.0137 mol), 4-bromophenylisocyanate (3.3 g, 0.0164), TEA (3.9 mL, 0.0274 mol) and DCM (50 mL) was added. The reaction mixture was stirred at room temperature for 12 h. After 12 h, the precipitate was formed and was collected by filtration. The solid was washed with diethyl ether and dried to get the title compound [3.0 g, 58%]. Calculated mass: 379.0; Observed mass: 380.0 (RT: 1.46 min). This compound was directly taken to the next step.

Step 4: 2-fluoro-N,N-dimethyl-4-(3-(4-(4,4,5,5-tetramethyl-1,3,2-dioxaborolan-2-yl)phenyl)ureido)-benzamide

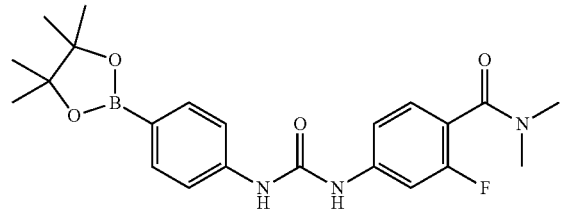

To a 100 mL round bottom flask, 4-(3-(4-bromophenyl)ureido)-2-fluoro-N,N-dimethyl-benzamide (3.0 g, 0.00789 mol), bis(pinacolato)diboron (3.02 g, 0.01179 mol), KOAc (2.32 g, 0.02363 mol) and 1,4-dioxane (30 mL) were added and degassed with nitrogen for 5-10 min. To the flask, Pd(dppf)Cl$_2$.DCM (0.45 g, 0.0005513 mol) was added and again degassed with nitrogen for 5-10 min. The reaction mixture was maintained at 105° C. for 12 h. To the cooled reaction mass, water was added and extracted with ethyl acetate. The ethyl acetate layer was dried over anhydrous sodium sulfate and evaporated under reduced pressure to obtain the crude product. The crude product was subjected to column chromatography using 60-120 silica gel and 2-5% MeOH in chloroform to get the title compound [1.1 g, 33%].

$^1$H NMR (300 MHz, DMSO-d$_6$): δ 8.41 (s, 1H), 8.23 (s, 1H), 7.74 (d, J=8.4 Hz, 2H), 7.44 (d, J=8.1 Hz, 2H), 7.28 (d, J=8.7 Hz, 2H), 7.09 (t, J=8.1 Hz, 1H), 6.55 (d, J=8.4 Hz, 1H), 3.16 (s, 3H), 2.91 (s, 3H), 1.33 (s, 12H); LC-MS (ESI): Calculated mass: 427.2; Observed mass: 428.2 (RT: 1.58 min).

Preparation 7: 4-(3-(2,3-difluoro-4-(4,4,5,5-tetramethyl-1,3,2-dioxaborolan-2-yl)phenyl)ureido)-N,N-dimethyl-benzamide

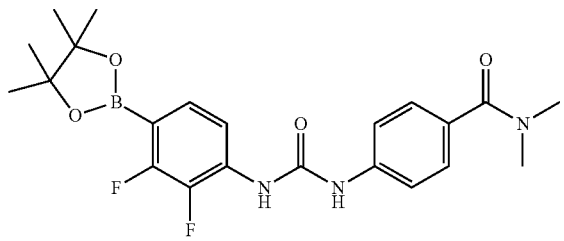

Step 1: 4-bromo-2,3-difluoroaniline

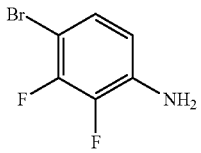

The procedure for preparing this compound was based on that described in International Patent Publication No. WO 2010/091272. To a 100 mL round bottom flask, 2,3-difluoroaniline (1 g, 0.0077 mol) and ACN (30 mL) were added. To the flask was added the solution of tetrabutylammonium tribromide (3.71 g, 0.0077 mol, in 10 mL of ACN). The reaction mixture was stirred at room temperature for 3 h. The reaction mass was diluted with water and extracted with ethyl acetate. The ethyl acetate layer was washed with brine and evaporated under reduced pressure to get the crude product. The crude product was purified by column chromatography using 60-12 silica gel and 30% ethyl acetate in hexane to get the title compound [0.55 g, 34%]. The obtained product was immediately taken to the next step.

Step 2: 4-(3-(4-bromo-2,3-difluorophenyl)ureido)-N,N-dimethyl-benzamide

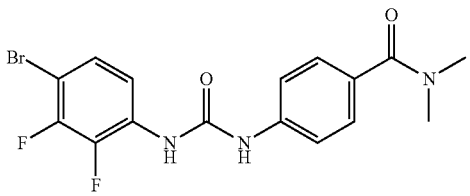 [SMILES: CN(C)C(=O)c1ccc(NC(=O)Nc2ccc(Br)c(F)c2F)cc1]

To a 50 mL round bottom flask, 4-bromo-2,3-difluoroaniline (0.5 g, 0.0024 mol), 2,2,2-trichloroethyl(4-(dimethylcarbamoyl)phenyl)carbamate (0.978 g, 0.00288 mol; from Preparation 5), TEA (1.01 mL, 0.0072 mol) and toluene (20 mL) were added. The reaction mixture was maintained at 105° C. for 12 h. The cooled reaction mixture was diluted with ethyl acetate and washed with water. The ethyl acetate layer was dried over anhydrous sodium sulfate and evaporated under reduced pressure to get the crude product. The crude was purified by column chromatography using 3% MeOH in chloroform to get the title compound [0.35 g, 36%]. $^1$H NMR (300 MHz, DMSO-d$_6$): δ 9.30 (s, 1H), 8.96 (s, 1H), 8.0-7.92 (m, 1H), 7.52-7.42 (m, 2H), 7.39 (d, J=8.4 Hz, 2H), 7.20-7.06 (m, 1H), 2.96 (s, 6H); LC-MS (ESI): Calculated mass: 397.0; Observed mass: 400.0 (RT: 1.49 min).

Step 3: 4-(3-(2,3-difluoro-4-(4,4,5,5-tetramethyl-1,3,2-dioxaborolan-2-yl)phenyl)ureido)-N,N-dimethyl-benzamide

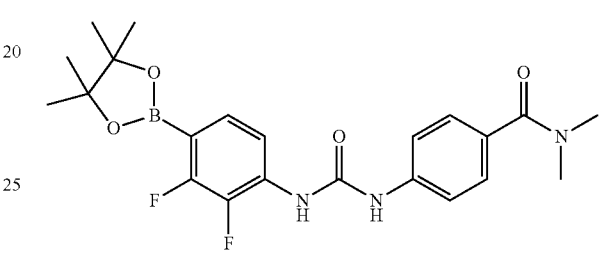

To a 50 mL round bottom flask, (3-(4-bromo-2,3-difluorophenyl)ureido)-N,N-dimethyl-benzamide (0.35 g, 0.00088 mol) and 1,4-dioxane (15 mL) were added. To the flask, bis(pinacolato)diboron (0.335 g, 0.00132 mol), Pd(dppf)Cl$_2$.DCM (0.05 g, 0.000062 mol) and KOAc (0.216 g, 0.0022 mol) was added. The reaction mixture was degassed with nitrogen for 5 min and maintained at 100° C. for 12 h. The reaction mass was cooled to room temperature and diluted with ethyl acetate. The ethyl acetate layer was washed with water, brine and dried over anhydrous sodium sulfate. The solvent was evaporated under reduced pressure to obtain the crude product. The crude product was subjected to column chromatography (60-120 silica gel, 5% MeOH in chloroform) to get the title compound [0.22 g, 56%]. $^1$H NMR (300 MHz, CDCl$_3$): δ 9.36 (s, 1H), 8.96 (s, 1H), 8.10-8.02 (m, 1H), 7.52 (d, J=8.1 Hz, 2H), 7.39 (d, J=7.5 Hz, 2H), 7.20-7.06 (m, 1H), 2.96 (s, 6H), 1.29 (s, 12H). LC-MS (ESI): Calculated mass: 445.2; Observed mass: 446.4 (RT: 1.12 min).

Example 1

N,N-Dimethyl-4-(3-{4-[4-morpholin-4-yl-7-pyrimidin-5-yl-quinazolin-2-yl)-phenyl]-ureido}-benzamide

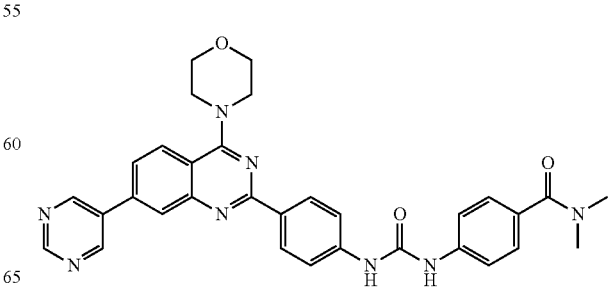

Step 1:
N-(3-Bromo-phenyl)-2-hydroxyimino-acetamide

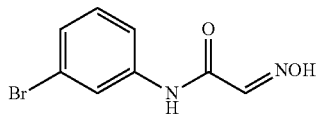

To a 3000 mL round bottom flask, 3-bromoaniline (50 g, 0.2907 mol), water (1500 mL), chloral hydrate (57.7 g, 0.3488 mol), hydroxylamine hydrochloride (64.6 g, 0.9302 mol) and sodium sulfate (250 g) were added. To this reaction mixture conc. HCl (76 mL) was slowly added. The reaction mixture was stirred at 90° C. for 2 h. The white precipitate was formed and was collected by filtration. The white solid was dried to get the title compound [60 g, 85%]. $^1$H NMR (300 MHz, DMSO-$d_6$): δ 12.28 (s, 1H), 10.38 (s, 1H), 8.03 (t, J=1.5 Hz, 1H), 7.62-7.65 (m, 2H), 7.29-7.31 (m, 2H). LC-MS (ESI): Calculated mass: 242.0; Observed mass: 243.0 [M+H]$^+$ (RT: 0.17 min).

Step 2: 6-Bromo-1H-indole-2,3-dione

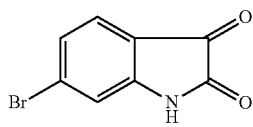

To the concentrated sulfuric acid (275 mL) at 50° C. was added N-(3-Bromo-phenyl)-2-hydroxyimino-acetamide (55 g, 0.2272 mol). The temperature was raised to 90° C. and maintained for 3 h. The reaction mixture was added to ice cold water to get yellow precipitate. The precipitate was filtered and dried to get the title compound as a yellow solid [50 g, 98%]. This material was taken to the next step without any further purification.

Step 3: 2-Amino-4-bromo-benzoic acid

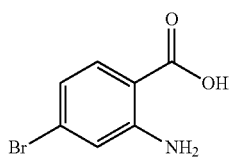

To a 500 mL round bottom flask, 6-bromo-1H-indole-2,3-dione (50 g, 0.2192 mol) and NaOH (20 g in 250 mL water) were added and cooled the reaction vessel to 0° C. To this reaction mixture 30% hydrogen peroxide (50 mL) was slowly added. The reaction mixture was stirred at 0° C. for 2 h. Subsequently, the reaction mixture was acidified with 2N HCl [pH-6] at 0° C. to afford the solid compound. The solid material was collected by filtration and dried to obtain the title compound [10 g, 21%]. $^1$H NMR (300 MHz, DMSO-$d_6$): δ 7.59 (d, J=8.7 Hz, 1H), 6.96 (d, J=2.1 Hz, 1H), 6.65 (dd, J'=8.7 Hz, J"=1.8 Hz, 1H) LC-MS (ESI): Calculated mass: 215.0; Observed mass: 215.9 [M+H]$^+$ (RT: 0.83 min).

Step 4: 7-Bromo-1H-quinazoline-2,4-dione

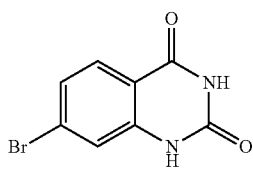

To a 250 mL round bottom flask, 2-amino-4-bromo-benzoic acid (10 g, 0.0463 mol) and urea (27.78 g, 0.4629 mol) were added. The reaction mixture was stirred at 195° C. for 3 h. The reaction mixture was allowed to reach 80° C. and water was added. The aqueous reaction mixture was stirred at 80° C. for 5-10 min then allowed to reach room temperature. The solid was filtered, dried and azeotroped with toluene to afford the title compound [10 g, 90%]. This material was taken to the next step without any further purification.

Step 5: 7-Bromo-2,4-dichloro-quinazoline

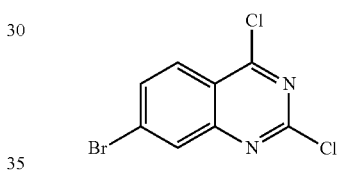

To a 250 mL round bottom flask, 7-bromo-1H-quinazoline-2,4-dione (10 g 0.0413 mol) was charged. To the same flask POCl$_3$ (100 mL) and DIPEA (6.5 mL, 0.0413 mol) were added. The reaction mixture was maintained at 130° C. for 12 h. The volatiles were evaporated and azeotroped with toluene to get the crude residue. The crude residue was purified using, column chromatography (60-120 silica gel, 10% ethyl acetate in hexane) to get the title compound (7 g, 60%). $^1$H NMR (300 MHz, CDCl$_3$): δ 8.41 (s, 1H), 8.00-8.09 (m, 1H), 7.89-7.91 (m, 1H): LC-MS (ESI): Calculated mass: 275.9; Observed mass: 276.8 [M+H]$^+$ (RT: 0.68 min).

Step 6:
7-Bromo-2-chloro-4-morpholin-4-yl-quinazoline

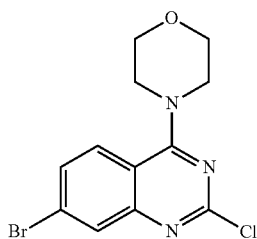 [SMILES: Clc1nc(N2CCOCC2)c2ccc(Br)cc2n1]

To an ice cold solution of 7-bromo-2,4-dichloro-quinazoline (7 g, 0.0255 mol) in DCM (150 mL), morpholine (4.43 mL, 0.0509 mol) was slowly added and the reaction was continued at 0° C. for 30 min. The solvent was evaporated to dryness to get the crude compound. The crude product was purified, using column chromatography (60-120 silica gel, 30% ethyl acetate in hexane) to get the title compound (7 g, 84%). ¹H NMR (300 MHz, CDCl₃): δ 8.17 (d, J=7.5 Hz, 1H), 8.04 (d, J=7.5 Hz, 1H), 7.63 (d, J=8.1 Hz, 1H), 3.72-3.74 (m, 8H): LC-MS (ESI): Calculated mass: 327.0; Observed mass: 329.8 [M+H]⁺ (RT: 0.45 min).

Step 7: 2-Chloro-4-morpholin-4-yl-7-pyrimidin-5-yl-quinazoline

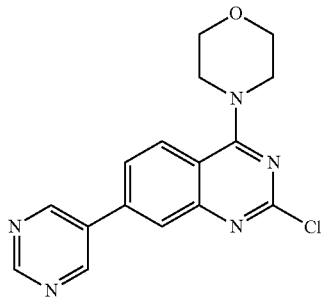 [SMILES: Clc1nc(N2CCOCC2)c2ccc(-c3cncnc3)cc2n1]

To a 50 mL round bottom flask, 7-bromo-2-chloro-4-morpholin-4-yl-quinazoline (0.2 g, 0.0006 mol), pyrimidine-5-boronic acid (0.068 g, 0.0005 mol), sodium carbonate (0.129 g, 0.0012 mol), DMF (10 mL) and water (3 mL) were added and degassed the reaction vessel with N₂ for 5-10 min. To the same reaction mixture, Pd(PPh₃)₂Cl₂ (0.029 g, 0.00004 mol) was added and again degassed with N₂ for 5-10 min. The reaction mixture was stirred at 95° C. for 2 h. The reaction mixture was cooled and diluted with ethyl acetate. The organic layer was washed with water, brine and dried over sodium sulfate. The solvent was removed under reduced pressure to afford the crude product. The crude product was purified; using column chromatography (60-120 silica gel, 60% ethyl acetate in hexane) to yield the desired product [150 mg, 75%]. ¹H NMR (300 MHz, CDCl₃): δ 9.27 (s, 1H), 9.04 (s, 2H), 7.85-8.45 (m, 2H), 7.60-7.64 (m, 1H), 3.82-3.91 (m, 8H); LC-MS (ESI): Calculated mass: 327.09; Observed mass: 328.0 [M+H]⁺ (RT: 0.98 min).

Step 8: N,N-Dimethyl-4-(3-{4-[4-morpholin-4-yl-7-pyrimidin-5-yl-quinazolin-2-yl)-phenyl]-ureido}-benzamide

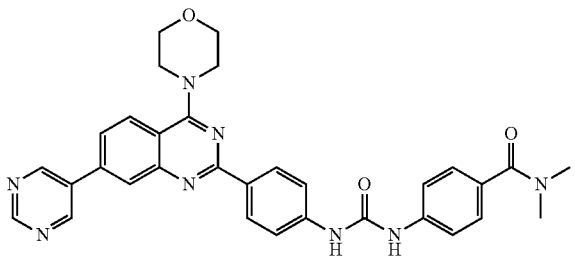

To a 50 mL round bottom flask, 2-chloro-4-morpholin-4-yl-7-pyrimidin-5-yl-quinazoline (150 mg, 0.00046 mol), N,N-Dimethyl-4-{3-[4-(4,4,5,5,-tetramethyl-[1,3,2]dioxaborolan-2-yl)-phenyl]-ureido}-benzamide (168 mg, 0.00041 mol), cesium carbonate (300 mg, 0.00092 mol), DMF (10 mL) and water (3 mL) were added. The reaction mixture was degassed with N₂ for 5-10 min. To the same reaction flask, Pd(PPh₃)₂Cl₂ (16 mg, 0.000023 mol) was added and again degassed with N₂ for 5-10 min. The reaction mixture was stirred at 95° C. for 2 h. The reaction mixture was cooled and diluted with ethyl acetate. The organic layer was washed with water, brine and dried over sodium sulfate. The solvent was removed under reduced pressure to afford the crude product. The crude product was purified using column chromatography (60-120 silica gel, 4% MeOH in chloroform) followed by preparative TLC (10% MeOH in chloroform) to yield the title compound [30 mg, 11%]. ¹H NMR (400 MHz, DMSO-d₆): δ 9.36 (s, 2H), 9.29 (s, 1H), 9.05 (s, 1H), 8.98 (s, 1H), 8.46 (d, J=8.8 Hz, 2H), 8.31 (d, J=2.0 Hz, 1H), 8.17 (d, J=8.8 Hz, 1H), 7.93 (dd, J'=8.4 Hz, J"=1.6 Hz, 1H), 7.64 (d, J=8.8 Hz, 2H), 7.53 (d, J=8.8 Hz, 2H), 7.38 (d, J=8.4 Hz, 2H), 3.87 (s, 8H), 2.96 (s, 6H); LC-MS (ESI): Calculated mass: 574.2; Observed mass: 575.1 [M+H]⁺ (RT: 0.26 min).

Example 2

N,N-Dimethyl-4-(3-{4-[7-(5-methyl-furan-2-yl)-4-morpholin-4-yl-quinazolin-2-yl]-phenyl}-ureido)-benzamide

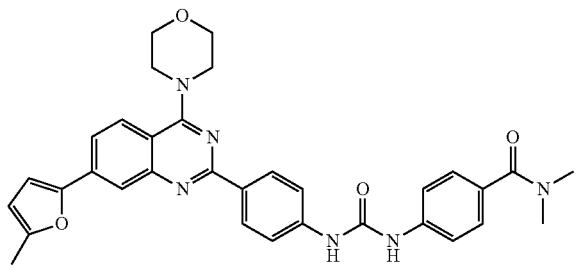 [SMILES: Cc1ccc(-c2ccc3c(N4CCOCC4)nc(-c4ccc(NC(=O)Nc5ccc(C(=O)N(C)C)cc5)cc4)nc3c2)o1]

Step 1: 2-Chloro-7-(5-methyl-furan-2-yl)-4-morpholin-4-yl-quinazoline

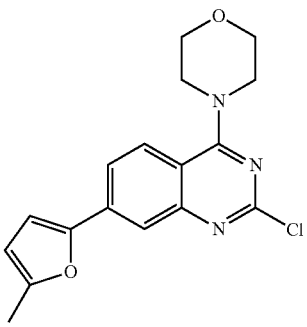 [SMILES: Cc1ccc(-c2ccc3c(N4CCOCC4)nc(Cl)nc3c2)o1]

To a 50 mL round bottom flask, 7-bromo-2-chloro-4-morpholin-4-yl-quinazoline (2 g, 0.0061 mol), 5-methyl-2-furanboronicacid pinacol ester (1.1 g, 0.0091 mol), sodium carbonate (0.969 g, 0.0092 mol), DMF (80 mL) and water (20 mL) were added and degassed the reaction vessel with nitrogen for 5-10 min. To the same reaction mixture, Pd(PPh₃)₂Cl₂ (0.213 g, 0.0003 mol) was added and again degassed with nitrogen for 5-10 min. The reaction mixture was stirred at 95°

C. for 2 h. The reaction mixture was cooled and diluted with ethyl acetate. The organic layer was washed with water, brine and dried over sodium sulfate. The solvent was removed under reduced pressure to afford the crude product. The crude product was purified; using column chromatography (60-120 silica gel, 0-20% ethyl acetate in hexane) to yield the desired product [1.4 g, 70%]. $^1$H NMR: (400 MHz, CDCl$_3$): δ 8.01 (d, J=1.6 Hz, 1H), 7.80 (d, J=8.8 Hz, 1H), 7.68 (dd, J'=8.8 Hz, J"=1.6 Hz, 1H), 6.78 (d, J=3.2 Hz, 1H), 6.14-6.45 (m, 1H), 3.88 (m, 8H), 2.42 (s, 3H); LC-MS (ESI): Calculated mass: 329.1; Observed mass: 330.0 [M+H]$^+$ (RT: 1.71 min).

Step 2: N,N-Dimethyl-4-(3-{4-[7-(5-methyl-furan-2-yl)-4-morpholin-4-yl-quinazolin-2-yl]-phenyl}-ureido)-benzamide

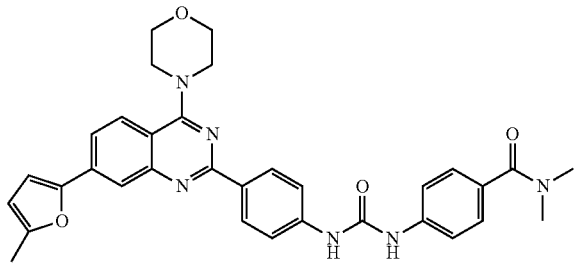 [SMILES: Cc1ccc(-c2ccc3c(N4CCOCC4)nc(-c4ccc(NC(=O)Nc5ccc(C(=O)N(C)C)cc5)cc4)nc3c2)o1]

To a 50 mL round bottom flask, 2-chloro-7-(5-methyl-furan-2-yl)-4-morpholin-4-yl-quinazoline (1.4 g, 0.0036 mol), N,N-dimethyl-4-{3-[4-(4,4,5,5,-tetramethyl-[1,3,2] dioxaborolan-2-yl)-phenyl]-ureido}-benzamide (2.25 g, 0.0055 mol), sodium carbonate (0.775 g, 0.0073 mol), toluene (12 mL), EtOH (12 mL) and water (12 mL) were added. The reaction mixture was degassed with nitrogen for 5-10 min. To the same reaction flask, Pd (PPh$_3$)$_2$Cl$_2$ (128 mg, 0.000023 mol) was added and again degassed with nitrogen for 5-10 min. The reaction mixture was stirred at 95° C. for 2 h. The reaction mixture was cooled and diluted with ethyl acetate. The organic layer was washed with water, brine and dried over sodium sulfate. The solvent was removed under reduced pressure to afford the crude product. The crude product was purified using column chromatography (60-120 silica gel, 0-4% MeOH in chloroform) followed by preparative HPLC (0.1% TFA in water and ACN) to yield the title compound [0.65 g, 27%]. $^1$H NMR (400 MHz, DMSO-d$_6$): δ 9.49 (brs, 1H), 9.27 (brs, 1H), 8.30 (d, J=8.8 Hz, 2H), 8.11 (t, J=9.2 Hz, 2H), 7.85 (d, J=8.8 Hz, 1H), 7.72 (d, J=8.8 Hz, 2H), 7.52 (d, J=8.8, 2H), 7.37 (d, J=8.4 Hz, 2H), 7.22 (d, J=3.2 Hz, 1H), 6.37 (s, 1H), 4.22 (brs, 4H), 3.83 (brs, 4H), 2.95 (s, 6H), 2.40 (s, 3H); LC-MS (ESI): Calculated mass: 576.2; Observed mass: 576.7 [M+H]$^+$ (RT: 0.64 min).

A mixture of N,N-dimethyl-4-(3-(4-(7-(5-methylfuran-2-yl)-4-morpholino-quinazolin-2-yl)phenyl)ureido)-benzamide (q eq.) and methanesulfonic acid (1 eq.) in acetone was maintained at 65° C. for 3 h. The reaction mass was cooled to room temperature and the solvent was evaporated under reduced pressure and azeotroped with toluene [3 times]. The obtained solid was triturated with ethyl acetate, filtered and dried to obtain the methanesulfonic acid salt of N,N-dimethyl-4-(3-(4-(7-(5-methylfuran-2-yl)-4-morpholino-quinazolin-2-yl)phenyl)ureido)-benzamide as a light yellow solid. $^1$H NMR (300 MHz, DMSO-d$_6$): δ 9.43 (s, 1H), 9.18 (s, 1H), 8.35 (d, J=8.7 Hz, 2H), 8.18 (d, J=8.1 Hz, 2H), 7.91 (d, J=9.3, 1H), 7.88 (d, J=8.7 Hz, 2H), 7.56 (d, J=8.7 Hz, 2H), 7.40 (d, J=8.7 Hz, 2H), 7.30 (d, J=3.3, 1H), 6.41 (d, J=2.4 Hz, 1H), 4.27 (s, 4H), 3.84 (s, 4H), 2.96 (s, 6H), 2.44 (s, 3H), 2.34 (s, 3H); LC-MS (ESI): Calculated mass: 576.2 (free base mass); Observed mass: 577.4 (RT=0.41 min)

A mixture of N,N-dimethyl-4-(3-(4-(7-(5-methylfuran-2-yl)-4-morpholino-quinazolin-2-yl)phenyl)ureido)-benzamide (1 eq.) and trifluoroacetic acid (1 eq.) in acetone was maintained at 65° C. for 3 h. The reaction mass was cooled to room temperature and the solvent was evaporated under reduced pressure azeotroped with toluene [3 times]. The obtained solid was triturated with ethyl acetate, filtered and dried to obtain the trifluoroacetic acid salt of N,N-dimethyl-4-(3-(4-(7-(5-methylfuran-2-yl)-4-morpholino-quinazolin-2-yl)phenyl)ureido)-benzamide as a light yellow solid. $^1$H NMR (400 MHz, DMSO-d$_6$): δ 9.53 (s, 1H), 9.31 (s, 1H), 8.36 (d, J=8.8 Hz, 2H), 8.14 (t, J=4 Hz, 2H), 7.88 (d, J=8.4 Hz, 1H), 7.76 (d, J=8.8 Hz, 2H), 7.56 (d, J=8.4 Hz, 2H), 7.39 (d, J=8.8 Hz, 2H), 7.27 (d, J=3.2 Hz, 1H), 6.38 (d, J=2.8 Hz, 1H), 4.22 (brs, 4H), 3.84 (s, 4H), 2.97 (s, 6H), 2.43 (s, 3H). LC-MS (ESI): Calculated mass: 576.2 (free base mass); Observed mass: 577.2 (RT=0.46 min)

Example 3

4-(3-{5-[7-(3-Methanesulfonyl-phenyl)-4-morpholin-4-yl-quinazolin-2-yl]-pyridin-2-yl}-ureido)-dimethyl-benzamide

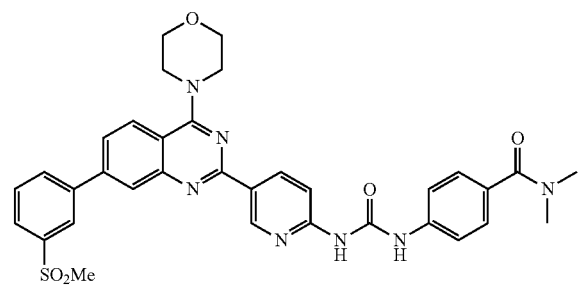 [SMILES: CN(C)C(=O)c1ccc(NC(=O)Nc2ccc(-c3nc(N4CCOCC4)c4ccc(-c5cccc(S(C)(=O)=O)c5)cc4n3)cn2)cc1]

Step 1: 2-Chloro-7-(3-methanesulfonyl-phenyl)-4-morpholin-4-yl-quinazoline

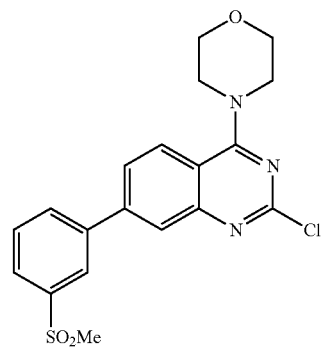 [SMILES: CS(=O)(=O)c1cccc(-c2ccc3c(N4CCOCC4)nc(Cl)nc3c2)c1]

To a 50 mL round bottom flask, 7-bromo-2-chloro-4-morpholin-4-yl-quinazoline (0.65 g, 0.0019 mol), 3-methylsulfonylphenylboronic acid (0.35 g, 0.0018 mol), sodium carbonate (0.314 g, 0.0029 mol), DMF (25 mL) and water (6 mL) were added and degassed the reaction vessel with nitrogen for 5-10 min. To the same reaction mixture, Pd(PPh$_3$)$_2$Cl$_2$ (0.069 g, 0.00099 mol) was added and again degassed with nitrogen for 5-10 min. The reaction mixture was stirred at 95° C. for 2 h. The reaction mixture was cooled and diluted with ethyl acetate. The organic layer was washed with water, brine and dried over sodium sulfate. The solvent was removed under reduced pressure to afford the crude product. The crude product was purified; using column chromatography (60-120 silica gel, 50% ethyl acetate in hexane) to yield the desired product [400 mg, 80%]. LC-MS (ESI): Calculated mass: 403.1; Observed mass: 404.0 [M+H]⁺ (RT: 1.36 min).

Step 2: 5-[7-(3-Methanesulfonyl-phenyl)-4-morpholin-4-yl-quinazolin-2-yl]-pyridin-2-ylamine

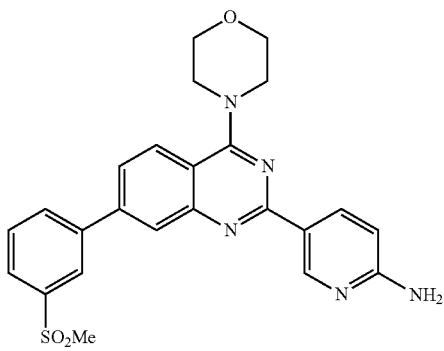 [SMILES: CS(=O)(=O)c1cccc(-c2ccc3c(N4CCOCC4)nc(-c4ccc(N)nc4)nc3c2)c1]

To a 50 mL round bottom flask, 2-chloro-7-(3-methanesulfonyl-phenyl)-4-morpholin-4-yl-quinazoline (0.15 g, 0.00037 mol), 2-aminopyridine-5-boronic acid pinacol ester (0.122 g, 0.0005568 mol), cesium carbonate (0.243 g, 0.00074 mol), DMF (4 mL) and water (2 mL) were added. The reaction mixture was degassed with nitrogen for 5-10 min. To the same reaction flask, Pd(PPh$_3$)$_2$Cl$_2$ (0.013 g, 0.000018 mol) was added and again degassed with nitrogen for 5-10 min. The reaction mixture was stirred at 95° C. for 2 h. The reaction mixture was cooled and diluted with ethyl acetate. The organic layer was washed with water, brine and dried over sodium sulfate. The solvent was removed under reduced pressure to afford the crude product. The crude product was purified using column chromatography (60-120 silica gel, 5% MeOH in chloroform) to yield the title compound (125 mg, 74%). LC-MS (ESI): Calculated mass: 461.2; Observed mass: 462.1 [M+H]⁺ (RT: 0.17 min).

Step 3: {5-[7-(3-Methanesulfonyl-phenyl)-4-morpholin-4-yl-quinazolin-2-yl]-pyridine-2-yl}-carbamic acid 2,2,2-trichloroethyl ester

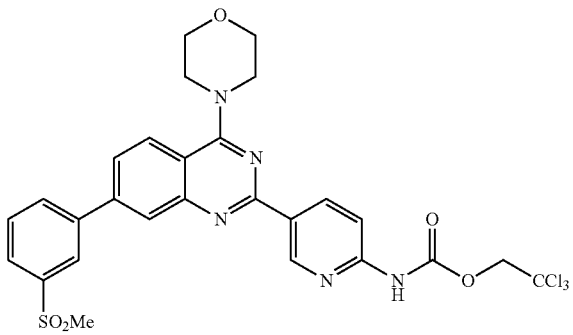

To a cooled solution (0° C.) of 5-[7-(3-methanesulfonyl-phenyl)-4-morpholin-4-yl-quinazolin-2-yl]-pyridin-2-ylamine (125 mg, 0.000271 mmol) in DCM (4 mL) was added 2,2,2-trichloroethylchloroformate (0.054 mL, 0.0004 mol) and TEA (0.056 mL, 0.0004 mol). The reaction mixture was allowed to stir at ambient temperature for 5 h. The volatiles were evaporated to get the crude product (100 mg). This material was taken to the next step without further purification.

Step 4: 4-(3-{5-[7-(3-Methanesulfonyl-phenyl)-4-morpholin-4-yl-quinazolin-2-yl]-pyridin-2-yl}-ureido)-dimethyl-benzamide

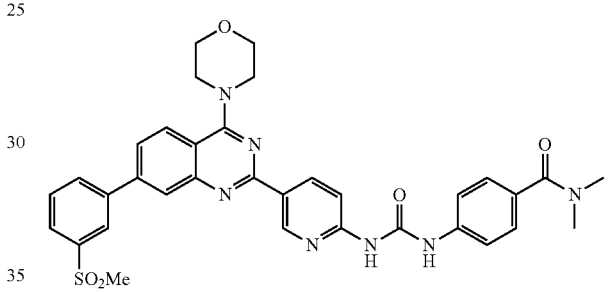

To a sealed tube, {5-[7-(3-methanesulfonyl-phenyl)-4-morpholin-4-yl-quinazolin-2-yl]-pyridine-2-yl}-carbamic acid 2,2,2-trichloroethyl ester (100 mg, 0.000312 mol), 4-amino-N,N-dimethyl-benzamide (258 mg, 0.00156 mol), TEA (0.218 mL, 0.00156 mol) and toluene (4 mL) were added, The reaction mixture was heated to 120° C. and maintained for 8 h. The reaction mixture was cooled and diluted with ethyl acetate. The organic layer was washed with water, brine and dried over sodium sulfate. The solvent was removed under reduced pressure to afford the crude product. The crude product was purified using column chromatography (60-120 silica gel, 0-3% MeOH and chloroform) to yield the desired product (15 mg, 15%). ¹H NMR (300 MHz, DMSO-d$_6$): δ 11.69 (brs, 1H), 9.52 (brs, 1H) 9.07 (brs, 1H), 8.89 (d, J=8.7 Hz, 1H), 8.40 (s, 1H), 8.24 (m, 3H), 8.07 (d, J=10.0 Hz, 1H), 7.83-7.91 (m, 2H), 7.78 (d, J=8.4 Hz, 2H), 7.40-7.45 (m, 3H), 3.91-3.96 (m, 8H), 3.27 (s, 3H), 3.04 (s, 6H); LC-MS (ESI): Calculated mass: 651.2; Observed mass: 652.2 (RT: 0.71 min).

Example 4

1-[4(6-Fluoro-4-morpholin-4-yl-7-pyridin-3-yl-quinazolin-2-yl)-phenyl]-3-[4-(4-methyl-piperazine-1-carbonyl)-phenyl]-urea

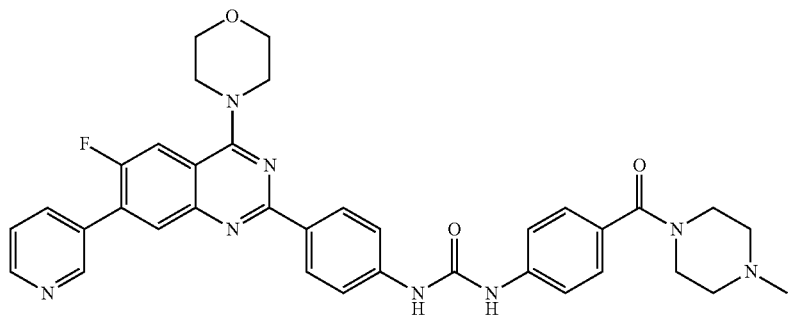 [SMILES: CN1CCN(C(=O)c2ccc(NC(=O)Nc3ccc(-c4nc(N5CCOCC5)c5cc(F)c(-c6cccnc6)cc5n4)cc3)cc2)CC1]

Step 1: N-(3-Bromo-4-fluoro-phenyl)-2-hydroxy-imino-acetamide

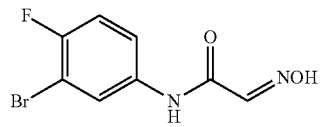

To a 500 mL round bottom flask, 3-bromo-4-fluoraniline (5 g, 0.0261 mol), water (300 mL), chloral hydrate (5.19 g, 0.0314 mol), hydroxylamine hydrochloride (5.8 g, 0.0835 mol) and sodium sulfate (25 g) were added. To this reaction mixture, conc. HCl (7.5 mL) was slowly added. The reaction mixture was stirred at 90° C. for 3 h. The precipitate was formed and was collected by filtration. The solid was dried to get the title compound (4.2 g, 61%). $^1$H NMR (300 MHz, DMSO-$d_6$): δ 12.28 (s, 1H), 10.51 (s, 1H), 8.12 (dd, J=2.4 Hz, J=2.7 Hz, 1H), 7.68 (m, 2H), 7.36 (t, J=8.7 Hz, 1H); LC-MS (ESI): Calculated mass: 260.0; Observed mass: 259.0 [M−H]$^+$ (RT: 0.88 min).

Step 2: 6-Bromo-5-fluoro-1H-indole-2,3-dione

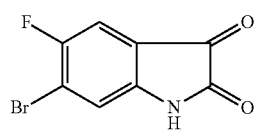

To the concentrated sulfuric acid (40 mL) at 50° C. was added N-(3-bromo-4-fluoro-phenyl)-2-hydroxyimino-acetamide (4 g, 0.0152 mol). The temperature was raised to 90° C. and maintained for 3 h. The reaction mixture was added to ice cold water to get the precipitate. The precipitate was filtered and dried to get the title compound (3.0 g, 80%). LC-MS (ESI): Calculated mass: 243.0; Observed mass: 242.1 [M−H]$^+$ (RT: 0.47 min).

Step 3: 2-Amino-4-bromo-5-fluoro-benzoic acid

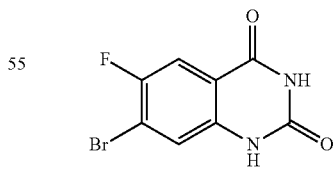

To a 100 mL round bottom flask, 6-bromo-5-fluoro-1H-indole-2,3-dione (3 g, 0.0121 mol) and 2N NaOH (15 mL) were added and cooled the reaction vessel to 0° C. To this reaction mixture 30% hydrogen peroxide (10.5 mL) was slowly added. The reaction mixture was stirred at 0° C. for 3 h. Subsequently, the reaction mixture was acidified with 2 N HCl at 0° C. [pH-5] to afford the solid compound. The solid material was collected by filtration and dried to obtain the title compound (700 mg, 25%). $^1$H NMR (300 MHz, DMSO-$d_6$): δ 7.52 (d, J=9.6 Hz, 1H), 7.09 (d, J=6.0 Hz, 1H); LC-MS (ESI): Calculated mass: 232.9; Observed mass: 231.9 [M−H]$^+$ (RT: 0.23 min).

Step 4: 7-Bromo-6-fluoro-1H-quinazoline-2,4-dione

To a 100 mL round bottom flask, 2-amino-4-bromo-5-fluoro-benzoic acid (0.7 g, 0.003 mol) and urea (1.07 g, 0.0018 mol) were added. The reaction mixture was stirred at 200° C. for 2 h. The reaction mixture was allowed to reach 100° C. and water was added. The aqueous reaction mixture was refluxed for 5-10 min, cooled to room temperature, to get the precipitate. The solid was filtered and dried to afford the title compound (400 mg, 51%). This material was taken for next step without any further purification.

Step 5: 7-Bromo-2,4-dichloro-6-fluoro-quinazoline

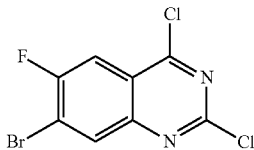 [SMILES: Fc1cc2c(Cl)nc(Cl)nc2cc1Br]

To a 100 mL round bottom flask was charged with 7-bromo-6-fluoro-1H-quinazoline-2,4-dione (0.4 g, 0.001532 mol). To the same flask POCl$_3$ (15 mL) and DIPEA (0.714 mL, 0.005 mol) were added. The reaction mixture was maintained at 140° C. for overnight. The volatiles were evaporated and azeotroped with toluene to get the residue. The crude residue was purified using column chromatography (60-120 silica gel, 20% ethyl acetate in hexane) to get the title compound (350 mg, 77%). This material was immediately taken to the next step.

Step 6: 7-Bromo-2-chloro-6-fluoro-4-morpholin-4-yl-quinazoline

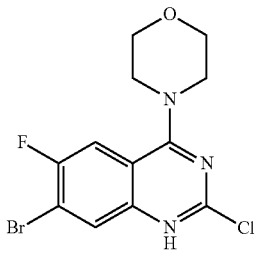 [SMILES: Fc1cc2c(N3CCOCC3)nc(Cl)nc2cc1Br]

To an ice cold solution of 7-bromo-2,4-dichloro-6-fluoro-quinazoline (0.35 g, 0.001178 mol) in DCM (15 mL), morpholine (0.247 mL, 2.946 mol) was slowly added and the reaction was continued for 20 min. The reaction mixture was diluted with DCM and washed with water. The organic layer was dried over sodium sulfate and evaporated to get the crude. The crude was purified using column chromatography (60-120 silica gel, 30% ethyl acetate in hexane) to get the title compound (220 mg, 57%). $^1$H NMR (300 MHz, DMSO-d$_6$): δ 8.16 (d, J=6.6 Hz, 1H), 8.01 (d, J=9.6 Hz, 1H), 3.83-3.86 (m, 4H), 3.76-3.73 (m, 4H); LC-MS (ESI): Calculated mass: 344.9; Observed mass: 347.8 [M+H]$^+$ (RT: 1.70 min).

Step 7: 2-Chloro-6-fluoro-4-morpholin-4-yl-7-pyridin-3-yl-quinazoline

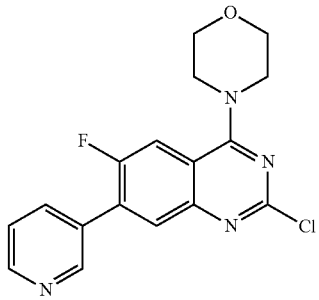 [SMILES: Fc1cc2c(N3CCOCC3)nc(Cl)nc2cc1-c1cccnc1]

To a 50 mL round bottom flask, 7-bromo-2-chloro-6-fluoro-4-morpholin-4-yl-quinazoline (200 mg, 0.0005764 mol), pyridine-3-boronic acid (63.3 mg, 0.0005188 mol), sodium carbonate (152.6 mg, 0.001441 mol), DMF (10 mL) and water (5 mL) were added and degassed the reaction vessel with nitrogen for 5-10 min. To the same reaction mixture, Pd(PPh$_3$)$_2$Cl$_2$ (20.1 mg, 0.0000288 mol) was added and again degassed with N$_2$ for 5-10 min. The reaction mixture was stirred at 95° C. for 2 h. The reaction mixture was cooled and diluted with ethyl acetate. The organic layer was washed with water, brine and dried over sodium sulfate. The solvent was removed under reduced pressure to afford the crude product. The crude product was purified using column chromatography (60-120 silica gel, 2% MeOH in chloroform) to yield the desired product (180 mg, 91%). $^1$H NMR (300 MHz, CD$_3$OD): δ 8.27-8.30 (m, 1H), 8.21-8.25 (m, 1H), 8.15-8.18 (m, 1H), 7.91-7.92 (m, 1H), 7.74-7.78 (m, 1H), 7.47-7.51 (m, 1H), 3.99-4.01 (m, 4H), 3.85-3.88 (m, 4H); LC-MS (ESI): Calculated mass: 344.1; Observed mass: 344.9 [M+H]$^+$ (RT: 1.3 min).

Step 8: 1-[4(6-Fluoro-4-morpholin-4-yl-7-pyridin-3-yl-quinazolin-2-yl)-phenyl]-3-[4-(4-methyl-piperazine-1-carbonyl)-phenyl]-urea

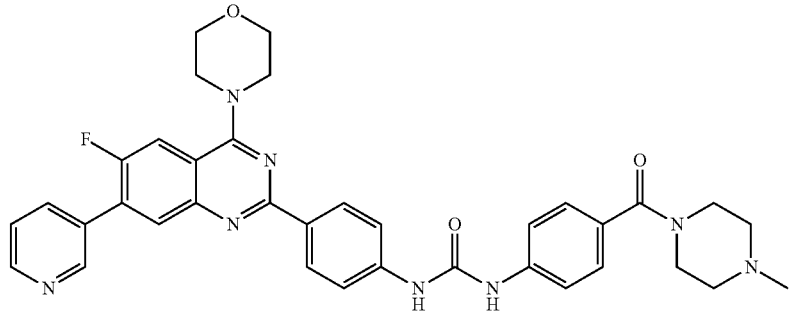 [SMILES: CN1CCN(C(=O)c2ccc(NC(=O)Nc3ccc(-c4nc(N5CCOCC5)c5cc(F)c(-c6cccnc6)cc5n4)cc3)cc2)CC1]

To a 50 mL round bottom flask, 2-chloro-6-fluoro-4-morpholin-4-yl-7-pyridin-3-yl-quinazoline (90 mg, 0.000259 mol), 1-[4-(4-methyl-piperazine-1-carbonyl)-phenyl]-3-[4-(4,4,5,5,-tetramethyl-[1,3,2]dioxaborolan-2-yl)-phenyl]-urea (144.7 mg, 0.0003114 mol), cesium carbonate (212.3 mg, 0.000647 mol), DMF (5 mL) and water (2.5 mL) were added. The reaction mixture was degassed with nitrogen for 5-10 min. To the same reaction flask, Pd(PPh$_3$)$_2$Cl$_2$ (9.07 mg, 0.0000131 mol) was added and again degassed with nitrogen for 5-10 min. The reaction mixture was stirred at 95° C. for 2 h. The reaction mixture was cooled and diluted with ethyl acetate. The organic layer was washed with water, brine and dried over sodium sulfate. The solvent was removed under reduced pressure to afford the crude product. The crude product was purified using column chromatography (60-120 silica gel, 5% MeOH in chloroform) to yield the title compound (15 mg, 6%) $^1$H NMR (300 MHz, DMSO-d$_6$): δ 9.05 (s, 1H), 9.0 (s, 1H), 8.93 (brs, 1H), 8.68-8.72 (m, 1H), 7.92-8.73 (m, 5H), 7.52-7.64 (m, 5H), 7.35 (d, J=8.1 Hz, 2H), 3.85 (s, 8H), 3.46-3.57 (m, 4H), 2.24-2.37 (m, 4H), 2.19 (s, 3H); LC-MS (ESI): Calculated mass: 646.2; Observed mass: 647.2 (RT: 0.11 min).

Example 5

4-(3-{4-[8-(3-Hydroxy-phenyl)-4-morpholin-4-yl-quinazolin-2-yl]-phenyl}-ureido)-N,N-dimethyl-benzamide

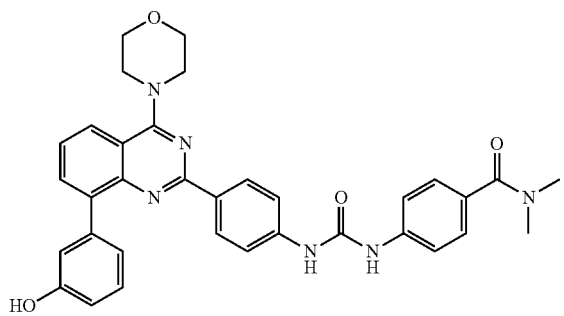 [SMILES: CN(C)C(=O)c1ccc(NC(=O)Nc2ccc(-c3nc(N4CCOCC4)c4cccc(-c5cccc(O)c5)c4n3)cc2)cc1]

Step 1:
N-(2-Bromo-phenyl)-2-hydroxyimino-acetamide

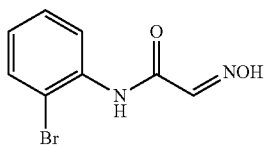

To a 1000 mL round bottom flask, 2-bromoaniline (15 g, 0.0872 mol), water (400 mL), chloral hydrate (17.05 g, 0.1046 mol), hydroxylamine hydrochloride (19.25 g, 0.279 mol) and sodium sulfate (57.81 g) were added. To this reaction mixture conc. HCl (21 mL) was slowly added. The reaction mixture was stirred at 100° C. for 3 h. The white precipitate was formed and was collected by filtration. The white solid was dried to get the title compound [7 g, 33%]. $^1$HNMR (300 MHz, DMSO-d$_6$): δ 12.46 (s, 1H), 9.48 (s, 1H), 7.89 (d, J=8.1 Hz, 1H), 7.69 (d, J=8.1 Hz, 1H), 7.66 (s, 1H), 7.42 (t, J=6.9 Hz, 1H), 7.15 (t, J=7.5 Hz, 1H); LC-MS (ESI): Calculated mass: 241.9; Observed mass: 243.0 [M+H]$^+$ (RT: 0.66 min).

Step 2: 8-Bromo-1H-indole-2,3-dione

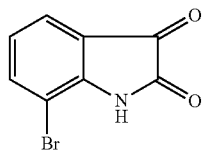 [SMILES: O=C1Nc2c(Br)cccc2C1=O]

To the concentrated sulfuric acid (70 mL) at 60° C. was added N-(2-bromo-phenyl)-2-hydroxyimino-acetamide (7 g, 0.028 mol). The temperature was raised to 90° C. and maintained for 3 h. The reaction mixture was added to ice cold water to get yellow precipitate. The precipitate was filtered and dried to get the title compound as a yellow solid [6.0 g, 92%]. $^1$H NMR (300 MHz, DMSO-d$_6$): δ 11.33 (s, 1H), 7.79 (d, J=8.1 Hz, 1H), 7.52 (d, J=7.2 Hz, 1H), 7.02 (t, J=7.5 Hz, 1H); LC-MS (ESI): Calculated mass: 224.9; Observed mass: 226.0 [M+H]$^+$ (RT: 0.39 min).

Step 3: 2-Amino-3-bromo-benzoic acid

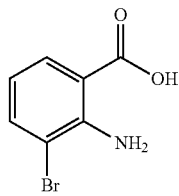 [SMILES: Nc1c(Br)cccc1C(=O)O]

To a 100 mL round bottom flask, 8-bromo-1H-indole-2,3-dione (6 g, 0.0234 mol) and 2N NaOH (66.8 mL) were added and the reaction vessel cooled to 0° C. To this reaction mixture 30% hydrogen peroxide (6 mL) was slowly added. The reaction mixture was stirred at 0° C. for 3 h. Subsequently, the reaction mixture was acidified with 2N HCl at 0° C. [pH-6] to afford the solid compound. The solid material was collected by filtration and dried to obtain the title compound [5 g, 88%]. $^1$H NMR (300 MHz, DMSO-d$_6$): δ 13.01 (brs, 1H), 7.79 (d, J=7.8 Hz, 1H), 7.65 (d, J=7.5 Hz, 1H), 6.75 (brs, 2H), 6.52 (t, J=8.1 Hz, 1H); LC-MS (ESI): Calculated mass: 214.9; Observed mass: 215.9 [M+H]$^+$ (RT: 0.88 min).

Step 4: 8-Bromo-1H-quinazoline-2,4-dione

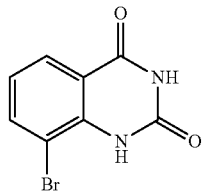 [SMILES: O=c1[nH]c(=O)c2cccc(Br)c2[nH]1]

To a 100 mL round bottom flask, 2-amino-3-bromo-benzoic acid (5 g, 0.0234 mol) and urea (7.33 g, 0.122 mol) were added. The reaction mixture was stirred at 195° C. for 3 h. The reaction mixture was allowed to reach 80° C. and water was added. The aqueous reaction mixture was stirred for 5-10 min and filtered to afford the title compound [5.4 g, 97%]. This material was taken to the next step without any further purification.

Step 5: 8-Bromo-2,4-dichloro-quinazoline

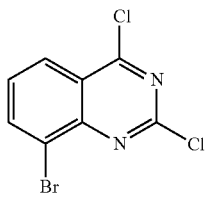 [SMILES: Clc1nc(Cl)c2cccc(Br)c2n1]

A 100 mL round bottom flask was charged with 8-bromo-1H-quinazoline-2,4-dione (5.4 g, 0.0224 mol). To the same flask POCl$_3$ (80 mL) and DIPEA (8 mL) were added. The reaction mixture was maintained at 130° C. for 12 h. The volatiles were evaporated and azeotroped with toluene (3×20 mL). The crude residue was purified using column chromatography (60-120 silica gel, 10% ethyl acetate in hexane) to get the title compound [5.5 g, 89%]. $^1$H NMR (300 MHz, CDCl$_3$): δ 8.53 (dd, J'=7.8 Hz, J"=1.2 Hz, 1H), 8.33 (dd, J'=8.4 Hz, J"=0.9 Hz, 1H), 7.81 (t, J=8.4 Hz, 1H); LC-MS (ESI): Calculated mass: 275.8; Observed mass: 277.0 [M+H]$^+$ (RT: 1.67 min).

Step 6:
8-Bromo-2-chloro-4-morpholin-4-yl-quinazoline

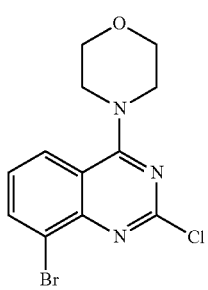 [SMILES: Clc1nc(N2CCOCC2)c2cccc(Br)c2n1]

To an ice cold solution of 8-bromo-2,4-dichloro-quinazoline (5.5 g, 0.0197 mol) in DCM (100 mL), morpholine (3.77 mL, 0.0433 mol) was slowly added and the reaction was continued for 15 min. The solvent was evaporated to dryness to get the crude compound. The crude product was purified, using column chromatography (60-120 silica gel, 5-30% ethyl acetate in hexane) to get the title compound [2.5 g, 39%]. $^1$H NMR (400 MHz, CDCl$_3$): δ 8.05 (dd, J'=7.8 Hz, J"=1.2 Hz, 1H), 7.81 (dd, J'=8.4 Hz, J"=0.9 Hz, 1H), 7.29 (t, J=8.4 Hz, 1H), 3.89 (s, 8H); LC-MS (ESI): Calculated mass: 326.9; Observed mass: 327.9 [M+H]$^+$ (RT: 1.57 min).

Step 7: 3-(2-Chloro-4-morpholin-4-ylquinazolin-8-yl)-phenol

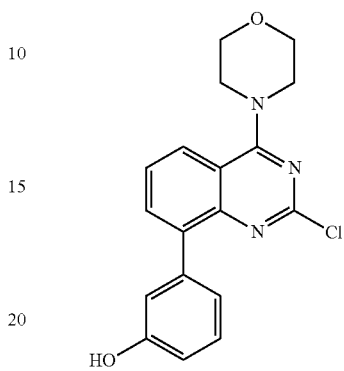

To a 50 mL round bottom flask, 8-bromo-2-chloro-4-morpholin-4-yl-quinazoline (150 mg, 0.00046 mol), 3-hydroxyphenylboronic acid (57 mg, 0.00041 mol), sodium carbonate (97 mg, 0.00091 mol), DMF (10 mL) and water (5 mL) were added. The reaction mixture was degassed with nitrogen for 5-10 min. To the same flask Pd(PPh$_3$)$_2$Cl$_2$ (16 mg, 0.000022 mol) was added and again degassed with nitrogen for 5-10 min. The reaction mixture was stirred at 95° C. for 2 h. The reaction mixture was cooled and diluted with ethyl acetate. The organic layer was washed with water, brine and dried over sodium sulfate. The solvent was removed under reduced pressure to afford the crude residue. The crude product was purified using column chromatography (60-120 silica gel, 1% MeOH in chloroform) to yield the desired title product (85 mg, 46%). $^1$H NMR: (300 MHz, CDCl$_3$): δ 7.70-7.78 (m, 2H), 7.40-7.44 (m, 1H), 7.20-7.26 (m, 1H), 7.03-7.05 (m, 2H), 6.78-6.83 (m, 1H), 3.81-3.83 (m, 8H); LC-MS (ESI): Calculated mass: 341.1; Observed mass: 342.1 [M+H]$^+$ (RT: 1.53 min).

Step 8: 4-(3-[4-{8-(3-Hydroxy-phenyl)-4-morpholin-4-yl-quinazolin-2-yl]-phenyl}-ureido)-N,N-dimethyl-benzamide

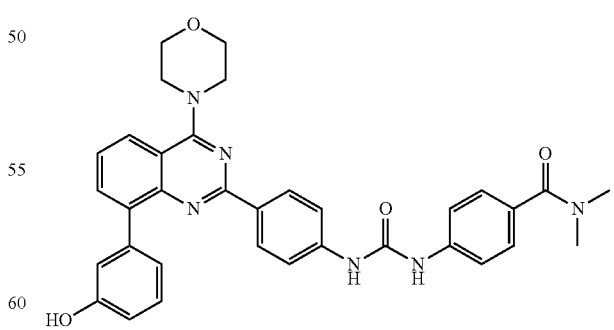

To a 50 mL round bottom flask, 3-(2-chloro-4-morpholin-4-ylquinazolin-8-yl)-phenol (80 mg, 0.000234 mol), N,N-dimethyl-4-[3-{4-(4,4,5,5,-tetramethyl-[1,3,2]dioxaborolan-2-yl)-phenyl]ureido}-benzamide (114 mg, 0.00028 mol), cesium carbonate (153 mg, 0.00047 mol), DMF (7 mL) and water (1 mL) were added. The reaction mixture was degassed with nitrogen for 5-10 min. To the same reaction flask, Pd(PPh$_3$)$_2$Cl$_2$ (8 mg, 0.0000011 mol) was added and again degassed with nitrogen for 5-10 min. The reaction mixture was stirred at 95° C. for 2 h. The reaction mixture was cooled and diluted with ethyl acetate. The organic layer was washed with water, brine and dried over sodium sulfate. The solvent was removed under reduced pressure to afford the crude product. The crude product was purified using column chromatography (60-120 silica gel, 2-5% MeOH in chloroform) to yield the title compound [15 mg, 6%]. $^1$H NMR: (300 MHz, DMSO-d$_6$): δ 9.49 (s, 1H), 9.00 (s, 1H), 8.97 (s, 1H), 8.31 (d, J=8.4 Hz, 2H), 8.00 (d, J=8.4 Hz, 1H), 7.82 (d, J=7.2 Hz, 1H), 7.50-7.59 (m, 5H), 7.29-7.35 (m, 3H), 7.16-7.22 (m, 2H), 6.83 (d, J=8.1 Hz, 1H), 3.83 (m, 8H), 2.97 (s, 6H); LC-MS (ESI): Calculated mass: 588.2; Observed mass: 588.8 [M+H]$^+$ (RT: 0.64 min).

Example 6

4-(3-{4-[8-(6-Fluoro-pyridin-3-yl)-4-morpholin-4-yl-quinazolin-2-yl]-phenyl}-ureido)-N,N-dimethyl-benzamide Step 1: 2-Chloro-8-(6-fluoro-pyridin-3-yl)-4-morpholin-4-yl-quinazoline

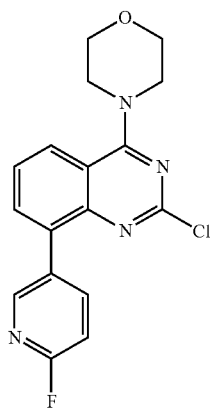 [SMILES: Fc1ccc(-c2cccc3c(N4CCOCC4)nc(Cl)nc23)cn1]

To a 50 mL round bottom flask, 8-bromo-2-chloro-4-morpholin-4-yl-quinazoline (150 mg, 0.00046 mol), 2-fluoropyridine-5-boronic acid (58 mg, 0.00041 mol), sodium carbonate (72 mg, 0.00068 mol), DMF (10 mL) and water (3 mL) were added and the reaction vessel was degassed with nitrogen for 5-10 min. To the same reaction mixture, PdCl$_2$(PPh$_3$)$_2$ (16 mg, 0.000023 mol) was added and again degassed with nitrogen for 5-10 min. The reaction mixture was stirred at 95° C. for 2 h. The reaction mixture was cooled and diluted with ethyl acetate. The organic layer was washed with water, brine and dried over sodium sulfate. The solvent was removed under reduced pressure to afford the crude product. The crude product was purified using column chromatography (60-120 silica gel, 60% ethyl acetate in hexane) to yield the desired product [90 mg, 60%]. $^1$H NMR (300 MHz, CDCl$_3$): δ 8.44 (s, 1H), 8.17-8.24 (m, 1H), 7.89 (d, J=8.1 Hz, 1H), 7.78 (d, J=7.5 Hz, 1H), 7.53 (t, J=7.5 Hz, 1H), 7.75 (dd, J'=2.7, J''=3.0 Hz, 1H), 3.89 (s, 8H). LC-MS (ESI): Calculated mass: 344.1; Observed mass: 345.0 [M+H]$^+$ (RT: 1.63 min).

Step 2: 4-(3-[4-{8-(6-Fluoro-pyridin-3-yl)-4-morpholin-4-yl-quinazolin-2-yl]-phenyl}-ureido)-N,N-dimethyl-benzamide

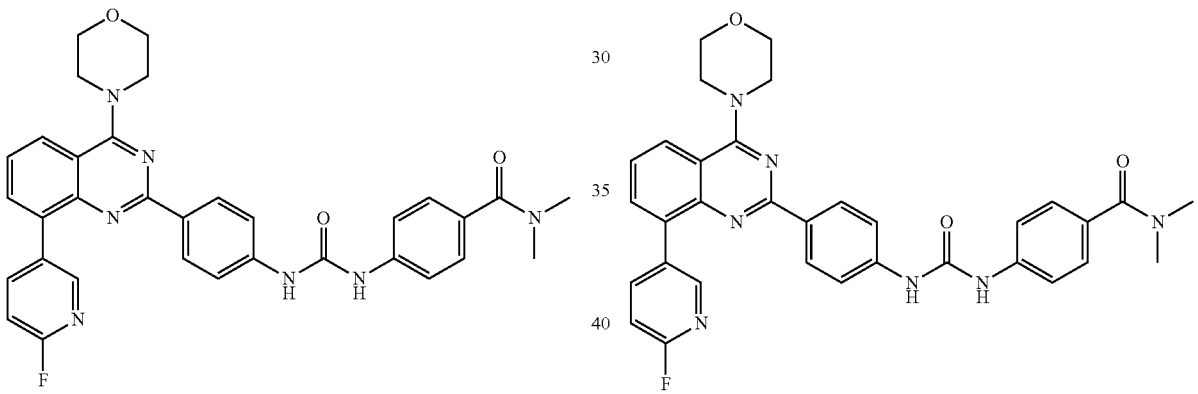

To a 50 mL round bottom flask, 2-chloro-8-(6-fluoro-pyridin-3-yl)-4-morpholin-4-yl-quinazoline (70 mg, 0.000203 mol), N,N-dimethyl-4-{3-{4-(4,4,5,5,-tetramethyl-[1,3,2]dioxaborolan-2-yl)-phenyl]-ureido]-benzamide (100 mg, 0.0002436 mol), cesium carbonate (133 mg, 0.000406 mol), DMF (3.5 mL) and water (0.9 mL) were added. The reaction mixture was degassed with nitrogen for 5-10 min. To the same reaction flask, Pd(PPh$_3$)$_2$Cl$_2$ (7 mg, 0.0000101 mol) was added and again degassed with nitrogen for 5-10 min. The reaction mixture was stirred at 95° C. for 2 h. The reaction mixture was cooled and diluted with ethyl acetate. The organic layer was washed with water, brine and dried over sodium sulfate. The solvent was removed under reduced pressure to afford the crude product. The crude product was purified using column chromatography (60-120 silica gel, 2% MeOH in chloroform) to yield the title compound as a light yellow solid [8 mg, 7%]. $^1$H NMR (400 MHz, DMSO-d$_6$): δ 8.99 (s, 1H), 8.95 (s, 1H), 8.60 (s, 1H), 8.43 (m, 1H), 8.28 (d, J=8.8 Hz, 2H), 8.07 (d, J=8.4 Hz, 1H), 7.95 (d, J=7.2 Hz, 1H), 7.58 (m, 3H), 7.49 (m, 2H), 7.39 (m, 3H), 3.84 (s, 8H), 2.95 (s, 6H); LC-MS (ESI): Calculated mass: 591.2; Observed mass: 591.9 [M+H]$^+$ (RT: 1.53 min).

Example 7

2-[4-{3-(4-Dimethycarbamoyl-phenyl)-Ureido]-phenyl}-4-morpholin-4-yl-quinazoline-7-carboxylic acid (2-dimethylamino-ethyl)-amide

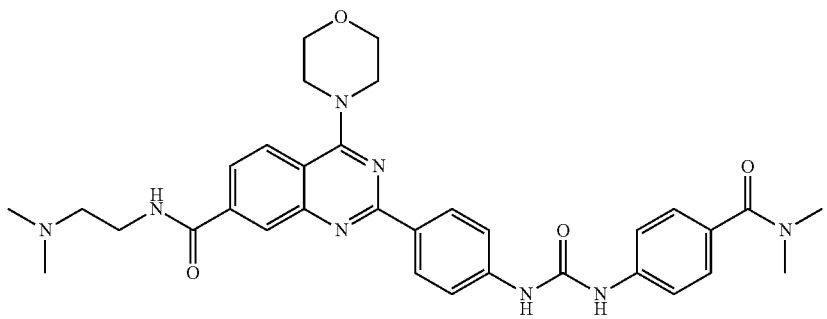

Step 1: 2,4-Dioxo-1,2,3,4-tetrahydro-quinazoline-7-carboxylic acid methyl ester

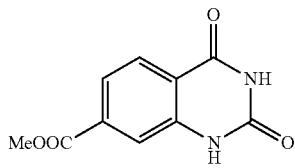 [SMILES: COC(=O)c1ccc2c(=O)[nH]c(=O)[nH]c2c1]

To a 250 mL round bottom flask, 2-amino dimethyl terephthalate (3 g, 0.0143 mol) and urea (4.3 g, 0.0717 mol) were added. The reaction mixture was stirred at 200° C. for 3 h. The reaction mixture was allowed to reach 100° C. and water was added. The aqueous reaction mixture was stirred at 100° C. for 5-10 min then allowed to reach room temperature. The solid was filtered, washed with chloroform dried and azeotroped with toluene to afford the title compound [2.5 g, 80%]. This material was taken to the next step without any further purification. $^1$H NMR; (400 MHz, DMSO-d$_6$): δ 11.25 (brs, 2H), 7.98 (d, 1H, J=8.2 Hz), 7.78 (s, 1H), 7.65 (d, J=8.2, 1.2 Hz, 1H), 3.98 (s, 3H): LC-MS (ESI): Calculated mass: 220.0; Observed mass: 221.0 [M+H]$^+$ (RT: 0.19 min).

Step 2: 2-Chloro-4-morpholine-4-yl-quinazoline-7-carboxylic acid methyl ester

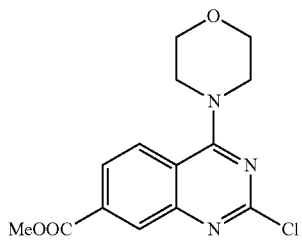 [SMILES: COC(=O)c1ccc2c(N3CCOCC3)nc(Cl)nc2c1]

To a 250 mL round bottom flask, 7-methylcarboxylate-1H-quinazoline-2,4-dione (1.4 g 0.00636 mol) was added. To the same flask POCl$_3$ (20 mL) and N,N-dimethylaniline (0.62 g, 0.00509 mol) were added. The reaction mixture was maintained at 120° C. for 5 h. The volatiles were evaporated and azeotroped with toluene to provide the crude residue. The crude residue was triturated with DCM and filtered through a Celite® pad. The filtrate was purified by column chromatography (60-120 silica gel, 50% ethyl acetate in hexane) to provide 7-methylcarboxylate-2,4-dichloro-quinazoline. To an ice cold solution of 7-methylcarboxylate-2,4-dichloro-quinazoline (0.65 g 0.00253 mol) in DCM (10 mL), morpholine (0.443 mL, 0.00507 mol) was slowly added and the reaction was continued at 0° C. for 30 min. The solvent was evaporated to dryness to get the crude compound. The crude product was purified, using column chromatography (60-120 silica gel, 50% ethyl acetate in hexane) to get the title compound (0.543 g, 70%). $^1$H NMR; (400 MHz, DMSO-d$_6$): δ 8.20 (d, 1H, J=1.2 Hz), 7.98 (d, 1H, J=8.2 Hz), 7.80 (dd, J=8.2, 1.2 Hz, 1H), 3.95 (s, 3H), 3.76-3.87 (m, 8H): LC-MS (ESI): Calculated mass: 307.0; Observed mass: 308.0 [M+H]$^+$ (RT: 1.21 min).

Step 3: 2-Chloro-4-morpholine-4-yl-quinazoline-7-carboxylic acid

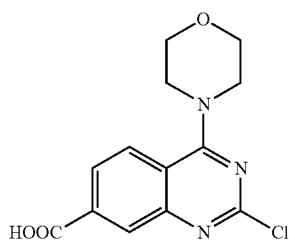 [SMILES: O=C(O)c1ccc2c(N3CCOCC3)nc(Cl)nc2c1]

To a 50 mL round bottom flask was added 7-methylcarboxylate-4-morpholine 2-chloro-quinazoline (0.5 g, 0.00162 mol) and THF:MeOH:H$_2$O (1:1:1, 9 mL). LiOH (0.273 g, 0.0065 mol) was then added and the reaction was stirred at room temperature for 1 h. After completion of the reaction, solvent were removed under reduced pressure and acidified with HCl. During the acidification, a white solid was formed, which was collected by filtration. The filter cake was washed with water (10 mL) and dried in a vacuum oven to give the title compound (0.38 g, 80%). $^1$H NMR (400 MHz, DMSO-d$_6$): δ 13.5 (brs, 1H), 8.20 (d, 1H, J=1.2 Hz), 7.98 (d, 1H, J=8.2 Hz), 7.80 (dd, J=8.2, 1.2 Hz, 1H), 3.76-3.87 (m, 8H): LC-MS (ESI): Calculated mass: 293.0; Observed mass: 294.0 [M+H]⁺ (RT: 0.44 min).

Step 4: 2-Chloro-4-morpholine-4-yl-quinazoline-7-carboxylic acid (2-dimethylamino-ethyl)-amide

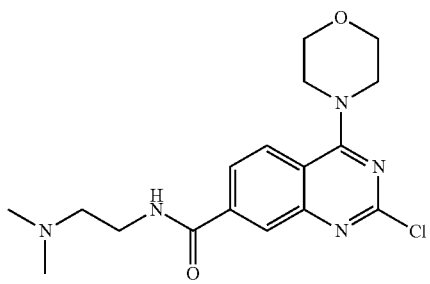 [SMILES: CN(C)CCNC(=O)c1ccc2c(N3CCOCC3)nc(Cl)nc2c1]

To a 50 mL round bottom flask, 7-carboxylic acid-4-morpholine-2-chloro-quinazoline (0.3 g, 0.00102 mol) in DMF (5 mL), N,N-dimethylethylene diamine (0.134 mL, 0.0012 mol), HATU (0.58 g, 0.0015 mol) and DIPEA (0.353 mL, 0.00204 mol) were added. The reaction mixture was stirred at room temperature for 12 h. The reaction mixture was diluted with water and extracted with ethyl acetate (3×500 mL). The organic layer was washed with water, brine and dried over sodium sulfate. The solvent was removed under reduced pressure and the crude product was purified, using column chromatography (60-120 silica gel, 1% MeOH in chloroform) to get the title compound (0.263 g, 70%). $^1$H NMR; (400 MHz, DMSO-d$_6$): δ 8.79 (brs, 1H), 8.12-8.16 (m, 2H), 7.90 (d, 1H, J=8.4 Hz), 3.77-3.87 (m, 8H), 3.44 (d, 2H, J=8.0 Hz), 2.50-2.56 (brs 2H), 2.29 (s, 6H): LC-MS (ESI): Calculated mass: 363.1; Observed mass: 364.0 [M+H]⁺ (RT: 0.09 min).

Step 5: 2-[4-{3-(4-Dimethycarbamoyl-phenyl)-Ureido]-phenyl}-4-morpholin-4-yl-quinazoline-7-carboxylic acid (2-dimethylamino-ethyl)-amide

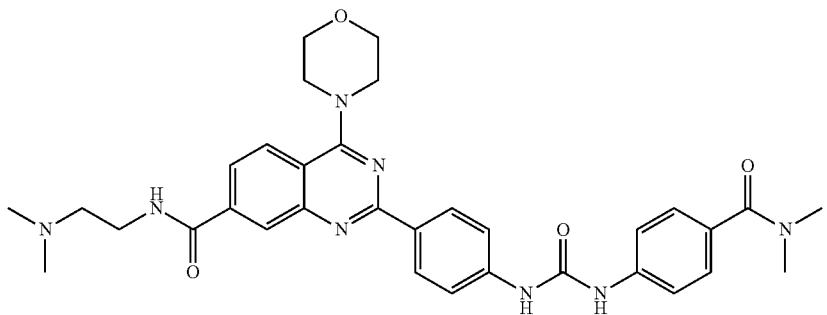

To a 50 mL round bottom flask, 2-chloro-4-morpholine-4-yl-quinazoline-7-carboxylic acid (2-dimethylamino-ethyl)-amide (0.08 g, 0.00022 mol), N,N-dimethyl-4-{3-{4-(4,4,5,5,-tetramethyl-[1,3,2] dioxaborolan-2-yl)-phenyl]-ureido}-benzamide (0.108 g, 0.000264 mol), cesium carbonate (0.143 g, 0.00044 mol), DMF (4 mL), water (1 mL) were added. The reaction mixture was degassed with nitrogen for 5-10 min. To the same reaction flask, Pd(PPh$_3$)$_2$Cl$_2$ (8 mg, 0.000011 mol) was added and again degassed with nitrogen for 5-10 min. The reaction mixture was stirred at 95° C. for 5 h. The reaction mixture was cooled and diluted with ethyl acetate. The organic layer was washed with water, brine and dried over sodium sulfate. The solvent was removed under reduced pressure to afford the crude product. The crude product was purified using column chromatography (60-120 silica gel, 15-20% MeOH in chloroform) to yield the crude title compound in 50% yield, followed by preparative HPLC (0.1% TFA in water and ACN) to yield the title compound [0.013 g, 10%]. $^1$H NMR; (400 MHz, DMSO-d$_6$): δ 9.65 (brs, 1H), 9.55 (s, 1H), 9.17 (s, 1H), 8.45 (brs, 1H), 8.43 (d, 2H, J=8.8 Hz), 8.16 (d, 1H, J=8.4 Hz), 7.96 (brs, 1H), 7.67 (d, 2H, J=8.0 Hz), 7.54 (d, 2H, J=8.4 Hz), 7.38 (d, 2H, J=8.4 Hz), 3.85-3.94 (m, 8H), 3.70 (d, 2H, J=5.2 Hz), 3.43 (brs, 2H), 2.95 (s, 6H), 2.86 (s, 6H): LC-MS (ESI): Calculated mass: 610.3; Observed mass: 611.1 [M+H]⁺ (RT: 0.08 min).

Example 8

4-(3-{2-Fluoro-4-[7-(5-methyl-furan-2-yl)-4-morpholin-4-yl-quinazolin-2-yl]-phenyl}ureido)dimethyl-benzamide

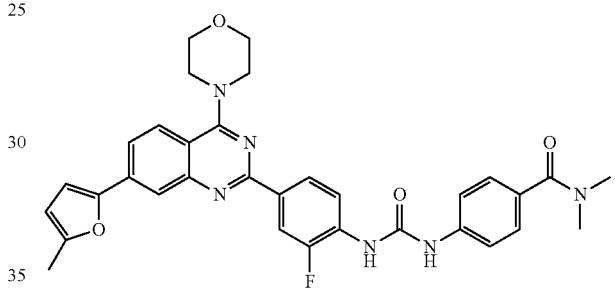

To a 50 mL round bottom flask, 2-chloro-7-(5-methyl-furan-2-yl)-4-morpholin-4-yl-quinazoline (0.05 g, 0.1519 mmol), 4-{3-[2-fluoro-4-(4,4,5,5-tetramethyl-[1,3,2]dioxaborolan-2-yl)phenyl]-ureido}-N,N-dimethyl-benzamide (0.097 g, 0.0002279 mol), cesium carbonate (0.099 g, 0.0003038 mol), toluene (4 mL), EtOH (4 mL) and water (2 mL) were added. The reaction mixture was degassed with nitrogen for 5-10 min. To the same reaction flask, Pd (PPh$_3$)$_2$Cl$_2$ (0.005 g, 0.0000076 mol) was added and again degassed with nitrogen for 5-10 min. The reaction mixture was stirred at 95° C. for 2 h. The reaction mixture was cooled and diluted with ethyl acetate. The organic layer was washed with water, brine and dried over sodium sulfate. The solvent was removed under reduced pressure to afford the crude product. The crude product was purified using column chromatography (60-120 silica gel, 0-4% MeOH in chloroform) followed by preparative HPLC using 10 mM ammonium acetate in water and ACN to yield the title compound [0.005 g, 6%]. $^1$H NMR (400 MHz, DMSO-$d_6$): δ 9.47 (s, 1H), 8.92 (d, J=2.0, 1H), 8.23-8.39 (m, 3H), 8.02 (d, J=8.8 Hz, 2H), 7.76 (dd, J'=8.8 Hz, J''=1.6 Hz, 1H), 7.54 (d, J=8.4 Hz, 2H), 7.39 (d, J=8.4 Hz, 2H), 7.18 (d, J=3.2 Hz, 1H), 6.32 (d, J=2.4 Hz, 1H), 3.84 (s, 8H), 2.97 (s, 6H), 2.42 (s, 3H): LC-MS (ESI): Calculated mass: 594.2; Observed mass: 595.2 [M+H]$^+$ (RT: 1.28 min).

Example 9

N,N-Dimethyl-4-{3-[4-(4-morpholin-4-yl-7-pyrimidin-5-yl-pyrido[3,2-d]-pyrimidin-2-yl)-phenyl]-ureido}-benzamide

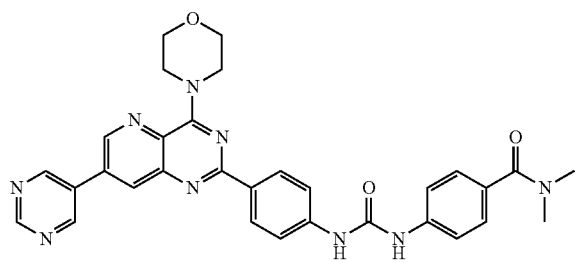 [SMILES: CN(C)C(=O)c1ccc(NC(=O)Nc2ccc(-c3nc(N4CCOCC4)c4ncc(-c5cncnc5)cc4n3)cc2)cc1]

Step 1: 3-Amino-5-bromo-pyridine-2-carboxylic acid amide

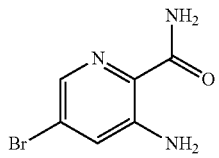

To a 100 mL round bottom flask, Raney Nickel (2.5 g) and EtOH (150 mL) were added. To the same flask was added 5-bromo-3-nitropyridine-2-carbonitrile (5 g, 0.0219 mol). The reaction mass was stirred under hydrogen for 14 h at ambient temperature. The catalyst was removed by filtration. The clear filtrate was evaporated to provide the crude product. The crude was subjected to column chromatography (60-120 silica gel, 30% ethyl acetate in hexane) to provide the title compound as a light yellow solid [1.1 g, 23%]. $^1$H NMR (300 MHz, DMSO-$d_6$): δ 7.89 (brs, 1H), 7.79 (d, J=1.8 Hz, 1H), 7.40 (brs, 1H), 7.38 (d, J=1.8 Hz, 1H), 7.04 (brs, 2H): LC-MS (ESI): Calculated mass: 215.0; Observed mass: 216.8 [M+H]$^+$ (RT: 0.38 min).

Step 2: 3-Amino-5-bromo-pyridine-2-carboxylic acid

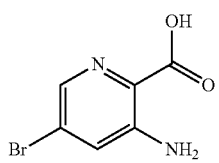

To a 100 mL round bottom flask, 3-amino-5-bromo-pyridine-2-carboxylic acid amide (1.05 g, 0.0049 mol) and aqueous sodium hydroxide solution (0.98 g in 10 mL water, 0.0245 mol) was added. The reaction mixture was stirred at reflux temperature for 5 h. The volatiles were evaporated under reduced pressure to get the residue. The residue was neutralized to pH=7.0, using 2N HCl at 0° C. to obtain the precipitate. The precipitate was filtered and dried to get the title compound as light yellow solid [1 g, 95%]. $^1$H NMR (300 MHz, DMSO-$d_6$): δ 7.65 (d, J=2.1 Hz, 1H), 7.20 (d, J=2.1 Hz, 1H), 7.01-7.16 (brs, 2H); LC-MS (ESI): Calculated mass: 215.9; Observed mass: 217.0 [M+H]$^+$ (RT: 0.43 min).

Step 3: 7-Bromo-pyrido[3,2-d]pyrimidine-2,4-diol

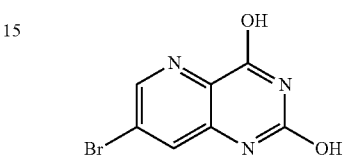

To a 100 mL round bottom flask, 3-amino-5-bromo-pyridine-2-carboxylic acid (1 g, 0.0046 mol) and urea (2.768 g, 0.4629 mol) were added. The reaction mixture was stirred at 200° C. for 2.5 h. The reaction mixture was cooled, water was added and stirred to provide a precipitate. The precipitate was filtered and dried to provide the title compound [1 g, 91%]. This material was taken to the next step without any further purification.

Step 4: 7-Bromo-2,4-dichloro-pyrido[3,2-d]pyrimidine

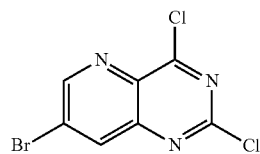

To a 100 mL round bottom flask, 7-bromo-pyrido[2,3-d]pyrimidine-2,4-diol (1 g, 0.0041 mol) was added. To the same flask, POCl$_3$ (10 mL) and DIPEA (1 mL) were added. The reaction mixture was maintained at 130° C. for 10 h. The volatiles were evaporated and azeotroped with toluene (2×10 mL). The obtained residue was treated with ethyl acetate and filtered through a Celite® pad. The filtrate was evaporated to get the crude title compound [0.9 g, 78% (crude yield)]. This material was taken to the next step without any further purification.

Step 5: 7-Bromo-2-chloro-4-morpholin-4-yl-pyrido[3,2-d]pyrimidine

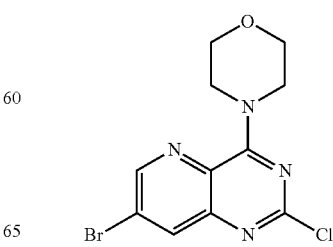

To an ice cold solution of crude 7-bromo-2,4-dichloro-pyrido[3,2-d]pyrimidine (2.85 g, 0.0102 mol) in DCM (25 mL) at 0° C. was added morpholine (1.8 g, 0.0204 mol). The reaction was continued at 0° C. for 30 min. The volatiles were evaporated and subjected to column chromatography (60-120 silica gel, 0-12% ethyl acetate in hexane) to get the title compound as a light yellow solid [0.35 g, 26%]. $^1$H NMR (300 MHz, DMSO-$d_6$): δ 8.68 (d, J=2.7 Hz, 1H), 8.19 (d, J=2.4 Hz, 1H), 3.86-3.89 (m, 8H); LC-MS (ESI): Calculated mass: 328.0; Observed mass: 330.8 [M+H]$^+$ (RT: 1.50 min).

Step 6: 2-Chloro-4-morpholin-4-yl-7-pyrimidin-5-yl-pyrido[3,2-d]pyrimidine

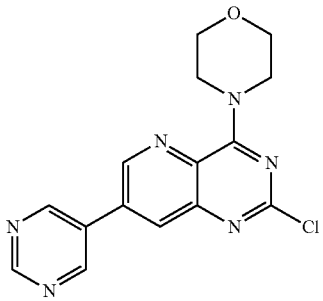 [SMILES: Clc1nc(N2CCOCC2)c2ncc(-c3cncnc3)cc2n1]

To a 50 mL round bottom flask, 7-bromo-2-chloro-4-morpholin-4-yl-pyrido[3,2-d]pyrimidine (120 mg, 0.0003647 mol), pyrimidine-5-boronic acid (40.4 mg, 0.0003282 mol), sodium carbonate (57.9 mg, 0.0005471 mol), DMF (5 mL) and water (3 mL) were added and the reaction vessel degassed with nitrogen for 5-10 min. To the same reaction mixture, Pd(PPh$_3$)$_2$Cl$_2$ (15 mg, 0.0003 mol) was added and again degassed with nitrogen for 5-10 min. The reaction mixture was stirred at 95° C. for 2 h. The reaction mixture was cooled and diluted with ethyl acetate. The organic layer was washed with water, brine and dried over sodium sulfate. The solvent was removed under reduced pressure to afford the crude product. The crude product was purified using column chromatography (60-120 silica gel, 0-1.5% MeOH in chloroform) to yield the desired product [55 mg, 43%]. $^1$H NMR (300 MHz, CDCl$_3$): δ 9.35 (s, 1H), 9.08 (s, 2H), 8.91 (d, J=2.1 Hz, 1H), 8.22 (d, J=2.7 Hz, 1H), 3.89-3.92 (m, 8H); LC-MS (ESI): Calculated mass: 328.1; Observed mass: 329.1 [M+H]$^+$ (RT: 0.56 min).

Step 7: N,N-Dimethyl-4-{3-[4-(4-morpholin-4-yl-7-pyrimidin-5-yl-pyrido[3,2-d]pyrimidin-2-yl)-phenyl]-ureido}-benzamide

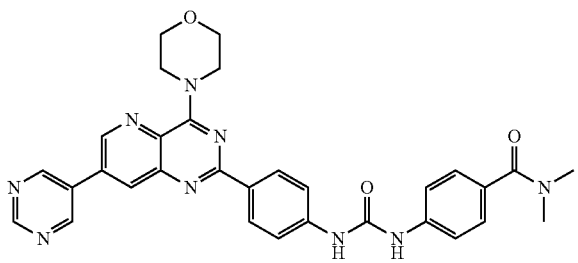 [SMILES: CN(C)C(=O)c1ccc(NC(=O)Nc2ccc(-c3nc(N4CCOCC4)c4ncc(-c5cncnc5)cc4n3)cc2)cc1]

To a 50 mL round bottom flask, 2-chloro-4-morpholin-4-yl-7-pyrimidin-5-yl-pyrido[3,2-d]pyrimidine (50 mg, 0.0001521 mol), N,N-dimethyl-4-{3-{4-(4,4,5,5,-tetramethyl-[1,3,2]dioxaborolan-2-yl)-phenyl]-ureido}-benzamide (93.4 mg, 0.0002282 mol), cesium carbonate (99.2 mg, 0.0003042 mol), DMF (5 mL) and water (2.5 mL) were added. The reaction mixture was degassed with nitrogen for 5-10 min. To the same reaction flask, Pd(PPh$_3$)$_2$Cl$_2$ (5.4 mg, 0.0000076 mol) was added and again degassed with nitrogen for 5-10 min. The reaction mixture was stirred at 90° C. for 2.5 h. The reaction mixture was cooled and diluted with ethyl acetate. The organic layer was washed with water, brine and dried over sodium sulfate. The solvent was removed under reduced pressure to afford the crude product. The crude product was purified using column chromatography (60-120 silica gel, 0-4% MeOH in chloroform) and preparative TLC (10% MeOH in chloroform) to afford pure compound (12 mg, 80%). This compound was subjected to prep HPLC using 10 mol % ammonium acetate in water to afford the title compound as light yellow solid [5 mg, 6%]. $^1$H NMR (300 MHz, DMSO-$d_6$): δ 9.30 (s, 1H) 9.18 (s, 2H), 9.00 (s, 1H), 8.93 (s, 1H), 8.44 (d, J=8.7 Hz, 2H), 8.22 (d, J=7.5 Hz, 1H), 7.95 (d, J=11.4 Hz, 1H), 7.63 (d, J=8.4 Hz, 2H), 7.51 (d, J=8.4 Hz, 2H), 7.36 (d, J=8.7 Hz, 2H), 3.86 (s, 8H), 2.97 (s, 6H); LC-MS (ESI): Calculated mass: 575.2; Observed mass: 576.2 [M+H]$^+$ (RT: 0.28 min).

Example 10

5-(2-(4-(3-(4-(dimethylcarbamoyl)phenyl)ureido)phenyl)-4-morpholino-quinazolin-7-yl)furan-2-carboxylic acid

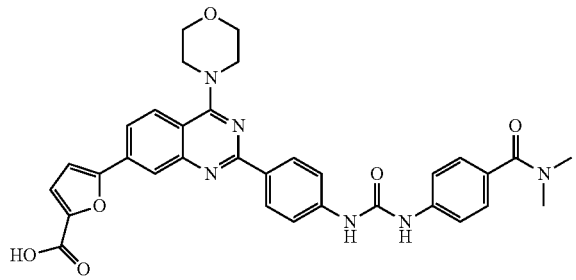 [SMILES: CN(C)C(=O)c1ccc(NC(=O)Nc2ccc(-c3nc(N4CCOCC4)c4ccc(-c5ccc(C(=O)O)o5)cc4n3)cc2)cc1]

Step 1: 5-(2-chloro-4-morpholino-quinazolin-7-yl)furan-2-carbaldehyde

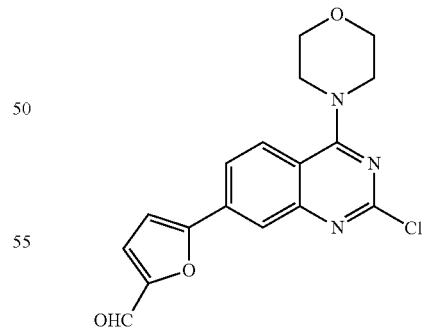

To a 50 mL round bottom flask, 7-bromo-2-chloro-4-morpholin-4-yl-quinazoline (Example 1; 1.0 g, 0.00304 mol) and 5-formyl-2-furanylboronic acid (0.384 g, 0.00274 mol), sodium carbonate (0.806 g, 0.0076 mol), toluene (15 mL), EtOH (15 mL) and water (5 mL) were added. The reaction mixture was degassed with nitrogen for 5-10 min. To the same reaction mixture, Pd(PPh$_3$)$_2$Cl$_2$ (0.105 g, 0.000152 mol) was added and again degassed with nitrogen for 5-10 min. The reaction mixture was stirred at 75° C. for 2.5 h. The reaction mixture was cooled and diluted with ethyl acetate. The organic layer was washed with water, brine and dried over anhydrous sodium sulfate. The solvent was removed under reduced pressure to afford the crude product. The crude product was purified; using column chromatography (60-120 silica gel, 75% ethyl acetate in hexane) to yield the desired product [0.65 g, 62%]. ¹H NMR (300 MHz, CDCl₃): δ 9.73 (s, 1H), 8.20 (s, 1H), 7.90 (s, 2H), 7.38 (d, J=3.6 Hz, 1H), 7.06 (d, J=3.6 Hz, 1H), 3.91 (s, 4H), 3.90 (s, 4H). LC-MS (ESI): Calculated mass: 343.0; Observed mass: 344.3 (RT: 1.21 min).

Step 2: methyl 5-(2-chloro-4-morpholino-quinazolin-7-yl)furan-2-carboxylate

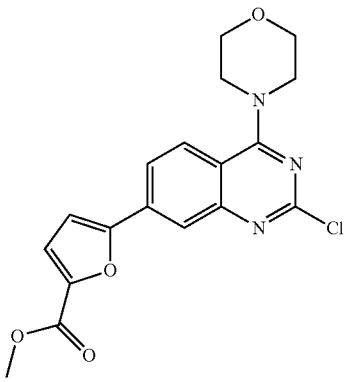 [SMILES: COC(=O)c1ccc(-c2ccc3c(N4CCOCC4)nc(Cl)nc3c2)o1]

To a 100 mL flask, 5-(2-chloro-4-morpholino-quinazolin-7-yl)furan-2-carbaldehyde (0.6 g, 0.0017 mol) in MeOH (60 mL) was added and cooled to 0° C. To the reaction flask, manganese (IV) oxide (0.74 g, 0.0085 mol) and sodium cyanide (0.429 g, 0.0085 mol) were added at 0° C. The reaction mixture was stirred at 25° C. for 3 h. The reaction mixture was diluted with chloroform and filtered through a pad of Celite® reagent. The filtrate was washed with water, brine, dried over anhydrous sodium sulfate and evaporated under reduced pressure to get the title compound as a solid [0.52 g, 79%]. ¹H NMR (300 MHz, CDCl₃): δ 8.18 (s, 1H), 7.87-7.86 (m, 2H), 7.29 (d, J=3.6 Hz, 1H), 6.95 (d, J=3.6 Hz, 1H), 3.93 (s, 3H), 3.89 (s, 8H). LC-MS (ESI): Calculated mass: 373.1; Observed mass: 374.1 (RT: 1.57 min).

Step 3: methyl 5-(2-(4-(3-(4-(dimethylcarbamoyl)phenyl)ureido)phenyl)-4-morpholino-quinazolin-7-yl) furan-2-carboxylate

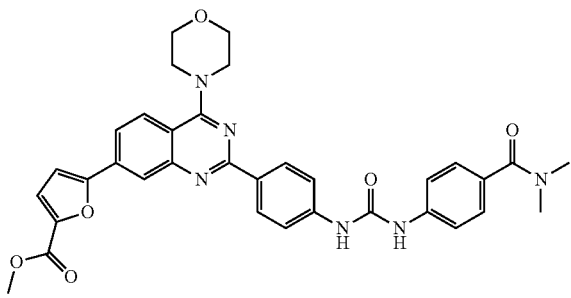

To a 50 mL round bottom flask, methyl 5-(2-chloro-4-morpholino-quinazolin-7-yl)furan-2-carboxylate (0.2 g, 0.00053 mol), N,N-dimethyl-4-{3-{4-(4,4,5,5,-tetramethyl-[1,3,2]dioxaborolan-2-yl)-phenyl]-ureido}-benzamide (0.262 g, 0.00064 mol), cesium carbonate (0.43 g, 0.00133 mol), toluene (10 mL), EtOH (10 mL), and water (5 mL) were added. The reaction mixture was degassed with nitrogen for 5-10 min. To the same reaction flask, Pd(PPh₃)₂Cl₂ (0.0186 g, 0.000026 mol) was added and again degassed with nitrogen for 5-10 min. The reaction mixture was stirred at 75° C. for 3 h. The reaction mixture was cooled, diluted with chloroform, washed with water, brine and dried over anhydrous sodium sulfate. The organic layer was evaporated under reduced pressure to afford the crude product. The crude product was purified using column chromatography using 60-120 silica gel and 4% MeOH in chloroform followed by recrystallization with MeOH to yield the title compound [0.18 g, 54%]. ¹H NMR (300 MHz, DMSO-d₆): δ 9.01 (s, 1H), 8.94 (s, 1H), 8.44 (d, J=8.7 Hz, 2H), 8.22 (s, 1H), 8.10 (d, J=9.0 Hz, 1H), 7.87 (dd, J'=8.7, J''=1.5 Hz, 1H), 7.62 (d, J=8.7 Hz, 2H), 7.52 (d, J=8.7 Hz, 2H), 7.42 (s, 1H), 7.37 (d, J=8.4 Hz, 2H), 7.31 (s, 1H), 3.86 (s, 3H), 3.83 (s, 8H), 2.94 (s, 6H). LC-MS (ESI): Calculated mass: 620.2; Observed mass: 621.1 (RT: 0.72 min).

Step 4: 5-(2-(4-(3-(4-(dimethylcarbamoyl)phenyl)ureido)phenyl)-4-morpholino-quinazolin-7-yl)furan-2-carboxylic acid (See, Scheme 11)

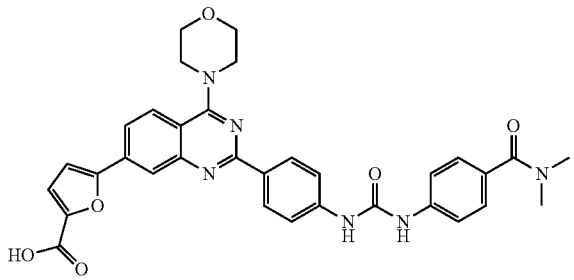 [SMILES: CN(C)C(=O)c1ccc(NC(=O)Nc2ccc(-c3nc(N4CCOCC4)c4ccc(-c5ccc(C(=O)O)o5)cc4n3)cc2)cc1]

To a 100 mL round bottom flask, methyl 5-(2-(4-(3-(4-(dimethylcarbamoyl)phenyl)ureido)phenyl)-4-morpholino-quinazolin-7-yl)furan-2-carboxylate (0.1 g, 0.00016 mol) in MeOH (2 mL), THF (2 mL) and water (2 mL) was added. Subsequently, lithium hydroxide monohydrate (0.034 g, 0.0008 mol) was added and stirred at 25° C. for 12 h. The volatiles were evaporated under reduced pressure, the residue redissolved in water and acidified with 2 N HCl to obtain a pH of 5.0. The volatiles were evaporated under reduced pressure and the residue was stirred with water and filtered. The obtained solid was washed with MeOH to yield the title compound [0.06 g, 61%]. ¹H NMR (300 MHz, DMSO-d₆): δ 12.12 (s, 1H), 8.57 (s, 1H), 8.54 (s, 1H), 8.25 (s, 1H), 8.05 (d, J=9.0 Hz, 2H), 7.97 (d, J=7.5 Hz, 2H), 7.87 (d, J=8.4 Hz, 1H), 7.79 (d, J=8.4 Hz, 2H), 7.37 (d, J=8.4 Hz, 2H), 7.28 (s, 2H), 7.04 (s, 1H), 3.85 (s, 8H), 2.98 (s, 6H). LC-MS (ESI): Calculated mass: 606.2; Observed mass: 607.2 (RT: 0.63 min).

Example 11

N,N-dimethyl-4-(3-(4-(7-(5-(4-methylpiperazine-1-carbonyl)furan-2-yl)-4-morpholino-quinazolin-2-yl)phenyl)ureido)-benzamide (See, Scheme 11)

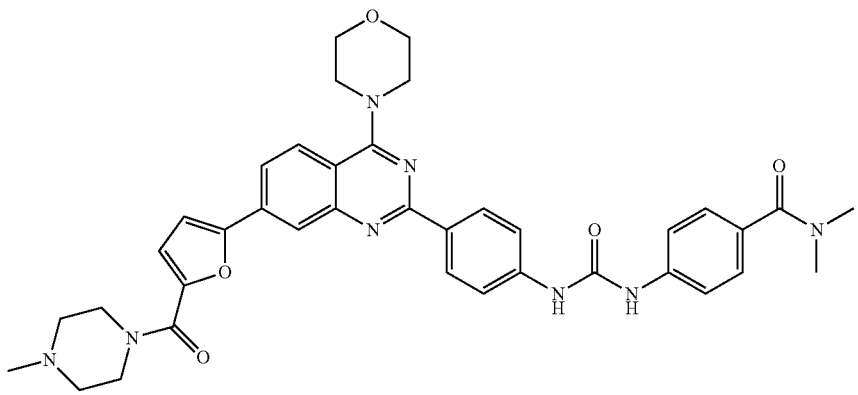

To a 50 mL round bottom flask, 5-(2-(4-(3-(4-(dimethylcarbamoyl)phenyl)ureido)phenyl)-4-morpholino-quinazolin-7-yl)furan-2-carboxylic acid (0.1 g, 0.00016 mol; Example 10) and N-methyl piperazine (0.024 g, 0.00024 mol) in DMF (5 mL) was added. To the flask, HATU (0.153 g, 0.0004 and TEA (0.067 mL, 0.00048 mol) were added. The reaction mass was stirred at room temperature for 12 h. To the reaction mass, ice cold water was added to provide the solid. The obtained solid was collected by filtration. The crude product was purified by column chromatography using 60-120 silica gel and 5% MeOH in chloroform. The solid was washed with MeOH and filtered to yield the desired product [0.01 g, 9%]. $^1$H NMR (300 MHz, DMSO-$d_6$): δ 9.11 (s, 1H), 9.05 (s, 1H), 8.43 (d, J=8.4 Hz, 2H), 8.14 (s, 1H), 8.07 (d, J=9.0 Hz, 1H), 7.81 (s, 1H), 7.62 (d, J=8.4 Hz, 2H), 7.52 (d, J=8.1 Hz, 2H), 7.43 (d, J=3.3 Hz, 1H), 7.36 (d, J=8.4 Hz, 2H), 7.16 (d, J=3.3 Hz, 1H), 3.82-3.54 (m, 16H), 2.94 (s, 6H), 2.39 (s, 3H). LC-MS (ESI): Calculated mass: 688.3; Observed mass: 689.3 (RT: 0.10 min).

Example 12

4-(3-(4-(7-(5-cyanofuran-2-yl)-4-morpholino-quinazolin-2-yl)-3-fluorophenyl)ureido)-N,N-dimethyl-benzamide (See, Scheme 11)

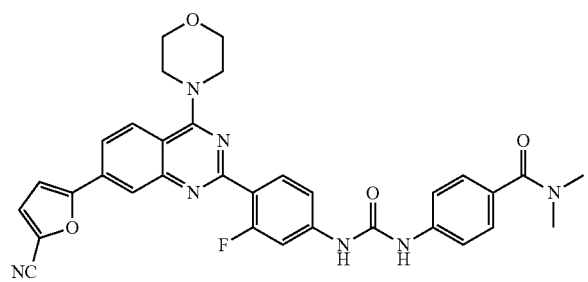 [SMILES: CN(C)C(=O)c1ccc(NC(=O)Nc2ccc(-c3nc(N4CCOCC4)c4ccc(-c5ccc(C#N)o5)cc4n3)c(F)c2)cc1]

Step 1: 5-(2-chloro-4-morpholino-quinazolin-7-yl)furan-2-carbonitrile

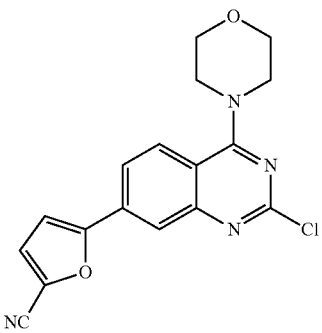 [SMILES: N#Cc1ccc(-c2ccc3c(N4CCOCC4)nc(Cl)nc3c2)o1]

To a 50 mL round bottom flask, 5-(2-chloro-4-morpholino-quinazolin-7-yl)furan-2-carbaldehyde (0.48 g, 0.0014 mol; prepared in a similar method to that described in Example 10) and THF (10 mL) were added. To the same flask, iodine (0.39 g, 0.00154 mol) and 30% aqueous ammonia (9.6 mL) were added. The reaction mixture was stirred at 25° C. The light brown reaction mixture turned yellow after 3 h. The reaction was quenched by adding ethyl acetate (100 mL) and 10% aqueous sodium thiosulfate (40 mL) and stirred for 5 min. The organic layer was separated, washed with water, dried over anhydrous sodium sulfate and evaporated under reduced pressure to get the crude product. The crude product was purified using column chromatography (60-120 silica gel, 10-50% ethyl acetate in hexane) to yield the desired product as an off white solid [0.31 g, 65%]. $^1$H NMR (300 MHz, CDCl$_3$): δ 8.11 (s, 1H), 7.92 (d, J=9.0 Hz, 1H), 7.78 (d, J=9.0

Hz, 1H), 7.24 (d, J=3.6 Hz, 1H), 6.95 (d, J=3.6 Hz, 1H), 3.95 (s, 8H). LC-MS (ESI): Calculated mass: 340.0; Observed mass: 341.0 (RT: 1.55 min).

Step 2: 4-(3-(4-(7-(5-cyanofuran-2-yl)-4-morpholino-quinazolin-2-yl)-3-fluorophenyl)ureido)-N,N-dimethyl-benzamide

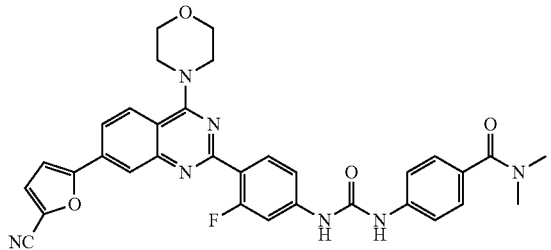 [SMILES: CN(C)C(=O)c1ccc(NC(=O)Nc2ccc(-c3nc(N4CCOCC4)c4ccc(-c5ccc(C#N)o5)cc4n3)c(F)c2)cc1]

To a 50 mL round bottom flask, 5-(2-chloro-4-morpholino-quinazolin-7-yl)furan-2-carbonitrile (0.12 g, 0.00035 mol), 4-(3-(3-fluoro-4-(4,4,5,5-tetramethyl-1,3,2-dioxaborolan-2-yl)phenyl)ureido)-N,N-dimethyl-benzamide (0.144 g, 0.00053 mol), cesium carbonate (0.228 g, 0.0007 mol), DMF (3 mL) and water (3 mL) were added. The reaction mixture was degassed with nitrogen for 5-10 min. To the same reaction flask, Pd(PPh$_3$)$_2$Cl$_2$ (0.013 g, 0.0000175 mol) was added and again degassed with nitrogen for 5-10 min. The reaction mixture was stirred at 95° C. for 2 h. To the cooled reaction mixture, water was added and extracted with ethyl acetate. The organic layer was separated, washed with water, brine and dried over anhydrous sodium sulfate. The organic layer was evaporated under reduced pressure to afford the crude product. The crude product was purified by column chromatography using 60-120 silica gel and 2-5% MeOH in chloroform to obtain the title compound [0.013 g, 6%]. $^1$H NMR (400 MHz, DMSO-d$_6$): δ 9.21 (s, 1H), 9.04 (s, 1H), 8.27 (d, J=2.0 Hz, 1H), 8.19-8.13 (m, 2H), 7.93 (dd, J'=1.6, J"=8.4 Hz, 1H), 7.82 (d, J=4.0 Hz, 1H), 7.64 (d, J=3.6 Hz, 2H), 7.61 (d, J=2.0 Hz, 1H), 7.54 (d, J=8.4 Hz, 2H), 7.28 (dd, J'=8.8 Hz, J"=2.0 Hz, 2H), 3.83 (s, 8H), 2.96 (s, 6H). LC-MS (ESI): Calculated mass: 605.2; Observed mass: 606.2 (RT: 1.17 min).

Example 13

4-(3-(4-(7-(5-acetylfuran-2-yl)-4-morpholino-quinazolin-2-yl)phenyl)ureido)-2-fluoro-N,N-dimethyl-benzamide (See, Scheme 11)

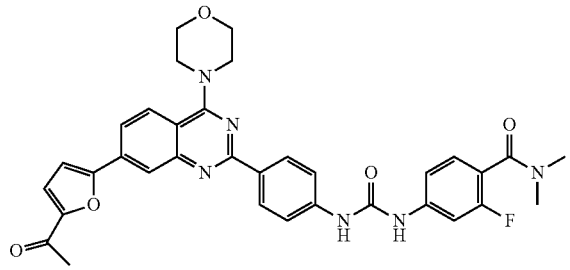 [SMILES: CC(=O)c1ccc(-c2ccc3c(N4CCOCC4)nc(-c4ccc(NC(=O)Nc5ccc(C(=O)N(C)C)c(F)c5)cc4)nc3c2)o1]

Step 1: 1-(5-(2-chloro-4-morpholino-quinazolin-7-yl)furan-2-yl)ethanol

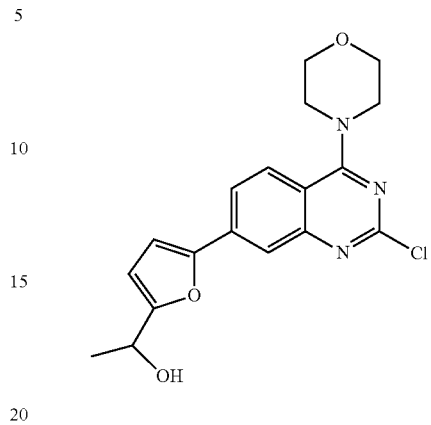

To a 50 mL round bottom flask, 5-(2-chloro-4-morpholino-quinazolin-7-yl)furan-2-carbaldehyde (0.5 g, 0.001457 mol) and THF (25 mL) was added and cooled to 0° C. To the flask was slowly added 1.5 M methyl magnesium bromide in diethyl ether (0.145 mL, 0.002186 mol). The resulting reaction mixture was stirred at room temperature for 3 h. The reaction was quenched with water and extracted with ethyl acetate (3×50 mL). The organic layer was dried over anhydrous sodium sulfate and evaporated to provide the crude product. The crude product was purified by column chromatography using 60-120 silica gel and 40% ethyl acetate in hexane [0.3 g, 57%]. $^1$H NMR (300 MHz, CDCl$_3$): δ 8.05 (d, J=1.2 Hz, 1H), 7.83 (d, J=6.3 Hz, 1H), 7.71 (dd, J'=6.6, J"=1.2 Hz, 1H), 6.82 (d, J=2.4 Hz, 1H), 6.40 (d, J=2.7 Hz, 1H), 4.91 (q, J=4.8 Hz, 1H), 3.89 (s, 8H), 1.63 (d, J=4.8 Hz, 3H). LC-MS (ESI): Calculated mass: 359.1; Observed mass: 360.1 (RT: 1.58 min).

Step 2: 1-(5-(2-chloro-4-morpholino-quinazolin-7-yl)furan-2-yl)ethanone

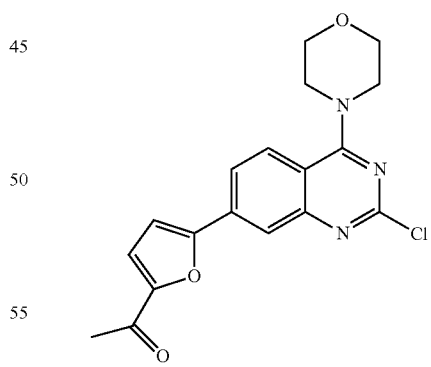

To a 50 mL round bottom flask, (5-(2-chloro-4-morpholino-quinazolin-7-yl) furan-2-yl) EtOH (0.3 g, 0.00084 mol) and DCM (50 mL) were added. To the flask, manganese (IV) oxide (0.36 g, 0.0042 mol) was added. The reaction mixture was stirred at room temperature for 12 h. The reaction mass was filtered through a pad of Celite® reagent. The filtrate was evaporated to get the title compound [0.25 g, 84%]. $^1$H NMR (300 MHz, CDCl$_3$): δ 8.20 (s, 1H), 7.91 (d, J=8.7 Hz, 1H), 7.84 (d, J=8.7 Hz, 1H), 7.30 (d, J=3.6 Hz, 1H), 6.99 (d, J=3.6 Hz, 1H), 3.90 (s, 8H), 2.56 (s, 3H). LC-MS (ESI): Calculated mass: 357.1; Observed mass: 358.1 (RT: 1.35 min).

Step 3: 4-(3-(4-(7-(5-acetylfuran-2-yl)-4-morpholino-quinazolin-2-yl)phenyl)ureido)-2-fluoro-N,N-dimethyl-benzamide

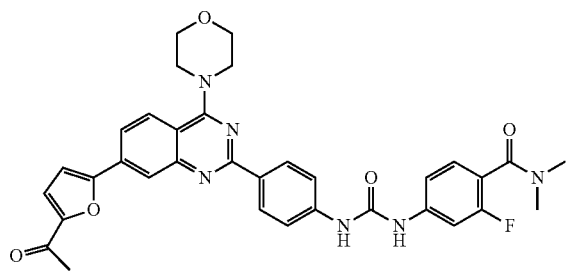 [SMILES: CC(=O)c1ccc(-c2ccc3c(N4CCOCC4)nc(-c4ccc(NC(=O)Nc5ccc(C(=O)N(C)C)c(F)c5)cc4)nc3c2)o1]

To a 50 mL round bottom flask, 1-(5-(2-chloro-4-morpholino-quinazolin-7-yl)furan-2-yl)ethanone (0.1 g, 0.00028 mol), 2-fluoro-N,N-dimethyl-4-(3-(4-(4,4,5,5-tetramethyl-1,3,2-dioxaborolan-2-yl)phenyl)ureido)-benzamide (0.144 g, 0.00034 mol), cesium carbonate (0.228 g, 0.0007 mol), toluene (7 mL) and EtOH (7 mL), and water (3 mL) were added. The reaction mixture was degassed with nitrogen for 5-10 min. To the same reaction flask, Pd(PPh$_3$)$_2$Cl$_2$ (0.0098 g, 0.000014 mol) was added and again degassed with nitrogen for 5-10 min. The reaction mixture was stirred at 75° C. for 3 h. The reaction mixture was cooled, diluted with chloroform, washed with water, brine and dried over anhydrous sodium sulfate. The organic layer was evaporated under reduced pressure to afford the crude product. The crude product was purified by column chromatography using 60-120 silica gel and 4% MeOH in chloroform. The compound was further purified by prep HPLC using 10 mM ammonium acetate in water and ACN to obtain the title compound [0.01 g, 6%]. $^1$H NMR (400 MHz, DMSO-d$_6$): δ 9.04 (s, 1H), 8.96 (s, 1H), 8.46 (d, J=8.4 Hz, 2H), 8.28 (s, 1H), 8.13 (d, 1H, J=8.8 Hz), 7.92 (d, J=8.4 Hz, 1H), 7.64 (d, J=8.4 Hz, 3H), 7.55-7.52 (m, 3H), 7.38 (d, J=8.0 Hz, 2H), 3.85 (s, 8H), 2.97 (s, 6H), 2.56 (s, 3H). LC-MS (ESI): Calculated mass: 622.2; Observed mass: 623.2 (RT: 0.45 min).

Example 14

4-(3-(2,3-difluoro-4-(7-(1-methyl-1H-pyrazol-4-yl)-4-morpholino-pyrido[3,2-d]pyrimidin-2-yl)phenyl)ureido)-N,N-dimethyl-benzamide

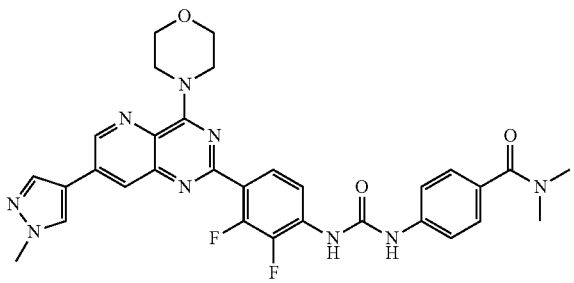 [SMILES: CN(C)C(=O)c1ccc(NC(=O)Nc2ccc(-c3nc(N4CCOCC4)c4ncc(-c5cnn(C)c5)cc4n3)c(F)c2F)cc1]

To a 50 mL round bottom flask, 4-(2-chloro-7-(1-methyl-1H-pyrazol-4-yl)pyrido[3,2-d]pyrimidin-4-yl)morpholine (0.1 g, 0.0003 mol), 4-(3-(2,3-difluoro-4-(4,4,5,5-tetramethyl-1,3,2-dioxaborolan-2-yl)phenyl)ureido)-N,N-dimethyl-benzamide (0.16 g, 0.00036 mol), cesium carbonate (0.244 g, 0.00075 mol), toluene (7 mL), EtOH (7 mL), and water (3 mL) were added. The reaction mixture was degassed with nitrogen for 5-10 min. To the same reaction flask, Pd(PPh$_3$)$_2$Cl$_2$ (0.0105 g, 0.000015 mol) was added and again degassed with nitrogen for 5-10 min. The reaction mixture was stirred at 75° C. for 3 h. To the cooled reaction mixture, ice cold water was added to obtain the solid. The crude product was obtained by the filtration of the solid. The crude product was purified by column chromatography using 60-120 silica gel and 4% MeOH in chloroform to isolate the product. The isolated product was washed with MeOH and filtered. The compound was further purified by prep TLC using 7% MeOH in chloroform to yield the title compound [0.02 g, 11%]. $^1$H NMR (400 MHz, DMSO-d$_6$): δ 9.38 (brs, 1H), 9.09 (d, J=2.0 Hz, 1H), 9.01 (brs, 1H), 8.53 (s, 1H), 8.32 (d, J=2.0 Hz, 1H), 8.24 (s, 1H), 8.14-7.97 (m, 2H), 7.54 (d, J=8.4 Hz, 2H), 7.40 (d, J=8.4 Hz, 2H), 4.49 (brs, 4H), 3.92 (s, 3H), 3.81 (brs, 1H), 2.96 (s, 6H). LC-MS (ESI): Calculated mass: 613.2; Observed mass: 614.2 (RT: 0.63 min).

Example 15

4-(3-(2-fluoro-4-(7-(5-(1-hydroxyethyl)furan-2-yl)-4-morpholino-pyrido[3,2-d]pyrimidin-2-yl)phenyl)ureido)-N,N-dimethyl-benzamide (See, Scheme 11)

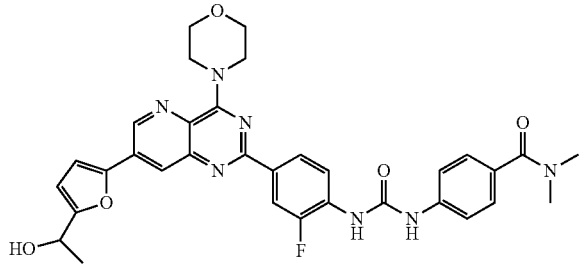 [SMILES: CC(O)c1ccc(-c2cnc3c(N4CCOCC4)nc(-c4ccc(NC(=O)Nc5ccc(C(=O)N(C)C)cc5)c(F)c4)nc3c2)o1]

Step 1: 5-(2-chloro-4-morpholino-pyrido[3,2-d]pyrimidin-7-yl)furan-2-carbaldehyde

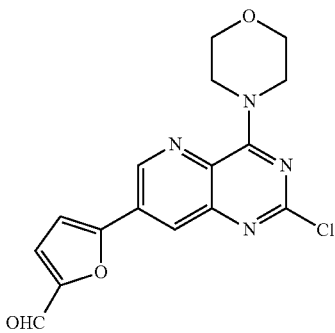 [SMILES: O=Cc1ccc(-c2cnc3c(N4CCOCC4)nc(Cl)nc3c2)o1]

To a 50 mL round bottom flask, 4-(7-bromo-2-chloropyrido[3,2-d]pyrimidin-4-yl)morpholine (1.0 g, 0.00303 mol; prepared as described in Scheme 7A) and 5-formyl-2-furanylboronic acid (0.38 g, 0.00273 mol), sodium carbonate (0.64 g, 0.00606 mol) toluene (5 mL), EtOH (5 mL) and water (5 mL) were added. The reaction vessel was degassed with nitrogen for 5-10 min. To the same reaction mixture, Pd(PPh$_3$)$_2$Cl$_2$ (0.106 g, 0.0001515 mol) was added and again degassed with nitrogen for 5-10 min. The reaction mixture was stirred at 90° C. for 2 h. The reaction mixture was cooled and diluted with chloroform. The organic layer was washed with water, brine and dried over sodium sulfate. The solvent was removed under the reduced pressure to afford the crude product. The crude product was purified using column chromatography (60-120 silica gel, chloroform) to yield the desired product as a yellow solid [0.48 g, 46%]. $^1$H NMR (300 MHz, CDCl$_3$): δ 9.77 (s, 1H), 9.12 (d, J=2.1 Hz, 1H), 8.34 (d, J=2.1 Hz, 1H), 7.40 (d, J=3.6 Hz, 1H), 7.11 (d, J=3.6 Hz, 1H), 4.50 (brs, 4H), 3.91-3.88 (m, 4H); LC-MS (ESI): Calculated mass: 344.1; Observed mass: 345.0 (RT: 1.39 min).

Step 2: 1-(5-(2-chloro-4-morpholino-pyrido[3,2-d]pyrimidin-7-yl)furan-2-yl)ethanol

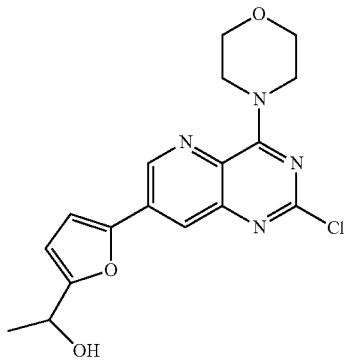 [SMILES: CC(O)c1ccc(-c2cnc3c(N4CCOCC4)nc(Cl)nc3c2)o1]

To a 50 mL round bottom flask, 5-(2-chloro-4-morpholino-pyrido[3,2-d]pyrimidin-7-yl)furan-2-carbaldehyde (0.4 g, 0.0012 mol) and THF (15 mL) were added and cooled to 0-5° C. To the flask was slowly added 3.0 M methyl magnesium bromide in diethyl ether (0.6 mL, 0.0036 mol). The resulting reaction mixture was stirred at room temperature for 2 h. To the reaction mass, water was added and extracted with DCM. The organic layer was dried over anhydrous sodium sulfate and evaporated under reduced to get the crude product. The crude product was purified by column chromatography using 1% MeOH in chloroform [0.17 g, 40%]. LC-MS (ESI): Calculated mass: 360.1; Observed mass: 361.1(RT: 1.29 min).

Step 3: 4-(3-(2-fluoro-4-(7-(5-(1-hydroxyethyl)furan-2-yl)-4-morpholino-pyrido[3,2-d]pyrimidin-2-yl)phenyl)ureido)-N,N-dimethyl-benzamide

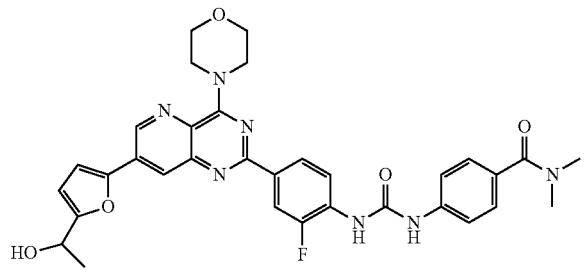 [SMILES: CC(O)c1ccc(-c2cnc3c(N4CCOCC4)nc(-c4ccc(NC(=O)Nc5ccc(C(=O)N(C)C)cc5)c(F)c4)nc3c2)o1]

This compound was prepared by the method as described in Scheme 7B. $^1$H NMR (400 MHz, DMSO-d$_6$): δ 9.38 (s, 1H), 9.12 (d, J=2 Hz, 1H), 8.89 (s, 1H), 8.36-8.34 (m, 1H), 8.28-8.26 (m, 2H), 8.24 (d, J=12.8 Hz, 1H), 7.54 (d, J=8.4 Hz, 2H), 7.40 (d, J=8.4 Hz, 2H), 7.36 (d, J=3.2 Hz, 1H), 6.50 (d, J=3.2 Hz, 1H), 5.51 (d, J=5.2 Hz, 1H), 4.83-4.82 (m, 1H), 4.52 (brs, 4H), 3.84 (brs, 4H), 2.97 (s, 6H), 1.48 (d, 3H, J=6.4 Hz); LC-MS (ESI): Calculated mass: 625.2; Observed mass: 626.2 (RT: 0.92 min).

Example 16

4-(3-(4-(7-(2-hydroxypropan-2-yl)-4-morpholino-quinazolin-2-yl)phenyl)ureido)-N,N-dimethyl-benzamide (See, Scheme 12)

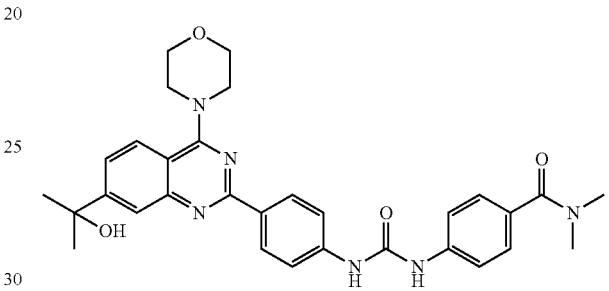

Step 1: 2-(2-chloro-4-morpholino-quinazolin-7-yl)propan-2-ol

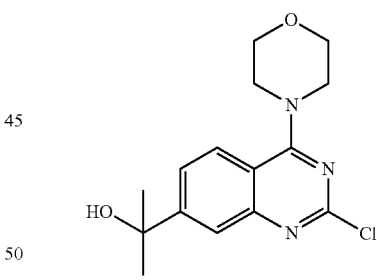

To a 25 mL round bottom flask, methyl 2-chloro-4-morpholino-quinazoline-7-carboxylate (0.5 g, 0.001628 mol; prepared as described in Example 7; Scheme 8A) and anhydrous THF were added and cooled to 0° C. To the flask was added methyl magnesium bromide (4.65 ml of 1.4 M in diethyl ether, 0.006514 mol) drop wise at 0° C. and the reaction mixture was stirred at room temperature for 12 h. The reaction mass was diluted with ethyl acetate and washed with water. The ethyl acetate layer was dried over anhydrous sodium sulfate and evaporated under reduced to get the crude product. The crude product was purified by column chromatography using 60-120 silica gel and 50% ethyl acetate in hexane to yield the title compound [0.28 g, 56%]. $^1$H NMR (300 MHz, CDCl$_3$): δ 7.85 (d, J=1.8 Hz, 1H), 7.87 (d, J=8.7

Hz 1H), 7.64 (dd, J'=2.1, J"=8.7 Hz, 1H), 3.87 (s, 8H), 1.63 (s, 6H). LC-MS (ESI): Calculated mass: 307.78; Observed mass: 308.1 (RT: 0.42 min).

Step 2: 4-(3-(4-(7-(2-hydroxypropan-2-yl)-4-morpholino-quinazolin-2-yl)phenyl)ureido)-N,N-dimethyl-benzamide

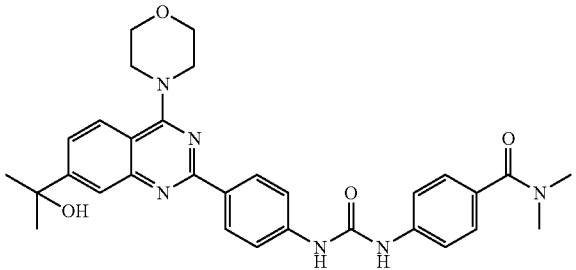 [SMILES: CN(C)C(=O)c1ccc(NC(=O)Nc2ccc(-c3nc(N4CCOCC4)c4ccc(C(C)(C)O)cc4n3)cc2)cc1]

To a 50 mL round bottom flask, 2-(2-chloro-4-morpholino-quinazolin-7-yl) propan-2-ol (0.08 g, 0.00026 mol), N,N-dimethyl-4-[3-{4-(4,4,5,5,-tetramethyl-[1,3,2]dioxaborolan-2-yl)-phenyl]ureido}-benzamide (0.128 g, 0.000312 mol), cesium carbonate (0.169 g, 0.00052 mol), DMF (3 mL) and water (1 mL) were added. The reaction mixture was degassed with nitrogen for 5-10 min. To the same reaction flask, Pd(PPh$_3$)$_2$Cl$_2$ (0.009 g, 0.000013 mol) was added and again degassed with nitrogen for 5-10 min. The reaction mixture was stirred at 95° C. for 5 h. To the cooled reaction mixture, water was added and extracted with ethyl acetate. The organic layer was separated, washed with water, brine and dried over anhydrous sodium sulfate. The organic layer was evaporated under reduced pressure to afford the crude product. The crude product was purified by column chromatography using 60-120 silica gel and 10% MeOH in chloroform. The compound was further purified by prep TLC using 10% MeOH in chloroform to obtain the title compound [0.007 g, 5%]. $^1$H NMR (400 MHz, DMSO-d$_6$): δ 9.02 (s, 1H), 8.97 (s, 1H), 8.44 (d, J=8.8 Hz, 2H), 7.97 (d, J=8.8 Hz, 1H), 7.91 (d, J=1.6 Hz, 1H), 7.97 (d, J=8.8 Hz, 3H), 7.54 (d, J=8.4 Hz, 2H), 7.38 (d, J=8.4 Hz, 2H), 5.30 (s, 1H), 3.83 (brs, 4H), 3.81 (brs, 4H), 2.96 (s, 6H), 1.52 (s, 6H). LC-MS (ESI): Calculated mass: 554.2; Observed mass: 555.1 (RT: 0.17 min).

Example 17

N-(4-(3-(4-(7-(5-methylfuran-2-yl)-4-morpholino-quinazolin-2-yl)phenyl)ureido)phenyl)acetamide (See, Scheme 10)

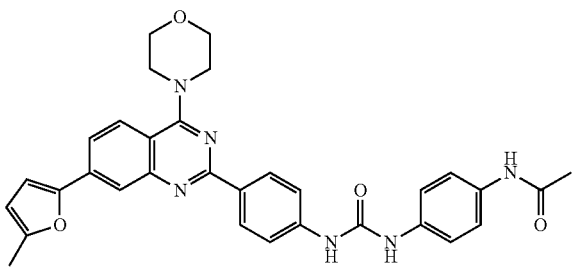 [SMILES: CC(=O)Nc1ccc(NC(=O)Nc2ccc(-c3nc(N4CCOCC4)c4ccc(-c5ccc(C)o5)cc4n3)cc2)cc1]

To a 50 mL round bottom flask, 2-chloro-7-(5-methylfuran-2-yl)-4-morpholin-4-yl-quinazoline (0.15 g, 0.00045 mol; prepared as described in Example 2; Scheme 6B), N-(4-(3-(4-(4,4,5,5-tetramethyl-1,3,2-dioxaborolan-2-yl)phenyl) ureido)phenyl)acetamide (0.23 g, 0.00059 mol; prepared according to the methods described in Scheme 9), cesium carbonate (0.44 g, 0.00135 mol), toluene (10 mL), EtOH (4 mL) and water (2 mL) were added. The reaction mixture was degassed with nitrogen for 5-10 min. To the same reaction flask, Pd (PPh$_3$)$_2$Cl$_2$ (0.022 g, 0.0000315 mol) was added and again degassed with nitrogen for 5-10 min. The reaction mixture was stirred at 95° C. for 3 h. The reaction mixture was cooled to room temperature to get the precipitate. The precipitate was collected by filtration to afford the crude product. The crude product was purified using column chromatography (60-120 silica gel, 3% MeOH in chloroform). The compound was further purified by flash column chromatography using 230-400 silica gel and 1.5% MeOH in chloroform to yield the title compound [0.0252 g, 10%]. $^1$H NMR (400 MHz, DMSO-d$_6$): δ 9.86 (s, 1H), 8.92 (s, 1H), 8.67 (s, 1H), 8.42 (d, J=8.8 Hz, 2H), 8.01 (d, J=8.8 Hz, 2H), 7.74 (d, J=8.4 Hz, 1H), 7.61 (d, J=8.8 Hz, 2H), 7.51 (d, J=8.8 Hz, 2H), 7.39 (d, J=8.8 Hz, 2H), 7.17 (d, J=3.2 Hz, 1H), 6.32 (d, J=2.8 Hz, 1H), 3.83 (s, 4H), 3.80 (s, 4H), 2.41 (s, 3H), 2.02 (s, 3H). LC-MS (ESI): Calculated mass: 562.2; Observed mass: 563.1 (RT: 0.64 min).

Example 18

1-(4-(7-(5-methylfuran-2-yl)-4-morpholino-quinazolin-2-yl)phenyl)-3-(4-(2-oxopyrrolidin-1-yl)phenyl) urea (See, Scheme 10)

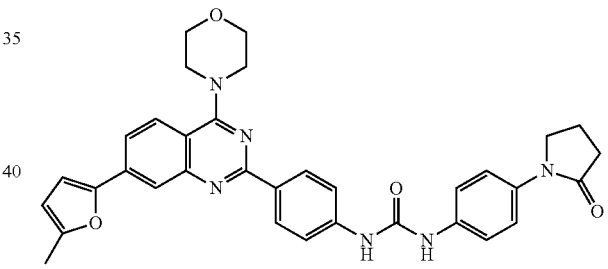

To a 50 mL round bottom flask, 2-Chloro-7-(5-methylfuran-2-yl)-4-morpholin-4-yl-quinazoline (0.12 g, 0.00036 mol; prepared as described in Example 2; Scheme 6B), 1-(4-(2-oxopyrrolidin-1-yl)phenyl)-3-(4-(4,4,5,5-tetramethyl-1,3,2-dioxaborolan-2-yl)phenyl)urea (0.184 g, 0.00043 mol; prepared according to the methods described in Scheme 9), cesium carbonate (0.296 g, 0.0009 mol), toluene (7 mL), EtOH (7 mL) and water (3 mL) were added. The reaction mixture was degassed with nitrogen for 5-10 min. To the same reaction flask, Pd (PPh$_3$)$_2$Cl$_2$ (0.0128 g, 0.000018 mol) was added and again degassed with nitrogen for 5-10 min. The reaction mixture was stirred at 95° C. for 3 h. The reaction mixture was cooled and diluted with chloroform. The organic layer was separated, washed with water, brine and dried over anhydrous sodium sulfate. The solvent was removed under reduced pressure to afford the crude product. The crude product was purified by flash column chromatography using 230-400 silica gel, 2% MeOH in chloroform. The compound was further purified by prep TLC using 4% MeOH in chloroform to yield the title compound [0.015 g, 7%]. $^1$H NMR (300 MHz, DMSO-d$_6$): δ 8.92 (s, 1H), 8.75 (s, 1H), 8.43 (d, J=7.2 Hz, 2H), 8.02 (d, J=8.1 Hz, 2H), 7.75 (d, J=8.4 Hz, 1H), 7.62 (t, J=8.7 Hz, 4H), 7.48 (d, J=9 Hz, 2H), 7.17 (d, J=3.3 Hz, 1H), 6.32 (d, J=2.4 Hz, 1H), 3.83 (m, 10H), 2.47 (d, J=8.4 Hz, 2H), 2.41 (s, 3H), 2.08 (m, 2H); LC-MS (ESI): Calculated mass: 588.2; Observed mass: 589.2 (RT: 0.13 min).

Examples 19-452

Additional compounds listed in Table 1 were prepared in a similar manner, using the methods described for Examples 1 to 18 and in the Schemes 1 to 15. In some cases, compounds were isolated and characterized as the trifluoroacetate salt.

LC-MS characterization data for Examples 1 to 294 are tabulated in Table 2, below. Further additional compounds of the invention, including those described in Examples 295-452, are prepared in a similar manner to the methods described for the Examples 1 to 18 and in Schemes 1 to 15.

TABLE 1

| Ex | Structure | Structure Name | Synthetic Scheme |
|----|-----------|----------------|------------------|
| 1 | 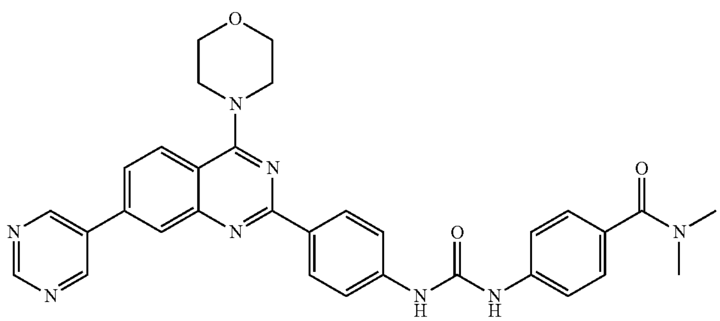 [SMILES: CN(C)C(=O)c1ccc(NC(=O)Nc2ccc(-c3nc(N4CCOCC4)c4ccc(-c5cncnc5)cc4n3)cc2)cc1] | N,N-dimethyl-4-{3-[4-(4-morpholin-4-yl-7-pyrimidin-5-yl-quinazolin-2-yl)-phenyl]-ureido}-benzamide | 6B |
| 2 | 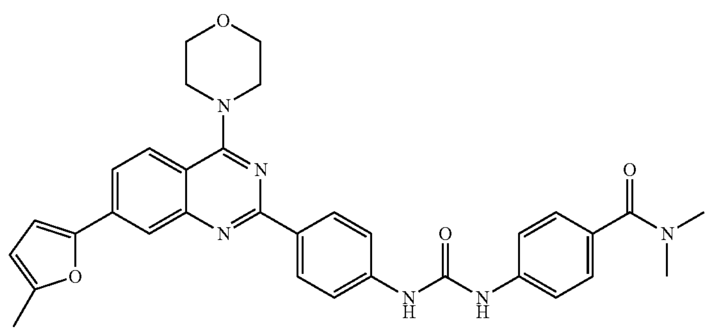 [SMILES: Cc1ccc(-c2ccc3c(N4CCOCC4)nc(-c4ccc(NC(=O)Nc5ccc(C(=O)N(C)C)cc5)cc4)nc3c2)o1] | N,N-dimethyl-4-(3-{4-[7-(5-methyl-furan-2-yl)-4-morpholin-4-yl-quinazolin-2-yl]-phenyl}-ureido)-benzamide | 6B |
| 3 | 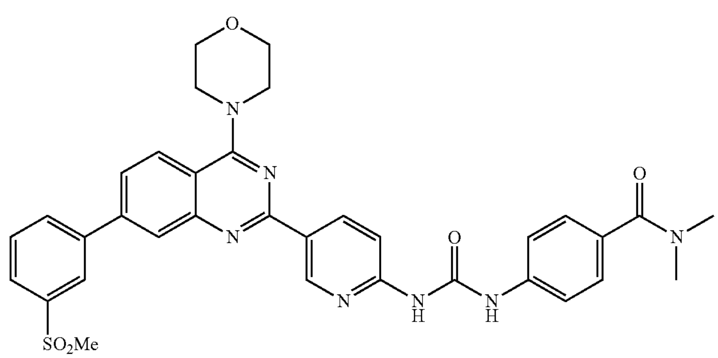 | 4-(3-{5-[7-(3-methanesulfonyl-phenyl)-4-morpholin-4-yl-quinazolin-2-yl]-pyridin-2-yl}-ureido)-N,N-dimethyl-benzamide | 6E |
| 4 | 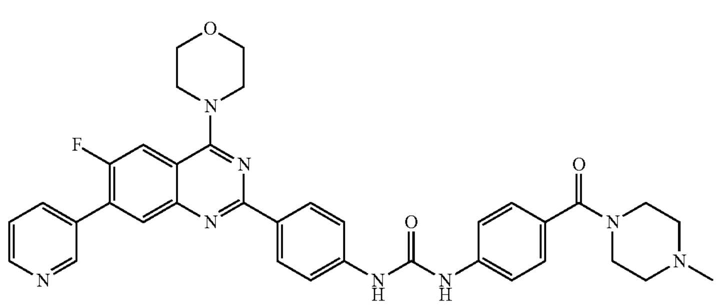 [SMILES: CN1CCN(C(=O)c2ccc(NC(=O)Nc3ccc(-c4nc(N5CCOCC5)c5cc(F)c(-c6cccnc6)cc5n4)cc3)cc2)CC1] | 1-[4-(6-fluoro-4-morpholin-4-yl-7-pyridin-3-yl-quinazolin-2-yl)-phenyl]-3-[4-(4-methyl-piperazine-1-carbonyl)-phenyl]-urea | 6G |

TABLE 1-continued

| Ex | Structure | Structure Name | Synthetic Scheme |
|---|---|---|---|
| 5 | 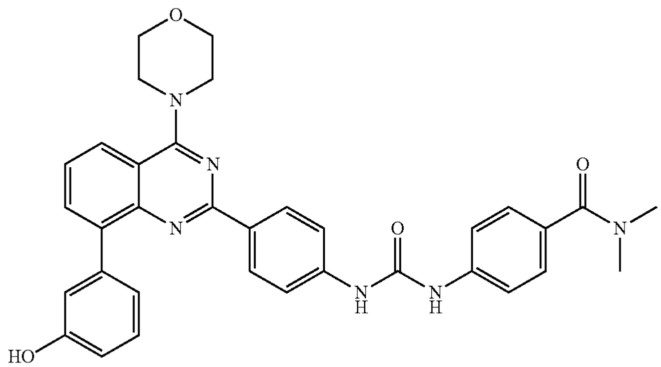 [SMILES: CN(C)C(=O)c1ccc(NC(=O)Nc2ccc(-c3nc(N4CCOCC4)c4cccc(-c5cccc(O)c5)c4n3)cc2)cc1] | 4-(3-{4-[8-(3-hydroxy-phenyl)-4-morpholin-4-yl-quinazolin-2-yl]-phenyl}-ureido)-N,N-dimethyl-benzamide | 6F |
| 6 | 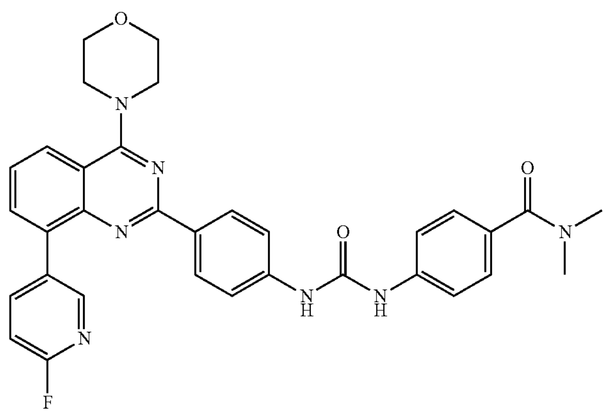 [SMILES: CN(C)C(=O)c1ccc(NC(=O)Nc2ccc(-c3nc(N4CCOCC4)c4cccc(-c5ccc(F)nc5)c4n3)cc2)cc1] | 4-(3-{4-[8-(6-fluoro-pyridin-3-yl)-4-morpholin-4-yl-quinazolin-2-yl]-phenyl}-ureido)-N,N-dimethyl-benzamide | 6F |
| 7 | 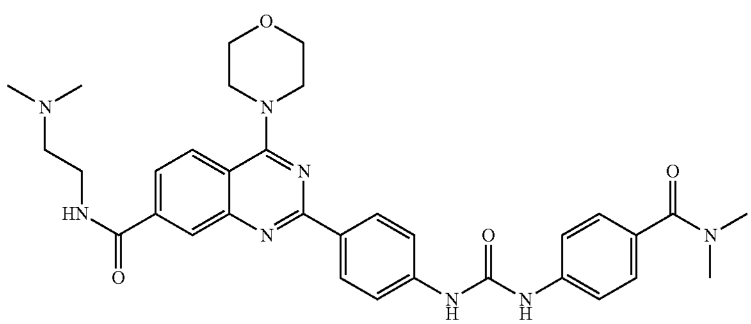 | 2-{4-[3-(4-dimethylcarbamoyl-phenyl)-ureido]-phenyl}-4-morpholin-4-yl-quinazoline-7-carboxylic acid (2-dimethylamino-ethyl)-amide | 8A |
| 8 | 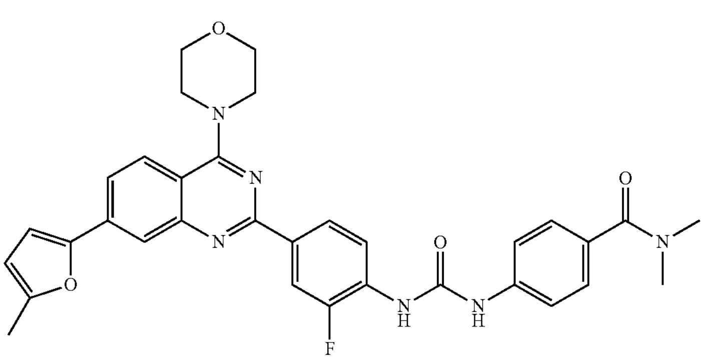 [SMILES: Cc1ccc(-c2ccc3c(N4CCOCC4)nc(-c4ccc(NC(=O)Nc5ccc(C(=O)N(C)C)cc5)c(F)c4)nc3c2)o1] | 4-(3-{2-fluoro-4-[7-(5-methyl-furan-2-yl)-4-morpholin-4-yl-quinazolin-2-yl]-phenyl}-ureido)-N,N-dimethyl-benzamide | 6D |

TABLE 1-continued

| Ex | Structure | Structure Name | Synthetic Scheme |
|---|---|---|---|
| 9 | 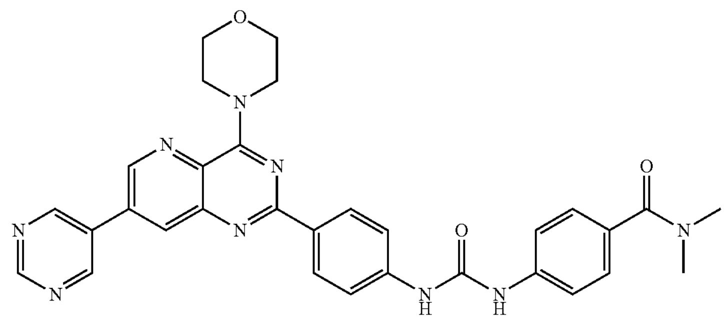 [SMILES: CN(C)C(=O)c1ccc(NC(=O)Nc2ccc(-c3nc(N4CCOCC4)c4ncc(-c5cncnc5)cc4n3)cc2)cc1] | N,N-dimethyl-4-{3-[4-(4-morpholin-4-yl-7-pyrimidin-5-yl-pyrido[3,2-d]pyrimidin-2-yl)-phenyl]-ureido}-benzamide | 7A |
| 10 | 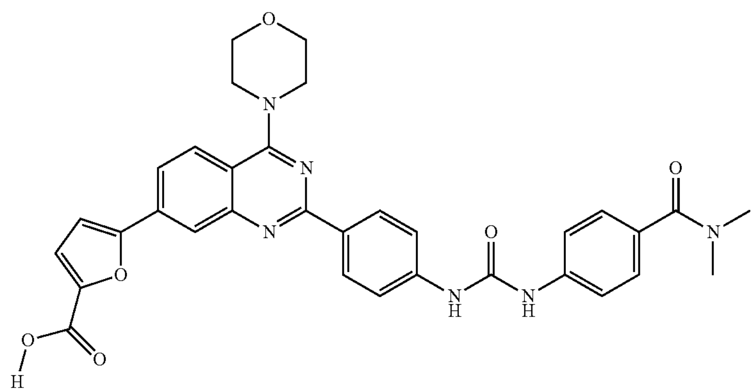 [SMILES: CN(C)C(=O)c1ccc(NC(=O)Nc2ccc(-c3nc(N4CCOCC4)c4ccc(-c5ccc(C(=O)O)o5)cc4n3)cc2)cc1] | 5-(2-(4-(3-(4-(dimethylcarbamoyl)phenyl)ureido)phenyl)-4-morpholine-quinazolin-7-yl)furan-2-carboxylic acid | 11 + 6B |
| 11 | 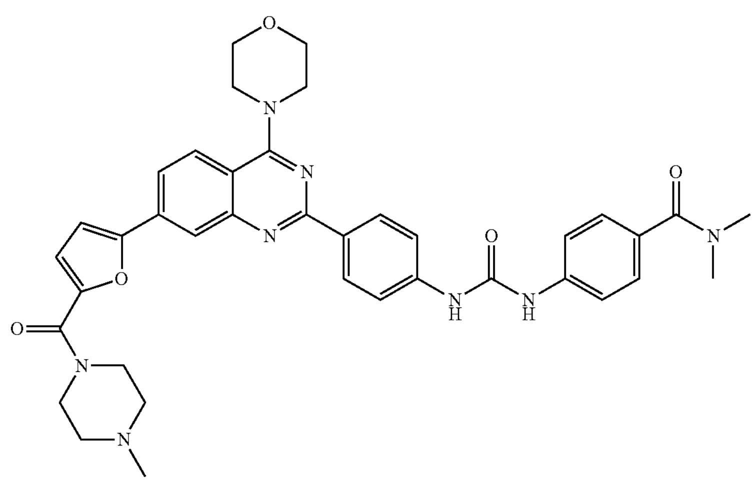 [SMILES: CN1CCN(C(=O)c2ccc(-c3ccc4c(N5CCOCC5)nc(-c5ccc(NC(=O)Nc6ccc(C(=O)N(C)C)cc6)cc5)nc4c3)o2)CC1] | N,N-dimethyl-4-(3-(4-(7-(5-(4-methylpiperazine-1-carbonyl)furan-2-yl)-4-morpholino-quinazolin-2-yl)phenyl)ureido)-benzamide | 11 + 6B |
| 12 | 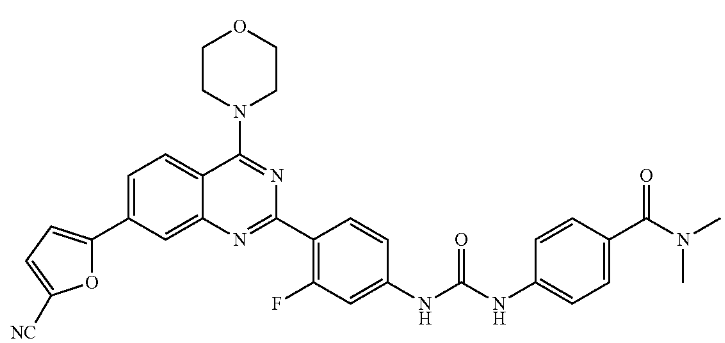 [SMILES: CN(C)C(=O)c1ccc(NC(=O)Nc2ccc(-c3nc(N4CCOCC4)c4ccc(-c5ccc(C#N)o5)cc4n3)c(F)c2)cc1] | 4-(3-(4-(7-(5-cyanofuran-2-yl)-4-morpholino-quinazolin-2-yl)-3-fluorophenyl)ureido)-N,N-dimethyl-benzamide | 11 + 6 |

TABLE 1-continued

| Ex | Structure | Structure Name | Synthetic Scheme |
|---|---|---|---|
| 13 | 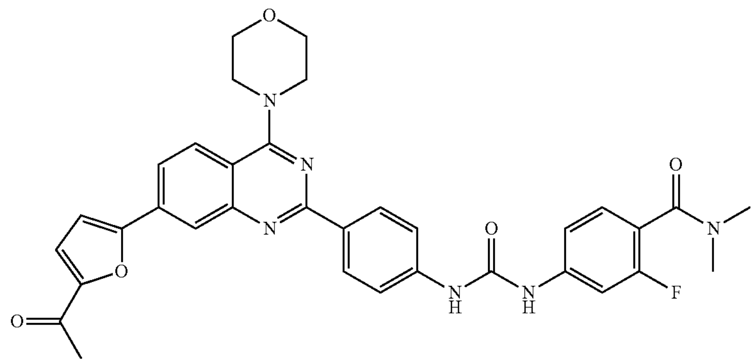 [SMILES: CC(=O)c1ccc(-c2ccc3c(N4CCOCC4)nc(-c4ccc(NC(=O)Nc5ccc(C(=O)N(C)C)c(F)c5)cc4)nc3c2)o1] | 4-(3-(4-(7-(5-acetylfuran-2-yl)-4-morpholino-quinazolin-2-yl)phenyl)ureido)-2-fluoro-N,N-dimethyl-benzamide | 11 + 6 |
| 14 | 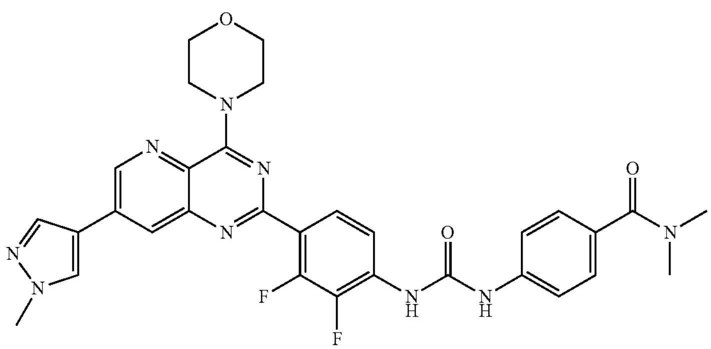 [SMILES: CN(C)C(=O)c1ccc(NC(=O)Nc2ccc(-c3nc(N4CCOCC4)c4ncc(-c5cnn(C)c5)cc4n3)c(F)c2F)cc1] | 4-(3-(2,3-difluoro-4-(7-(1-methyl-1H-pyrazol-4-yl)-4-morpholino-pyrido[3,2-d]pyrimidin-2-yl)phenyl)ureido)-N,N-dimethyl-benzamide | 2 + 7 |
| 15 | 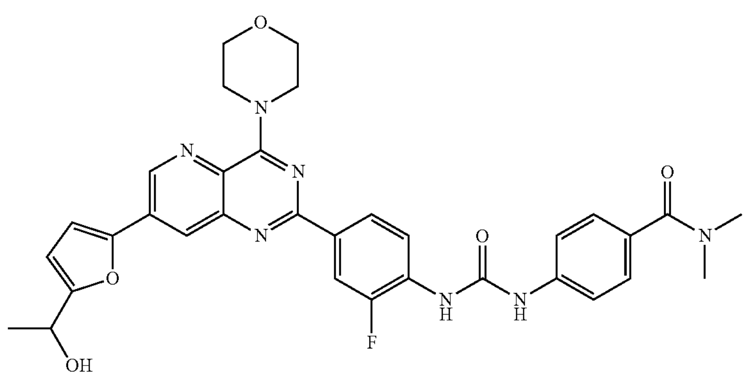 [SMILES: CC(O)c1ccc(-c2cnc3c(N4CCOCC4)nc(-c4ccc(NC(=O)Nc5ccc(C(=O)N(C)C)cc5)c(F)c4)nc3c2)o1] | 4-(3-(2-fluoro-4-(7-(5-(1-hydroxyethyl)furan-2-yl)-4-morpholino-pyrido[3,2-d]pyrimidin-2-yl)phenyl)ureido)-N,N-dimethyl-benzamide | 11 + 7B |
| 16 | 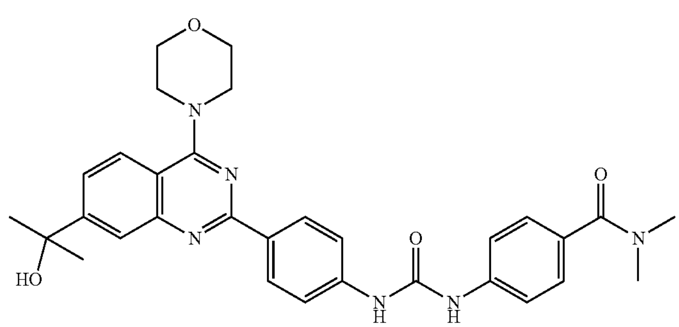 [SMILES: CN(C)C(=O)c1ccc(NC(=O)Nc2ccc(-c3nc(N4CCOCC4)c4ccc(C(C)(C)O)cc4n3)cc2)cc1] | 4-(3-(4-(7-(2-hydroxypropan-2-yl)-4-morpholino-quinazolin-2-yl)phenyl)ureido)-N,N-dimethyl-benzamide | 8A + 12 |

TABLE 1-continued

| Ex | Structure | Structure Name | Synthetic Scheme |
|---|---|---|---|
| 17 | 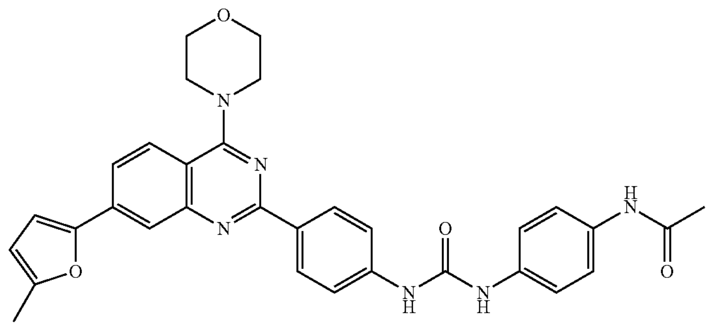 [SMILES: CC(=O)Nc1ccc(NC(=O)Nc2ccc(-c3nc(N4CCOCC4)c4ccc(-c5ccc(C)o5)cc4n3)cc2)cc1] | N-(4-(3-(4-(7-(5-methylfuran-2-yl)-4-morpholino-quinazolin-2-yl)phenyl)ureido)-phenyl)-acetamide | 10 |
| 18 | 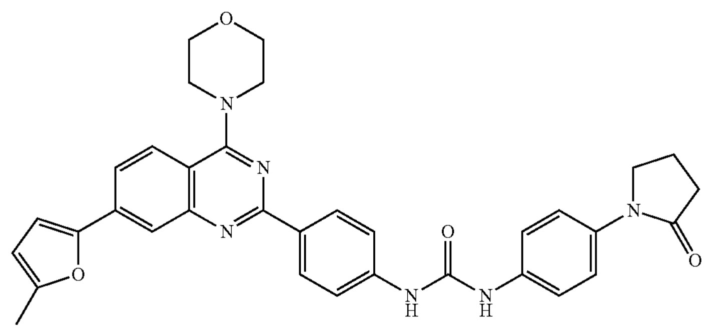 [SMILES: Cc1ccc(-c2ccc3c(N4CCOCC4)nc(-c4ccc(NC(=O)Nc5ccc(N6CCCC6=O)cc5)cc4)nc3c2)o1] | 1-(4-(7-(5-methylfuran-2-yl)-4-morpholino-quinazolin-2-yl)phenyl)-3-(4-(2-oxopyrrolidin-1-yl)phenyl)urea | 10 |
| 19 | 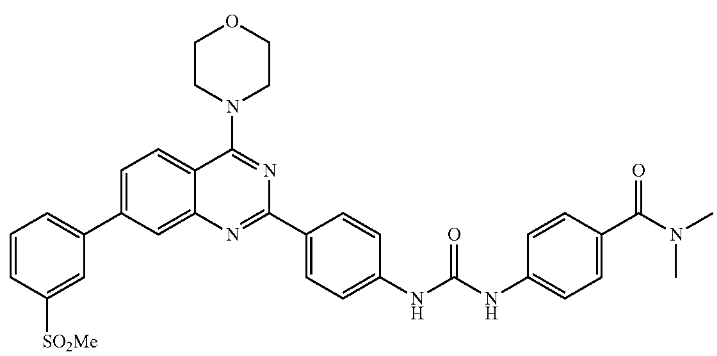 [SMILES: CN(C)C(=O)c1ccc(NC(=O)Nc2ccc(-c3nc(N4CCOCC4)c4ccc(-c5cccc(S(C)(=O)=O)c5)cc4n3)cc2)cc1] | 4-(3-{4-[7-(3-methanesulfonyl-phenyl)-4-morpholin-4-yl-quinazolin-2-yl]-phenyl}-ureido)-N,N-dimethyl-benzamide | 6B |
| 20 | 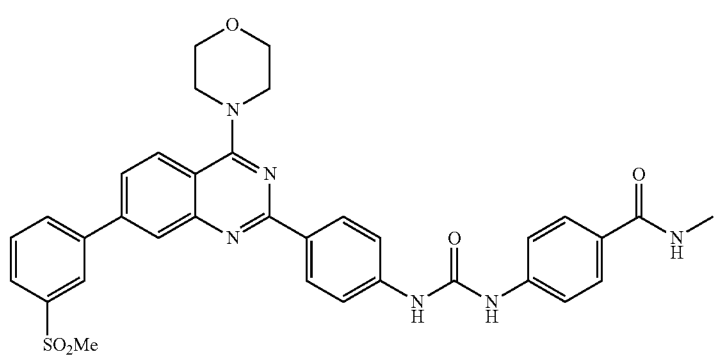 [SMILES: CNC(=O)c1ccc(NC(=O)Nc2ccc(-c3nc(N4CCOCC4)c4ccc(-c5cccc(S(C)(=O)=O)c5)cc4n3)cc2)cc1] | 4-(3-{4-[7-(3-methanesulfonyl-phenyl)-4-morpholin-4-yl-quinazolin-2-yl]-phenyl}-ureido)-N-methyl-benzamide | 6B |

TABLE 1-continued

| Ex | Structure | Structure Name | Synthetic Scheme |
|---|---|---|---|
| 21 | 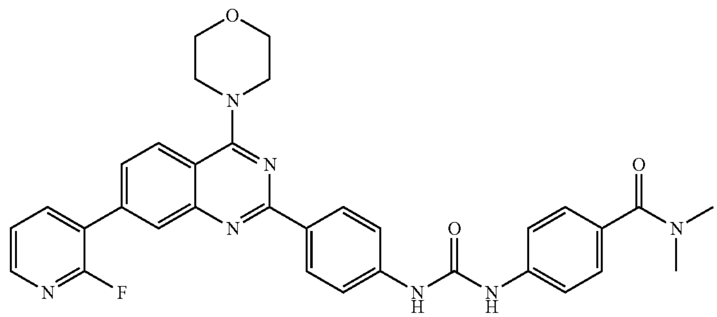 | 4-(3-{4-[7-(2-fluoro-pyridin-3-yl)-4-morpholin-4-yl-quinazolin-2-yl]-phenyl}-ureido)-N,N-dimethyl-benzamide | 6B |
| 22 | 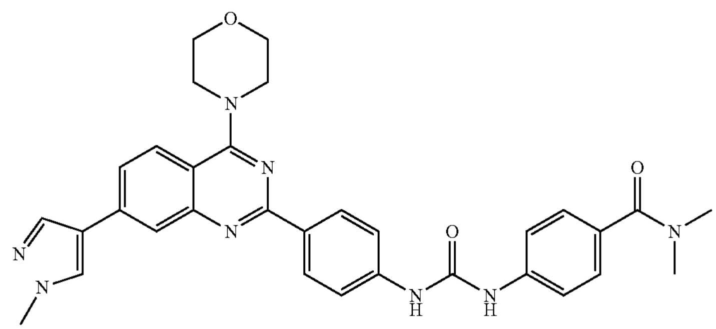 [SMILES: CN/C=C(\C=N)c1ccc2c(N3CCOCC3)nc(-c3ccc(NC(=O)Nc4ccc(C(=O)N(C)C)cc4)cc3)nc2c1] | N,N-dimethyl-4-(3-{4-[7-(1-methyl-1H-pyrazol-4-yl)-4-morpholin-4-yl-quinazolin-2-yl]-phenyl}-ureido)-benzamide | 6B |
| 23 | 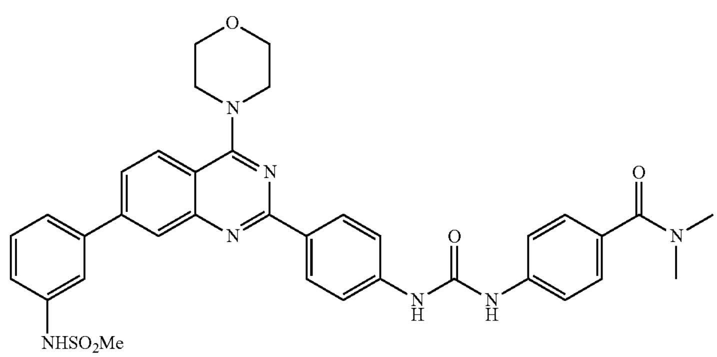 | 4-(3-{4-[7-(3-methanesulfonylamino-phenyl)-4-morpholin-4-yl-quinazolin-2-yl]-phenyl}-ureido)-N,N-dimethyl-benzamide | 6B |
| 24 | 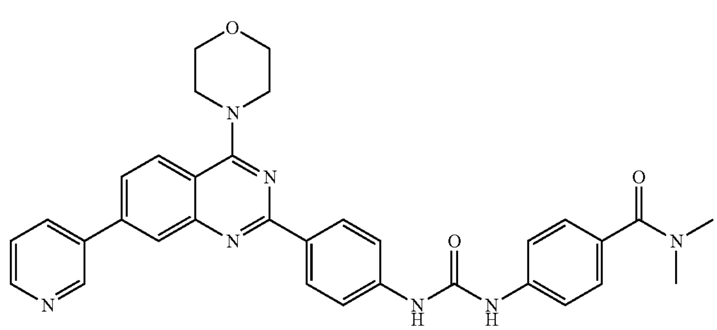 [SMILES: CN(C)C(=O)c1ccc(NC(=O)Nc2ccc(-c3nc(N4CCOCC4)c4ccc(-c5cccnc5)cc4n3)cc2)cc1] | N,N-dimethyl-4-{3-[4-(4-morpholin-4-yl-7-pyridin-3-yl-quinazolin-2-yl)-phenyl]-ureido}-benzamide | 6B |

TABLE 1-continued

| Ex | Structure Name | Synthetic Scheme |
|---|---|---|
| 25 | 4-(3-{4-[7-(3-methanesulfonyl-phenyl)-4-morpholin-4-yl-quinazolin-2-yl]-phenyl}-ureido)-benzamide | 6B |
| 26 | 1-{4-[7-(2-fluoro-pyridin-3-yl)-4-morpholin-4-yl-quinazolin-2-yl]-phenyl}-3-[4-(4-methyl-piperazine-1-carbonyl)-phenyl]-urea | 6B |
| 27 | 1-[4-(4-methyl-piperazine-1-carbonyl)-phenyl]-3-{4-[7-(1-methyl-1H-pyrazol-4-yl)-4-morpholin-4-yl-quinazolin-2-yl]-phenyl}-urea | 6B |
| 28 | 5-(3-{4-[7-(2-fluoro-pyridin-3-yl)-4-morpholin-4-yl-quinazolin-2-yl]-phenyl}-ureido)-pyridine-2-carboxylic acid dimethylamide | 6B |
| 29 | 4-{3-[4-(6-fluoro-4-morpholin-4-yl-7-pyridin-3-yl-quinazolin-2-yl)-phenyl]-ureido}-N,N-dimethyl-benzamide | 6G |

TABLE 1-continued

| Ex | Structure | Structure Name | Synthetic Scheme |
|---|---|---|---|
| 30 | 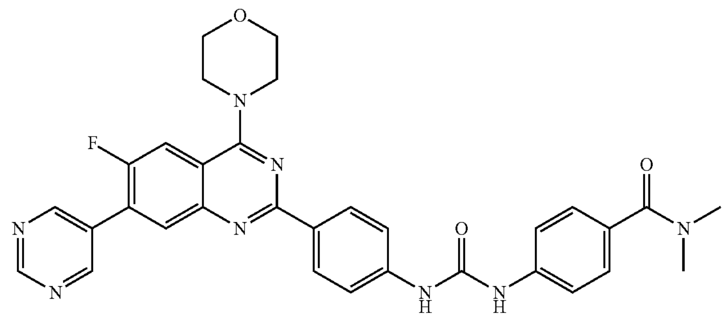 [SMILES: CN(C)C(=O)c1ccc(NC(=O)Nc2ccc(-c3nc(N4CCOCC4)c4cc(F)c(-c5cncnc5)cc4n3)cc2)cc1] | 4-{3-[4-(6-fluoro-4-morpholin-4-yl-7-pyrimidin-5-yl-quinazolin-2-yl)-phenyl]-ureido}-N,N-dimethyl-benzamide | 6G |
| 31 | 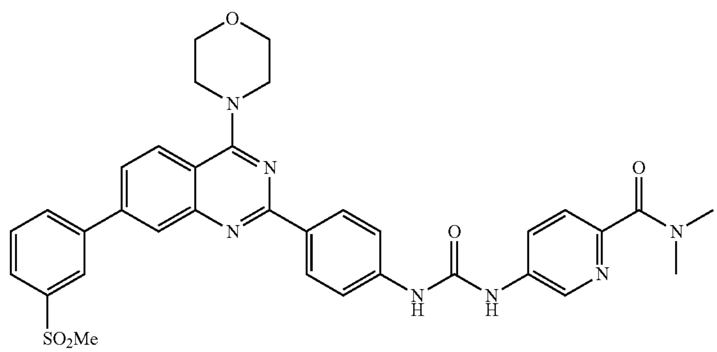 [SMILES: CN(C)C(=O)c1ccc(NC(=O)Nc2ccc(-c3nc(N4CCOCC4)c4ccc(-c5cccc(S(C)(=O)=O)c5)cc4n3)cc2)cn1] | 5-(3-{4-[7-(3-methanesulfonyl-phenyl)-4-morpholin-4-yl-quinazolin-2-yl]-phenyl}-ureido)-pyridine-2-carboxylic acid dimethylamide | 6B |
| 32 | 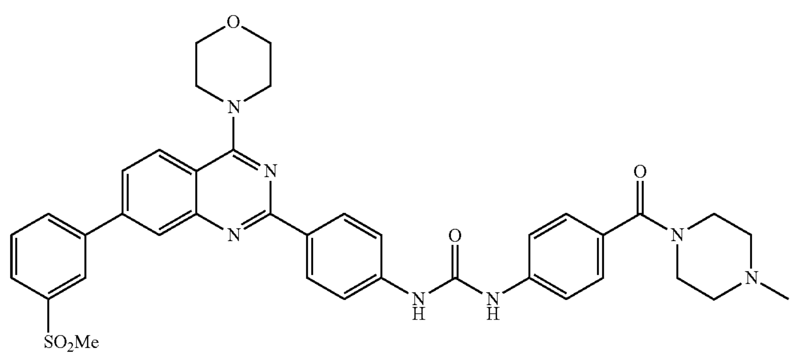 [SMILES: CN1CCN(C(=O)c2ccc(NC(=O)Nc3ccc(-c4nc(N5CCOCC5)c5ccc(-c6cccc(S(C)(=O)=O)c6)cc5n4)cc3)cc2)CC1] | 1-(4-(4-methylpiperazine-1-carbonyl)phenyl)-3-(4-(7-(3-(methylsulfonyl)phenyl)-4-morpholino-quinazolin-2-yl)phenyl)urea | 6B |
| 33 | 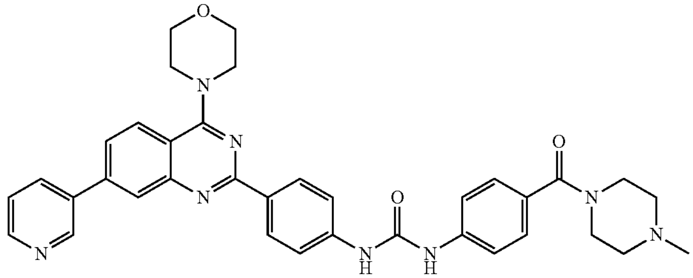 [SMILES: CN1CCN(C(=O)c2ccc(NC(=O)Nc3ccc(-c4nc(N5CCOCC5)c5ccc(-c6cccnc6)cc5n4)cc3)cc2)CC1] | 1-[4-(4-methyl-piperazine-1-carbonyl)-phenyl]-3-[4-(4-morpholin-4-yl-7-pyridin-3-yl-quinazolin-2-yl)-phenyl]-urea | 6B |

TABLE 1-continued

| Ex | Structure | Structure Name | Synthetic Scheme |
|---|---|---|---|
| 34 | 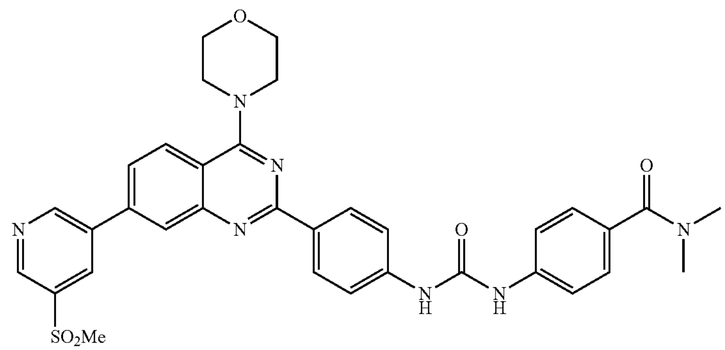 [SMILES: CN(C)C(=O)c1ccc(NC(=O)Nc2ccc(-c3nc(N4CCOCC4)c4ccc(-c5cncc(S(C)(=O)=O)c5)cc4n3)cc2)cc1] | 4-(3-{4-[7-(5-methanesulfonyl-pyridin-3-yl)-4-morpholin-4-yl-qinazolin-2-yl]-phenyl}-ureido)-N,N-dimethyl-benzamide | 6B |
| 35 | 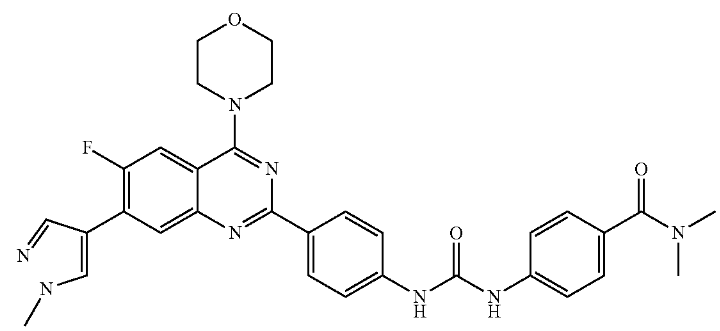 [SMILES: CN/C=C(\C=N)c1cc2nc(-c3ccc(NC(=O)Nc4ccc(C(=O)N(C)C)cc4)cc3)nc(N3CCOCC3)c2cc1F] | 4-(3-{4-[6-Fluoro-7-(1-methyl-1H-pyrazol-4-yl)-4-morpholin-4-yl-quinazolin-2-yl]-phenyl)-ureido)-N,N-dimethyl-benzamide | 6G |
| 36 | 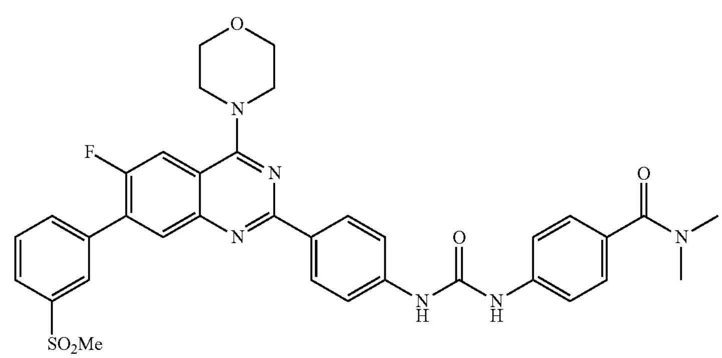 [SMILES: CN(C)C(=O)c1ccc(NC(=O)Nc2ccc(-c3nc(N4CCOCC4)c4cc(F)c(-c5cccc(S(C)(=O)=O)c5)cc4n3)cc2)cc1] | 4-(3-{4-[6-fluoro-7-(3-methanesulfonyl-phenyl)-4-morpholin-4-yl-quinazolin-2-yl]-phenyl}-ureido)-N,N-dimethyl-benzamide | 6G |
| 37 | 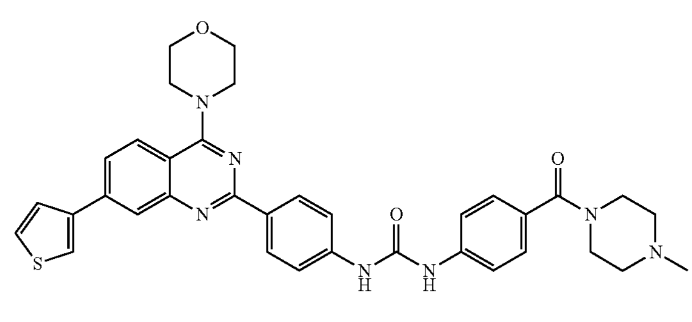 [SMILES: CN1CCN(C(=O)c2ccc(NC(=O)Nc3ccc(-c4nc(N5CCOCC5)c5ccc(-c6ccsc6)cc5n4)cc3)cc2)CC1] | 1-[4-(4-methyl-piperazine-1-carbonyl)-phenyl]-3-[4-(4-morpholin-4-yl-7-thiophen-3-yl-quinazolin-2-yl)-phenyl]-urea | 6B |

TABLE 1-continued

| Ex | Structure | Structure Name | Synthetic Scheme |
|---|---|---|---|
| 38 | 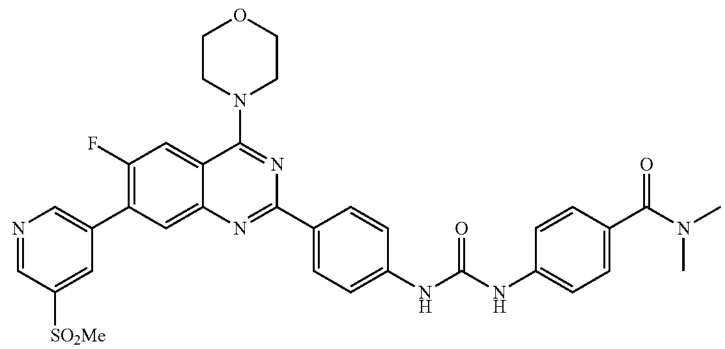 [SMILES: CN(C)C(=O)c1ccc(NC(=O)Nc2ccc(-c3nc(N4CCOCC4)c4cc(F)c(-c5cncc(S(C)(=O)=O)c5)cc4n3)cc2)cc1] | 4-(3-{4-[6-fluoro-7-(5-methanesulfonyl-pyridin-3-yl)-4-morpholin-4-yl-quinazolin-2-yl]-phenyl}-ureido)-N,N-dimethyl-benzamide | 6G |
| 39 | 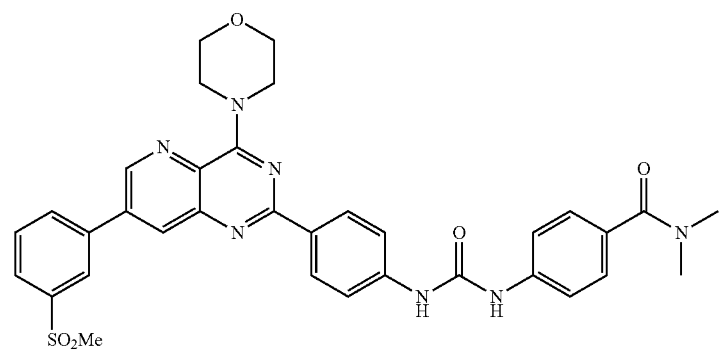 [SMILES: CN(C)C(=O)c1ccc(NC(=O)Nc2ccc(-c3nc(N4CCOCC4)c4ncc(-c5cccc(S(C)(=O)=O)c5)cc4n3)cc2)cc1] | 4-(3-{4-[7-(3-methanesulfonyl-phenyl)-4-morpholin-4-yl-pyrido[3,2-d]pyrimidin-2-yl]-phenyl}-ureido)-N,N-dimethyl-benzamide | 7A |
| 40 | 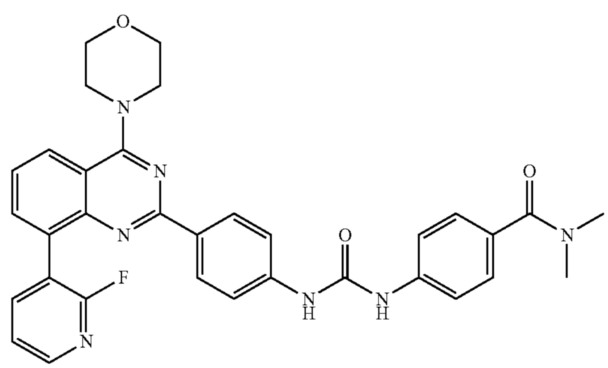 [SMILES: CN(C)C(=O)c1ccc(NC(=O)Nc2ccc(-c3nc(N4CCOCC4)c4cccc(-c5cccnc5F)c4n3)cc2)cc1] | 4-(3-{4-[8-(2-fluoro-pyridin-3-yl)-4-morpholin-4-yl-quinazolin-2-yl]-phenyl}-ureido)-N,N-dimethyl-benzamide | 6F |
| 41 | 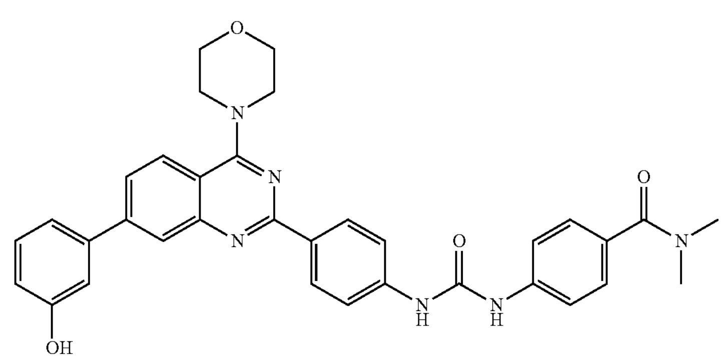 [SMILES: CN(C)C(=O)c1ccc(NC(=O)Nc2ccc(-c3nc(N4CCOCC4)c4ccc(-c5cccc(O)c5)cc4n3)cc2)cc1] | 4-(3-{4-[7-(3-hydroxy-phenyl)-4-morpholin-4-yl-quinazolin-2-yl]-phenyl}-ureido)-N,N-dimethyl-benzamide | 6B |

TABLE 1-continued

| Ex | Structure | Structure Name | Synthetic Scheme |
|---|---|---|---|
| 42 | 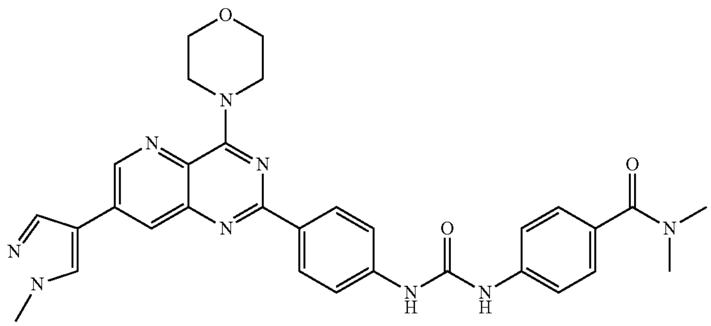 [SMILES: CN/C=C(\C=N)c1cnc2c(N3CCOCC3)nc(-c3ccc(NC(=O)Nc4ccc(C(=O)N(C)C)cc4)cc3)nc2c1] | N,N-dimethyl-4-(3-{4-[7-(1-methyl-1H-pyrazol-4-yl)-4-morpholin-4-yl-pyrido[3,2-d]pyrimidin-2-yl]-phenyl}-ureido)-benzamide | 7A |
| 43 | 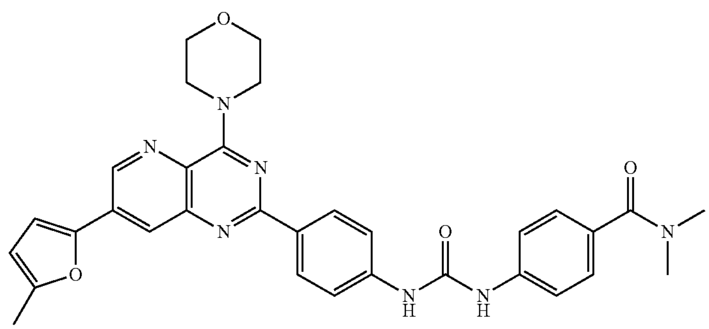 [SMILES: Cc1ccc(-c2cnc3c(N4CCOCC4)nc(-c4ccc(NC(=O)Nc5ccc(C(=O)N(C)C)cc5)cc4)nc3c2)o1] | N,N-dimethyl-4-(3-{4-[7-(5-methyl-furan-2-yl)-4-morpholin-4-yl-pyrido[3,2-d]pyrimidin-2-yl]-phenyl}-ureido)-benzamide | 7A |
| 44 | 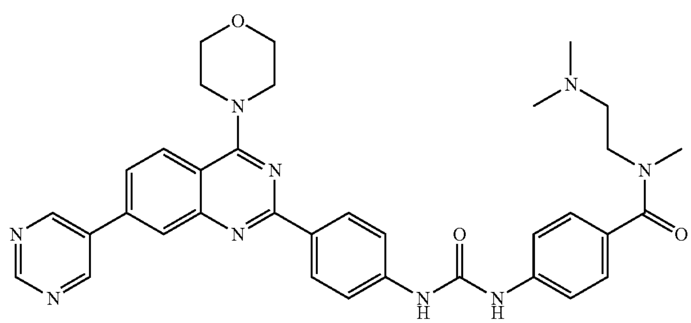 [SMILES: CN(C)CCN(C)C(=O)c1ccc(NC(=O)Nc2ccc(-c3nc(N4CCOCC4)c4ccc(-c5cncnc5)cc4n3)cc2)cc1] | N-(2-dimethylamino-ethyl)-N-methyl-4-{3-[4-(4-morpholin-4-yl-7-pyrimidin-5-yl-quinazolin-2-yl)-phenyl]-ureido}-benzamide | 6B |
| 45 | 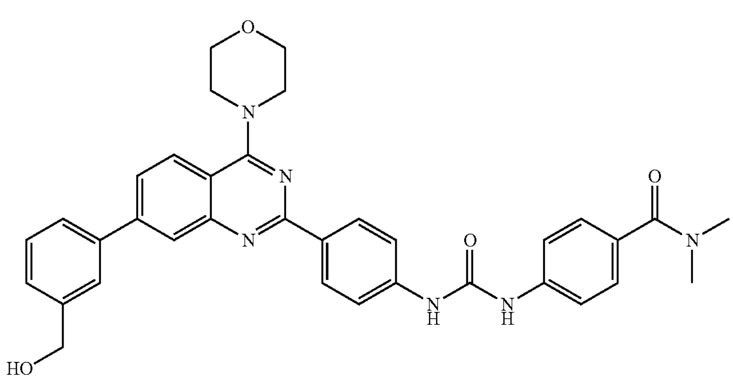 [SMILES: CN(C)C(=O)c1ccc(NC(=O)Nc2ccc(-c3nc(N4CCOCC4)c4ccc(-c5cccc(CO)c5)cc4n3)cc2)cc1] | 4-(3-{4-[7-(3-hydroxymethyl-phenyl)-4-morpholin-4-yl-quinazolin-2-yl]-phenyl}-ureido)-N,N-dimethyl-benzamide | 6B |

TABLE 1-continued

| Ex | Structure | Structure Name | Synthetic Scheme |
|---|---|---|---|
| 46 | 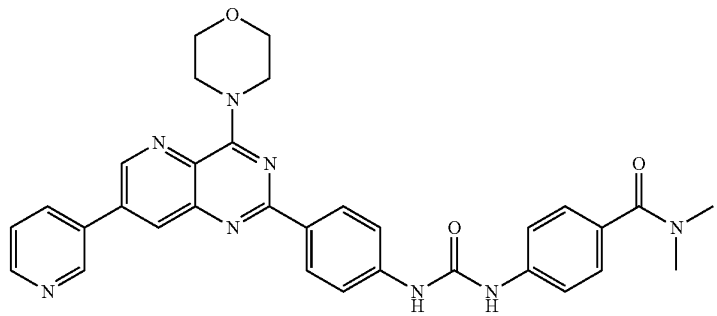 [SMILES: CN(C)C(=O)c1ccc(NC(=O)Nc2ccc(-c3nc(N4CCOCC4)c4ncc(-c5cccnc5)cc4n3)cc2)cc1] | N,N-dimethyl-4-{3-[4-(4-morpholin-4-yl-7-pyridin-3-yl-pyrido[3,2-d]pyrimidin-2-yl)-phenyl]-ureido}-benzamide | 7A |
| 47 | 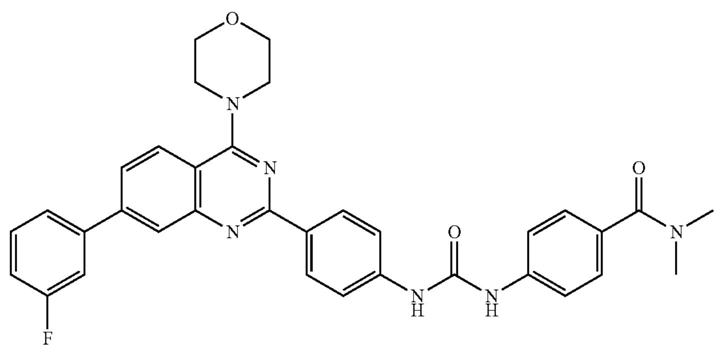 [SMILES: CN(C)C(=O)c1ccc(NC(=O)Nc2ccc(-c3nc(N4CCOCC4)c4ccc(-c5cccc(F)c5)cc4n3)cc2)cc1] | 4-(3-{4-[7-(3-fluoro-phenyl)-4-morpholin-4-yl-quinazolin-2-yl]-phenyl}-ureido)-N,N-dimethyl-benzamide | 6B |
| 48 | 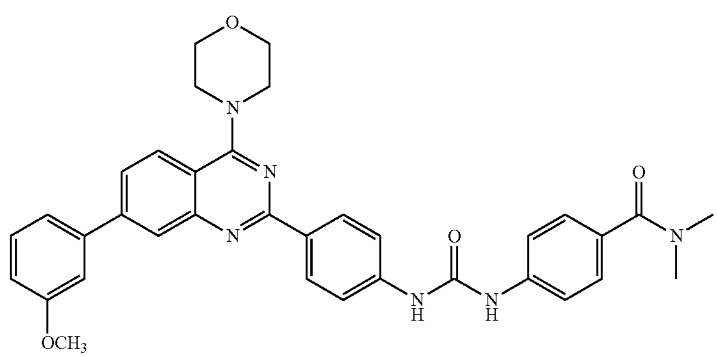 [SMILES: COc1cccc(-c2ccc3c(N4CCOCC4)nc(-c4ccc(NC(=O)Nc5ccc(C(=O)N(C)C)cc5)cc4)nc3c2)c1] | 4-(3-{4-[7-(3-methoxy-phenyl)-4-morpholin-4-yl-quinazolin-2-yl]-phenyl}-ureido)-N,N-dimethyl-benzamide | 6B |
| 49 | 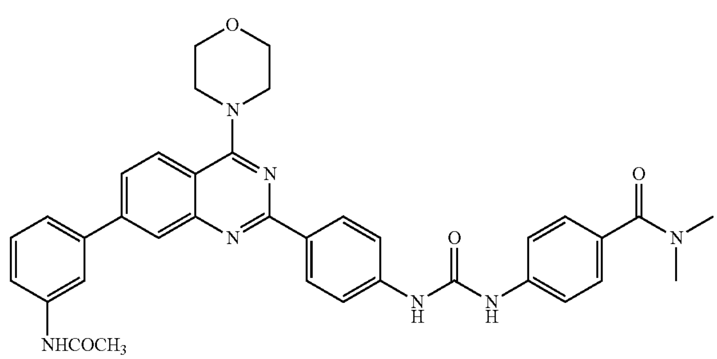 | 4-(3-{4-[7-(3-acetylamino-phenyl)-4-morpholin-4-yl-quinazolin-2-yl]-phenyl}-ureido)-N,N-dimethyl-benzamide | 6B |

TABLE 1-continued

| Ex | Structure | Structure Name | Synthetic Scheme |
|---|---|---|---|
| 50 | 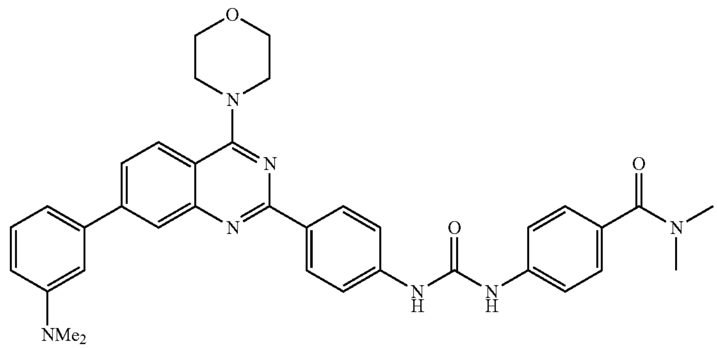 [SMILES: CN(C)C(=O)c1ccc(NC(=O)Nc2ccc(-c3nc(N4CCOCC4)c4ccc(-c5cccc(N(C)C)c5)cc4n3)cc2)cc1] | 4-(3-{4-[7-(3-dimethylamino-phenyl)-4-morpholin-4-yl-quinazolin-2-yl]-phenyl}-ureido)-N,N-dimethyl-benzamide | 6B |
| 51 | 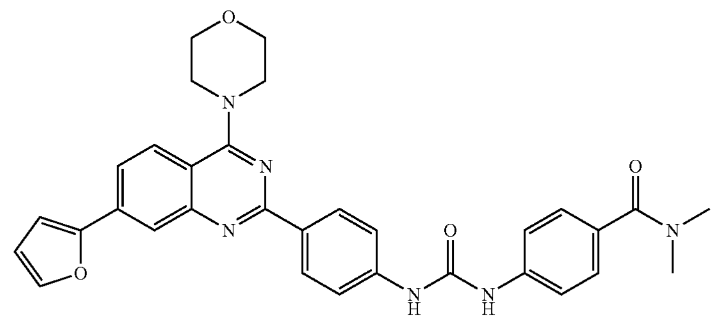 [SMILES: CN(C)C(=O)c1ccc(NC(=O)Nc2ccc(-c3nc(N4CCOCC4)c4ccc(-c5ccco5)cc4n3)cc2)cc1] | 4-{3-[4-(7-furan-2-yl-4-morpholin-4-yl-quinazolin-2-yl)-phenyl]-ureido}-N,N-dimethyl-benzamide | 6B |
| 52 | 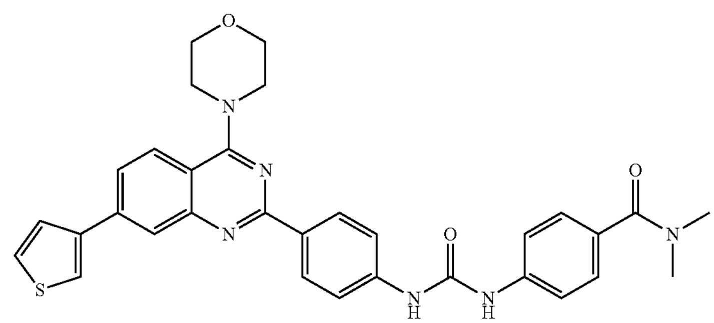 | N,N-dimethyl-4-{3-[4-(4-morpholin-4-yl-7-thiophen-3-yl-quinazolin-2-yl)-phenyl]-ureido}-benzamide | 6B |
| 53 | 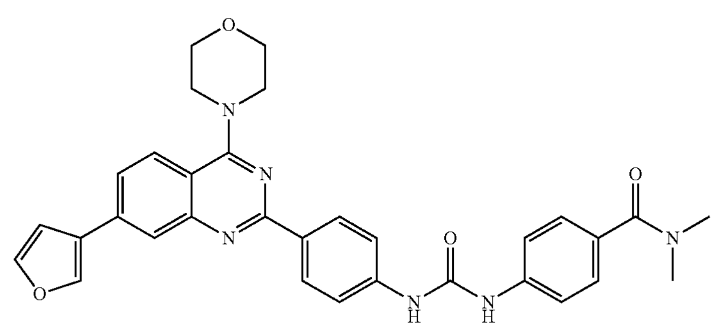 [SMILES: CN(C)C(=O)c1ccc(NC(=O)Nc2ccc(-c3nc(N4CCOCC4)c4ccc(-c5ccsc5)cc4n3)cc2)cc1] | 4-{3-[4-(7-furan-3-yl-4-morpholin-4-yl-quinazolin-2-yl)-phenyl]-ureido}-N,N-dimethyl-benzamide | 6B |

TABLE 1-continued

| Ex | Structure | Structure Name | Synthetic Scheme |
|---|---|---|---|
| 54 | 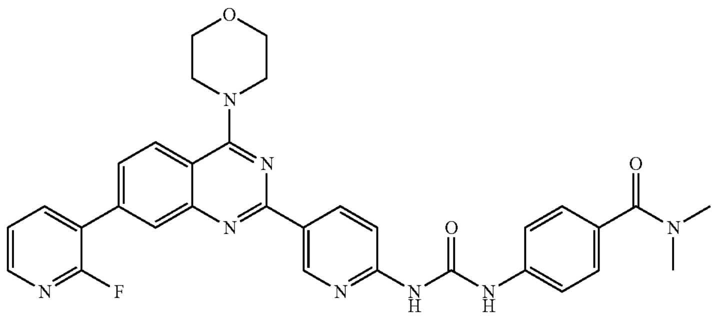 [SMILES: CN(C)C(=O)c1ccc(NC(=O)Nc2ccc(-c3nc(N4CCOCC4)c4ccc(-c5cccnc5F)cc4n3)cn2)cc1] | 4-(3-{5-[7-(2-fluoro-pyridin-3-yl)-4-morpholin-4-yl-quinazolin-2-yl]-pyridin-2-yl}-ureido)-N,N-dimethyl-benzamide | 6E |
| 55 | 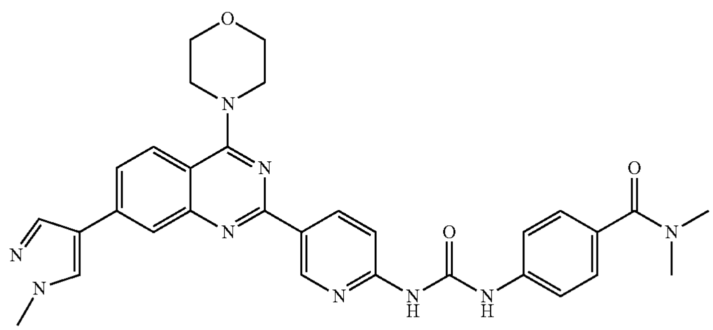 | N,N-dimethyl-4-(3-{5-[7-(1-methyl-1H-pyrazol-4-yl)-4-morpholin-4-yl-quinazolin-2-yl]-pyridin-2-yl}-ureido)-benzamide | 6E |
| 56 | 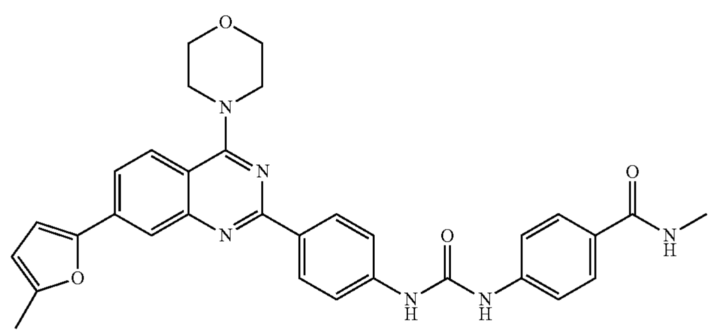 [SMILES: CNC(=O)c1ccc(NC(=O)Nc2ccc(-c3nc(N4CCOCC4)c4ccc(-c5ccc(C)o5)cc4n3)cc2)cc1] | N-methyl-4-(3-{4-[7-(5-methyl-furan-2-yl)-4-morpholin-4-yl-quinazolin-2-yl]-phenyl}-ureido)-benzamide | 6B |
| 57 | 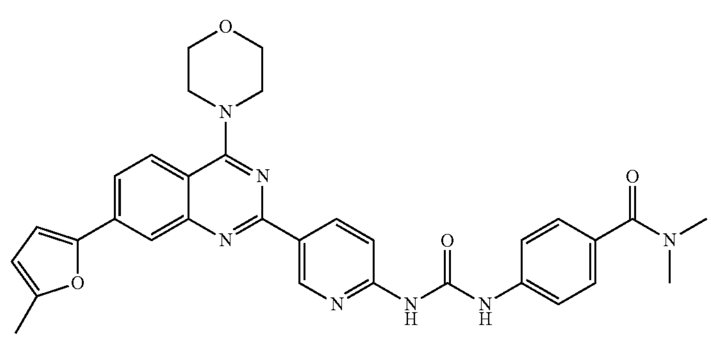 [SMILES: Cc1ccc(-c2ccc3c(N4CCOCC4)nc(-c4ccc(NC(=O)Nc5ccc(C(=O)N(C)C)cc5)nc4)nc3c2)o1] | N,N-dimethyl-4-(3-{5-[7-(5-methyl-furan-2-yl)-4-morpholin-4-yl-quinazolin-2-yl]-pyridin-2-yl}-ureido)-benzamide | 6E |

TABLE 1-continued

| Ex | Structure Name | Synthetic Scheme |
|---|---|---|
| 58 | N,N-dimethyl-4-{3-[4-(4-morpholin-4-yl-7-pyridin-4-yl-quinazolin-2-yl)-phenyl]-ureido}-benzamide | 6B |
| 59 | N,N-dimethyl-4-{3-[4-(4-morpholin-4-yl-7-quinolin-3-yl-quinazolin-2-yl)-phenyl]-ureido}-benzamide | 6B |
| 60 | 4-(3-{4-[7-(6-methoxy-pyridin-3-yl)-4-morpholin-4-yl-quinazolin-2-yl]-phenyl}-ureido)-N,N-dimethyl-benzamide | 6B |
| 61 | N,N-dimethyl-4-(3-{4-[7-(5-methyl-thiophen-2-yl)-4-morpholin-4-yl-quinazolin-2-yl]-phenyl}-ureido)-benzamide | 6B |
| 62 | N,N-dimethyl-4-(3-{4-[7-(4-methyl-pyridin-3-yl)-4-morpholin-4-yl-quinazolin-2-yl]-phenyl}-ureido)-benzamide | 6B |

TABLE 1-continued

| Ex | Structure | Structure Name | Synthetic Scheme |
|---|---|---|---|
| 63 | 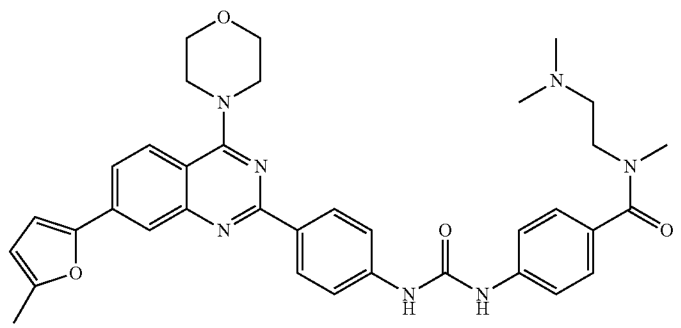 [SMILES: Cc1ccc(-c2ccc3c(N4CCOCC4)nc(-c4ccc(NC(=O)Nc5ccc(C(=O)N(C)CCN(C)C)cc5)cc4)nc3c2)o1] | N-(2-dimethylamino-ethyl)-N-methyl-4-(3-{4-[7-(5-methyl-furan-2-yl)-4-morpholin-4-yl-quinazolin-2-yl]-phenyl}-ureido)-benzamide | 6B |
| 64 | 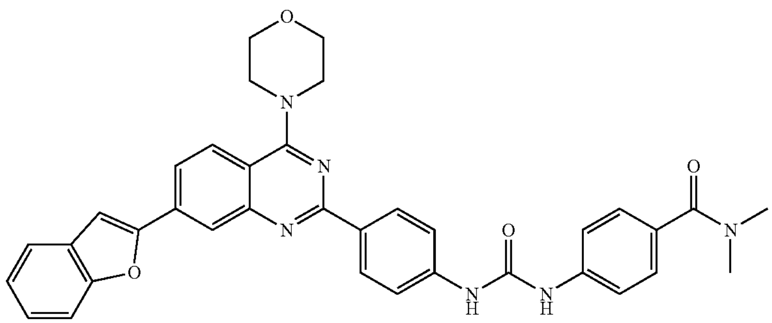 [SMILES: CN(C)C(=O)c1ccc(NC(=O)Nc2ccc(-c3nc(N4CCOCC4)c4ccc(-c5cc6ccccc6o5)cc4n3)cc2)cc1] | 4-{3-[4-(7-benzofuran-2-yl-4-morpholin-4-yl-quinazolin-2-yl)-phenyl]-ureido}-N,N-dimethyl-benzamide | 6B |
| 65 | 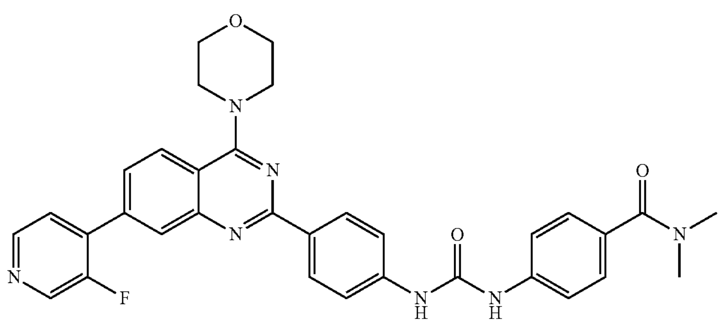 [SMILES: CN(C)C(=O)c1ccc(NC(=O)Nc2ccc(-c3nc(N4CCOCC4)c4ccc(-c5ccncc5F)cc4n3)cc2)cc1] | 4-(3-{4-[7-(3-fluoro-pyridin-4-yl)-4-morpholin-4-yl-quinazolin-2-yl]-phenyl}-ureido)-N,N-dimethyl-benzamide | 6B |
| 66 | 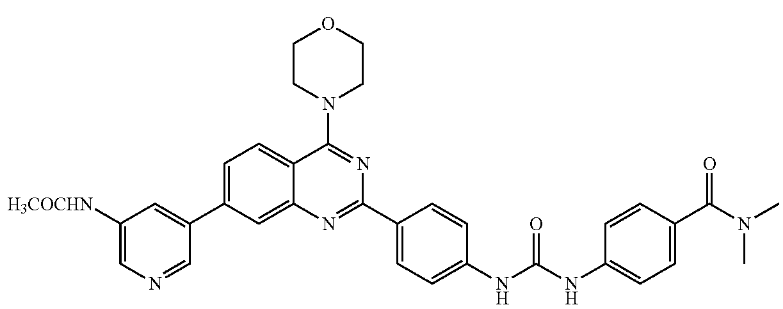 | 4-(3-{4-[7-(5-acetylamino-pyridin-3-yl)-4-morpholin-4-yl-quinazolin-2-yl]-phenyl}-ureido)-N,N-dimethyl-benzamide | 6B |
| 67 | 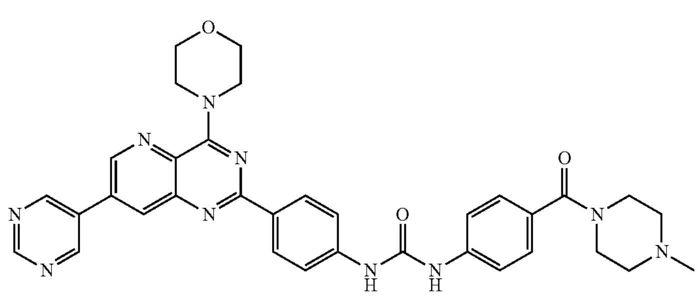 [SMILES: CN1CCN(C(=O)c2ccc(NC(=O)Nc3ccc(-c4nc(N5CCOCC5)c5ncc(-c6cncnc6)cc5n4)cc3)cc2)CC1] | 1-[4-(4-methyl-piperazine-1-carbonyl)-phenyl]-3-[4-(4-morpholin-4-yl-7-pyrimidin-5-yl-pyrido[3,2-d]pyrimidin-2-yl)-phenyl]-urea | 7A |

TABLE 1-continued

| Ex | Structure | Structure Name | Synthetic Scheme |
|---|---|---|---|
| 68 | 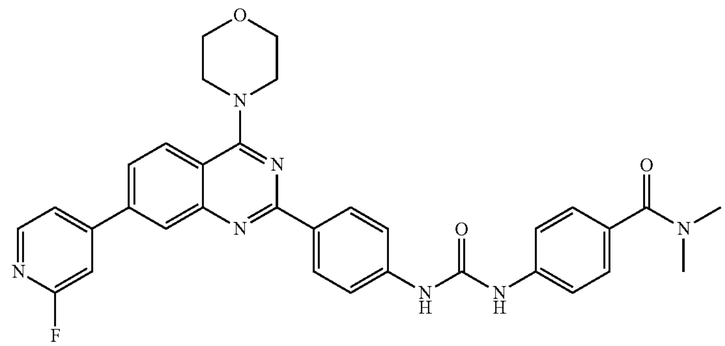 [SMILES: CN(C)C(=O)c1ccc(NC(=O)Nc2ccc(-c3nc(N4CCOCC4)c4ccc(-c5ccnc(F)c5)cc4n3)cc2)cc1] | 4-(3-{4-[7-(2-fluoro-pyridin-4-yl)-4-morpholin-4-yl-quinazolin-2-yl]-phenyl}-ureido)-N,N-dimethyl-benzamide | 6B |
| 69 | 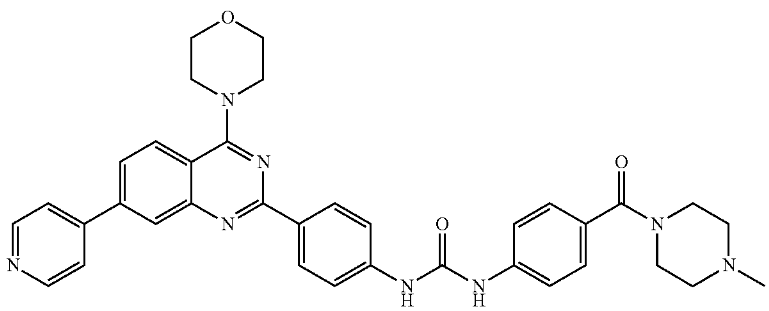 [SMILES: CN1CCN(C(=O)c2ccc(NC(=O)Nc3ccc(-c4nc(N5CCOCC5)c5ccc(-c6ccncc6)cc5n4)cc3)cc2)CC1] | 1-[4-(4-methyl-piperazine-1-carbonyl)-phenyl]-3-[4-(4-morpholin-4-yl-7-pyridin-4-yl-quinazolin-2-yl)-phenyl]-urea | 6B |
| 70 | 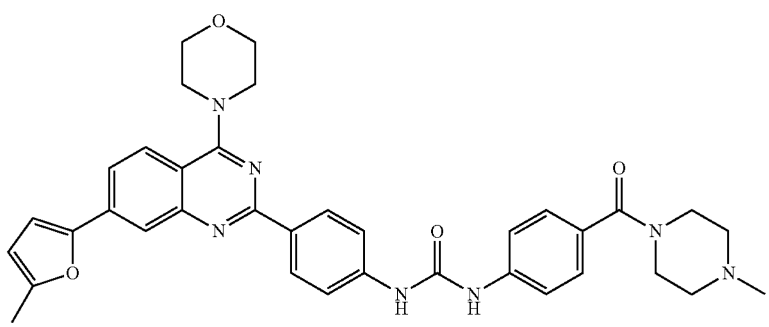 [SMILES: Cc1ccc(-c2ccc3c(N4CCOCC4)nc(-c4ccc(NC(=O)Nc5ccc(C(=O)N6CCN(C)CC6)cc5)cc4)nc3c2)o1] | 1-{4-[7-(5-methyl-furan-2-yl)-4-morpholin-4-yl-quinazolin-2-yl]-phenyl}-3-[4-(4-methyl-piperazine-1-carbonyl)-phenyl]-urea | 6B |
| 71 | 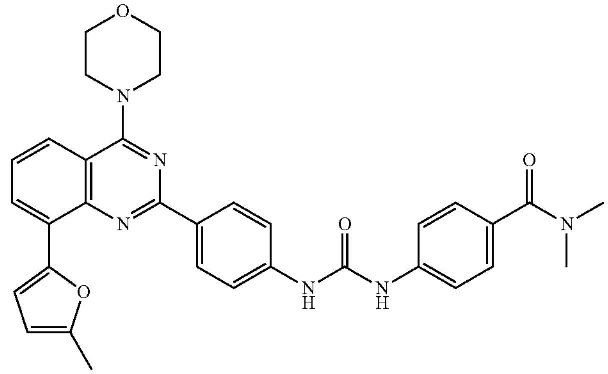 [SMILES: Cc1ccc(-c2cccc3c(N4CCOCC4)nc(-c4ccc(NC(=O)Nc5ccc(C(=O)N(C)C)cc5)cc4)nc23)o1] | N,N-dimethyl-4-(3-{4-[8-(5-methyl-furan-2-yl)-4-morpholin-4-yl-quinazolin-2-yl]-phenyl}-ureido)-benzamide | 6F |

TABLE 1-continued

| Ex | Structure | Structure Name | Synthetic Scheme |
|---|---|---|---|
| 72 | 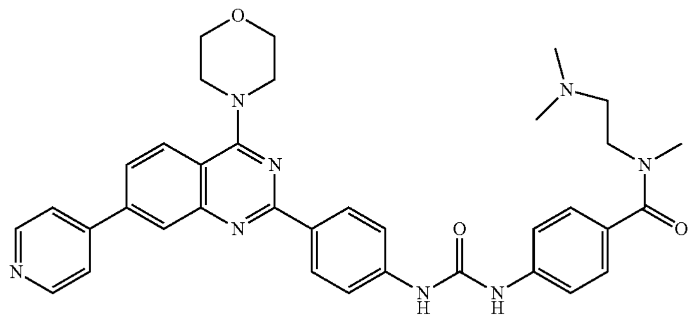 [SMILES: CN(C)CCN(C)C(=O)c1ccc(NC(=O)Nc2ccc(-c3nc(N4CCOCC4)c4ccc(-c5ccncc5)cc4n3)cc2)cc1] | N-(2-dimethylamino-ethyl)-N-methyl-4-{3-[4-(4-morpholin-4-yl-7-pyridin-4-yl-quinazolin-2-yl)-phenyl]-ureido}-benzamide | 6B |
| 73 | 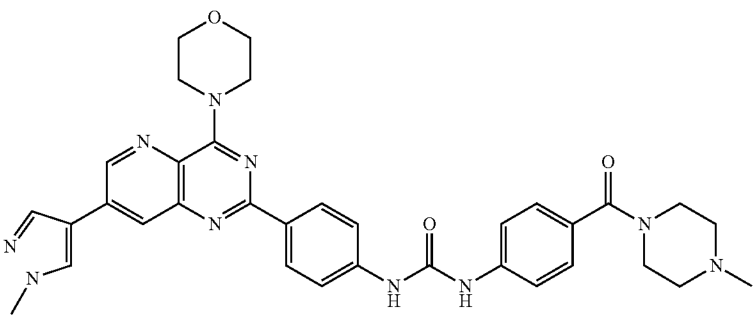 [SMILES: CN/C=C(\C=N)c1cnc2c(N3CCOCC3)nc(-c3ccc(NC(=O)Nc4ccc(C(=O)N5CCN(C)CC5)cc4)cc3)nc2c1] | 1-[4-(4-methyl-piperazine-1-carbonyl)-phenyl]-3-{4-[7-(1-methyl-1H-pyrazol-4-yl)-4-morpholin-4-yl-pyrido[3,2-d]pyrimidin-2-yl]-phenyl}-urea | 7A |
| 74 | 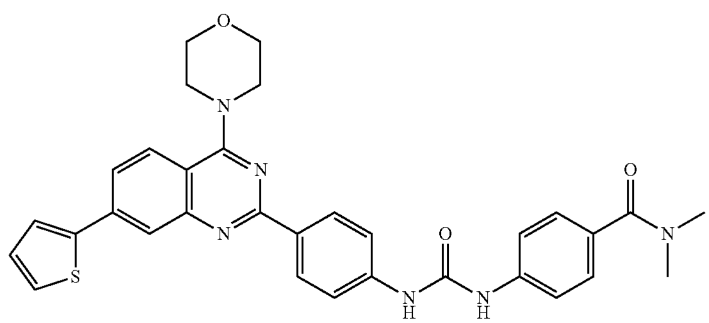 [SMILES: CN(C)C(=O)c1ccc(NC(=O)Nc2ccc(-c3nc(N4CCOCC4)c4ccc(-c5cccs5)cc4n3)cc2)cc1] | N,N-dimethyl-4-{3-[4-(4-morpholin-4-yl-7-thiophen-2-yl-quinazolin-2-yl)-phenyl]-ureido}-benzamide | 6B |
| 75 | 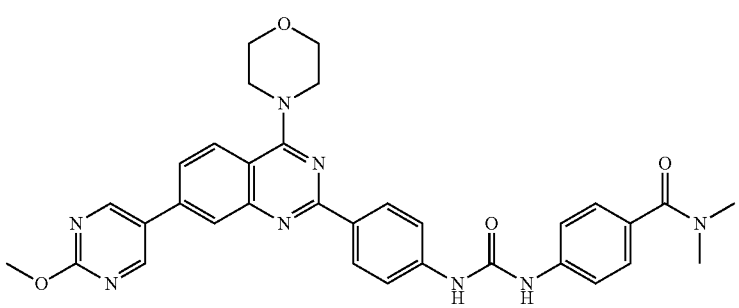 | 4-(3-{4-[7-(2-methoxy-pyrimidin-5-yl)-4-morpholin-4-yl-quinazolin-2-yl]-phenyl}-ureido)-N,N-dimethyl-benzamide | 6B |
| 76 | 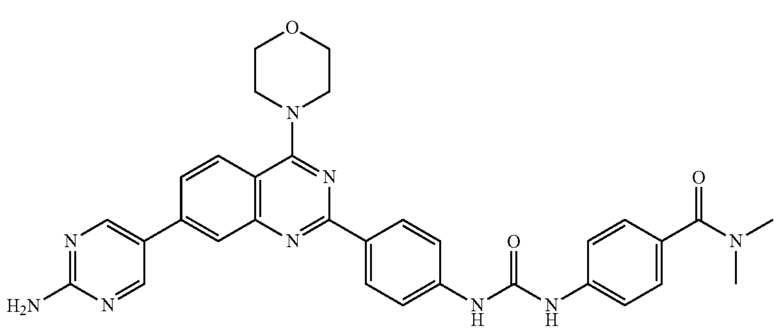 [SMILES: CN(C)C(=O)c1ccc(NC(=O)Nc2ccc(-c3nc(N4CCOCC4)c4ccc(-c5cnc(N)nc5)cc4n3)cc2)cc1] | 4-(3-{4-[7-(2-amino-pyrimidin-5-yl)-4-morpholin-4-yl-quinazolin-2-yl]-phenyl}-ureido)-N,N-dimethyl-benzamide | 6B |

TABLE 1-continued

| Ex | Structure | Structure Name | Synthetic Scheme |
|---|---|---|---|
| 77 | 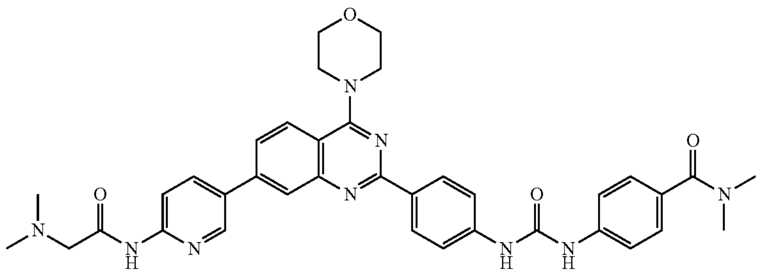 | 4-(3-(4-(7-(5-(2-(dimethylamino)acetamido)pyridin-3-yl)-4-morpholino-quinazolin-2-yl)phenyl)ureido]-N,N-dimethyl-benzamide | 6B |
| 78 | 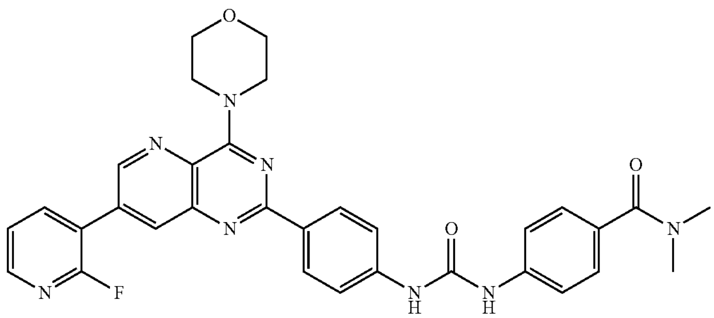 | 4-(3-{4-[7-(2-fluoro-pyridin-3-yl)-4-morpholin-4-yl-pyrido[3,2-d]pyrimidin-2-yl]-phenyl}-ureido)-N,N-dimethyl-benzamide | 7A |
| 79 | 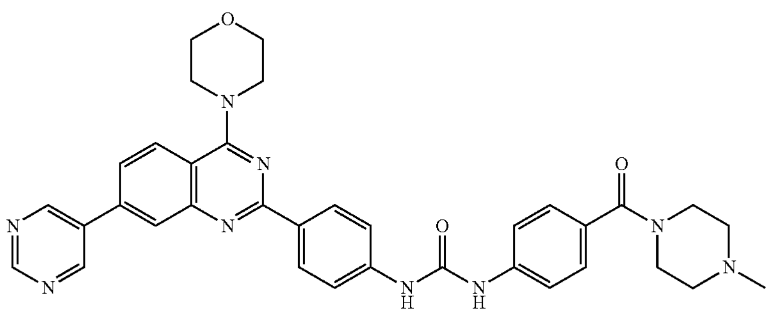 [SMILES: CN1CCN(C(=O)c2ccc(NC(=O)Nc3ccc(-c4nc(N5CCOCC5)c5ccc(-c6cncnc6)cc5n4)cc3)cc2)CC1] | 1-[4-(4-methyl-piperazine-1-carbonyl)-phenyl]-3-[4-(4-morpholin-4-yl-7-pyrimidin-5-yl-quinazolin-2-yl)-phenyl]-urea | 6B |
| 80 | 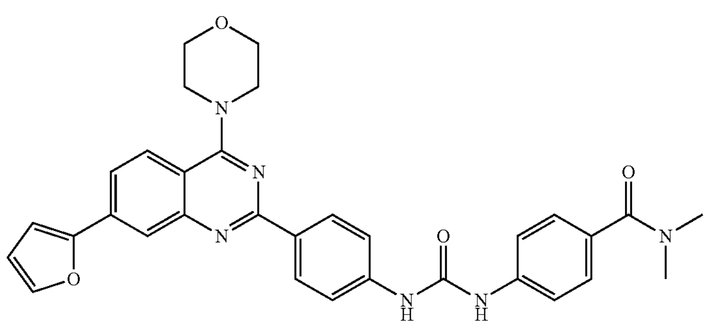 [SMILES: CN(C)C(=O)c1ccc(NC(=O)Nc2ccc(-c3nc(N4CCOCC4)c4ccc(-c5ccco5)cc4n3)cc2)cc1] | N,N-dimethyl-4-(3-{4-[7-(furan-2-yl)-4-morpholin-4-yl-quinazolin-2-yl]-phenyl}-ureido)-benzamide | 6B |
| 81 | 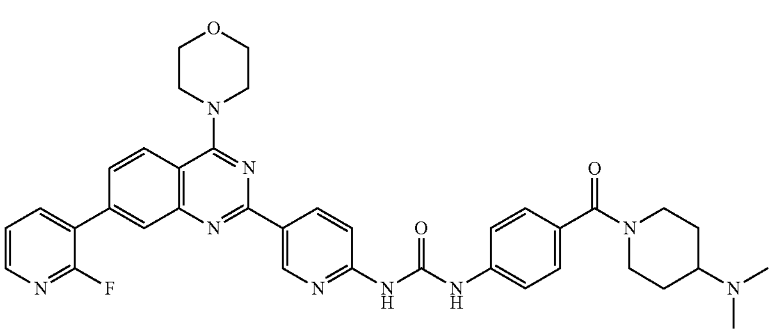 [SMILES: CN(C)C1CCN(C(=O)c2ccc(NC(=O)Nc3ccc(-c4nc(N5CCOCC5)c5ccc(-c6cccnc6F)cc5n4)cn3)cc2)CC1] | 1-(4-(4-(dimethylamino)piperidine-1-carbonyl)phenyl)-3-(5-(7-(2-fluoropyridin-3-yl)-4-morpholine-quinazolin-2-yl)pyridin-2-yl)urea | 6E |

TABLE 1-continued

| Ex | Structure Name | Synthetic Scheme |
|---|---|---|
| 82 | 4-(3-(2-fluoro-4-(7-(1-methyl-1H-pyrazol-4-yl)-4-morpholino-pyrido[3,2-d]pyrimidin-2-yl)phenyl)ureido)-N,N-dimethyl-benzamide | 7B |
| 83 | 4-(3-(4-(7-(1-(2-(dimethylamino)ethyl)-1H-pyrazol-4-yl)-4-morpholino-quinazolin-2-yl)phenyl)ureido)-N,N-dimethyl-benzamide | 6B |
| 84 | 4-(3-(2-fluoro-4-(4-morpholino-7-(pyrimidin-5-yl)quinazolin-2-yl)phenyl)ureido)-N,N-dimethyl-benzamide | 6D |
| 85 | N,N-dimethyl-4-(3-(5-(7-(1-methyl-1H-pyrazol-4-yl)-4-morpholino-pyrido[3,2-d]pyrimidin-2-yl)pyridin-2-yl)ureido)-benzamide | 7 + 6E |

TABLE 1-continued

| Ex | Structure | Structure Name | Synthetic Scheme |
|---|---|---|---|
| 86 | 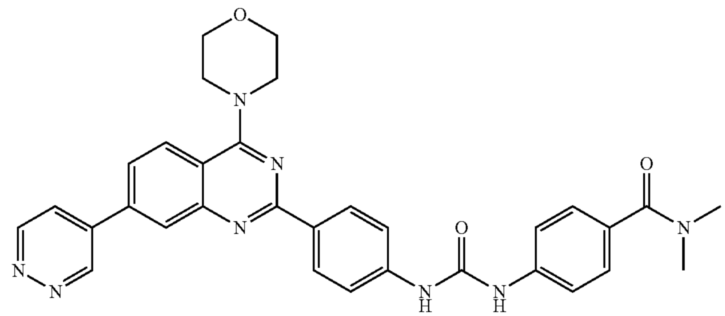 [SMILES: CN(C)C(=O)c1ccc(NC(=O)Nc2ccc(-c3nc(N4CCOCC4)c4ccc(-c5ccnnc5)cc4n3)cc2)cc1] | N,N-dimethyl-4-(3-(4-(4-morpholino-7-(pyridazin-4-yl)quinazolin-2-yl)phenyl)ureido)-benzamide | 6 + 6B |
| 87 | 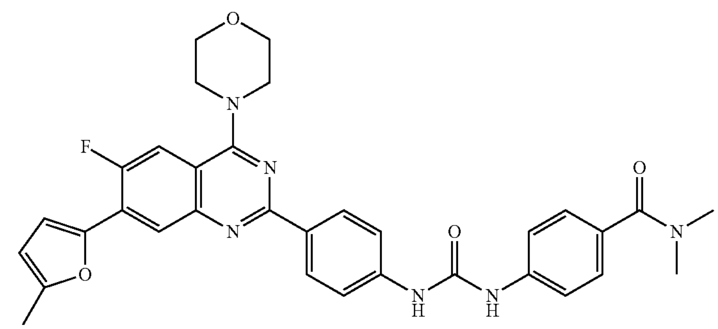 [SMILES: Cc1ccc(-c2cc3nc(-c4ccc(NC(=O)Nc5ccc(C(=O)N(C)C)cc5)cc4)nc(N4CCOCC4)c3cc2F)o1] | 4-(3-(4-(6-fluoro-7-(5-methylfuran-2-yl)-4-morpholino-quinazolin-2-yl)phenyl)ureido)-N,N-dimethyl-benzamide | 6G |
| 88 | 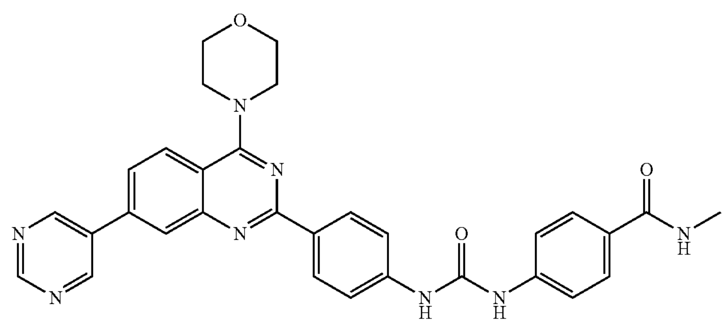 | N-methyl-4-(3-(4-(4-morpholino-7-(pyrimidin-5-yl)quinazolin-2-yl)phenyl)ureido)-benzamide | 6B |
| 89 | 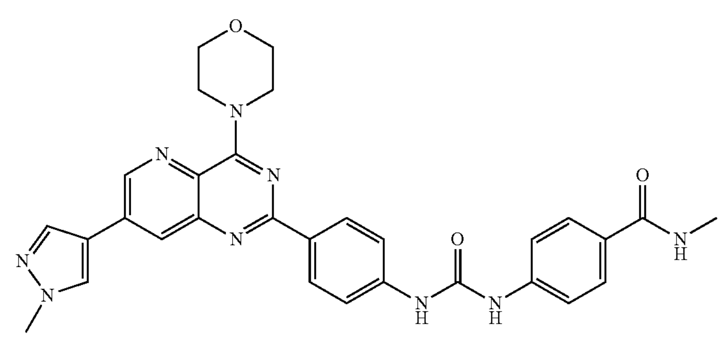 [SMILES: CNC(=O)c1ccc(NC(=O)Nc2ccc(-c3nc(N4CCOCC4)c4ncc(-c5cnn(C)c5)cc4n3)cc2)cc1] | N-methyl-4-(3-(4-(7-(1-methyl-1H-pyrazol-4-yl)-4-morpholino-pyrido[3,2-d]pyrimidin-2-yl)phenyl)ureido)-benzamide | 7A |

TABLE 1-continued

| Ex | Structure | Structure Name | Synthetic Scheme |
|---|---|---|---|
| 90 | 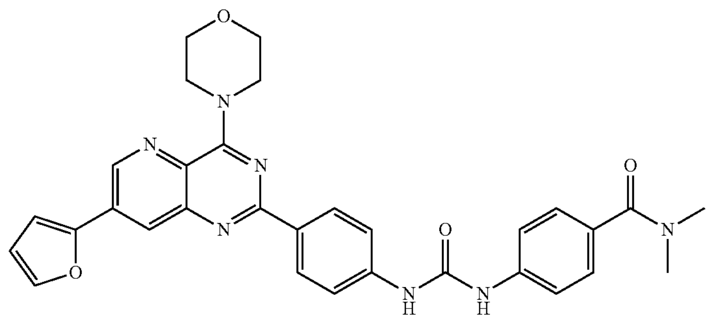 [SMILES: CN(C)C(=O)c1ccc(NC(=O)Nc2ccc(-c3nc(N4CCOCC4)c4ncc(-c5ccco5)cc4n3)cc2)cc1] | 4-(3-(4-(7-(furan-2-yl)-4-morpholino-pyrido[3,2-d]pyrimidin-2-yl)phenyl)ureido)-N,N-dimethyl-benzamide | 7A |
| 91 | 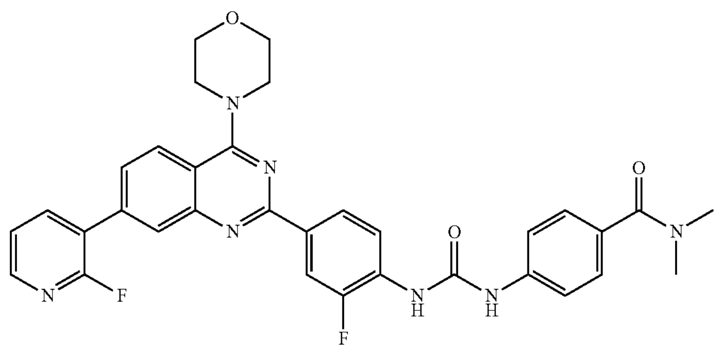 [SMILES: CN(C)C(=O)c1ccc(NC(=O)Nc2ccc(-c3nc(N4CCOCC4)c4ccc(-c5cccnc5F)cc4n3)cc2F)cc1] | 4-(3-(2-fluoro-4-(7-(2-fluoropyridin-3-yl)-4-morpholino-quinazolin-2-yl)phenyl)ureido)-N,N-dimethyl-benzamide | 6D |
| 92 | 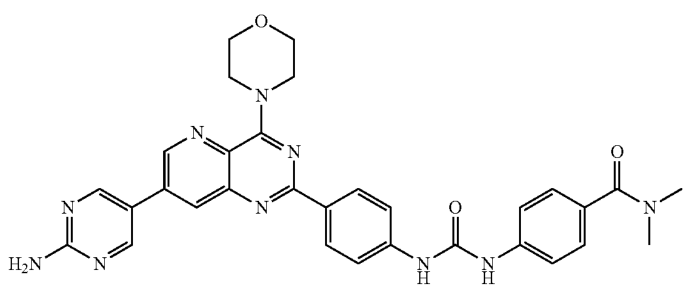 [SMILES: CN(C)C(=O)c1ccc(NC(=O)Nc2ccc(-c3nc(N4CCOCC4)c4ncc(-c5cnc(N)nc5)cc4n3)cc2)cc1] | 4-(3-(4-(7-(2-aminopyrimidin-5-yl)-4-morpholino-pyrido[3,2-d]pyrimidin-2-yl)phenyl)ureido)-N,N-dimethyl-benzamide | 7A |
| 93 | 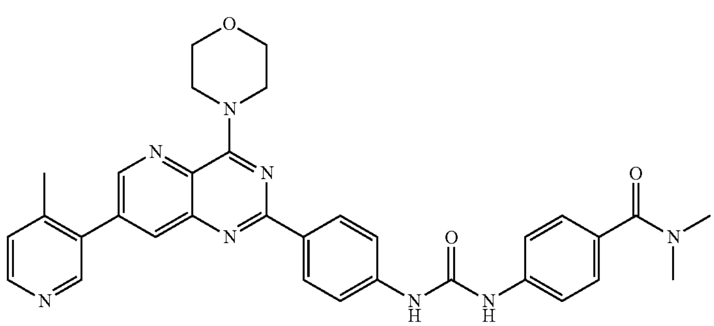 [SMILES: Cc1ccncc1-c1cnc2c(N3CCOCC3)nc(-c3ccc(NC(=O)Nc4ccc(C(=O)N(C)C)cc4)cc3)nc2c1] | N,N-dimethyl-4-(3-(4-(7-(4-methylpyridin-3-yl)-4-morpholino-pyrido[3,2-d]pyrimidin-2-yl)phenyl)ureido)-benzamide | 7A |
| 94 | 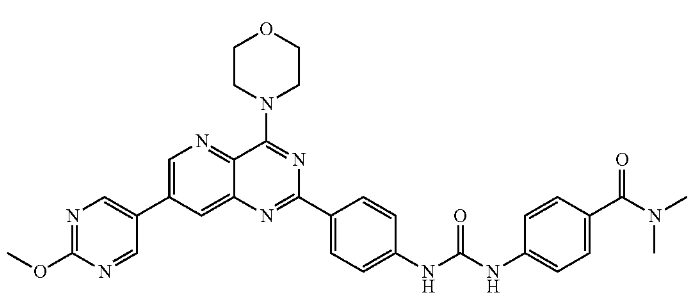 | 4-(3-(4-(7-(2-methoxypyrimidin-5-yl)-4-morpholino-pyrido[3,2-d]pyrimidin-2-yl)phenyl)ureido)-N,N-dimethyl-benzamide | 7A |

TABLE 1-continued

| Ex | Structure | Structure Name | Synthetic Scheme |
|---|---|---|---|
| 95 | 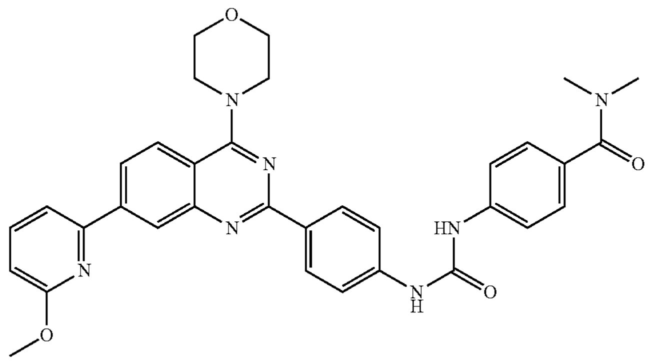 [SMILES: COc1cccc(-c2ccc3c(N4CCOCC4)nc(-c4ccc(NC(=O)Nc5ccc(C(=O)N(C)C)cc5)cc4)nc3c2)n1] | 4-(3-(4-(7-(6-methoxypyridin-2-yl)-4-morpholino-quinazolin-2-yl)phenyl)ureido)-N,N-dimethyl-benzamide | 6B |
| 96 | 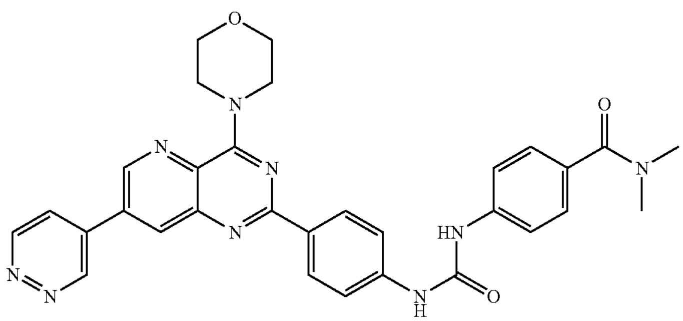 [SMILES: CN(C)C(=O)c1ccc(NC(=O)Nc2ccc(-c3nc(N4CCOCC4)c4ncc(-c5ccnnc5)cc4n3)cc2)cc1] | N,N-dimethyl-4-(3-(4-(4-morpholino-7-(pyridazin-4-yl)pyrido[3,2-d]pyrimidin-2-yl)phenyl)ureido)-benzamide | 7 |
| 97 | 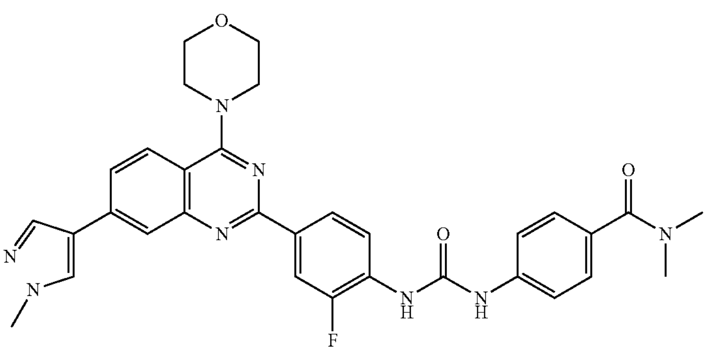 [SMILES: CN/C=C(\C=N)c1ccc2c(N3CCOCC3)nc(-c3ccc(NC(=O)Nc4ccc(C(=O)N(C)C)cc4)c(F)c3)nc2c1] | 4-(3-(2-fluoro-4-(7-(1-methyl-1H-pyrazol-4-yl)-4-morpholino-quinazolin-2-yl)phenyl)ureido)-N,N-dimethyl-benzamide | 6D |
| 98 | 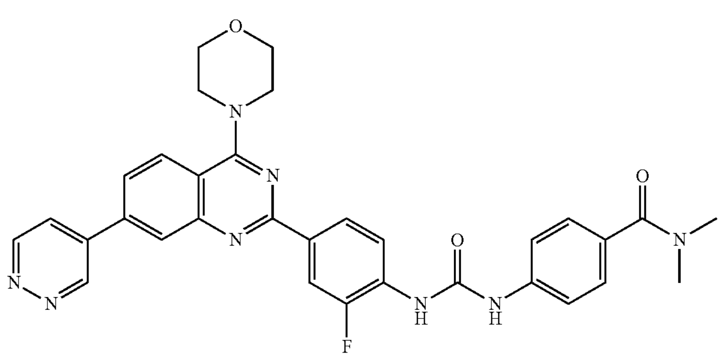 [SMILES: CN(C)C(=O)c1ccc(NC(=O)Nc2ccc(-c3nc(N4CCOCC4)c4ccc(-c5ccnnc5)cc4n3)cc2F)cc1] | 4-(3-(2-fluoro-4-(4-morpholino-7-(pyridazin-4-yl)quinazolin-2-yl)phenyl)ureido)-N,N-dimethyl-benzamide | 6 + 6D |

TABLE 1-continued

| Ex | Structure | Structure Name | Synthetic Scheme |
|---|---|---|---|
| 99 | 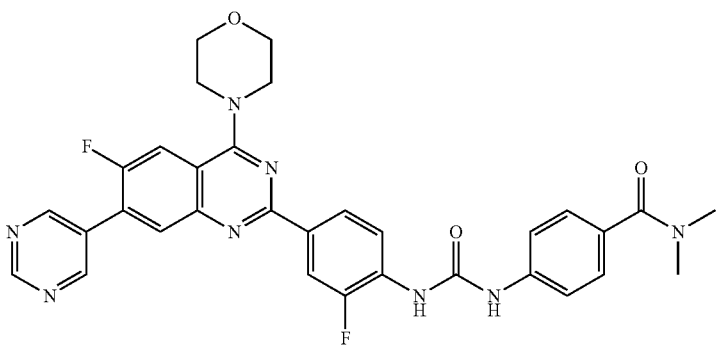 [SMILES: CN(C)C(=O)c1ccc(NC(=O)Nc2ccc(-c3nc(N4CCOCC4)c4cc(F)c(-c5cncnc5)cc4n3)cc2F)cc1] | 4-(3-(2-fluoro-4-(6-fluoro-4-morpholino-7-(pyrimidin-5-yl)quinazolin-2-yl)phenyl)ureido)-N,N-dimethyl-benzamide | 6G + 6D |
| 100 | 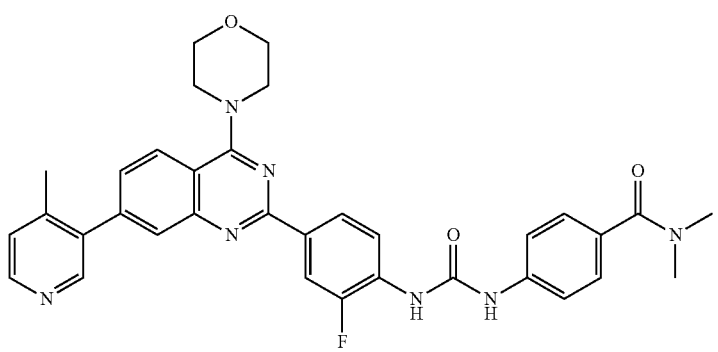 [SMILES: Cc1ccncc1-c1ccc2c(N3CCOCC3)nc(-c3ccc(NC(=O)Nc4ccc(C(=O)N(C)C)cc4)c(F)c3)nc2c1] | 4-(3-(2-fluoro-4-(7-(4-methylpyridin-3-yl)-4-morpholino-quinazolin-2-yl)phenyl)ureido)-N,N-dimethyl-benzamide | 6D |
| 101 | 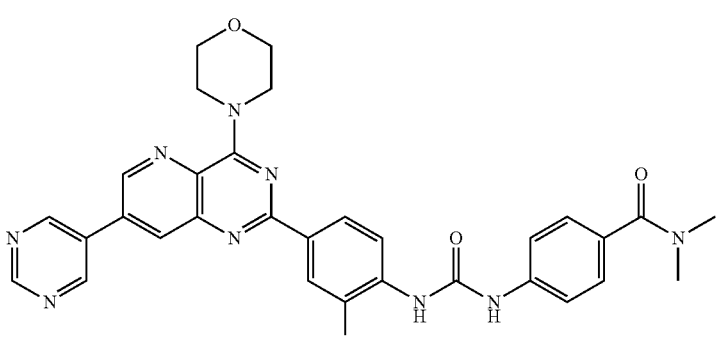 | 4-(3-(2-fluoro-4-(4-morpholino-7-(pyrimidin-5-yl)pyrido[3,2-d]pyrimidin-2-yl)phenyl)ureido)-N,N-dimethyl-benzamide | 7B |
| 102 | 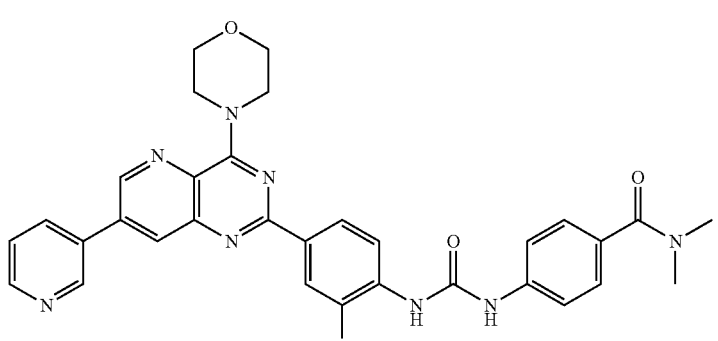 | 4-(3-(2-fluoro-4-(4-morpholino-7-(pyridin-3-yl)pyrido[3,2-d]pyrimidin-2-yl)phenyl)ureido)-N,N-dimethyl-benzamide | 7B |

TABLE 1-continued

| Ex | Structure | Structure Name | Synthetic Scheme |
|---|---|---|---|
| 103 | 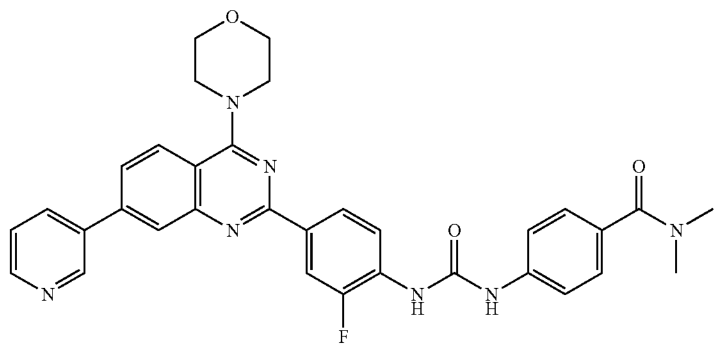 [SMILES: CN(C)C(=O)c1ccc(NC(=O)Nc2ccc(-c3nc(N4CCOCC4)c4ccc(-c5cccnc5)cc4n3)cc2F)cc1] | 4-(3-(2-fluoro-4-(4-morpholino-7-(pyridin-3-yl)quinazolin-2-yl)phenyl)ureido)-N,N-dimethyl-benzamide | 6D |
| 104 | 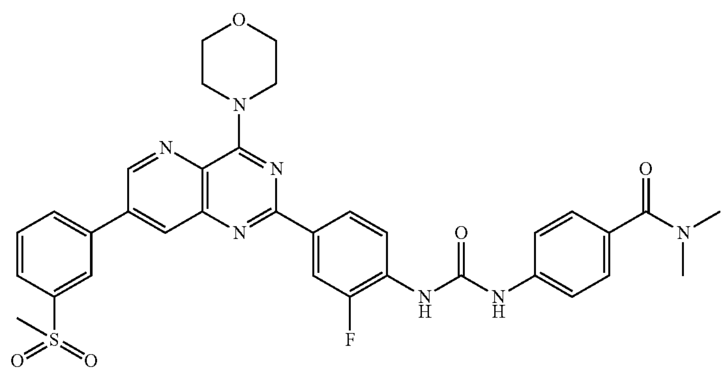 [SMILES: CN(C)C(=O)c1ccc(NC(=O)Nc2ccc(-c3nc(N4CCOCC4)c4ncc(-c5cccc(S(C)(=O)=O)c5)cc4n3)cc2F)cc1] | 4-(3-(2-fluoro-4-(7-(3-(methylsulfonyl)phenyl)-4-morpholino-pyrido[3,2-d]pyrimidin-2-yl)phenyl)ureido)-N,N-dimethyl-benzamide | 7B |
| 105 | 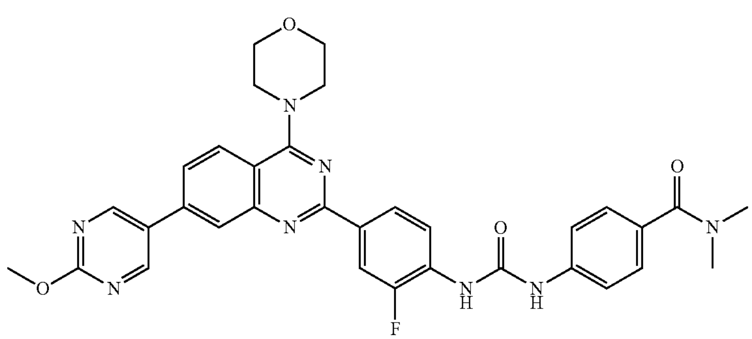 | 4-(3-(2-fluoro-4-(7-(2-methoxypyrimidin-5-yl)-4-morpholino-quinazolin-2-yl)phenyl)ureido)-N,N-dimethyl-benzamide | 6D |
| 106 | 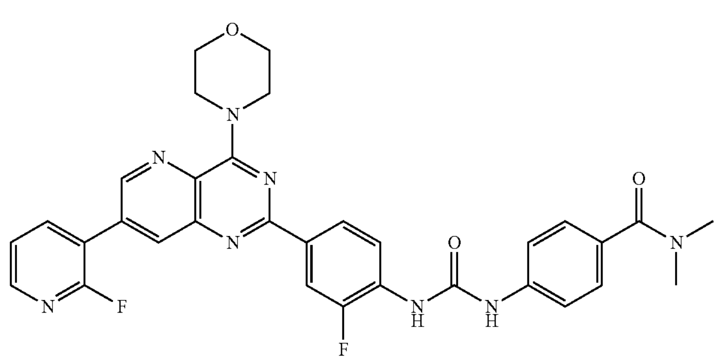 [SMILES: CN(C)C(=O)c1ccc(NC(=O)Nc2ccc(-c3nc(N4CCOCC4)c4ncc(-c5cccnc5F)cc4n3)cc2F)cc1] | 4-(3-(2-fluoro-4-(7-(2-fluoropyridin-3-yl)-4-morpholino-pyrido[3,2-d]pyrimidin-2-yl)phenyl)ureido)-N,N-dimethyl-benzamide | 7B |

TABLE 1-continued

| Ex | Structure | Structure Name | Synthetic Scheme |
|---|---|---|---|
| 107 | 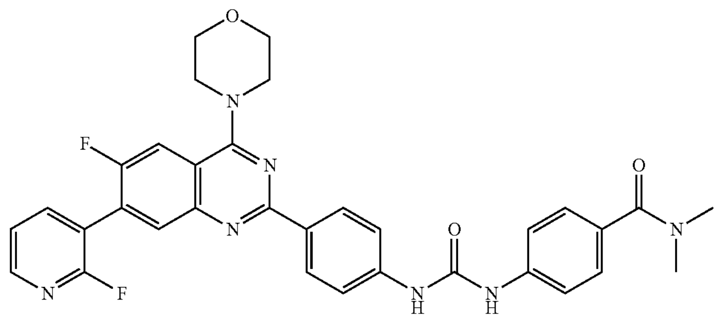 [SMILES: CN(C)C(=O)c1ccc(NC(=O)Nc2ccc(-c3nc(N4CCOCC4)c4cc(F)c(-c5cccnc5F)cc4n3)cc2)cc1] | 4-(3-(4-(6-fluoro-7-(2-fluoropyridin-3-yl)-4-morpholino-quinazolin-2-yl)phenyl)ureido)-N,N-dimethyl-benzamide | 6G |
| 108 | 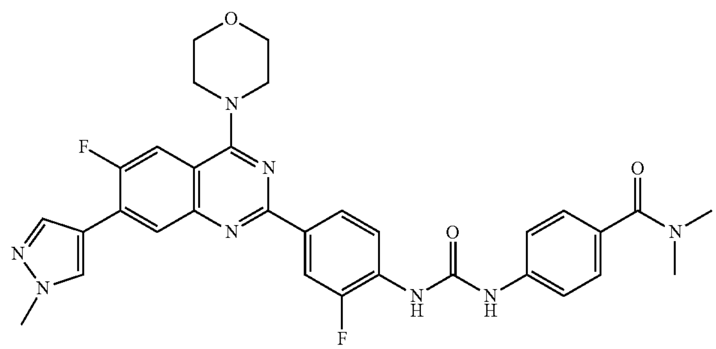 [SMILES: CN(C)C(=O)c1ccc(NC(=O)Nc2ccc(-c3nc(N4CCOCC4)c4cc(F)c(-c5cnn(C)c5)cc4n3)cc2F)cc1] | 4-(3-(2-fluoro-4-(6-fluoro-7-(1-methyl-1H-pyrazol-4-yl)-4-morpholino-quinazolin-2-yl)phenyl)ureido dimethyl-benzamide)-N,N-dimethyl-benzamide | 6D + 6G |
| 109 | 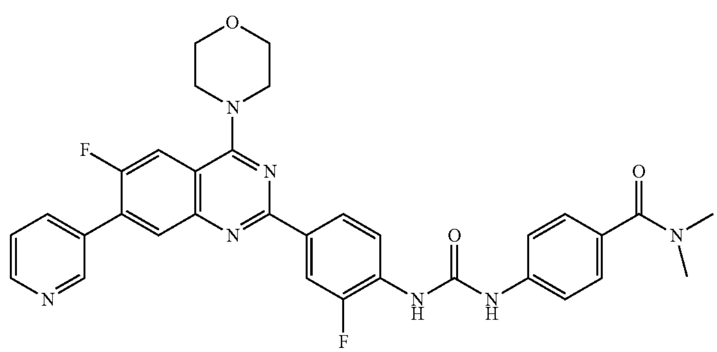 [SMILES: CN(C)C(=O)c1ccc(NC(=O)Nc2ccc(-c3nc(N4CCOCC4)c4cc(F)c(-c5cccnc5)cc4n3)cc2F)cc1] | 4-(3-(2-fluoro-4-(6-fluoro-4-morpholino-7-(pyridin-3-yl)quinazolin-2-yl)phenyl)ureido)-N,N-dimethyl-benzamide | 6D + 6G |
| 110 | 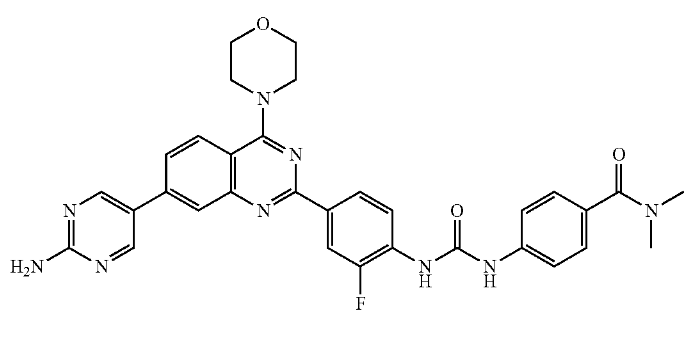 [SMILES: CN(C)C(=O)c1ccc(NC(=O)Nc2ccc(-c3nc(N4CCOCC4)c4ccc(-c5cnc(N)nc5)cc4n3)cc2F)cc1] | 4-(3-(4-(7-(2-aminopyrimidin-5-yl)-4-morpholino-quinazolin-2-yl)-2-fluorophenyl)ureido)-N,N-dimethyl-benzamide | 6D |

TABLE 1-continued

| Ex | Structure | Structure Name | Synthetic Scheme |
|---|---|---|---|
| 111 | 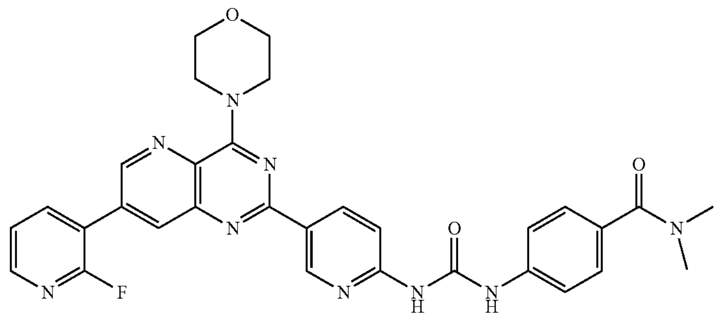 [SMILES: CN(C)C(=O)c1ccc(NC(=O)Nc2ccc(-c3nc(N4CCOCC4)c4ncc(-c5cccnc5F)cc4n3)cn2)cc1] | 4-(3-(5-(7-(2-fluoropyridin-3-yl)-4-morpholino-pyrido[3,2-d]pyrimidin-2-yl)pyridin-2-yl)ureido)-N,N-dimethyl-benzamide | 7A + 6E |
| 112 | 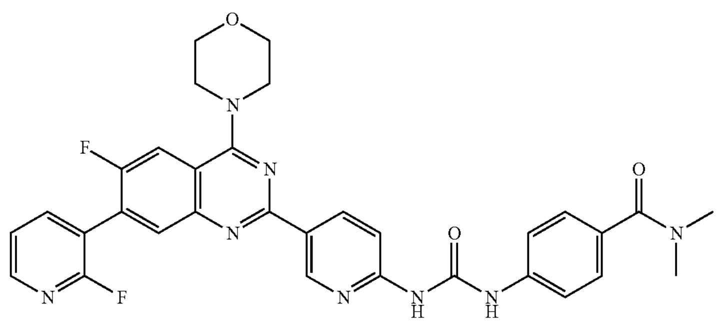 [SMILES: CN(C)C(=O)c1ccc(NC(=O)Nc2ccc(-c3nc(N4CCOCC4)c4cc(F)c(-c5cccnc5F)cc4n3)cn2)cc1] | 4-(3-(5-(6-fluoro-7-(2-fluoropyridin-3-yl)-4-morpholino-quinazolin-2-yl)pyridin-2-yl)ureido)-N,N-dimethyl-benzamide | 6E + 6G |
| 113 | 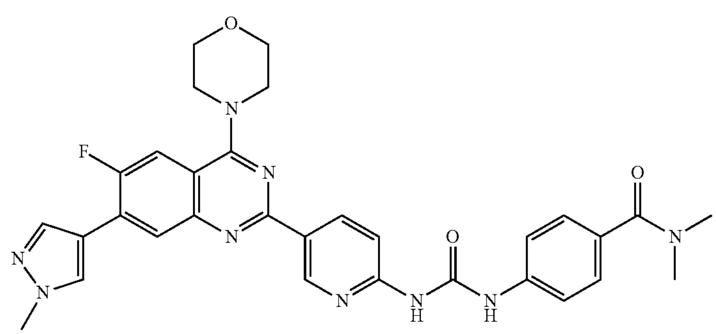 [SMILES: CN(C)C(=O)c1ccc(NC(=O)Nc2ccc(-c3nc(N4CCOCC4)c4cc(F)c(-c5cnn(C)c5)cc4n3)cn2)cc1] | 4-(3-(5-(6-fluoro-7-(1-methyl-1H-pyrazol-4-yl)-4-morpholino-quinazolin-2-yl)pyridin-2-yl)ureido)-N,N-dimethyl-benzamide | 6E + 6G |
| 114 | 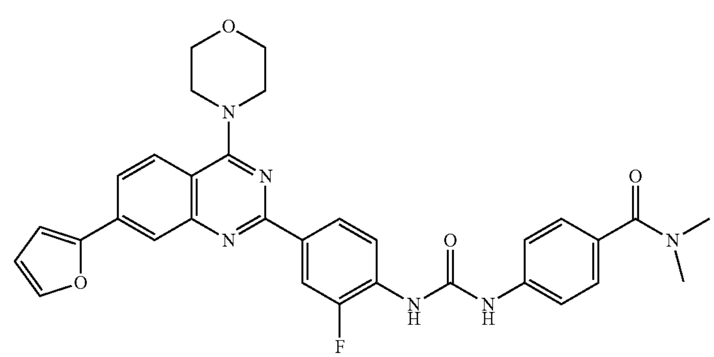 [SMILES: CN(C)C(=O)c1ccc(NC(=O)Nc2ccc(-c3nc(N4CCOCC4)c4ccc(-c5ccco5)cc4n3)cc2F)cc1] | 4-(3-(2-fluoro-4-(7-(furan-2-yl)-4-morpholino-quinazolin-2-yl)phenyl)ureido)-N,N-dimethyl-benzamide | 6D |

TABLE 1-continued

| Ex | Structure | Structure Name | Synthetic Scheme |
|---|---|---|---|
| 115 | 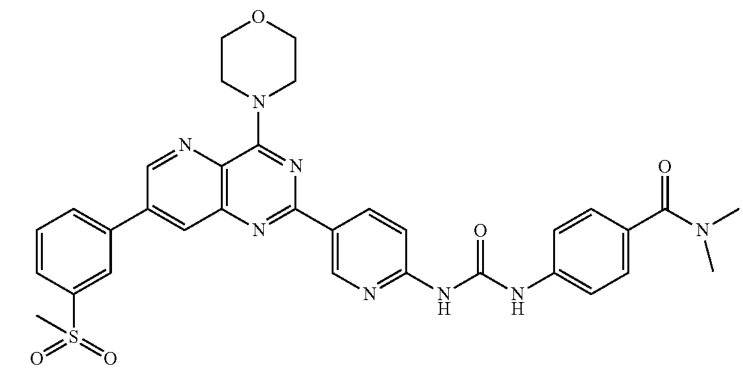 [SMILES: CN(C)C(=O)c1ccc(NC(=O)Nc2ccc(-c3nc(N4CCOCC4)c4ncc(-c5cccc(S(C)(=O)=O)c5)cc4n3)cn2)cc1] | N,N-dimethyl-4-(3-(5-(7-(3-(methylsulfonyl)phenyl)-4-morpholino-pyrido[3,2-d]pyrimidin-2-yl)pyridin-2-yl)ureido)-benzamide | 7A + 6E |
| 116 | 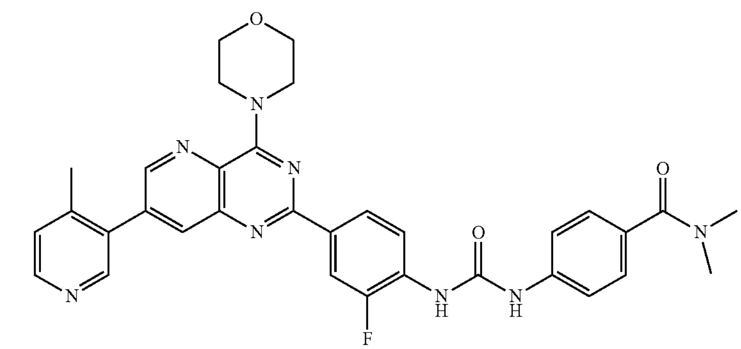 [SMILES: Cc1ccncc1-c1cnc2c(N3CCOCC3)nc(-c3ccc(NC(=O)Nc4ccc(C(=O)N(C)C)cc4)c(F)c3)nc2c1] | 4-(3-(2-fluoro-4-(7-(4-methylpyridin-3-yl)-4-morpholino-pyrido[3,2-d]pyrimidin-2-yl)phenyl)ureido)-N,N-dimethyl-benzamide | 7B |
| 117 | 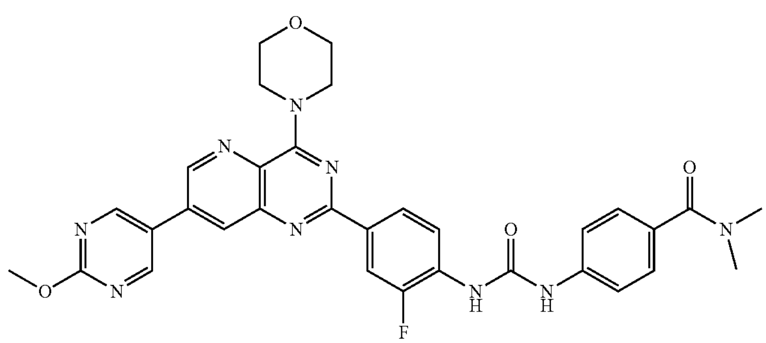 | 4-(3-(2-fluoro-4-(7-(2-methoxypyrimidin-5-yl)-4-morpholino-pyrido[3,2-d]pyrimidin-2-yl)phenyl)ureido)-N,N-dimethyl-benzamide | 7B |
| 118 | 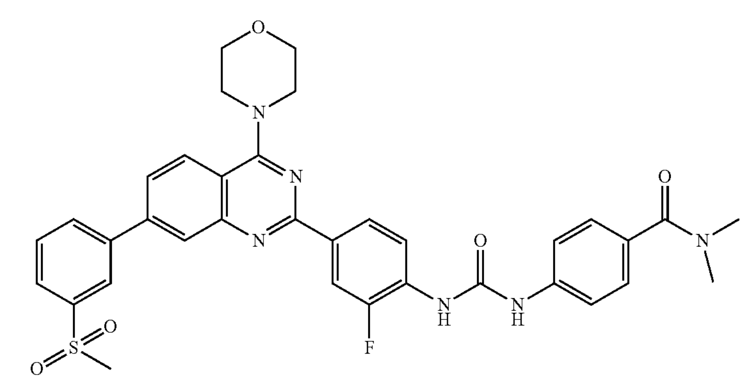 [SMILES: CN(C)C(=O)c1ccc(NC(=O)Nc2ccc(-c3nc(N4CCOCC4)c4ccc(-c5cccc(S(C)(=O)=O)c5)cc4n3)cc2F)cc1] | 4-(3-(2-fluoro-4-(7-(3-(methylsulfonyl)phenyl)-4-morpholino-quinazolin-2-yl)phenyl)ureido)-N,N-dimethyl-benzamide | 6D |

TABLE 1-continued

| Ex | Structure | Structure Name | Synthetic Scheme |
|---|---|---|---|
| 119 | 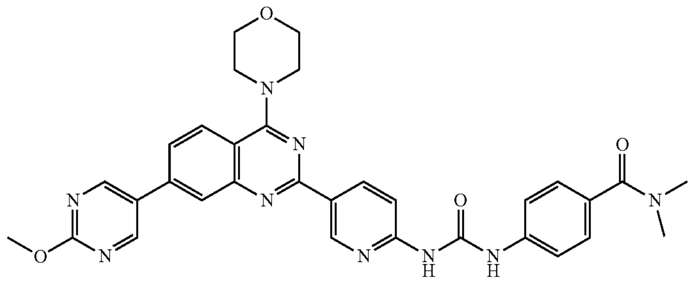 | 4-(3-(5-(7-(2-methoxypyrimidin-5-yl)-4-morpholino-quinazolin-2-yl)pyridin-2-yl)ureido)-N,N-dimethyl-benzamide | 6E |
| 120 | 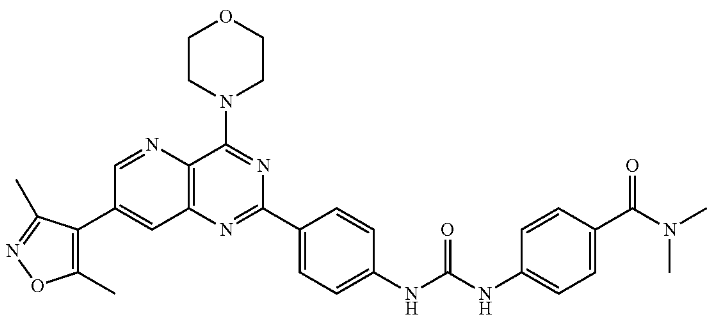 [SMILES: Cc1noc(C)c1-c1cnc2c(N3CCOCC3)nc(-c3ccc(NC(=O)Nc4ccc(C(=O)N(C)C)cc4)cc3)nc2c1] | 4-(3-(4-(7-(3,5-dimethylisoxazol-4-yl)-4-morpholino-pyrido[3,2-d]pyrimidin-2-yl)phenyl)ureido)-N,N-dimethyl-benzamide | 7A |
| 121 | 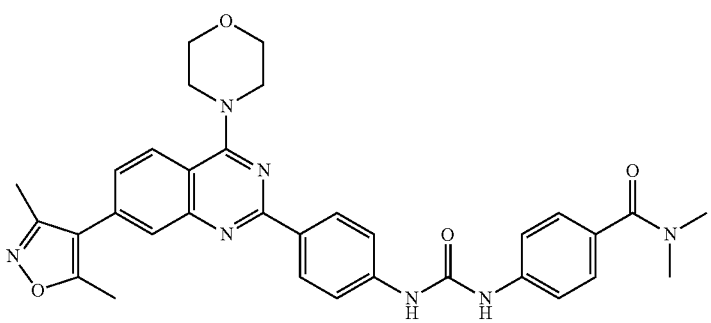 [SMILES: Cc1noc(C)c1-c1ccc2c(N3CCOCC3)nc(-c3ccc(NC(=O)Nc4ccc(C(=O)N(C)C)cc4)cc3)nc2c1] | 4-(3-(4-(7-(3,5-dimethylisoxazol-4-yl)-4-morpholino-quinazolin-2-yl)phenyl)ureido)-N,N-dimethyl-benzamide | 6B |
| 122 | 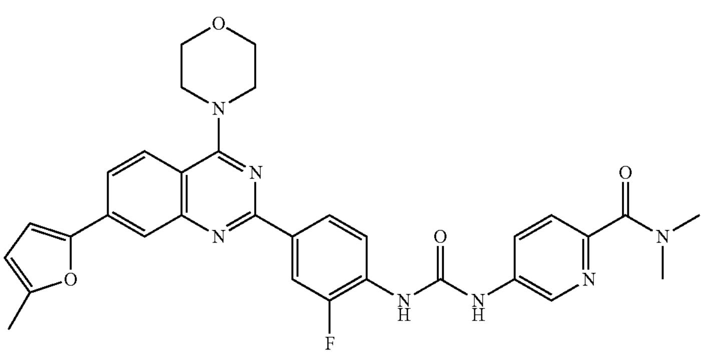 [SMILES: Cc1ccc(-c2ccc3c(N4CCOCC4)nc(-c4ccc(NC(=O)Nc5ccc(C(=O)N(C)C)nc5)c(F)c4)nc3c2)o1] | 5-(3-(2-fluoro-4-(7-(5-methylfuran-2-yl)-4-morpholino-quinazolin-2-yl)phenyl)ureido)-N,N-dimethylpicolinamide | 6B + 4 |

TABLE 1-continued

| Ex | Structure | Structure Name | Synthetic Scheme |
|---|---|---|---|
| 123 | 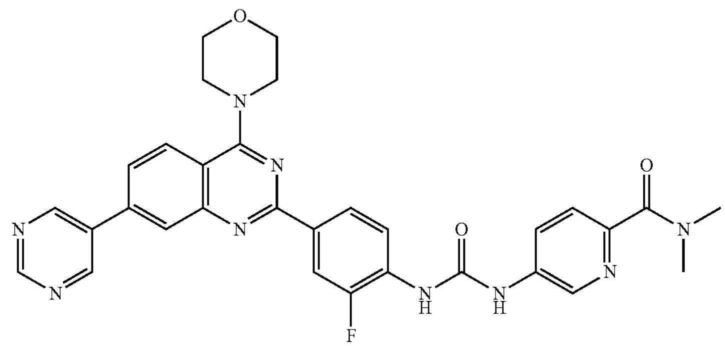 | 5-(3-(2-fluoro-4-(4-morpholino-7-(pyrimidin-5-yl)quinazolin-2-yl)phenyl)ureido)-N,N-dimethylpicolinamide | 6B + 4 |
| 124 | 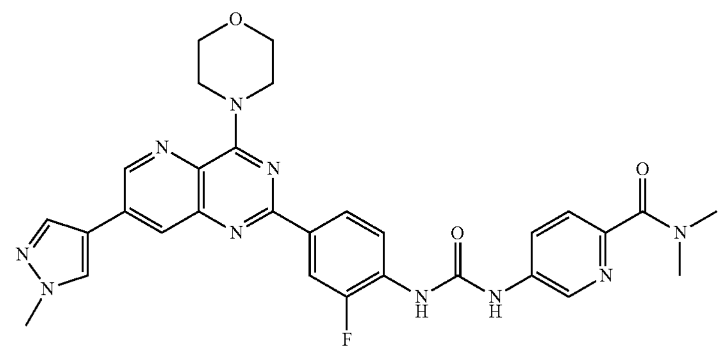 | 5-(3-(2-fluoro-4-(7-(1-methyl-1H-pyrazol-4-yl)-4-morpholino-pyrido[3,2-d]pyrimidin-2-yl)phenyl)ureido)-N,N-dimethylpicolinamide | 7A + 4 |
| 125 | 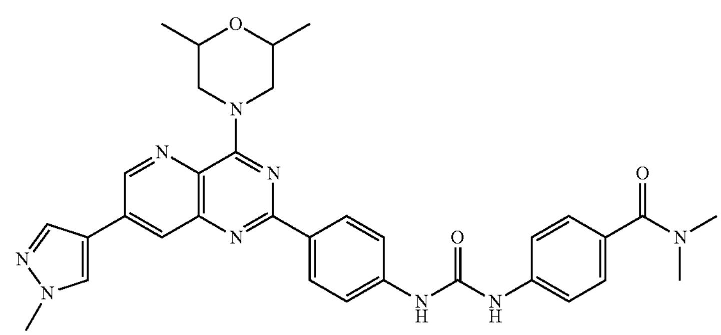 [SMILES: CC1CN(c2nc(-c3ccc(NC(=O)Nc4ccc(C(=O)N(C)C)cc4)cc3)nc3cc(-c4cnn(C)c4)cnc23)CC(C)O1] | 4-(3-(4-(4-(2,6-dimethylmorpholino)-7-(1-methyl-1H-pyrazol-4-yl)pyrido[3,2-d]pyrimidin-2-yl)phenyl)ureido)-N,N-dimethyl-benzamide | 7 |
| 126 | 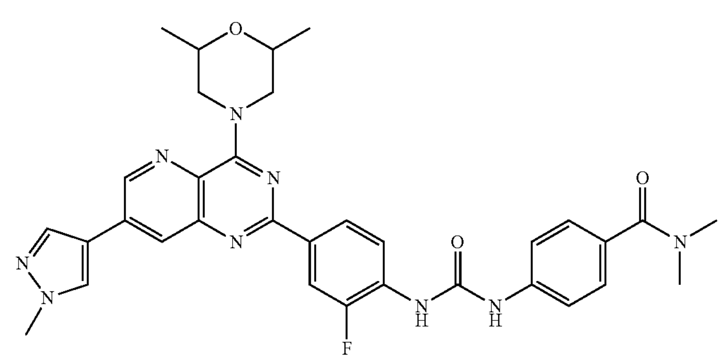 [SMILES: CC1CN(c2nc(-c3ccc(NC(=O)Nc4ccc(C(=O)N(C)C)cc4)c(F)c3)nc3cc(-c4cnn(C)c4)cnc23)CC(C)O1] | 4-(3-(4-(4-(2,6-dimethylmorpholino)-7-(1-methyl-1H-pyrazol-4-yl)pyrido[3,2-d]pyrimidin-2-yl)-2-fluorophenyl)ureido)-N,N-dimethyl-benzamide | 7 |

TABLE 1-continued

| Ex | Structure | Structure Name | Synthetic Scheme |
|---|---|---|---|
| 127 | 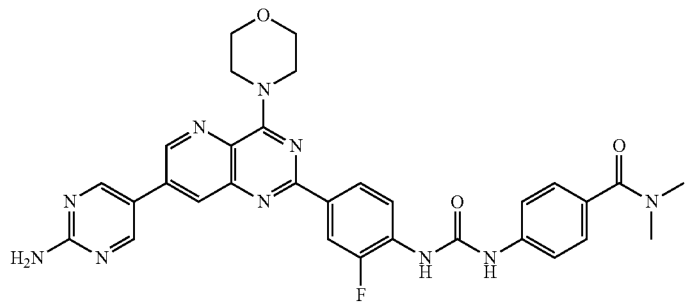 [SMILES: CN(C)C(=O)c1ccc(NC(=O)Nc2ccc(-c3nc(N4CCOCC4)c4ncc(-c5cnc(N)nc5)cc4n3)cc2F)cc1] | 4-(3-(4-(7-(2-aminopyrimidin-5-yl)-4-morpholinopyrido[3,2-d]pyrimidin-2-yl)-2-fluorophenyl)ureido)-N,N-dimethyl-benzamide | 7B |
| 128 | 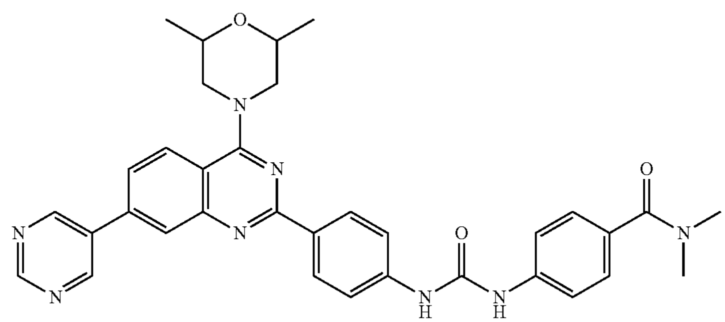 [SMILES: CC1CN(c2nc(-c3ccc(NC(=O)Nc4ccc(C(=O)N(C)C)cc4)cc3)nc3cc(-c4cncnc4)ccc23)CC(C)O1] | 4-(3-(4-(4-(2,6-dimethylmorpholino)-7-(pyrimidin-5-yl)quinazolin-2-yl)phenyl)ureido)-N,N-dimethyl-benzamide | 6 |
| 129 | 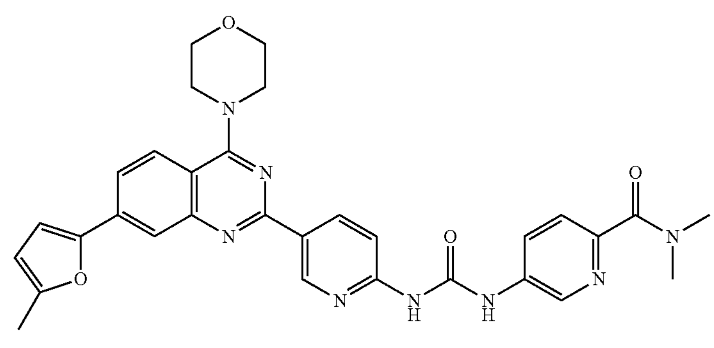 [SMILES: Cc1ccc(-c2ccc3c(N4CCOCC4)nc(-c4ccc(NC(=O)Nc5ccc(C(=O)N(C)C)nc5)nc4)nc3c2)o1] | N,N-dimethyl-5-(3-(5-(7-(5-methylfuran-2-yl)-4-morpholino-quinazolin-2-yl)pyridin-2-yl)ureido)picolinamide | 6 |
| 130 | 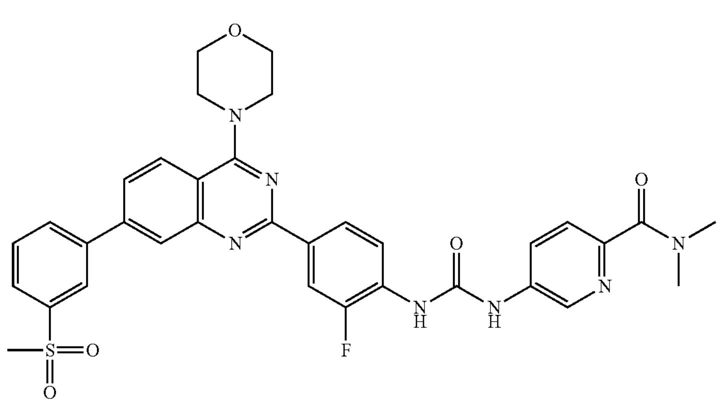 | 5-(3-(2-fluoro-4-(7-(3-(methylsulfonyl)phenyl)-4-morpholino-quinazolin-2-yl)phenyl)ureido)-N,N-dimethylpicolinamide | 6B + 4 |

TABLE 1-continued

| Ex | Structure | Structure Name | Synthetic Scheme |
|---|---|---|---|
| 131 | 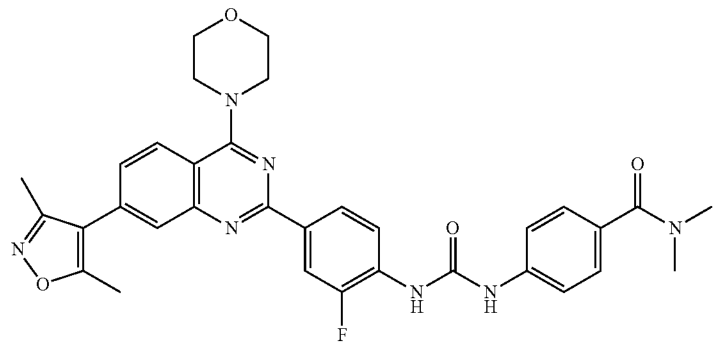 [SMILES: Cc1noc(C)c1-c1ccc2c(N3CCOCC3)nc(-c3ccc(NC(=O)Nc4ccc(C(=O)N(C)C)cc4)c(F)c3)nc2c1] | 4-(3-(4-(7-(3,5-dimethylisoxazol-4-yl)-4-morpholino-quinazolin-2-yl)-2-fluorophenyl)ureido)-N,N-dimethyl-benzamide | 6D |
| 132 | 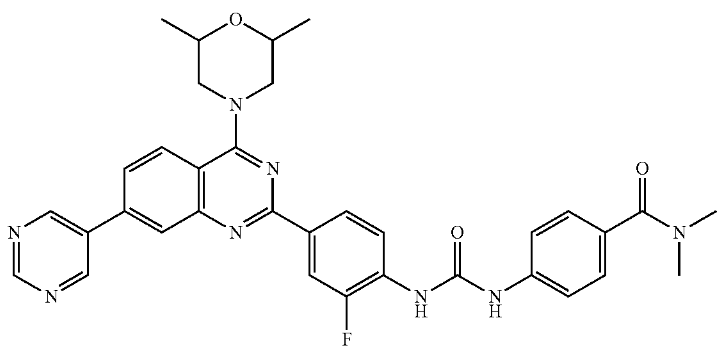 [SMILES: CC1CN(c2nc(-c3ccc(NC(=O)Nc4ccc(C(=O)N(C)C)cc4)c(F)c3)nc3cc(-c4cncnc4)ccc23)CC(C)O1] | 4-(3-(4-(4-(2,6-dimethylmorpholino)-7-(pyrimidin-5-yl)quinazolin-2-yl)-2-fluorophenyl)ureido)-N,N-dimethyl-benzamide | 6 |
| 133 | 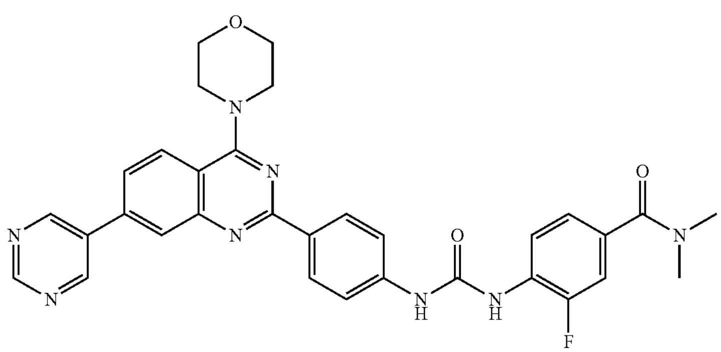 [SMILES: CN(C)C(=O)c1ccc(NC(=O)Nc2ccc(-c3nc(N4CCOCC4)c4ccc(-c5cncnc5)cc4n3)cc2)c(F)c1] | 3-fluoro-N,N-dimethyl-4-(3-(4-(4-morpholino-7-(pyrimidin-5-yl)quinazolin-2-yl)phenyl)ureido)-benzamide | 6C |
| 134 | 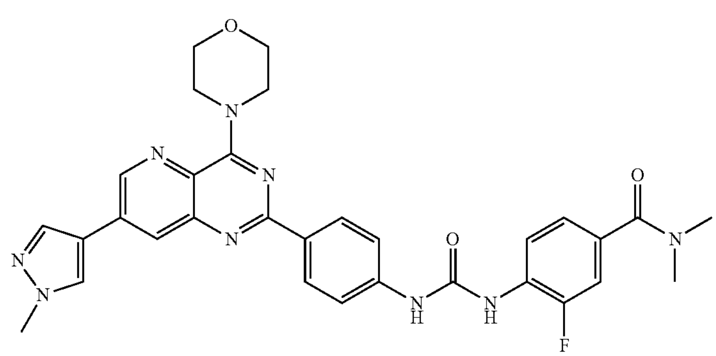 [SMILES: CN(C)C(=O)c1ccc(NC(=O)Nc2ccc(-c3nc(N4CCOCC4)c4ncc(-c5cnn(C)c5)cc4n3)cc2)c(F)c1] | 3-fluoro-N,N-dimethyl-4-(3-(4-(7-(1-methyl-1H-pyrazol-4-yl)-4-morpholino-pyrido[3,2-d]pyrimidin-2-yl)phenyl)ureido)-benzamide | 7A |

TABLE 1-continued

| Ex | Structure | Structure Name | Synthetic Scheme |
|---|---|---|---|
| 135 | 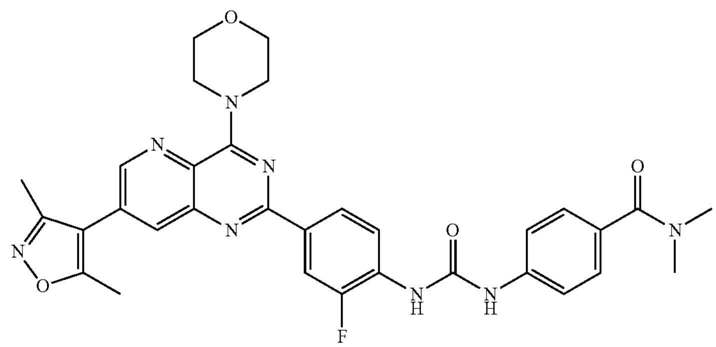 [SMILES: Cc1noc(C)c1-c1cnc2c(N3CCOCC3)nc(-c3ccc(NC(=O)Nc4ccc(C(=O)N(C)C)cc4)c(F)c3)nc2c1] | 4-(3-(4-(7-(3,5-dimethylisoxazol-4-yl)-4-morpholino-pyrido[3,2-d]pyrimidin-2-yl)-2-fluorophenyl)ureido)-N,N-dimethyl-benzamide | 7B |
| 136 | 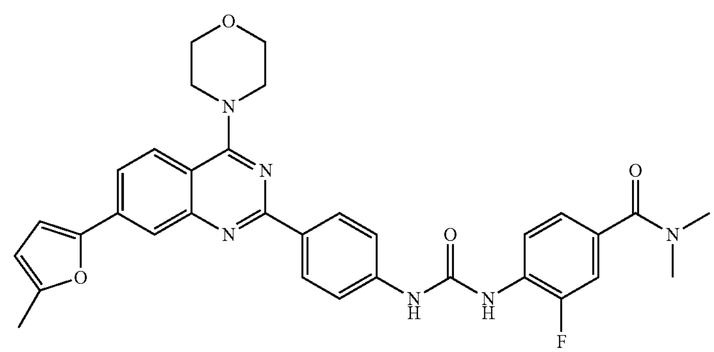 [SMILES: Cc1ccc(-c2ccc3c(N4CCOCC4)nc(-c4ccc(NC(=O)Nc5ccc(C(=O)N(C)C)cc5F)cc4)nc3c2)o1] | 3-fluoro-N,N-dimethyl-4-(3-(4-(7-(5-methylfuran-2-yl)-4-morpholino-quinazolin-2-yl)phenyl)ureido)-benzamide | 6C |
| 137 | 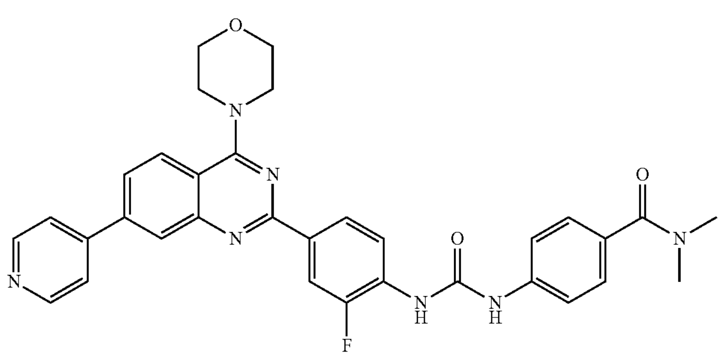 [SMILES: CN(C)C(=O)c1ccc(NC(=O)Nc2ccc(-c3nc(N4CCOCC4)c4ccc(-c5ccncc5)cc4n3)cc2F)cc1] | 4-(3-(2-fluoro-4-(4-morpholino-7-(pyridin-4-yl)quinazolin-2-yl)phenyl)ureido)-N,N-dimethyl-benzamide | 6D |
| 138 | 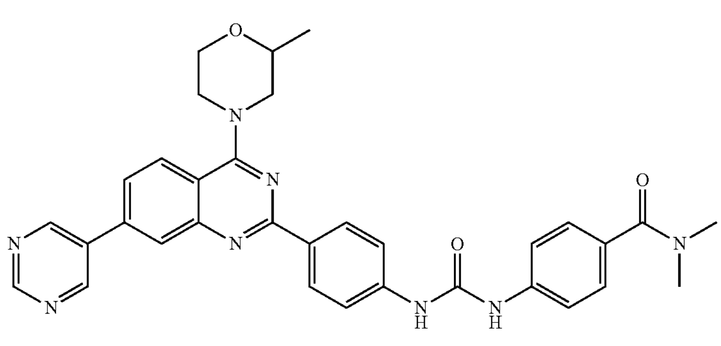 [SMILES: CC1CN(c2nc(-c3ccc(NC(=O)Nc4ccc(C(=O)N(C)C)cc4)cc3)nc3cc(-c4cncnc4)ccc23)CCO1] | N,N-dimethyl-4-(3-(4-(4-(2-methylmorpholino)-7-(pyrimidin-5-yl)quinazolin-2-yl)phenyl)ureido)-benzamide | 6 |

TABLE 1-continued

| Ex | Structure | Structure Name | Synthetic Scheme |
|---|---|---|---|
| 139 | 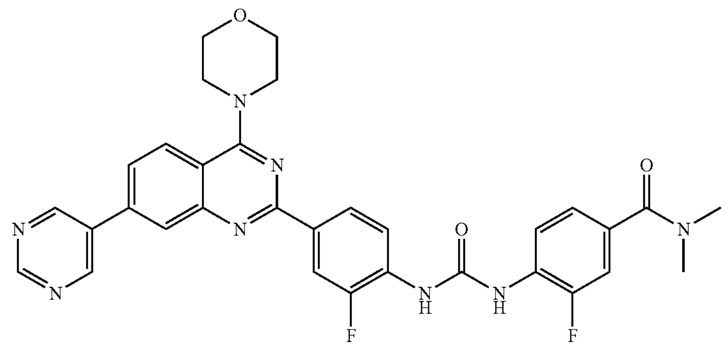 [SMILES: CN(C)C(=O)c1ccc(NC(=O)Nc2ccc(-c3nc(N4CCOCC4)c4ccc(-c5cncnc5)cc4n3)cc2F)c(F)c1] | 3-fluoro-4-(3-(2-fluoro-4-(4-morpholino-7-(pyrimidin-5-yl)quinazolin-2-yl)phenyl)ureido)-N,N-dimethyl-benzamide | 6B |
| 140 | 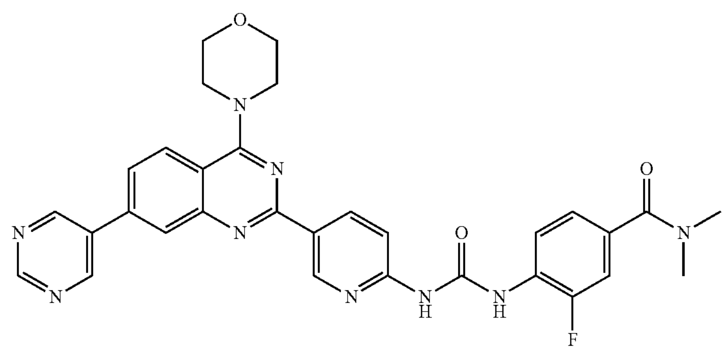 [SMILES: CN(C)C(=O)c1ccc(NC(=O)Nc2ccc(-c3nc(N4CCOCC4)c4ccc(-c5cncnc5)cc4n3)cn2)c(F)c1] | 3-fluoro-N,N-dimethyl-4-(3-(5-(4-morpholino-7-(pyrimidin-5-yl)quinazolin-2-yl)pyridin-2-yl)ureido)-benzamide | 6E |
| 141 | 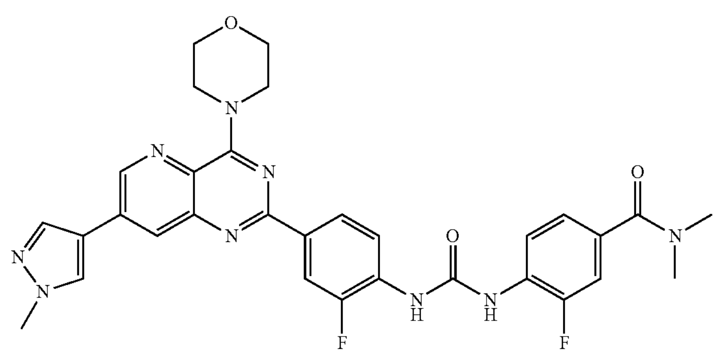 [SMILES: CN(C)C(=O)c1ccc(NC(=O)Nc2ccc(-c3nc(N4CCOCC4)c4ncc(-c5cnn(C)c5)cc4n3)cc2F)c(F)c1] | 3-fluoro-4-(3-(2-fluoro-4-(7-(1-methyl-1H-pyrazol-4-yl)-4-morpholino-pyrido[3,2-d]pyrimidin-2-yl)phenyl)ureido)-N,N-dimethyl-benzamide | 7A |
| 142 | 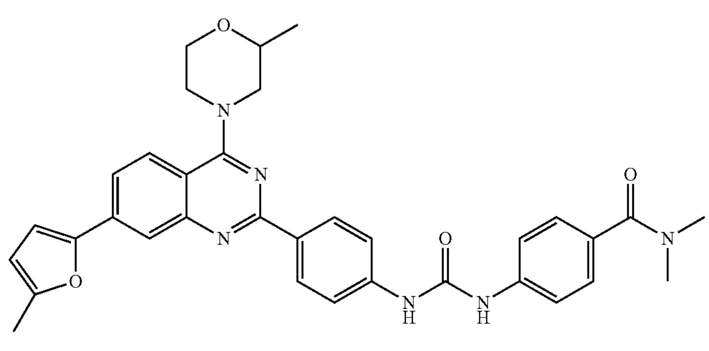 [SMILES: Cc1ccc(-c2ccc3c(N4CCOC(C)C4)nc(-c4ccc(NC(=O)Nc5ccc(C(=O)N(C)C)cc5)cc4)nc3c2)o1] | N,N-dimethyl-4-(3-(4-(7-(5-methylfuran-2-yl)-4-(2-methylmorpholino)quinazolin-2-yl)phenyl)ureido)-benzamide | 6 |

TABLE 1-continued

| Ex | Structure | Structure Name | Synthetic Scheme |
|---|---|---|---|
| 143 | 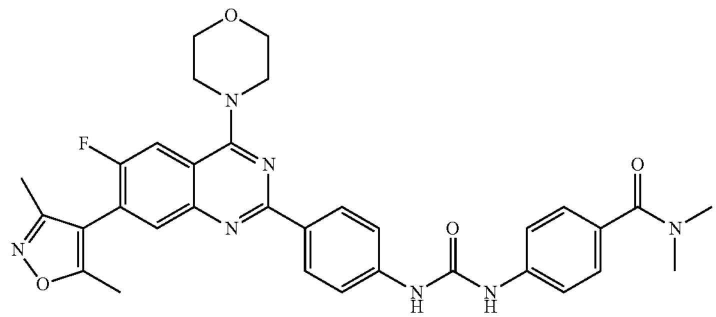 [SMILES: Cc1noc(C)c1-c1cc2nc(-c3ccc(NC(=O)Nc4ccc(C(=O)N(C)C)cc4)cc3)nc(N3CCOCC3)c2cc1F] | 4-(3-(4-(7-(3,5-dimethylisoxazol-4-yl)-6-fluoro-4-morpholino-quinazolin-2-yl)phenyl)ureido)-N,N-dimethyl-benzamide | 6G |
| 144 | 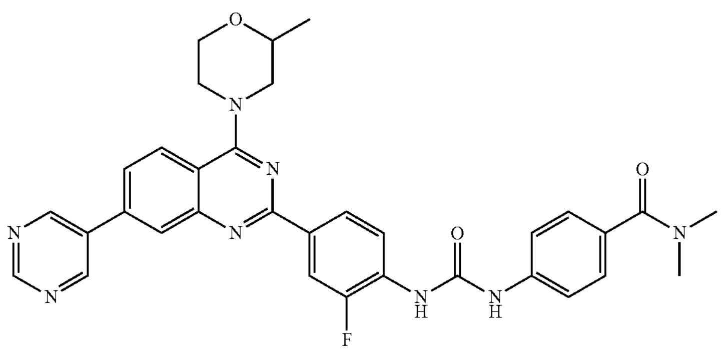 [SMILES: CC1CN(c2nc(-c3ccc(NC(=O)Nc4ccc(C(=O)N(C)C)cc4)c(F)c3)nc3cc(-c4cncnc4)ccc23)CCO1] | 4-(3-(2-fluoro-4-(4-(2-methylmorpholino)-7-(pyrimidin-5-yl)quinazolin-2-yl)phenyl)ureido)-N,N-dimethyl-benzamide | 6 |
| 145 | 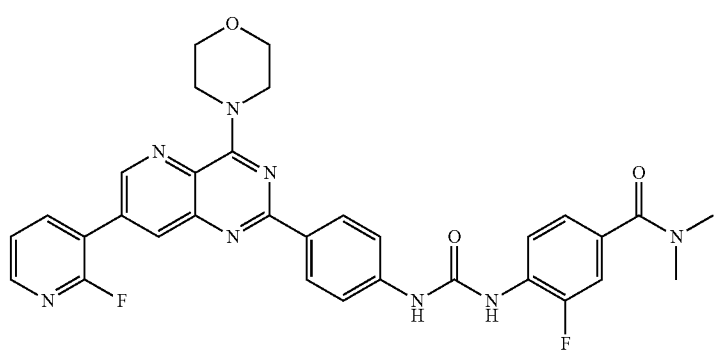 [SMILES: CN(C)C(=O)c1ccc(NC(=O)Nc2ccc(-c3nc(N4CCOCC4)c4ncc(-c5cccnc5F)cc4n3)cc2)c(F)c1] | 3-fluoro-4-(3-(4-(7-(2-fluoropyridin-3-yl)-4-morpholino-pyrido[3,2-d]pyrimidin-2-yl)phenyl)ureido)-N,N-dimethyl-benzamide | 7A |
| 146 | 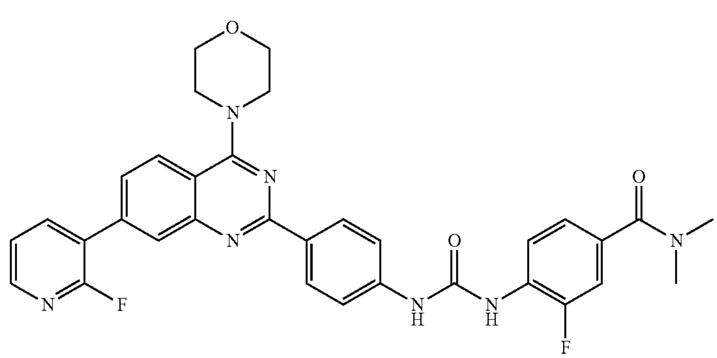 [SMILES: CN(C)C(=O)c1ccc(NC(=O)Nc2ccc(-c3nc(N4CCOCC4)c4ccc(-c5cccnc5F)cc4n3)cc2)c(F)c1] | 3-fluoro-4-(3-(4-(7-(2-fluoropyridin-3-yl)-4-morpholino-quinazolin-2-yl)phenyl)ureido)-N,N-dimethyl-benzamide | 6C |

TABLE 1-continued

| Ex | Structure Name | Synthetic Scheme |
|---|---|---|
| 147 | 3-fluoro-4-(3-(4-(7-(2-methoxypyrimidin-5-yl)-4-morpholino-quinazolin-2-yl)phenyl)ureido)-N,N-dimethyl-benzamide | 6C |
| 148 | N,N-dimethyl-4-(3-(4-(7-(1-methyl-1H-pyrazol-4-yl)-4-(2-methylmorpholino)pyrido[3,2-d]pyrimidin-2-yl)phenyl)ureido)-benzamide | 7 |
| 149 | 4-(3-(4-(6-fluoro-7-(furan-2-yl)-4-morpholino-quinazolin-2-yl)phenyl)ureido)-N,N-dimethyl-benzamide | 6G |
| 150 | 4-(3-(4-(7-(2-hydroxypyrimidin-5-yl)-4-morpholino-quinazolin-2-yl)phenyl)ureido)-N,N-dimethyl-benzamide | 6B |

TABLE 1-continued

| Ex | Structure | Structure Name | Synthetic Scheme |
|---|---|---|---|
| 151 | 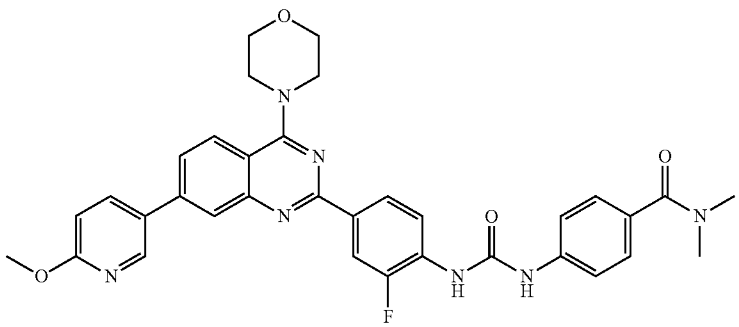 | 4-(3-(2-fluoro-4-(7-(6-methoxypyridin-3-yl)-4-morpholino-quinazolin-2-yl)phenyl)ureido)-N,N-dimethyl-benzamide | 6D |
| 152 | 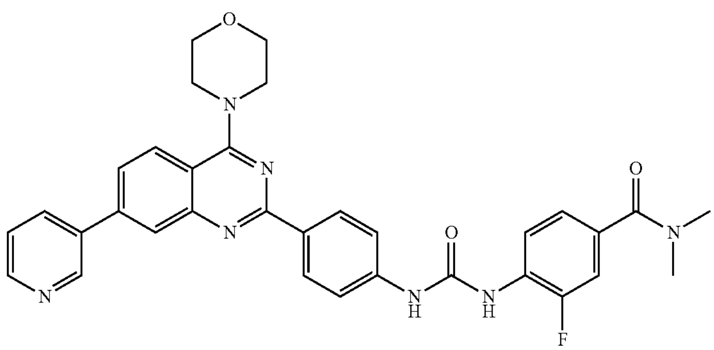 [SMILES: CN(C)C(=O)c1ccc(NC(=O)Nc2ccc(-c3nc(N4CCOCC4)c4ccc(-c5cccnc5)cc4n3)cc2)c(F)c1] | 3-fluoro-N,N-dimethyl-4-(3-(4-(4-morpholino-7-(pyridin-3-yl)quinazolin-2-yl)phenyl)ureido)-benzamide | 6C |
| 153 | 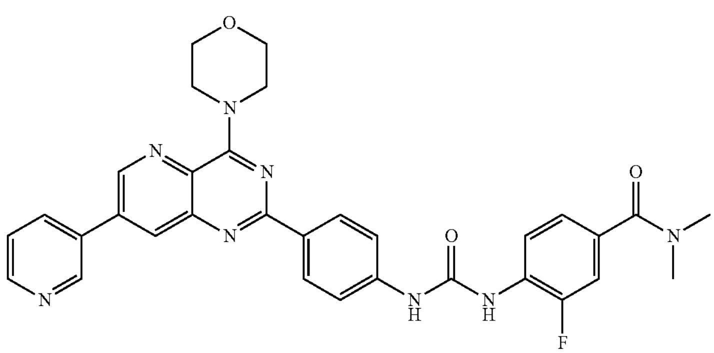 [SMILES: CN(C)C(=O)c1ccc(NC(=O)Nc2ccc(-c3nc(N4CCOCC4)c4ncc(-c5cccnc5)cc4n3)cc2)c(F)c1] | 3-fluoro-N,N-dimethyl-4-(3-(4-(4-morpholino-7-(pyridin-3-yl)pyrido[3,2-d]pyrimidin-2-yl)phenyl)ureido)-benzamide | 7A |
| 154 | 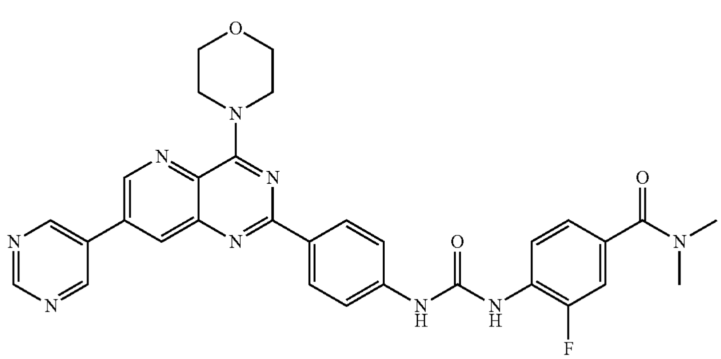 [SMILES: CN(C)C(=O)c1ccc(NC(=O)Nc2ccc(-c3nc(N4CCOCC4)c4ncc(-c5cncnc5)cc4n3)cc2)c(F)c1] | 3-fluoro-N,N-dimethyl-4-(3-(4-(4-morpholino-7-(pyrimidin-5-yl)pyrido[3,2-d]pyrimidin-2-yl)phenyl)ureido)-benzamide | 7A |

TABLE 1-continued

| Ex | Structure | Structure Name | Synthetic Scheme |
|---|---|---|---|
| 155 | 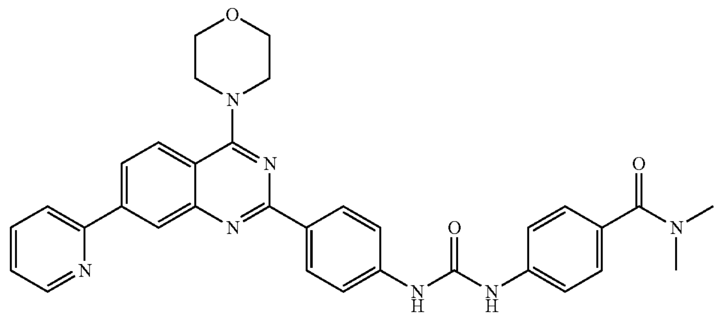 [SMILES: CN(C)C(=O)c1ccc(NC(=O)Nc2ccc(-c3nc(N4CCOCC4)c4ccc(-c5ccccn5)cc4n3)cc2)cc1] | N,N-dimethyl-4-(3-(4-(4-morpholino-7-(pyridin-2-yl)quinazolin-2-yl)phenyl)ureido)-benzamide | 6 + 6B |
| 156 | 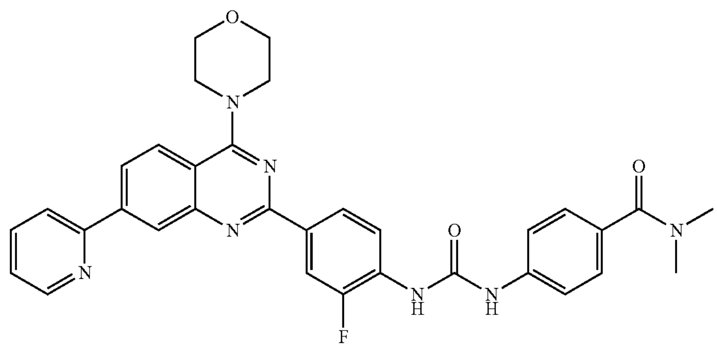 [SMILES: CN(C)C(=O)c1ccc(NC(=O)Nc2ccc(-c3nc(N4CCOCC4)c4ccc(-c5ccccn5)cc4n3)cc2F)cc1] | 4-(3-(2-fluoro-4-(4-morpholino-7-(pyridin-2-yl)quinazolin-2-yl)phenyl)ureido)-N,N-dimethyl-benzamide | 6 + 6D |
| 157 | 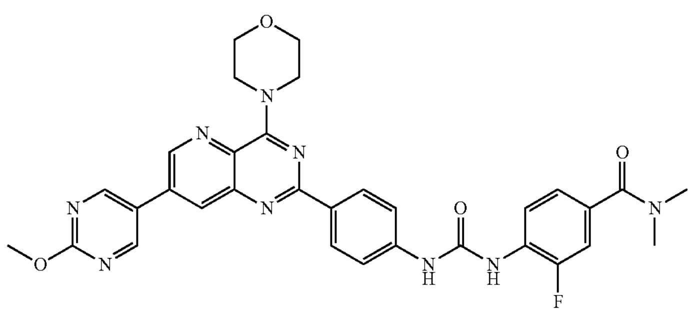 | 3-fluoro-4-(3-(4-(7-(2-methoxypyrimidin-5-yl)-4-morpholino-pyrido[3,2-d]pyrimidin-2-yl)phenyl)ureido)-N,N-dimethyl-benzamide | 7A |
| 158 | 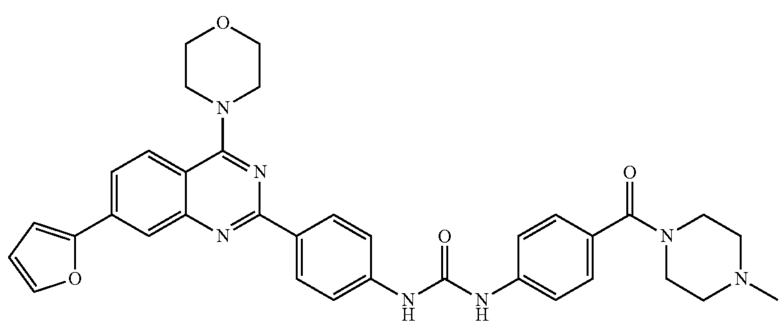 [SMILES: CN1CCN(C(=O)c2ccc(NC(=O)Nc3ccc(-c4nc(N5CCOCC5)c5ccc(-c6ccco6)cc5n4)cc3)cc2)CC1] | 1-(4-(7-(furan-2-yl)-4-morpholino-quinazolin-2-yl)phenyl)-3-(4-(4-methylpiperazine-1-carbonyl)phenyl)urea | 6B |

TABLE 1-continued

| Ex | Structure | Structure Name | Synthetic Scheme |
|---|---|---|---|
| 159 | 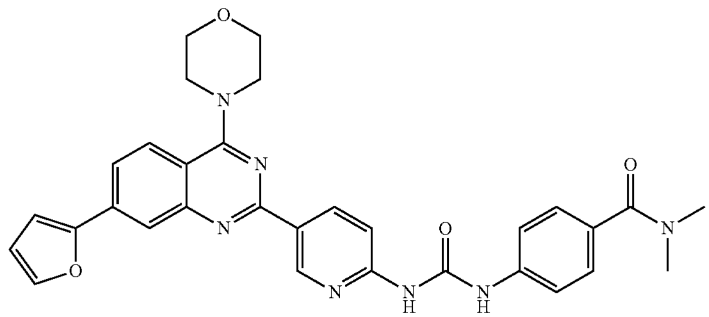 [SMILES: CN(C)C(=O)c1ccc(NC(=O)Nc2ccc(-c3nc(N4CCOCC4)c4ccc(-c5ccco5)cc4n3)cn2)cc1] | 4-(3-(5-(7-(furan-2-yl)-4-morpholino-quinazolin-2-yl)pyridin-2-yl)ureido)-N,N-dimethyl-benzamide | 6E |
| 160 | 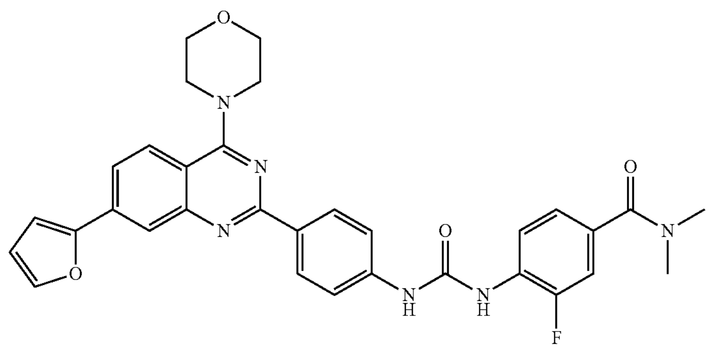 [SMILES: CN(C)C(=O)c1ccc(NC(=O)Nc2ccc(-c3nc(N4CCOCC4)c4ccc(-c5ccco5)cc4n3)cc2)c(F)c1] | 3-fluoro-4-(3-(4-(7-(furan-2-yl)-4-morpholino-quinazolin-2-yl)phenyl)ureido)-N,N-dimethyl-benzamide | 6C |
| 161 | 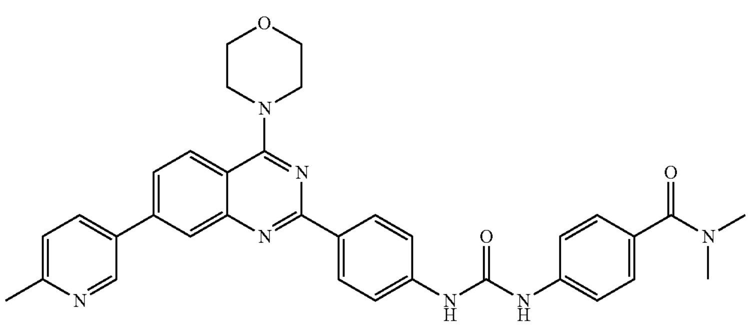 | N,N-dimethyl-4-(3-(4-(7-(6-methylpyridin-3-yl)-4-morpholino-quinazolin-2-yl)phenyl)ureido)-benzamide | 6B |
| 162 | 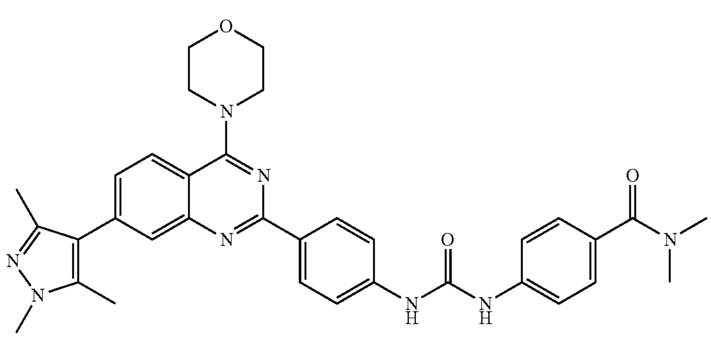 [SMILES: Cc1nn(C)c(C)c1-c1ccc2c(N3CCOCC3)nc(-c3ccc(NC(=O)Nc4ccc(C(=O)N(C)C)cc4)cc3)nc2c1] | N,N-dimethyl-4-(3-(4-(4-morpholino-7-(1,3,5-trimethyl-1H-pyrazol-4-yl)quinazolin-2-yl)phenyl)ureido)-benzamide | 6B |

TABLE 1-continued

| Ex | Structure | Structure Name | Synthetic Scheme |
|---|---|---|---|
| 163 | 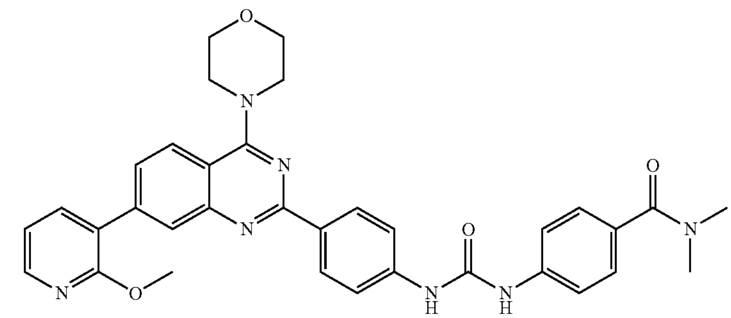 [SMILES: COc1ncccc1-c1ccc2c(N3CCOCC3)nc(-c3ccc(NC(=O)Nc4ccc(C(=O)N(C)C)cc4)cc3)nc2c1] | 4-(3-(4-(7-(2-methoxypyridin-3-yl)-4-morpholino-quinazolin-2-yl)phenyl)ureido)-N,N-dimethyl-benzamide | 6B |
| 164 | 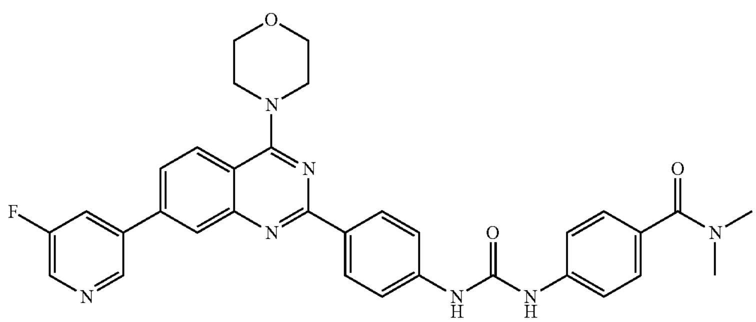 [SMILES: CN(C)C(=O)c1ccc(NC(=O)Nc2ccc(-c3nc(N4CCOCC4)c4ccc(-c5cncc(F)c5)cc4n3)cc2)cc1] | 4-(3-(4-(7-(5-fluoropyridin-3-yl)-4-morpholino-quinazolin-2-yl)phenyl)ureido)-N,N-dimethyl-benzamide | 6B |
| 165 | 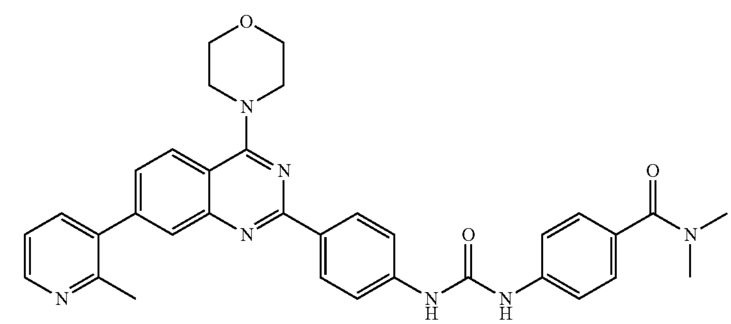 [SMILES: Cc1ncccc1-c1ccc2c(N3CCOCC3)nc(-c3ccc(NC(=O)Nc4ccc(C(=O)N(C)C)cc4)cc3)nc2c1] | N,N-dimethyl-4-(3-(4-(7-(2-methylpyridin-3-yl)-4-morpholino-quinazolin-2-yl)phenyl)ureido)-benzamide | 6B |
| 166 | 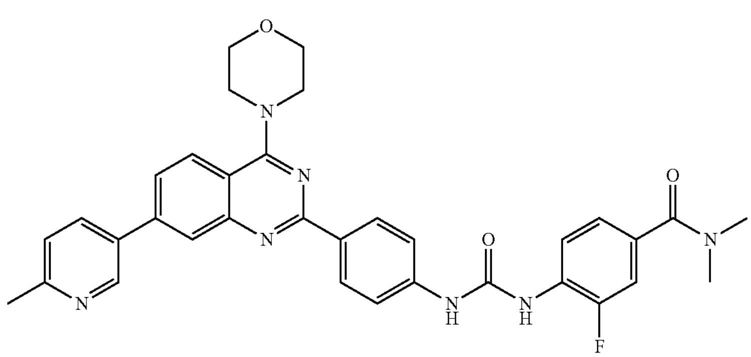 | 3-fluoro-N,N-dimethyl-4-(3-(4-(7-(6-methylpyridin-3-yl)-4-morpholino-quinazolin-2-yl)phenyl)ureido)-benzamide | 6C |

TABLE 1-continued

| Ex | Structure | Structure Name | Synthetic Scheme |
|---|---|---|---|
| 167 | 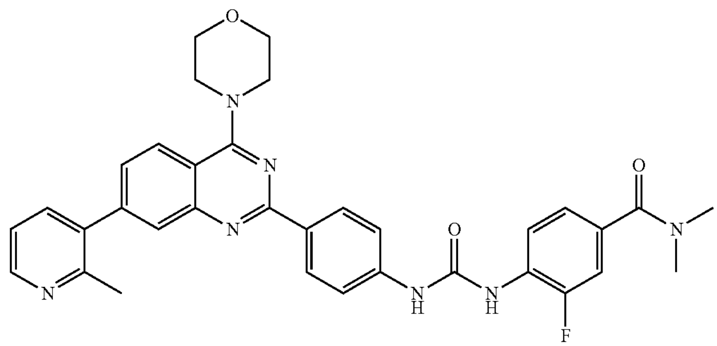 [SMILES: Cc1ncccc1-c1ccc2c(N3CCOCC3)nc(-c3ccc(NC(=O)Nc4ccc(C(=O)N(C)C)cc4F)cc3)nc2c1] | 3-fluoro-N,N-dimethyl-4-(3-(4-(7-(2-methylpyridin-3-yl)-4-morpholino-quinazolin-2-yl)phenyl)ureido)-benzamide | 6C |
| 168 | 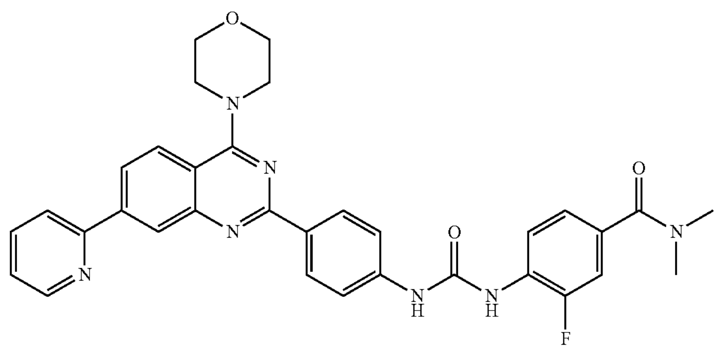 [SMILES: CN(C)C(=O)c1ccc(NC(=O)Nc2ccc(-c3nc(N4CCOCC4)c4ccc(-c5ccccn5)cc4n3)cc2)c(F)c1] | 3-fluoro-N,N-dimethyl-4-(3-(4-(4-morpholino-7-(pyridin-2-yl)quinazolin-2-yl)phenyl)ureido)-benzamide | 6 + 6C |
| 169 | 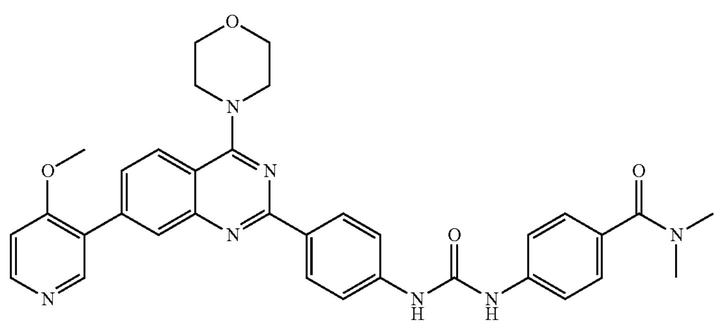 [SMILES: COc1ccncc1-c1ccc2c(N3CCOCC3)nc(-c3ccc(NC(=O)Nc4ccc(C(=O)N(C)C)cc4)cc3)nc2c1] | 4-(3-(4-(7-(4-methoxypyridin-3-yl)-4-morpholino-quinazolin-2-yl)phenyl)ureido)-N,N-dimethyl-benzamide | 6B |
| 170 | 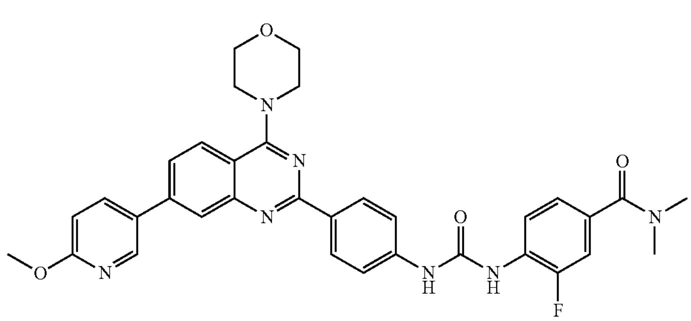 | 3-fluoro-4-(3-(4-(7-(6-methoxypyridin-3-yl)-4-morpholino-quinazolin-2-yl)phenyl)ureido)-N,N-dimethyl-benzamide | 6C |

TABLE 1-continued

| Ex | Structure Name | Synthetic Scheme |
|---|---|---|
| 171 | 3-chloro-4-(3-(4-(7-(furan-2-yl)-4-morpholino-quinazolin-2-yl)phenyl)ureido)-N,N-dimethyl-benzamide | 6B |
| 172 | 3-fluoro-N,N-dimethyl-4-(3-(5-(7-(1-methyl-1H-pyrazol-4-yl)-4-morpholino-quinazolin-2-yl)pyridin-2-yl)ureido)-benzamide | 6E |
| 173 | 3-fluoro-4-(3-(4-(6-fluoro-4-morpholino-7-(pyridin-3-yl)quinazolin-2-yl)phenyl)ureido)-N,N-dimethyl-benzamide | 6G |
| 174 | 3-fluoro-4-(3-(4-(6-fluoro-4-morpholino-7-(pyrimidin-5-yl)quinazolin-2-yl)phenyl)ureido)-N,N-dimethyl-benzamide | 6G |

TABLE 1-continued

| Ex | Structure Name | Synthetic Scheme |
|---|---|---|
| 175 | 4-(3-(5-(6-fluoro-4-morpholino-7-(pyridin-3-yl)quinazolin-2-yl)pyridin-2-yl)ureido)-N,N-dimethyl-benzamide | 6G + 6E |
| 176 | 4-(3-(5-(6-fluoro-4-morpholino-7-(pyrimidin-5-yl)quinazolin-2-yl)pyridin-2-yl)ureido)-N,N-dimethyl-benzamide | 6G + 6E |
| 177 | 4-(3-(4-(7-(6-aminopyridin-3-yl)-4-morpholino-quinazolin-2-yl)phenyl)ureido)-N,N-dimethyl-benzamide | 6B |
| 178 | 4-(3-(4-(7-(6-aminopyridin-3-yl)-4-morpholino-quinazolin-2-yl)phenyl)ureido)-3-fluoro-N,N-dimethyl-benzamide | 6C |
| 179 | N,N-dimethyl-4-(3-(4-(4-morpholino-quinazolin-2-yl)phenyl)ureido)-benzamide | 15 |

TABLE 1-continued

| Ex | Structure | Structure Name | Synthetic Scheme |
|---|---|---|---|
| 180 | 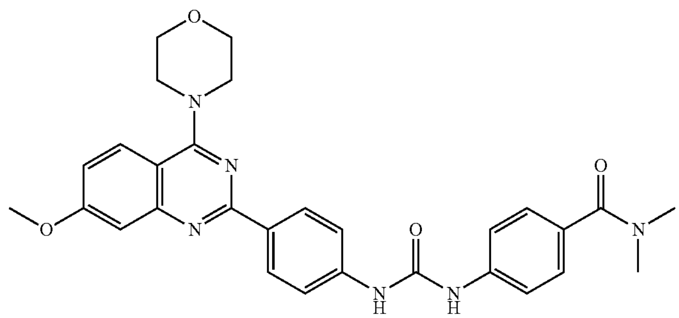 | 4-(3-(4-(7-methoxy-4-morpholino-quinazolin-2-yl)phenyl)ureido)-N,N-dimethyl-benzamide | 15 |
| 181 | 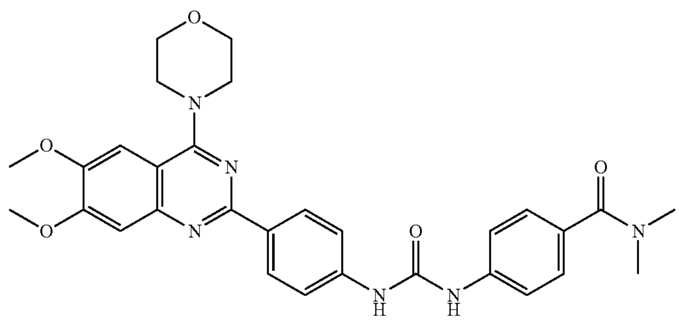 | 4-(3-(4-(6,7-dimethoxy-4-morpholino-quinazolin-2-yl)phenyl)ureido)-N,N-dimethyl-benzamide | 15 |
| 182 | 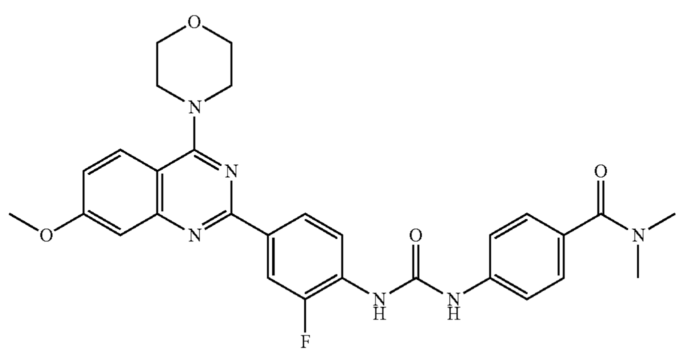 | 4-(3-(2-fluoro-4-(7-methoxy-4-morpholino-quinazolin-2-yl)phenyl)ureido)-N,N-dimethyl-benzamide | 15 |
| 183 | 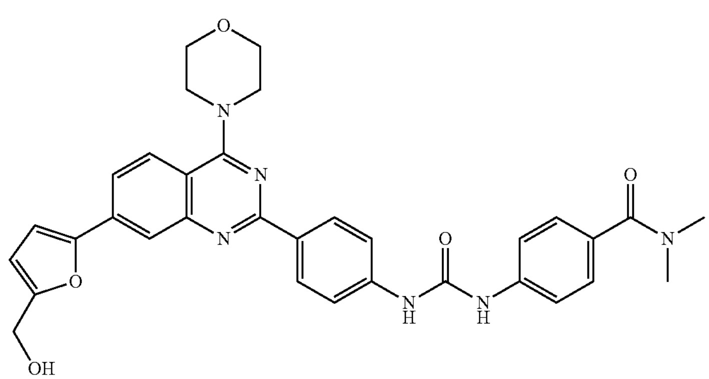 [SMILES: CN(C)C(=O)c1ccc(NC(=O)Nc2ccc(-c3nc(N4CCOCC4)c4ccc(-c5ccc(CO)o5)cc4n3)cc2)cc1] | 4-(3-(4-(7-(5-(hydroxymethyl)furan-2-yl)-4-morpholino-quinazolin-2-yl)phenyl)ureido)-N,N-dimethyl-benzamide | 11 + 6b |

TABLE 1-continued

| Ex | Structure | Structure Name | Synthetic Scheme |
|---|---|---|---|
| 184 | 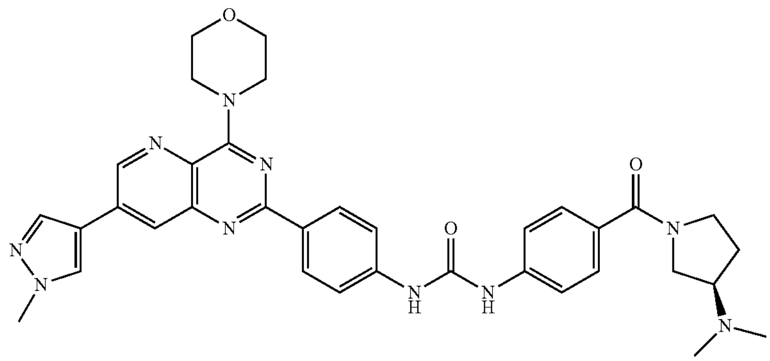 [SMILES: CN(C)[C@@H]1CCN(C(=O)c2ccc(NC(=O)Nc3ccc(-c4nc(N5CCOCC5)c5ncc(-c6cnn(C)c6)cc5n4)cc3)cc2)C1] | (R)-1-(4-(3-(dimethylamino)pyrrolidine-1-carbonyl)phenyl)-3-(4-(7-(1-methyl-1H-pyrazol-4-yl)-4-morpholino-pyrido[3,2-d]pyrimidin-2-yl)phenyl)urea | 7A,13 + 14 |
| 185 | 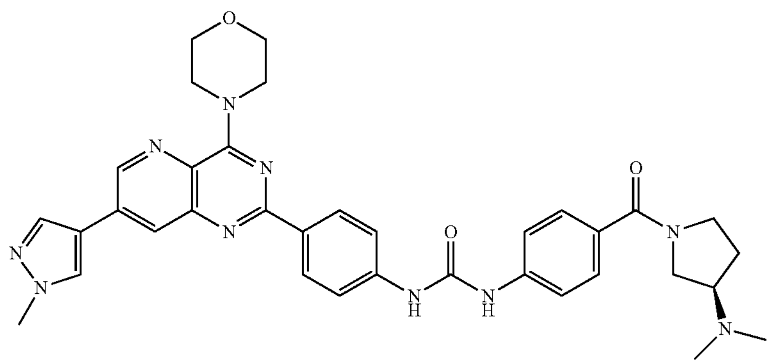 [SMILES: CN(C)[C@@H]1CCN(C(=O)c2ccc(NC(=O)Nc3ccc(-c4nc(N5CCOCC5)c5ncc(-c6cnn(C)c6)cc5n4)cc3)cc2)C1] | (S)-1-(4-(3-(dimethylamino)pyrrolidine-1-carbonyl)phenyl)-3-(4-(7-(1-methyl-1H-pyrazol-4-yl)-4-morpholino-pyrido[3,2-d]pyrimidin-2-yl)phenyl)urea | 7A,13 + 14 |
| 186 | 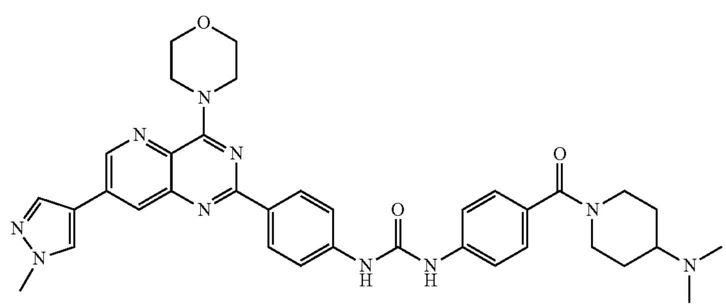 [SMILES: CN(C)C1CCN(C(=O)c2ccc(NC(=O)Nc3ccc(-c4nc(N5CCOCC5)c5ncc(-c6cnn(C)c6)cc5n4)cc3)cc2)CC1] | 1-(4-(4-(dimethylamino)piperidine-1-carbonyl)phenyl)-3-(4-(7-(1-methyl-1H-pyrazol-4-yl)-4-morpholino-pyrido[3,2-d]pyrimidin-2-yl)phenyl)urea | 7A,13 + 14 |
| 187 | 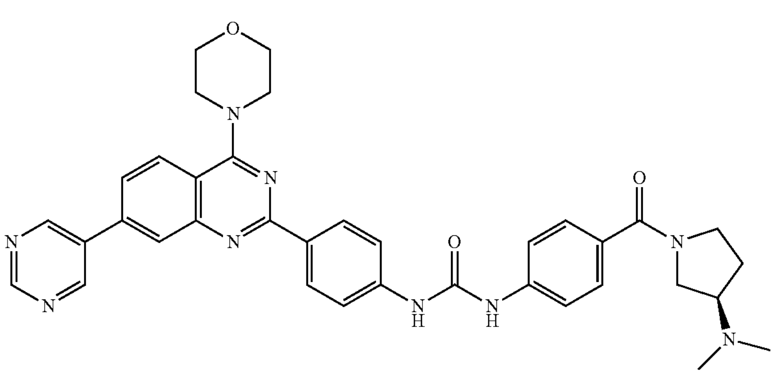 [SMILES: CN(C)[C@@H]1CCN(C(=O)c2ccc(NC(=O)Nc3ccc(-c4nc(N5CCOCC5)c5ccc(-c6cncnc6)cc5n4)cc3)cc2)C1] | (R)-1-(4-(3-(dimethylamino)pyrrolidine-1-carbonyl)phenyl)-3-(4-(4-morpholino-7-(pyrimidin-5-yl)quinazolin-2-yl)phenyl)urea | 6B,13 + 14 |

TABLE 1-continued

| Ex | Structure Name | Synthetic Scheme |
|---|---|---|
| 188 | (S)-1-(4-(3-(dimethylamino)pyrrolidine-1-carbonyl)phenyl)-3-(4-(4-morpholino-7-(pyrimidin-5-yl)quinazolin-2-yl)phenyl)urea | 6B,13 + 14 |
| 189 | 1-(4-(3-hydroxypyrrolidine-1-carbonyl)phenyl)-3-(4-(4-morpholino-7-(pyrimidin-5-yl)quinazolin-2-yl)phenyl)urea | 6B,13 + 14 |
| 190 | 4-(3-(4-(7-(5-((dimethylamino)methyl)furan-2-yl)-4-morpholino-quinazolin-2-yl)phenyl)ureido)-N,N-dimethyl-benzamide | 11 + 6B |
| 191 | 1-(4-(4-(dimethylamino)piperidine-1-carbonyl)phenyl)-3-(4-(7-(5-methylfuran-2-yl)-4-morpholino-quinazolin-2-yl)phenyl)urea | 6B,13 + 14 |

TABLE 1-continued

| Ex | Structure | Structure Name | Synthetic Scheme |
|---|---|---|---|
| 192 | 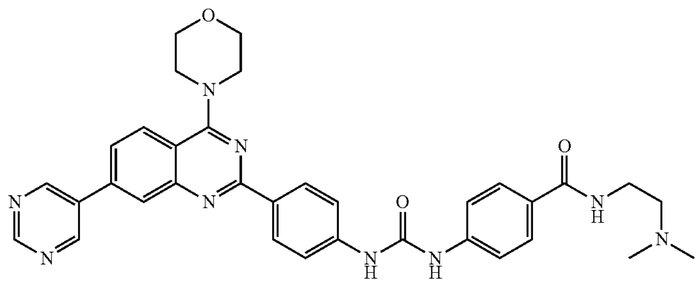 [SMILES: CN(C)CCNC(=O)c1ccc(NC(=O)Nc2ccc(-c3nc(N4CCOCC4)c4ccc(-c5cncnc5)cc4n3)cc2)cc1] | N-(2-(dimethylamino)ethyl)-4-(3-(4-(4-morpholino-7-(pyrimidin-5-yl)quinazolin-2-yl)phenyl)ureido)-benzamide | 6B,13 + 14 |
| 193 | 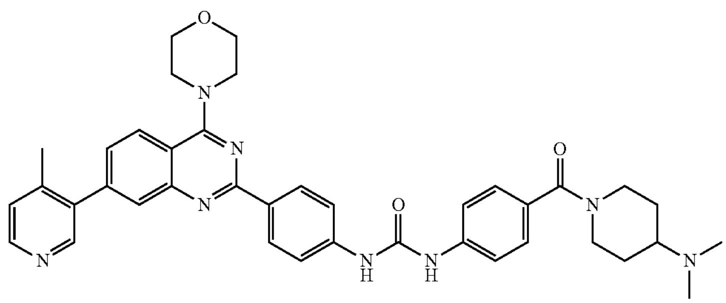 [SMILES: Cc1ccncc1-c1ccc2c(N3CCOCC3)nc(-c3ccc(NC(=O)Nc4ccc(C(=O)N5CCC(N(C)C)CC5)cc4)cc3)nc2c1] | 1-(4-(4-(dimethylamino)piperidine-1-carbonyl)phenyl)-3-(4-(7-(4-methylpyridin-3-yl)-4-morpholino-quinazolin-2-yl)phenyl)urea | 6B,13 + 14 |
| 194 | 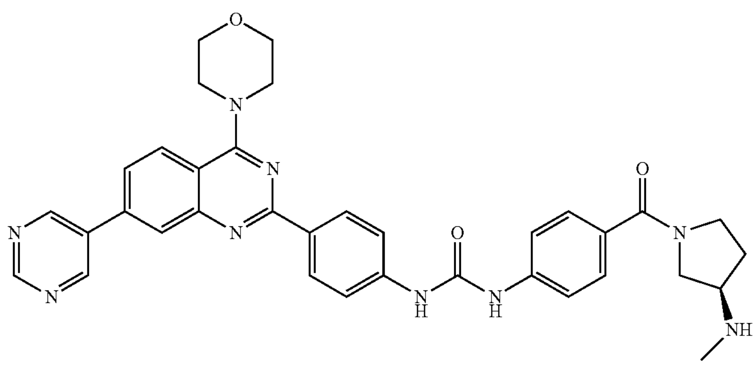 [SMILES: CN[C@@H]1CCN(C(=O)c2ccc(NC(=O)Nc3ccc(-c4nc(N5CCOCC5)c5ccc(-c6cncnc6)cc5n4)cc3)cc2)C1] | (S)-1-(4-(3-aminopyrrolidine-1-carbonyl)phenyl)-3-(4-(4-morpholino-7-(pyrimidin-5-yl)quinazolin-2-yl)phenyl)urea | 6B,13 + 14 |
| 195 | 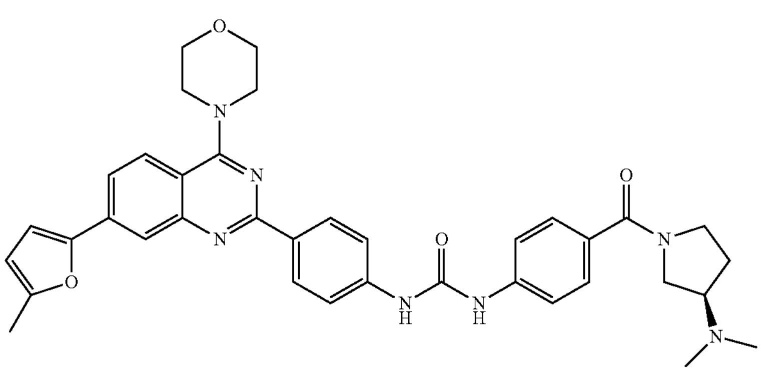 [SMILES: Cc1ccc(-c2ccc3c(N4CCOCC4)nc(-c4ccc(NC(=O)Nc5ccc(C(=O)N6CC[C@@H](N(C)C)C6)cc5)cc4)nc3c2)o1] | (S)-1-(4-(3-(dimethylamino)pyrrolidine-1-carbonyl)phenyl)-3-(4-(7-(5-methylfuran-2-yl)-4-morpholino-quinazolin-2-yl)phenyl)urea | 6B,13 + 14 |

TABLE 1-continued

| Ex | Structure | Structure Name | Synthetic Scheme |
|---|---|---|---|
| 196 | 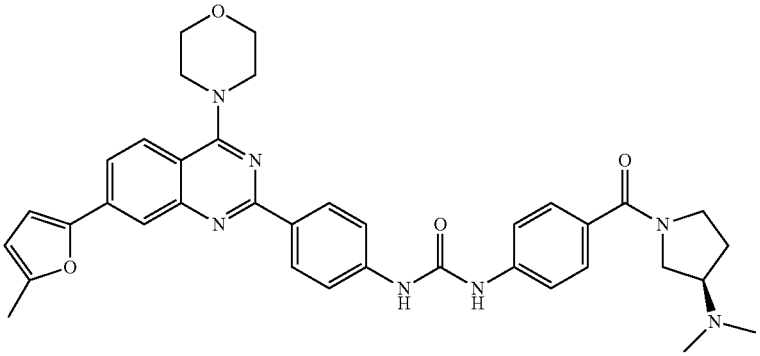 [SMILES: Cc1ccc(-c2ccc3c(N4CCOCC4)nc(-c4ccc(NC(=O)Nc5ccc(C(=O)N6CC[C@@H](N(C)C)C6)cc5)cc4)nc3c2)o1] | (R)-1-(4-(3-(dimethylamino)pyrrolidine-1-carbonyl)phenyl)-3-(4-(7-(5-methylfuran-2-yl)-4-morpholino-quinazolin-2-yl)phenyl)urea | 6B,13 + 14 |
| 197 | 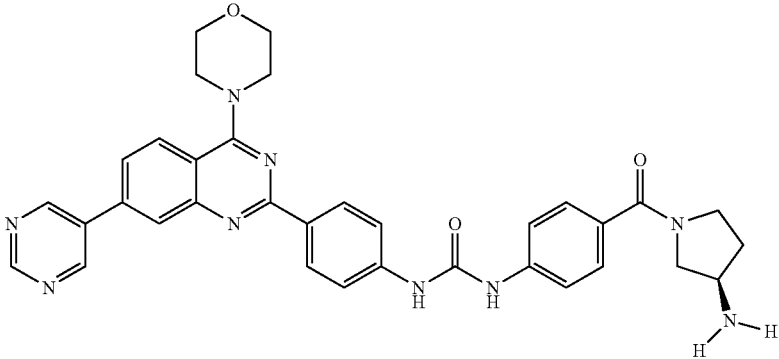 [SMILES: N[C@@H]1CCN(C(=O)c2ccc(NC(=O)Nc3ccc(-c4nc(N5CCOCC5)c5ccc(-c6cncnc6)cc5n4)cc3)cc2)C1] | (R)-1-(4-(3-aminopyrrolidine-1-carbonyl)phenyl)-3-(4-(4-morpholino-7-(pyrimidin-5-yl)quinazolin-2-yl)phenyl)urea | 6B,13 + 14 |
| 198 | 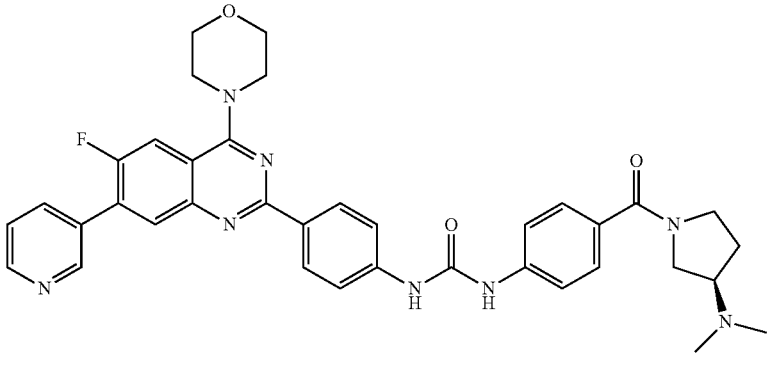 [SMILES: CN(C)[C@@H]1CCN(C(=O)c2ccc(NC(=O)Nc3ccc(-c4nc(N5CCOCC5)c5cc(F)c(-c6cccnc6)cc5n4)cc3)cc2)C1] | (S)-1-(4-(3-(dimethylamino)pyrrolidine-1-carbonyl)phenyl)-3-(4-(6-fluoro-4-morpholino-7-(pyridin-3-yl)quinazolin-2-yl)phenyl)urea | 6G,13 + 14 |
| 199 | 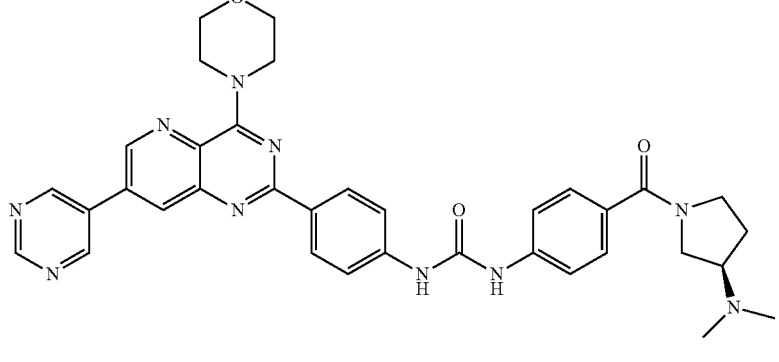 | (S)-1-(4-(3-(dimethylamino)pyrrolidine-1-carbonyl)phenyl)-3-(4-(4-morpholino-7-(pyrimidin-5-yl)pyrido[3,2-d]pyrimidin-2-yl)phenyl)urea | 7A,13 + 14 |

TABLE 1-continued

| Ex | Structure | Structure Name | Synthetic Scheme |
|---|---|---|---|
| 200 | 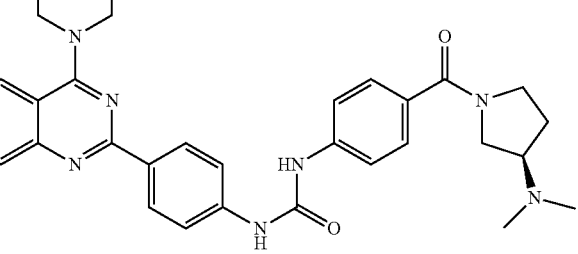 | (R)-1-(4-(3-(dimethylamino)pyrrolidine-1-carbonyl)phenyl)-3-(4-(6-fluoro-4-morpholino-7-(pyridin-3-yl)quinazolin-2-yl)phenyl)urea | 6G,13 + 14 |
| 201 | 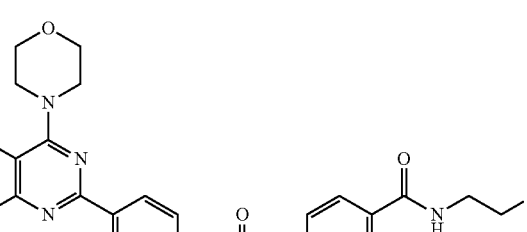 | N-(2-(dimethylamino)ethyl)-4-(3-(4-(7-(5-methylfuran-2-yl)-4-morpholino-quinazolin-2-yl)phenyl)ureido)-benzamide | 6B,13 + 14 |
| 202 | 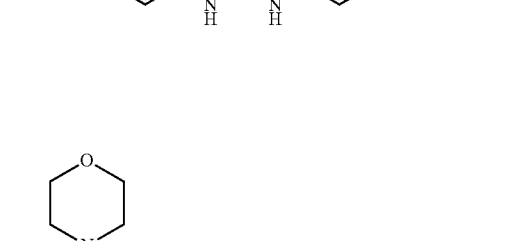 | 4-(3-(4-(7-(1-methyl-1H-pyrazol-4-yl)-4-morpholino-pyrido[3,2-d]pyrimidin-2-yl)phenyl)ureido)-benzamide | 7A,13 + 14 |
| 203 | 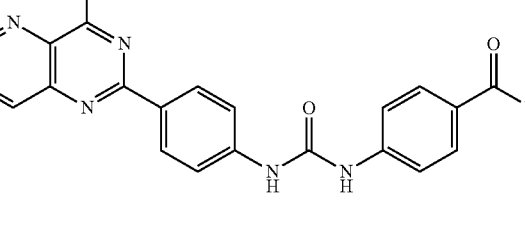 | 4-(3-(2-fluoro-4-(7-(5-(hydroxymethyl)furan-2-yl)-4-morpholino-quinazolin-2-yl)phenyl)ureido)-N,N-dimethyl-benzamide | 11 + 6D |

TABLE 1-continued

| Ex | Structure | Structure Name | Synthetic Scheme |
|---|---|---|---|
| 204 | 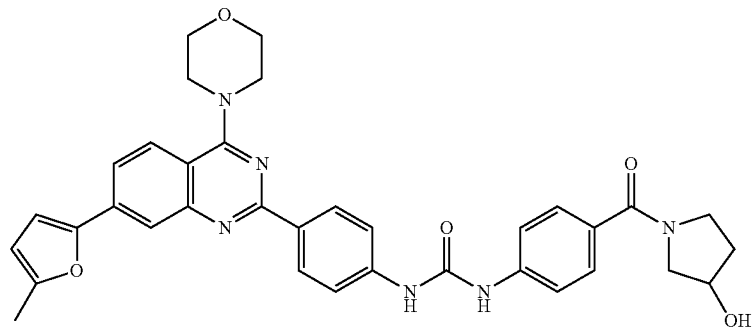 [SMILES: Cc1ccc(-c2ccc3c(N4CCOCC4)nc(-c4ccc(NC(=O)Nc5ccc(C(=O)N6CCC(O)C6)cc5)cc4)nc3c2)o1] | 1-(4-(3-hydroxypyrrolidine-1-carbonyl)phenyl)-3-(4-(7-(5-methylfuran-2-yl)-4-morpholino-quinazolin-2-yl)phenyl)urea | 6B,13 + 14 |
| 205 | 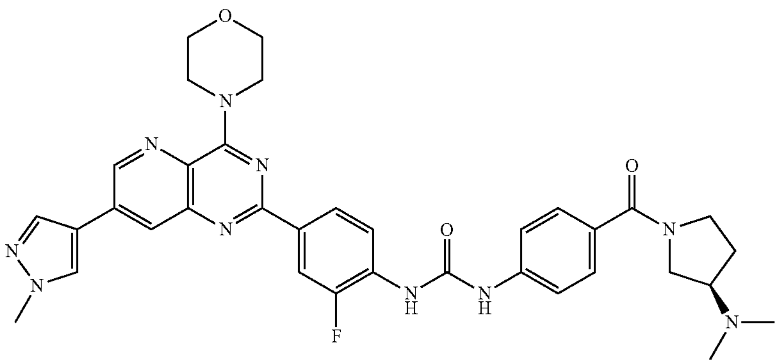 [SMILES: CN(C)[C@@H]1CCN(C(=O)c2ccc(NC(=O)Nc3ccc(-c4nc(N5CCOCC5)c5ncc(-c6cnn(C)c6)cc5n4)cc3F)cc2)C1] | (R)-1-(4-(3-(dimethylamino)pyrrolidine-1-carbonyl)phenyl)-3-(2-fluoro-4-(7-(1-methyl-1H-pyrazol-4-yl)-4-morpholino-pyrido[3,2-d]pyrimidin-2-yl)phenyl)urea | 7A,13 + 14 |
| 206 | 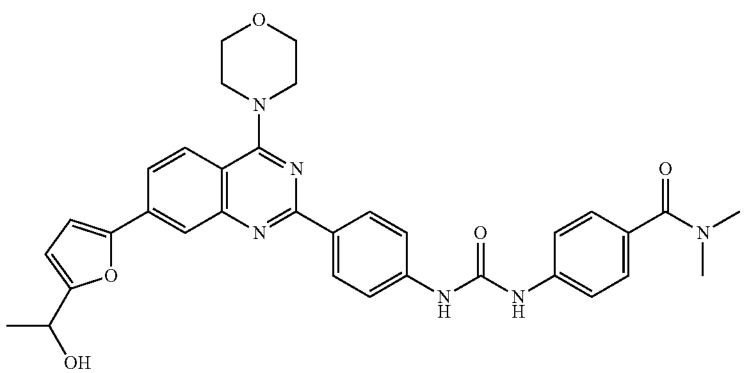 [SMILES: CC(O)c1ccc(-c2ccc3c(N4CCOCC4)nc(-c4ccc(NC(=O)Nc5ccc(C(=O)N(C)C)cc5)cc4)nc3c2)o1] | 4-(3-(4-(7-(5-(1-hydroxyethyl)furan-2-yl)-4-morpholino-quinazolin-2-yl)phenyl)ureido)-N,N-dimethyl-benzamide | 11 + 6B |
| 207 | 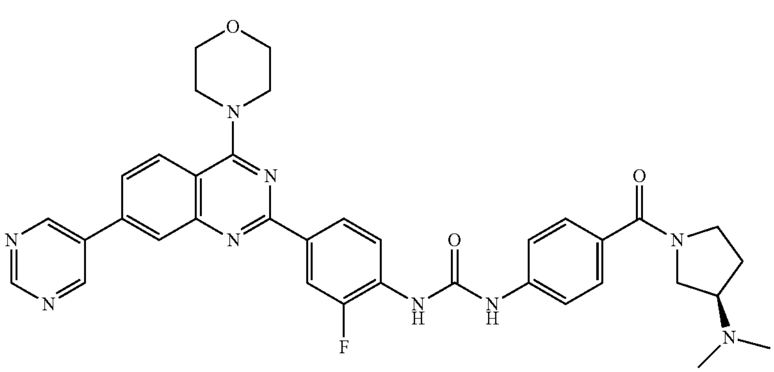 [SMILES: CN(C)[C@@H]1CCN(C(=O)c2ccc(NC(=O)Nc3ccc(-c4nc(N5CCOCC5)c5ccc(-c6cncnc6)cc5n4)cc3F)cc2)C1] | (S)-1-(4-(3-(dimethylamino)pyrrolidine-1-carbonyl)phenyl)-3-(2-fluoro-4-(4-morpholino-7-(pyrimidin-5-yl)quinazolin-2-yl)phenyl)urea | 6B,13 + 14 |

TABLE 1-continued

| Ex | Structure | Structure Name | Synthetic Scheme |
|---|---|---|---|
| 208 | 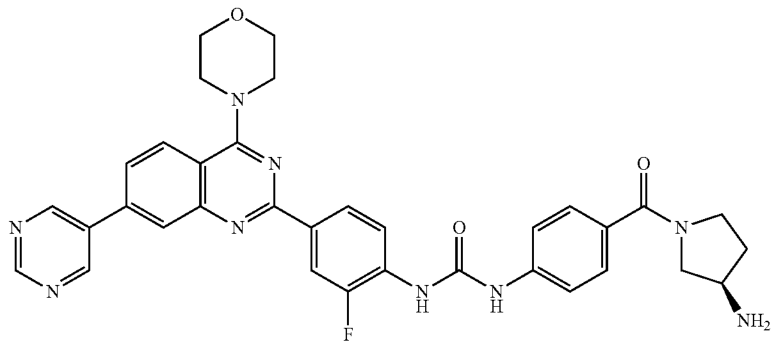 [SMILES: N[C@@H]1CCN(C(=O)c2ccc(NC(=O)Nc3ccc(-c4nc(N5CCOCC5)c5ccc(-c6cncnc6)cc5n4)cc3F)cc2)C1] | (S)-1-(4-(3-aminopyrrolidine-1-carbonyl)phenyl)-3-(2-fluoro-4-(4-morpholino-7-(pyrimidin-5-yl)quinazolin-2-yl)phenyl)urea | 6B,13 + 14 |
| 209 | 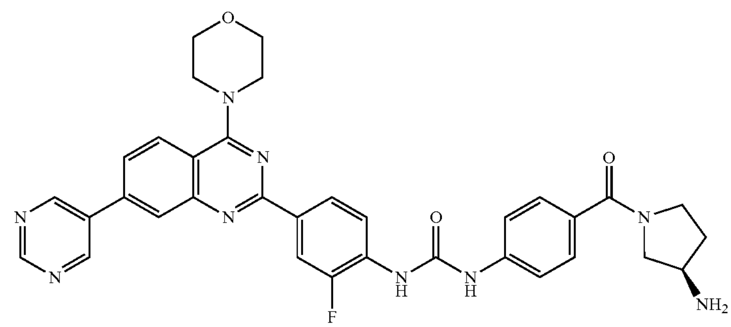 [SMILES: N[C@@H]1CCN(C(=O)c2ccc(NC(=O)Nc3ccc(-c4nc(N5CCOCC5)c5ccc(-c6cncnc6)cc5n4)cc3F)cc2)C1] | (R)-1-(4-(3-aminopyrrolidine-1-carbonyl)phenyl)-3-(2-fluoro-4-(4-morpholino-7-(pyrimidin-5-yl)quinazolin-2-yl)phenyl)urea | 6B,13 + 14 |
| 210 | 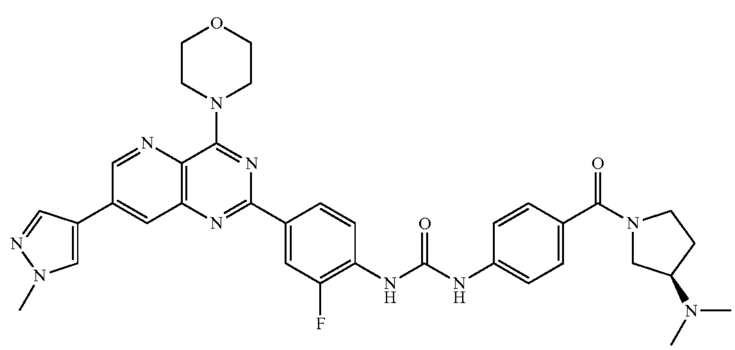 [SMILES: CN(C)[C@@H]1CCN(C(=O)c2ccc(NC(=O)Nc3ccc(-c4nc(N5CCOCC5)c5ncc(-c6cnn(C)c6)cc5n4)cc3F)cc2)C1] | (S)-1-(4-(3-(dimethylamino)pyrrolidine-1-carbonyl)phenyl)-3-(2-fluoro-4-(7-(1-methyl-1H-pyrazol-4-yl)-4-morpholino-pyrido[3,2-d]pyrimidin-2-yl)phenyl)urea | 7A,13 + 14 |
| 211 | 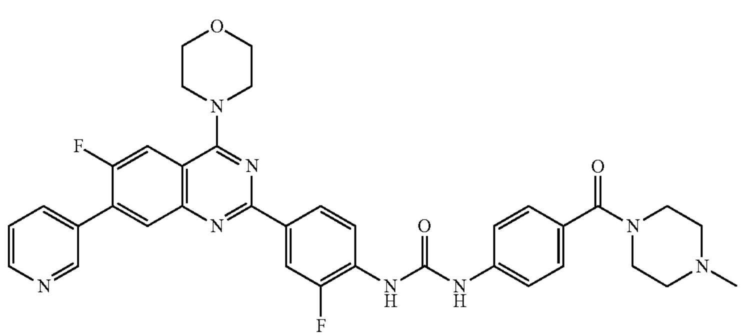 [SMILES: CN1CCN(C(=O)c2ccc(NC(=O)Nc3ccc(-c4nc(N5CCOCC5)c5cc(F)c(-c6cccnc6)cc5n4)cc3F)cc2)CC1] | 1-(2-fluoro-4-(6-fluoro-4-morpholino-7-(pyridin-3-yl)quinazolin-2-yl)phenyl)-3-(4-(4-methylpiperazine-1-carbonyl)phenyl)urea | 6G,13 + 14 |

TABLE 1-continued

| Ex | Structure | Structure Name | Synthetic Scheme |
|---|---|---|---|
| 212 | 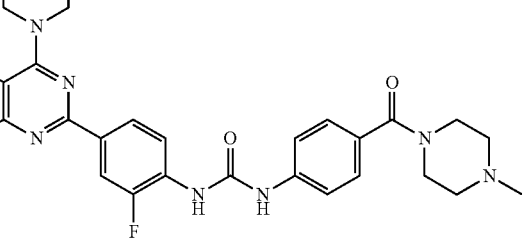 | 1-(2-fluoro-4-(4-morpholino-7-(pyridin-4-yl)quinazolin-2-yl)phenyl)-3-(4-(4-methylpiperazine-1-carbonyl)phenyl)urea | 6B,13 + 14 |
| 213 | 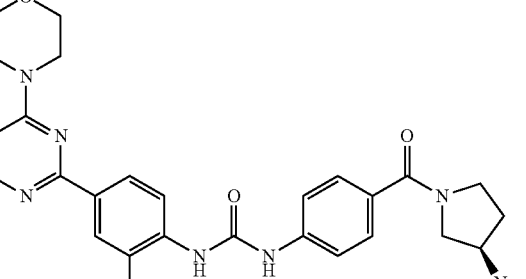 | (S)-1-(4-(3-(dimethylamino)pyrrolidine-1-carbonyl)phenyl)-3-(2-fluoro-4-(7-(2-fluoropyridin-3-yl)-4-morpholino-pyrido[3,2-d]pyrimidin-2-yl)phenyl)urea | 7A,13 + 14 |
| 214 | 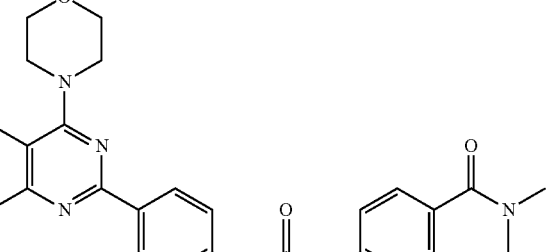 | 4-(3-(2-fluoro-4-(7-(5-(1-hydroxyethyl)furan-2-yl)-4-morpholino-quinazolin-2-yl)phenyl)ureido)-N,N-dimethyl-benzamide | 11 + 6D |
| 215 | 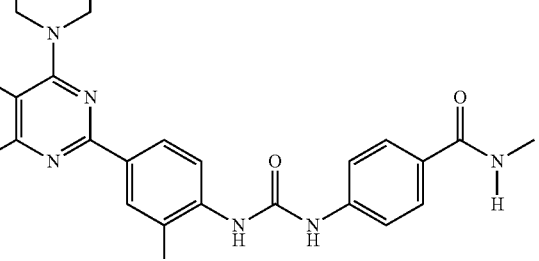 | 4-(3-(2-fluoro-4-(4-morpholino-7-(pyrimidin-5-yl)quinazolin-2-yl)phenyl)ureido)-N-methyl-benzamide | 6B,13 + 14 |

TABLE 1-continued

| Ex | Structure Name | Synthetic Scheme |
|---|---|---|
| 216 | 4-(3-(4-(7-(5-(1-hydroxyethyl)furan-2-yl)-4-morpholino-pyrido[3,2-d]pyrimidin-2-yl)phenyl)ureido)-N,N-dimethyl-benzamide | 11 + 7A |
| 217 | N-(2-(dimethylamino)ethyl)-4-(3-(2-fluoro-4-(4-morpholino-7-(pyrimidin-5-yl)quinazolin-2-yl)phenyl)ureido)-benzamide | 6B,13 + 14 |
| 218 | 4-(3-(2-fluoro-4-(7-(5-(hydroxymethyl)furan-2-yl)-4-morpholino-pyrido[3,2-d]pyrimidin-2-yl)phenyl)ureido)-N,N-dimethyl-benzamide | 11 + 7B |
| 219 | 3-fluoro-4-(3-(4-(7-(5-(hydroxymethyl)furan-2-yl)-4-morpholino-quinazolin-2-yl)phenyl)ureido)-N,N-dimethyl-benzamide | 11 + 6C |

| Ex | Structure | Structure Name | Synthetic Scheme |
|---|---|---|---|
| 220 | 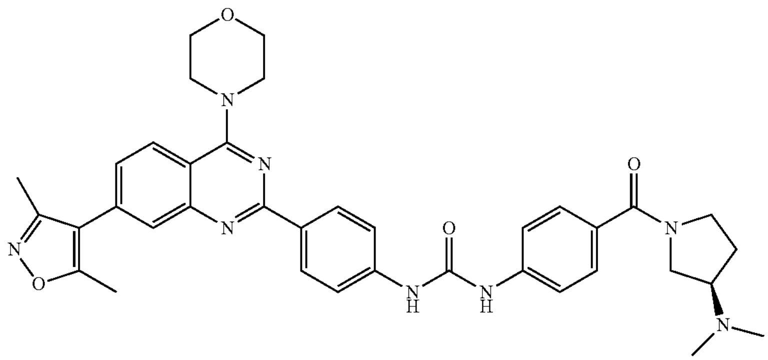 [SMILES: Cc1noc(C)c1-c1ccc2c(N3CCOCC3)nc(-c3ccc(NC(=O)Nc4ccc(C(=O)N5CC[C@@H](N(C)C)C5)cc4)cc3)nc2c1] | (S)-1-(4-(3-(dimethylamino)pyrrolidine-1-carbonyl)phenyl)-3-(4-(7-(3,5-dimethylisoxazol-4-yl)-4-morpholino-quinazolin-2-yl)phenyl)urea | 6B,13 + 14 |
| 221 | 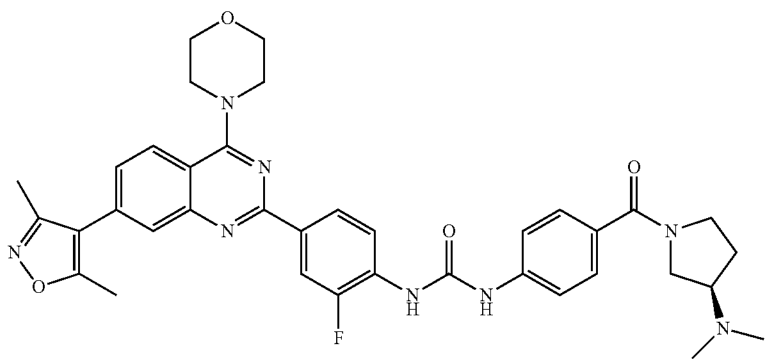 [SMILES: Cc1noc(C)c1-c1ccc2c(N3CCOCC3)nc(-c3ccc(NC(=O)Nc4ccc(C(=O)N5CC[C@@H](N(C)C)C5)cc4)c(F)c3)nc2c1] | (S)-1-(4-(3-(dimethylamino)pyrrolidine-1-carbonyl)phenyl)-3-(4-(7-(3,5-dimethylisoxazol-4-yl)-4-morpholino-quinazolin-2-yl)-2-fluorophenyl)urea | 6B,13 + 14 |
| 222 | 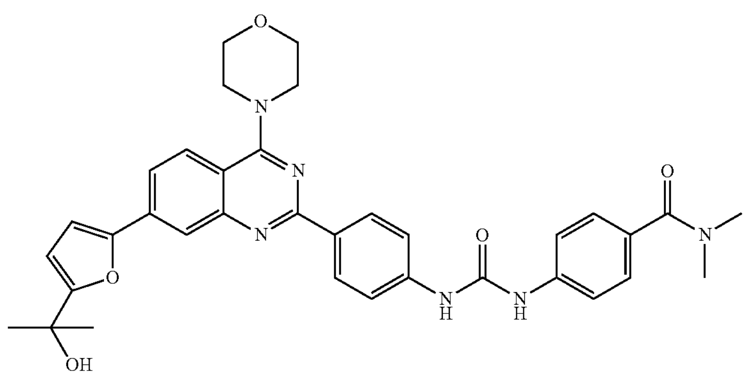 [SMILES: CN(C)C(=O)c1ccc(NC(=O)Nc2ccc(-c3nc(N4CCOCC4)c4ccc(-c5ccc(C(C)(C)O)o5)cc4n3)cc2)cc1] | 4-(3-(4-(7-(5-(2-hydroxypropan-2-yl)furan-2-yl)-4-morpholino-quinazolin-2-yl)phenyl)ureido)-N,N-dimethyl-benzamide | 11 + 6B |
| 223 | 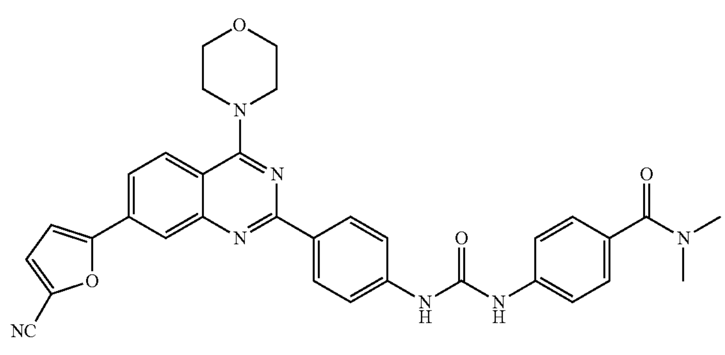 [SMILES: CN(C)C(=O)c1ccc(NC(=O)Nc2ccc(-c3nc(N4CCOCC4)c4ccc(-c5ccc(C#N)o5)cc4n3)cc2)cc1] | 4-(3-(4-(7-(5-cyanofuran-2-yl)-4-morpholino-quinazolin-2-yl)phenyl)ureido)-N,N-dimethyl-benzamide | 11 + 6B |

TABLE 1-continued

| Ex | Structure | Structure Name | Synthetic Scheme |
|---|---|---|---|
| 224 | 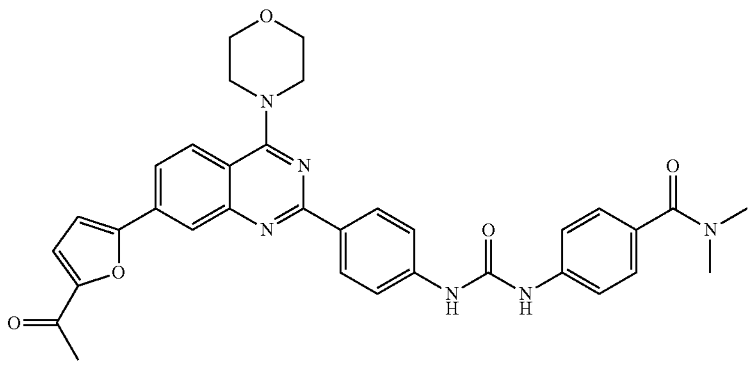 [SMILES: CC(=O)c1ccc(-c2ccc3c(N4CCOCC4)nc(-c4ccc(NC(=O)Nc5ccc(C(=O)N(C)C)cc5)cc4)nc3c2)o1] | 4-(3-(4-(7-(5-acetylfuran-2-yl)-4-morpholino-quinazolin-2-yl)phenyl)ureido)-N,N-dimethyl-benzamide | 11 + 6B |
| 225 | 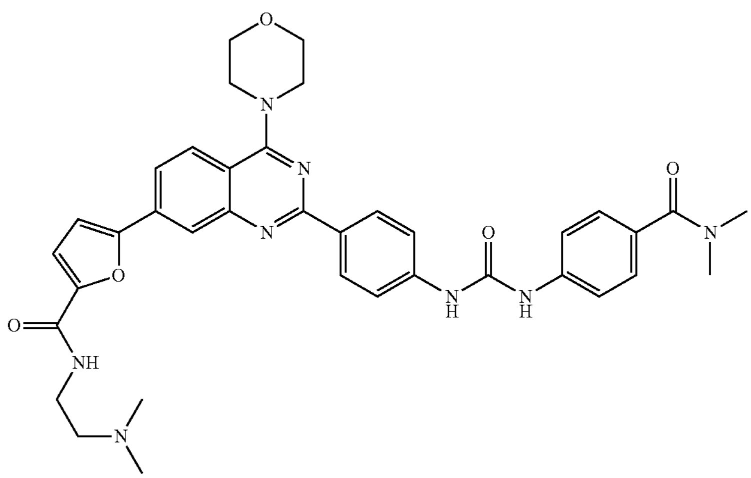 [SMILES: CN(C)CCNC(=O)c1ccc(-c2ccc3c(N4CCOCC4)nc(-c4ccc(NC(=O)Nc5ccc(C(=O)N(C)C)cc5)cc4)nc3c2)o1] | N-(2-(dimethylamino)ethyl)-5-(2-(4-(3-(4-(dimethylcarbamoyl)phenyl)ureido)phenyl)-4-morpholino-quinazolin-7-yl)furan-2-carboxamide | 11 + 6B |
| 226 | 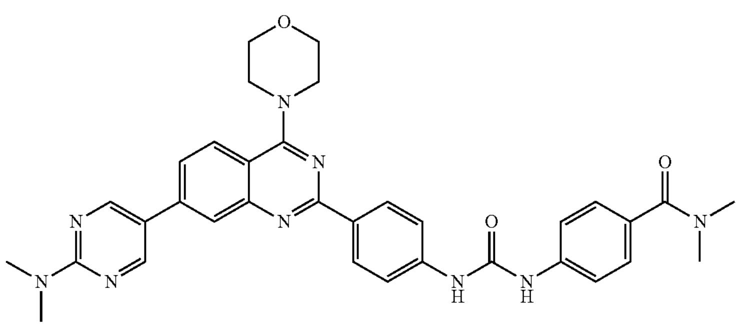 | 4-(3-(4-(7-(2-(dimethylamino)pyrimidin-5-yl)-4-morpholino-quinazolin-2-yl)phenyl)ureido)-N,N-dimethyl-benzamide | 6B |
| 227 | 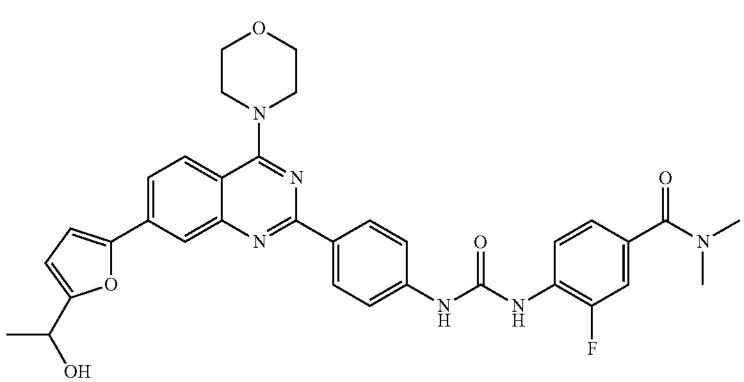 [SMILES: CC(O)c1ccc(-c2ccc3c(N4CCOCC4)nc(-c4ccc(NC(=O)Nc5ccc(C(=O)N(C)C)cc5F)cc4)nc3c2)o1] | 3-fluoro-4-(3-(4-(7-(5-(1-hydroxyethyl)furan-2-yl)-4-morpholino-quinazolin-2-yl)phenyl)ureido)-N,N-dimethyl-benzamide | 11 + 6C |

TABLE 1-continued

| Ex | Structure Name | Synthetic Scheme |
|---|---|---|
| 228 | 3-fluoro-4-(3-(4-(7-(5-(hydroxymethyl)furan-2-yl)-4-morpholino-quinazolin-2-yl)phenyl)ureido)-N,N-dimethyl-benzamide | 11 + 6C |
| 229 | 5-(2-(4-(3-(4-(dimethylcarbamoyl)phenyl)ureido)phenyl)-4-morpholine-quinazolin-7-yl)-N,N-dimethylfuran-2-carboxamide | 11 + 6B |
| 230 | 4-(3-(4-(7-(2-(dimethylamino)pyrimidin-5-yl)-4-morpholino-pyrido[3,2-d]pyrimidin-2-yl)phenyl)ureido)-N,N-dimethyl-benzamide | 7A |
| 231 | 4-(3-(4-(7-(2-(dimethylamino)pyrimidin-5-yl)-4-morpholino-quinazolin-2-yl)-2-fluorophenyl)ureido)-N,N-dimethyl-benzamide | 6D |

TABLE 1-continued

| Ex | Structure | Structure Name | Synthetic Scheme |
|---|---|---|---|
| 232 | 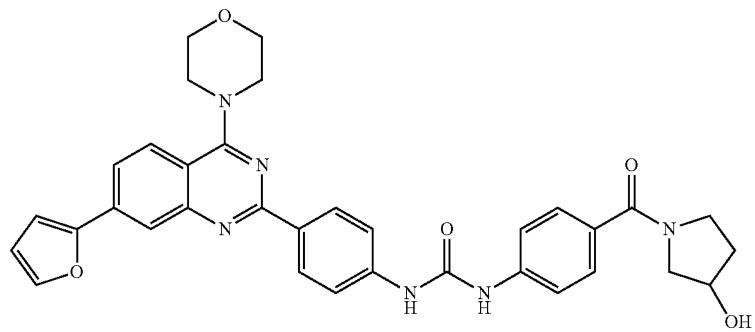 [SMILES: O=C(Nc1ccc(C(=O)N2CCC(O)C2)cc1)Nc1ccc(-c2nc(N3CCOCC3)c3ccc(-c4ccco4)cc3n2)cc1] | 1-(4-(7-(furan-2-yl)-4-morpholino-quinazolin-2-yl)phenyl)-3-(4-(3-hydroxypyrrolidine-1-carbonyl)phenyl)urea | 6B,13 + 14 |
| 233 | 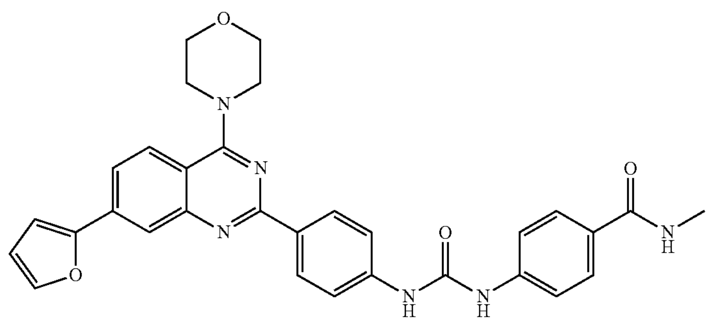 [SMILES: CNC(=O)c1ccc(NC(=O)Nc2ccc(-c3nc(N4CCOCC4)c4ccc(-c5ccco5)cc4n3)cc2)cc1] | 4-(3-(4-(7-(furan-2-yl)-4-morpholine-quinazolin-2-yl)phenyl)ureido)-N-methyl-benzamide | 6B,13 + 14 |
| 234 | 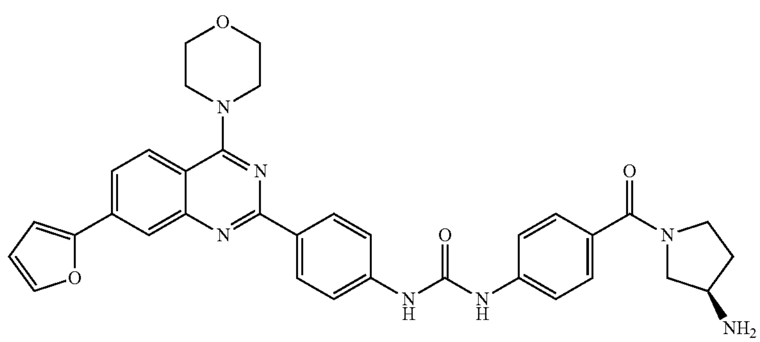 [SMILES: N[C@@H]1CCN(C(=O)c2ccc(NC(=O)Nc3ccc(-c4nc(N5CCOCC5)c5ccc(-c6ccco6)cc5n4)cc3)cc2)C1] | (S)-1-(4-(3-aminopyrrolidine-1-carbonyl)phenyl)-3-(4-(7-(furan-2-yl)-4-morpholino-quinazolin-2-yl)phenyl)urea | 6B,13 + 14 |
| 235 | 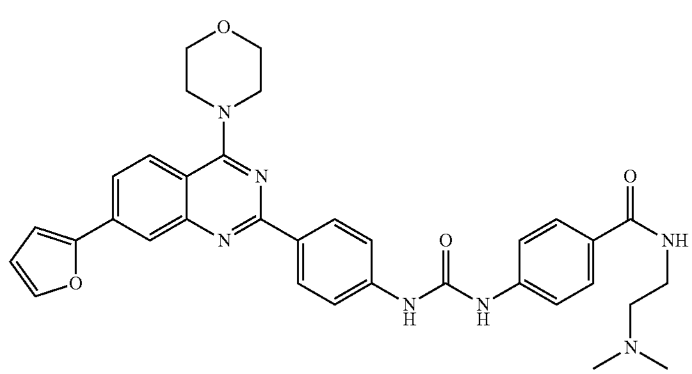 [SMILES: CN(C)CCNC(=O)c1ccc(NC(=O)Nc2ccc(-c3nc(N4CCOCC4)c4ccc(-c5ccco5)cc4n3)cc2)cc1] | N-(2-(dimethylamino)ethyl)-4-(3-(4-(7-(furan-2-yl)-4-morpholino-quinazolin-2-yl)phenyl)ureido)-benzamide | 6B,13 + 14 |

TABLE 1-continued

| Ex | Structure | Structure Name | Synthetic Scheme |
|---|---|---|---|
| 236 | 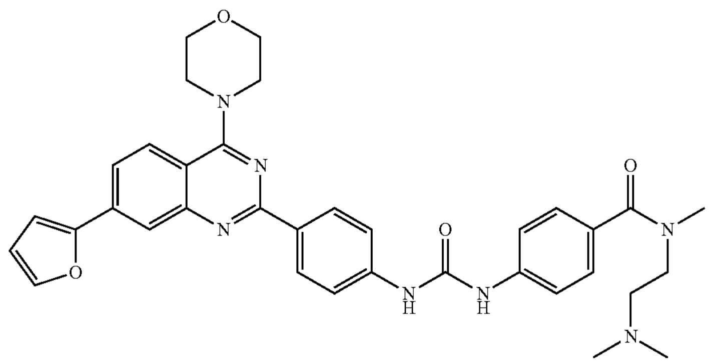 [SMILES: CN(C)CCN(C)C(=O)c1ccc(NC(=O)Nc2ccc(-c3nc(N4CCOCC4)c4ccc(-c5ccco5)cc4n3)cc2)cc1] | N-(2-(dimethylamino)ethyl)-4-(3-(4-(7-(furan-2-yl)-4-morpholino-quinazolin-2-yl)phenyl)ureido)-N-methyl-benzamide | 6B,13 + 14 |
| 237 | 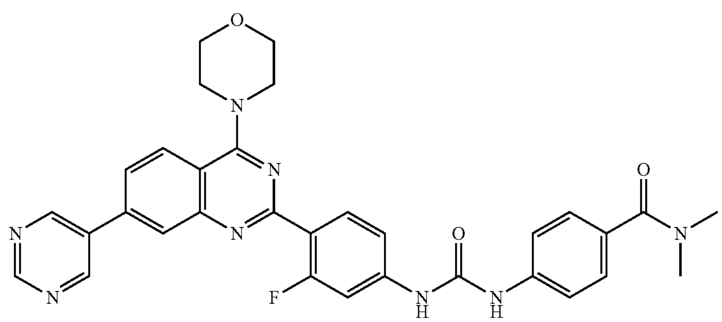 [SMILES: CN(C)C(=O)c1ccc(NC(=O)Nc2ccc(-c3nc(N4CCOCC4)c4ccc(-c5cncnc5)cc4n3)c(F)c2)cc1] | 4-(3-(3-fluoro-4-(4-morpholino-7-(pyrimidin-5-yl)quinazolin-2-yl)phenyl)ureido)-N,N-dimethyl-benzamide | 6 |
| 238 | 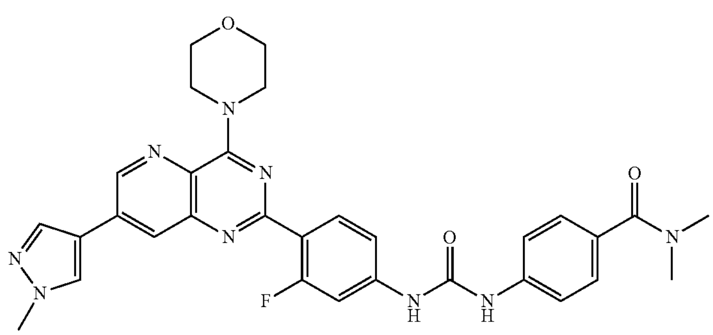 [SMILES: CN(C)C(=O)c1ccc(NC(=O)Nc2ccc(-c3nc(N4CCOCC4)c4ncc(-c5cnn(C)c5)cc4n3)c(F)c2)cc1] | 4-(3-(3-fluoro-4-(7-(1-methyl-1H-pyrazol-4-yl)-4-morpholino-pyrido[3,2-d]pyrimidin-2-yl)phenyl)ureido)-N,N-dimethyl-benzamide | 7 |
| 239 | 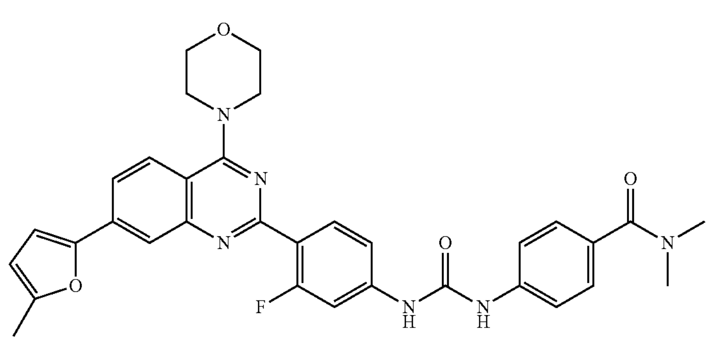 [SMILES: Cc1ccc(-c2ccc3c(N4CCOCC4)nc(-c4ccc(NC(=O)Nc5ccc(C(=O)N(C)C)cc5)cc4F)nc3c2)o1] | 4-(3-(3-fluoro-4-(7-(5-methylfuran-2-yl)-4-morpholino-quinazolin-2-yl)phenyl)ureido)-N,N-dimethyl-benzamide | 6 |

TABLE 1-continued

| Ex | Structure | Structure Name | Synthetic Scheme |
|---|---|---|---|
| 240 | 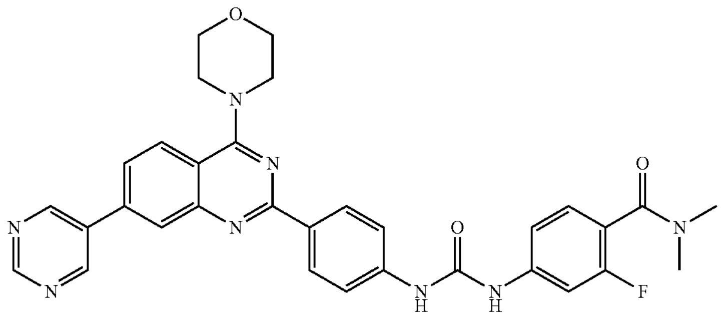 [SMILES: CN(C)C(=O)c1ccc(NC(=O)Nc2ccc(-c3nc(N4CCOCC4)c4ccc(-c5cncnc5)cc4n3)cc2)cc1F] | 2-fluoro-N,N-dimethyl-4-(3-(4-(4-morpholino-7-(pyrimidin-5-yl)quinazolin-2-yl)phenyl)ureido)-benzamide | 6 |
| 241 | 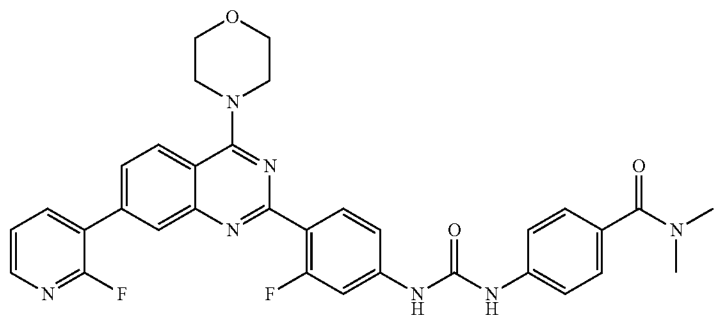 [SMILES: CN(C)C(=O)c1ccc(NC(=O)Nc2ccc(-c3nc(N4CCOCC4)c4ccc(-c5cccnc5F)cc4n3)c(F)c2)cc1] | 4-(3-(3-fluoro-4-(7-(2-fluoropyridin-3-yl)-4-morpholino-quinazolin-2-yl)phenyl)ureido)-N,N-dimethyl-benzamide | 6 |
| 242 | 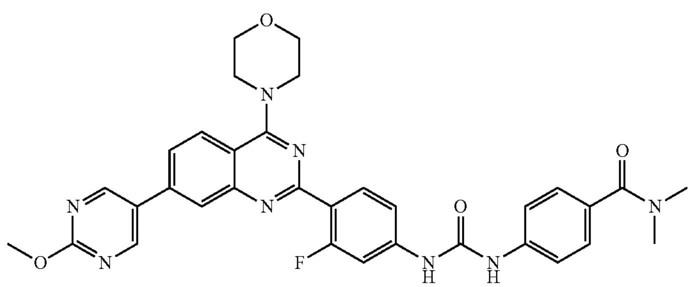 | 4-(3-(3-fluoro-4-(7-(2-methoxypyrimidin-5-yl)-4-morpholino-quinazolin-2-yl)phenyl)ureido)-N,N-dimethyl-benzamide | 6 |
| 243 | 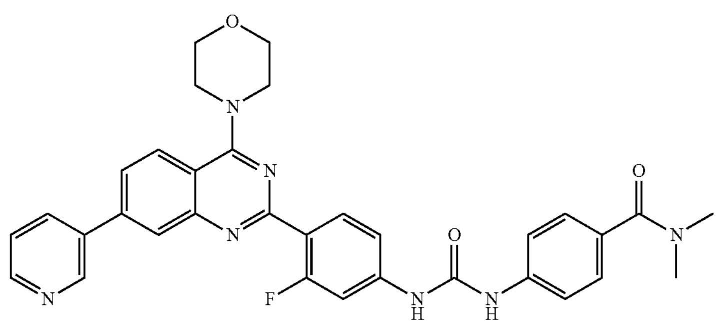 [SMILES: CN(C)C(=O)c1ccc(NC(=O)Nc2ccc(-c3nc(N4CCOCC4)c4ccc(-c5cccnc5)cc4n3)c(F)c2)cc1] | 4-(3-(3-fluoro-4-(4-morpholino-7-(pyridin-3-yl)quinazolin-2-yl)phenyl)ureido)-N,N-dimethyl-benzamide | 6 |
| 244 | 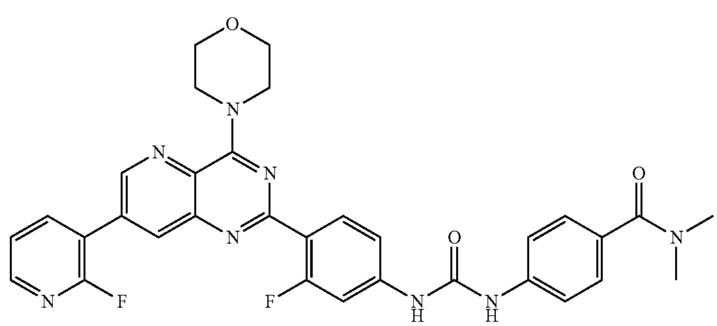 [SMILES: CN(C)C(=O)c1ccc(NC(=O)Nc2ccc(-c3nc(N4CCOCC4)c4ncc(-c5cccnc5F)cc4n3)c(F)c2)cc1] | 4-(3-(3-fluoro-4-(7-(2-fluoropyridin-3-yl)-4-morpholino-pyrido[3,2-d]pyrimidin-2-yl)phenyl)ureido)-N,N-dimethyl-benzamide | 7 |

TABLE 1-continued

| Ex | Structure | Structure Name | Synthetic Scheme |
|---|---|---|---|
| 245 | 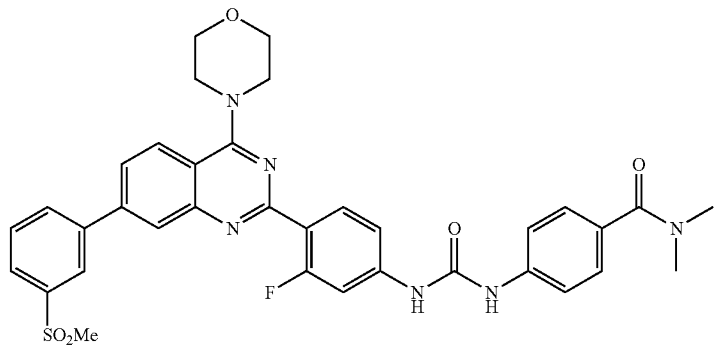 [SMILES: CN(C)C(=O)c1ccc(NC(=O)Nc2ccc(-c3nc(N4CCOCC4)c4ccc(-c5cccc(S(C)(=O)=O)c5)cc4n3)c(F)c2)cc1] | 4-(3-(3-fluoro-4-(7-(3-(methylsulfonyl)phenyl)-4-morpholino-quinazolin-2-yl)phenyl)ureido)-N,N-dimethyl-benzamide | 6 |
| 246 | 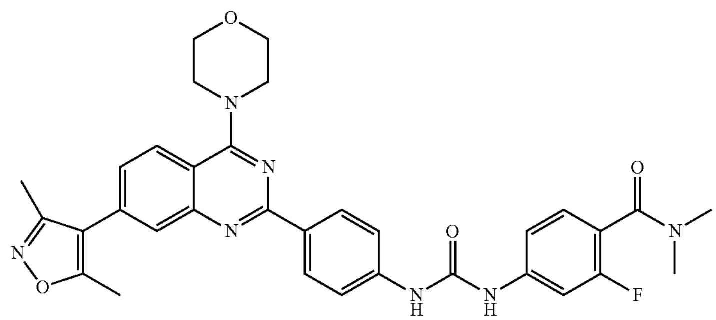 [SMILES: Cc1noc(C)c1-c1ccc2c(N3CCOCC3)nc(-c3ccc(NC(=O)Nc4ccc(C(=O)N(C)C)c(F)c4)cc3)nc2c1] | 4-(3-(4-(7-(3,5-dimethylisoxazol-4-yl)-4-morpholino-quinazolin-2-yl)phenyl)ureido)-2-fluoro-N,N-dimethyl-benzamide | 6 |
| 247 | 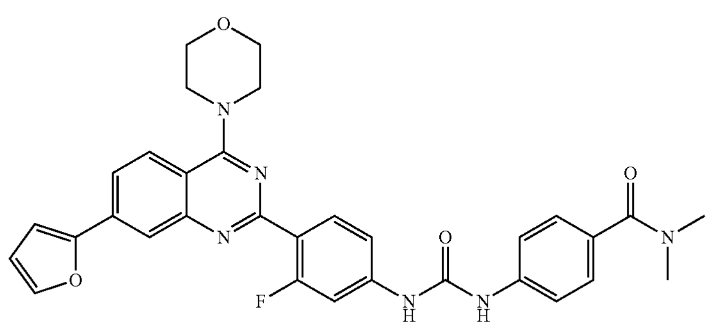 [SMILES: CN(C)C(=O)c1ccc(NC(=O)Nc2ccc(-c3nc(N4CCOCC4)c4ccc(-c5ccco5)cc4n3)c(F)c2)cc1] | 4-(3-(3-fluoro-4-(7-(furan-2-yl)-4-morpholino-quinazolin-2-yl)phenyl)ureido)-N,N-dimethyl-benzamide | 6 |
| 248 | 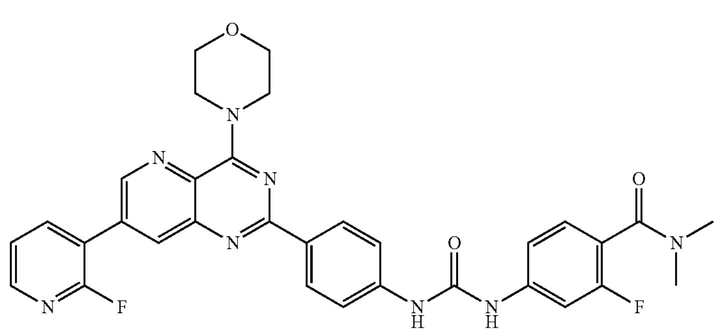 [SMILES: CN(C)C(=O)c1ccc(NC(=O)Nc2ccc(-c3nc(N4CCOCC4)c4ncc(-c5cccnc5F)cc4n3)cc2)cc1F] | 2-fluoro-4-(3-(4-(7-(2-fluoropyridin-3-yl)-4-morpholino-pyrido[3,2-d]pyrimidin-2-yl)phenyl)ureido)-N,N-dimethyl-benzamide | 7 |

TABLE 1-continued

| Ex | Structure Name | Synthetic Scheme |
|---|---|---|
| 249 | 4-(3-(3-fluoro-4-(7-(1-methyl-1H-pyrazol-4-yl)-4-morpholino-quinazolin-2-yl)phenyl)ureido)-N,N-dimethyl-benzamide | 6 |
| 250 | 4-(3-(3-fluoro-4-(4-morpholino-7-(pyrimidin-5-yl)pyrido[3,2-d]pyrimidin-2-yl)phenyl)ureido)-N,N-dimethyl-benzamide | 7 |
| 251 | 5-(3-(3-fluoro-4-(4-morpholino-7-(pyrimidin-5-yl)quinazolin-2-yl)phenyl)ureido)-N,N-dimethylpicolinamide | 6 |
| 252 | 4-(3-(4-(7-(3,5-dimethylisoxazol-4-yl)-4-morpholino-quinazolin-2-yl)-3-fluorophenyl)ureido)-N,N-dimethyl-benzamide | 6 |

TABLE 1-continued

| Ex | Structure | Structure Name | Synthetic Scheme |
|---|---|---|---|
| 253 | 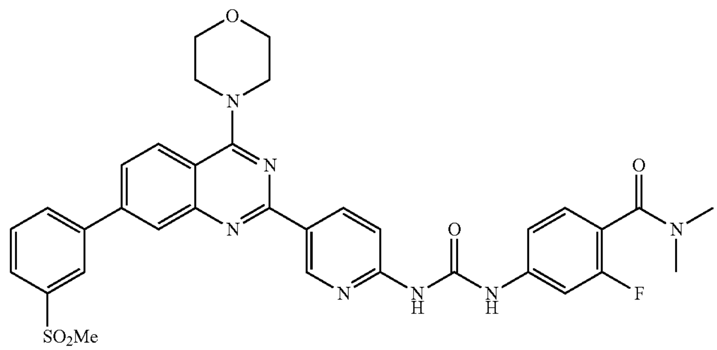 [SMILES: CN(C)C(=O)c1ccc(NC(=O)Nc2ccc(-c3nc(N4CCOCC4)c4ccc(-c5cccc(S(C)(=O)=O)c5)cc4n3)cn2)cc1F] | 2-fluoro-N,N-dimethyl-4-(3-(5-(7-(3-(methylsulfonyl)phenyl)-4-morpholino-quinazolin-2-yl)pyridin-2-yl)ureido)-benzamide | 6 + 6E |
| 254 | 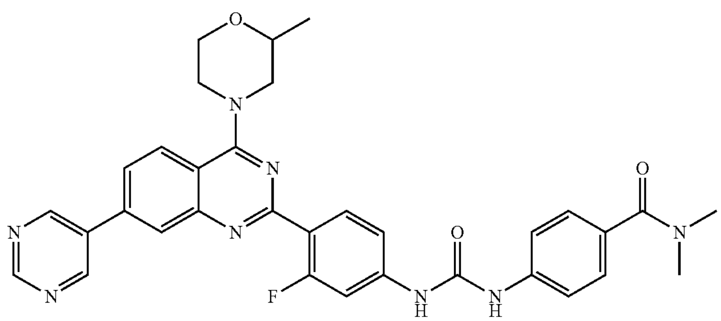 [SMILES: CC1CN(c2nc(-c3ccc(NC(=O)Nc4ccc(C(=O)N(C)C)cc4)cc3F)nc3cc(-c4cncnc4)ccc23)CCO1] | 4-(3-(3-fluoro-4-(4-(2-methylmorpholino)-7-(pyrimidin-5-yl)quinazolin-2-yl)phenyl)ureido)-N,N-dimethyl-benzamide | 6 |
| 255 | 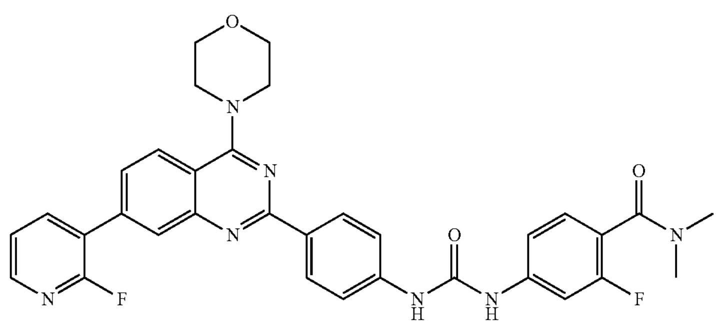 [SMILES: CN(C)C(=O)c1ccc(NC(=O)Nc2ccc(-c3nc(N4CCOCC4)c4ccc(-c5cccnc5F)cc4n3)cc2)cc1F] | 2-fluoro-4-(3-(4-(7-(2-fluoropyridin-3-yl)-4-morpholino-quinazolin-2-yl)phenyl)ureido)-N,N-dimethyl-benzamide | 6 |
| 256 | 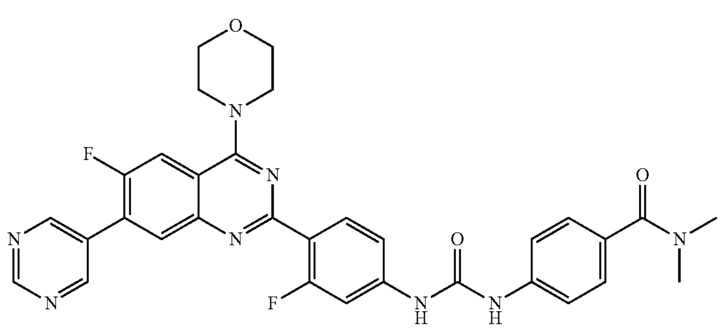 [SMILES: CN(C)C(=O)c1ccc(NC(=O)Nc2ccc(-c3nc(N4CCOCC4)c4cc(F)c(-c5cncnc5)cc4n3)c(F)c2)cc1] | 4-(3-(3-fluoro-4-(6-fluoro-4-morpholino-7-(pyrimidin-5-yl)quinazolin-2-yl)phenyl)ureido)-N,N-dimethyl-benzamide | 6 + 6G |

TABLE 1-continued

| Ex | Structure | Structure Name | Synthetic Scheme |
|---|---|---|---|
| 257 | 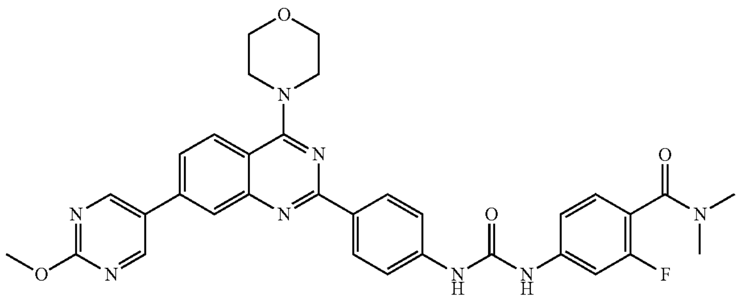 | 2-fluoro-4-(3-(4-(7-(2-methoxypyrimidin-5-yl)-4-morpholino-quinazolin-2-yl)phenyl)ureido)-N,N-dimethyl-benzamide | 6 |
| 258 | 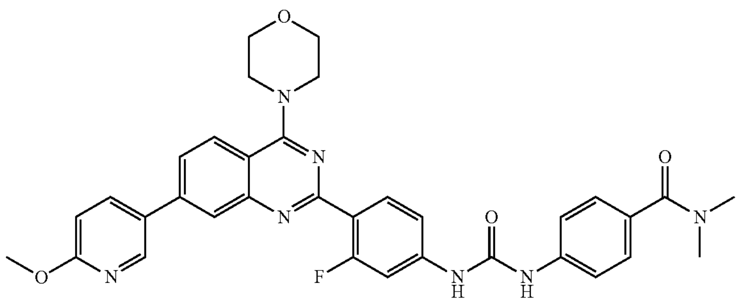 | 4-(3-(3-fluoro-4-(7-(6-methoxypyridin-3-yl)-4-morpholino-quinazolin-2-yl)phenyl)ureido)-N,N-dimethyl-benzamide | 6 |
| 259 | 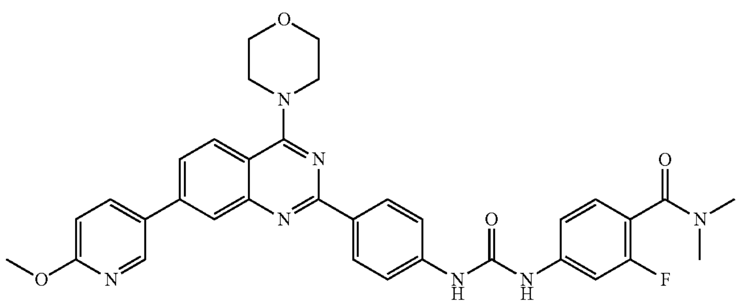 | 2-fluoro-4-(3-(4-(7-(6-methoxypyridin-3-yl)-4-morpholino-quinazolin-2-yl)phenyl)ureido)-N,N-dimethyl-benzamide | 6 |
| 260 | 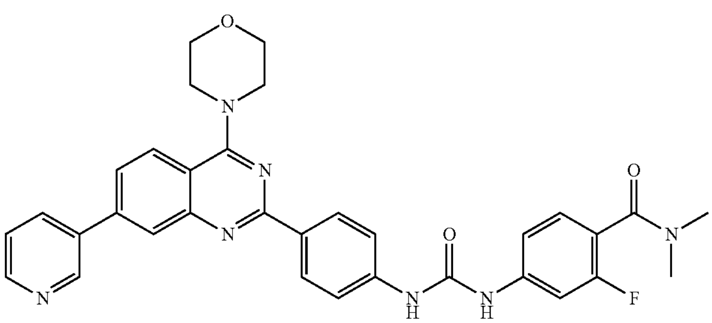 [SMILES: CN(C)C(=O)c1ccc(NC(=O)Nc2ccc(-c3nc(N4CCOCC4)c4ccc(-c5cccnc5)cc4n3)cc2)cc1F] | 2-fluoro-N,N-dimethyl-4-(3-(4-(4-morpholino-7-(pyridin-3-yl)quinazolin-2-yl)phenyl)ureido)-benzamide | 6 |
| 261 | 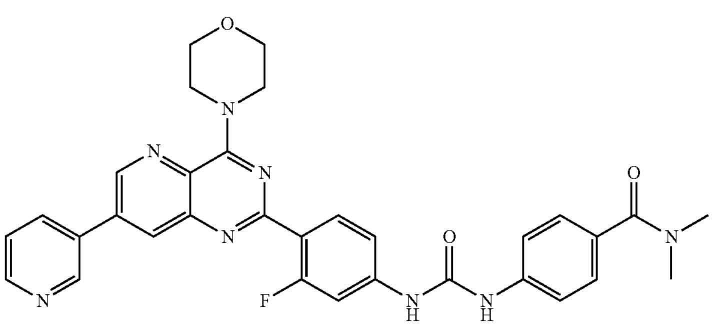 [SMILES: CN(C)C(=O)c1ccc(NC(=O)Nc2ccc(-c3nc(N4CCOCC4)c4ncc(-c5cccnc5)cc4n3)c(F)c2)cc1] | 4-(3-(3-fluoro-4-(4-morpholino-7-(pyridin-3-yl)pyrido[3,2-d]pyrimidin-2-yl)phenyl)ureido)-N,N-dimethyl-benzamide | 7 |

TABLE 1-continued

| Ex | Structure | Structure Name | Synthetic Scheme |
|---|---|---|---|
| 262 | 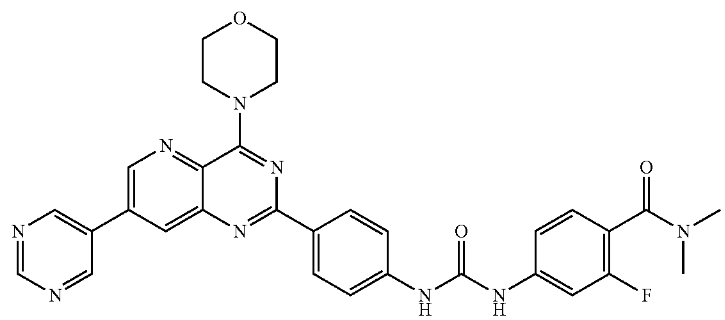 [SMILES: CN(C)C(=O)c1ccc(NC(=O)Nc2ccc(-c3nc(N4CCOCC4)c4ncc(-c5cncnc5)cc4n3)cc2)cc1F] | 2-fluoro-N,N-dimethyl-4-(3-(4-(4-morpholino-7-(pyrimidin-5-yl)pyrido[3,2-d]pyrimidin-2-yl)phenyl)ureido)-benzamide | 7 |
| 263 | 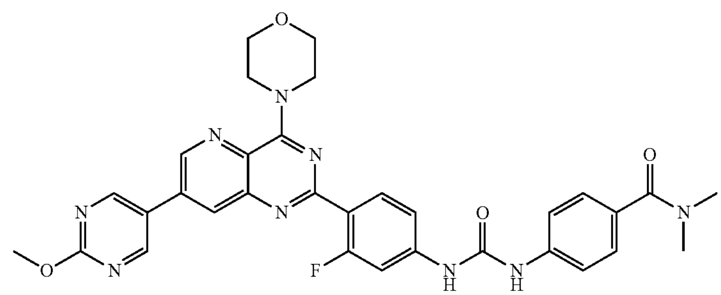 | 4-(3-(3-fluoro-4-(7-(2-methoxypyrimidin-5-yl)-4-morpholino-pyrido[3,2-d]pyrimidin-2-yl)phenyl)ureido)-N,N-dimethyl-benzamide | 7 |
| 264 | 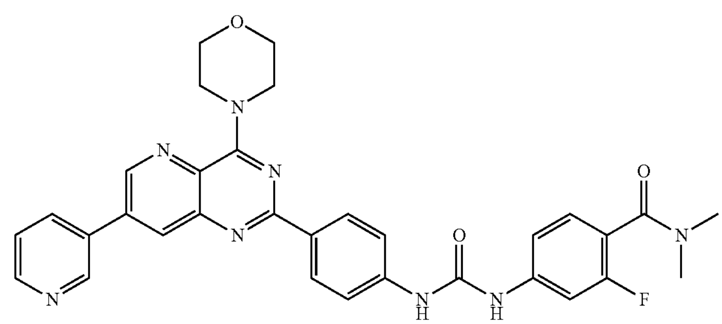 [SMILES: CN(C)C(=O)c1ccc(NC(=O)Nc2ccc(-c3nc(N4CCOCC4)c4ncc(-c5cccnc5)cc4n3)cc2)cc1F] | 2-fluoro-N,N-dimethyl-4-(3-(4-(4-morpholino-7-(pyridin-3-yl)pyrido[3,2-d]pyrimidin-2-yl)phenyl)ureido)-benzamide | 7 |
| 265 | 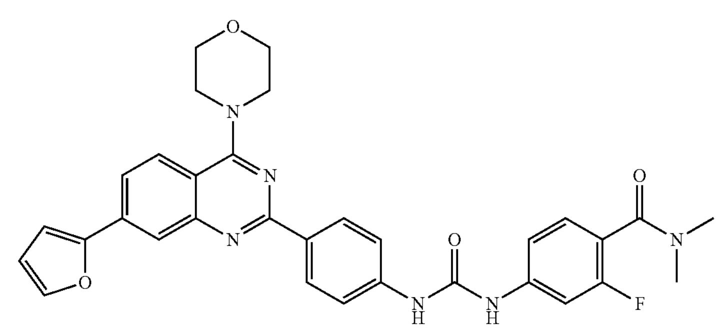 [SMILES: CN(C)C(=O)c1ccc(NC(=O)Nc2ccc(-c3nc(N4CCOCC4)c4ccc(-c5ccco5)cc4n3)cc2)cc1F] | 2-fluoro-4-(3-(4-(7-(furan-2-yl)-4-morpholino-quinazolin-2-yl)phenyl)ureido)-N,N-dimethyl-benzamide | 6 |
| 266 | 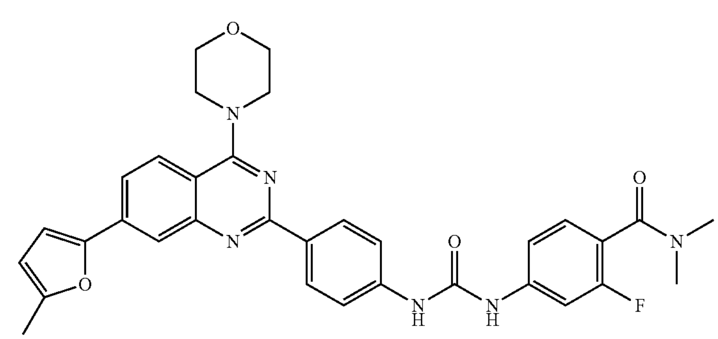 [SMILES: Cc1ccc(-c2ccc3c(N4CCOCC4)nc(-c4ccc(NC(=O)Nc5ccc(C(=O)N(C)C)c(F)c5)cc4)nc3c2)o1] | 2-fluoro-N,N-dimethyl-4-(3-(4-(7-(5-methylfuran-2-yl)-4-morpholino-quinazolin-2-yl)phenyl)ureido)-benzamide | 6 |

TABLE 1-continued

| Ex | Structure | Structure Name | Synthetic Scheme |
|---|---|---|---|
| 267 | 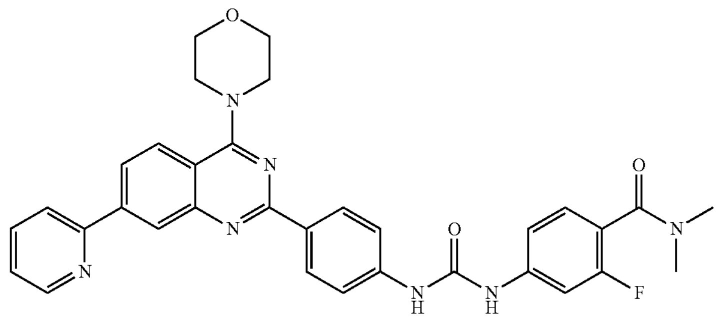 [SMILES: CN(C)C(=O)c1ccc(NC(=O)Nc2ccc(-c3nc(N4CCOCC4)c4ccc(-c5ccccn5)cc4n3)cc2)cc1F] | 2-fluoro-N,N-dimethyl-4-(3-(4-(4-morpholino-7-(pyridin-2-yl)quinazolin-2-yl)phenyl)ureido)-benzamide | 6 |
| 268 | 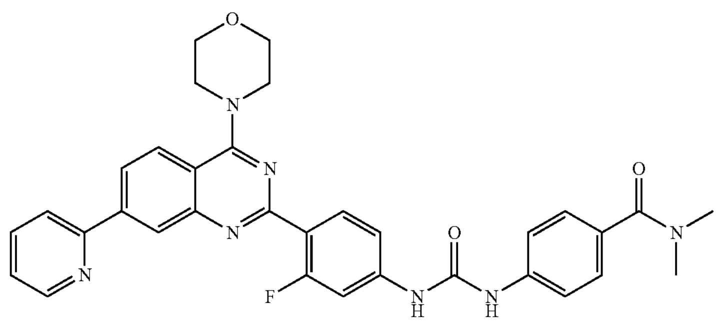 [SMILES: CN(C)C(=O)c1ccc(NC(=O)Nc2ccc(-c3nc(N4CCOCC4)c4ccc(-c5ccccn5)cc4n3)c(F)c2)cc1] | 4-(3-(3-fluoro-4-(4-morpholino-7-(pyridin-2-yl)quinazolin-2-yl)phenyl)ureido)-N,N-dimethyl-benzamide | 6 |
| 269 | 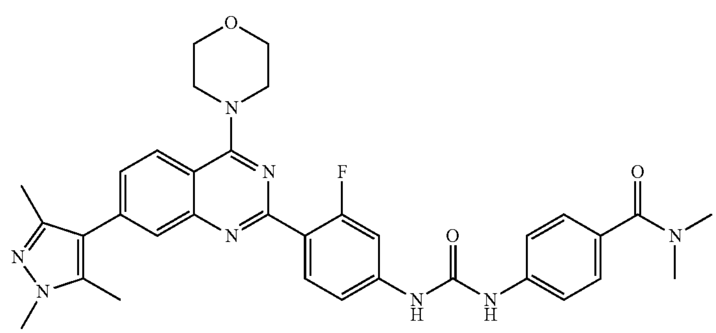 [SMILES: Cc1nn(C)c(C)c1-c1ccc2c(N3CCOCC3)nc(-c3ccc(NC(=O)Nc4ccc(C(=O)N(C)C)cc4)cc3F)nc2c1] | 4-(3-(3-fluoro-4-(4-morpholino-7-(1,3,5-trimethyl-1H-pyrazol-4-yl)quinazolin-2-yl)phenyl)ureido)-N,N-dimethyl-benzamide | 6 |
| 270 | 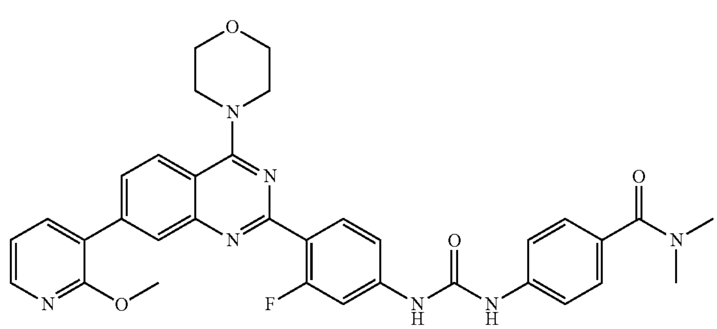 [SMILES: COc1ncccc1-c1ccc2c(N3CCOCC3)nc(-c3ccc(NC(=O)Nc4ccc(C(=O)N(C)C)cc4)cc3F)nc2c1] | 4-(3-(3-fluoro-4-(7-(2-methoxypyridin-3-yl)-4-morpholino-quinazolin-2-yl)phenyl)ureido)-N,N-dimethyl-benzamide | 6 |

TABLE 1-continued

| Ex | Structure | Structure Name | Synthetic Scheme |
|---|---|---|---|
| 271 | 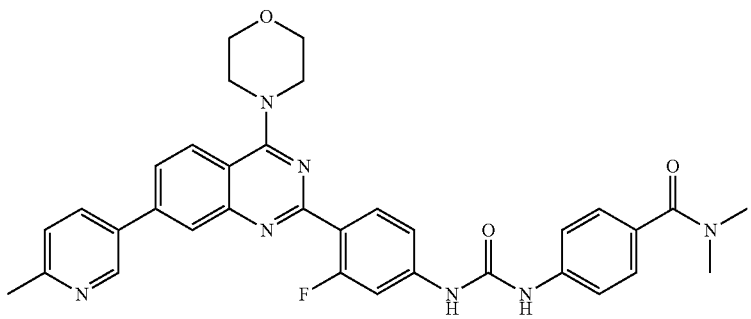 | 4-(3-(3-fluoro-4-(7-(6-methylpyridin-3-yl)-4-morpholino-quinazolin-2-yl)phenyl)ureido)-N,N-dimethyl-benzamide | 6 |
| 272 | 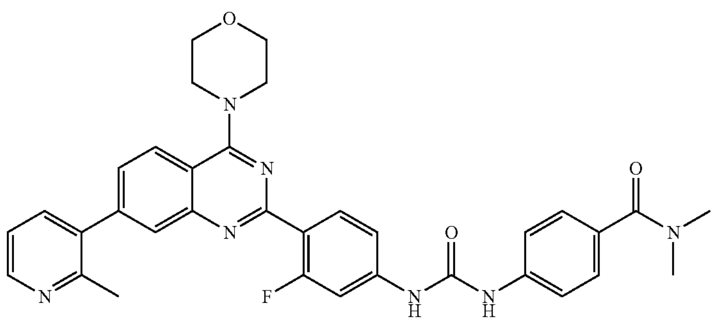 [SMILES: Cc1ncccc1-c1ccc2c(N3CCOCC3)nc(-c3ccc(NC(=O)Nc4ccc(C(=O)N(C)C)cc4)cc3F)nc2c1] | 4-(3-(3-fluoro-4-(7-(2-methylpyridin-3-yl)-4-morpholino-quinazolin-2-yl)phenyl)ureido)-N,N-dimethyl-benzamide | 6 |
| 273 | 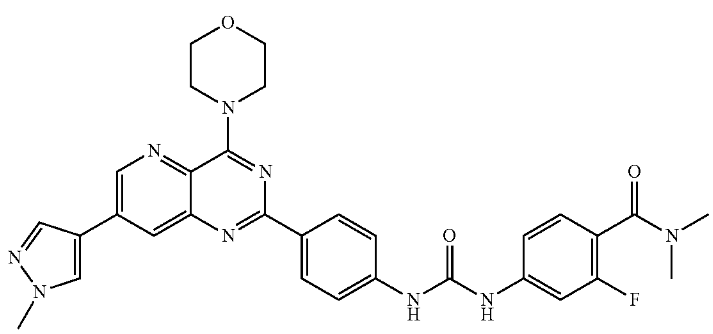 [SMILES: CN(C)C(=O)c1ccc(NC(=O)Nc2ccc(-c3nc(N4CCOCC4)c4ncc(-c5cnn(C)c5)cc4n3)cc2)cc1F] | 2-fluoro-N,N-dimethyl-4-(3-(4-(7-(1-methyl-1H-pyrazol-4-yl)-4-morpholino-pyrido[3,2-d]pyrimidin-2-yl)phenyl)ureido)-benzamide | 7 |
| 274 | 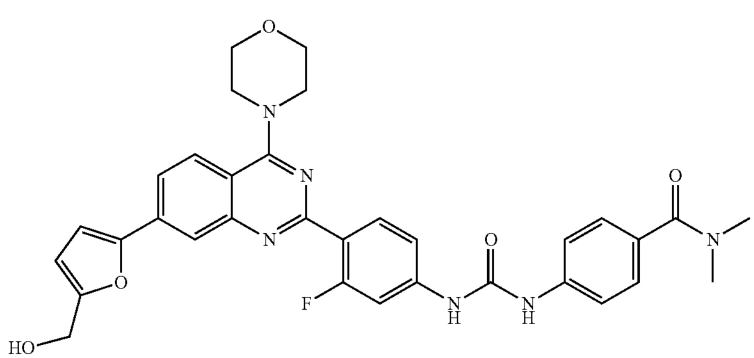 [SMILES: CN(C)C(=O)c1ccc(NC(=O)Nc2ccc(-c3nc(N4CCOCC4)c4ccc(-c5ccc(CO)o5)cc4n3)c(F)c2)cc1] | 4-(3-(3-fluoro-4-(7-(5-(hydroxymethyl)furan-2-yl)-4-morpholino-quinazolin-2-yl)phenyl)ureido)-N,N-dimethyl-benzamide | 11 + 6 |

TABLE 1-continued

| Ex | Structure Name | Synthetic Scheme |
|----|----------------|------------------|
| 275 | 4-(3-(3-fluoro-4-(7-(5-(1-hydroxyethyl)furan-2-yl)-4-morpholino-quinazolin-2-yl)phenyl)ureido)-N,N-dimethyl-benzamide | 11 + 6 |
| 276 | 4-(3-(3-fluoro-4-(7-(5-(2-hydroxypropan-2-yl)furan-2-yl)-4-morpholino-quinazolin-2-yl)phenyl)ureido)-N,N-dimethyl-benzamide | 11 + 6 |
| 277 | 4-(3-(4-(7-(2-(dimethylamino)pyrimidin-5-yl)-4-morpholino-quinazolin-2-yl)-3-fluorophenyl)ureido)-N,N-dimethyl-benzamide | 6 |
| 278 | 2-fluoro-4-(3-(4-(7-(5-(hydroxymethyl)furan-2-yl)-4-morpholino-quinazolin-2-yl)phenyl)ureido)-N,N-dimethyl-benzamide | 11 + 6 |

TABLE 1-continued

| Ex | Structure | Structure Name | Synthetic Scheme |
|---|---|---|---|
| 279 | 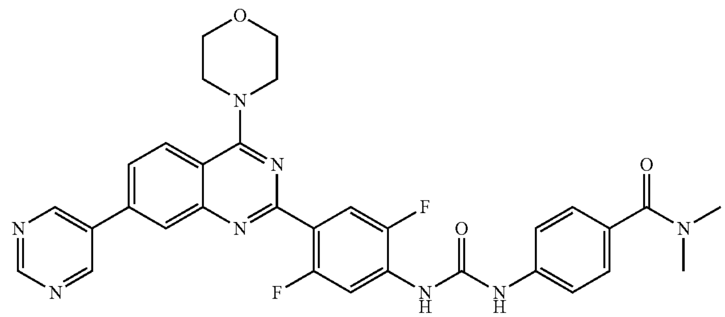 [SMILES: CN(C)C(=O)c1ccc(NC(=O)Nc2cc(F)c(-c3nc(N4CCOCC4)c4ccc(-c5cncnc5)cc4n3)cc2F)cc1] | 4-(3-(2,5-difluoro-4-(4-morpholino-7-(pyrimidin-5-yl)quinazolin-2-yl)phenyl)ureido)-N,N-dimethyl-benzamide | 2 + 6 |
| 280 | 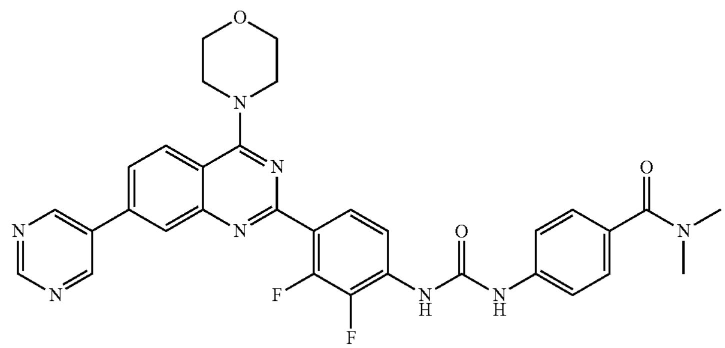 [SMILES: CN(C)C(=O)c1ccc(NC(=O)Nc2ccc(-c3nc(N4CCOCC4)c4ccc(-c5cncnc5)cc4n3)c(F)c2F)cc1] | 4-(3-(2,3-difluoro-4-(4-morpholino-7-(pyrimidin-5-yl)quinazolin-2-yl)phenyl)ureido)-N,N-dimethyl-benzamide | 2 + 6 |
| 281 | 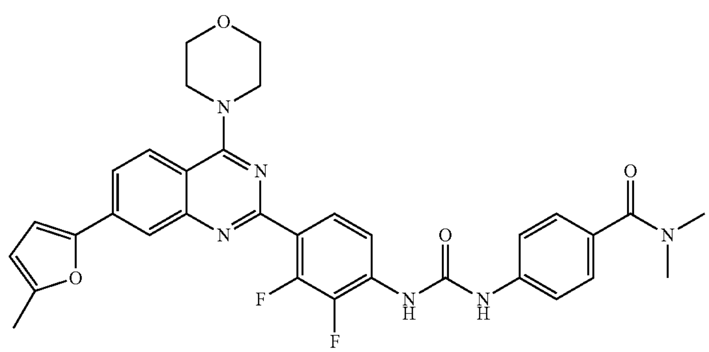 [SMILES: Cc1ccc(-c2ccc3c(N4CCOCC4)nc(-c4ccc(NC(=O)Nc5ccc(C(=O)N(C)C)cc5)c(F)c4F)nc3c2)o1] | 4-(3-(2,3-difluoro-4-(7-(5-methylfuran-2-yl)-4-morpholino-quinazolin-2-yl)phenyl)ureido)-N,N-dimethyl-benzamide | 2 + 6 |
| 282 | 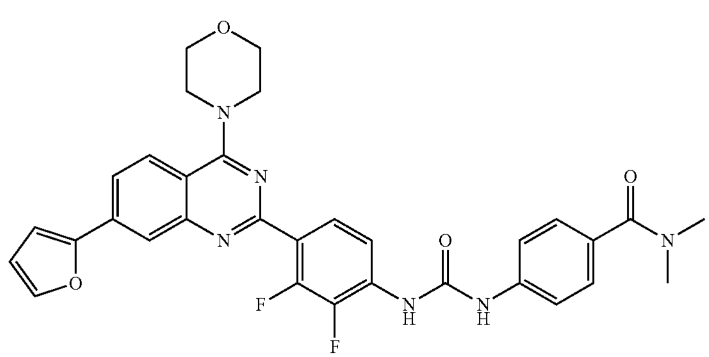 [SMILES: CN(C)C(=O)c1ccc(NC(=O)Nc2ccc(-c3nc(N4CCOCC4)c4ccc(-c5ccco5)cc4n3)c(F)c2F)cc1] | -(3-(2,3-difluoro-4-(7-(furan-2-yl)-4-morpholino-quinazolin-2-yl)phenyl)ureido)-N,N-dimethyl-benzamide | 2 + 6 |

TABLE 1-continued

| Ex | Structure | Structure Name | Synthetic Scheme |
|---|---|---|---|
| 283 | 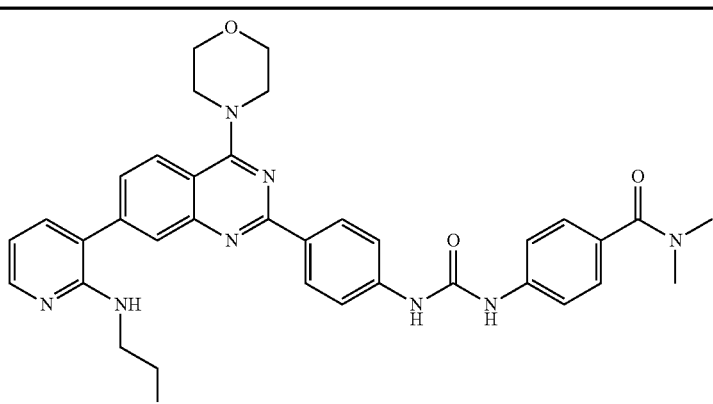 | 4-(3-(4-(7-(2-((2-hydroxyethyl)amino)pyridin-3-yl)-4-morpholine-quinazolin-2-yl)phenyl)ureido)-N,N-dimethyl-benzamide | 6B |
| 284 | 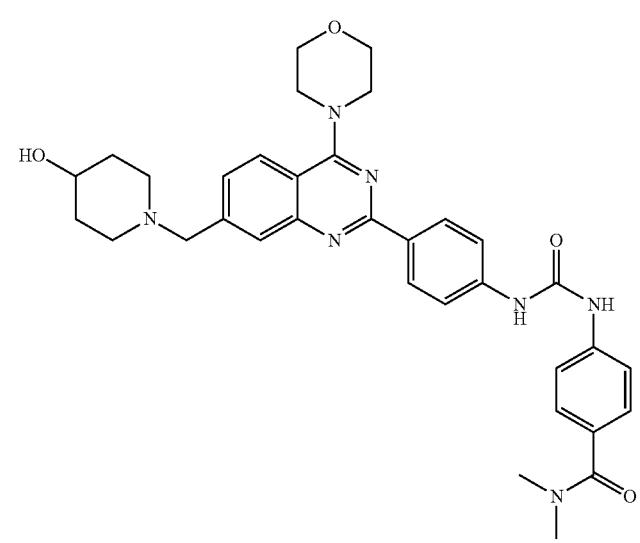 [SMILES: CN(C)C(=O)c1ccc(NC(=O)Nc2ccc(-c3nc(N4CCOCC4)c4ccc(CN5CCC(O)CC5)cc4n3)cc2)cc1] | 4-(3-(4-(7-((4-hydroxypiperidin-1-yl)methyl)-4-morpholino-quinazolin-2-yl)phenyl)ureido)-N,N-dimethyl-benzamide | 6B + methods related to 11 |
| 285 | 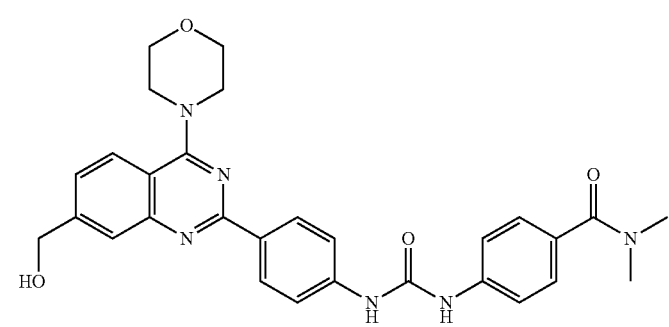 [SMILES: CN(C)C(=O)c1ccc(NC(=O)Nc2ccc(-c3nc(N4CCOCC4)c4ccc(CO)cc4n3)cc2)cc1] | 4-(3-(4-(7-(hydroxymethyl)-4-morpholino-quinazolin-2-yl)phenyl)ureido)-N,N-dimethyl-benzamide | 8A + 12 |
| 286 | 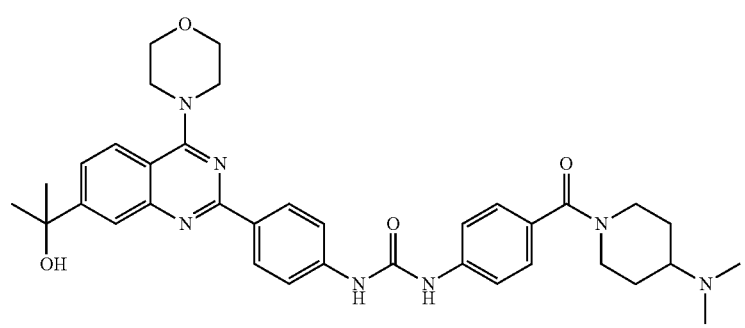 [SMILES: CN(C)C1CCN(C(=O)c2ccc(NC(=O)Nc3ccc(-c4nc(N5CCOCC5)c5ccc(C(C)(C)O)cc5n4)cc3)cc2)CC1] | 1-(4-(4-(dimethylamino)piperidine-1-carbonyl)phenyl)-3-(4-(7-(2-hydroxypropan-2-yl)-4-morpholino-quinazolin-2-yl)phenyl)urea | 8A,13 + 12 |

TABLE 1-continued

| Ex | Structure Name | Synthetic Scheme |
|---|---|---|
| 287 | 4-(3-(4-(7-(4-(dimethylamino)piperidine-1-carbonyl)-4-morpholino-quinazolin-2-yl)phenyl)ureido)-N,N-dimethyl-benzamide | 8A |
| 288 | (R)-1-(4-(3-(dimethylamino)pyrrolidine-1-carbonyl)phenyl)-3-(4-(7-(2-hydroxypropan-2-yl)-4-morpholino-quinazolin-2-yl)phenyl)urea | 8A,13 + 12 |
| 289 | (S)-1-(4-(3-(dimethylamino)pyrrolidine-1-carbonyl)phenyl)-3-(4-(7-(2-hydroxypropan-2-yl)-4-morpholino-quinazolin-2-yl)phenyl)urea | 8A,13 + 12 |
| 290 | 4-(3-(2-fluoro-4-(7-(2-hydroxypropan-2-yl)-4-morpholino-quinazolin-2-yl)phenyl)ureido)-N,N-dimethyl-benzamide | 8A,12 + 6 |

TABLE 1-continued

| Ex | Structure | Structure Name | Synthetic Scheme |
|---|---|---|---|
| 291 | 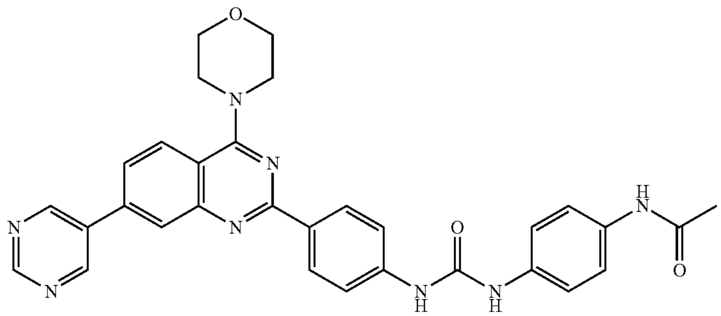 [SMILES: CC(=O)Nc1ccc(NC(=O)Nc2ccc(-c3nc(N4CCOCC4)c4ccc(-c5cncnc5)cc4n3)cc2)cc1] | N-(4-(3-(4-(4-morpholino-7-(pyrimidin-5-yl)quinazolin-2-yl)phenyl)ureido)phenyl)-acetamide | 10 |
| 292 | 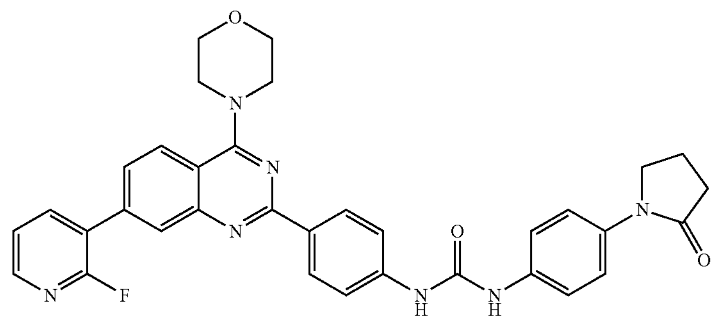 [SMILES: O=C(Nc1ccc(-c2nc(N3CCOCC3)c3ccc(-c4cccnc4F)cc3n2)cc1)Nc1ccc(N2CCCC2=O)cc1] | 1-(4-(7-(2-fluoropyridin-3-yl)-4-morpholinoquinazolin-2-yl)phenyl)-3-(4-(2-oxopyrrolidin-1-yl)phenyl)urea | 10 |
| 293 | 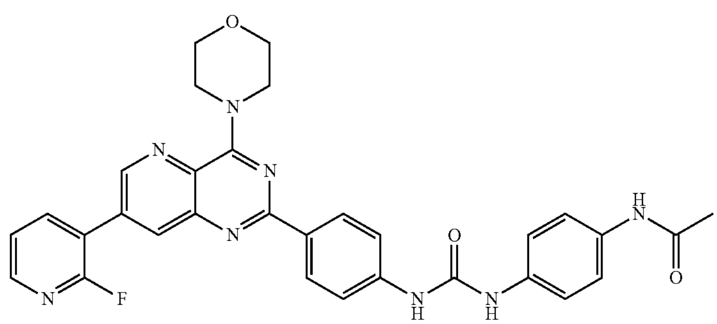 [SMILES: CC(=O)Nc1ccc(NC(=O)Nc2ccc(-c3nc(N4CCOCC4)c4ncc(-c5cccnc5F)cc4n3)cc2)cc1] | N-(4-(3-(4-(7-(2-fluoropyridin-3-yl)-4-morpholinopyrido[3,2-d]pyrimidin-2-yl)phenyl)ureido)phenyl)acetamide | 7A + 9 |
| 294 | 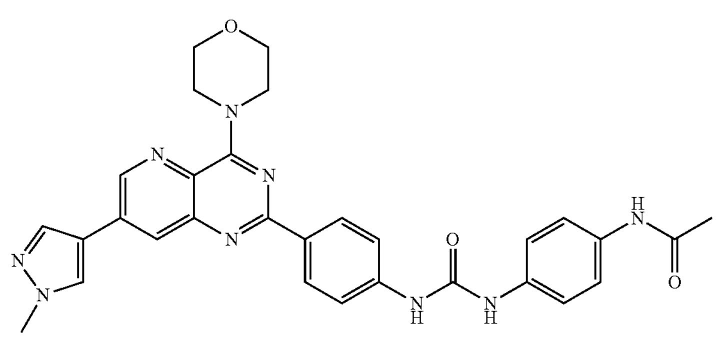 [SMILES: CC(=O)Nc1ccc(NC(=O)Nc2ccc(-c3nc(N4CCOCC4)c4ncc(-c5cnn(C)c5)cc4n3)cc2)cc1] | N-(4-(3-(4-(7-(1-methyl-1H-pyrazol-4-yl)-4-morpholinopyrido[3,2-d]pyrimidin-2-yl)phenyl)ureido)phenyl)acetamide | 7A + 9 |

TABLE 1-continued

| Ex | Structure Name | Synthetic Scheme |
|---|---|---|
| 295 | N,N-dimethyl-4-(3-(4-(4-morpholino-7-(1,3,5-trimethyl-1H-pyrazol-4-yl)pyrido[3,2-d]pyrimidin-2-yl)phenyl)ureido)-benzamide | 7A |
| 296 | 4-(3-(2-fluoro-4-(4-morpholino-7-(1,3,5-trimethyl-1H-pyrazol-4-yl)pyrido[3,2-d]pyrimidin-2-yl)phenyl)ureido)-N,N-dimethyl-benzamide | 7B |
| 297 | N,N-dimethyl-4-(3-(4-(7-(2-methylpyridin-3-yl)-4-morpholinopyrido[3,2-d]pyrimidin-2-yl)phenyl)ureido)-benzamide | 7A |
| 298 | 4-(3-(2-fluoro-4-(7-(2-methylpyridin-3-yl)-4-morpholinopyrido[3,2-d]pyrimidin-2-yl)phenyl)ureido)-N,N-dimethyl-benzamide | 7B |

TABLE 1-continued

| Ex | Structure | Structure Name | Synthetic Scheme |
|---|---|---|---|
| 299 | 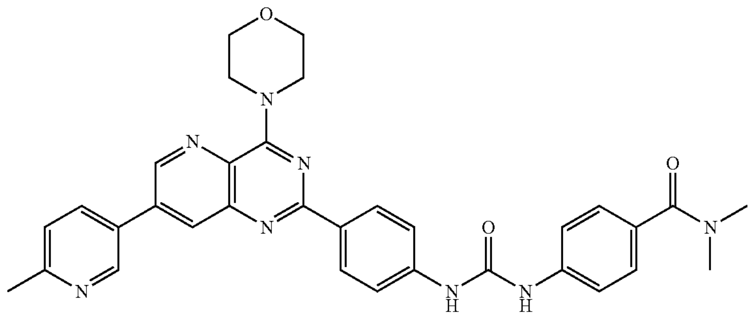 | N,N-dimethyl-4-(3-(4-(7-(6-methylpyridin-3-yl)-4-morpholinopyrido[3,2-d]pyrimidin-2-yl)phenyl)ureido)-benzamide | 7A |
| 300 | 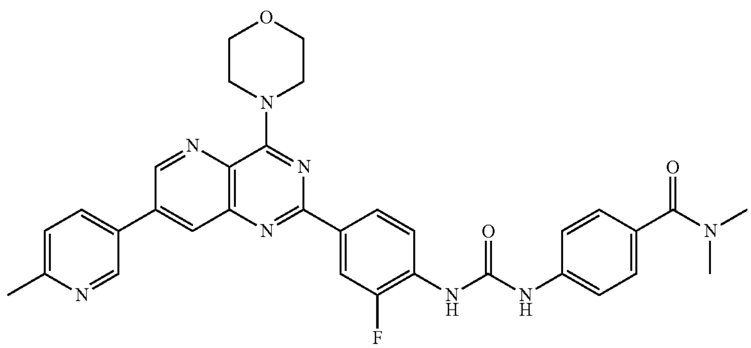 | 4-(3-(2-fluoro-4-(7-(6-methylpyridin-3-yl)-4-morpholinopyrido[3,2-d]pyrimidin-2-yl)phenyl)ureido)-N,N-dimethyl-benzamide | 7B |
| 301 | 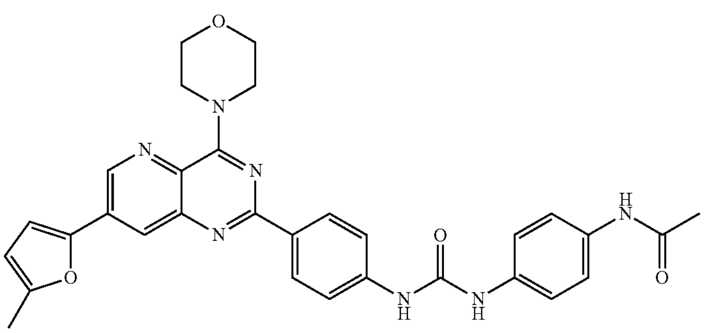 [SMILES: CC(=O)Nc1ccc(NC(=O)Nc2ccc(-c3nc(N4CCOCC4)c4ncc(-c5ccc(C)o5)cc4n3)cc2)cc1] | N-(4-(3-(4-(7-(5-methylfuran-2-yl)-4-morpholinopyrido[3,2-d]pyrimidin-2-yl)phenyl)ureido)phenyl)acetamide | 7A + 9 |
| 302 | 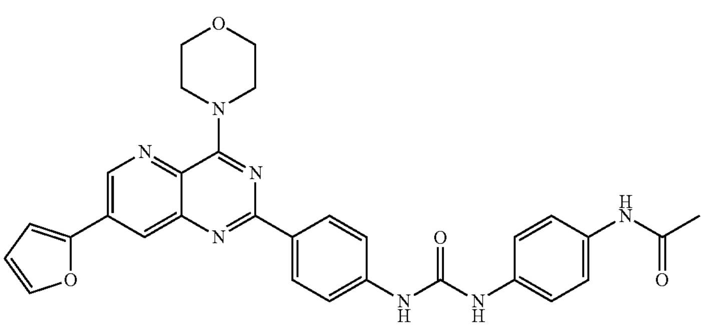 [SMILES: CC(=O)Nc1ccc(NC(=O)Nc2ccc(-c3nc(N4CCOCC4)c4ncc(-c5ccco5)cc4n3)cc2)cc1] | N-(4-(3-(4-(7-(2-fluoropyridin-3-yl)-4-morpholinopyrido[3,2-d]pyrimidin-2-yl)phenyl)ureido)phenyl)acetamide | 7A + 9 |

TABLE 1-continued

| Ex | Structure | Structure Name | Synthetic Scheme |
|---|---|---|---|
| 303 | 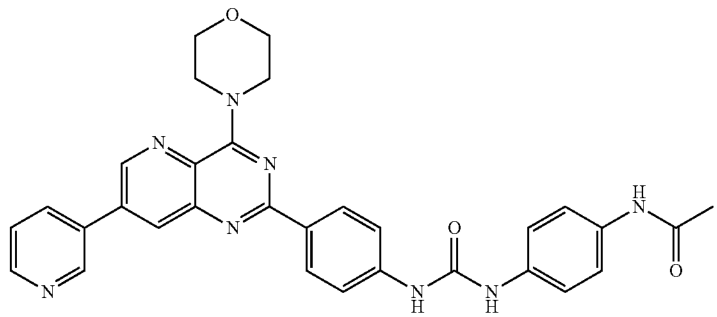 [SMILES: CC(=O)Nc1ccc(NC(=O)Nc2ccc(-c3nc(N4CCOCC4)c4ncc(-c5cccnc5)cc4n3)cc2)cc1] | N-(4-(3-(4-(4-morpholino-7-(pyridin-3-yl)pyrido[3,2-d]pyrimidin-2-yl)phenyl)ureido)phenyl)acetamide | 7A + 9 |
| 304 | 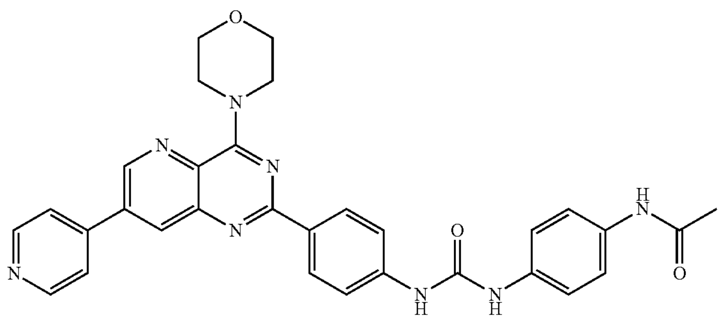 [SMILES: CC(=O)Nc1ccc(NC(=O)Nc2ccc(-c3nc(N4CCOCC4)c4ncc(-c5ccncc5)cc4n3)cc2)cc1] | N-(4-(3-(4-(4-morpholino-7-(pyridin-4-yl)pyrido[3,2-d]pyrimidin-2-yl)phenyl)ureido)phenyl)acetamide | 7A + 9 |
| 305 | 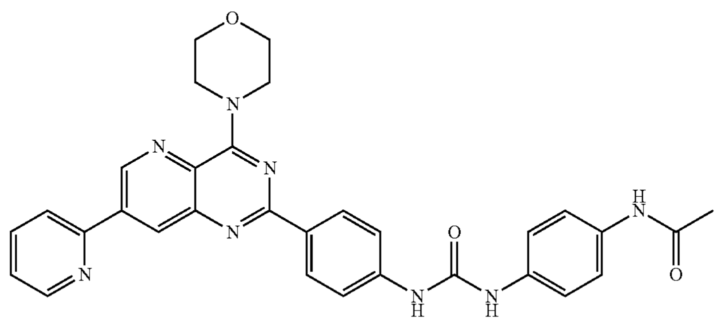 [SMILES: CC(=O)Nc1ccc(NC(=O)Nc2ccc(-c3nc(N4CCOCC4)c4ncc(-c5ccccn5)cc4n3)cc2)cc1] | N-(4-(3-(4-(4-morpholino-7-(pyridin-2-yl)pyrido[3,2-d]pyrimidin-2-yl)phenyl)ureido)phenyl)acetamide | 7A + 9 |
| 306 | 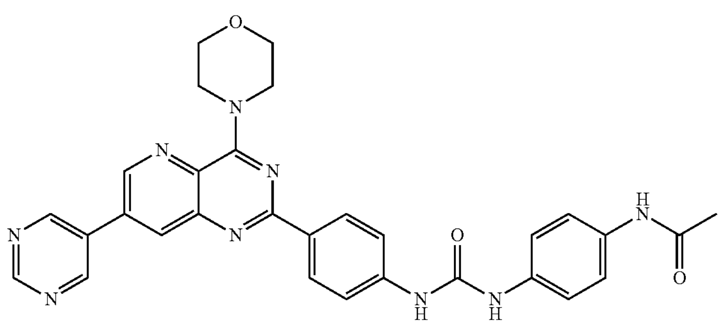 [SMILES: CC(=O)Nc1ccc(NC(=O)Nc2ccc(-c3nc(N4CCOCC4)c4ncc(-c5cncnc5)cc4n3)cc2)cc1] | N-(4-(3-(4-(4-morpholino-7-(pyrimidin-5-yl)pyrido[3,2-d]pyrimidin-2-yl)phenyl)ureido)phenyl)acetamide | 7A + 9 |
| 307 | 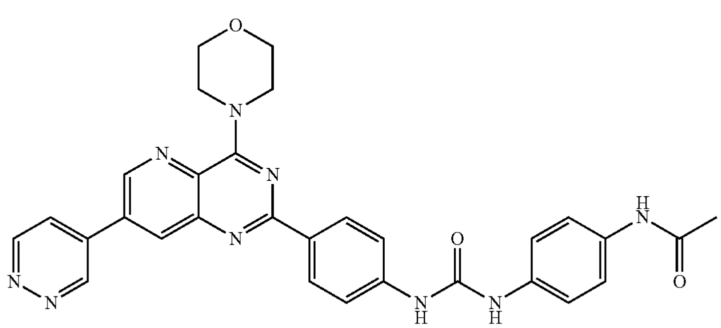 [SMILES: CC(=O)Nc1ccc(NC(=O)Nc2ccc(-c3nc(N4CCOCC4)c4ncc(-c5ccnnc5)cc4n3)cc2)cc1] | N-(4-(3-(4-(4-morpholino-7-(pyridazin-4-yl)pyrido[3,2-d]pyrimidin-2-yl)phenyl)ureido)phenyl)acetamide | 7A + 9 |

TABLE 1-continued

| Ex | Structure | Structure Name | Synthetic Scheme |
|---|---|---|---|
| 308 | 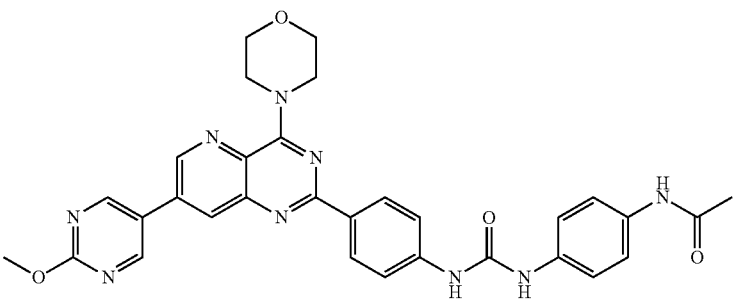 [SMILES: COc1ncc(-c2cnc3c(N4CCOCC4)nc(-c4ccc(NC(=O)Nc5ccc(NC(C)=O)cc5)cc4)nc3c2)cn1] | N-(4-(3-(4-(7-(2-methoxypyrimidin-5-yl)-4-morpholinopyrido[3,2-d]pyrimidin-2-yl)phenyl)ureido)phenyl)acetamide | 7A + 9 |
| 309 | 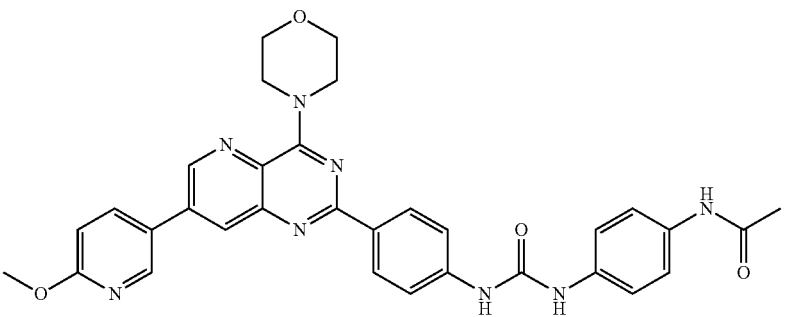 [SMILES: COc1ccc(-c2cnc3c(N4CCOCC4)nc(-c4ccc(NC(=O)Nc5ccc(NC(C)=O)cc5)cc4)nc3c2)cn1] | N-(4-(3-(4-(7-(6-methoxypyridin-3-yl)-4-morpholinopyrido[3,2-d]pyrimidin-2-yl)phenyl)ureido)phenyl)acetamide | 7A + 9 |
| 310 | 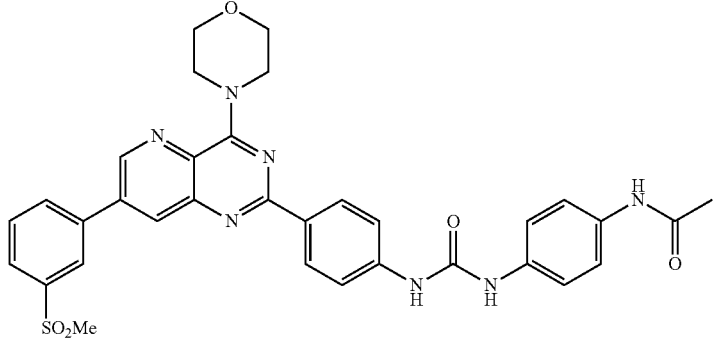 | N-(4-(3-(4-(7-(3-(methylsulfonyl)phenyl)-4-morpholinopyrido[3,2-d]pyrimidin-2-yl)phenyl)ureido)phenyl)acetamide | 7A + 9 |
| 311 | 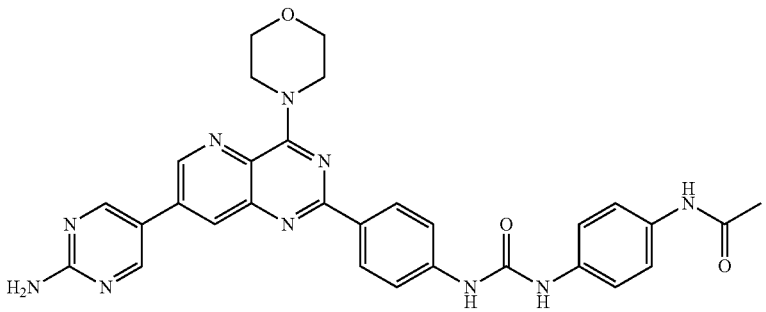 [SMILES: CC(=O)Nc1ccc(NC(=O)Nc2ccc(-c3nc(N4CCOCC4)c4ncc(-c5cnc(N)nc5)cc4n3)cc2)cc1] | N-(4-(3-(4-(7-(2-aminopyrimidin-5-yl)-4-morpholinopyrido[3,2-d]pyrimidin-2-yl)phenyl)ureido)phenyl)acetamide | 7A + 9 |

TABLE 1-continued

| Ex | Structure | Structure Name | Synthetic Scheme |
|---|---|---|---|
| 312 | 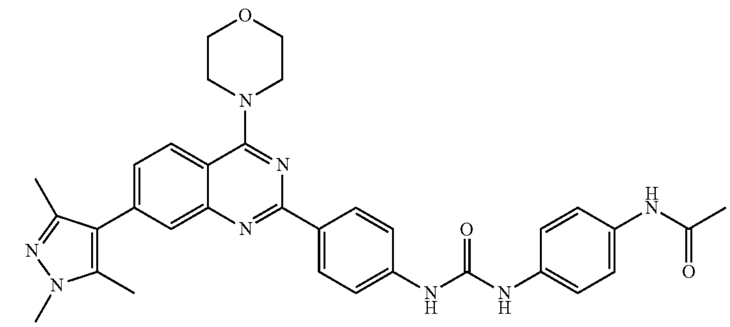 [SMILES: CC(=O)Nc1ccc(NC(=O)Nc2ccc(-c3nc(N4CCOCC4)c4ccc(-c5c(C)nn(C)c5C)cc4n3)cc2)cc1] | N-(4-(3-(4-(4-morpholino-7-(1,3,5-trimethyl-1H-pyrazol-4-yl)quinazolin-2-yl)phenyl)ureido)phenyl)acetamide | 7A + 9 |
| 313 | 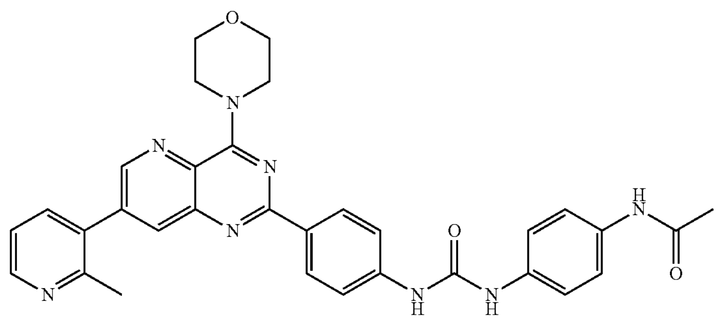 | N-(4-(3-(4-(7-(2-methylpyridin-3-yl)-4-morpholinopyrido[3,2-d]pyrimidin-2-yl)phenyl)ureido)phenyl)acetamide | 7A + 9 |
| 314 | 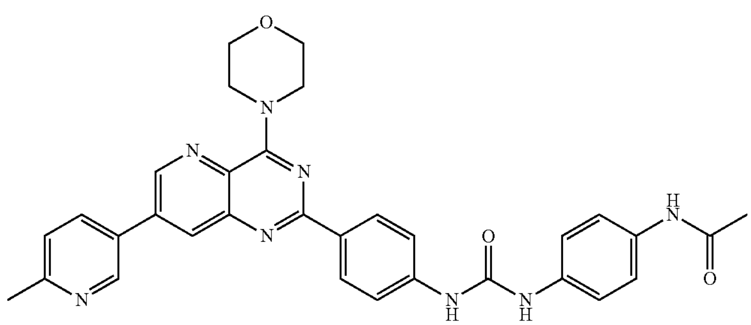 [SMILES: CC(=O)Nc1ccc(NC(=O)Nc2ccc(-c3nc(N4CCOCC4)c4ncc(-c5ccc(C)nc5)cc4n3)cc2)cc1] | N-(4-(3-(4-(7-(6-methylpyridin-3-yl)-4-morpholinopyrido[3,2-d]pyrimidin-2-yl)phenyl)ureido)phenyl)acetamide | 7A + 9 |
| 315 | 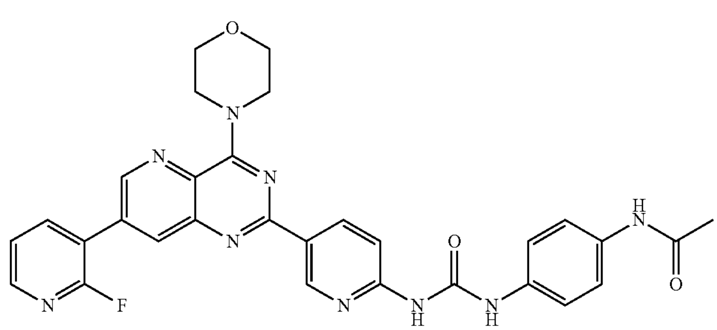 [SMILES: CC(=O)Nc1ccc(NC(=O)Nc2ccc(-c3nc(N4CCOCC4)c4ncc(-c5cccnc5F)cc4n3)cn2)cc1] | N-(4-(3-(5-(7-(2-fluoropyridin-3-yl)-4-morpholinopyrido[3,2-d]pyrimidin-2-yl)pyridin-2-yl)ureido)phenyl)acetamide | 7A + 6E + 9 |

TABLE 1-continued

| Ex | Structure | Structure Name | Synthetic Scheme |
|---|---|---|---|
| 316 | 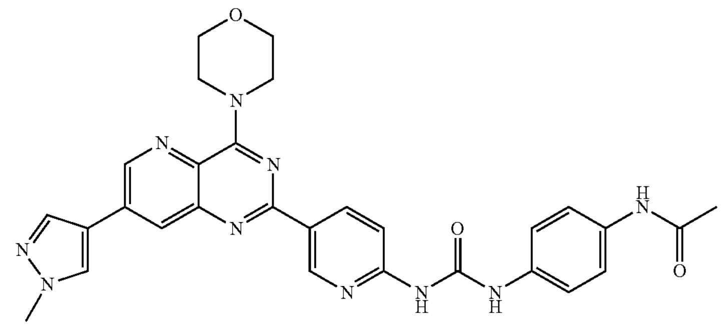 [SMILES: CC(=O)Nc1ccc(NC(=O)Nc2ccc(-c3nc(N4CCOCC4)c4ncc(-c5cnn(C)c5)cc4n3)cn2)cc1] | N-(4-(3-(5-(7-(1-methyl-1H-pyrazol-4-yl)-4-morpholinopyrido[3,2-d]pyrimidin-2-yl)pyridin-2-yl)ureido)phenyl)acetamide | 7A + 6E + 9 |
| 317 | 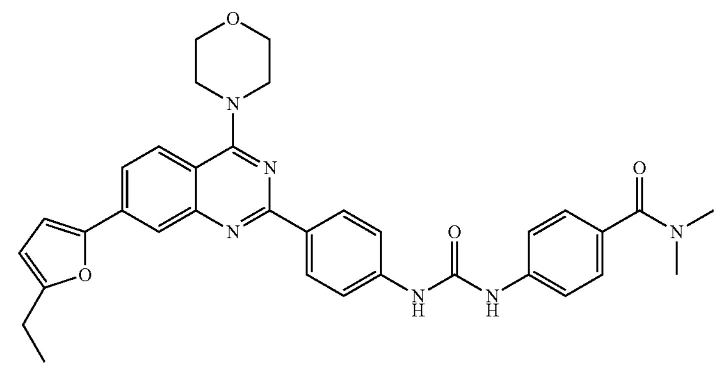 [SMILES: CCc1ccc(-c2ccc3c(N4CCOCC4)nc(-c4ccc(NC(=O)Nc5ccc(C(=O)N(C)C)cc5)cc4)nc3c2)o1] | 4-(3-(4-(7-(5-ethylfuran-2-yl)-4-morpholinoquinazolin-2-yl)phenyl)ureido)-N,N-dimethyl-benzamide | 6B + 11 |
| 318 | 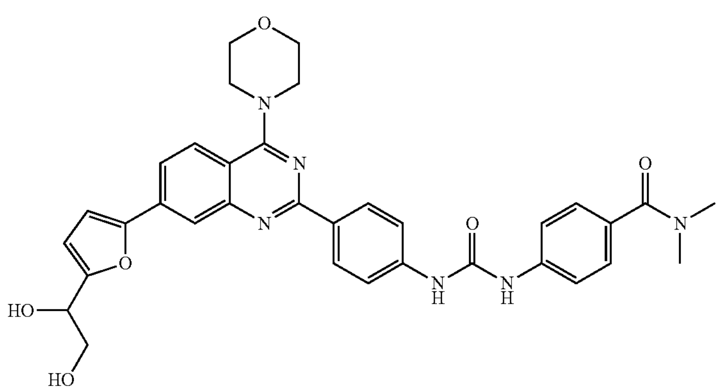 [SMILES: CN(C)C(=O)c1ccc(NC(=O)Nc2ccc(-c3nc(N4CCOCC4)c4ccc(-c5ccc(C(O)CO)o5)cc4n3)cc2)cc1] | 4-(3-(4-(7-(5-(1,2-dihydroxyethyl)furan-2-yl)-4-morpholinoquinazolin-2-yl)phenyl)ureido)-N,N-dimethyl-benzamide | 6B + 11 |
| 319 | 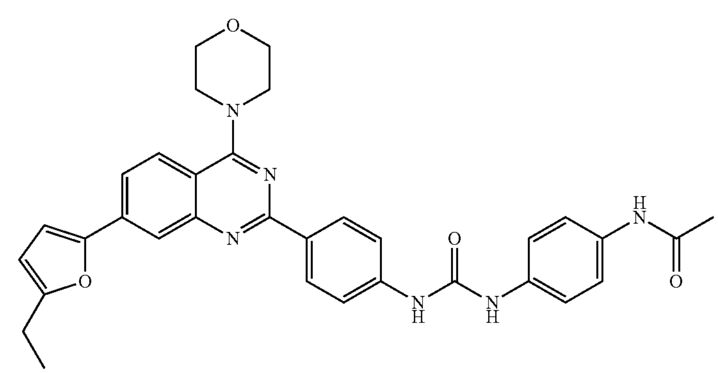 [SMILES: CCc1ccc(-c2ccc3c(N4CCOCC4)nc(-c4ccc(NC(=O)Nc5ccc(NC(C)=O)cc5)cc4)nc3c2)o1] | N-(4-(3-(4-(7-(5-ethylfuran-2-yl)-4-morpholinoquinazolin-2-yl)phenyl)ureido)phenyl)acetamide | 10 |

TABLE 1-continued

| Ex | Structure | Structure Name | Synthetic Scheme |
|---|---|---|---|
| 320 | 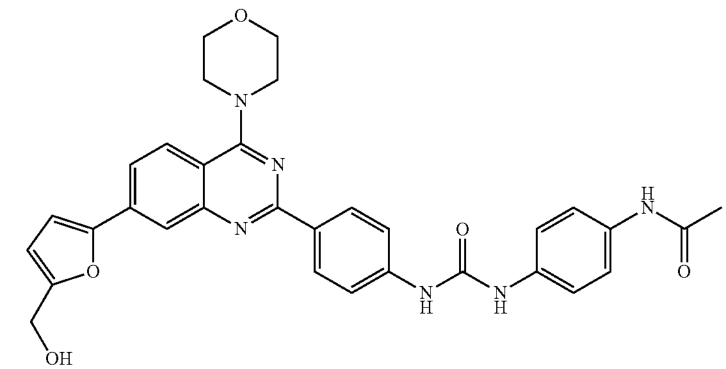 [SMILES: CC(=O)Nc1ccc(NC(=O)Nc2ccc(-c3nc(N4CCOCC4)c4ccc(-c5ccc(CO)o5)cc4n3)cc2)cc1] | N-(4-(3-(4-(7-(5-(hydroxymethyl)furan-2-yl)-4-morpholinoquinazolin-2-yl)phenyl)ureido)phenyl)acetamide | 11 + 10 |
| 321 | 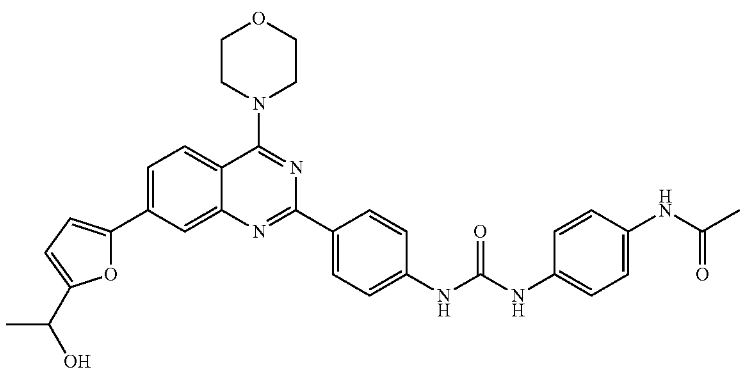 [SMILES: CC(=O)Nc1ccc(NC(=O)Nc2ccc(-c3nc(N4CCOCC4)c4ccc(-c5ccc(C(C)O)o5)cc4n3)cc2)cc1] | N-(4-(3-(4-(7-(5-(1-hydroxyethyl)furan-2-yl)-4-morpholinoquinazolin-2-yl)phenyl)ureido)phenyl)acetamide | 11 + 10 |
| 322 | 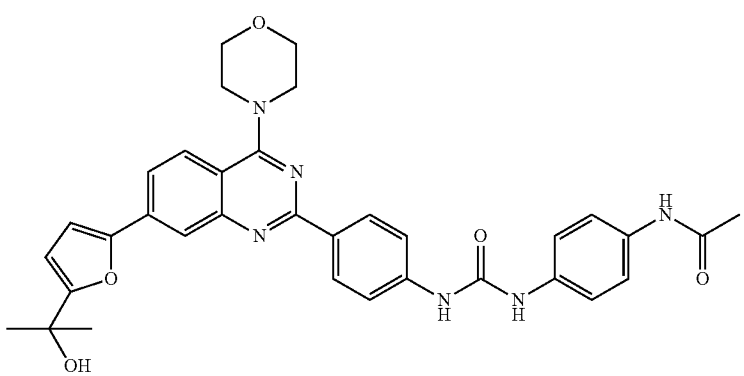 [SMILES: CC(=O)Nc1ccc(NC(=O)Nc2ccc(-c3nc(N4CCOCC4)c4ccc(-c5ccc(C(C)(C)O)o5)cc4n3)cc2)cc1] | N-(4-(3-(4-(7-(5-(2-hydroxypropan-2-yl)furan-2-yl)-4-morpholinoquinazolin-2-yl)phenyl)ureido)phenyl)acetamide | 11 + 10 |
| 323 | 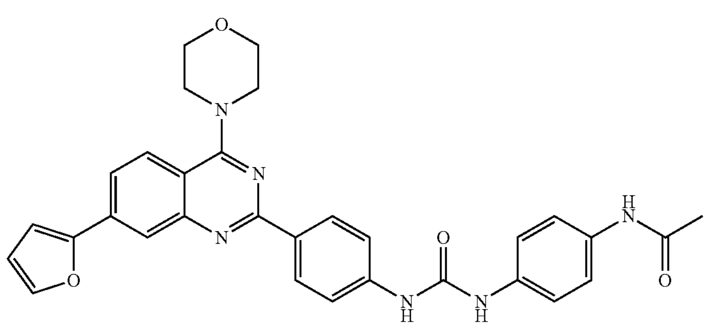 | N-(4-(3-(4-(7-(furan-2-yl)-4-morpholinoquinazolin-2-yl)phenyl)ureido)phenyl)acetamide | 10 |

TABLE 1-continued

| Ex | Structure | Structure Name | Synthetic Scheme |
|---|---|---|---|
| 324 | 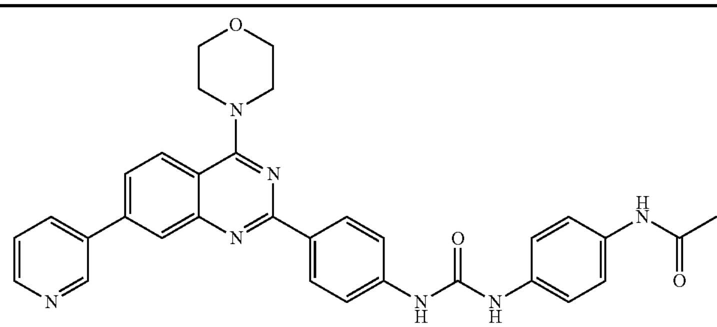 | N-(4-(3-(4-(4-morpholino-7-(pyridin-3-yl)quinazolin-2-yl)phenyl)ureido)phenyl)acetamide | 10 |
| 325 | 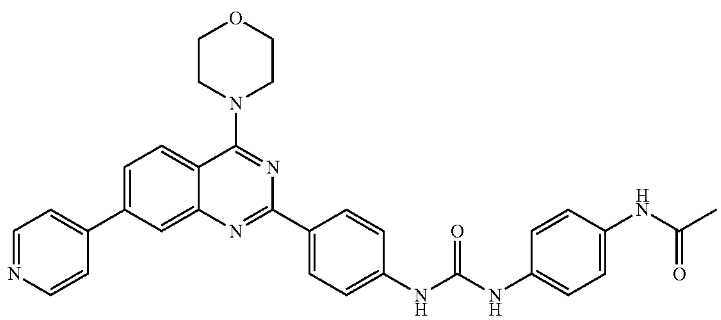 [SMILES: CC(=O)Nc1ccc(NC(=O)Nc2ccc(-c3nc(N4CCOCC4)c4ccc(-c5ccncc5)cc4n3)cc2)cc1] | N-(4-(3-(4-(4-morpholino-7-(pyridin-4-yl)quinazolin-2-yl)phenyl)ureido)phenyl)acetamide | 10 |
| 326 | 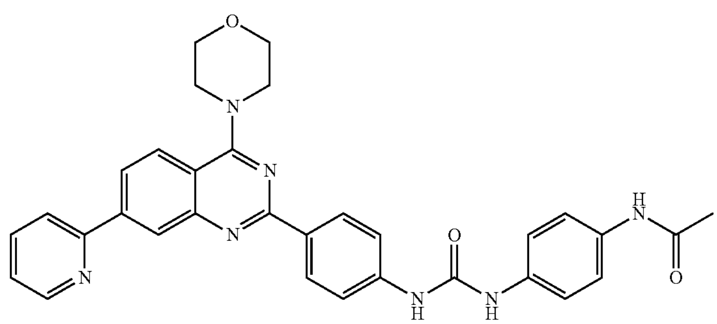 [SMILES: CC(=O)Nc1ccc(NC(=O)Nc2ccc(-c3nc(N4CCOCC4)c4ccc(-c5ccccn5)cc4n3)cc2)cc1] | N-(4-(3-(4-(4-morpholino-7-(pyridin-2-yl)quinazolin-2-yl)phenyl)ureido)phenyl)acetamide | 6B + 10 |
| 327 | 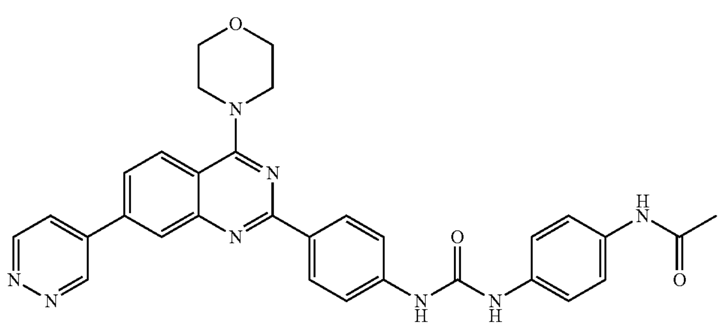 [SMILES: CC(=O)Nc1ccc(NC(=O)Nc2ccc(-c3nc(N4CCOCC4)c4ccc(-c5ccnnc5)cc4n3)cc2)cc1] | N-(4-(3-(4-(4-morpholino-7-(pyridazin-4-yl)quinazolin-2-yl)phenyl)ureido)phenyl)acetamide | 6B + 10 |
| 328 | 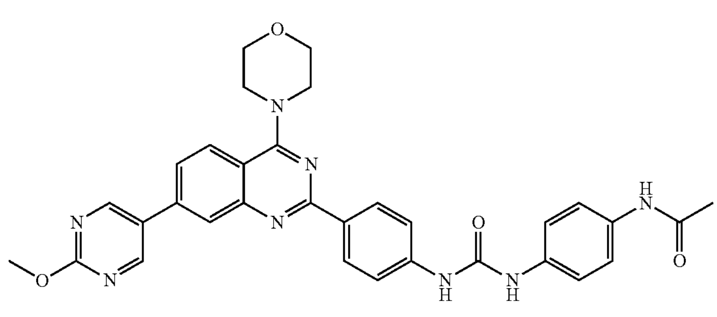 [SMILES: COc1ncc(-c2ccc3c(N4CCOCC4)nc(-c4ccc(NC(=O)Nc5ccc(NC(C)=O)cc5)cc4)nc3c2)cn1] | N-(4-(3-(4-(7-(2-methoxypyrimidin-5-yl)-4-morpholinoquinazolin-2-yl)phenyl)ureido)phenyl)acetamide | 10 |

TABLE 1-continued

| Ex | Structure | Structure Name | Synthetic Scheme |
|---|---|---|---|
| 329 | 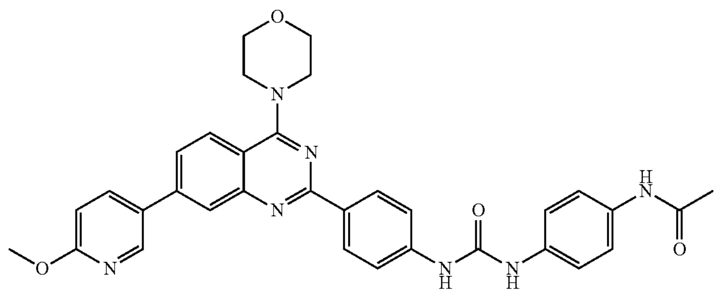 [SMILES: COc1ccc(-c2ccc3c(N4CCOCC4)nc(-c4ccc(NC(=O)Nc5ccc(NC(C)=O)cc5)cc4)nc3c2)cn1] | N-(4-(3-(4-(7-(6-methoxypyridin-3-yl)-4-morpholinoquinazolin-2-yl)phenyl)ureido)phenyl)acetamide | 10 |
| 330 | 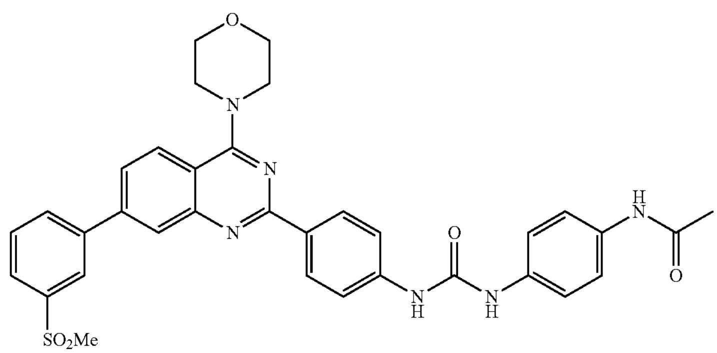 | N-(4-(3-(4-(7-(3-(methylsulfonyl)phenyl)-4-morpholinoquinazolin-2-yl)phenyl)ureido)phenyl)acetamide | 10 |
| 331 | 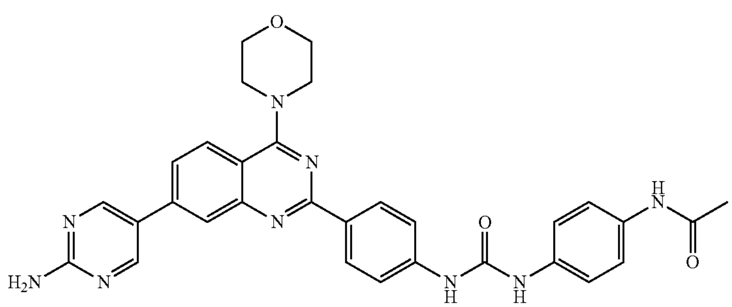 [SMILES: CC(=O)Nc1ccc(NC(=O)Nc2ccc(-c3nc(N4CCOCC4)c4ccc(-c5cnc(N)nc5)cc4n3)cc2)cc1] | N-(4-(3-(4-(7-(2-aminopyrimidin-5-yl)-4-morpholinoquinazolin-2-yl)phenyl)ureido)phenyl)acetamide | 10 |
| 332 | 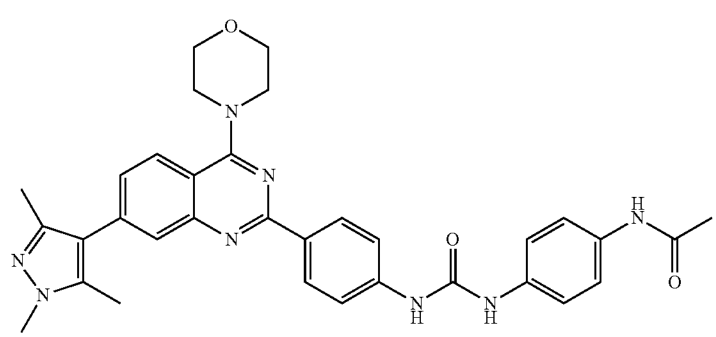 [SMILES: CC(=O)Nc1ccc(NC(=O)Nc2ccc(-c3nc(N4CCOCC4)c4ccc(-c5c(C)nn(C)c5C)cc4n3)cc2)cc1] | N-(4-(3-(4-(4-morpholino-7-(1,3,5-trimethyl-1H-pyrazol-4-yl)quinazolin-2-yl)phenyl)ureido)phenyl)acetamide | 10 |

TABLE 1-continued

| Ex | Structure | Structure Name | Synthetic Scheme |
|---|---|---|---|
| 333 | 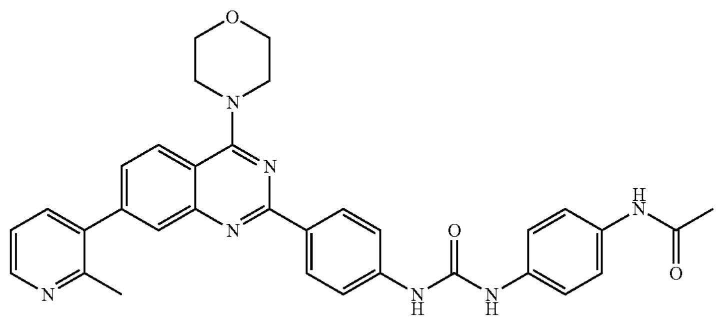 [SMILES: CC(=O)Nc1ccc(NC(=O)Nc2ccc(-c3nc(N4CCOCC4)c4ccc(-c5cccnc5C)cc4n3)cc2)cc1] | N-(4-(3-(4-(7-(2-methylpyridin-3-yl)-4-morpholinoquinazolin-2-yl)phenyl)ureido)phenyl)acetamide | 10 |
| 334 | 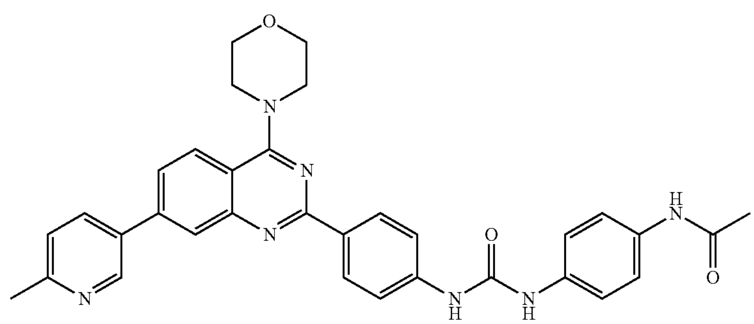 [SMILES: CC(=O)Nc1ccc(NC(=O)Nc2ccc(-c3nc(N4CCOCC4)c4ccc(-c5ccc(C)nc5)cc4n3)cc2)cc1] | N-(4-(3-(4-(7-(6-methylpyridin-3-yl)-4-morpholinoquinazolin-2-yl)phenyl)ureido)phenyl)acetamide | 10 |
| 335 | 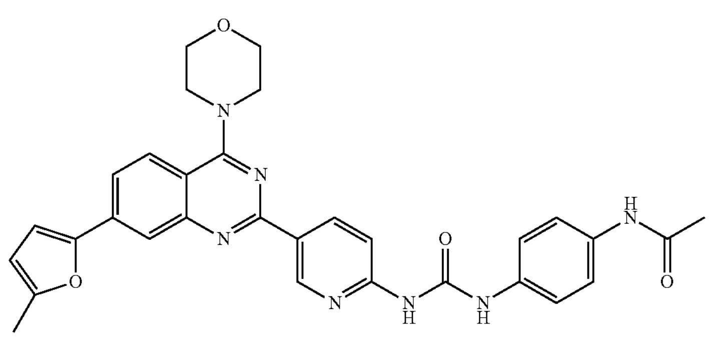 | N-(4-(3-(5-(7-(5-methylfuran-2-yl)-4-morpholinoquinazolin-2-yl)pyridin-2-yl)ureido)phenyl)acetamide | 6E + 9 |
| 336 | 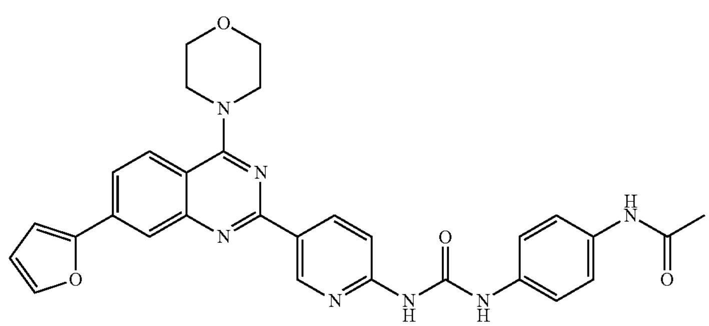 [SMILES: CC(=O)Nc1ccc(NC(=O)Nc2ccc(-c3nc(N4CCOCC4)c4ccc(-c5ccco5)cc4n3)cn2)cc1] | N-(4-(3-(5-(7-(furan-2-yl)-4-morpholinoquinazolin-2-yl)pyridin-2-yl)ureido)phenyl)acetamide | 6E + 9 |

TABLE 1-continued

| Ex | Structure | Structure Name | Synthetic Scheme |
|---|---|---|---|
| 337 | 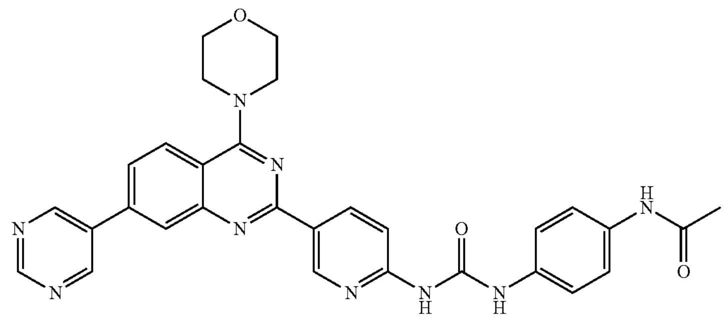 [SMILES: CC(=O)Nc1ccc(NC(=O)Nc2ccc(-c3nc(N4CCOCC4)c4ccc(-c5cncnc5)cc4n3)cn2)cc1] | N-(4-(3-(5-(4-morpholino-7-(pyrimidin-5-yl)quinazolin-2-yl)pyridin-2-yl)ureido)phenyl)acetamide | 6E + 9 |
| 338 | 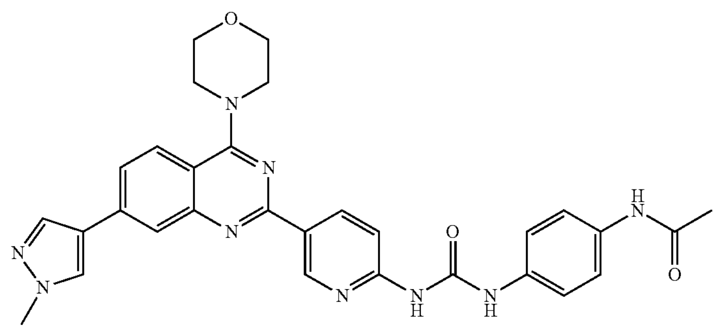 [SMILES: CC(=O)Nc1ccc(NC(=O)Nc2ccc(-c3nc(N4CCOCC4)c4ccc(-c5cnn(C)c5)cc4n3)cn2)cc1] | N-(4-(3-(5-(7-(1-methyl-1H-pyrazol-4-yl)-4-morpholinoquinazolin-2-yl)pyridin-2-yl)ureido)phenyl)acetamide | 6E + 9 |
| 339 | 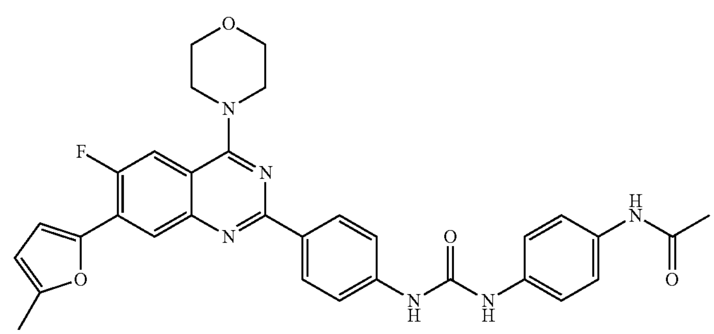 | N-(4-(3-(4-(6-fluoro-7-(5-methylfuran-2-yl)-4-morpholinoquinazolin-2-yl)phenyl)ureido)phenyl)acetamide | 10 |
| 340 | 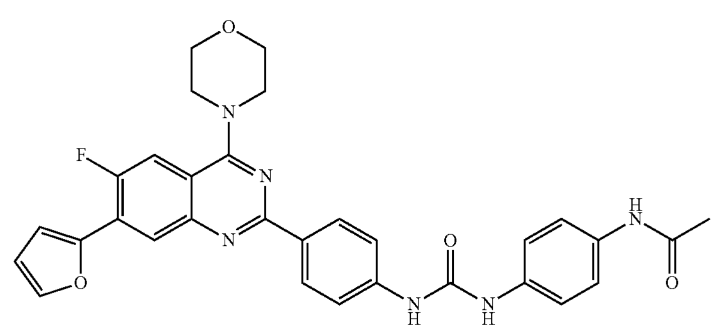 [SMILES: CC(=O)Nc1ccc(NC(=O)Nc2ccc(-c3nc(N4CCOCC4)c4cc(F)c(-c5ccco5)cc4n3)cc2)cc1] | N-(4-(3-(4-(6-fluoro-7-(furan-2-yl)-4-morpholinoquinazolin-2-yl)phenyl)ureido)phenyl)acetamide | 10 |

TABLE 1-continued

| Ex | Structure | Structure Name | Synthetic Scheme |
|---|---|---|---|
| 341 | 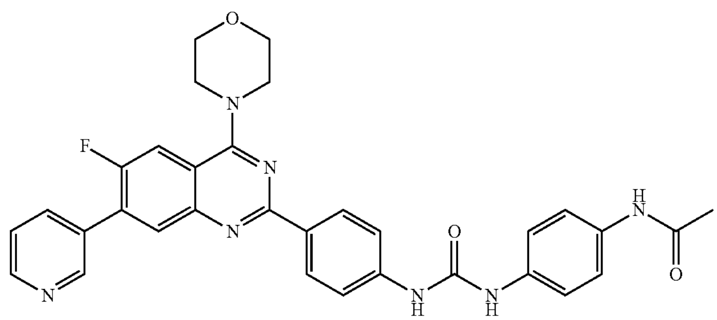 [SMILES: CC(=O)Nc1ccc(NC(=O)Nc2ccc(-c3nc(N4CCOCC4)c4cc(F)c(-c5cccnc5)cc4n3)cc2)cc1] | N-(4-(3-(4-(6-fluoro-4-morpholino-7-(pyridin-3-yl)quinazolin-2-yl)phenyl)ureido)phenyl)acetamide | 10 |
| 342 | 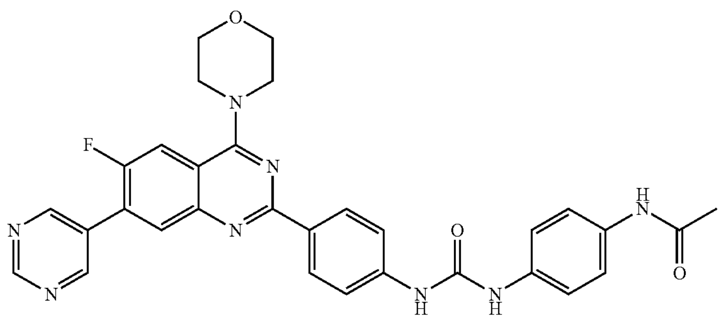 [SMILES: CC(=O)Nc1ccc(NC(=O)Nc2ccc(-c3nc(N4CCOCC4)c4cc(F)c(-c5cncnc5)cc4n3)cc2)cc1] | N-(4-(3-(4-(6-fluoro-4-morpholino-7-(pyrimidin-5-yl)quinazolin-2-yl)phenyl)ureido)phenyl)acetamide | 10 |
| 343 | 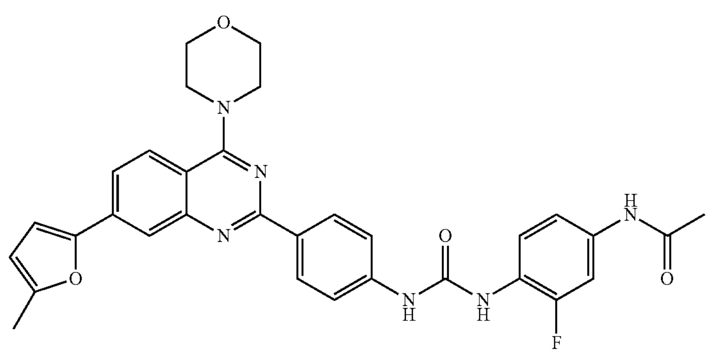 [SMILES: CC(=O)Nc1ccc(NC(=O)Nc2ccc(-c3nc(N4CCOCC4)c4ccc(-c5ccc(C)o5)cc4n3)cc2)c(F)c1] | N-(3-fluoro-4-(3-(4-(7-(5-methylfuran-2-yl)-4-morpholinoquinazolin-2-yl)phenyl)ureido)phenyl)acetamide | 10 |
| 344 | 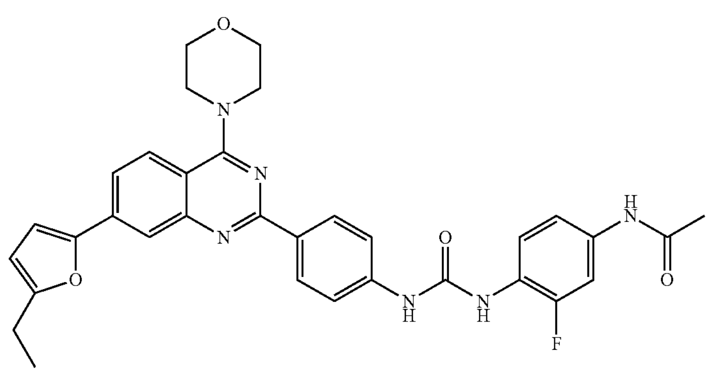 [SMILES: CCc1ccc(-c2ccc3c(N4CCOCC4)nc(-c4ccc(NC(=O)Nc5ccc(NC(C)=O)cc5F)cc4)nc3c2)o1] | N-(4-(3-(4-(7-(5-ethylfuran-2-yl)-4-morpholinoquinazolin-2-yl)phenyl)ureido)-3-fluorophenyl)acetamide | 10 + 11 |

TABLE 1-continued

| Ex | Structure | Structure Name | Synthetic Scheme |
|---|---|---|---|
| 345 | 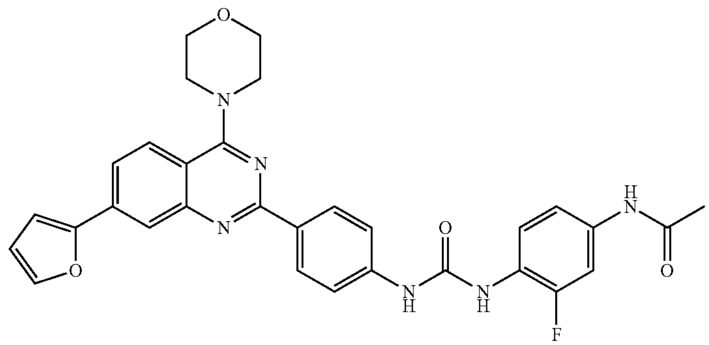 [SMILES: CC(=O)Nc1ccc(NC(=O)Nc2ccc(-c3nc(N4CCOCC4)c4ccc(-c5ccco5)cc4n3)cc2)c(F)c1] | N-(3-fluoro-4-(3-(4-(7-(furan-2-yl)-4-morpholinoquinazolin-2-yl)phenyl)ureido)phenyl)acetamide | 10 |
| 346 | 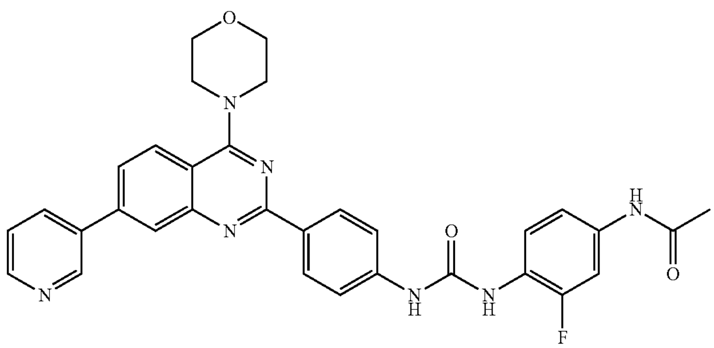 [SMILES: CC(=O)Nc1ccc(NC(=O)Nc2ccc(-c3nc(N4CCOCC4)c4ccc(-c5cccnc5)cc4n3)cc2)c(F)c1] | N-(3-fluoro-4-(3-(4-(4-morpholino-7-(pyridin-3-yl)quinazolin-2-yl)phenyl)ureido)phenyl)acetamide | 10 |
| 347 | 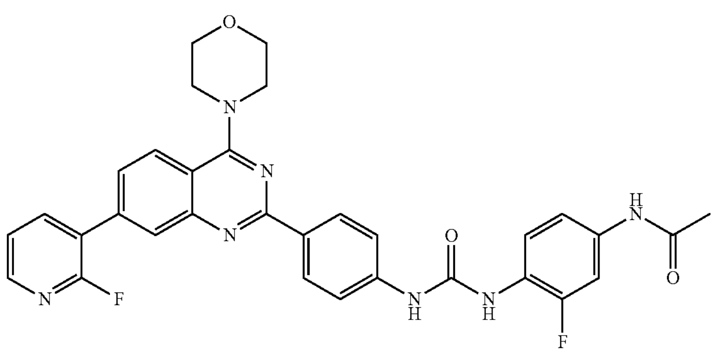 | N-(3-fluoro-4-(3-(4-(7-(2-fluoropyridin-3-yl)-4-morpholinoquinazolin-2-yl)phenyl)ureido)phenyl)acetamide | 10 |
| 348 | 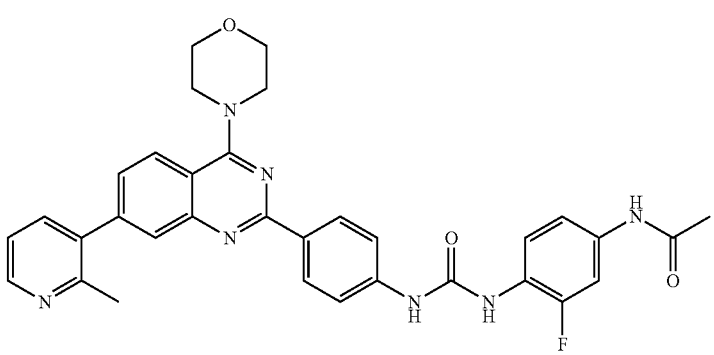 [SMILES: CC(=O)Nc1ccc(NC(=O)Nc2ccc(-c3nc(N4CCOCC4)c4ccc(-c5cccnc5C)cc4n3)cc2)c(F)c1] | N-(3-fluoro-4-(3-(4-(7-(2-methylpyridin-3-yl)-4-morpholinoquinazolin-2-yl)phenyl)ureido)phenyl)acetamide | 10 |

TABLE 1-continued

| Ex | Structure | Structure Name | Synthetic Scheme |
|---|---|---|---|
| 349 | 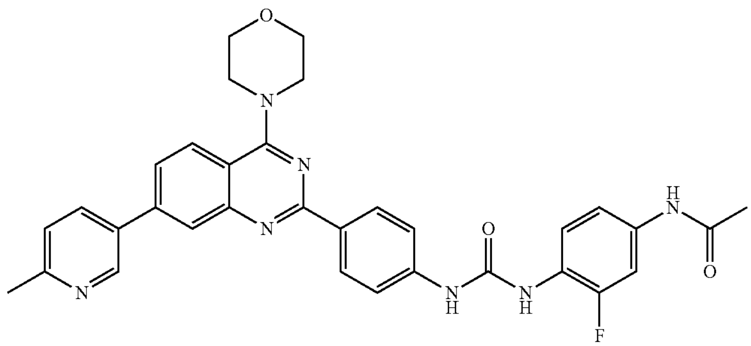 [SMILES: CC(=O)Nc1ccc(NC(=O)Nc2ccc(-c3nc(N4CCOCC4)c4ccc(-c5ccc(C)nc5)cc4n3)cc2)c(F)c1] | N-(3-fluoro-4-(3-(4-(7-(6-methylpyridin-3-yl)-4-morpholinoquinazolin-2-yl)phenyl)ureido)phenyl)acetamide | 10 |
| 350 | 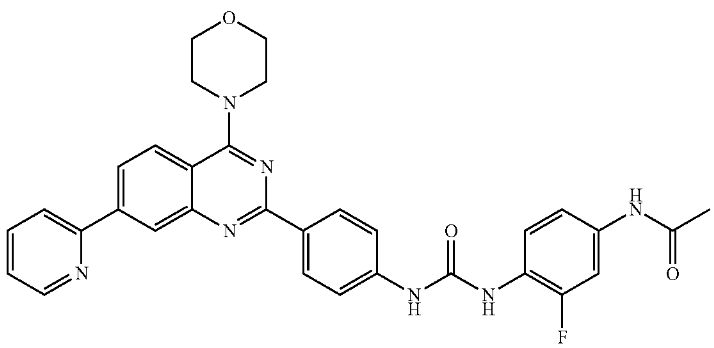 [SMILES: CC(=O)Nc1ccc(NC(=O)Nc2ccc(-c3nc(N4CCOCC4)c4ccc(-c5ccccn5)cc4n3)cc2)c(F)c1] | N-(3-fluoro-4-(3-(4-(4-morpholino-7-(pyridin-2-yl)quinazolin-2-yl)phenyl)ureido)phenyl)acetamide | 6A + 10 |
| 351 | 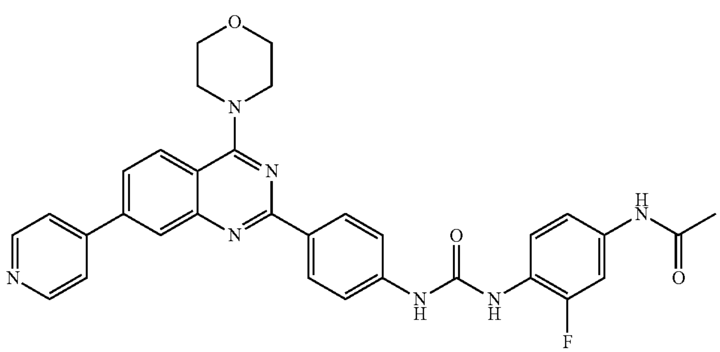 [SMILES: CC(=O)Nc1ccc(NC(=O)Nc2ccc(-c3nc(N4CCOCC4)c4ccc(-c5ccncc5)cc4n3)cc2)c(F)c1] | N-(3-fluoro-4-(3-(4-(4-morpholino-7-(pyridin-4-yl)quinazolin-2-yl)phenyl)ureido)phenyl)acetamide | 10 |
| 352 | 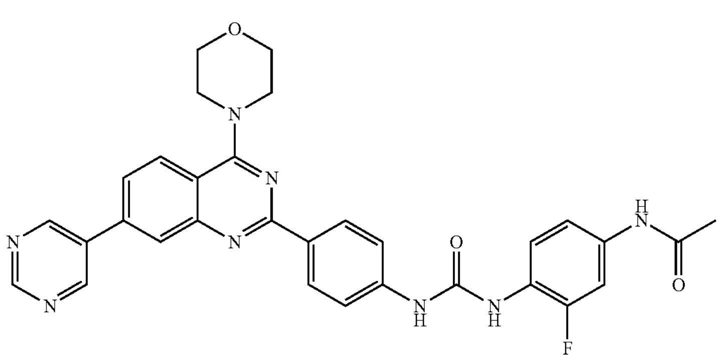 [SMILES: CC(=O)Nc1ccc(NC(=O)Nc2ccc(-c3nc(N4CCOCC4)c4ccc(-c5cncnc5)cc4n3)cc2)c(F)c1] | N-(3-fluoro-4-(3-(4-(4-morpholino-7-(pyrimidin-5-yl)quinazolin-2-yl)phenyl)ureido)phenyl)acetamide | 10 |

TABLE 1-continued

| Ex | Structure | Structure Name | Synthetic Scheme |
|---|---|---|---|
| 353 | 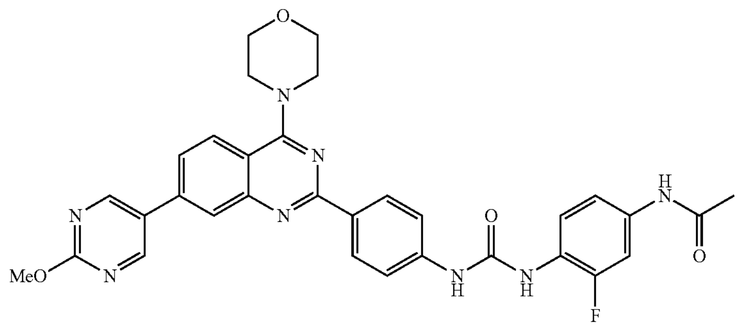 [SMILES: COc1ncc(-c2ccc3c(N4CCOCC4)nc(-c4ccc(NC(=O)Nc5ccc(NC(C)=O)cc5F)cc4)nc3c2)cn1] | N-(3-fluoro-4-(3-(4-(7-(2-methoxypyrimidin-5-yl)-4-morpholinoquinazolin-2-yl)phenyl)ureido)phenyl)acetamide | 10 |
| 354 | 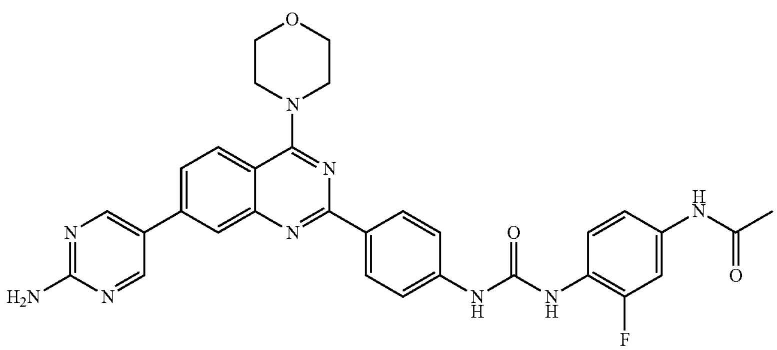 [SMILES: CC(=O)Nc1ccc(NC(=O)Nc2ccc(-c3nc(N4CCOCC4)c4ccc(-c5cnc(N)nc5)cc4n3)cc2)c(F)c1] | N-(4-(3-(4-(7-(2-aminopyrimidin-5-yl)-4-morpholinoquinazolin-2-yl)phenyl)ureido)-3-fluorophenyl)acetamide | 10 |
| 355 | 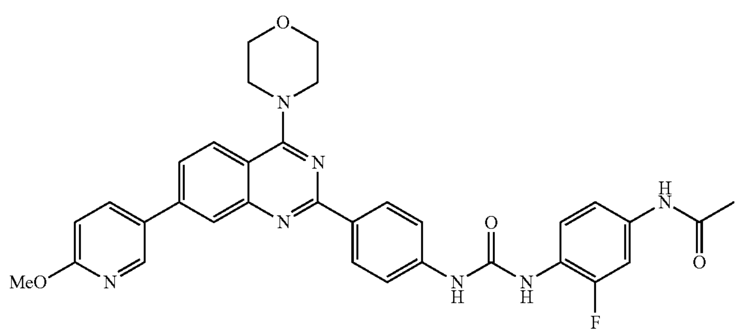 [SMILES: COc1ccc(-c2ccc3c(N4CCOCC4)nc(-c4ccc(NC(=O)Nc5ccc(NC(C)=O)cc5F)cc4)nc3c2)cn1] | N-(3-fluoro-4-(3-(4-(7-(6-methoxypyridin-3-yl)-4-morpholinoquinazolin-2-yl)phenyl)ureido)phenyl)acetamide | 10 |
| 356 | 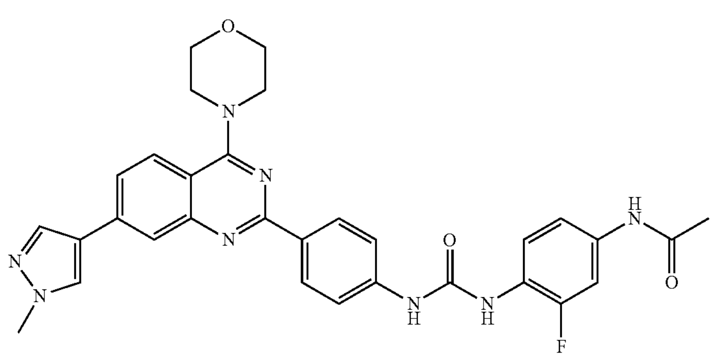 [SMILES: CC(=O)Nc1ccc(NC(=O)Nc2ccc(-c3nc(N4CCOCC4)c4ccc(-c5cnn(C)c5)cc4n3)cc2)c(F)c1] | N-(3-fluoro-4-(3-(4-(7-(1-methyl-1H-pyrazol-4-yl)-4-morpholinoquinazolin-2-yl)phenyl)ureido)phenyl)acetamide | 10 |

TABLE 1-continued

| Ex | Structure | Structure Name | Synthetic Scheme |
|---|---|---|---|
| 357 | 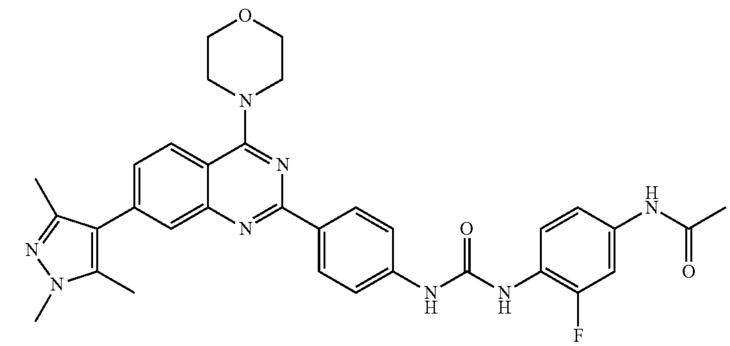 [SMILES: CC(=O)Nc1ccc(NC(=O)Nc2ccc(-c3nc(N4CCOCC4)c4ccc(-c5c(C)nn(C)c5C)cc4n3)cc2)c(F)c1] | N-(3-fluoro-4-(3-(4-(4-morpholino-7-(1,3,5-trimethyl-1H-pyrazol-4-yl)quinazolin-2-yl)phenyl)ureido)phenyl)acetamide | 10 |
| 358 | 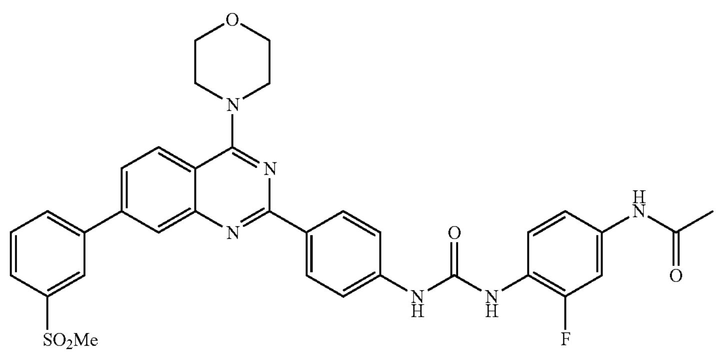 [SMILES: CC(=O)Nc1ccc(NC(=O)Nc2ccc(-c3nc(N4CCOCC4)c4ccc(-c5cccc(S(C)(=O)=O)c5)cc4n3)cc2)c(F)c1] | N-(3-fluoro-4-(3-(4-(7-(3-(methylsulfonyl)phenyl)-4-morpholinoquinazolin-2-yl)phenyl)ureido)phenyl)acetamide | 10 |
| 359 | 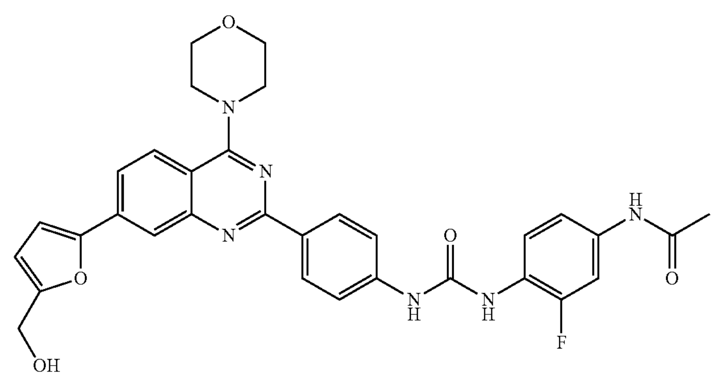 [SMILES: CC(=O)Nc1ccc(NC(=O)Nc2ccc(-c3nc(N4CCOCC4)c4ccc(-c5ccc(CO)o5)cc4n3)cc2)c(F)c1] | N-(3-fluoro-4-(3-(4-(7-(5-(hydroxymethyl)furan-2-yl)-4-morpholinoquinazolin-2-yl)phenyl)ureido)phenyl)acetamide | 10 + 11 |
| 360 | 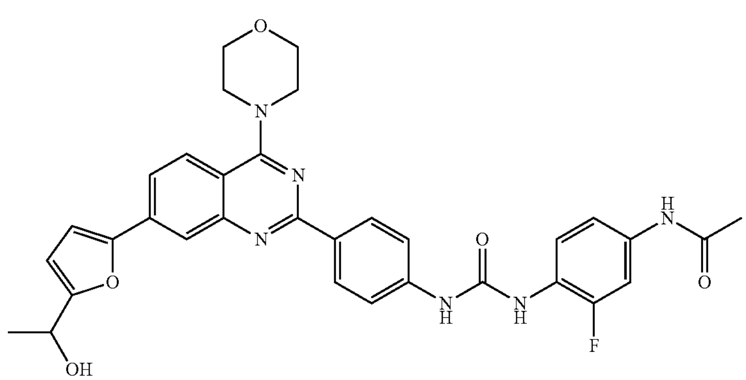 [SMILES: CC(=O)Nc1ccc(NC(=O)Nc2ccc(-c3nc(N4CCOCC4)c4ccc(-c5ccc(C(C)O)o5)cc4n3)cc2)c(F)c1] | N-(3-fluoro-4-(3-(4-(7-(5-(1-hydroxyethyl)furan-2-yl)-4-morpholinoquinazolin-2-yl)phenyl)ureido)phenyl)acetamide | 10 + 11 |

TABLE 1-continued

| Ex | Structure Name | Synthetic Scheme |
|---|---|---|
| 361 | N-(3-fluoro-4-(3-(4-(7-(5-(2-hydroxypropan-2-yl)furan-2-yl)-4-morpholinoquinazolin-2-yl)phenyl)ureido)phenyl)acetamide | 10 + 11 |
| 362 | N-(2-fluoro-4-(3-(4-(7-(5-methylfuran-2-yl)-4-morpholinoquinazolin-2-yl)phenyl)ureido)phenyl)acetamide | 10 |
| 363 | N-(4-(3-(4-(7-(5-ethylfuran-2-yl)-4-morpholinoquinazolin-2-yl)phenyl)ureido)-2-fluorophenyl)acetamide | 10 + 11 |
| 364 | N-(2-fluoro-4-(3-(4-(7-(furan-2-yl)-4-morpholinoquinazolin-2-yl)phenyl)ureido)phenyl)acetamide | 10 |

TABLE 1-continued

| Ex | Structure | Structure Name | Synthetic Scheme |
|---|---|---|---|
| 365 | 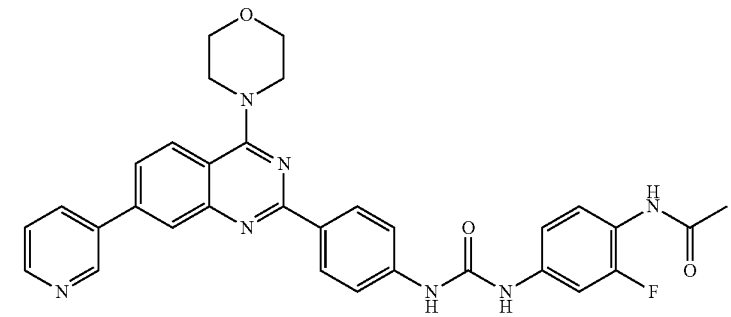 [SMILES: CC(=O)Nc1ccc(NC(=O)Nc2ccc(-c3nc(N4CCOCC4)c4ccc(-c5cccnc5)cc4n3)cc2)cc1F] | N-(2-fluoro-4-(3-(4-(4-morpholino-7-(pyridin-3-yl)quinazolin-2-yl)phenyl)ureido)phenyl)acetamide | 10 |
| 366 | 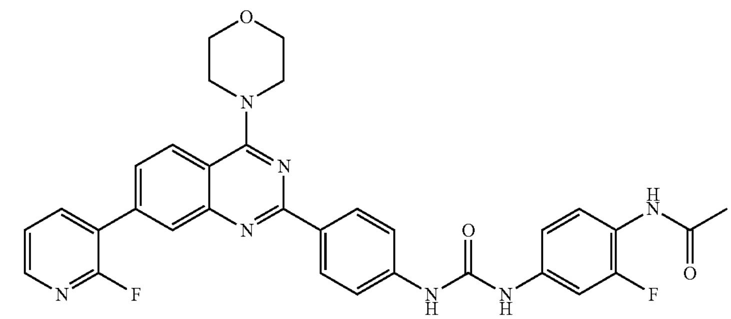 [SMILES: CC(=O)Nc1ccc(NC(=O)Nc2ccc(-c3nc(N4CCOCC4)c4ccc(-c5cccnc5F)cc4n3)cc2)cc1F] | N-(2-fluoro-4-(3-(4-(7-(2-fluoropyridin-3-yl)-4-morpholinoquinazolin-2-yl)phenyl)ureido)phenyl)acetamide | 10 |
| 367 | 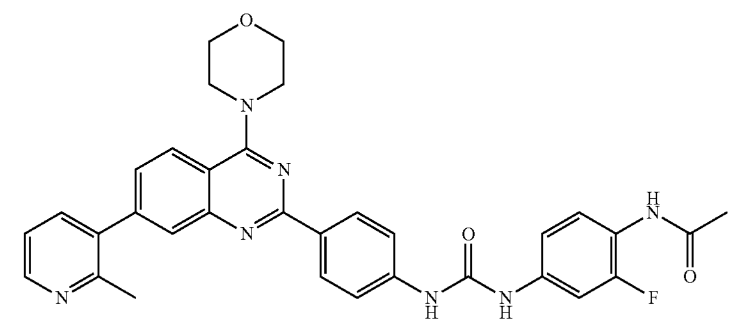 [SMILES: CC(=O)Nc1ccc(NC(=O)Nc2ccc(-c3nc(N4CCOCC4)c4ccc(-c5cccnc5C)cc4n3)cc2)cc1F] | N-(2-fluoro-4-(3-(4-(7-(2-methylpyridin-3-yl)-4-morpholinoquinazolin-2-yl)phenyl)ureido)phenyl)acetamide | 10 |
| 368 | 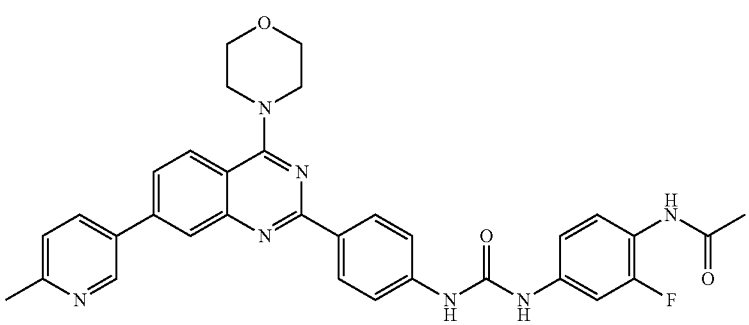 [SMILES: CC(=O)Nc1ccc(NC(=O)Nc2ccc(-c3nc(N4CCOCC4)c4ccc(-c5ccc(C)nc5)cc4n3)cc2)cc1F] | N-(2-fluoro-4-(3-(4-(7-(6-methylpyridin-3-yl)-4-morpholinoquinazolin-2-yl)phenyl)ureido)phenyl)acetamide | 10 |
| 369 | 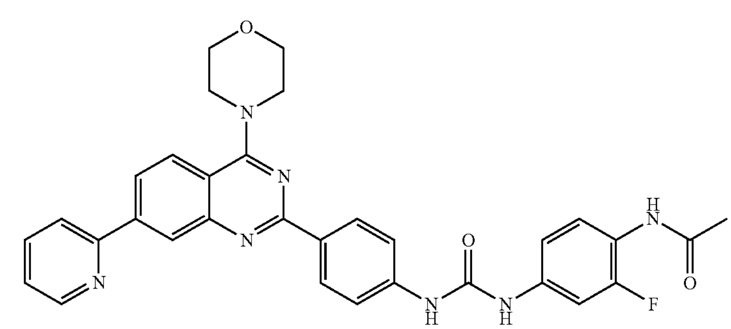 [SMILES: CC(=O)Nc1ccc(NC(=O)Nc2ccc(-c3nc(N4CCOCC4)c4ccc(-c5ccccn5)cc4n3)cc2)cc1F] | N-(2-fluoro-4-(3-(4-(4-morpholino-7-(pyridin-2-yl)quinazolin-2-yl)phenyl)ureido)phenyl)acetamide | 10 + 6A |

TABLE 1-continued

| Ex | Structure Name | Synthetic Scheme |
|---|---|---|
| 370 | N-(2-fluoro-4-(3-(4-(4-morpholino-7-(pyridin-4-yl)quinazolin-2-yl)phenyl)ureido)phenyl)acetamide | 10 |
| 371 | N-(2-fluoro-4-(3-(4-(4-morpholino-7-(pyrimidin-5-yl)quinazolin-2-yl)phenyl)ureido)phenyl)acetamide | 10 |
| 372 | N-(2-fluoro-4-(3-(4-(7-(2-methoxypyrimidin-5-yl)-4-morpholinoquinazolin-2-yl)phenyl)ureido)phenyl)acetamide | 10 |
| 373 | N-(4-(3-(4-(7-(2-aminopyrimidin-5-yl)-4-morpholinoquinazolin-2-yl)phenyl)ureido)-2-fluorophenyl)acetamide | 10 |
| 374 | N-(2-fluoro-4-(3-(4-(7-(6-methoxypyridin-3-yl)-4-morpholinoquinazolin-2-yl)phenyl)ureido)phenyl)acetamide | 10 |

TABLE 1-continued

| Ex | Structure Name | Synthetic Scheme |
|---|---|---|
| 375 | N-(2-fluoro-4-(3-(4-(7-(1-methyl-1H-pyrazol-4-yl)-4-morpholinoquinazolin-2-yl)phenyl)ureido)phenyl)acetamide | 10 |
| 376 | N-(2-fluoro-4-(3-(4-(4-morpholino-7-(1,3,5-trimethyl-1H-pyrazol-4-yl)quinazolin-2-yl)phenyl)ureido)phenyl)acetamide | 10 |
| 377 | N-(2-fluoro-4-(3-(4-(7-(3-(methylsulfonyl)phenyl)-4-morpholinoquinazolin-2-yl)phenyl)ureido)phenyl)acetamide | 10 |
| 378 | N-(2-fluoro-4-(3-(4-(7-(5-(hydroxymethyl)furan-2-yl)-4-morpholinoquinazolin-2-yl)phenyl)ureido)phenyl)acetamide | 10 + 11 |

TABLE 1-continued

| Ex | Structure Name | Synthetic Scheme |
|---|---|---|
| 379 | N-(2-fluoro-4-(3-(4-(7-(5-(1-hydroxyethyl)furan-2-yl)-4-morpholinoquinazolin-2-yl)phenyl)ureido)phenyl)acetamide | 10 + 11 |
| 380 | N-(2-fluoro-4-(3-(4-(7-(5-(2-hydroxypropan-2-yl)furan-2-yl)-4-morpholinoquinazolin-2-yl)phenyl)ureido)phenyl)acetamide | 10 + 11 |
| 381 | N-methyl-N-(4-(3-(4-(7-(5-methylfuran-2-yl)-4-morpholinoquinazolin-2-yl)phenyl)ureido)phenyl)acetamide | 10 |
| 382 | N-(4-(3-(4-(7-(5-ethylfuran-2-yl)-4-morpholinoquinazolin-2-yl)phenyl)ureido)phenyl)-N-methylacetamide | 10 + 11 |

TABLE 1-continued

| Ex | Structure | Structure Name | Synthetic Scheme |
|---|---|---|---|
| 383 | 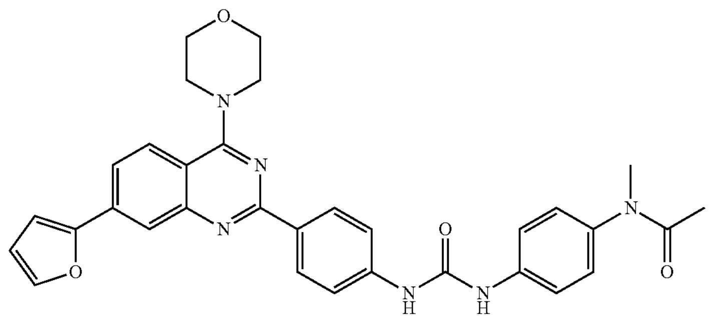 [SMILES: CC(=O)N(C)c1ccc(NC(=O)Nc2ccc(-c3nc(N4CCOCC4)c4ccc(-c5ccco5)cc4n3)cc2)cc1] | N-(4-(3-(4-(7-(furan-2-yl)-4-morpholinoquinazolin-2-yl)phenyl)ureido)phenyl)-N-methylacetamide | 10 |
| 384 | 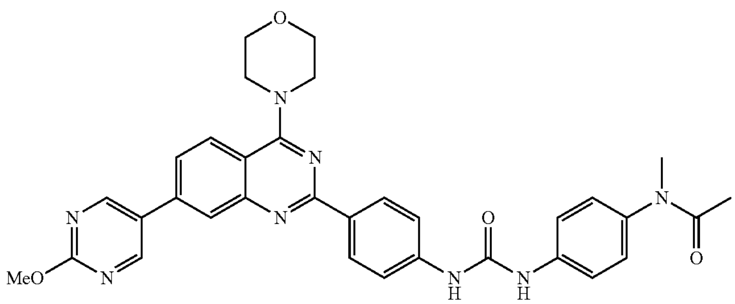 [SMILES: COc1ncc(-c2ccc3c(N4CCOCC4)nc(-c4ccc(NC(=O)Nc5ccc(N(C)C(C)=O)cc5)cc4)nc3c2)cn1] | N-(4-(3-(4-(7-(2-methoxypyrimidin-5-yl)-4-morpholinoquinazolin-2-yl)phenyl)ureido)phenyl)-N-methylacetamide | 10 |
| 385 | 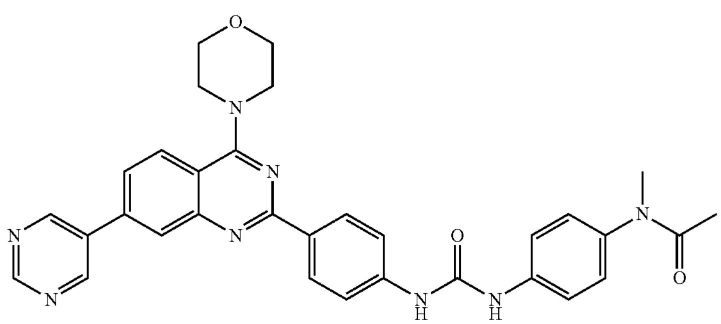 [SMILES: CC(=O)N(C)c1ccc(NC(=O)Nc2ccc(-c3nc(N4CCOCC4)c4ccc(-c5cncnc5)cc4n3)cc2)cc1] | N-methyl-N-(4-(3-(4-(4-morpholino-7-(pyrimidin-5-yl)quinazolin-2-yl)phenyl)ureido)phenyl)acetamide | 10 |
| 386 | 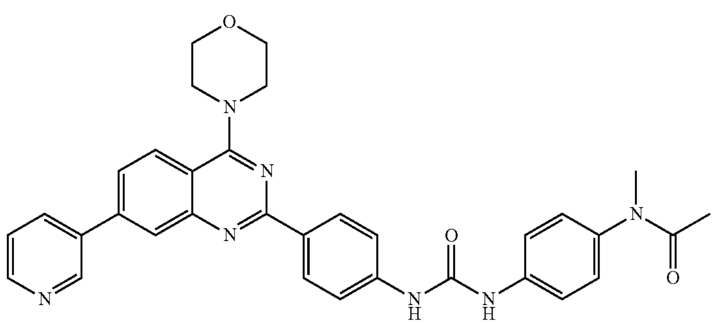 [SMILES: CC(=O)N(C)c1ccc(NC(=O)Nc2ccc(-c3nc(N4CCOCC4)c4ccc(-c5cccnc5)cc4n3)cc2)cc1] | N-methyl-N-(4-(3-(4-(4-morpholino-7-(pyridin-3-yl)quinazolin-2-yl)phenyl)ureido)phenyl)acetamide | 10 |
| 387 | 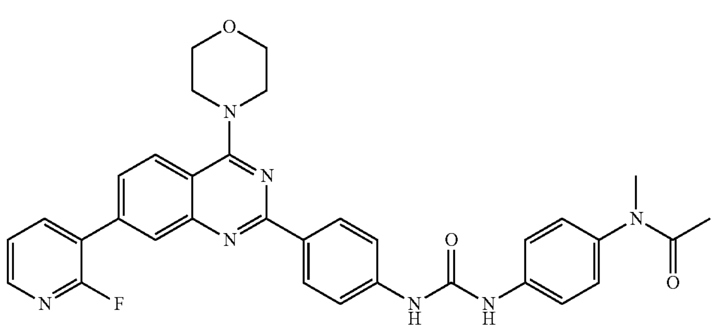 [SMILES: CC(=O)N(C)c1ccc(NC(=O)Nc2ccc(-c3nc(N4CCOCC4)c4ccc(-c5cccnc5F)cc4n3)cc2)cc1] | N-(4-(3-(4-(7-(2-fluoropyridin-3-yl)-4-morpholinoquinazolin-2-yl)phenyl)ureido)phenyl)-N-methylacetamide | 10 |

TABLE 1-continued

| Ex | Structure | Structure Name | Synthetic Scheme |
|---|---|---|---|
| 388 | 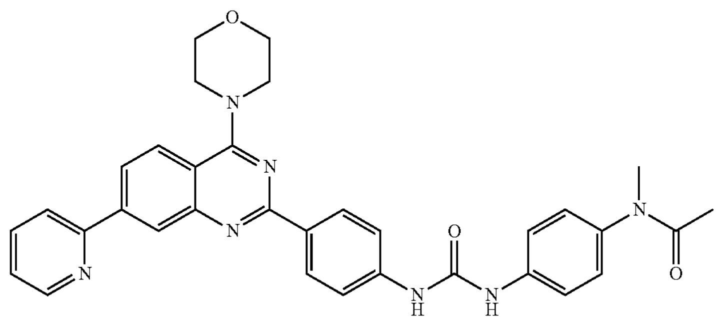 [SMILES: CC(=O)N(C)c1ccc(NC(=O)Nc2ccc(-c3nc(N4CCOCC4)c4ccc(-c5ccccn5)cc4n3)cc2)cc1] | N-methyl-N-(4-(3-(4-(4-morpholino-7-(pyridin-2-yl)quinazolin-2-yl)phenyl)ureido)phenyl)acetamide | 6A + 10 |
| 389 | 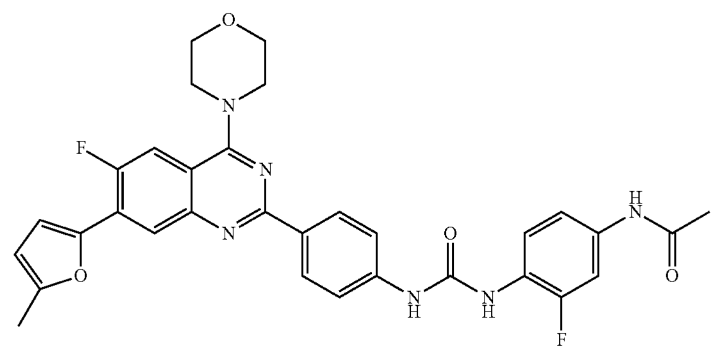 | N-(3-fluoro-4-(3-(4-(6-fluoro-7-(5-methylfuran-2-yl)-4-morpholinoquinazolin-2-yl)phenyl)ureido)phenyl)acetamide | 10 |
| 390 | 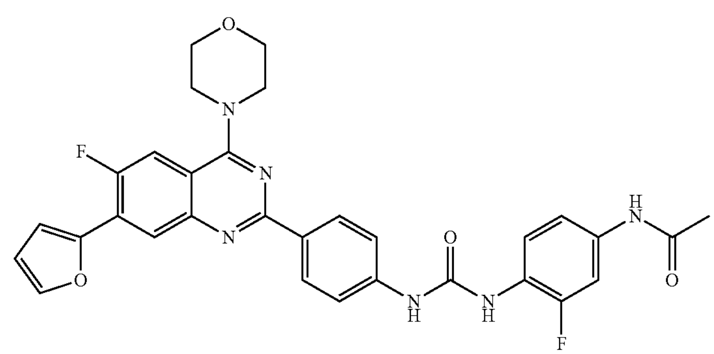 [SMILES: CC(=O)Nc1ccc(NC(=O)Nc2ccc(-c3nc(N4CCOCC4)c4cc(F)c(-c5ccco5)cc4n3)cc2)c(F)c1] | N-(3-fluoro-4-(3-(4-(6-fluoro-7-(furan-2-yl)-4-morpholinoquinazolin-2-yl)phenyl)ureido)phenyl)acetamide | 10 |
| 391 | 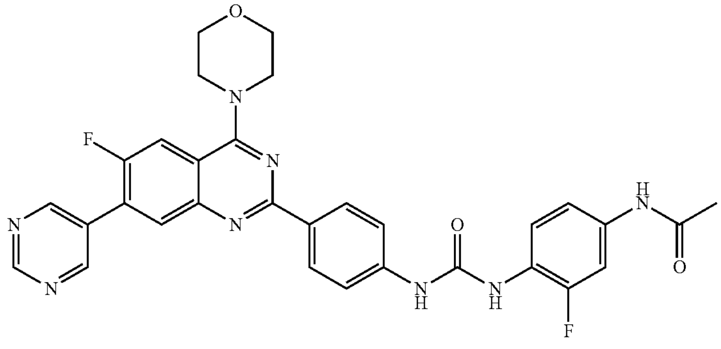 [SMILES: CC(=O)Nc1ccc(NC(=O)Nc2ccc(-c3nc(N4CCOCC4)c4cc(F)c(-c5cncnc5)cc4n3)cc2)c(F)c1] | N-(3-fluoro-4-(3-(4-(6-fluoro-4-morpholino-7-(pyrimidin-5-yl)quinazolin-2-yl)phenyl)ureido)phenyl)acetamide | 10 |

TABLE 1-continued

| Ex | Structure | Structure Name | Synthetic Scheme |
|---|---|---|---|
| 392 | 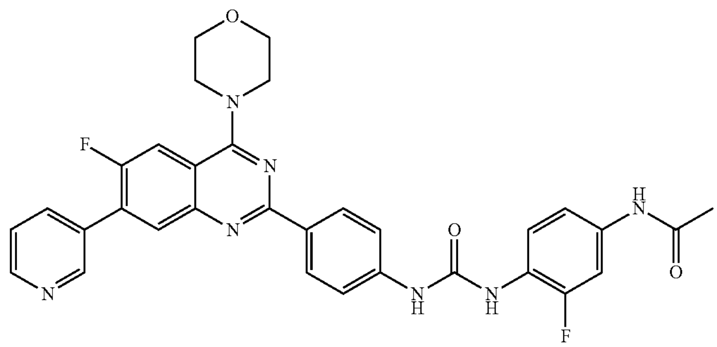 [SMILES: CC(=O)Nc1ccc(NC(=O)Nc2ccc(-c3nc(N4CCOCC4)c4cc(F)c(-c5cccnc5)cc4n3)cc2)c(F)c1] | N-(3-fluoro-4-(3-(4-(6-fluoro-4-morpholino-7-(pyridin-3-yl)quinazolin-2-yl)phenyl)ureido)phenyl)acetamide | 10 |
| 393 | 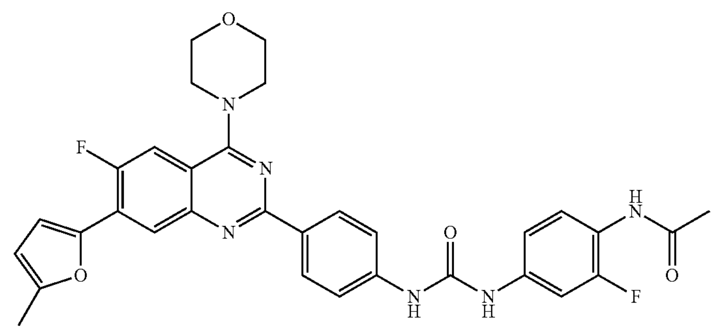 [SMILES: CC(=O)Nc1ccc(NC(=O)Nc2ccc(-c3nc(N4CCOCC4)c4cc(F)c(-c5ccc(C)o5)cc4n3)cc2)cc1F] | N-(2-fluoro-4-(3-(4-(6-fluoro-7-(5-methylfuran-2-yl)-4-morpholinoquinazolin-2-yl)phenyl)ureido)phenyl)acetamide | 10 |
| 394 | 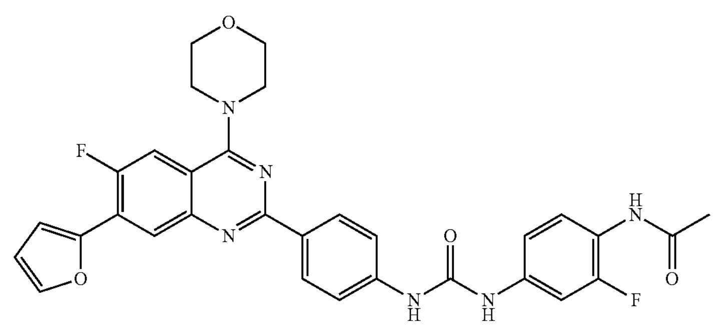 [SMILES: CC(=O)Nc1ccc(NC(=O)Nc2ccc(-c3nc(N4CCOCC4)c4cc(F)c(-c5ccco5)cc4n3)cc2)cc1F] | N-(2-fluoro-4-(3-(4-(6-fluoro-7-(furan-2-yl)-4-morpholinoquinazolin-2-yl)phenyl)ureido)phenyl)acetamide | 10 |
| 395 | 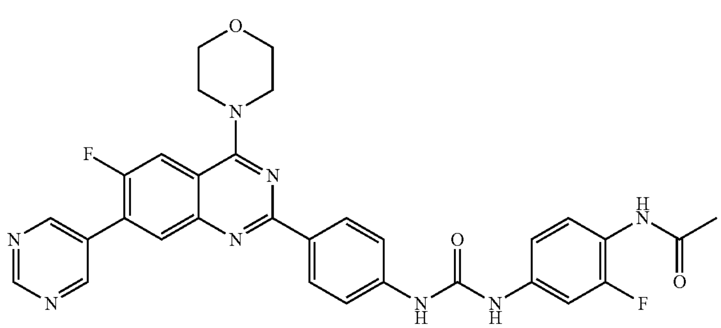 [SMILES: CC(=O)Nc1ccc(NC(=O)Nc2ccc(-c3nc(N4CCOCC4)c4cc(F)c(-c5cncnc5)cc4n3)cc2)cc1F] | N-(2-fluoro-4-(3-(4-(6-fluoro-4-morpholino-7-(pyrimidin-5-yl)quinazolin-2-yl)phenyl)ureido)phenyl)acetamide | 10 |

TABLE 1-continued

| Ex | Structure | Structure Name | Synthetic Scheme |
|---|---|---|---|
| 396 | 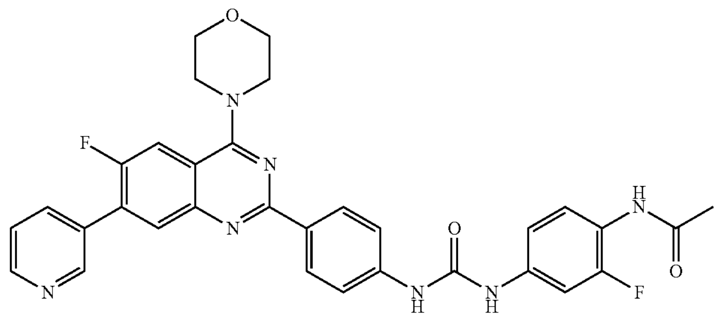 [SMILES: CC(=O)Nc1ccc(NC(=O)Nc2ccc(-c3nc(N4CCOCC4)c4cc(F)c(-c5cccnc5)cc4n3)cc2)cc1F] | N-(2-fluoro-4-(3-(4-(6-fluoro-4-morpholino-7-(pyridin-3-yl)quinazolin-2-yl)phenyl)ureido)phenyl) acetamide | 10 |
| 397 | 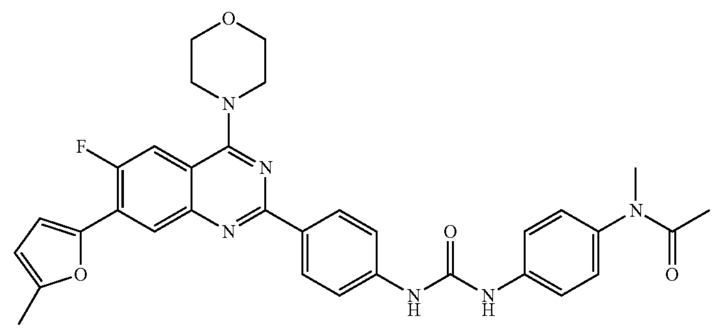 [SMILES: CC(=O)N(C)c1ccc(NC(=O)Nc2ccc(-c3nc(N4CCOCC4)c4cc(F)c(-c5ccc(C)o5)cc4n3)cc2)cc1] | N-(4-(3-(4-(6-fluoro-7-(5-methylfuran-2-yl)-4-morpholinoquinazolin-2-yl)phenyl)ureido)phenyl)-N-methylacetamide | 10 |
| 398 | 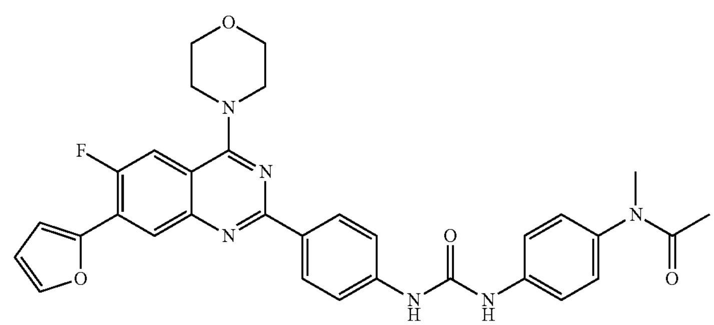 [SMILES: CC(=O)N(C)c1ccc(NC(=O)Nc2ccc(-c3nc(N4CCOCC4)c4cc(F)c(-c5ccco5)cc4n3)cc2)cc1] | N-(4-(3-(4-(6-fluoro-7-(furan-2-yl)-4-morpholinoquinazolin-2-yl)phenyl)ureido)phenyl)-N-methylacetamide | 10 |
| 399 | 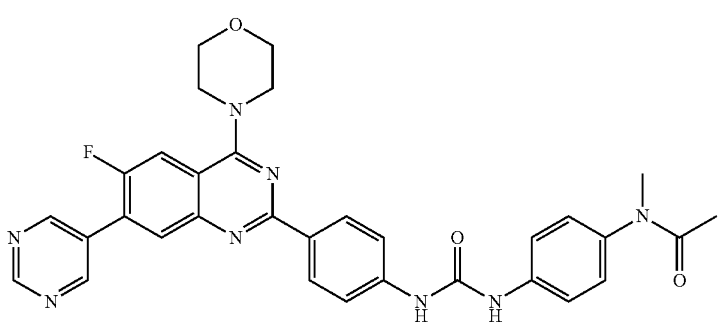 [SMILES: CC(=O)N(C)c1ccc(NC(=O)Nc2ccc(-c3nc(N4CCOCC4)c4cc(F)c(-c5cncnc5)cc4n3)cc2)cc1] | N-(4-(3-(4-(6-fluoro-4-morpholino-7-(pyrimidin-5-yl)quinazolin-2-yl)phenyl)ureido)phenyl)-N-methylacetamide | 10 |

TABLE 1-continued

| Ex | Structure | Structure Name | Synthetic Scheme |
|---|---|---|---|
| 400 | 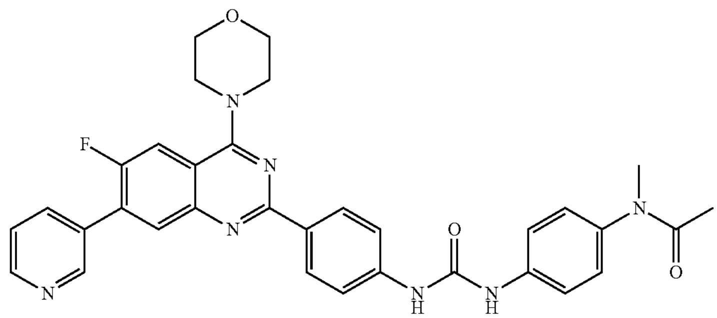 [SMILES: CC(=O)N(C)c1ccc(NC(=O)Nc2ccc(-c3nc(N4CCOCC4)c4cc(F)c(-c5cccnc5)cc4n3)cc2)cc1] | N-(4-(3-(4-(6-fluoro-4-morpholino-7-(pyridin-3-yl)quinazolin-2-yl)phenyl)ureido)phenyl)-N-methylacetamide | 10 |
| 401 | 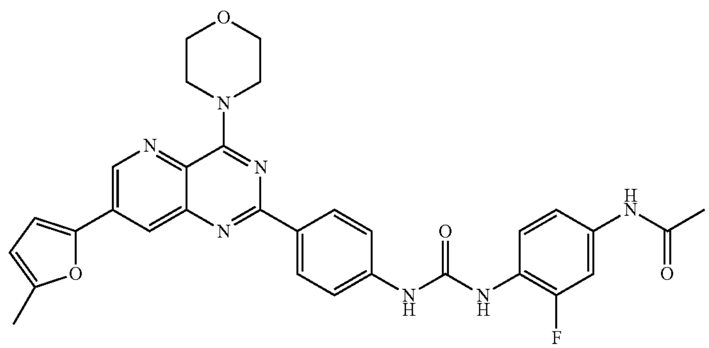 [SMILES: CC(=O)Nc1ccc(NC(=O)Nc2ccc(-c3nc(N4CCOCC4)c4ncc(-c5ccc(C)o5)cc4n3)cc2)c(F)c1] | N-(3-fluoro-4-(3-(4-(7-(5-methylfuran-2-yl)-4-morpholinopyrido[3,2-d]pyrimidin-2-yl)phenyl)ureido)phenyl) acetamide | 7A + 9 |
| 402 | 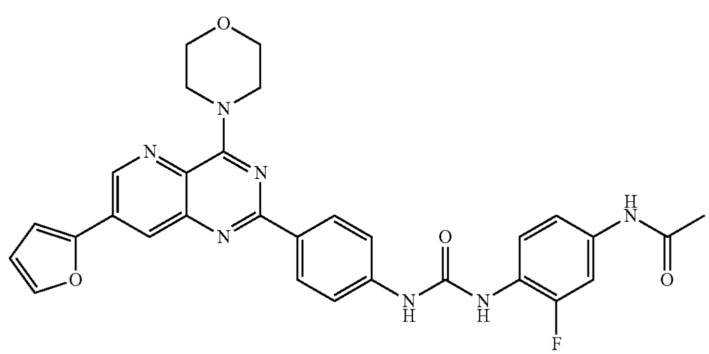 [SMILES: CC(=O)Nc1ccc(NC(=O)Nc2ccc(-c3nc(N4CCOCC4)c4ncc(-c5ccco5)cc4n3)cc2)c(F)c1] | N-(3-fluoro-4-(3-(4-(7-(furan-2-yl)-4-morpholinopyrido[3,2-d]pyrimidin-2-yl)phenyl)ureido)phenyl) acetamide | 7A + 9 |
| 403 | 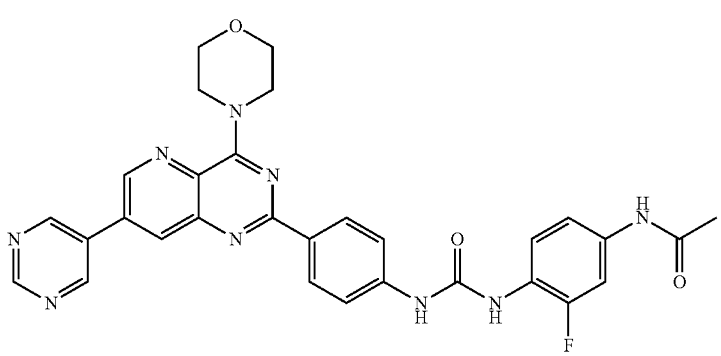 [SMILES: CC(=O)Nc1ccc(NC(=O)Nc2ccc(-c3nc(N4CCOCC4)c4ncc(-c5cncnc5)cc4n3)cc2)c(F)c1] | N-(3-fluoro-4-(3-(4-(4-morpholino-7-(pyrimidin-5-yl)pyrido[3,2-d]pyrimidin-2-yl)phenyl)ureido)phenyl) acetamide | 7A + 9 |

TABLE 1-continued

| Ex | Structure | Structure Name | Synthetic Scheme |
|---|---|---|---|
| 404 | 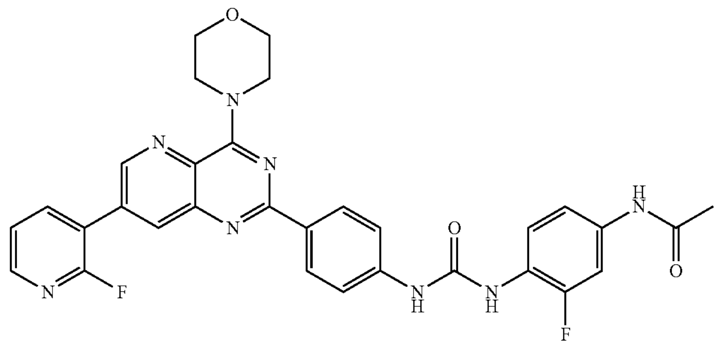 [SMILES: CC(=O)Nc1ccc(NC(=O)Nc2ccc(-c3nc(N4CCOCC4)c4ncc(-c5cccnc5F)cc4n3)cc2)c(F)c1] | N-(3-fluoro-4-(3-(4-(7-(2-fluoropyridin-3-yl)-4-morpholinopyrido[3,2-d]pyrimidin-2-yl)phenyl)ureido)phenyl)acetamide | 7A + 9 |
| 405 | 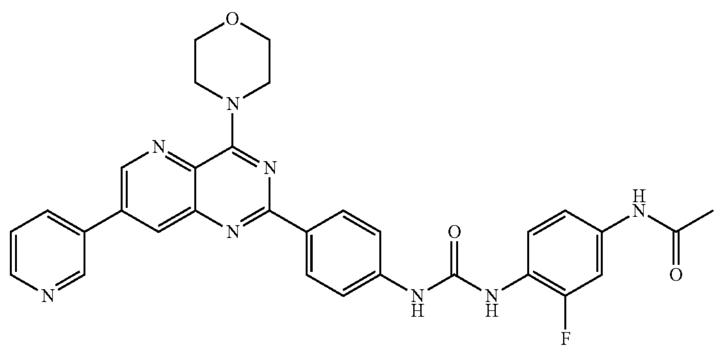 [SMILES: CC(=O)Nc1ccc(NC(=O)Nc2ccc(-c3nc(N4CCOCC4)c4ncc(-c5cccnc5)cc4n3)cc2)c(F)c1] | N-(3-fluoro-4-(3-(4-(4-morpholino-7-(pyridin-3-yl)pyrido[3,2-d]pyrimidin-2-yl)phenyl)ureido)phenyl)acetamide | 7A + 9 |
| 406 | 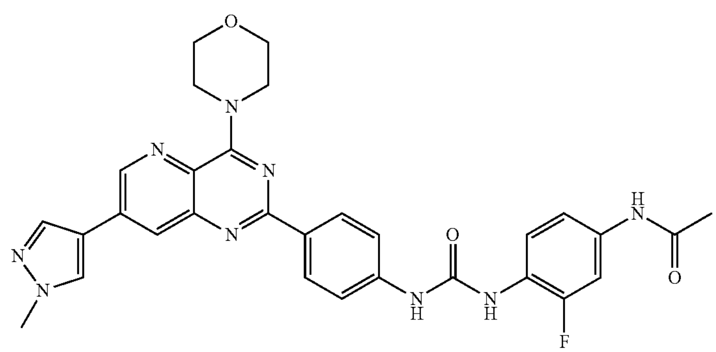 | N-(3-fluoro-4-(3-(4-(7-(1-methyl-1H-pyrazol-4-yl)-4-morpholinopyrido[3,2-d]pyrimidin-2-yl)phenyl)ureido)phenyl)acetamide | 7A + 9 |
| 407 | 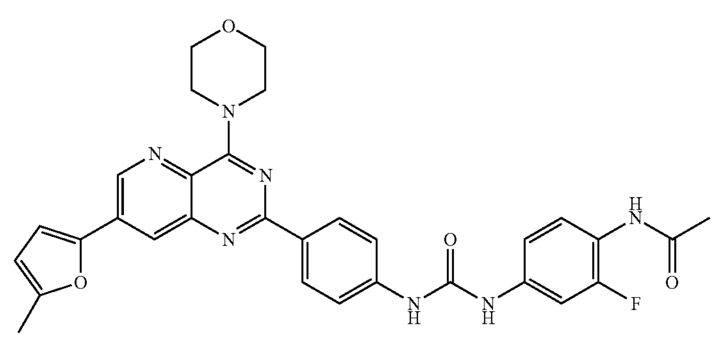 [SMILES: CC(=O)Nc1ccc(NC(=O)Nc2ccc(-c3nc(N4CCOCC4)c4ncc(-c5ccc(C)o5)cc4n3)cc2)cc1F] | N-(2-fluoro-4-(3-(4-(7-(5-methylfuran-2-yl)-4-morpholinopyrido[3,2-d]pyrimidin-2-yl)phenyl)ureido)phenyl)acetamide | 7A + 9 |

TABLE 1-continued

| Ex | Structure | Structure Name | Synthetic Scheme |
|---|---|---|---|
| 408 | 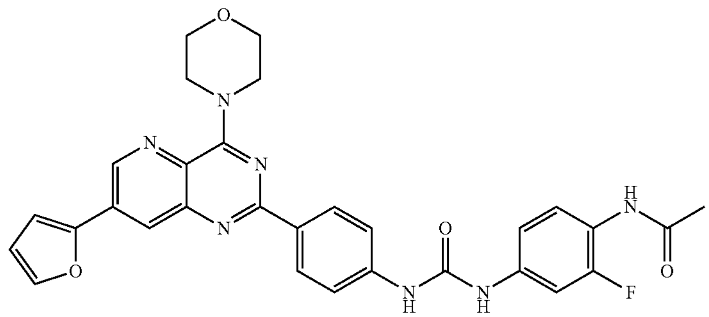 [SMILES: CC(=O)Nc1ccc(NC(=O)Nc2ccc(-c3nc(N4CCOCC4)c4ncc(-c5ccco5)cc4n3)cc2)cc1F] | N-(2-fluoro-4-(3-(4-(7-(furan-2-yl)-4-morpholinopyrido[3,2-d]pyrimidin-2-yl)phenyl)ureido)phenyl)acetamide | 7A + 9 |
| 409 | 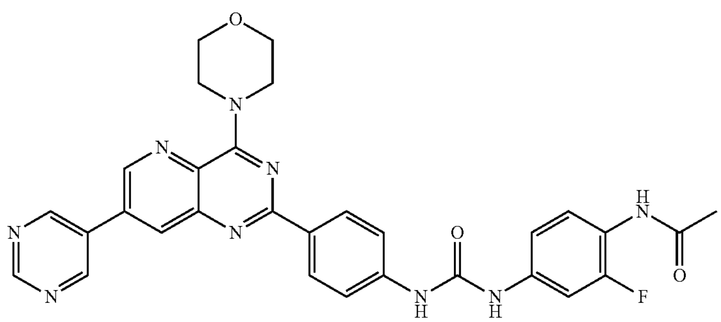 | N-(2-fluoro-4-(3-(4-(4-morpholino-7-(pyrimidin-5-yl)pyrido[3,2-d]pyrimidin-2-yl)phenyl)ureido)phenyl)acetamide | 7A + 9 |
| 410 | 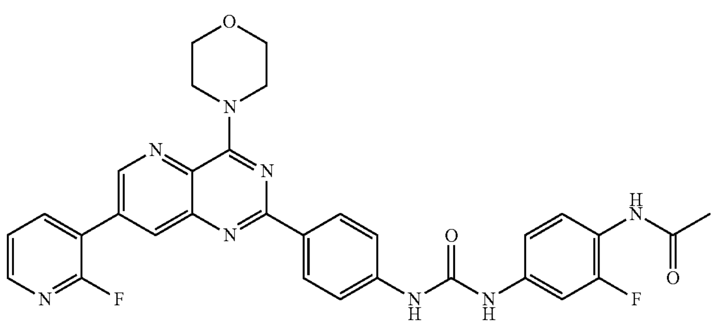 [SMILES: CC(=O)Nc1ccc(NC(=O)Nc2ccc(-c3nc(N4CCOCC4)c4ncc(-c5cccnc5F)cc4n3)cc2)cc1F] | N-(2-fluoro-4-(3-(4-(7-(2-fluoropyridin-3-yl)-4-morpholinopyrido[3,2-d]pyrimidin-2-yl)phenyl)ureido)phenyl)acetamide | 7A + 9 |
| 411 | 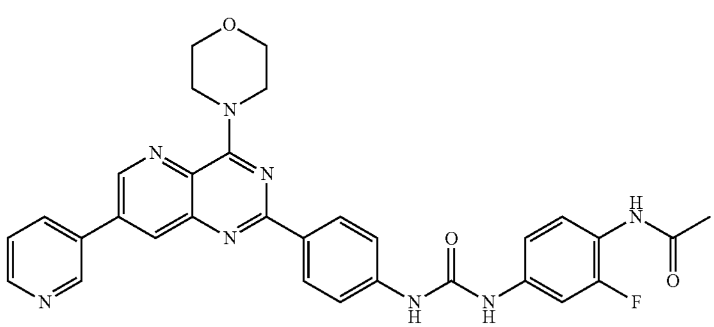 | N-(2-fluoro-4-(3-(4-(4-morpholino-7-(pyridin-3-yl)pyrido[3,2-d]pyrimidin-2-yl)phenyl)ureido)phenyl)acetamide | 7A + 9 |

TABLE 1-continued

| Ex | Structure | Structure Name | Synthetic Scheme |
|---|---|---|---|
| 412 | 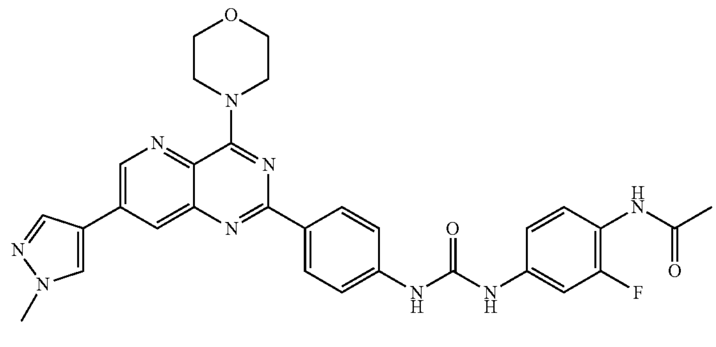 [SMILES: CC(=O)Nc1ccc(NC(=O)Nc2ccc(-c3nc(N4CCOCC4)c4ncc(-c5cnn(C)c5)cc4n3)cc2)cc1F] | N-(2-fluoro-4-(3-(4-(7-(1-methyl-1H-pyrazol-4-yl)-4-morpholinopyrido[3,2-d]pyrimidin-2-yl)phenyl)ureido)phenyl)acetamide | 7A + 9 |
| 413 | 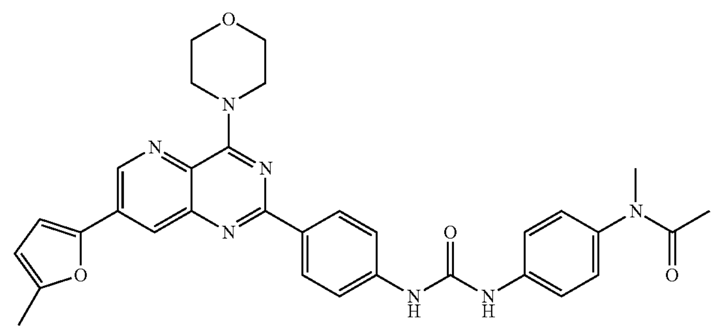 [SMILES: CC(=O)N(C)c1ccc(NC(=O)Nc2ccc(-c3nc(N4CCOCC4)c4ncc(-c5ccc(C)o5)cc4n3)cc2)cc1] | N-methyl-N-(4-(3-(4-(7-(5-methylfuran-2-yl)-4-morpholinopyrido[3,2-d]pyrimidin-2-yl)phenyl)ureido)phenyl)acetamide | 7A + 9 |
| 414 | 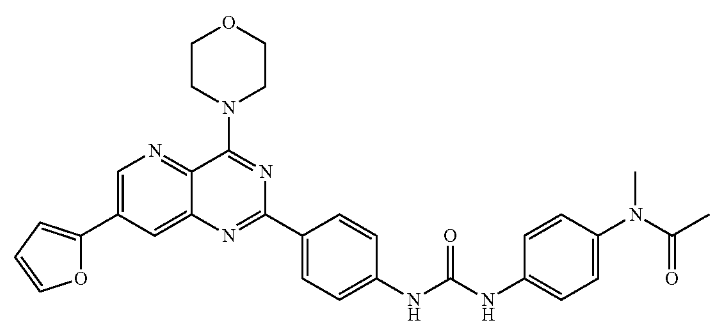 | N-(4-(3-(4-(7-(furan-2-yl)-4-morpholinopyrido[3,2-d]pyrimidin-2-yl)phenyl)ureido)phenyl)-N-methylacetamide | 7A + 9 |
| 415 | 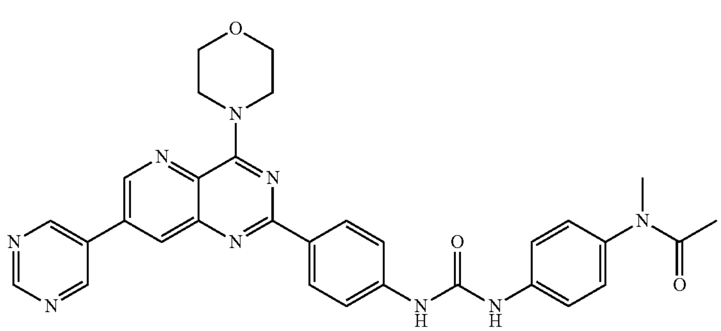 [SMILES: CC(=O)N(C)c1ccc(NC(=O)Nc2ccc(-c3nc(N4CCOCC4)c4ncc(-c5cncnc5)cc4n3)cc2)cc1] | N-methyl-N-(4-(3-(4-(4-morpholino-7-(pyrimidin-5-yl)pyrido[3,2-d]pyrimidin-2-yl)phenyl)ureido)phenyl)acetamide | 7A + 9 |

TABLE 1-continued

| Ex | Structure | Structure Name | Synthetic Scheme |
|---|---|---|---|
| 416 | 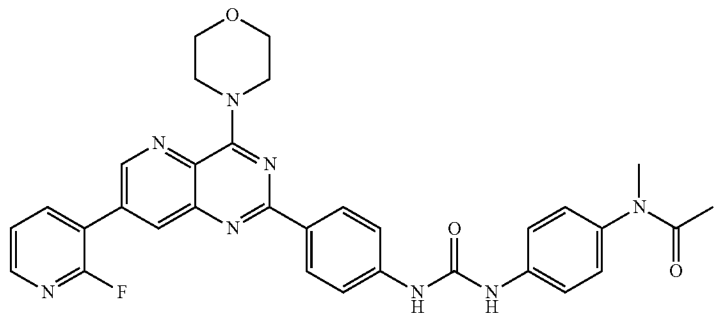 [SMILES: CC(=O)N(C)c1ccc(NC(=O)Nc2ccc(-c3nc(N4CCOCC4)c4ncc(-c5cccnc5F)cc4n3)cc2)cc1] | N-(4-(3-(4-(7-(2-fluoropyridin-3-yl)-4-morpholinopyrido[3,2-d]pyrimidin-2-yl)phenyl)ureido)phenyl)-N-methylacetamide | 7A + 9 |
| 417 | 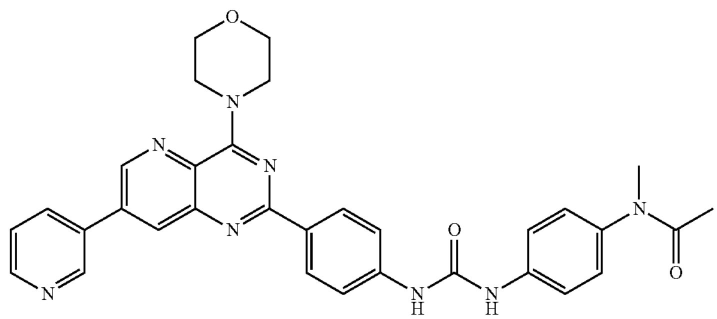 [SMILES: CC(=O)N(C)c1ccc(NC(=O)Nc2ccc(-c3nc(N4CCOCC4)c4ncc(-c5cccnc5)cc4n3)cc2)cc1] | N-methyl-N-(4-(3-(4-(4-morpholino-7-(pyridin-3-yl)pyrido[3,2-d]pyrimidin-2-yl)phenyl)ureido)phenyl)acetamide | 7A + 9 |
| 418 | 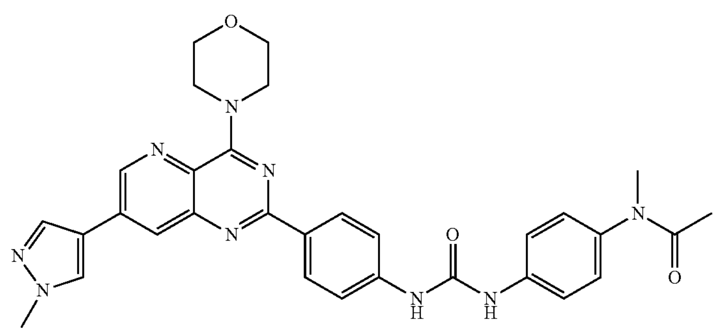 [SMILES: CC(=O)N(C)c1ccc(NC(=O)Nc2ccc(-c3nc(N4CCOCC4)c4ncc(-c5cnn(C)c5)cc4n3)cc2)cc1] | N-methyl-N-(4-(3-(4-(7-(1-methyl-1H-pyrazol-4-yl)-4-morpholinopyrido[3,2-d]pyrimidin-2-yl)phenyl)ureido)phenyl)acetamide | 7A + 9 |
| 419 | 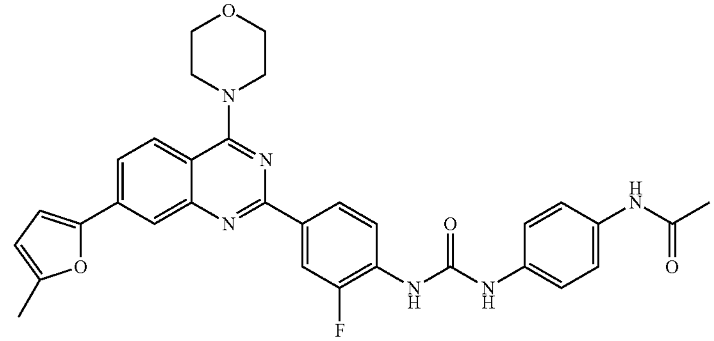 [SMILES: CC(=O)Nc1ccc(NC(=O)Nc2ccc(-c3nc(N4CCOCC4)c4ccc(-c5ccc(C)o5)cc4n3)cc2F)cc1] | N-(4-(3-(2-fluoro-4-(7-(5-methylfuran-2-yl)-4-morpholinoquinazolin-2-yl)phenyl)ureido)phenyl)acetamide | 6D + 9 + 10 |

TABLE 1-continued

| Ex | Structure | Structure Name | Synthetic Scheme |
|---|---|---|---|
| 420 | 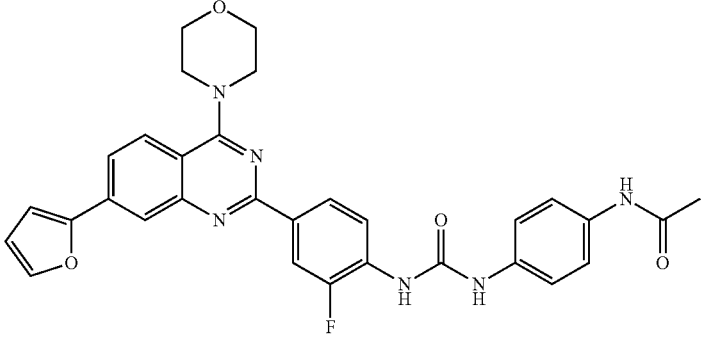 [SMILES: CC(=O)Nc1ccc(NC(=O)Nc2ccc(-c3nc(N4CCOCC4)c4ccc(-c5ccco5)cc4n3)cc2F)cc1] | N-(4-(3-(2-fluoro-4-(7-(furan-2-yl)-4-morpholinoquinazolin-2-yl)phenyl)ureido)phenyl)acetamide | 6D + 9 + 10 |
| 421 | 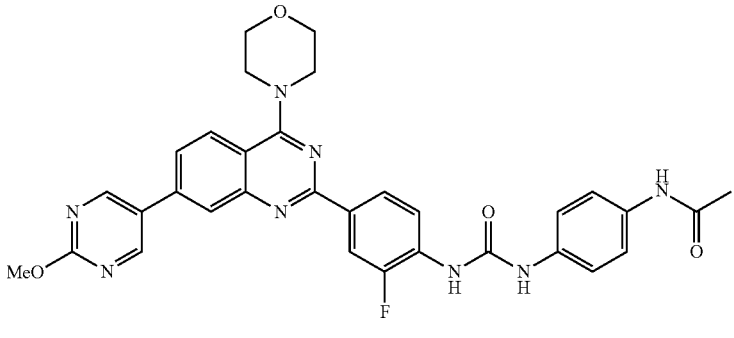 [SMILES: COc1ncc(-c2ccc3c(N4CCOCC4)nc(-c4ccc(NC(=O)Nc5ccc(NC(C)=O)cc5)c(F)c4)nc3c2)cn1] | N-(4-(3-(2-fluoro-4-(7-(2-methoxypyrimidin-5-yl)-4-morpholinoquinazolin-2-yl)phenyl)ureido)phenyl)acetamide | 6D + 9 + 10 |
| 422 | 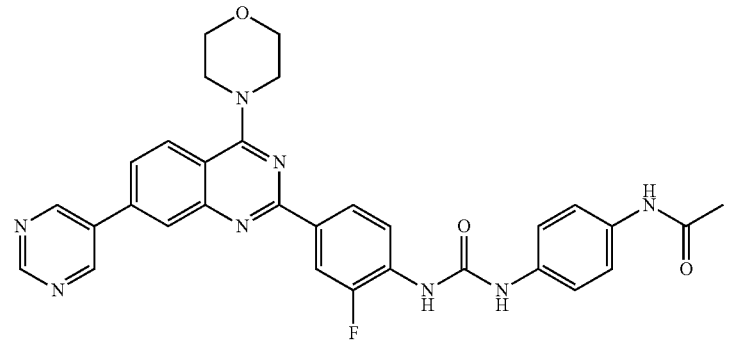 [SMILES: CC(=O)Nc1ccc(NC(=O)Nc2ccc(-c3nc(N4CCOCC4)c4ccc(-c5cncnc5)cc4n3)cc2F)cc1] | N-(4-(3-(2-fluoro-4-(4-morpholino-7-(pyrimidin-5-yl)quinazolin-2-yl)phenyl)ureido)phenyl)acetamide | 6D + 9 + 10 |
| 423 | 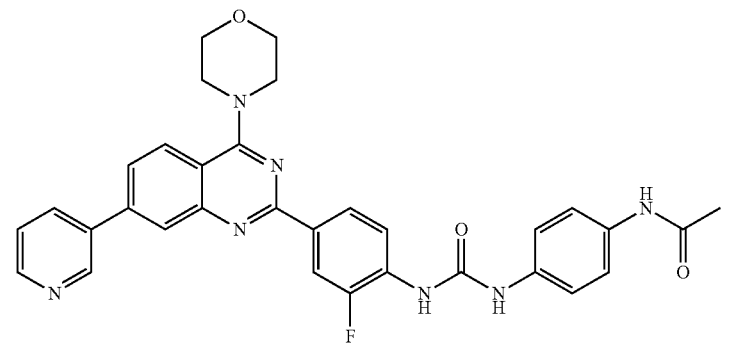 | N-(4-(3-(2-fluoro-4-(4-morpholino-7-(pyridin-3-yl)quinazolin-2-yl)phenyl)ureido)phenyl)acetamide | 6D + 9 + 10 |

TABLE 1-continued

| Ex | Structure | Structure Name | Synthetic Scheme |
|---|---|---|---|
| 424 | 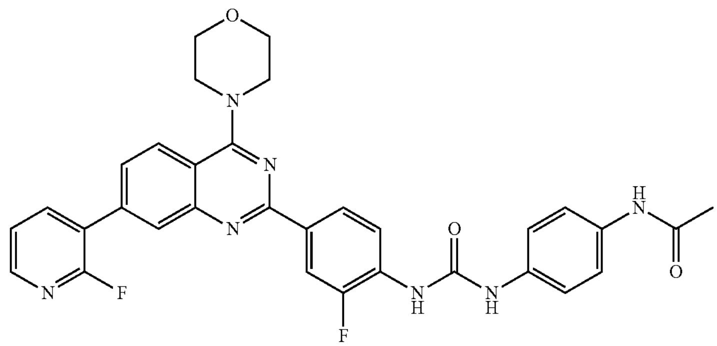 [SMILES: CC(=O)Nc1ccc(NC(=O)Nc2ccc(-c3nc(N4CCOCC4)c4ccc(-c5cccnc5F)cc4n3)cc2F)cc1] | N-(4-(3-(2-fluoro-4-(7-(2-fluoropyridin-3-yl)-4-morpholinoquinazolin-2-yl)phenyl)ureido)phenyl)acetamide | 6D + 9 + 10 |
| 425 | 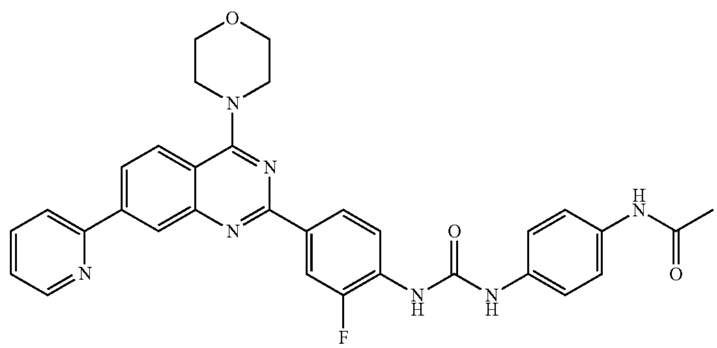 [SMILES: CC(=O)Nc1ccc(NC(=O)Nc2ccc(-c3nc(N4CCOCC4)c4ccc(-c5ccccn5)cc4n3)cc2F)cc1] | N-(4-(3-(2-fluoro-4-(4-morpholino-7-(pyridin-2-yl)quinazolin-2-yl)phenyl)ureido)phenyl)acetamide | 6D + 9 + 10 |
| 426 | 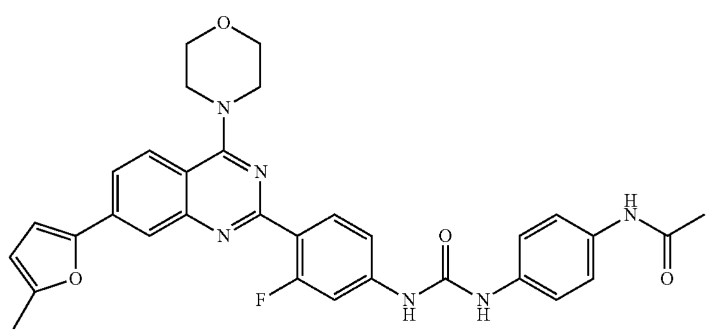 [SMILES: CC(=O)Nc1ccc(NC(=O)Nc2ccc(-c3nc(N4CCOCC4)c4ccc(-c5ccc(C)o5)cc4n3)c(F)c2)cc1] | N-(4-(3-(3-fluoro-4-(7-(5-methylfuran-2-yl)-4-morpholinoquinazolin-2-yl)phenyl)ureido)phenyl)acetamide | 6 + 9 + 10 |
| 427 | 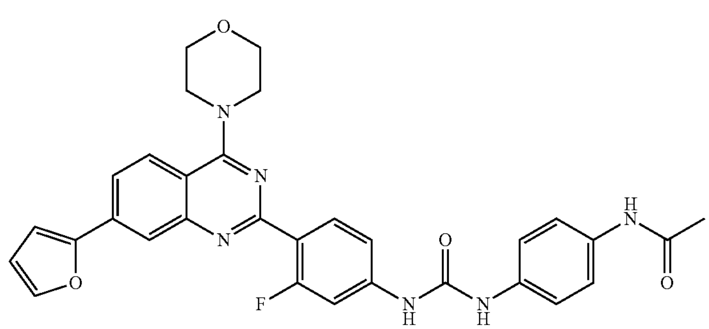 [SMILES: CC(=O)Nc1ccc(NC(=O)Nc2ccc(-c3nc(N4CCOCC4)c4ccc(-c5ccco5)cc4n3)c(F)c2)cc1] | N-(4-(3-(3-fluoro-4-(7-(furan-2-yl)-4-morpholinoquinazolin-2-yl)phenyl)ureido)phenyl)acetamide | 6 + 9 + 10 |

TABLE 1-continued

| Ex | Structure | Structure Name | Synthetic Scheme |
|---|---|---|---|
| 428 | 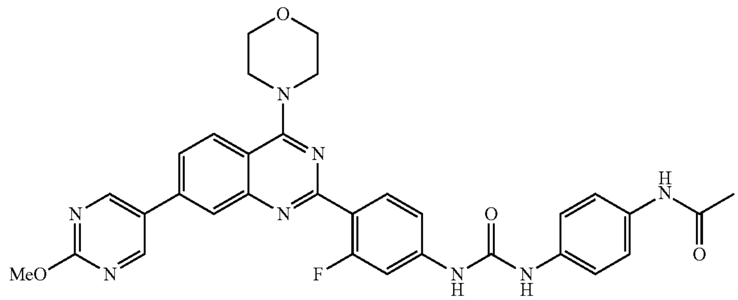 [SMILES: COc1ncc(-c2ccc3c(N4CCOCC4)nc(-c4ccc(NC(=O)Nc5ccc(NC(C)=O)cc5)cc4F)nc3c2)cn1] | N-(4-(3-(3-fluoro-4-(7-(2-methoxypyrimidin-5-yl)-4-morpholinoquinazolin-2-yl)phenyl)ureido)phenyl)acetamide | 6 + 9 + 10 |
| 429 | 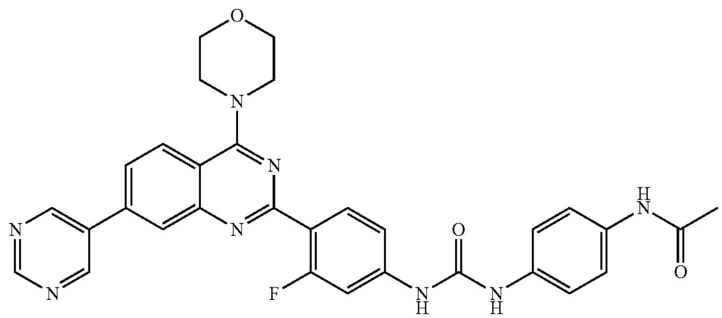 [SMILES: CC(=O)Nc1ccc(NC(=O)Nc2ccc(-c3nc(N4CCOCC4)c4ccc(-c5cncnc5)cc4n3)c(F)c2)cc1] | N-(4-(3-(3-fluoro-4-(4-morpholino-7-(pyrimidin-5-yl)quinazolin-2-yl)phenyl)ureido)phenyl)acetamide | 6 + 9 + 10 |
| 430 | 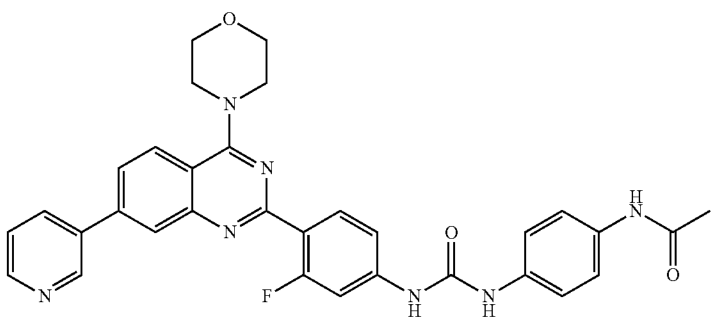 [SMILES: CC(=O)Nc1ccc(NC(=O)Nc2ccc(-c3nc(N4CCOCC4)c4ccc(-c5cccnc5)cc4n3)c(F)c2)cc1] | N-(4-(3-(3-fluoro-4-(4-morpholino-7-(pyridin-3-yl)quinazolin-2-yl)phenyl)ureido)phenyl)acetamide | 6 + 9 + 10 |
| 431 | 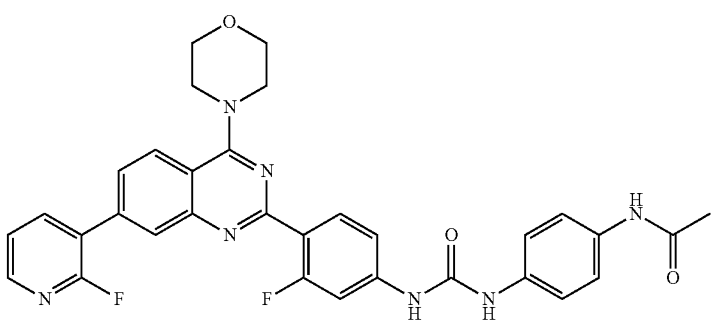 [SMILES: CC(=O)Nc1ccc(NC(=O)Nc2ccc(-c3nc(N4CCOCC4)c4ccc(-c5cccnc5F)cc4n3)c(F)c2)cc1] | N-(4-(3-(3-fluoro-4-(7-(2-fluoropyridin-3-yl)-4-morpholinoquinazolin-2-yl)phenyl)ureido)phenyl)acetamide | 6 + 9 + 10 |
| 432 | 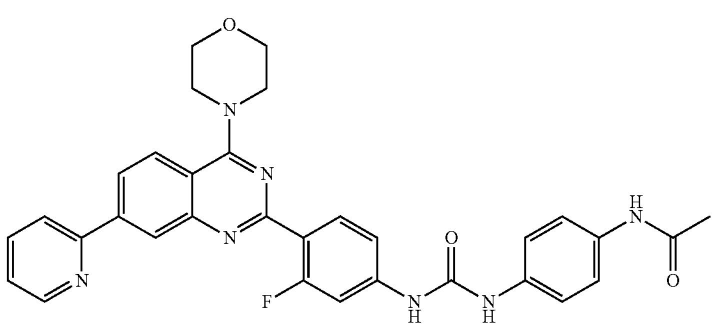 [SMILES: CC(=O)Nc1ccc(NC(=O)Nc2ccc(-c3nc(N4CCOCC4)c4ccc(-c5ccccn5)cc4n3)c(F)c2)cc1] | N-(4-(3-(3-fluoro-4-(4-morpholino-7-(pyridin-2-yl)quinazolin-2-yl)phenyl)ureido)phenyl)acetamide | 6 + 9 + 10 |

TABLE 1-continued

| Ex | Structure | Structure Name | Synthetic Scheme |
|---|---|---|---|
| 433 | 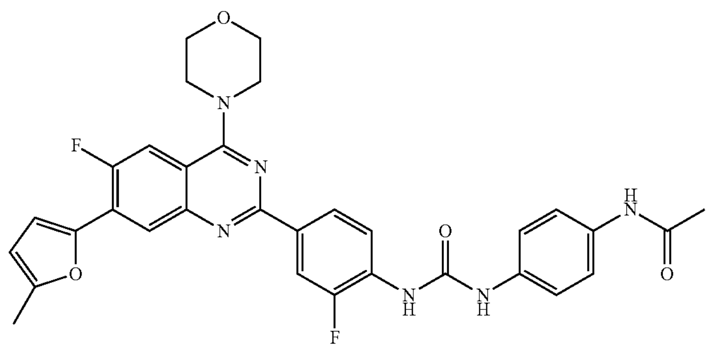 [SMILES: CC(=O)Nc1ccc(NC(=O)Nc2ccc(-c3nc(N4CCOCC4)c4cc(F)c(-c5ccc(C)o5)cc4n3)cc2F)cc1] | N-(4-(3-(2-fluoro-4-(6-fluoro-7-(5-methylfuran-2-yl)-4-morpholinoquinazolin-2-yl)phenyl)ureido)phenyl)acetamide | 6G + 6D + 9 + 10 |
| 434 | 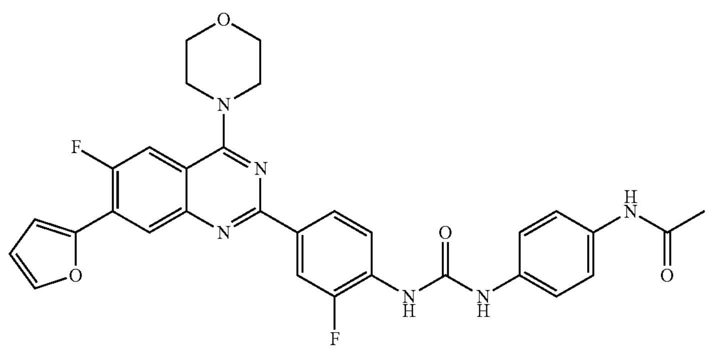 [SMILES: CC(=O)Nc1ccc(NC(=O)Nc2ccc(-c3nc(N4CCOCC4)c4cc(F)c(-c5ccco5)cc4n3)cc2F)cc1] | N-(4-(3-(2-fluoro-4-(6-fluoro-7-(furan-2-yl)-4-morpholinoquinazolin-2-yl)phenyl)ureido)phenyl)acetamide | 6G + 6D + 9 + 10 |
| 435 | 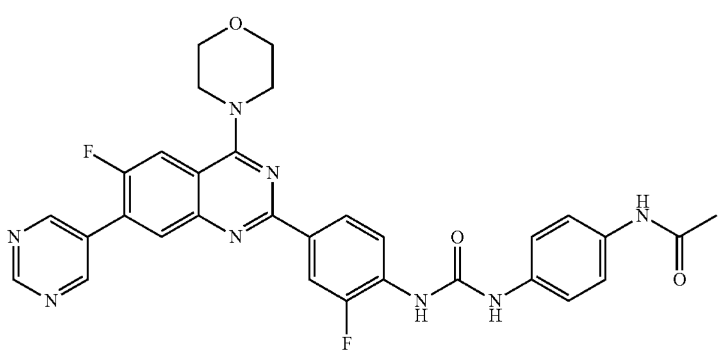 [SMILES: CC(=O)Nc1ccc(NC(=O)Nc2ccc(-c3nc(N4CCOCC4)c4cc(F)c(-c5cncnc5)cc4n3)cc2F)cc1] | N-(4-(3-(2-fluoro-4-(6-fluoro-4-morpholino-7-(pyrimidin-5-yl)quinazolin-2-yl)phenyl)ureido)phenyl)acetamide | 6G + 6D + 9 + 10 |
| 436 | 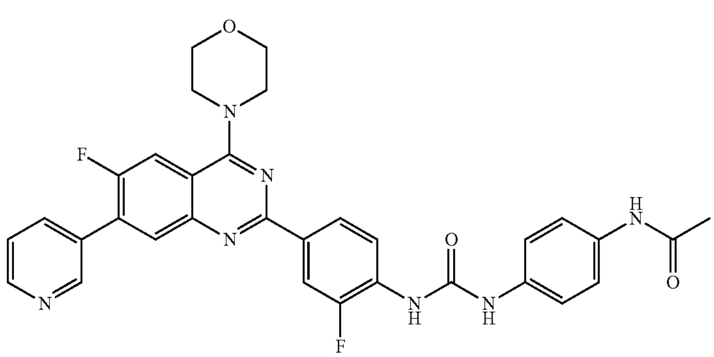 [SMILES: CC(=O)Nc1ccc(NC(=O)Nc2ccc(-c3nc(N4CCOCC4)c4cc(F)c(-c5cccnc5)cc4n3)cc2F)cc1] | N-(4-(3-(2-fluoro-4-(6-fluoro-4-morpholino-7-(pyridin-3-yl)quinazolin-2-yl)phenyl)ureido)phenyl)acetamide | 6G + 6D + 9 + 10 |

TABLE 1-continued

| Ex | Structure | Structure Name | Synthetic Scheme |
|---|---|---|---|
| 437 | 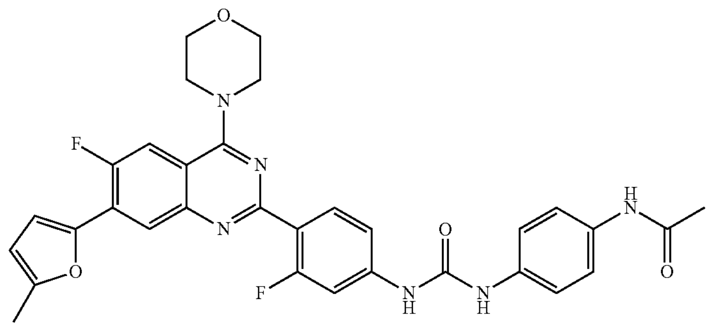 [SMILES: CC(=O)Nc1ccc(NC(=O)Nc2ccc(-c3nc(N4CCOCC4)c4cc(F)c(-c5ccc(C)o5)cc4n3)c(F)c2)cc1] | N-(4-(3-(3-fluoro-4-(6-fluoro-7-(5-methylfuran-2-yl)-4-morpholinoquinazolin-2-yl)phenyl)ureido)phenyl)acetamide | 6 + 6G + 9 + 10 |
| 438 | 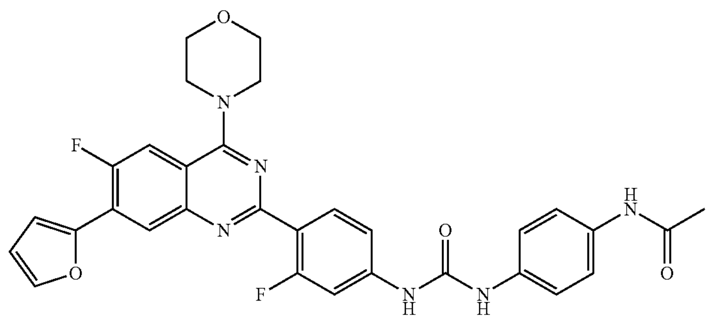 [SMILES: CC(=O)Nc1ccc(NC(=O)Nc2ccc(-c3nc(N4CCOCC4)c4cc(F)c(-c5ccco5)cc4n3)c(F)c2)cc1] | N-(4-(3-(3-fluoro-4-(6-fluoro-7-(furan-2-yl)-4-morpholinoquinazolin-2-yl)phenyl)ureido)phenyl)acetamide | 6 + 6G + 9 + 10 |
| 439 | 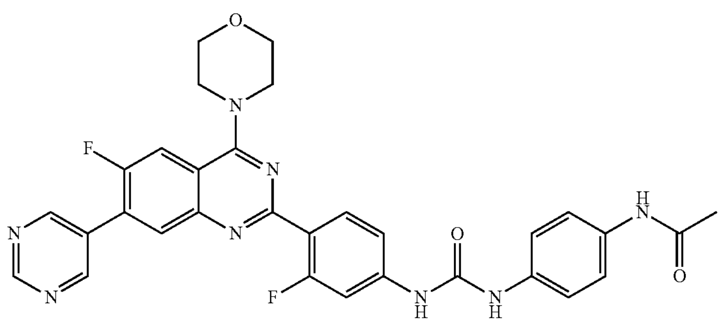 [SMILES: CC(=O)Nc1ccc(NC(=O)Nc2ccc(-c3nc(N4CCOCC4)c4cc(F)c(-c5cncnc5)cc4n3)c(F)c2)cc1] | N-(4-(3-(3-fluoro-4-(6-fluoro-4-morpholino-7-(pyrimidin-5-yl)quinazolin-2-yl)phenyl)ureido)phenyl)acetamide | 6 + 6G + 9 + 10 |
| 440 | 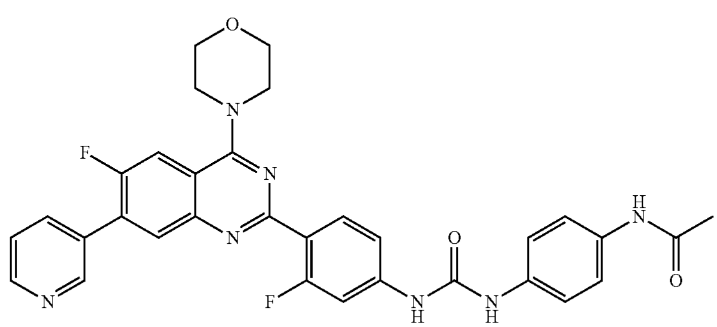 [SMILES: CC(=O)Nc1ccc(NC(=O)Nc2ccc(-c3nc(N4CCOCC4)c4cc(F)c(-c5cccnc5)cc4n3)c(F)c2)cc1] | N-(4-(3-(3-fluoro-4-(6-fluoro-4-morpholino-7-(pyridin-3-yl)quinazolin-2-yl)phenyl)ureido)phenyl)acetamide | 6 + 6G + 9 + 10 |

TABLE 1-continued

| Ex | Structure | Structure Name | Synthetic Scheme |
|---|---|---|---|
| 441 | 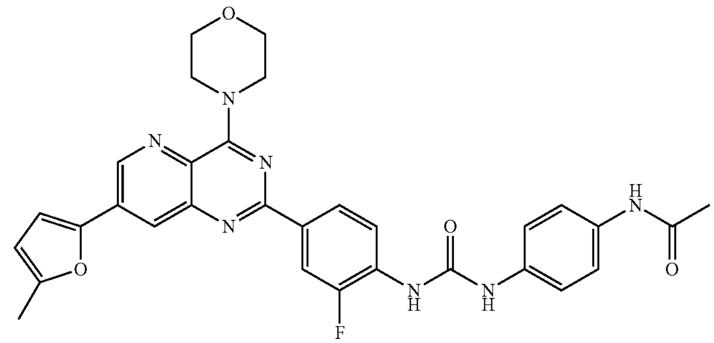 | N-(4-(3-(2-fluoro-4-(7-(5-methylfuran-2-yl)-4-morpholinopyrido[3,2-d]pyrimidin-2-yl)phenyl)ureido)phenyl)acetamide | 7B + 9 + 10 |
| 442 | 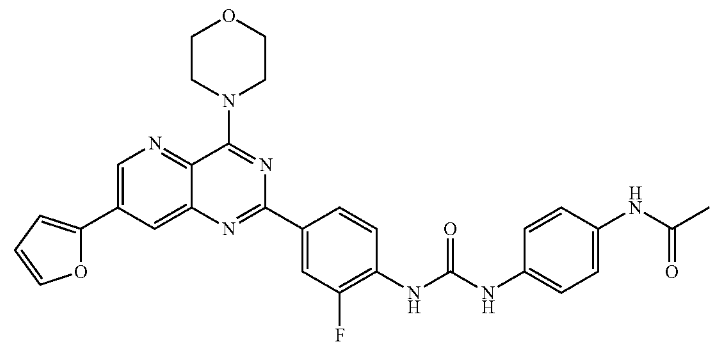 [SMILES: CC(=O)Nc1ccc(NC(=O)Nc2ccc(-c3nc(N4CCOCC4)c4ncc(-c5ccco5)cc4n3)cc2F)cc1] | N-(4-(3-(2-fluoro-4-(7-(furan-2-yl)-4-morpholinopyrido[3,2-d]pyrimidin-2-yl)phenyl)ureido)phenyl)acetamide | 7B + 9 + 10 |
| 443 | 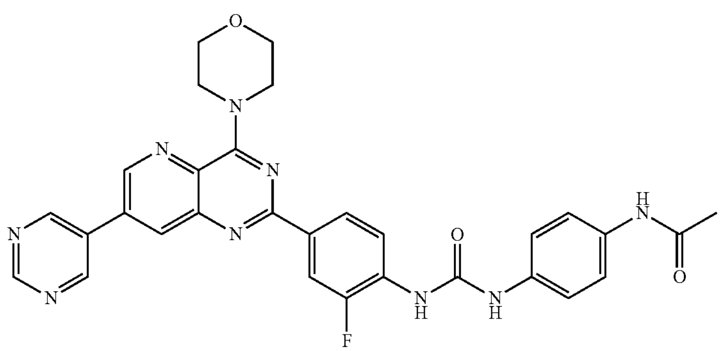 [SMILES: CC(=O)Nc1ccc(NC(=O)Nc2ccc(-c3nc(N4CCOCC4)c4ncc(-c5cncnc5)cc4n3)cc2F)cc1] | N-(4-(3-(2-fluoro-4-(4-morpholino-7-(pyrimidin-5-yl)pyrido[3,2-d]pyrimidin-2-yl)phenyl)ureido)phenyl)acetamide | 7B + 9 + 10 |
| 444 | 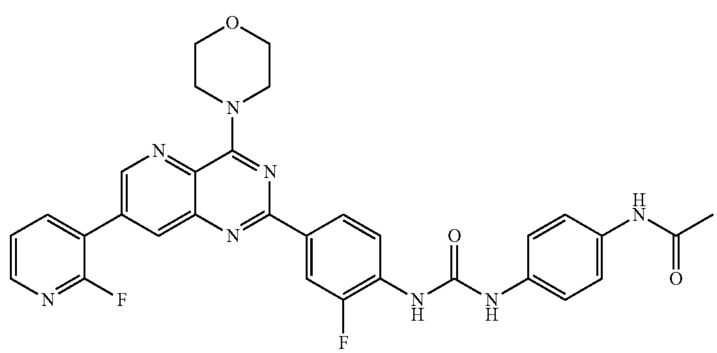 [SMILES: CC(=O)Nc1ccc(NC(=O)Nc2ccc(-c3nc(N4CCOCC4)c4ncc(-c5cccnc5F)cc4n3)cc2F)cc1] | N-(4-(3-(2-fluoro-4-(7-(2-fluoropyridin-3-yl)-4-morpholinopyrido[3,2-d]pyrimidin-2-yl)phenyl)ureido)phenyl)acetamide | 7B + 9 + 10 |

TABLE 1-continued

| Ex | Structure | Structure Name | Synthetic Scheme |
|---|---|---|---|
| 445 | 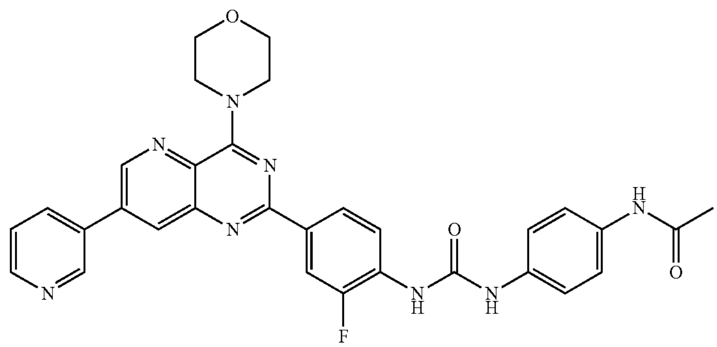 [SMILES: CC(=O)Nc1ccc(NC(=O)Nc2ccc(-c3nc(N4CCOCC4)c4ncc(-c5cccnc5)cc4n3)cc2F)cc1] | N-(4-(3-(2-fluoro-4-(4-morpholino-7-(pyridin-3-yl)pyrido[3,2-d]pyrimidin-2-yl)phenyl)ureido)phenyl)acetamide | 7B + 9 + 10 |
| 446 | 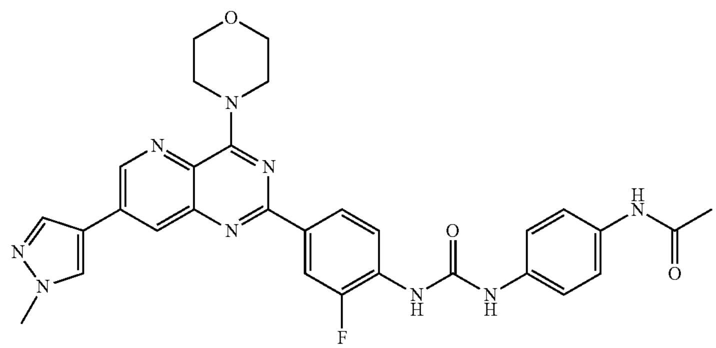 [SMILES: CC(=O)Nc1ccc(NC(=O)Nc2ccc(-c3nc(N4CCOCC4)c4ncc(-c5cnn(C)c5)cc4n3)cc2F)cc1] | N-(4-(3-(2-fluoro-4-(7-(1-methyl-1H-pyrazol-4-yl)-4-morpholinopyrido[3,2-d]pyrimidin-2-yl)phenyl)ureido)phenyl)acetamide | 7B + 9 + 10 |
| 447 | 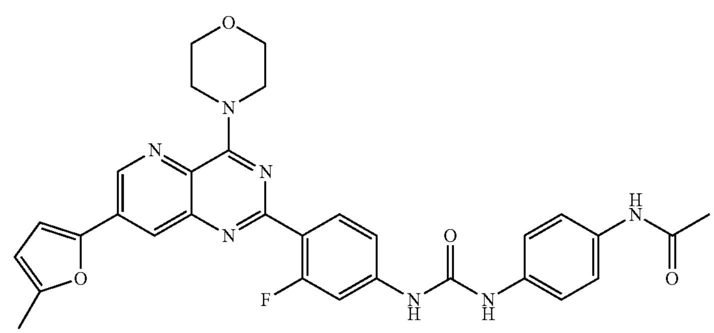 [SMILES: CC(=O)Nc1ccc(NC(=O)Nc2ccc(-c3nc(N4CCOCC4)c4ncc(-c5ccc(C)o5)cc4n3)c(F)c2)cc1] | N-(4-(3-(3-fluoro-4-(7-(5-methylfuran-2-yl)-4-morpholinopyrido[3,2-d]pyrimidin-2-yl)phenyl)ureido)phenyl)acetamide | 7 + 9 + 10 |
| 448 | 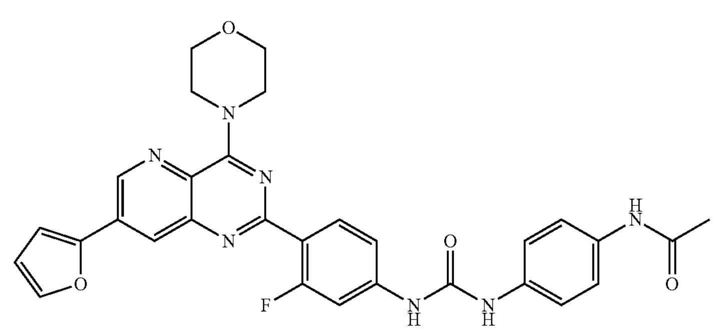 [SMILES: CC(=O)Nc1ccc(NC(=O)Nc2ccc(-c3nc(N4CCOCC4)c4ncc(-c5ccco5)cc4n3)c(F)c2)cc1] | N-(4-(3-(3-fluoro-4-(7-(furan-2-yl)-4-morpholinopyrido[3,2-d]pyrimidin-2-yl)phenyl)ureido)phenyl)acetamide | 7 + 9 + 10 |

| Ex | Structure | Structure Name | Synthetic Scheme |
|---|---|---|---|
| 449 | 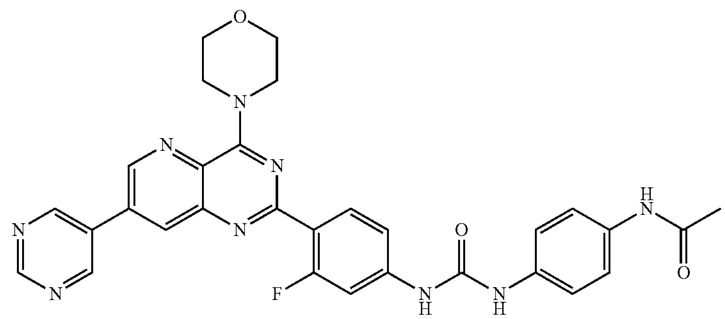 [SMILES: CC(=O)Nc1ccc(NC(=O)Nc2ccc(-c3nc(N4CCOCC4)c4ncc(-c5cncnc5)cc4n3)c(F)c2)cc1] | N-(4-(3-(3-fluoro-4-(4-morpholino-7-(pyrimidin-5-yl)pyrido[3,2-d]pyrimidin-2-yl)phenyl)ureido)phenyl)acetamide | 7 + 9 + 10 |
| 450 | 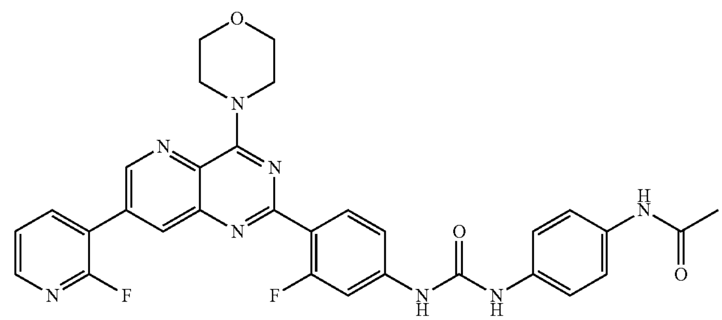 [SMILES: CC(=O)Nc1ccc(NC(=O)Nc2ccc(-c3nc(N4CCOCC4)c4ncc(-c5cccnc5F)cc4n3)c(F)c2)cc1] | N-(4-(3-(3-fluoro-4-(7-(2-fluoropyridin-3-yl)-4-morpholinopyrido[3,2-d]pyrimidin-2-yl)phenyl)ureido)phenyl)acetamide | 7 + 9 + 10 |
| 451 | 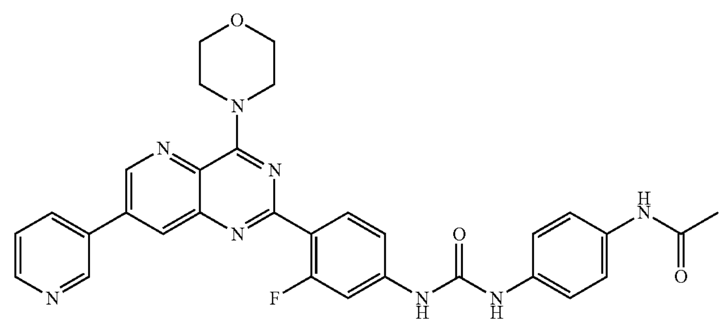 [SMILES: CC(=O)Nc1ccc(NC(=O)Nc2ccc(-c3nc(N4CCOCC4)c4ncc(-c5cccnc5)cc4n3)c(F)c2)cc1] | N-(4-(3-(3-fluoro-4-(4-morpholino-7-(pyridin-3-yl)pyrido[3,2-d]pyrimidin-2-yl)phenyl)ureido)phenyl)acetamide | 7 + 9 + 10 |
| 452 | 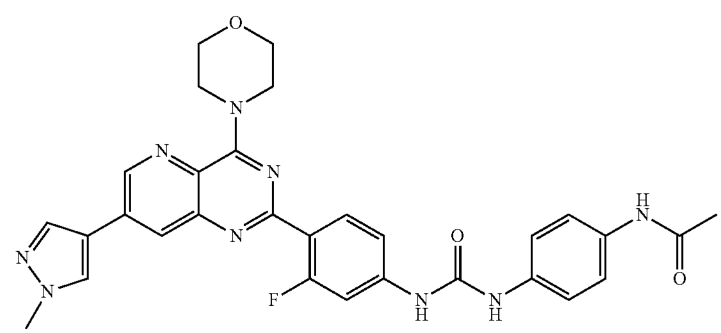 [SMILES: CC(=O)Nc1ccc(NC(=O)Nc2ccc(-c3nc(N4CCOCC4)c4ncc(-c5cnn(C)c5)cc4n3)c(F)c2)cc1] | N-(4-(3-(3-fluoro-4-(7-(1-methyl-1H-pyrazol-4-yl)-4-morpholinopyrido[3,2-d]pyrimidin-2-yl)phenyl)ureido)phenyl)acetamide | 7 + 9 + 10 |

Example 72

Biological Assays (i) PI3 Kinase Time-Resolved Fluorescence Resonance Energy Transfer (TR-FRET) Assay The ability of compounds of the invention to inhibit PI3K activity was determined in a homogeneous TR-FRET assay using a PI3K assay kit (Millipore, USA; cat #33-016) according to manufacturer's instructions. PI3-Kinases (isoforms $\alpha$, $\beta$, $\gamma$ and $\delta$) catalyze the phosphorylation of phosphatidylinositol, PIP2 to PIP3 in the presence of ATP and $Mg^{2+}$. The PIP3 product is detected by displacement of biotin-PIP3 from an energy transfer complex consisting of Europium labeled anti-GST monoclonal antibody, a GST-tagged PH domain, biotinylated PIP3 and Streptavidin-APC. Excitation of Europium in the complex results in an energy transfer to the APC and a fluorescence emission at 665 nm. The PIP3 product displaces biotin-PIP3 from the complex resulting in a loss of energy transfer and thus a decrease in signal.

To test for the ability of compounds to inhibit the activity of PI3K$\alpha$ (wild-type), exemplary compounds of formula (I)

were dissolved in DMSO and directly distributed into 384-well plates at a volume of 0.5 μL. 14.5 μL of P110/P85α/PIP2 mixture in buffer (obtained from the Millipore kit) containing $MgCl_2$ (40 mM) and DTT (5 mM) was added to compound wells and incubated for 60 min at room temperature. P110/P85α was expressed in SF9 insect cells and purified nickel column extraction. Five ng of wild-type P110/P85α was used in the assay. The kinase reaction was started by the addition of ATP. The assay concentrations of both PIP2 and ATP were 10 μM. The reaction mixture was incubated for 30 min at room temperature and was terminated by the addition of stop mix and detection mix. Fluorescence was measured at 615 and 665 nm upon excitation at 340 nm in a Victor™ V5 fluorometer (Perkin Elmer, USA). The fluorescence emission ratio at 665 to 615 nm, proportional to the kinase activity, was plotted against the compound concentration to generate dose-response curves and $IC_{50}$ values were determined using Graph-Pad Prism® 5 software.

Inhibition of PI3Kα activity was observed for compounds of formula (I) as determined by this assay. See, Table 2.

The activity of PI3 kinase isoforms β, γ and δ were assayed in a similar manner to the assay protocol described above for PI3Kα, by substituting the appropriate p110/p85 isoform for the p110α/p85α. Compounds of formula (I) caused inhibition of PI3 kinase isoforms β, γ and δ as determined by these assays. For example, the compounds of examples 3, 51, 54, 111, 113, 115, and 253 each caused inhibition of PI3 kinase isoform β with $IC_{50}$ values <50 nM. The compounds of examples 104, 133, 146 and 152 each caused inhibition of PI3 kinase isoform β with $IC_{50}$ values <500 nM. The compounds of examples 3, 51, 54, 104, 111, 113, 115, 133, 253, and 152 each caused inhibition of PI3 kinase isoform γ with $IC_{50}$ values <500 nM. The compound of Example 2 caused inhibition of PI3 kinase isoform β and isoform γ with $IC_{50}$ values <1 μM. The compounds of examples 2, 3, 51, 54, 111, 113, and 253 each caused inhibition of PI3 kinase isoform δ with $IC_{50}$ values >1 μM.

The activity of PI3Kα mutations H1047R and E545K were assayed in a similar manner to the assay protocol described above for PI3Kα (wild type). The compounds of formula (I) caused inhibition of PI3Kα mutations H1047R (a mutation associated with breast and gastric cancers) and E545K (a mutation associated with colorectal tumors, glioblastomas, gastric cancers, breast cancers, and lung cancers). For example, each of the compounds of examples 1, 2, 3, 51, 54, 104, 111, 113, 115, and 253 caused inhibition of each of the PI3Kα mutations H1047R and E545K with $IC_{50}$ values <50 nM. Each of the compounds of examples 133, 146, and 152 caused inhibition of each of the PI3Kα mutations H1047R and E545K with $IC_{50}$ values <500 nM.

(ii) mTOR Kinase TR-FRET Assay

Compound inhibition for mTOR kinase was determined in a homogeneous TR-FRET assay using the Lance® ULight-p70 S6K (Thr 389) peptide (obtained from Perkin-Elmer). The ULight™-labeled synthetic peptide contains the amino acid residues surrounding Thr389 of human p70 S6K. The ULight-p70 S6K peptide is phosphorylated at Thr389 by mTOR. Phosphorylation motif: LGF<u>T</u>YVAP as substrate.

The compound dilution was carried out in 100% DMSO followed by a buffer dilution. The reaction buffer was HEPES (50 mM pH 7.5), EGTA (1 mM), $MnCl_2$ (3 mM). Test compounds at various concentrations were pre-incubated with mTOR (Millipore, USA; 5 ng) for 60 min, and then the Lance® ULight-p70 S6K (Thr 389) peptide (50 nM) was added along with ATP (20 μM). After incubating the reaction mixture for 60 min at room temperature, the kinase reaction was terminated by the addition of EDTA (10 mM) followed by the addition of detection mix, i.e., 1 nM Eu-labeled anti-phospho-substrate antibody (Perkin Elmer, USA). The fluorescence emission at 615 and 665 nM was measured upon excitation at 340 nM. $IC_{50}$ values were subsequently determined using a sigmoidal dose-response curve (variable slope) in GraphPad Prism® 5 software.

Compounds of formula (I) caused inhibition of mTOR kinase activity as determined by this assay. See Table 2.

(iii) In-Cell Western Assay

Cells from human prostate cancer cell line PC3 (American Type Culture Collection (ATCC), Manassas, Va. 20108 USA) were seeded at an optimal density of 22,000 cell/well in 96-well plates containing Ham's F12K medium (90 μL) and incubated overnight. The compound dilutions were carried out in 100% DMSO followed by a dilution in the medium. Test compounds were added in serial dilutions to the wells and incubated for 2 h. The cells were washed and fixed with 4% paraformaldehyde. After incubation at room temperature for 1 h in the dark, blocking was done for 2 h at room temperature. Primary antibodies for phosphorylated (p) AKT (5473) (phosphorylated at serine 473), pAKT(T308) (phosphorylated at threonine 308) and for pS6RP(S235/236) (phosphorylated at serine 235/236) (commercially available from Cell Signaling Technology®, whose protocol was followed for the in-cell western assay, were diluted to the required concentration and added to the corresponding wells followed by overnight incubation at 4° C. Eu-labeled rabbit (PE) (Perkin-Elmer USA catalog #AD0106) secondary antibody was added and incubated for 2 h at room temperature. Delfia® enhancement solution (cat #1244-105, Perkin Elmer USA) was subsequently added to the plate before taking the reading at 615 nm with excitation wavelength of 340 nm, after which 0.5 μg/mL of Hoechst® 33258 dye (Catalog #86140-5, Sigma) was added to the plate and fluorescence emission was read at 460 nm with 355 nm excitation, to evaluate the correction factor. $IC_{50}$ values were calculated using a sigmoidal dose-response curve fit in GraphPad Prism® v5 software. Compounds of formula (I) inhibited phosphorylation of Akt (5473), Akt(T308) and S6RP, as shown in Table 2. These results indicate the ability of the tested compounds to inhibit an PI3K/Akt-pathway dependent prostate neoplasm.

In-cell Western assays for pAkt(5473) and pS6RP are also carried out in a breast cancer cell line with PI3K mutations (PIK3CA-K111N mutation) which overexpresses HER 2 (BT474) cells and a human ductal breast epithelial cell line (T47D cells), in a similar manner to the protocol described above for PC3 cells, in order to assess the ability of the compounds to inhibit the Akt-pathway in two breast cancer cell lines. Compounds of the invention caused inhibition of pAkt(5473) and pS6RP in BT474 and T47D cell lines as determined by these assays. For example, the compound of Example 1 caused inhibition of pAkt(5473) in BT474 and T47D cell lines with $IC_{50}$ values <300 nM, and this compound also caused inhibition of pS6RP in BT474 and T47D cell lines with $IC_{50}$ values <50 nM.

(iv) XTT Assay for Cell Viability

Using a commercial kit from Sigma Aldrich (Catalog #X34251) and following its protocol, PC3 cells in the log phase of growth were employed and seeded at an optimal density of 1000 cell/well on to 96 well plates and incubated for 24 h followed by the addition of compounds of formula (I) in serial dilutions. Compound dilutions were made in DMSO. The cells were incubated with the compounds of formula (I) for 96 h and XTT tetrazolium dye (Sigma, USA) was subsequently added and incubated at 37° C. After the color formation, absorbance was measured at 465 nm in a Spectramax® Gemini spectrophotometer. $EC_{50}$ values were calculated using a sigmoidal dose response curve fit in GraphPad Prism® v5 software. The tested compounds of formula (I) which caused inhibition of PC3 cell proliferation as determined by this assay protocol are shown in Table 2.

XTT assays for cell viability are also determined in BT474 cells and T47D cells, in a similar manner to the protocol described above. The compounds caused inhibition of BT474 and T47D cell proliferation as determined by these assays. For example, the compound of Example 1 caused inhibition of BT474 and T47D cell proliferation with $IC_{50}$ values <100 nM.

(v) In Vivo Pharmacokinetic/Pharmacodynamic (PK/PD) Studies for Oncology

PC3 cells were cultured at 37° C. in a 5% $CO_2$ incubator using Hams F12 K medium. Ten million ($10^7$) cells were injected subcutaneously to the right flank region of athymic male mice (Harlan, age: 6-7 weeks, weight: about 20 g). Tumor bearing mice were randomized when the tumor volume reached about 250 mm$^3$ and three mice were used per each time point. Test compounds of formula (I) were formulated in 40% HPCD in 1×PBS, pH 7.4 and dosed orally at 50 mg/kg single dose (dose volume–10 mL/kg). Plasma and tumor samples were collected at 0 (vehicle control animals), 1, 4 and 24 hours post dosing. Blood was drawn (retro orbital) to a tube containing 0.2% EDTA for plasma collection. The tumor was excised from the mouse and immediately frozen in liquid nitrogen for PD analysis. Tumor and plasma drug concentrations were measured for PK analysis using LC-MS.

Snap frozen tumor samples were pulverized in a mortar (Belart) containing liquid nitrogen and tumor powder was stored at –80° C. until analysis. Pre coated ELISA kits (Cell Signaling Technology; pAKT(T308), CST#7135; pAKT (5473), CST#7134 and pS6RP, CST#7205) were used for PD analysis. Tumor powder was transferred to Eppendorf® tubes and lysis buffer (1 mL) was added to the powder. Protease and phosphatase inhibitors (SIGMA) and phenylmethanesulfonylfluoride (PMSF) were added to tumor powder and mixed by vortexing followed by sonication (15 sec). Samples were kept on an ice bath for 30 min. Supernatant was separated after centrifugation at 10,000 rpm for 20 min at 4° C. Supernatant was re-centrifuged and fresh supernatant was aliquoted to different tubes. Total protein was estimated using a BCA kit (Thermo Scientific) and 50 µg total protein was loaded to each well. ELISA analysis was carried out as per manufacturer's instructions. The detection for pAKT was based on chemiluminescence and pS6RP was based on absorbance. Qualitative assessments of the suppression of pAKT (T308), pAKT(5473), and pS6RP were also carried out by standard Western blot analyses.

The compounds caused suppression of pAkt and pS6RP as measured at 1, 4 and 24 hours after a single dose of 30-50 mg/kg po. For example, the compound of Example 1, at 50 mg/kg po, caused about 50% inhibition of pAkt(5473) at 1 and 4 hours and >50% inhibition of pS6RP at 1, 4 and 24 hours. Also, the compound of Example 2, at 50 mg/kg po, caused about 25-30% inhibition of pAkt(5473) at 4 and 24 hours and >50% inhibition of pS6RP at 1, 4 and 24 hours. The compound of example 51, at 30 mg/kg po, caused >50% inhibition of pS6RP at 2, 4 and 24 hours. Also, the compounds of examples 133, 146, 147, and 228, at 50 mg/kg po, each caused >50% inhibition of pS6RP at 3 and 8 hours. The compounds of examples 133 and 146, at 50 mg/kg po, each showed significant suppression of pAkt(T308) at 8 hours by Western blot analysis.

In vivo pharmacokinetic/pharmacodynamic (PK/PD) studies were also carried out using BT474 tumor cells and the corresponding tumor-bearing xenograft mice, and compounds of the invention were determined to be active in this assay. For example, the compound of example 51, at 30 mg/kg po, caused 30-40% inhibition of pS6RP at 4 and 24 hours. After dosing the compounds for 2 weeks at 40 mg/kg bid po, the compounds of examples 2 and 51 caused significant suppression of pAkt(T308), pAkt(5473) and pS6RP in tumor tissue samples by Western blot analyses.

(vi) In Vivo Efficacy Studies for Oncology (Tumor Growth Suppression)

PC3 cells were cultured at 37° C. in a 5% $CO_2$ incubator using Hams F12 K medium. Five million ($5\times10^6$) cells were implanted subcutaneously to the right flank of athymic male mice (Harlan, age: 6-7 weeks, weight: about 20 g). Tumor bearing mice were randomized when the tumor volume reached about 100 mm$^3$. Ten mice were used per group. Dosage regimen of compounds of formula (I) were scheduled on the basis of the PK, PK-PD and maximum tolerated dose studies. Compounds of formula (I) were formulated using HPCD in PBS, pH 7.4 and dosed orally (dose volume, 10 mL/kg). Solutions of the compounds were prepared immediately before dosing the animals. A vehicle control and a reference compound were included along with test compounds.

The tumor size was measured on alternate days using Vernier® calipers. Assuming tumors to be ellipsoid, the tumor volume was calculated using the formula:

$$V=(D\times d^2)/2$$

where:
V (mm$^3$) is tumor volume
D is longest diameter in mm
d is shortest diameter in mm.

Changes in tumor volume (Δ volumes) for each treated (T) and control (C) group were calculated by subtracting the mean tumor volume on the first day of treatment (starting day) from the mean tumor volume on the specified observation day. These values were used to calculate a percentage growth (% T/C) using the formula:

$$\% \ T/C=(\Delta T/\Delta C)\times 100$$

where ΔT>0, or $$\% \ T/C=(\Delta T/\Delta Ti)\times 100$$

where ΔT<0 and Ti is the mean tumor volume at the start of the experiment.

Percentage tumor growth inhibition was calculated as [100–% T/C]. Percentage body weight change was calculated as [(Body weight on specified observation day–Body weight on starting day)/Body weight on starting day]×100. The compounds suppressed tumor growth in this in vivo efficacy model. For example, the compound of Example 1 caused more than 70% tumor growth inhibition as measured relative to vehicle control group, after 14 days of dosing at 60 mg/kg qd po or at 30 mg/kg bid po, and the compound of Example 2 caused more than 70% tumor growth inhibition as measured relative to vehicle control group after 14 days of dosing at 30 or 60 mg/kg qd po. The compounds of examples 82 and 183 each caused about 60% tumor growth inhibition as measured relative to vehicle control group after 14 days of dosing at 40 mg/kg bid po.

In vivo efficacy studies were also carried out using BT474 tumor cells, in a similar manner to the protocol described above for the PC3 tumor cell in vivo efficacy study. Compounds of the invention suppressed tumor growth in the in vivo BT474 efficacy model. For example, relative to vehicle control group after 14 days of dosing, the compound of Example 2 at 40 mg/kg bid po caused about 65% tumor growth inhibition, and the compound of example 51 at 40 mg/kg bid po caused about 70% tumor growth inhibition.

(vii) In Vivo Efficacy Studies for Inflammation

The ability of compounds of the invention to reduce inflammation is determined by using various animal models that are known in the art. Some examples are as follows:

(a) Inflammatory arthritis. The ability of compounds of the invention to reduce inflammation in inflammatory arthritis is determined by following procedures for the collagen-induced arthritis (CIA) mouse model. See, e.g., the procedure described in Camps et al., Nature Med. 2005, 11, 936-943, which is incorporated herein by reference.

(b) Pulmonary fibrosis. The ability of compounds of the invention to prevent bleomycin-induced pulmonary fibrosis in rats is determined by following the procedures described in Wei et al., Biochem. Biophys. Res. Comm. 2010, 397, 311-317 and Brent et al., Toxicology 2000, 147, 1-13, which are incorporated herein by reference.

(c) Myocardial infarction. The ability of compounds of the invention to reduce inflammation and/or improve healing after myocardial infarction is determined by following the procedures for a mouse model described in Siragusa et al., Circ. Res. 2010, 106, 757-768, which is incorporated herein by reference.

(d) Peritonitis. The ability of compounds of the invention to reduce inflammation in peritonitis is determined by following procedures for the RANTES-induced or thioglycollate-induced peritonitis mouse model, for example as described in Camps et al., Nature Med. 2005, 11, 936-943, which is incorporated herein by reference.

TABLE 2

Data for the Compounds of Examples 1-294

| Ex. | LC-MS M+H+ | LC-MS ret. time (min) | PI3Kα | mTOR | pAkt-T308 | pAkt-S473 | pS6RP | XTT |
|---|---|---|---|---|---|---|---|---|
| 1 | 575.1 | 0.26 | A | A | F | E | D | E |
| 2 | 576.7 | 0.64 | A | A | E | E | E | D |
| 3 | 652.2 | 0.71 | A | B | | | | E |
| 4 | 647.2 | 0.11 | A | A | | | | D |
| 5 | 588.8 | 0.64 | B | A | | | | D |
| 6 | 591.9 | 1.53 | B | A | | | | E |
| 7 | 611.1 | 0.08 | B | A | | | | |
| 8 | 595.2 | 1.28 | C | B | | | | |
| 9 | 576.2 | 0.28 | A | A | | | | D |
| 10 | 607.2 | 0.63 | A | A | | | | |
| 11 | 689.3 | 0.10 | A | A | | | | |
| 12 | 606.2 | 1.17 | A | A | | | | |
| 13 | 623.2 | 0.45 | A | A | | | | |
| 14 | 614.2 | 0.63 | A | A | | | | |
| 15 | 626.2 | 0.92 | A | A | | | | |
| 16 | 555.1 | 0.17 | A | A | | | C | C |
| 17 | 563.1 | 0.64 | B | B | | | | E |
| 18 | 589.2 | 0.13 | C | A | | | | |
| 19 | 651.2 | 0.44 | A | A | E | E | D | D |
| 20 | 637.0 | 0.44 | A | A | E | E | E | E |
| 21 | 592.1 | 0.49 | B | A | | | | E |
| 22 | 577.2 | 0.35 | A | A | E | E | D | D |
| 23 | 666.2 | 0.55 | A | B | | | | F |
| 24 | 574.2 | 0.19 | A | B | E | E | D | D |
| 25 | 622.9 | 0.37 | B | B | | | | F |
| 26 | 647.0 | 0.23 | A | A | | | | D |
| 27 | 632.0 | 0.21 | B | A | | | | D |
| 28 | 592.9 | 0.28 | B | A | | | | D |
| 29 | 592.0 | 0.38 | A | A | | | | D |
| 30 | 592.9 | 0.35 | A | A | | | | D |
| 31 | 651.8 | 0.34 | B | A | | | | E |
| 32 | 705.9 | 0.21 | A | A | | | | F |
| 33 | 629.2 | 0.10 | A | A | E | E | D | D |
| 34 | 652.2 | 0.10 | A | A | | | | D |
| 35 | 595.2 | 0.40 | A | A | E | E | D | D |
| 36 | 668.8 | 0.72 | A | A | | | | D |
| 37 | 633.9 | 0.23 | B | B | | | | E |
| 38 | 669.1 | 0.80 | A | A | | | | D |
| 39 | 651.7 | 0.61 | A | A | | | | D |
| 40 | 591.9 | 1.43 | B | A | | | D | E |
| 41 | 589.2 | 0.27 | A | B | | | D | E |
| 42 | 578.2 | 0.36 | A | A | E | D | E | D |
| 43 | 578.1 | 1.18 | A | A | | | | E |
| 44 | 632.2 | 0.09 | A | A | D | D | D | D |
| 45 | 602.7 | 0.26 | A | A | | | | D |
| 46 | 575.0 | 0.37 | A | A | E | D | D | D |
| 47 | 590.7 | 0.87 | B | C | | | | |
| 48 | 602.9 | 1.35 | B | B | | | | |
| 49 | 629.8 | 0.39 | A | A | E | E | D | D |
| 50 | 615.7 | 0.54 | A | B | | | | |
| 51 | 563.1 | 1.49 | A | A | | | F | E |
| 52 | 579.1 | 0.64 | A | B | | | | E |
| 53 | 562.7 | 0.42 | B | B | | | | E |
| 54 | 592.7 | 0.65 | A | B | | | | E |
| 55 | 577.9 | 0.30 | A | A | | | D | E |
| 56 | 563.0 | 0.70 | B | A | | | | |
| 57 | 578.0 | 1.26 | A | C | | | | |
| 58 | 573.8 | 0.27 | A | A | | | | F |
| 59 | 624.2 | 0.45 | A | A | | | | D |
| 60 | 603.8 | 0.44 | A | A | | | | E |
| 61 | 593.2 | 1.22 | B | C | | | | |
| 62 | 588.3 | 0.11 | A | A | | | D | E |
| 63 | 634.2 | 0.11 | A | A | | | E | E |
| 64 | 613.2 | 1.28 | C | C | | | | |
| 65 | 592.2 | 0.27 | A | A | | | D | E |
| 66 | 631.2 | 0.12 | A | A | | | D | E |
| 67 | 631.3 | 0.08 | A | A | | | | E |
| 68 | 592.2 | 0.39 | A | A | | | | F |
| 69 | 629.2 | 0.10 | A | A | | | D | E |
| 70 | 632.3 | 0.16 | B | B | | | | F |
| 71 | 577.2 | 1.62 | B | A | | | | |
| 72 | 631.2 | 0.10 | A | A | | | D | E |
| 73 | 633.3 | 0.16 | A | A | | | | F |
| 74 | 579.2 | 0.71 | A | B | | | | F |
| 75 | 605.1 | 0.45 | A | A | | | | D |
| 76 | 590.1 | 0.29 | A | A | | | | |
| 77 | 674.4 | 0.16 | A | A | | | | |
| 78 | 593.2 | 1.20 | A | A | | | | |
| 79 | 630.8 | 0.10 | C | A | | | | F |
| 80 | 563.1 | 1.49 | A | A | | | D | D |
| 81 | 676.0 | 0.10 | A | A | | | D | F |
| 82 | 596.2 | 0.52 | A | A | | | C | C |
| 83 | 634.3 | 0.14 | B | A | | | C | C |
| 84 | 593.2 | 0.25 | B | A | | | C | C |
| 85 | 579.1 | 0.46 | A | A | | | C | C |
| 86 | 575.2 | 0.13 | B | A | | | C | C |
| 87 | 595.2 | 1.32 | B | A | | | D | D |
| 88 | 561.1 | 0.13 | B | A | | | D | C |
| 89 | 564.2 | 0.21 | A | A | | | C | C |
| 90 | 564.2 | 0.73 | blank | | | | | |
| 91 | 610.2 | 0.69 | A | A | | | C | C |
| 92 | 591.2 | 0.17 | A | A | | | C | C |
| 93 | 589.3 | 0.18 | A | A | | | C | C |
| 94 | 606.2 | 0.35 | A | A | | | C | C |
| 95 | 604.3 | 1.34 | B | B | | | F | D |
| 96 | 576.2 | 0.24 | A | A | | | C | C |
| 97 | 595.2 | 0.31 | A | A | | | C | C |
| 98 | 593.2 | 0.25 | B | A | | | C | C |
| 99 | 611.3 | 0.80 | A | A | | | C | C |
| 100 | 606.3 | 0.19 | A | A | | | C | C |
| 101 | 594.3 | 0.61 | A | A | | | C | C |
| 102 | 593.5 | 0.73 | A | A | | | C | C |
| 103 | 592.2 | 0.28 | A | A | | | C | C |
| 104 | 670.2 | 1.30 | A | A | | | D | C |
| 105 | 623.2 | 0.44 | B | A | | | C | C |

TABLE 2-continued

Data for the Compounds of Examples 1-294

| Ex. | LC-MS M + H⁺ | LC-MS ret. time (min) | PI3Kα | mTOR | pAkt-T308 | pAkt-S473 | pS6RP | XTT |
|---|---|---|---|---|---|---|---|---|
| 106 | 611.3 | 1.37 | A | A | | | C | C |
| 107 | 610.3 | 0.81 | A | A | | | C | C |
| 108 | 613.2 | 0.68 | B | A | | | | |
| 109 | 610.2 | 0.81 | B | B | | | | |
| 110 | 608.2 | 0.21 | C | A | | | | |
| 111 | 594.3 | 1.38 | A | A | | C | C | C |
| 112 | 611.2 | 1.43 | A | C | | | F | D |
| 113 | 596.3 | 0.64 | A | B | D | D | D | C |
| 114 | 581.3 | 1.09 | B | B | | | | |
| 115 | 653.3 | 1.30 | A | B | | | C | C |
| 116 | 607.2 | 0.49 | B | B | | | | F |
| 117 | 624.2 | 1.43 | A | A | | | C | D |
| 118 | 669.1 | 0.77 | A | A | | F | C | C |
| 119 | 606.3 | 0.45 | A | C | | | | |
| 120 | 593.2 | 0.65 | A | A | | | C | C |
| 121 | 592.2 | 0.42 | A | A | | | C | C |
| 122 | 596.2 | 0.86 | B | B | | | | |
| 123 | 594.2 | 0.18 | B | A | | | C | C |
| 124 | 597.4 | 0.17 | A | A | | | | C |
| 125 | 606.3 | 0.80 | C | B | | | | |
| 126 | 624.2 | 1.30 | C | C | | | | |
| 127 | 609.1 | 0.36 | A | A | | | C | C |
| 128 | 603.4 | 0.48 | C | A | | | C | D |
| 129 | 579.3 | 0.86 | A | B | | | D | F |
| 130 | 670.2 | 0.40 | A | A | | | C | C |
| 131 | 610.3 | 0.74 | A | B | | | C | C |
| 132 | 621.4 | 0.74 | C | B | | | C | C |
| 133 | 593.2 | 0.20 | A | A | D | F | C | C |
| 134 | 596.2 | 0.35 | A | A | | | C | C |
| 135 | 611.2 | 1.39 | A | A | | | | C |
| 136 | 595.2 | 1.36 | C | C | | | | |
| 137 | 592.2 | 0.24 | B | B | | | C | C |
| 138 | 589.4 | 0.36 | A | A | | | | C |
| 139 | 611.2 | 049 | C | C | | | | |
| 140 | 594.4 | 0.42 | A | C | | | | |
| 141 | 614.2 | 0.80 | C | B | | | | |
| 142 | 591.3 | 1.44 | B | B | | | | |
| 143 | 610.2 | 1.04 | B | A | | | | C |
| 144 | 607.2 | 0.57 | B | A | | | | |
| 145 | 611.2 | 0.92 | A | A | | | | |
| 146 | 610.2 | 0.55 | B | A | D | D | | C |
| 147 | 623.2 | 0.37 | B | A | C | D | | |
| 148 | 592.2 | 0.36 | A | A | | | | |
| 149 | 581.2 | 1.21 | B | B | | | | |
| 150 | 591.2 | 0.24 | A | A | | | | |
| 151 | 622.2 | 0.57 | B | B | | | | |
| 152 | 592.2 | 0.20 | A | A | D | F | | D |
| 153 | 593.5 | 0.38 | A | A | | | | |
| 154 | 594.3 | 0.32 | A | A | | | | |
| 155 | 574.2 | 0.35 | A | A | | D | | C |
| 156 | 592.4 | 0.49 | B | B | | | | |
| 157 | 624.2 | 0.52 | A | A | | | | |
| 158 | 618.4 | 0.13 | A | B | | | | |
| 159 | 563.8 | 0.13 | A | C | | D | | D |
| 160 | 581.5 | 0.77 | A | B | | F | | D |
| 161 | 588.4 | 0.10 | A | A | | | | |
| 162 | 605.4 | 0.20 | A | A | | | | |
| 163 | 603.8 | 0.38 | A | A | | | | |
| 164 | 591.9 | 0.27 | A | A | | | | |
| 165 | 588.2 | 0.12 | A | A | | | | |
| 166 | 606.3 | 0.17 | A | A | | | | |
| 167 | 606.2 | 0.10 | A | A | | | | |
| 168 | 592.3 | 0.34 | A | A | | | | |
| 169 | 603.8 | 0.11 | A | A | | | | |
| 170 | 621.8 | 0.52 | A | B | | | | |
| 171 | 597.1 | 0.14 | C | C | | | | |
| 172 | 596.3 | 0.29 | A | C | | | | |
| 173 | 610.3 | 0.35 | A | A | | | | |
| 174 | 611.3 | 0.30 | B | A | | | | |
| 175 | 593.3 | 0.63 | A | B | | | | |
| 176 | 594.4 | 0.44 | A | B | | | | |
| 177 | 589.2 | 0.09 | A | A | | | | |
| 178 | 607.3 | 0.09 | B | A | | | | |
| 179 | 497.2 | 0.17 | B | A | | | C | C |
| 180 | 527.2 | 0.22 | A | A | | | C | C |
| 181 | 557.3 | 0.27 | B | A | | | C | C |
| 182 | 545.2 | 0.35 | B | A | | | | |
| 183 | 593.1 | 0.23 | A | A | | | C | C |
| 184 | 647.2 | 0.11 | A | A | | | C | C |
| 185 | 647.3 | 0.08 | A | A | | | C | C |
| 186 | 661.3 | 0.10 | A | A | | | C | C |
| 187 | 644.1 | 0.09 | A | A | | | C | C |
| 188 | 644.3 | 0.07 | A | A | | | C | C |
| 189 | 617.2 | 0.11 | C | A | | | C | C |
| 190 | 619.9 | 0.09 | B | A | | | C | C |
| 191 | 660.3 | 0.18 | C | B | | | C | C |
| 192 | 618.3 | 0.10 | B | A | | | | |
| 193 | 617.3 | 0.09 | A | A | | | C | C |
| 194 | 616.3 | 0.07 | A | A | | | C | C |
| 195 | 646.5 | 0.17 | B | A | | | | D |
| 196 | 646.3 | 0.25 | B | A | | | D | D |
| 197 | 616.3 | 0.08 | A | A | | | C | C |
| 198 | 661.5 | 0.10 | A | A | | | C | C |
| 199 | 645.4 | 0.08 | A | A | | | C | C |
| 200 | 661.3 | 0.13 | A | A | | | C | C |
| 201 | 620.3 | 0.35 | B | A | | | F | F |
| 202 | 550.3 | 0.28 | A | A | | | C | C |
| 203 | 611.3 | 0.34 | A | A | | | C | C |
| 204 | 619.2 | 0.51 | A | A | | | D | D |
| 205 | 665.4 | 0.10 | A | A | | | C | C |
| 206 | 607.3 | 0.35 | A | A | | | C | C |
| 207 | 662.3 | 0.11 | A | A | | | C | D |
| 208 | 634.2 | 0.11 | A | A | | | C | C |
| 209 | 634.3 | 0.10 | A | A | | | C | C |
| 210 | 665.3 | 0.14 | A | A | | | C | C |
| 211 | 665.4 | 0.22 | A | A | | | C | D |
| 212 | 647.4 | 0.09 | B | B | | | | |
| 213 | 680.3 | 0.33 | A | A | | | C | C |
| 214 | 625.2 | 0.48 | A | A | | | C | D |
| 215 | 579.4 | 0.21 | B | B | | | C | C |
| 216 | 608.2 | 0.45 | A | A | | | C | C |
| 217 | 636.1 | 0.08 | A | A | | | C | C |
| 218 | 612.1 | 0.81 | A | B | | | | |
| 219 | 611.2 | 0.44 | B | B | | | | |
| 220 | 661.4 | 0.19 | B | A | | | C | C |
| 221 | 679.4 | 0.21 | B | B | | | | |
| 222 | 621.1 | 1.15 | A | A | | | C | C |
| 223 | 588.2 | 1.34 | A | A | | | C | C |
| 224 | 604.9 | 1.04 | A | A | | | C | C |
| 225 | 677.2 | 0.51 | B | A | | | | |
| 226 | 618.3 | 0.40 | A | A | | | | C |
| 227 | 625.2 | 0.41 | C | B | | | | |
| 228 | 611.2 | 0.34 | A | A | | F | | |
| 229 | 634.2 | 0.36 | A | A | | | | |
| 230 | 619.1 | 0.58 | A | A | | | | |
| 231 | 636.3 | 0.83 | B | A | | | | |
| 232 | 605.1 | 0.30 | A | A | | | | |
| 233 | 549.7 | 0.55 | A | B | | | | D |
| 234 | 603.8 | 0.11 | A | A | | | | C |
| 235 | 606.7 | 0.20 | A | A | | | | |
| 236 | 620.6 | 0.19 | A | A | | | | |
| 237 | 593.2 | 0.19 | A | A | | | C | C |
| 238 | 596.3 | 0.50 | A | A | | | C | C |
| 239 | 595.2 | 1.23 | B | B | | | | |
| 240 | 593.2 | 0.23 | A | A | | | | C |
| 241 | 610.1 | 0.71 | A | B | | | C | C |
| 242 | 623.2 | 0.42 | A | A | | | C | C |
| 243 | 592.2 | 0.32 | A | A | | | C | C |
| 244 | 611.3 | 1.03 | A | A | | | C | C |
| 245 | 669.1 | 0.70 | A | B | | | C | C |
| 246 | 610.2 | 0.62 | B | A | | | C | C |
| 247 | 581.2 | 0.66 | B | B | | | C | C |
| 248 | 611.2 | 1.16 | A | A | | | | |
| 249 | 595.2 | 0.29 | B | A | | | | |

TABLE 2-continued

Data for the Compounds of Examples 1-294

| Ex. | LC-MS M + H⁺ | LC-MS ret. time (min) | PI3Kα | mTOR | pAkt-T308 | pAkt-S473 | pS6RP | XTT |
|---|---|---|---|---|---|---|---|---|
| 250 | 594.2 | 0.28 | A | A | | | | C |
| 251 | 594.2 | 0.14 | C | A | | | | |
| 252 | 610.1 | 1.33 | B | B | | | | |
| 253 | 670.2 | 1.00 | A | C | | D | | |
| 254 | 607.2 | 0.28 | C | B | | | | |
| 255 | 610.2 | 0.70 | B | A | | | | C |
| 256 | 611.2 | 0.33 | B | B | | | | C |
| 257 | 623.2 | 0.46 | A | A | | | | C |
| 258 | 622.2 | 0.88 | B | B | | | | |
| 259 | 622.2 | 0.56 | B | A | | | | C |
| 260 | 592.3 | 0.30 | A | A | | | | C |
| 261 | 593.2 | 0.31 | A | A | | | | |
| 262 | 593.7 | 0.16 | A | A | | | | |
| 263 | 624.2 | 0.46 | A | A | | | | |
| 264 | 592.8 | 0.28 | A | A | | | | |
| 265 | 581.4 | 0.95 | B | B | | | | D |
| 266 | 595.2 | 1.28 | B | B | | | | |
| 267 | 592.4 | 0.50 | A | A | | F | | C |
| 268 | 592.4 | 0.40 | A | A | | F | | C |
| 269 | 623.4 | 0.26 | A | A | | | | |
| 270 | 621.8 | 0.44 | B | B | | | | |
| 271 | 605.8 | 0.12 | A | A | | | | |
| 272 | 606.3 | 0.11 | A | B | | | | |
| 273 | 595.9 | 0.29 | A | A | | | | |
| 274 | 611.1 | 0.60 | A | B | | | | C |
| 275 | 625.1 | 0.72 | B | A | | | | C |
| 276 | 639.2 | 0.61 | B | B | | | | |
| 277 | 636.3 | 0.62 | A | A | | | | |
| 278 | 611.2 | 0.40 | A | A | | | | |
| 279 | 611.2 | 0.22 | B | B | | | | |
| 280 | 611.2 | 0.37 | B | A | | D | | |
| 281 | 613.4 | 1.30 | C | C | | | | |
| 282 | 599.4 | 1.18 | B | C | | | D | |
| 283 | 633.3 | 0.12 | C | B | | | C | C |
| 284 | 610.6 | 0.14 | C | B | | | | |
| 285 | 527.1 | 0.09 | A | A | | | C | D |
| 286 | 638.2 | 0.08 | A | A | | | C | C |
| 287 | 650.9 | 0.10 | C | C | | | | |
| 288 | 624.0 | 0.07 | B | A | | | | |
| 289 | 623.8 | 0.07 | B | A | | | C | C |
| 290 | 573.3 | 0.24 | B | A | | | | |
| 291 | 561.2 | 0.12 | A | A | F | | E | E |
| 292 | 604.2 | 0.34 | | A | | | | |
| 293 | 579.2 | 0.73 | A | A | | | | |
| 294 | 564.2 | 0.19 | A | A | | | | |

Activities (nM):
A: IC₅₀ <50;
B: IC₅₀ = 50-200;
C: IC₅₀ = 201-10,000;
D: IC₅₀ <100;
E: IC₅₀ = 100-500;
F: IC₅₀ = 501-5000.

The present application thereby provides a compound of formula (I):

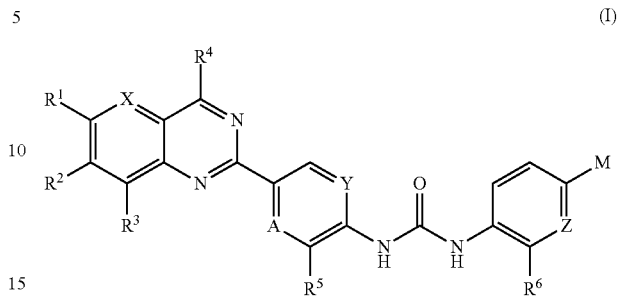

wherein, $R^1$ is H, F, Cl, or $OCH_3$; $R^2$ is H, optionally substituted aryl, optionally substituted heterocycle, optionally substituted heteroaryl, optionally substituted alkyl, optionally substituted alkenyl, optionally substituted alkynyl, optionally substituted alkylamino, optionally substituted dialkylamino, optionally substituted arylamino, optionally substituted heteroarylamino, optionally substituted heterocycle-amino, optionally substituted alkylcarbonylamino, optionally substituted alkylsulfonylamino, optionally substituted alkylthio, optionally substituted alkylsulfonyl, optionally substituted alkoxy, optionally substituted hydroxyalkyl, optionally substituted aryloxy, optionally substituted heteroaryloxy, optionally substituted heterocycle-oxy, optionally substituted alkylaminocarbonyl, optionally substituted arylaminocarbonyl, optionally substituted heteroarylaminocarbonyl, optionally substituted heterocycle-aminocarbonyl, or C(O)-(optionally substituted heterocycle) and $R^3$ is H, halogen, CN, OH, $NH_2$, $NHCH_3$, or $OCH_3$; or $R^2$ is H, halogen, CN, OH, $NH_2$, $NHCH_3$, or $OCH_3$ and $R^3$ is H, optionally substituted aryl, optionally substituted heterocycle, optionally substituted heteroaryl, optionally substituted alkyl, optionally substituted alkenyl, optionally substituted alkynyl, optionally substituted alkylamino, optionally substituted dialkylamino, optionally substituted arylamino, optionally substituted heteroarylamino, optionally substituted heterocycle-amino, optionally substituted alkylcarbonylamino, optionally substituted alkylsulfonylamino, optionally substituted alkylthio, optionally substituted alkylsulfonyl, optionally substituted alkoxy, optionally substituted hydroxyalkyl, optionally substituted aryloxy, optionally substituted heteroaryloxy, optionally substituted heterocycle-oxy, optionally substituted alkylaminocarbonyl, optionally substituted arylaminocarbonyl, optionally substituted heteroarylaminocarbonyl, optionally substituted heterocycle-aminocarbonyl, or C(O)-(optionally substituted heterocycle); $R^4$ is optionally substituted morpholine or thiomorpholine; $R^5$ is H, F, or Cl; $R^6$ is H, F or Cl; M is selected from the group consisting of

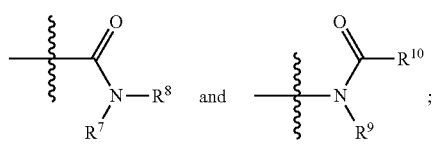

$R^7$ and $R^8$ are, independently, H, or optionally substituted alkyl; or $R^7$ and $R^8$ are joined to form an optionally-substituted heterocycle containing 1 or 2 nitrogen atoms, 0 or 1 oxygen atom, 0 or 1 sulfur atom, 0 or 1 S(O) fragment, 0 or 1 S(O)₂ fragment, and 3 to 6 carbon atoms; $R^9$ is H or alkyl; $R^{10}$ is H or alkyl optionally substituted with OH, NH$_2$, NHCH$_3$, N(CH$_3$)$_2$, halogen, alkoxy, CF$_3$, OCF$_3$, or CN; or R$^9$ and R$^{10}$ are joined to form an optionally-substituted heterocycle wherein the fragment —R$^9$-R$^{10}$— is optionally substituted —CH$_2$CH$_2$CH$_2$—, —CH$_2$CH$_2$CH$_2$CH$_2$—, or —CH$_2$CH$_2$CH$_2$ CH$_2$CH$_2$—; A is CH or C—F; X is N, CH, C—F or C—Cl; Y is N, CH, C—F or C—Cl; and Z is N, CH, C—F, or C—Cl; or a pharmaceutically acceptable salt or solvate thereof. In one embodiment, R$^4$ is morpholine. In another embodiment, R$^4$ is morpholine substituted by one or more methyl. In a further embodiment, R$^4$ is:

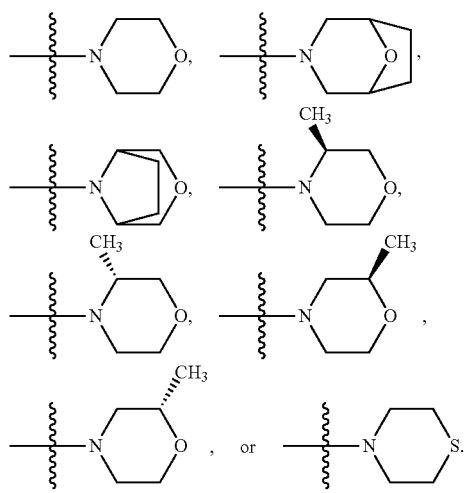

In still another embodiment, R$^7$ and R$^8$ are joined to form an optionally substituted ring containing at least 1 nitrogen atom. In yet a further embodiment, R$^7$ and R$^8$ are joined to form optionally substituted piperidinyl, pyrrolidinyl, azepanyl, piperazinyl, homopiperazinyl, morpholinyl, or thiomorpholinyl. In another embodiment,
R$^7$ and R$^8$ are, independently, H or alkyl optionally substituted with OH, halogen, alkoxy, CF$_3$, OCF$_3$, CN, alkylamino, dialkylamino, amino, alkylsulfonyl, alkylthio, alkylcarbonylamino, alkylsulfonylamino, alkylaminocarbonyl, or alkylaminosulfonyl. In still a further embodiment, R$^7$ and R$^8$ are, independently, H or alkyl optionally substituted with CH$_2$OH, CH$_2$CH$_2$OH, F, Cl, CN, NH$_2$, NH(CH$_3$), N(CH$_3$)$_2$, CONHCH$_3$, NHCOCH$_3$, NHSO$_2$CH$_3$, OCH$_3$, OCF$_3$, or SO$_2$CH$_3$. In yet another embodiment, R$^7$ and R$^8$ are joined to form a heterocycle optionally substituted with 1 to 3 groups independently selected from the group consisting of OH, halogen, alkoxy, CF$_3$, OCF$_3$, CN, alkylamino, dialkylamino, amino, hydroxyalkyl, alkylsulfonyl, alkylthio, aminoalkyl, alkylaminoalkyl, dialkylaminoalkyl, alkylcarbonylamino, alkylsulfonylamino, alkylsulfonylalkyl, alkylaminocarbonyl, alkylaminosulfonyl, and cyanoalkyl. In a further embodiment, the R$^7$+R$^8$ heterocycle is substituted with 1 to 3 groups independently selected from the group consisting of OH, CH$_2$OH, CH$_2$CH$_2$OH, F, Cl, CN, NH$_2$, NH(CH$_3$), N(CH$_3$)$_2$, CH$_2$N(CH$_3$)$_2$, CH$_2$CH$_2$N(CH$_3$)$_2$, CONHCH$_3$, NHCOCH$_3$, NHSO$_2$CH$_3$, CH$_2$CN, CH(CH$_3$)CN, C(CH$_3$)$_2$CN, OCH$_3$, OCF$_3$, and SO$_2$CH$_3$. In yet another embodiment, R$^5$ and R$^6$ are both H. In a further embodiment, R$^7$ and R$^8$ are both CH$_3$. In a further embodiment, R$^2$ or R$^3$ is of the structure

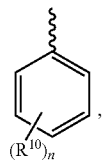

wherein n is 1 to 5; each R$^{10}$ is independently selected from the group consisting of OH, halogen, alkoxy, CF$_3$, OCF$_3$, CN, alkylamino, dialkylamino, hydroxyalkyl, alkylsulfonyl, alkylthio, aminoalkyl, alkylaminoalkyl, dialkylaminoalkyl, alkylcarbonylamino, alkylsulfonylamino, alkylsulfonylalkyl, alkylaminocarbonyl, alkylaminosulfonyl, or cyanoalkyl. In still another embodiment, the R$^2$ or R$^3$ substituted phenyl is 3- or 4-substituted. In yet a further embodiment, the R2 or R$^3$ phenyl is substituted with OH, CH$_2$OH, CH$_2$CH$_2$OH, F, Cl, CN, N(CH$_3$)$_2$, CH$_2$N(CH$_3$)$_2$, CH$_2$CH$_2$N(CH$_3$)$_2$, CONHCH$_3$, NHCOCH$_3$, NHSO$_2$CH$_3$, CH$_2$CN, CH(CH$_3$)CN, C(CH$_3$)$_2$CN, OCH$_3$, OCF$_3$, or SO$_2$CH$_3$. In another embodiment, R$^2$ or R$^3$ is optionally substituted heterocycle or heteroaryl. In still a further embodiment, R$^2$ or R$^3$ is heteroaryl substituted with 1 to 3 R$^{11}$ groups independently selected from the group consisting of OH, halogen, alkoxy, CF$_3$, OCF$_3$, CN, alkylamino, dialkylamino, hydroxyalkyl, alkylsulfonyl, alkylthio, aminoalkyl, alkylaminoalkyl, dialkylaminoalkyl, alkylcarbonylamino, alkylsulfonylamino, alkylsulfonylalkyl, alkylaminocarbonyl, alkylaminosulfonyl, and cyanoalkyl. In yet another embodiment, R$^2$ or R$^3$ is of the formula

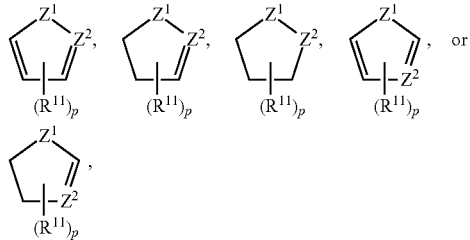

wherein Z$^1$ is O, S, or NR$^{12}$; Z$^2$ is CH or N; R$^{12}$ is absent, H or alkyl; p is 0 to 2; and each R$^{11}$ is, independently, selected from the group consisting of OH, halogen, alkoxy, CF$_3$, OCF$_3$, CN, alkylamino, dialkylamino, hydroxyalkyl, alkylsulfonyl, alkylthio, aminoalkyl, alkylaminoalkyl, dialkylaminoalkyl, alkylcarbonylamino, alkylsulfonylamino, alkylsulfonylalkyl, alkylaminocarbonyl, alkylaminosulfonyl, and cyanoalkyl. In a further embodiment, R$^2$ or R$^3$ is selected from the group consisting of pyrazole, imidazole, pyrrole, thiophene and furan. In a further embodiment, R$^2$ or R$^3$ is selected from the group consisting of pyrazole and imidazole. In another embodiment, R$^2$ or R$^3$ is substituted with CH$_2$OH, CH$_2$CH$_2$OH, F, Cl, CN, N(CH$_3$)$_2$, CH$_2$N(CH$_3$)$_2$, CH$_2$CH$_2$N (CH$_3$)$_2$, CONHCH$_3$, NHCOCH$_3$, NHSO$_2$CH$_3$, CH$_2$CN, CH(CH$_3$)CN, C(CH$_3$)$_2$CN, OCH$_3$, OCF$_3$, or SO$_2$CH$_3$. In a further embodiment, R$^2$ or R$^3$ is selected from the group consisting of

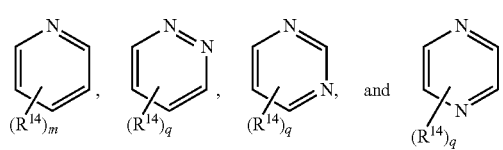

wherein, m is 0 to 4; q is 0 to 3; each $R^{14}$ is, independently, selected from the group consisting of OH, halogen, alkoxy, $CF_3$, $OCF_3$, CN, alkylamino, dialkylamino, hydroxyalkyl, alkylsulfonyl, alkylthio, aminoalkyl, alkylaminoalkyl, dialkylaminoalkyl, alkylcarbonylamino, alkylsulfonylamino, alkylsulfonylalkyl, alkylaminocarbonyl, alkylaminosulfonyl, and cyanoalkyl. In yet another embodiment, $R^2$ or $R^3$ is selected from the group consisting of piperidine, piperazine, morpholine, pyridine, pyrimidine, and pyridazine. In still a further embodiment, $R^2$ or $R^3$ is substituted with $CH_2OH$, $CH_2CH_2OH$, F, Cl, CN, $N(CH_3)_2$, $CH_2N(CH_3)_2$, $CH_2CH_2N(CH_3)_2$, $CONHCH_3$, $NHCOCH_3$, $NHSO_2CH_3$, $CH_2CN$, $CH(CH_3)CN$, $C(CH_3)_2CN$, $OCH_3$, $OCF_3$, or $SO_2CH_3$. In another embodiment, the compound of formula (II), wherein $R^1$ is H or F

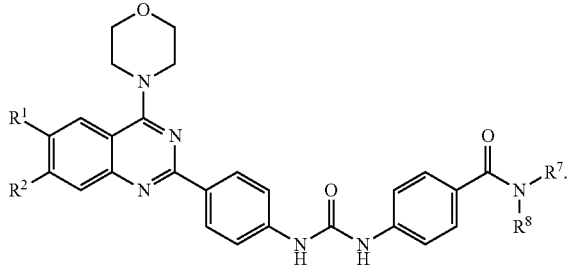

(II)

In a further embodiment, the compound is of formula (III), wherein $R^1$ is H or F

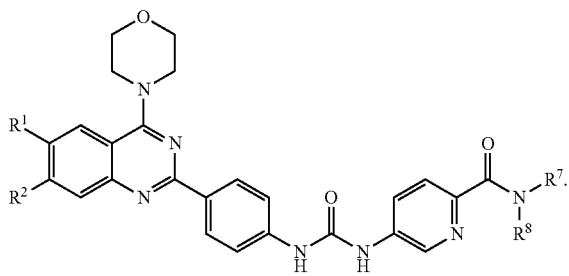

(III)

In another embodiment, the compound is of formula (IV)

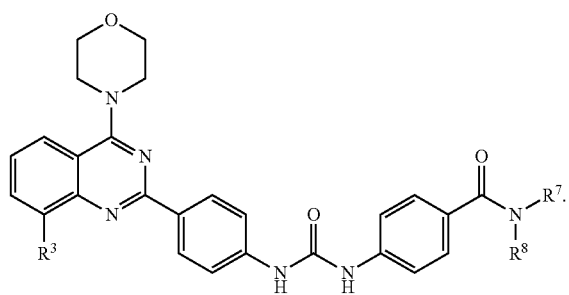

(IV)

In still a further embodiment, the compound is of formula (V), wherein $R^1$ and $R^6$ are independently H or F

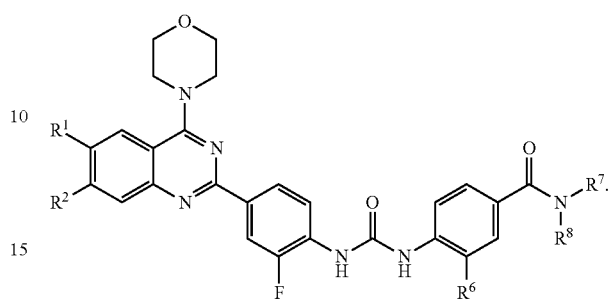

(V)

In yet a further embodiment, the compound is of formula (VI), wherein one of $R^5$ or $R^6$ is F

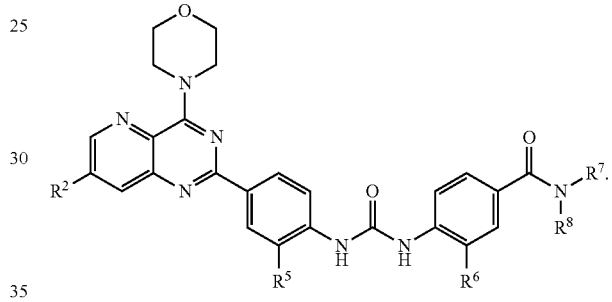

(VI)

In still another embodiment, M is

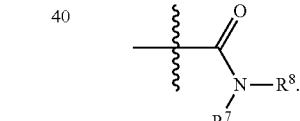

In yet another embodiment, M is

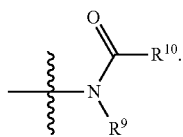

In a further embodiment, the compound is a salt of an acid. In another embodiment, the compound is a salt of an acid is selected from the group consisting of acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, trifluoroacetic, and camphorsulfonic. In yet a further embodiment, the compound d is N,N-Dimethyl-4-{3-[4-(4-morpholin-4-yl-7-pyrimidin-5-yl-quinazolin-2-yl)-phenyl]-ureido}-benzamide; N,N-Dimethyl-4-(3-{4-[7-(5-methyl-furan-2-yl)-4-morpholin-4-yl-quinazolin-2-yl]-phenyl}-ureido)-benzamide; 4-(3-{5-[7-

(3-Methanesulfonyl-phenyl)-4-morpholin-4-yl-quinazolin-2-yl}-pyridin-2-yl]-ureido)-N,N-dimethyl-benzamide; 1-[4-(6-Fluoro-4-morpholin-4-yl-7-pyridin-3-yl-quinazolin-2-yl)-phenyl]-3-[4-(4-methyl-piperazine-1-carbonyl)-phenyl]-urea; 4-(3-{4-[8-(3-Hydroxy-phenyl)-4-morpholin-4-yl-quinazolin-2-yl]-phenyl}-ureido)-N,N-dimethyl-benzamide; 4-(3-{4-[8-(6-Fluoro-pyridin-3-yl)-4-morpholin-4-yl-quinazolin-2-yl]-phenyl}-ureido)-N,N-dimethyl-benzamide; 2-{4-[3-(4-Dimethylcarbamoyl-phenyl)-ureido]-phenyl}-4-morpholin-4-yl-quinazoline-7-carboxylic acid (2-dimethylamino-ethyl)-amide; 4-(3-{2-Fluoro-4-[7-(5-methyl-furan-2-yl)-4-morpholin-4-yl-quinazolin-2-yl]-phenyl}-ureido)-N,N-dimethyl-benzamide; N,N-Dimethyl-4-{3-[4-(4-morpholin-4-yl-7-pyrimidin-5-yl-pyrido[3,2-d]pyrimidin-2-yl)-phenyl]-ureido}-benzamide; 5-(2-(4-(3-(4-(dimethylcarbamoyl)phenyl)ureido)phenyl)-4-morpholino-quinazolin-7-yl)furan-2-carboxylic acid; N,N-dimethyl-4-(3-(4-(7-(5-(4-methylpiperazine-1-carbonyl)furan-2-yl)-4-morpholino-quinazolin-2-yl)phenyl)ureido)-benzamide; 4-(3-(4-(7-(5-cyanofuran-2-yl)-4-morpholino-quinazolin-2-yl)-3-fluorophenyl)ureido)-N,N-dimethyl-benzamide; 4-(3-(4-(7-(5-acetylfuran-2-yl)-4-morpholino-quinazolin-2-yl)phenyl)ureido)-2-fluoro-N,N-dimethyl-benzamide; 4-(3-(2,3-difluoro-4-(7-(1-methyl-1H-pyrazol-4-yl)-4-morpholino-pyrido[3,2-d]pyrimidin-2-yl)phenyl)ureido)-N,N-dimethyl-benzamide; 4-(3-(2-fluoro-4-(7-(5-(1-hydroxyethyl)furan-2-yl)-4-morpholino-pyrido[3,2-d]pyrimidin-2-yl)phenyl)ureido)-N,N-dimethyl-benzamide; 4-(3-(4-(7-(2-hydroxypropan-2-yl)-4-morpholino-quinazolin-2-yl)phenyl)ureido)-N,N-dimethyl-benzamide; N-(4-(3-(4-(7-(5-methylfuran-2-yl)-4-morpholino-quinazolin-2-yl)phenyl)ureido)-phenyl)-acetamide; 1-(4-(7-(5-methylfuran-2-yl)-4-morpholino-quinazolin-2-yl)phenyl)-3-(4-(2-oxopyrrolidin-1-yl)phenyl)urea; 4-(3-{4-[7-(3-Methanesulfonyl-phenyl)-4-morpholin-4-yl-quinazolin-2-yl]-phenyl}-ureido)-N,N-dimethyl-benzamide; 4-(3-{4-[7-(3-Methanesulfonyl-phenyl)-4-morpholin-4-yl-quinazolin-2-yl]-phenyl}-ureido)-N-methyl-benzamide; 4-(3-{4-[7-(2-Fluoro-pyridin-3-yl)-4-morpholin-4-yl-quinazolin-2-yl]-phenyl}-ureido)-N,N-dimethyl-benzamide; N,N-Dimethyl-4-(3-{4-[7-(1-methyl-1H-pyrazol-4-yl)-4-morpholin-4-yl-quinazolin-2-yl]-phenyl}-ureido)-benzamide; 4-(3-{4-[7-(3-Methanesulfonylamino-phenyl)-4-morpholin-4-yl-quinazolin-2-yl]-phenyl}-ureido)-N,N-dimethyl-benzamide; N,N-Dimethyl-4-{3-[4-(4-morpholin-4-yl-7-pyridin-3-yl-quinazolin-2-yl)-phenyl]-ureido}-benzamide; 4-(3-{4-[7-(3-Methanesulfonyl-phenyl)-4-morpholin-4-yl-quinazolin-2-yl]-phenyl}-ureido)-benzamide; 1-{4-[7-(2-Fluoro-pyridin-3-yl)-4-morpholin-4-yl-quinazolin-2-yl]-phenyl}-3-[4-(4-methyl-piperazine-1-carbonyl)-phenyl]-urea; 1-[4-(4-Methyl-piperazine-1-carbonyl)-phenyl]-3-{4-[7-(1-methyl-1H-pyrazol-4-yl)-4-morpholin-4-yl-quinazolin-2-yl]-phenyl}-urea; 5-(3-{4-[7-(2-Fluoro-pyridin-3-yl)-4-morpholin-4-yl-quinazolin-2-yl]-phenyl}-ureido)-pyridine-2-carboxylic acid dimethylamide; 4-{3-[4-(6-Fluoro-4-morpholin-4-yl-7-pyridin-3-yl-quinazolin-2-yl)-phenyl]-ureido}-N,N-dimethyl-benzamide; 4-{3-[4-(6-Fluoro-4-morpholin-4-yl-7-pyrimidin-5-yl-quinazolin-2-yl)-phenyl]-ureido}-N,N-dimethyl-benzamide; 5-(3-{4-[7-(3-Methanesulfonyl-phenyl)-4-morpholin-4-yl-quinazolin-2-yl]-phenyl}-ureido)-pyridine-2-carboxylic acid dimethylamide; 1-(4-(4-methylpiperazine-1-carbonyl)phenyl)-3-(4-(7-(3-(methylsulfonyl)phenyl)-4-morpholino-quinazolin-2-yl)phenyl)urea; 1-[4-(4-Methyl-piperazine-1-carbonyl)-phenyl]-3-[4-(4-morpholin-4-yl-7-pyridin-3-yl-quinazolin-2-yl)-phenyl]-urea; 4-(3-{4-[7-(5-Methanesulfonyl-pyridin-3-yl)-4-morpholin-4-yl-quinazolin-2-yl]-phenyl}-ureido)-N,N-dimethyl-benzamide; 4-(3-[4-{6-Fluoro-7-(1-methyl-1H-pyrazol-4-yl)-4-morpholin-4-yl-quinazolin-2-yl]-phenyl}-ureido)-N,N-dimethyl-benzamide; 4-(3-{4-[6-Fluoro-7-(3-methanesulfonyl-phenyl)-4-morpholin-4-yl-quinazolin-2-yl]-phenyl}-ureido)-N,N-dimethyl-benzamide; 1-[4-(4-Methyl-piperazine-1-carbonyl)-phenyl]-3-[4-(4-morpholin-4-yl-7-thiophen-3-yl-quinazolin-2-yl)-phenyl]-urea; 4-(3-{4-[6-Fluoro-7-(5-methanesulfonyl-pyridin-3-yl)-4-morpholin-4-yl-quinazolin-2-yl]-phenyl}-ureido)-N,N-dimethyl-benzamide; 4-(3-{4-[7-(3-Methanesulfonyl-phenyl)-4-morpholin-4-yl-pyrido[3,2-d]pyrimidin-2-yl]-phenyl}-ureido)-N,N-dimethyl-benzamide; 4-(3-[4-{8-(2-Fluoro-pyridin-3-yl)-4-morpholin-4-yl-quinazolin-2-yl]-phenyl}-ureido)-N,N-dimethyl-benzamide; 4-(3-{4-[7-(3-Hydroxy-phenyl)-4-morpholin-4-yl-quinazolin-2-yl]-phenyl}-ureido)-N,N-dimethyl-benzamide; N,N-Dimethyl-4-(3-{4-[7-(1-methyl-1H-pyrazol-4-yl)-4-morpholin-4-yl-pyrido[3,2-d]pyrimidin-2-yl]-phenyl}-ureido)-benzamide; N,N-Dimethyl-4-(3-[4-{7-(5-methyl-furan-2-yl)-4-morpholin-4-yl-pyrido[3,2-d]pyrimidin-2-yl]-phenyl}-ureido)-benzamide; N-(2-Dimethylamino-ethyl)-N-methyl-4-{3-[4-(4-morpholin-4-yl-7-pyrimidin-5-yl-quinazolin-2-yl)-phenyl]-ureido}-benzamide; 4-(3-{4-[7-(3-Hydroxymethyl-phenyl)-4-morpholin-4-yl-quinazolin-2-yl]-phenyl}-ureido)-N,N-dimethyl-benzamide; N,N-Dimethyl-4-{3-[4-(4-morpholin-4-yl-7-pyridin-3-yl-pyrido[3,2-d]pyrimidin-2-yl)-phenyl]-ureido}-benzamide; 4-(3-[4-{7-(3-Fluoro-phenyl)-4-morpholin-4-yl-quinazolin-2-yl]-phenyl}-ureido)-N,N-dimethyl-benzamide; 4-(3-{4-[7-(3-Methoxy-phenyl)-4-morpholin-4-yl-quinazolin-2-yl]-phenyl}-ureido)-N,N-dimethyl-benzamide; 4-(3-{4-[7-(3-Acetylamino-phenyl)-4-morpholin-4-yl-quinazolin-2-yl]-phenyl}-ureido)-N,N-dimethyl-benzamide; 4-(3-{4-[7-(3-Dimethylamino-phenyl)-4-morpholin-4-yl-quinazolin-2-yl]-phenyl}-ureido)-N,N-dimethyl-benzamide; 4-{3-[4-(7-Furan-2-yl-4-morpholin-4-yl-quinazolin-2-yl)-phenyl]-ureido}-N,N-dimethyl-benzamide; N,N-Dimethyl-4-{3-[4-(4-morpholin-4-yl-7-thiophen-3-yl-quinazolin-2-yl)-phenyl]-ureido}-benzamide; 4-{3-[4-(7-Furan-3-yl-4-morpholin-4-yl-quinazolin-2-yl)-phenyl]-ureido}-N,N-dimethyl-benzamide; 4-(3-{5-[7-(2-Fluoro-pyridin-3-yl)-4-morpholin-4-yl-quinazolin-2-yl]-pyridin-2-yl}-ureido)-N,N-dimethyl-benzamide; N,N-Dimethyl-4-(3-{5-[7-(1-methyl-1H-pyrazol-4-yl)-4-morpholin-4-yl-quinazolin-2-yl]-pyridin-2-yl}-ureido)-benzamide; N-Methyl-4-(3-{4-[7-(5-methyl-furan-2-yl)-4-morpholin-4-yl-quinazolin-2-yl]-phenyl}-ureido)-benzamide; N,N-Dimethyl-4-(3-{5-[7-(5-methyl-furan-2-yl)-4-morpholin-4-yl-quinazolin-2-yl]-pyridin-2-yl}-ureido)-benzamide; N,N-Dimethyl-4-{3-[4-(4-morpholin-4-yl-7-pyridin-4-yl-quinazolin-2-yl)-phenyl]-ureido}-benzamide; N,N-Dimethyl-4-{3-[4-(4-morpholin-4-yl-7-quinolin-3-yl-quinazolin-2-yl)-phenyl]-ureido}-benzamide; 4-(3-{4-[7-(6-Methoxy-pyridin-3-yl)-4-morpholin-4-yl-quinazolin-2-yl]-phenyl}-ureido)-N,N-dimethyl-benzamide; N,N-Dimethyl-4-(3-{4-[7-(5-methyl-thiophen-2-yl)-4-morpholin-4-yl-quinazolin-2-yl]-phenyl}-ureido)-benzamide; N,N-Dimethyl-4-(3-{4-[7-(4-methyl-pyridin-3-yl)-4-morpholin-4-yl-quinazolin-2-yl]-phenyl}-ureido)-benzamide; N-(2-Dimethylamino-ethyl)-N-methyl-4-(3-{4-[7-(5-methyl-furan-2-yl)-4-morpholin-4-yl-quinazolin-2-yl]-phenyl}-ureido)-benzamide; 4-{3-[4-(7-Benzofuran-2-yl-4-morpholin-4-yl-quinazolin-2-yl)-phenyl]-ureido}-N,N-dimethyl-benzamide; 4-(3-{4-[7-(3-Fluoro-pyridin-4-yl)-4-morpholin-4-yl-quinazolin-2-yl]-phenyl}-ureido)-N,N-dimethyl-benzamide; 4-(3-[4-{7-(5-Acetylamino-pyridin-3-yl)-4-morpholin-4-yl-quinazolin-2-yl]-phenyl}-ureido)-N,N-dimethyl-benzamide; 1-[4-(4-Methyl-piperazine-1-carbonyl)-phenyl]-3-[4-(4-morpholin- 4-yl-7-pyrimidin-5-yl-pyrido[3,2-d]pyrimidin-2-yl)-phenyl]-urea; 4-(3-{4-[7-(2-Fluoro-pyridin-4-yl)-4-morpholin-4-yl-quinazolin-2-yl]-phenyl}-ureido)-N,N-dimethyl-benzamide; 1-[4-(4-Methyl-piperazine-1-carbonyl)-phenyl]-3-[4-(4-morpholin-4-yl-7-pyridin-4-yl-quinazolin-2-yl)-phenyl]-urea; 1-{4-[7-(5-Methyl-furan-2-yl)-4-morpholin-4-yl-quinazolin-2-yl]-phenyl}-3-[4-(4-methyl-piperazine-1-carbonyl)-phenyl]-urea; N,N-Dimethyl-4-(3-{4-[8-(5-methyl-furan-2-yl)-4-morpholin-4-yl-quinazolin-2-yl]-phenyl}-ureido)-benzamide; N-(2-Dimethylamino-ethyl)-N-methyl-4-{3-[4-(4-morpholin-4-yl-7-pyridin-4-yl-quinazolin-2-yl)-phenyl]-ureido}-benzamide; 1-[4-(4-Methyl-piperazine-1-carbonyl)-phenyl]-3-{4-[7-(1-methyl-1H-pyrazol-4-yl)-4-morpholin-4-yl-pyrido[3,2-d]pyrimidin-2-yl]-phenyl}-urea; N,N-Dimethyl-4-{3-[4-(4-morpholin-4-yl-7-thiophen-2-yl-quinazolin-2-yl)-phenyl]-ureido}-benzamide; 4-(3-{4-[7-(2-Methoxy-pyrimidin-5-yl)-4-morpholin-4-yl-quinazolin-2-yl]-phenyl}-ureido)-N,N-dimethyl-benzamide; 4-(3-{4-[7-(2-Amino-pyrimidin-5-yl)-4-morpholin-4-yl-quinazolin-2-yl]-phenyl}-ureido)-N,N-dimethyl-benzamide; 4-(3-(4-(7-(5-(2-(Dimethylamino)acetamido)pyridin-3-yl)-4-morpholino-quinazolin-2-yl)phenyl)ureido]-N,N-dimethyl-benzamide; 4-(3-{4-[7-(2-Fluoro-pyridin-3-yl)-4-morpholin-4-yl-pyrido[3,2-d]pyrimidin-2-yl]-phenyl}-ureido)-N,N-dimethyl-benzamide; 1-[4-(4-Methyl-piperazine-1-carbonyl)-phenyl]-3-[4-(4-morpholin-4-yl-7-pyrimidin-5-yl-quinazolin-2-yl)-phenyl]-urea; N,N-Dimethyl-4-(3-{4-[7-(furan-2-yl)-4-morpholin-4-yl-quinazolin-2-yl]-phenyl}-ureido)-benzamide; 1-(4-(4-(dimethylamino)piperidine-1-carbonyl)phenyl)-3-(5-(7-(2-fluoropyridin-3-yl)-4-morpholino-quinazolin-2-yl)pyridin-2-yl)urea; 4-(3-(2-fluoro-4-(7-(1-methyl-1H-pyrazol-4-yl)-4-morpholino-pyrido[3,2-d]pyrimidin-2-yl)phenyl)ureido)-N,N-dimethyl-benzamide; 4-(3-(4-(7-(1-(2-(dimethylamino)ethyl)-1H-pyrazol-4-yl)-4-morpholino-quinazolin-2-yl)phenyl)ureido)-N,N-dimethyl-benzamide; 4-(3-(2-fluoro-4-(4-morpholino-7-(pyrimidin-5-yl)quinazolin-2-yl)phenyl)ureido)-N,N-dimethyl-benzamide; N,N-dimethyl-4-(3-(5-(7-(1-methyl-1H-pyrazol-4-yl)-4-morpholino-pyrido[3,2-d]pyrimidin-2-yl)pyridin-2-yl)ureido)-benzamide; N,N-dimethyl-4-(3-(4-(4-morpholino-7-(pyridazin-4-yl)quinazolin-2-yl)phenyl)ureido)-benzamide; 4-(3-(4-(6-fluoro-7-(5-methylfuran-2-yl)-4-morpholino-quinazolin-2-yl)phenyl)ureido)-N,N-dimethyl-benzamide; N-methyl-4-(3-(4-(4-morpholino-7-(pyrimidin-5-yl)quinazolin-2-yl)phenyl)ureido)-benzamide; N-methyl-4-(3-(4-(7-(1-methyl-1H-pyrazol-4-yl)-4-morpholino-pyrido[3,2-d]pyrimidin-2-yl)phenyl)ureido)-benzamide; 4-(3-(4-(7-(furan-2-yl)-4-morpholino-pyrido[3,2-d]pyrimidin-2-yl)phenyl)ureido)-N,N-dimethyl-benzamide; 4-(3-(2-fluoro-4-(7-(2-fluoropyridin-3-yl)-4-morpholino-quinazolin-2-yl)phenyl)ureido)-N,N-dimethyl-benzamide; 4-(3-(4-(7-(2-aminopyrimidin-5-yl)-4-morpholino-pyrido[3,2-d]pyrimidin-2-yl)phenyl)ureido)-N,N-dimethyl-benzamide; N,N-dimethyl-4-(3-(4-(7-(4-methylpyridin-3-yl)-4-morpholino-pyrido[3,2-d]pyrimidin-2-yl)phenyl)ureido)-benzamide; 4-(3-(4-(7-(2-methoxypyrimidin-5-yl)-4-morpholino-pyrido[3,2-d]pyrimidin-2-yl)phenyl)ureido)-N,N-dimethyl-benzamide; 4-(3-(4-(7-(6-methoxypyridin-2-yl)-4-morpholino-quinazolin-2-yl)phenyl)ureido)-N,N-dimethyl-benzamide; N,N-dimethyl-4-(3-(4-(4-morpholino-7-(pyridazin-4-yl)pyrido[3,2-d]pyrimidin-2-yl)phenyl)ureido)-benzamide; 4-(3-(2-fluoro-4-(7-(1-methyl-1H-pyrazol-4-yl)-4-morpholino-quinazolin-2-yl)phenyl)ureido)-N,N-dimethyl-benzamide; 4-(3-(2-fluoro-4-(4-morpholino-7-(pyridazin-4-yl)quinazolin-2-yl)phenyl)ureido)-N,N-dimethyl-benzamide; 4-(3-(2-fluoro-4-(6-fluoro-4-morpholino-7-(pyrimidin-5-yl)quinazolin-2-yl)phenyl)ureido)-N,N-dimethyl-benzamide; 4-(3-(2-fluoro-4-(7-(4-methylpyridin-3-yl)-4-morpholino-quinazolin-2-yl)phenyl)ureido)-N,N-dimethyl-benzamide; 4-(3-(2-fluoro-4-(4-morpholino-7-(pyrimidin-5-yl)pyrido[3,2-d]pyrimidin-2-yl)phenyl)ureido)-N,N-dimethyl-benzamide; 4-(3-(2-fluoro-4-(4-morpholino-7-(pyridin-3-yl)pyrido[3,2-d]pyrimidin-2-yl)phenyl)ureido)-N,N-dimethyl-benzamide; 4-(3-(2-fluoro-4-(4-morpholino-7-(pyridin-3-yl)quinazolin-2-yl)phenyl)ureido)-N,N-dimethyl-benzamide; 4-(3-(2-fluoro-4-(7-(3-(methylsulfonyl)phenyl)-4-morpholino-pyrido[3,2-d]pyrimidin-2-yl)phenyl)ureido)-N,N-dimethyl-benzamide; 4-(3-(2-fluoro-4-(7-(2-methoxypyrimidin-5-yl)-4-morpholino-quinazolin-2-yl)phenyl)ureido)-N,N-dimethyl-benzamide; 4-(3-(2-fluoro-4-(7-(2-fluoropyridin-3-yl)-4-morpholino-pyrido[3,2-d]pyrimidin-2-yl)phenyl)ureido)-N,N-dimethyl-benzamide; 4-(3-(4-(6-fluoro-7-(2-fluoropyridin-3-yl)-4-morpholino-quinazolin-2-yl)phenyl)ureido)-N,N-dimethyl-benzamide; 4-(3-(2-fluoro-4-(6-fluoro-7-(1-methyl-1H-pyrazol-4-yl)-4-morpholino-quinazolin-2-yl)phenyl)ureido dimethyl-benzamide)-N,N-dimethyl-benzamide; 4-(3-(2-fluoro-4-(6-fluoro-4-morpholino-7-(pyridin-3-yl)quinazolin-2-yl)phenyl)ureido)-N,N-dimethyl-benzamide; 4-(3-(4-(7-(2-aminopyrimidin-5-yl)-4-morpholino-quinazolin-2-yl)-2-fluorophenyl)ureido)-N,N-dimethyl-benzamide; 4-(3-(5-(7-(2-fluoropyridin-3-yl)-4-morpholino-pyrido[3,2-d]pyrimidin-2-yl)pyridin-2-yl)ureido)-N,N-dimethyl-benzamide; 4-(3-(5-(6-fluoro-7-(2-fluoropyridin-3-yl)-4-morpholino-quinazolin-2-yl)pyridin-2-yl)ureido)-N,N-dimethyl-benzamide; 4-(3-(5-(6-fluoro-7-(1-methyl-1H-pyrazol-4-yl)-4-morpholino-quinazolin-2-yl)pyridin-2-yl)ureido)-N,N-dimethyl-benzamide; 4-(3-(2-fluoro-4-(7-(furan-2-yl)-4-morpholino-quinazolin-2-yl)phenyl)ureido)-N,N-dimethyl-benzamide; N,N-dimethyl-4-(3-(5-(7-(3-(methylsulfonyl)phenyl)-4-morpholino-pyrido[3,2-d]pyrimidin-2-yl)pyridin-2-yl)ureido)-benzamide; 4-(3-(2-fluoro-4-(7-(4-methylpyridin-3-yl)-4-morpholino-pyrido[3,2-d]pyrimidin-2-yl)phenyl)ureido)-N,N-dimethyl-benzamide; 4-(3-(2-fluoro-4-(7-(2-methoxypyrimidin-5-yl)-4-morpholino-pyrido[3,2-d]pyrimidin-2-yl)phenyl)ureido)-N,N-dimethyl-benzamide; 4-(3-(2-fluoro-4-(7-(3-(methylsulfonyl)phenyl)-4-morpholino-quinazolin-2-yl)phenyl)ureido)-N,N-dimethyl-benzamide; 4-(3-(5-(7-(2-methoxypyrimidin-5-yl)-4-morpholino-quinazolin-2-yl)pyridin-2-yl)ureido)-N,N-dimethyl-benzamide; 4-(3-(4-(7-(3,5-dimethylisoxazol-4-yl)-4-morpholino-pyrido[3,2-d]pyrimidin-2-yl)phenyl)ureido)-N,N-dimethyl-benzamide; 4-(3-(4-(7-(3,5-dimethylisoxazol-4-yl)-4-morpholino-quinazolin-2-yl)phenyl)ureido)-N,N-dimethyl-benzamide; 5-(3-(2-fluoro-4-(7-(5-methylfuran-2-yl)-4-morpholino-quinazolin-2-yl)phenyl)ureido)-N,N-dimethylpicolinamide; 5-(3-(2-fluoro-4-(4-morpholino-7-(pyrimidin-5-yl)quinazolin-2-yl)phenyl)ureido)-N,N-dimethylpicolinamide; 5-(3-(2-fluoro-4-(7-(1-methyl-1H-pyrazol-4-yl)-4-morpholino-pyrido[3,2-d]pyrimidin-2-yl)phenyl)ureido)-N,N-dimethylpicolinamide; 4-(3-(4-(4-(2,6-dimethylmorpholino)-7-(1-methyl-1H-pyrazol-4-yl)pyrido[3,2-d]pyrimidin-2-yl)phenyl)ureido)-N,N-dimethyl-benzamide; 4-(3-(4-(4-(2,6-dimethylmorpholino)-7-(1-methyl-1H-pyrazol-4-yl)pyrido[3,2-d]pyrimidin-2-yl)-2-fluorophenyl)ureido)-N,N-dimethyl-benzamide; 4-(3-(4-(7-(2-aminopyrimidin-5-yl)-4-morpholinopyrido[3,2-d]pyrimidin-2-yl)-2-fluorophenyl)ureido)-N,N-dimethyl-benzamide; 4-(3-(4-(4-(2,6-dimethylmorpholino)-7-(pyrimidin-5-yl)quinazolin-2-yl)phenyl)ureido)-N,N-dimethyl-benzamide; N,N-dimethyl-5-(3-(5-(7-(5-methylfuran-2-yl)-4-morpholino-quinazolin-2-yl)pyridin-2- yl)ureido)picolinamide; 5-(3-(2-fluoro-4-(7-(3-(methylsulfonyl)phenyl)-4-morpholino-quinazolin-2-yl)phenyl)ureido)-N,N-dimethylpicolinamide; 4-(3-(4-(7-(3,5-dimethylisoxazol-4-yl)-4-morpholino-quinazolin-2-yl)-2-fluorophenyl)ureido)-N,N-dimethyl-benzamide; 4-(3-(4-(4-(2,6-dimethylmorpholino)-7-(pyrimidin-5-yl)quinazolin-2-yl)-2-fluorophenyl)ureido)-N,N-dimethyl-benzamide; 3-fluoro-N,N-dimethyl-4-(3-(4-(4-morpholino-7-(pyrimidin-5-yl)quinazolin-2-yl)phenyl)ureido)-benzamide; 3-fluoro-N,N-dimethyl-4-(3-(4-(7-(1-methyl-1H-pyrazol-4-yl)-4-morpholino-pyrido[3,2-d]pyrimidin-2-yl)phenyl)ureido)-benzamide; 4-(3-(4-(7-(3,5-dimethylisoxazol-4-yl)-4-morpholino-pyrido[3,2-d]pyrimidin-2-yl)-2-fluorophenyl)ureido)-N,N-dimethyl-benzamide; 3-fluoro-N,N-dimethyl-4-(3-(4-(7-(5-methylfuran-2-yl)-4-morpholino-quinazolin-2-yl)phenyl)ureido)-benzamide; 4-(3-(2-fluoro-4-(4-morpholino-7-(pyridin-4-yl)quinazolin-2-yl)phenyl)ureido)-N,N-dimethyl-benzamide; N,N-dimethyl-4-(3-(4-(4-(2-methylmorpholino)-7-(pyrimidin-5-yl)quinazolin-2-yl)phenyl)ureido)-benzamide; 3-fluoro-4-(3-(2-fluoro-4-(4-morpholino-7-(pyrimidin-5-yl)quinazolin-2-yl)phenyl)ureido)-N,N-dimethyl-benzamide; 3-fluoro-N,N-dimethyl-4-(3-(5-(4-morpholino-7-(pyrimidin-5-yl)quinazolin-2-yl)pyridin-2-yl)ureido)-benzamide; 3-fluoro-4-(3-(2-fluoro-4-(7-(1-methyl-1H-pyrazol-4-yl)-4-morpholino-pyrido[3,2-d]pyrimidin-2-yl)phenyl)ureido)-N,N-dimethyl-benzamide; N,N-dimethyl-4-(3-(4-(7-(5-methylfuran-2-yl)-4-(2-methylmorpholino)quinazolin-2-yl)phenyl)ureido)-benzamide; 4-(3-(4-(7-(3,5-dimethylisoxazol-4-yl)-6-fluoro-4-morpholino-quinazolin-2-yl)phenyl)ureido)-N,N-dimethyl-benzamide; 4-(3-(2-fluoro-4-(4-(2-methylmorpholino)-7-(pyrimidin-5-yl)quinazolin-2-yl)phenyl)ureido)-N,N-dimethyl-benzamide; 3-fluoro-4-(3-(4-(7-(2-fluoropyridin-3-yl)-4-morpholino-pyrido[3,2-d]pyrimidin-2-yl)phenyl)ureido)-N,N-dimethyl-benzamide; 3-fluoro-4-(3-(4-(7-(2-fluoropyridin-3-yl)-4-morpholino-quinazolin-2-yl)phenyl)ureido)-N,N-dimethyl-benzamide; 3-fluoro-4-(3-(4-(7-(2-methoxypyrimidin-5-yl)-4-morpholino-quinazolin-2-yl)phenyl)ureido)-N,N-dimethyl-benzamide; N,N-dimethyl-4-(3-(4-(7-(1-methyl-1H-pyrazol-4-yl)-4-(2-methylmorpholino)pyrido[3,2-d]pyrimidin-2-yl)phenyl)ureido)-benzamide; 4-(3-(4-(6-fluoro-7-(furan-2-yl)-4-morpholino-quinazolin-2-yl)phenyl)ureido)-N,N-dimethyl-benzamide; 4-(3-(4-(7-(2-hydroxypyrimidin-5-yl)-4-morpholino-quinazolin-2-yl)phenyl)ureido)-N,N-dimethyl-benzamide; 4-(3-(2-fluoro-4-(7-(6-methoxypyridin-3-yl)-4-morpholino-quinazolin-2-yl)phenyl)ureido)-N,N-dimethyl-benzamide; 3-fluoro-N,N-dimethyl-4-(3-(4-(4-morpholino-7-(pyridin-3-yl)quinazolin-2-yl)phenyl)ureido)-benzamide; 3-fluoro-N,N-dimethyl-4-(3-(4-(4-morpholino-7-(pyridin-3-yl)pyrido[3,2-d]pyrimidin-2-yl)phenyl)ureido)-benzamide; 3-fluoro-N,N-dimethyl-4-(3-(4-(4-morpholino-7-(pyrimidin-5-yl)pyrido[3,2-d]pyrimidin-2-yl)phenyl)ureido)-benzamide; N,N-dimethyl-4-(3-(4-(4-morpholino-7-(pyridin-2-yl)quinazolin-2-yl)phenyl)ureido)-benzamide; 4-(3-(2-fluoro-4-(4-morpholino-7-(pyrimidin-2-yl)quinazolin-2-yl)phenyl)ureido)-N,N-dimethyl-benzamide; 3-fluoro-4-(3-(4-(7-(2-methoxypyrimidin-5-yl)-4-morpholino-pyrido[3,2-d]pyrimidin-2-yl)phenyl)ureido)-N,N-dimethyl-benzamide; 1-(4-(7-(furan-2-yl)-4-morpholino-quinazolin-2-yl)phenyl)-3-(4-(4-methylpiperazine-1-carbonyl)phenyl)urea; 4-(3-(5-(7-(furan-2-yl)-4-morpholino-quinazolin-2-yl)pyridin-2-yl)ureido)-N,N-dimethyl-benzamide; 3-fluoro-4-(3-(4-(7-(furan-2-yl)-4-morpholino-quinazolin-2-yl)phenyl)ureido)-N,N-dimethyl-benzamide; N,N-dimethyl-4-(3-(4-(7-(6-methylpyridin-3-yl)-4-morpholino-quinazolin-2-yl)phenyl)ureido)-benzamide; N,N-dimethyl-4-(3-(4-(4-morpholino-7-(1,3,5-trimethyl-1H-pyrazol-4-yl)quinazolin-2-yl)phenyl)ureido)-benzamide; 4-(3-(4-(7-(2-methoxypyridin-3-yl)-4-morpholino-quinazolin-2-yl)phenyl)ureido)-N,N-dimethyl-benzamide; 4-(3-(4-(7-(5-fluoropyridin-3-yl)-4-morpholino-quinazolin-2-yl)phenyl)ureido)-N,N-dimethyl-benzamide; N,N-dimethyl-4-(3-(4-(7-(2-methylpyridin-3-yl)-4-morpholino-quinazolin-2-yl)phenyl)ureido)-benzamide; 3-fluoro-N,N-dimethyl-4-(3-(4-(7-(6-methylpyridin-3-yl)-4-morpholino-quinazolin-2-yl)phenyl)ureido)-benzamide; 3-fluoro-N,N-dimethyl-4-(3-(4-(7-(2-methylpyridin-3-yl)-4-morpholino-quinazolin-2-yl)phenyl)ureido)-benzamide; 3-fluoro-N,N-dimethyl-4-(3-(4-(4-morpholino-7-(pyridin-2-yl)quinazolin-2-yl)phenyl)ureido)-benzamide; 4-(3-(4-(7-(4-methoxypyridin-3-yl)-4-morpholino-quinazolin-2-yl)phenyl)ureido)-N,N-dimethyl-benzamide; 3-fluoro-4-(3-(4-(7-(6-methoxypyridin-3-yl)-4-morpholino-quinazolin-2-yl)phenyl)ureido)-N,N-dimethyl-benzamide; 3-chloro-4-(3-(4-(7-(furan-2-yl)-4-morpholino-quinazolin-2-yl)phenyl)ureido)-N,N-dimethyl-benzamide; 3-fluoro-N,N-dimethyl-4-(3-(5-(7-(1-methyl-1H-pyrazol-4-yl)-4-morpholino-quinazolin-2-yl)pyridin-2-yl)ureido)-benzamide; 3-fluoro-4-(3-(4-(6-fluoro-4-morpholino-7-(pyridin-3-yl)quinazolin-2-yl)phenyl)ureido)-N,N-dimethyl-benzamide; 3-fluoro-4-(3-(4-(6-fluoro-4-morpholino-7-(pyrimidin-5-yl)quinazolin-2-yl)phenyl)ureido)-N,N-dimethyl-benzamide; 4-(3-(5-(6-fluoro-4-morpholino-7-(pyridin-3-yl)quinazolin-2-yl)pyridin-2-yl)ureido)-N,N-dimethyl-benzamide; 4-(3-(5-(6-fluoro-4-morpholino-7-(pyrimidin-5-yl)quinazolin-2-yl)pyridin-2-yl)ureido)-N,N-dimethyl-benzamide; 4-(3-(4-(7-(6-aminopyridin-3-yl)-4-morpholino-quinazolin-2-yl)phenyl)ureido)-N,N-dimethyl-benzamide; 4-(3-(4-(7-(6-aminopyridin-3-yl)-4-morpholino-quinazolin-2-yl)phenyl)ureido)-3-fluoro-N,N-dimethyl-benzamide; N,N-dimethyl-4-(3-(4-(4-morpholino-quinazolin-2-yl)phenyl)ureido)-benzamide; 4-(3-(4-(7-methoxy-4-morpholino-quinazolin-2-yl)phenyl)ureido)-N,N-dimethyl-benzamide; 4-(3-(4-(6,7-dimethoxy-4-morpholino-quinazolin-2-yl)phenyl)ureido)-N,N-dimethyl-benzamide; 4-(3-(2-fluoro-4-(7-methoxy-4-morpholino-quinazolin-2-yl)phenyl)ureido)-N,N-dimethyl-benzamide; 4-(3-(4-(7-(5-(hydroxymethyl)furan-2-yl)-4-morpholino-quinazolin-2-yl)phenyl)ureido)-N,N-dimethyl-benzamide; (R)-1-(4-(3-(dimethylamino)pyrrolidine-1-carbonyl)phenyl)-3-(4-(7-(1-methyl-1H-pyrazol-4-yl)-4-morpholino-pyrido[3,2-d]pyrimidin-2-yl)phenyl)urea; (S)-1-(4-(3-(dimethylamino)pyrrolidine-1-carbonyl)phenyl)-3-(4-(7-(1-methyl-1H-pyrazol-4-yl)-4-morpholino-pyrido[3,2-d]pyrimidin-2-yl)phenyl)urea; 1-(4-(4-(dimethylamino)piperidine-1-carbonyl)phenyl)-3-(4-(7-(1-methyl-1H-pyrazol-4-yl)-4-morpholino-pyrido[3,2-d]pyrimidin-2-yl)phenyl)urea; (R)-1-(4-(3-(dimethylamino)pyrrolidine-1-carbonyl)phenyl)-3-(4-(4-morpholino-7-(pyrimidin-5-yl)quinazolin-2-yl)phenyl)urea; (S)-1-(4-(3-(dimethylamino)pyrrolidine-1-carbonyl)phenyl)-3-(4-(4-morpholino-7-(pyrimidin-5-yl)quinazolin-2-yl)phenyl)urea; 1-(4-(3-hydroxypyrrolidine-1-carbonyl)phenyl)-3-(4-(4-morpholino-7-(pyrimidin-5-yl)quinazolin-2-yl)phenyl)urea; 4-(3-(4-(7-(5-((dimethylamino)methyl)furan-2-yl)-4-morpholino-quinazolin-2-yl)phenyl)ureido)-N,N-dimethyl-benzamide; 1-(4-(4-(dimethylamino)piperidine-1-carbonyl)phenyl)-3-(4-(7-(5-methylfuran-2-yl)-4-morpholino-quinazolin-2-yl)phenyl)urea; N-(2-(dimethylamino)ethyl)-4-(3-(4-(4-morpholino-7-(pyrimidin-5-yl)quinazolin-2-yl)phenyl)ureido)-benzamide; 1-(4-(4-(dimethylamino)piperidine-1-carbonyl)phenyl)-3-(4-(7-(4-methylpyridin-3-yl)-4-morpholino-quinazolin-2-yl)phenyl)urea; (S)-1-(4-(3-aminopyrrolidine-1-carbonyl)phenyl)-3-(4-(4-morpholino- 7-(pyrimidin-5-yl)quinazolin-2-yl)phenyl)urea; (S)-1-(4-(3-(dimethylamino)pyrrolidine-1-carbonyl)phenyl)-3-(4-(7-(5-methylfuran-2-yl)-4-morpholino-quinazolin-2-yl)phenyl)urea; (R)-1-(4-(3-(dimethylamino)pyrrolidine-1-carbonyl)phenyl)-3-(4-(7-(5-methylfuran-2-yl)-4-morpholino-quinazolin-2-yl)phenyl)urea; (R)-1-(4-(3-aminopyrrolidine-1-carbonyl)phenyl)-3-(4-(4-morpholino-7-(pyrimidin-5-yl)quinazolin-2-yl)phenyl)urea; (S)-1-(4-(3-(dimethylamino)pyrrolidine-1-carbonyl)phenyl)-3-(4-(6-fluoro-4-morpholino-7-(pyridin-3-yl)quinazolin-2-yl)phenyl)urea; (S)-1-(4-(3-(dimethylamino)pyrrolidine-1-carbonyl)phenyl)-3-(4-(4-morpholino-7-(pyrimidin-5-yl)pyrido[3,2-d]pyrimidin-2-yl)phenyl)urea; (R)-1-(4-(3-(dimethylamino)pyrrolidine-1-carbonyl)phenyl)-3-(4-(6-fluoro-4-morpholino-7-(pyridin-3-yl)quinazolin-2-yl)phenyl)urea; N-(2-(dimethylamino)ethyl)-4-(3-(4-(7-(5-methylfuran-2-yl)-4-morpholino-quinazolin-2-yl)phenyl)ureido)-benzamide; 4-(3-(4-(7-(1-methyl-1H-pyrazol-4-yl)-4-morpholino-pyrido[3,2-d]pyrimidin-2-yl)phenyl)ureido)-benzamide; 4-(3-(2-fluoro-4-(7-(5-(hydroxymethyl)furan-2-yl)-4-morpholino-quinazolin-2-yl)phenyl)ureido)-N,N-dimethyl-benzamide; 1-(4-(3-hydroxypyrrolidine-1-carbonyl)phenyl)-3-(4-(7-(5-methylfuran-2-yl)-4-morpholino-quinazolin-2-yl)phenyl)urea; (R)-1-(4-(3-(dimethylamino)pyrrolidine-1-carbonyl)phenyl)-3-(2-fluoro-4-(7-(1-methyl-1H-pyrazol-4-yl)-4-morpholino-pyrido[3,2-d]pyrimidin-2-yl)phenyl)urea; 4-(3-(4-(7-(5-(1-hydroxyethyl)furan-2-yl)-4-morpholino-quinazolin-2-yl)phenyl)ureido)-N,N-dimethyl-benzamide; (S)-1-(4-(3-(dimethylamino)pyrrolidine-1-carbonyl)phenyl)-3-(2-fluoro-4-(4-morpholino-7-(pyrimidin-5-yl)quinazolin-2-yl)phenyl)urea; (S)-1-(4-(3-aminopyrrolidine-1-carbonyl)phenyl)-3-(2-fluoro-4-(4-morpholino-7-(pyrimidin-5-yl)quinazolin-2-yl)phenyl)urea; (R)-1-(4-(3-aminopyrrolidine-1-carbonyl)phenyl)-3-(2-fluoro-4-(4-morpholino-7-(pyrimidin-5-yl)quinazolin-2-yl)phenyl)urea; (S)-1-(4-(3-(dimethylamino)pyrrolidine-1-carbonyl)phenyl)-3-(2-fluoro-4-(7-(1-methyl-1H-pyrazol-4-yl)-4-morpholino-pyrido[3,2-d]pyrimidin-2-yl)phenyl)urea; 1-(2-fluoro-4-(6-fluoro-4-morpholino-7-(pyridin-3-yl)quinazolin-2-yl)phenyl)-3-(4-(4-methylpiperazine-1-carbonyl)phenyl)urea; 1-(2-fluoro-4-(4-morpholino-7-(pyridin-4-yl)quinazolin-2-yl)phenyl)-3-(4-(4-methylpiperazine-1-carbonyl)phenyl)urea; (S)-1-(4-(3-(dimethylamino)pyrrolidine-1-carbonyl)phenyl)-3-(2-fluoro-4-(7-(2-fluoropyridin-3-yl)-4-morpholino-pyrido[3,2-d]pyrimidin-2-yl)phenyl)urea; 4-(3-(2-fluoro-4-(7-(5-(1-hydroxyethyl)furan-2-yl)-4-morpholino-quinazolin-2-yl)phenyl)ureido)-N,N-dimethyl-benzamide; 4-(3-(2-fluoro-4-(4-morpholino-7-(pyrimidin-5-yl)quinazolin-2-yl)phenyl)ureido)-N-methyl-benzamide; 4-(3-(4-(7-(5-(1-hydroxyethyl)furan-2-yl)-4-morpholino-pyrido[3,2-d]pyrimidin-2-yl)phenyl)ureido)-N,N-dimethyl-benzamide; N-(2-(dimethylamino)ethyl)-4-(3-(2-fluoro-4-(4-morpholino-7-(pyrimidin-5-yl)quinazolin-2-yl)phenyl)ureido)-benzamide; 4-(3-(2-fluoro-4-(7-(5-(hydroxymethyl)furan-2-yl)-4-morpholino-pyrido[3,2-d]pyrimidin-2-yl)phenyl)ureido)-N,N-dimethyl-benzamide; 3-fluoro-4-(3-(4-(7-(5-(hydroxymethyl)furan-2-yl)-4-morpholino-quinazolin-2-yl)phenyl)ureido)-N,N-dimethyl-benzamide; (S)-1-(4-(3-(dimethylamino)pyrrolidine-1-carbonyl)phenyl)-3-(4-(7-(3,5-dimethylisoxazol-4-yl)-4-morpholino-quinazolin-2-yl)phenyl)urea; (S)-1-(4-(3-(dimethylamino)pyrrolidine-1-carbonyl)phenyl)-3-(4-(7-(3,5-dimethylisoxazol-4-yl)-4-morpholino-quinazolin-2-yl)-2-fluorophenyl)urea; 4-(3-(4-(7-(5-(2-hydroxypropan-2-yl)furan-2-yl)-4-morpholino-quinazolin-2-yl)phenyl)ureido)-N,N-dimethyl-benzamide; 4-(3-(4-(7-(5-cyanofuran-2-yl)-4-morpholino-quinazolin-2-yl)phenyl)ureido)-N,N-dimethyl-benzamide; 4-(3-(4-(7-(5-acetylfuran-2-yl)-4-morpholino-quinazolin-2-yl)phenyl)ureido)-N,N-dimethyl-benzamide; N-(2-(dimethylamino)ethyl)-5-(2-(4-(3-(4-(dimethylcarbamoyl)phenyl)ureido)phenyl)-4-morpholino-quinazolin-7-yl)furan-2-carboxamide; 4-(3-(4-(7-(2-(dimethylamino)pyrimidin-5-yl)-4-morpholino-quinazolin-2-yl)phenyl)ureido)-N,N-dimethyl-benzamide; 3-fluoro-4-(3-(4-(7-(5-(1-hydroxyethyl)furan-2-yl)-4-morpholino-quinazolin-2-yl)phenyl)ureido)-N,N-dimethyl-benzamide; 3-fluoro-4-(3-(4-(7-(5-(hydroxymethyl)furan-2-yl)-4-morpholino-quinazolin-2-yl)phenyl)ureido)-N,N-dimethyl-benzamide; 5-(2-(4-(3-(4-(dimethylcarbamoyl)phenyl)ureido)phenyl)-4-morpholino-quinazolin-7-yl)-N,N-dimethylfuran-2-carboxamide; 4-(3-(4-(7-(2-(dimethylamino)pyrimidin-5-yl)-4-morpholino-pyrido[3,2-d]pyrimidin-2-yl)phenyl)ureido)-N,N-dimethyl-benzamide; 4-(3-(4-(7-(2-(dimethylamino)pyrimidin-5-yl)-4-morpholino-quinazolin-2-yl)-2-fluorophenyl)ureido)-N,N-dimethyl-benzamide; 1-(4-(7-(furan-2-yl)-4-morpholino-quinazolin-2-yl)phenyl)-3-(4-(3-hydroxypyrrolidine-1-carbonyl)phenyl)urea; 4-(3-(4-(7-(furan-2-yl)-4-morpholino-quinazolin-2-yl)phenyl)ureido)-N-methyl-benzamide; (S)-1-(4-(3-aminopyrrolidine-1-carbonyl)phenyl)-3-(4-(7-(furan-2-yl)-4-morpholino-quinazolin-2-yl)phenyl)urea; N-(2-(dimethylamino)ethyl)-4-(3-(4-(7-(furan-2-yl)-4-morpholino-quinazolin-2-yl)phenyl)ureido)-benzamide; N-(2-(dimethylamino)ethyl)-4-(3-(4-(7-(furan-2-yl)-4-morpholino-quinazolin-2-yl)phenyl)ureido)-N-methyl-benzamide; 4-(3-(3-fluoro-4-(4-morpholino-7-(pyrimidin-5-yl)quinazolin-2-yl)phenyl)ureido)-N,N-dimethyl-benzamide; 4-(3-(3-fluoro-4-(7-(1-methyl-1H-pyrazol-4-yl)-4-morpholino-pyrido[3,2-d]pyrimidin-2-yl)phenyl)ureido)-N,N-dimethyl-benzamide; 4-(3-(3-fluoro-4-(7-(5-methylfuran-2-yl)-4-morpholino-quinazolin-2-yl)phenyl)ureido)-N,N-dimethyl-benzamide; 2-fluoro-N,N-dimethyl-4-(3-(4-(4-morpholino-7-(pyrimidin-5-yl)quinazolin-2-yl)phenyl)ureido)-benzamide; 4-(3-(3-fluoro-4-(7-(2-fluoropyridin-3-yl)-4-morpholino-quinazolin-2-yl)phenyl)ureido)-N,N-dimethyl-benzamide; 4-(3-(3-fluoro-4-(7-(2-methoxypyrimidin-5-yl)-4-morpholino-quinazolin-2-yl)phenyl)ureido)-N,N-dimethyl-benzamide; 4-(3-(3-fluoro-4-(4-morpholino-7-(pyridin-3-yl)quinazolin-2-yl)phenyl)ureido)-N,N-dimethyl-benzamide; 4-(3-(3-fluoro-4-(7-(2-fluoropyridin-3-yl)-4-morpholino-pyrido[3,2-d]pyrimidin-2-yl)phenyl)ureido)-N,N-dimethyl-benzamide; 4-(3-(3-fluoro-4-(7-(3-(methylsulfonyl)phenyl)-4-morpholino-quinazolin-2-yl)phenyl)ureido)-N,N-dimethyl-benzamide; 4-(3-(4-(7-(3,5-dimethylisoxazol-4-yl)-4-morpholino-quinazolin-2-yl)phenyl)ureido)-2-fluoro-N,N-dimethyl-benzamide; 4-(3-(3-fluoro-4-(7-(furan-2-yl)-4-morpholino-quinazolin-2-yl)phenyl)ureido)-N,N-dimethyl-benzamide; 2-fluoro-4-(3-(4-(7-(2-fluoropyridin-3-yl)-4-morpholino-pyrido[3,2-d]pyrimidin-2-yl)phenyl)ureido)-N,N-dimethyl-benzamide; 4-(3-(3-fluoro-4-(7-(1-methyl-1H-pyrazol-4-yl)-4-morpholino-quinazolin-2-yl)phenyl)ureido)-N,N-dimethyl-benzamide; 4-(3-(3-fluoro-4-(4-morpholino-7-(pyrimidin-5-yl)pyrido[3,2-d]pyrimidin-2-yl)phenyl)ureido)-N,N-dimethyl-benzamide; 5-(3-(3-fluoro-4-(4-morpholino-7-(pyrimidin-5-yl)quinazolin-2-yl)phenyl)ureido)-N,N-dimethylpicolinamide; 4-(3-(4-(7-(3,5-dimethylisoxazol-4-yl)-4-morpholino-quinazolin-2-yl)-3-fluorophenyl)ureido)-N,N-dimethyl-benzamide; 2-fluoro-N,N-dimethyl-4-(3-(5-(7-(3-(methylsulfonyl)phenyl)-4-morpholino-quinazolin-2-yl)pyridin-2-yl)ureido)-benzamide; 4-(3-(3-fluoro-4-(4-(2-methylmorpholino)-7-

(pyrimidin-5-yl)quinazolin-2-yl)phenyl)ureido)-N,N-dimethyl-benzamide; 2-fluoro-4-(3-(4-(7-(2-fluoropyridin-3-yl)-4-morpholino-quinazolin-2-yl)phenyl)ureido)-N,N-dimethyl-benzamide; 4-(3-(3-fluoro-4-(6-fluoro-4-morpholino-7-(pyrimidin-5-yl)quinazolin-2-yl)phenyl)ureido)-N,N-dimethyl-benzamide; 2-fluoro-4-(3-(4-(7-(2-methoxypyrimidin-5-yl)-4-morpholino-quinazolin-2-yl)phenyl)ureido)-N,N-dimethyl-benzamide; 4-(3-(3-fluoro-4-(7-(6-methoxypyridin-3-yl)-4-morpholino-quinazolin-2-yl)phenyl)ureido)-N,N-dimethyl-benzamide; 2-fluoro-4-(3-(4-(7-(6-methoxypyridin-3-yl)-4-morpholino-quinazolin-2-yl)phenyl)ureido)-N,N-dimethyl-benzamide; 2-fluoro-N,N-dimethyl-4-(3-(4-(4-morpholino-7-(pyridin-3-yl)quinazolin-2-yl)phenyl)ureido)-benzamide; 4-(3-(3-fluoro-4-(4-morpholino-7-(pyridin-3-yl)pyrido[3,2-d]pyrimidin-2-yl)phenyl)ureido)-N,N-dimethyl-benzamide; 2-fluoro-N,N-dimethyl-4-(3-(4-(4-morpholino-7-(pyrimidin-5-yl)pyrido[3,2-d]pyrimidin-2-yl)phenyl)ureido)-benzamide; 4-(3-(3-fluoro-4-(7-(2-methoxypyrimidin-5-yl)-4-morpholino-pyrido[3,2-d]pyrimidin-2-yl)phenyl)ureido)-N,N-dimethyl-benzamide; 2-fluoro-N,N-dimethyl-4-(3-(4-(4-morpholino-7-(pyridin-3-yl)pyrido[3,2-d]pyrimidin-2-yl)phenyl)ureido)-benzamide; 2-fluoro-4-(3-(4-(7-(furan-2-yl)-4-morpholino-quinazolin-2-yl)phenyl)ureido)-N,N-dimethyl-benzamide; 2-fluoro-N,N-dimethyl-4-(3-(4-(7-(5-methylfuran-2-yl)-4-morpholino-quinazolin-2-yl)phenyl)ureido)-benzamide; 2-fluoro-N,N-dimethyl-4-(3-(4-(4-morpholino-7-(pyridin-2-yl)quinazolin-2-yl)phenyl)ureido)-benzamide; 4-(3-(3-fluoro-4-(4-morpholino-7-(pyridin-2-yl)quinazolin-2-yl)phenyl)ureido)-N,N-dimethyl-benzamide; 4-(3-(3-fluoro-4-(4-morpholino-7-(1,3,5-trimethyl-1H-pyrazol-4-yl)quinazolin-2-yl)phenyl)ureido)-N,N-dimethyl-benzamide; 4-(3-(3-fluoro-4-(7-(2-methoxypyridin-3-yl)-4-morpholino-quinazolin-2-yl)phenyl)ureido)-N,N-dimethyl-benzamide; 4-(3-(3-fluoro-4-(7-(6-methylpyridin-3-yl)-4-morpholino-quinazolin-2-yl)phenyl)ureido)-N,N-dimethyl-benzamide; 4-(3-(3-fluoro-4-(7-(2-methylpyridin-3-yl)-4-morpholino-quinazolin-2-yl)phenyl)ureido)-N,N-dimethyl-benzamide; 2-fluoro-N,N-dimethyl-4-(3-(4-(7-(1-methyl-1H-pyrazol-4-yl)-4-morpholino-pyrido[3,2-d]pyrimidin-2-yl)phenyl)ureido)-benzamide; 4-(3-(3-fluoro-4-(7-(5-(hydroxymethyl)furan-2-yl)-4-morpholino-quinazolin-2-yl)phenyl)ureido)-N,N-dimethyl-benzamide; 4-(3-(3-fluoro-4-(7-(5-(1-hydroxyethyl)furan-2-yl)-4-morpholino-quinazolin-2-yl)phenyl)ureido)-N,N-dimethyl-benzamide; 4-(3-(3-fluoro-4-(7-(5-(2-hydroxypropan-2-yl)furan-2-yl)-4-morpholino-quinazolin-2-yl)phenyl)ureido)-N,N-dimethyl-benzamide; 4-(3-(4-(7-(2-(dimethylamino)pyrimidin-5-yl)-4-morpholino-quinazolin-2-yl)-3-fluorophenyl)ureido)-N,N-dimethyl-benzamide; 2-fluoro-4-(3-(4-(7-(5-(hydroxymethyl)furan-2-yl)-4-morpholino-quinazolin-2-yl)phenyl)ureido)-N,N-dimethyl-benzamide; 4-(3-(2,5-difluoro-4-(4-morpholino-7-(pyrimidin-5-yl)quinazolin-2-yl)phenyl)ureido)-N,N-dimethyl-benzamide; 4-(3-(2,3-difluoro-4-(4-morpholino-7-(pyrimidin-5-yl)quinazolin-2-yl)phenyl)ureido)-N,N-dimethyl-benzamide; 4-(3-(2,3-difluoro-4-(7-(5-methylfuran-2-yl)-4-morpholino-quinazolin-2-yl)phenyl)ureido)-N,N-dimethyl-benzamide; -(3-(2,3-difluoro-4-(7-(furan-2-yl)-4-morpholino-quinazolin-2-yl)phenyl)ureido)-N,N-dimethyl-benzamide; 4-(3-(4-(7-(2-((2-hydroxyethyl)amino)pyridin-3-yl)-4-morpholino-quinazolin-2-yl)phenyl)ureido)-N,N-dimethyl-benzamide; 4-(3-(4-(7-((4-hydroxypiperidin-1-yl)methyl)-4-morpholino-quinazolin-2-yl)phenyl)ureido)-N,N-dimethyl-benzamide; 4-(3-(4-(7-(hydroxymethyl)-4-morpholino-quinazolin-2-yl)phenyl)ureido)-N,N-dimethyl-benzamide; 1-(4-(4-(dimethylamino)piperidine-1-carbonyl)phenyl)-3-(4-(7-(2-hydroxypropan-2-yl)-4-morpholino-quinazolin-2-yl)phenyl)urea; 4-(3-(4-(7-(4-(dimethylamino)piperidine-1-carbonyl)-4-morpholino-quinazolin-2-yl)phenyl)ureido)-N,N-dimethyl-benzamide; (R)-1-(4-(3-(dimethylamino)pyrrolidine-1-carbonyl)phenyl)-3-(4-(7-(2-hydroxypropan-2-yl)-4-morpholino-quinazolin-2-yl)phenyl)urea; (S)-1-(4-(3-(dimethylamino)pyrrolidine-1-carbonyl)phenyl)-3-(4-(7-(2-hydroxypropan-2-yl)-4-morpholino-quinazolin-2-yl)phenyl)urea; 4-(3-(2-fluoro-4-(7-(2-hydroxypropan-2-yl)-4-morpholino-quinazolin-2-yl)phenyl)ureido)-N,N-dimethyl-benzamide; N-(4-(3-(4-(4-morpholino-7-(pyrimidin-5-yl)quinazolin-2-yl)phenyl)ureido)phenyl)-acetamide; 1-(4-(7-(2-fluoropyridin-3-yl)-4-morpholinoquinazolin-2-yl)phenyl)-3-(4-(2-oxopyrrolidin-1-yl)phenyl)urea; N-(4-(3-(4-(7-(2-fluoropyridin-3-yl)-4-morpholinopyrido[3,2-d]pyrimidin-2-yl)phenyl)ureido)phenyl)acetamide; N-(4-(3-(4-(7-(1-methyl-1H-pyrazol-4-yl)-4-morpholinopyrido[3,2-d]pyrimidin-2-yl)phenyl)ureido)phenyl)acetamide; N,N-dimethyl-4-(3-(4-(4-morpholino-7-(1,3,5-trimethyl-1H-pyrazol-4-yl)pyrido[3,2-d]pyrimidin-2-yl)phenyl)ureido)-benzamide; 4-(3-(2-fluoro-4-(4-morpholino-7-(1,3,5-trimethyl-1H-pyrazol-4-yl)pyrido[3,2-d]pyrimidin-2-yl)phenyl)ureido)-N,N-dimethyl-benzamide; N,N-dimethyl-4-(3-(4-(7-(2-methylpyridin-3-yl)-4-morpholinopyrido[3,2-d]pyrimidin-2-yl)phenyl)ureido)-benzamide; 4-(3-(2-fluoro-4-(7-(2-methylpyridin-3-yl)-4-morpholinopyrido[3,2-d]pyrimidin-2-yl)phenyl)ureido)-N,N-dimethyl-benzamide; N,N-dimethyl-4-(3-(4-(7-(6-methylpyridin-3-yl)-4-morpholinopyrido[3,2-d]pyrimidin-2-yl)phenyl)ureido)-benzamide; 4-(3-(2-fluoro-4-(7-(6-methylpyridin-3-yl)-4-morpholinopyrido[3,2-d]pyrimidin-2-yl)phenyl)ureido)-N,N-dimethyl-benzamide; N-(4-(3-(4-(7-(5-methylfuran-2-yl)-4-morpholinopyrido[3,2-d]pyrimidin-2-yl)phenyl)ureido)phenyl)acetamide; N-(4-(3-(4-(7-(2-fluoropyridin-3-yl)-4-morpholinopyrido[3,2-d]pyrimidin-2-yl)phenyl)ureido)phenyl)acetamide; N-(4-(3-(4-(4-morpholino-7-(pyridin-3-yl)pyrido[3,2-d]pyrimidin-2-yl)phenyl)ureido)phenyl)acetamide; N-(4-(3-(4-(4-morpholino-7-(pyridin-4-yl)pyrido[3,2-d]pyrimidin-2-yl)phenyl)ureido)phenyl)acetamide; N-(4-(3-(4-(4-morpholino-7-(pyridin-2-yl)pyrido[3,2-d]pyrimidin-2-yl)phenyl)ureido)phenyl)acetamide; N-(4-(3-(4-(4-morpholino-7-(pyrimidin-5-yl)pyrido[3,2-d]pyrimidin-2-yl)phenyl)ureido)phenyl)acetamide; N-(4-(3-(4-(4-morpholino-7-(pyridazin-4-yl)pyrido[3,2-d]pyrimidin-2-yl)phenyl)ureido)phenyl)acetamide; N-(4-(3-(4-(7-(2-methoxypyrimidin-5-yl)-4-morpholinopyrido[3,2-d]pyrimidin-2-yl)phenyl)ureido)phenyl)acetamide; N-(4-(3-(4-(7-(6-methoxypyridin-3-yl)-4-morpholinopyrido[3,2-d]pyrimidin-2-yl)phenyl)ureido)phenyl)acetamide; N-(4-(3-(4-(7-(3-(methylsulfonyl)phenyl)-4-morpholinopyrido[3,2-d]pyrimidin-2-yl)phenyl)ureido)phenyl)acetamide; N-(4-(3-(4-(7-(2-aminopyrimidin-5-yl)-4-morpholinopyrido[3,2-d]pyrimidin-2-yl)phenyl)ureido)phenyl)acetamide; N-(4-(3-(4-(4-morpholino-7-(1,3,5-trimethyl-1H-pyrazol-4-yl)quinazolin-2-yl)phenyl)ureido)phenyl)acetamide; N-(4-(3-(4-(7-(2-methylpyridin-3-yl)-4-morpholinopyrido[3,2-d]pyrimidin-2-yl)phenyl)ureido)phenyl)acetamide; N-(4-(3-(4-(7-(6-methylpyridin-3-yl)-4-morpholinopyrido[3,2-d]pyrimidin-2-yl)phenyl)ureido)phenyl)acetamide; N-(4-(3-(5-(7-(2-fluoropyridin-3-yl)-4-morpholinopyrido[3,2-d]pyrimidin-2-yl)pyridin-2-yl)ureido)phenyl)acetamide; N-(4-(3-(5-(7-(1-methyl-1H-pyrazol-4-yl)-4-morpholinopyrido[3,2-d]pyrimidin-2-yl)pyridin-2-yl)ureido)phenyl)acetamide; 4-(3-(4-(7-(5-ethylfuran-2-yl)-4-morpholinoquinazolin-2-yl)phenyl)ureido)-N,N-dimethyl-benzamide; 4-(3-(4-(7-(5-(1,2-dihydroxyethyl)furan-2-yl)-

4-morpholinoquinazolin-2-yl)phenyl)ureido)-N,N-dimethyl-benzamide; N-(4-(3-(4-(7-(5-ethylfuran-2-yl)-4-morpholinoquinazolin-2-yl)phenyl)ureido)phenyl)acetamide; N-(4-(3-(4-(7-(5-(hydroxymethyl)furan-2-yl)-4-morpholinoquinazolin-2-yl)phenyl)ureido)phenyl)acetamide; N-(4-(3-(4-(7-(5-(1-hydroxyethyl)furan-2-yl)-4-morpholinoquinazolin-2-yl)phenyl)ureido)phenyl)acetamide; N-(4-(3-(4-(7-(5-(2-hydroxypropan-2-yl)furan-2-yl)-4-morpholinoquinazolin-2-yl)phenyl)ureido)phenyl)acetamide; N-(4-(3-(4-(7-(furan-2-yl)-4-morpholinoquinazolin-2-yl)phenyl)ureido)phenyl)acetamide; N-(4-(3-(4-(4-morpholino-7-(pyridin-3-yl)quinazolin-2-yl)phenyl)ureido)phenyl)acetamide; N-(4-(3-(4-(4-morpholino-7-(pyridin-4-yl)quinazolin-2-yl)phenyl)ureido)phenyl)acetamide; N-(4-(3-(4-(4-morpholino-7-(pyridin-2-yl)quinazolin-2-yl)phenyl)ureido)phenyl)acetamide; N-(4-(3-(4-(4-morpholino-7-(pyridazin-4-yl)quinazolin-2-yl)phenyl)ureido)phenyl)acetamide; N-(4-(3-(4-(7-(2-methoxypyrimidin-5-yl)-4-morpholinoquinazolin-2-yl)phenyl)ureido)phenyl)acetamide; N-(4-(3-(4-(7-(6-methoxypyridin-3-yl)-4-morpholinoquinazolin-2-yl)phenyl)ureido)phenyl)acetamide; N-(4-(3-(4-(7-(3-(methylsulfonyl)phenyl)-4-morpholinoquinazolin-2-yl)phenyl)ureido)phenyl)acetamide; N-(4-(3-(4-(7-(2-aminopyrimidin-5-yl)-4-morpholinoquinazolin-2-yl)phenyl)ureido)phenyl)acetamide; N-(4-(3-(4-(4-morpholino-7-(1,3,5-trimethyl-1H-pyrazol-4-yl)quinazolin-2-yl)phenyl)ureido)phenyl)acetamide; N-(4-(3-(4-(7-(2-methylpyridin-3-yl)-4-morpholinoquinazolin-2-yl)phenyl)ureido)phenyl)acetamide; N-(4-(3-(4-(7-(6-methylpyridin-3-yl)-4-morpholinoquinazolin-2-yl)phenyl)ureido)phenyl)acetamide; N-(4-(3-(5-(7-(5-methylfuran-2-yl)-4-morpholinoquinazolin-2-yl)pyridin-2-yl)ureido)phenyl)acetamide; N-(4-(3-(5-(7-(furan-2-yl)-4-morpholinoquinazolin-2-yl)pyridin-2-yl)ureido)phenyl)acetamide; N-(4-(3-(5-(4-morpholino-7-(pyrimidin-5-yl)quinazolin-2-yl)pyridin-2-yl)ureido)phenyl)acetamide; N-(4-(3-(5-(7-(1-methyl-1H-pyrazol-4-yl)-4-morpholinoquinazolin-2-yl)pyridin-2-yl)ureido)phenyl)acetamide; N-(4-(3-(4-(6-fluoro-7-(5-methylfuran-2-yl)-4-morpholinoquinazolin-2-yl)phenyl)ureido)phenyl)acetamide; N-(4-(3-(4-(6-fluoro-7-(furan-2-yl)-4-morpholinoquinazolin-2-yl)phenyl)ureido)phenyl)acetamide; N-(4-(3-(4-(6-fluoro-4-morpholino-7-(pyridin-3-yl)quinazolin-2-yl)phenyl)ureido)phenyl)acetamide; N-(4-(3-(4-(6-fluoro-4-morpholino-7-(pyrimidin-5-yl)quinazolin-2-yl)phenyl)ureido)phenyl)acetamide; N-(3-fluoro-4-(3-(4-(7-(5-methylfuran-2-yl)-4-morpholinoquinazolin-2-yl)phenyl)ureido)phenyl)acetamide; N-(4-(3-(4-(7-(5-ethylfuran-2-yl)-4-morpholinoquinazolin-2-yl)phenyl)ureido)-3-fluorophenyl)acetamide; N-(3-fluoro-4-(3-(4-(7-(furan-2-yl)-4-morpholinoquinazolin-2-yl)phenyl)ureido)phenyl)acetamide; N-(3-fluoro-4-(3-(4-(4-morpholino-7-(pyridin-3-yl)quinazolin-2-yl)phenyl)ureido)phenyl)acetamide; N-(3-fluoro-4-(3-(4-(7-(2-fluoropyridin-3-yl)-4-morpholinoquinazolin-2-yl)phenyl)ureido)phenyl)acetamide; N-(3-fluoro-4-(3-(4-(7-(2-methylpyridin-3-yl)-4-morpholinoquinazolin-2-yl)phenyl)ureido)phenyl)acetamide; N-(3-fluoro-4-(3-(4-(7-(6-methylpyridin-3-yl)-4-morpholinoquinazolin-2-yl)phenyl)ureido)phenyl)acetamide; N-(3-fluoro-4-(3-(4-(4-morpholino-7-(pyridin-2-yl)quinazolin-2-yl)phenyl)ureido)phenyl)acetamide; N-(3-fluoro-4-(3-(4-(4-morpholino-7-(pyridin-4-yl)quinazolin-2-yl)phenyl)ureido)phenyl)acetamide; N-(3-fluoro-4-(3-(4-(4-morpholino-7-(pyrimidin-5-yl)quinazolin-2-yl)phenyl)ureido)phenyl)acetamide; N-(3-fluoro-4-(3-(4-(7-(2-methoxypyrimidin-5-yl)-4-morpholinoquinazolin-2-yl)phenyl)ureido)phenyl)acetamide; N-(4-(3-(4-(7-(2-aminopyrimidin-5-yl)-4-morpholinoquinazolin-2-yl)phenyl)ureido)-3-fluorophenyl)acetamide; N-(3-fluoro-4-(3-(4-(7-(6-methoxypyridin-3-yl)-4-morpholinoquinazolin-2-yl)phenyl)ureido)phenyl)acetamide; N-(3-fluoro-4-(3-(4-(7-(1-methyl-1H-pyrazol-4-yl)-4-morpholinoquinazolin-2-yl)phenyl)ureido)phenyl)acetamide; N-(3-fluoro-4-(3-(4-(4-morpholino-7-(1,3,5-trimethyl-1H-pyrazol-4-yl)quinazolin-2-yl)phenyl)ureido)phenyl)acetamide; N-(3-fluoro-4-(3-(4-(7-(3-(methyl sulfonyl)phenyl)-4-morpholinoquinazolin-2-yl)phenyl)ureido)phenyl)acetamide; N-(3-fluoro-4-(3-(4-(7-(5-(hydroxymethyl)furan-2-yl)-4-morpholinoquinazolin-2-yl)phenyl)ureido)phenyl)acetamide; N-(3-fluoro-4-(3-(4-(7-(5-(1-hydroxyethyl)furan-2-yl)-4-morpholinoquinazolin-2-yl)phenyl)ureido)phenyl)acetamide; N-(3-fluoro-4-(3-(4-(7-(5-(2-hydroxypropan-2-yl)furan-2-yl)-4-morpholinoquinazolin-2-yl)phenyl)ureido)phenyl)acetamide; N-(2-fluoro-4-(3-(4-(7-(5-methylfuran-2-yl)-4-morpholinoquinazolin-2-yl)phenyl)ureido)phenyl)acetamide; N-(4-(3-(4-(7-(5-ethylfuran-2-yl)-4-morpholinoquinazolin-2-yl)phenyl)ureido)-2-fluorophenyl)acetamide; N-(2-fluoro-4-(3-(4-(7-(furan-2-yl)-4-morpholinoquinazolin-2-yl)phenyl)ureido)phenyl)acetamide; N-(2-fluoro-4-(3-(4-(4-morpholino-7-(pyridin-3-yl)quinazolin-2-yl)phenyl)ureido)phenyl)acetamide; N-(2-fluoro-4-(3-(4-(7-(2-fluoropyridin-3-yl)-4-morpholinoquinazolin-2-yl)phenyl)ureido)phenyl)acetamide; N-(2-fluoro-4-(3-(4-(7-(2-methylpyridin-3-yl)-4-morpholinoquinazolin-2-yl)phenyl)ureido)phenyl)acetamide; N-(2-fluoro-4-(3-(4-(7-(6-methylpyridin-3-yl)-4-morpholinoquinazolin-2-yl)phenyl)ureido)phenyl)acetamide; N-(2-fluoro-4-(3-(4-(4-morpholino-7-(pyridin-2-yl)quinazolin-2-yl)phenyl)ureido)phenyl)acetamide; N-(2-fluoro-4-(3-(4-(4-morpholino-7-(pyridin-4-yl)quinazolin-2-yl)phenyl)ureido)phenyl)acetamide; N-(2-fluoro-4-(3-(4-(4-morpholino-7-(pyrimidin-5-yl)quinazolin-2-yl)phenyl)ureido)phenyl)acetamide; N-(2-fluoro-4-(3-(4-(7-(2-methoxypyrimidin-5-yl)-4-morpholinoquinazolin-2-yl)phenyl)ureido)phenyl)acetamide; N-(4-(3-(4-(7-(2-aminopyrimidin-5-yl)-4-morpholinoquinazolin-2-yl)phenyl)ureido)-2-fluorophenyl)acetamide; N-(2-fluoro-4-(3-(4-(7-(6-methoxypyridin-3-yl)-4-morpholinoquinazolin-2-yl)phenyl)ureido)phenyl)acetamide; N-(2-fluoro-4-(3-(4-(7-(1-methyl-1H-pyrazol-4-yl)-4-morpholinoquinazolin-2-yl)phenyl)ureido)phenyl)acetamide; N-(2-fluoro-4-(3-(4-(4-morpholino-7-(1,3,5-trimethyl-1H-pyrazol-4-yl)quinazolin-2-yl)phenyl)ureido)phenyl)acetamide; N-(2-fluoro-4-(3-(4-(7-(3-(methylsulfonyl)phenyl)-4-morpholinoquinazolin-2-yl)phenyl)ureido)phenyl)acetamide; N-(2-fluoro-4-(3-(4-(7-(5-(hydroxymethyl)furan-2-yl)-4-morpholinoquinazolin-2-yl)phenyl)ureido)phenyl)acetamide; N-(2-fluoro-4-(3-(4-(7-(5-(1-hydroxyethyl)furan-2-yl)-4-morpholinoquinazolin-2-yl)phenyl)ureido)phenyl)acetamide; N-(2-fluoro-4-(3-(4-(7-(5-(2-hydroxypropan-2-yl)furan-2-yl)-4-morpholinoquinazolin-2-yl)phenyl)ureido)phenyl)acetamide; N-methyl-N-(4-(3-(4-(7-(5-methylfuran-2-yl)-4-morpholinoquinazolin-2-yl)phenyl)ureido)phenyl)acetamide; N-(4-(3-(4-(7-(5-ethylfuran-2-yl)-4-morpholinoquinazolin-2-yl)phenyl)ureido)phenyl)-N-methylacetamide; N-(4-(3-(4-(7-(furan-2-yl)-4-morpholinoquinazolin-2-yl)phenyl)ureido)phenyl)-N-methylacetamide; N-(4-(3-(4-(7-(2-methoxypyrimidin-5-yl)-4-morpholinoquinazolin-2-yl)phenyl)ureido)phenyl)-N-methylacetamide; N-methyl-N-(4-(3-(4-(4-morpholino-7-(pyrimidin-5-yl)quinazolin-2-yl)phenyl)ureido)phenyl)acetamide; N-methyl-N-(4-(3-(4-(4-morpholino-7-(pyridin- 3-yl)quinazolin-2-yl)phenyl)ureido)phenyl)acetamide; N-(4-(3-(4-(7-(2-fluoropyridin-3-yl)-4-morpholinoquinazolin-2-yl)phenyl)ureido)phenyl)-N-methylacetamide; N-methyl-N-(4-(3-(4-(4-morpholino-7-(pyridin-2-yl)quinazolin-2-yl)phenyl)ureido)phenyl)acetamide; N-(3-fluoro-4-(3-(4-(6-fluoro-7-(5-methylfuran-2-yl)-4-morpholinoquinazolin-2-yl)phenyl)ureido)phenyl)acetamide; N-(3-fluoro-4-(3-(4-(6-fluoro-7-(furan-2-yl)-4-morpholinoquinazolin-2-yl)phenyl)ureido)phenyl)acetamide; N-(3-fluoro-4-(3-(4-(6-fluoro-4-morpholino-7-(pyrimidin-5-yl)quinazolin-2-yl)phenyl)ureido)phenyl)acetamide; N-(3-fluoro-4-(3-(4-(6-fluoro-4-morpholino-7-(pyridin-3-yl)quinazolin-2-yl)phenyl)ureido)phenyl)acetamide; N-(2-fluoro-4-(3-(4-(6-fluoro-7-(5-methylfuran-2-yl)-4-morpholinoquinazolin-2-yl)phenyl)ureido)phenyl)acetamide; N-(2-fluoro-4-(3-(4-(6-fluoro-7-(furan-2-yl)-4-morpholinoquinazolin-2-yl)phenyl)ureido)phenyl)acetamide; N-(2-fluoro-4-(3-(4-(6-fluoro-4-morpholino-7-(pyrimidin-5-yl)quinazolin-2-yl)phenyl)ureido)phenyl)acetamide; N-(2-fluoro-4-(3-(4-(6-fluoro-4-morpholino-7-(pyridin-3-yl)quinazolin-2-yl)phenyl)ureido)phenyl)acetamide; N-(4-(3-(4-(6-fluoro-7-(5-methylfuran-2-yl)-4-morpholinoquinazolin-2-yl)phenyl)ureido)phenyl)-N-methylacetamide; N-(4-(3-(4-(6-fluoro-7-(furan-2-yl)-4-morpholinoquinazolin-2-yl)phenyl)ureido)phenyl)-N-methylacetamide; N-(4-(3-(4-(6-fluoro-4-morpholino-7-(pyrimidin-5-yl)quinazolin-2-yl)phenyl)ureido)phenyl)-N-methylacetamide; N-(4-(3-(4-(6-fluoro-4-morpholino-7-(pyridin-3-yl)quinazolin-2-yl)phenyl)ureido)phenyl)-N-methylacetamide; N-(3-fluoro-4-(3-(4-(7-(5-methylfuran-2-yl)-4-morpholinopyrido[3,2-d]pyrimidin-2-yl)phenyl)ureido)phenyl)acetamide; N-(3-fluoro-4-(3-(4-(7-(furan-2-yl)-4-morpholinopyrido[3,2-d]pyrimidin-2-yl)phenyl)ureido)phenyl)acetamide; N-(3-fluoro-4-(3-(4-(4-morpholino-7-(pyrimidin-5-yl)pyrido[3,2-d]pyrimidin-2-yl)phenyl)ureido)phenyl)acetamide; N-(3-fluoro-4-(3-(4-(7-(2-fluoropyridin-3-yl)-4-morpholinopyrido[3,2-d]pyrimidin-2-yl)phenyl)ureido)phenyl)acetamide; N-(3-fluoro-4-(3-(4-(4-morpholino-7-(pyridin-3-yl)pyrido[3,2-d]pyrimidin-2-yl)phenyl)ureido)phenyl)acetamide; N-(3-fluoro-4-(3-(4-(7-(1-methyl-1H-pyrazol-4-yl)-4-morpholinopyrido[3,2-d]pyrimidin-2-yl)phenyl)ureido)phenyl)acetamide; N-(2-fluoro-4-(3-(4-(7-(5-methylfuran-2-yl)-4-morpholinopyrido[3,2-d]pyrimidin-2-yl)phenyl)ureido)phenyl)acetamide; N-(2-fluoro-4-(3-(4-(7-(furan-2-yl)-4-morpholinopyrido[3,2-d]pyrimidin-2-yl)phenyl)ureido)phenyl)acetamide; N-(2-fluoro-4-(3-(4-(4-morpholino-7-(pyrimidin-5-yl)pyrido[3,2-d]pyrimidin-2-yl)phenyl)ureido)phenyl)acetamide; N-(2-fluoro-4-(3-(4-(7-(2-fluoropyridin-3-yl)-4-morpholinopyrido[3,2-d]pyrimidin-2-yl)phenyl)ureido)phenyl)acetamide; N-(2-fluoro-4-(3-(4-(4-morpholino-7-(pyridin-3-yl)pyrido[3,2-d]pyrimidin-2-yl)phenyl)ureido)phenyl)acetamide; N-(2-fluoro-4-(3-(4-(7-(1-methyl-1H-pyrazol-4-yl)-4-morpholinopyrido[3,2-d]pyrimidin-2-yl)phenyl)ureido)phenyl)acetamide; N-methyl-N-(4-(3-(4-(7-(5-methylfuran-2-yl)-4-morpholinopyrido[3,2-d]pyrimidin-2-yl)phenyl)ureido)phenyl)acetamide; N-(4-(3-(4-(7-(furan-2-yl)-4-morpholinopyrido[3,2-d]pyrimidin-2-yl)phenyl)ureido)phenyl)-N-methylacetamide; N-methyl-N-(4-(3-(4-(4-morpholino-7-(pyrimidin-5-yl)pyrido[3,2-d]pyrimidin-2-yl)phenyl)ureido)phenyl)acetamide; N-(4-(3-(4-(7-(2-fluoropyridin-3-yl)-4-morpholinopyrido[3,2-d]pyrimidin-2-yl)phenyl)ureido)phenyl)-N-methylacetamide; N-methyl-N-(4-(3-(4-(4-morpholino-7-(pyridin-3-yl)pyrido[3,2-d]pyrimidin-2-yl)phenyl)ureido)phenyl)acetamide; N-methyl-N-(4-(3-(4-(7-(1-methyl-1H-pyrazol-4-yl)-4-morpholinopyrido[3,2-d]pyrimidin-2-yl)phenyl)ureido)phenyl)acetamide; N-(4-(3-(2-fluoro-4-(7-(5-methylfuran-2-yl)-4-morpholinoquinazolin-2-yl)phenyl)ureido)phenyl)acetamide; N-(4-(3-(2-fluoro-4-(7-(furan-2-yl)-4-morpholinoquinazolin-2-yl)phenyl)ureido)phenyl)acetamide; N-(4-(3-(2-fluoro-4-(7-(2-methoxypyrimidin-5-yl)-4-morpholinoquinazolin-2-yl)phenyl)ureido)phenyl)acetamide; N-(4-(3-(2-fluoro-4-(4-morpholino-7-(pyrimidin-5-yl)quinazolin-2-yl)phenyl)ureido)phenyl)acetamide; N-(4-(3-(2-fluoro-4-(4-morpholino-7-(pyridin-3-yl)quinazolin-2-yl)phenyl)ureido)phenyl)acetamide; N-(4-(3-(2-fluoro-4-(7-(2-fluoropyridin-3-yl)-4-morpholinoquinazolin-2-yl)phenyl)ureido)phenyl)acetamide; N-(4-(3-(2-fluoro-4-(4-morpholino-7-(pyridin-2-yl)quinazolin-2-yl)phenyl)ureido)phenyl)acetamide; N-(4-(3-(3-fluoro-4-(7-(5-methylfuran-2-yl)-4-morpholinoquinazolin-2-yl)phenyl)ureido)phenyl)acetamide; N-(4-(3-(3-fluoro-4-(7-(furan-2-yl)-4-morpholinoquinazolin-2-yl)phenyl)ureido)phenyl)acetamide; N-(4-(3-(3-fluoro-4-(7-(2-methoxypyrimidin-5-yl)-4-morpholinoquinazolin-2-yl)phenyl)ureido)phenyl)acetamide; N-(4-(3-(3-fluoro-4-(4-morpholino-7-(pyrimidin-5-yl)quinazolin-2-yl)phenyl)ureido)phenyl)acetamide; N-(4-(3-(3-fluoro-4-(4-morpholino-7-(pyridin-3-yl)quinazolin-2-yl)phenyl)ureido)phenyl)acetamide; N-(4-(3-(3-fluoro-4-(7-(2-fluoropyridin-3-yl)-4-morpholinoquinazolin-2-yl)phenyl)ureido)phenyl)acetamide; N-(4-(3-(3-fluoro-4-(4-morpholino-7-(pyridin-2-yl)quinazolin-2-yl)phenyl)ureido)phenyl)acetamide; N-(4-(3-(2-fluoro-4-(6-fluoro-7-(5-methylfuran-2-yl)-4-morpholinoquinazolin-2-yl)phenyl)ureido)phenyl)acetamide; N-(4-(3-(2-fluoro-4-(6-fluoro-7-(furan-2-yl)-4-morpholinoquinazolin-2-yl)phenyl)ureido)phenyl)acetamide; N-(4-(3-(2-fluoro-4-(6-fluoro-4-morpholino-7-(pyrimidin-5-yl)quinazolin-2-yl)phenyl)ureido)phenyl)acetamide; N-(4-(3-(2-fluoro-4-(6-fluoro-4-morpholino-7-(pyridin-3-yl)quinazolin-2-yl)phenyl)ureido)phenyl)acetamide; N-(4-(3-(3-fluoro-4-(6-fluoro-7-(5-methylfuran-2-yl)-4-morpholinoquinazolin-2-yl)phenyl)ureido)phenyl)acetamide; N-(4-(3-(3-fluoro-4-(6-fluoro-7-(furan-2-yl)-4-morpholinoquinazolin-2-yl)phenyl)ureido)phenyl)acetamide; N-(4-(3-(3-fluoro-4-(6-fluoro-4-morpholino-7-(pyrimidin-5-yl)quinazolin-2-yl)phenyl)ureido)phenyl)acetamide; N-(4-(3-(3-fluoro-4-(6-fluoro-4-morpholino-7-(pyridin-3-yl)quinazolin-2-yl)phenyl)ureido)phenyl)acetamide; N-(4-(3-(2-fluoro-4-(7-(5-methylfuran-2-yl)-4-morpholinopyrido[3,2-d]pyrimidin-2-yl)phenyl)ureido)phenyl)acetamide; N-(4-(3-(2-fluoro-4-(7-(furan-2-yl)-4-morpholinopyrido[3,2-d]pyrimidin-2-yl)phenyl)ureido)phenyl)acetamide; N-(4-(3-(2-fluoro-4-(4-morpholino-7-(pyrimidin-5-yl)pyrido[3,2-d]pyrimidin-2-yl)phenyl)ureido)phenyl)acetamide; N-(4-(3-(2-fluoro-4-(7-(2-fluoropyridin-3-yl)-4-morpholinopyrido[3,2-d]pyrimidin-2-yl)phenyl)ureido)phenyl)acetamide; N-(4-(3-(2-fluoro-4-(4-morpholino-7-(pyridin-3-yl)pyrido[3,2-d]pyrimidin-2-yl)phenyl)ureido)phenyl)acetamide; N-(4-(3-(2-fluoro-4-(7-(1-methyl-1H-pyrazol-4-yl)-4-morpholinopyrido[3,2-d]pyrimidin-2-yl)phenyl)ureido)phenyl)acetamide; N-(4-(3-(3-fluoro-4-(7-(5-methylfuran-2-yl)-4-morpholinopyrido[3,2-d]pyrimidin-2-yl)phenyl)ureido)phenyl)acetamide; N-(4-(3-(3-fluoro-4-(7-(furan-2-yl)-4-morpholinopyrido[3,2-d]pyrimidin-2-yl)phenyl)ureido)phenyl)acetamide; N-(4-(3-(3-fluoro-4-(4-morpholino-7-(pyrimidin-5-yl)pyrido[3,2-d]pyrimidin-2-yl)phenyl)ureido)phenyl)acetamide; N-(4-(3-(3-fluoro-4-(7-(2-fluoropyridin-3-yl)-4-morpholinopyrido[3,2-d]pyrimidin-2-yl)phenyl)ureido)phenyl)acetamide; N-(4-(3-(3-fluoro-4-(4-morpholino-7-(pyridin-3-yl)pyrido[3,2-d]pyrimidin-2-yl)phenyl)ureido)phenyl)acetamide; and N-(4-(3-(3-fluoro-4-(7-(1-methyl-1H-pyrazol-4-yl)-4-morpholinopyrido[3,2-d]pyrimidin-2-yl)phenyl)ureido)phenyl)acetamide.

Further provided are pharmaceutical compositions comprising a compound described herein and a pharmaceutically acceptable carrier.

Additionally provided is a kit comprising a compound described herein.

Also provided are the following methods:

(i) A method for co-regulating PI3K and mTOR, said method comprising administering a therapeutically effective amount of a compound described herein to a patient in need thereof. In one embodiment, co-regulation comprises inhibition of the PI3K/AKT/mTOR pathway.

(ii) A method for treating a condition treatable by inhibiting the PI3K/AKT/pathway, said method comprising administering a therapeutically effective amount of a compound described herein to a patient in need thereof. In one embodiment, said condition is an inflammatory disorder. In another embodiment, said inflammatory disorder is selected from the group consisting of arthritis, pulmonary fibrosis, myocardial infarction, and peritonitis.

(iii) A method for treating a disease characterized by an abnormal cellular proliferation resulting from a dysregulated PI3K/AKT/mTOR pathway, said method comprising administering of a therapeutically effective amount of a compound of claim 1 to a patient in need thereof. In one embodiment, said disease is cancer. In a further embodiment, said cancer is of the prostate, head, neck, eye, mouth, throat, esophagus, bronchus, larynx, pharynx, chest, bone, lung, colon, rectum, stomach, bladder, uterus, cervix, breast, ovaries, vagina, testicles, skin, thyroid, blood, lymph nodes, kidney, liver, intestines, pancreas, brain, central nervous system, adrenal gland, or skin or a leukemia. In another embodiment, said cancer is cancer of the prostate. In still a further embodiment, said patient has at least one solid tumor.

All publications and priority applications, including U.S. patent application Ser. No. 14/076,765, filed Nov. 11, 2013, U.S. patent application Ser. No. 13/787,946, filed Mar. 7, 2013, U.S. patent application Ser. No. 13/285,227, filed Oct. 31, 2011, U.S. Provisional Patent Application No. 61/408, 620, filed Oct. 31, 2010 and U.S. Provisional Patent Application No. 61/501,901, filed Jun. 28, 2011, cited in this specification are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A method for co-regulating PI3K and mTOR, said method comprising: administering a therapeutically effective amount of a compound to a patient in need thereof, wherein the compound is selected from the group consisting of:

N,N-Dimethyl-4-{3-[4-(4-morpholin-4-yl-7-pyrimidin-5-yl-quinazolin-2-yl)-phenyl]-ureido}-benzamide;

N,N-Dimethyl-4-(3-{4-[7-(5-methyl-furan-2-yl)-4-morpholin-4-yl-quinazolin-2-yl]-phenyl}-ureido)-benzamide;

4-(3-{5-[7-(3-Methanesulfonyl-phenyl)-4-morpholin-4-yl-quinazolin-2-yl]-pyridin-2-yl}-ureido)-N,N-dimethyl-benzamide;

1-[4-(6-Fluoro-4-morpholin-4-yl-7-pyridin-3-yl-quinazolin-2-yl)-phenyl]-3-[4-(4-methyl-piperazine-1-carbonyl)-phenyl]-urea;

4-(3-{4-[8-(3-Hydroxy-phenyl)-4-morpholin-4-yl-quinazolin-2-yl]-phenyl}-ureido)-N,N-dimethyl-benzamide;

4-(3-{4-[8-(6-Fluoro-pyridin-3-yl)-4-morpholin-4-yl-quinazolin-2-yl]-phenyl}-ureido)-N,N-dimethyl-benzamide;

2-{4-[3-(4-Dimethylcarbamoyl-phenyl)-ureido]-phenyl}-4-morpholin-4-yl-quinazoline-7-carboxylic acid (2-dimethylamino-ethyl)-amide;

4-(3-{2-Fluoro-4-[7-(5-methyl-furan-2-yl)-4-morpholin-4-yl-quinazolin-2-yl]-phenyl}-ureido)-N,N-dimethyl-benzamide;

N,N-Dimethyl-4-{3-[4-(4-morpholin-4-yl-7-pyrimidin-5-yl-pyrido[3,2-d]pyrimidin-2-yl)-phenyl]-ureido}-benzamide;

5-(2-(4-(3-(4-(dimethylcarbamoyl)phenyl)ureido)phenyl)-4-morpholino-quinazolin-7-yl)furan-2-carboxylic acid;

N,N-dimethyl-4-(3-(4-(7-(5-(4-methylpiperazine-1-carbonyl)furan-2-yl)-4-morpholino-quinazolin-2-yl)phenyl)ureido)-benzamide;

4-(3-(4-(7-(5-cyanofuran-2-yl)-4-morpholino-quinazolin-2-yl)-3-fluorophenyl)ureido)-N,N-dimethyl-benzamide;

4-(3-(4-(7-(5-acetylfuran-2-yl)-4-morpholino-quinazolin-2-yl)phenyl)ureido)-2-fluoro-N,N-dimethyl-benzamide;

4-(3-(2,3-difluoro-4-(7-(1-methyl-1H-pyrazol-4-yl)-4-morpholino-pyrido[3,2-d]pyrimidin-2-yl)phenyl)ureido)-N,N-dimethyl-benzamide;

4-(3-(2-fluoro-4-(7-(5-(1-hydroxyethyl)furan-2-yl)-4-morpholino-pyrido[3,2-d]pyrimidin-2-yl)phenyl)ureido)-N,N-dimethyl-benzamide;

4-(3-(4-(7-(2-hydroxypropan-2-yl)-4-morpholino-quinazolin-2-yl)phenyl)ureido)-N,N-dimethyl-benzamide;

N-(4-(3-(4-(7-(5-methylfuran-2-yl)-4-morpholino-quinazolin-2-yl)phenyl)ureido)-phenyl)-acetamide;

1-(4-(7-(5-methylfuran-2-yl)-4-morpholino-quinazolin-2-yl)phenyl)-3-(4-(2-oxopyrrolidin-1-yl)phenyl)urea;

4-(3-{4-[7-(3-Methanesulfonyl-phenyl)-4-morpholin-4-yl-quinazolin-2-yl]-phenyl}-ureido)-N,N-dimethyl-benzamide;

4-(3-{4-[7-(3-Methanesulfonyl-phenyl)-4-morpholin-4-yl-quinazolin-2-yl]-phenyl}-ureido)-N-methyl-benzamide;

4-(3-{4-[7-(2-Fluoro-pyridin-3-yl)-4-morpholin-4-yl-quinazolin-2-yl]-phenyl}-ureido)-N,N-dimethyl-benzamide;

N,N-Dimethyl-4-(3-{4-[7-(1-methyl-1H-pyrazol-4-yl)-4-morpholin-4-yl-quinazolin-2-yl]-phenyl}-ureido)-benzamide;

4-(3-{4-[7-(3-Methanesulfonylamino-phenyl)-4-morpholin-4-yl-quinazolin-2-yl]-phenyl}-ureido)-N,N-dimethyl-benzamide;

N,N-Dimethyl-4-{3-[4-(4-morpholin-4-yl-7-pyridin-3-yl-quinazolin-2-yl)-phenyl]-ureido}-benzamide;

4-(3-{4-[7-(3-Methanesulfonyl-phenyl)-4-morpholin-4-yl-quinazolin-2-yl]-phenyl}-ureido)-benzamide;

1-{4-[7-(2-Fluoro-pyridin-3-yl)-4-morpholin-4-yl-quinazolin-2-yl]-phenyl}-3-[4-(4-methyl-piperazine-1-carbonyl)-phenyl]-urea;

1-[4-(4-Methyl-piperazine-1-carbonyl)-phenyl]-3-{4-[7-(1-methyl-1H-pyrazol-4-yl)-4-morpholin-4-yl-quinazolin-2-yl]-phenyl}-urea;

5-(3-{4-[7-(2-Fluoro-pyridin-3-yl)-4-morpholin-4-yl-quinazolin-2-yl]-phenyl}-ureido)-pyridine-2-carboxylic acid dimethylamide;

4-{3-[4-(6-Fluoro-4-morpholin-4-yl-7-pyridin-3-yl-quinazolin-2-yl)-phenyl]-ureido}-N,N-dimethyl-benzamide;

4-{3-[4-(6-Fluoro-4-morpholin-4-yl-7-pyrimidin-5-yl-quinazolin-2-yl)-phenyl]-ureido}-N,N-dimethyl-benzamide;

5-(3-{4-[7-(3-Methanesulfonyl-phenyl)-4-morpholin-4-yl-quinazolin-2-yl]-phenyl}-ureido)-pyridine-2-carboxylic acid dimethylamide;

1-(4-(4-methylpiperazine-1-carbonyl)phenyl)-3-(4-(7-(3-(methylsulfonyl)phenyl)-4-morpholino-quinazolin-2-yl)phenyl)urea;

1-[4-(4-Methyl-piperazine-1-carbonyl)-phenyl]-3-[4-(4-morpholin-4-yl-7-pyridin-3-yl-quinazolin-2-yl)-phenyl]-urea;

4-(3-{4-[7-(5-Methanesulfonyl-pyridin-3-yl)-4-morpholin-4-yl-quinazolin-2-yl]-phenyl}-ureido)-N,N-dimethyl-benzamide;

4-(3-{4-[6-Fluoro-7-(1-methyl-1H-pyrazol-4-yl)-4-morpholin-4-yl-quinazolin-2-yl]-phenyl}-ureido)-N,N-dimethyl-benzamide;

4-(3-{4-[6-Fluoro-7-(3-methanesulfonyl-phenyl)-4-morpholin-4-yl-quinazolin-2-yl]-phenyl}-ureido)-N,N-dimethyl-benzamide;

1-[4-(4-Methyl-piperazine-1-carbonyl)-phenyl]-3-[4-(4-morpholin-4-yl-7-thiophen-3-yl-quinazolin-2-yl)-phenyl]-urea;

4-(3-{4-[6-Fluoro-7-(5-methanesulfonyl-pyridin-3-yl)-4-morpholin-4-yl-quinazolin-2-yl]-phenyl}-ureido)-N,N-dimethyl-benzamide;

4-(3-{4-[7-(3-Methanesulfonyl-phenyl)-4-morpholin-4-yl-pyrido[3,2-d]pyrimidin-2-yl]-phenyl}-ureido)-N,N-dimethyl-benzamide;

4-(3-{4-[8-(2-Fluoro-pyridin-3-yl)-4-morpholin-4-yl-quinazolin-2-yl]-phenyl}-ureido)-N,N-dimethyl-benzamide;

4-(3-{4-[7-(3-Hydroxy-phenyl)-4-morpholin-4-yl-quinazolin-2-yl]-phenyl}-ureido)-N,N-dimethyl-benzamide;

N,N-Dimethyl-4-(3-{4-[7-(1-methyl-1H-pyrazol-4-yl)-4-morpholin-4-yl-pyrido[3,2-d]pyrimidin-2-yl]-phenyl}-ureido)-benzamide;

N,N-Dimethyl-4-(3-{4-[7-(5-methyl-furan-2-yl)-4-morpholin-4-yl-pyrido[3,2-d]pyrimidin-2-yl]-phenyl}-ureido)-benzamide;

N-(2-Dimethylamino-ethyl)-N-methyl-4-{3-[4-(4-morpholin-4-yl-7-pyrimidin-5-yl-quinazolin-2-yl)-phenyl]-ureido}-benzamide;

4-(3-{4-[7-(3-Hydroxymethyl-phenyl)-4-morpholin-4-yl-quinazolin-2-yl]-phenyl}-ureido)-N,N-dimethyl-benzamide;

N,N-Dimethyl-4-{3-[4-(4-morpholin-4-yl-7-pyridin-3-yl-pyrido[3,2-d]pyrimidin-2-yl)-phenyl]-ureido}-benzamide;

4-(3-{4-[7-(3-Fluoro-phenyl)-4-morpholin-4-yl-quinazolin-2-yl]-phenyl}-ureido)-N,N-dimethyl-benzamide;

4-(3-{4-[7-(3-Methoxy-phenyl)-4-morpholin-4-yl-quinazolin-2-yl]-phenyl}-ureido)-N,N-dimethyl-benzamide;

4-(3-{4-[7-(3-Acetylamino-phenyl)-4-morpholin-4-yl-quinazolin-2-yl]-phenyl}-ureido)-N,N-dimethyl-benzamide;

4-(3-{4-[7-(3-Dimethylamino-phenyl)-4-morpholin-4-yl-quinazolin-2-yl]-phenyl}-ureido)-N,N-dimethyl-benzamide;

4-{3-[4-(7-Furan-2-yl-4-morpholin-4-yl-quinazolin-2-yl)-phenyl]-ureido}-N,N-dimethyl-benzamide;

N,N-Dimethyl-4-{3-[4-(4-morpholin-4-yl-7-thiophen-3-yl-quinazolin-2-yl)-phenyl]-ureido}-benzamide;

4-{3-[4-(7-Furan-3-yl-4-morpholin-4-yl-quinazolin-2-yl)-phenyl]-ureido}-N,N-dimethyl-benzamide;

4-(3-{5-[7-(2-Fluoro-pyridin-3-yl)-4-morpholin-4-yl-quinazolin-2-yl]-pyridin-2-yl}-ureido)-N,N-dimethyl-benzamide;

N,N-Dimethyl-4-(3-{5-[7-(1-methyl-1H-pyrazol-4-yl)-4-morpholin-4-yl-quinazolin-2-yl]-pyridin-2-yl}-ureido)-benzamide;

N-Methyl-4-(3-{4-[7-(5-methyl-furan-2-yl)-4-morpholin-4-yl-quinazolin-2-yl]-phenyl}-ureido)-benzamide;

N,N-Dimethyl-4-(3-{5-[7-(5-methyl-furan-2-yl)-4-morpholin-4-yl-quinazolin-2-yl]-pyridin-2-yl}-ureido)-benzamide;

N,N-Dimethyl-4-{3-[4-(4-morpholin-4-yl-7-pyridin-4-yl-quinazolin-2-yl)-phenyl]-ureido}-benzamide;

N,N-Dimethyl-4-{3-[4-(4-morpholin-4-yl-7-quinolin-3-yl-quinazolin-2-yl)-phenyl]-ureido}-benzamide;

4-(3-{4-[7-(6-Methoxy-pyridin-3-yl)-4-morpholin-4-yl-quinazolin-2-yl]-phenyl}-ureido)-N,N-dimethyl-benzamide;

N,N-Dimethyl-4-(3-{4-[7-(5-methyl-thiophen-2-yl)-4-morpholin-4-yl-quinazolin-2-yl]-phenyl}-ureido)-benzamide;

N,N-Dimethyl-4-(3-{4-[7-(4-methyl-pyridin-3-yl)-4-morpholin-4-yl-quinazolin-2-yl]-phenyl}-ureido)-benzamide;

N-(2-Dimethylamino-ethyl)-N-methyl-4-(3-{4-[7-(5-methyl-furan-2-yl)-4-morpholin-4-yl-quinazolin-2-yl]-phenyl}-ureido)-benzamide;

4-{3-[4-(7-Benzofuran-2-yl-4-morpholin-4-yl-quinazolin-2-yl)-phenyl]-ureido}-N,N-dimethyl-benzamide;

4-(3-{4-[7-(3-Fluoro-pyridin-4-yl)-4-morpholin-4-yl-quinazolin-2-yl]-phenyl}-ureido)-N,N-dimethyl-benzamide;

4-(3-{4-[7-(5-Acetylamino-pyridin-3-yl)-4-morpholin-4-yl-quinazolin-2-yl]-phenyl}-ureido)-N,N-dimethyl-benzamide;

1-[4-(4-Methyl-piperazine-1-carbonyl)-phenyl]-3-[4-(4-morpholin-4-yl-7-pyrimidin-5-yl-pyrido[3,2-d]pyrimidin-2-yl)-phenyl]-urea;

4-(3-{4-[7-(2-Fluoro-pyridin-4-yl)-4-morpholin-4-yl-quinazolin-2-yl]-phenyl}-ureido)-N,N-dimethyl-benzamide;

1-[4-(4-Methyl-piperazine-1-carbonyl)-phenyl]-3-[4-(4-morpholin-4-yl-7-pyridin-4-yl-quinazolin-2-yl)-phenyl]-urea;

1-{4-[7-(5-Methyl-furan-2-yl)-4-morpholin-4-yl-quinazolin-2-yl]-phenyl}-3-[4-(4-methyl-piperazine-1-carbonyl)-phenyl]-urea;

N,N-Dimethyl-4-(3-{4-[8-(5-methyl-furan-2-yl)-4-morpholin-4-yl-quinazolin-2-yl]-phenyl}-ureido)-benzamide;

N-(2-Dimethylamino-ethyl)-N-methyl-4-{3-[4-(4-morpholin-4-yl-7-pyridin-4-yl-quinazolin-2-yl)-phenyl]-ureido}-benzamide;

1-[4-(4-Methyl-piperazine-1-carbonyl)-phenyl]-3-{4-[7-(1-methyl-1H-pyrazol-4-yl)-4-morpholin-4-yl-pyrido[3,2-d]pyrimidin-2-yl]-phenyl}-urea;

N,N-Dimethyl-4-{3-[4-(4-morpholin-4-yl-7-thiophen-2-yl-quinazolin-2-yl)-phenyl]-ureido}-benzamide;

4-(3-{4-[7-(2-Methoxy-pyrimidin-5-yl)-4-morpholin-4-yl-quinazolin-2-yl]-phenyl}-ureido)-N,N-dimethyl-benzamide;

4-(3-{4-[7-(2-Amino-pyrimidin-5-yl)-4-morpholin-4-yl-quinazolin-2-yl]-phenyl}-ureido)-N,N-dimethyl-benzamide;

4-(3-(4-(7-(5-(2-(Dimethylamino)acetamido)pyridin-3-yl)-4-morpholino-quinazolin-2-yl)phenyl)ureido}-N,N-dimethyl-benzamide;

4-(3-{4-[7-(2-Fluoro-pyridin-3-yl)-4-morpholin-4-yl-pyrido[3,2-d]pyrimidin-2-yl]-phenyl}-ureido)-N,N-dimethyl-benzamide;

1-[4-(4-Methyl-piperazine-1-carbonyl)-phenyl]-3-[4-(4-morpholin-4-yl-7-pyrimidin-5-yl-quinazolin-2-yl)-phenyl]-urea;

N,N-Dimethyl-4-(3-{4-[7-(furan-2-yl)-4-morpholin-4-yl-quinazolin-2-yl]-phenyl}-ureido)-benzamide;

1-(4-(4-(dimethylamino)piperidine-1-carbonyl)phenyl)-3-(5-(7-(2-fluoropyridin-3-yl)-4-morpholino-quinazolin-2-yl)pyridin-2-yl)urea;

4-(3-(2-fluoro-4-(7-(1-methyl-1H-pyrazol-4-yl)-4-morpholino-pyrido[3,2-d]pyrimidin-2-yl)phenyl)ureido)-N,N-dimethyl-benzamide;

4-(3-(4-(7-(1-(2-(dimethylamino)ethyl)-1H-pyrazol-4-yl)-4-morpholino-quinazolin-2-yl)phenyl)ureido)-N,N-dimethyl-benzamide;

4-(3-(2-fluoro-4-(4-morpholino-7-(pyrimidin-5-yl)quinazolin-2-yl)phenyl)ureido)-N,N-dimethyl-benzamide;

N,N-dimethyl-4-(3-(5-(7-(1-methyl-1H-pyrazol-4-yl)-4-morpholino-pyrido[3,2-d]pyrimidin-2-yl)pyridin-2-yl)ureido)-benzamide;

N,N-dimethyl-4-(3-(4-(4-morpholino-7-(pyridazin-4-yl)quinazolin-2-yl)phenyl)ureido)-benzamide;

4-(3-(4-(6-fluoro-7-(5-methylfuran-2-yl)-4-morpholino-quinazolin-2-yl)phenyl)ureido)-N,N-dimethyl-benzamide;

N-methyl-4-(3-(4-(4-morpholino-7-(pyrimidin-5-yl)quinazolin-2-yl)phenyl)ureido)-benzamide;

N-methyl-4-(3-(4-(7-(1-methyl-1H-pyrazol-4-yl)-4-morpholino-pyrido[3,2-d]pyrimidin-2-yl)phenyl)ureido)-benzamide;

4-(3-(4-(7-(furan-2-yl)-4-morpholino-pyrido[3,2-d]pyrimidin-2-yl)phenyl)ureido)-N,N-dimethyl-benzamide;

4-(3-(2-fluoro-4-(7-(2-fluoropyridin-3-yl)-4-morpholino-quinazolin-2-yl)phenyl)ureido)-N,N-dimethyl-benzamide;

4-(3-(4-(7-(2-aminopyrimidin-5-yl)-4-morpholino-pyrido[3,2-d]pyrimidin-2-yl)phenyl)ureido)-N,N-dimethyl-benzamide;

N,N-dimethyl-4-(3-(4-(7-(4-methylpyridin-3-yl)-4-morpholino-pyrido[3,2-d]pyrimidin-2-yl)phenyl)ureido)-benzamide;

4-(3-(4-(7-(2-methoxypyrimidin-5-yl)-4-morpholino-pyrido[3,2-d]pyrimidin-2-yl)phenyl)ureido)-N,N-dimethyl-benzamide;

4-(3-(4-(7-(6-methoxypyridin-2-yl)-4-morpholino-quinazolin-2-yl)phenyl)ureido)-N,N-dimethyl-benzamide;

N,N-dimethyl-4-(3-(4-(4-morpholino-7-(pyridazin-4-yl)pyrido[3,2-d]pyrimidin-2-yl)phenyl)ureido)-benzamide;

4-(3-(2-fluoro-4-(7-(1-methyl-1H-pyrazol-4-yl)-4-morpholino-quinazolin-2-yl)phenyl)ureido)-N,N-dimethyl-benzamide;

4-(3-(2-fluoro-4-(4-morpholino-7-(pyridazin-4-yl)quinazolin-2-yl)phenyl)ureido)-N,N-dimethyl-benzamide;

4-(3-(2-fluoro-4-(6-fluoro-4-morpholino-7-(pyrimidin-5-yl)quinazolin-2-yl)phenyl)ureido)-N,N-dimethyl-benzamide;

4-(3-(2-fluoro-4-(7-(4-methylpyridin-3-yl)-4-morpholino-quinazolin-2-yl)phenyl)ureido)-N,N-dimethyl-benzamide;

4-(3-(2-fluoro-4-(4-morpholino-7-(pyrimidin-5-yl)pyrido[3,2-d]pyrimidin-2-yl)phenyl)ureido)-N,N-dimethyl-benzamide;

4-(3-(2-fluoro-4-(4-morpholino-7-(pyridin-3-yl)pyrido[3,2-d]pyrimidin-2-yl)phenyl)ureido)-N,N-dimethyl-benzamide;

4-(3-(2-fluoro-4-(4-morpholino-7-(pyridin-3-yl)quinazolin-2-yl)phenyl)ureido)-N,N-dimethyl-benzamide;

4-(3-(2-fluoro-4-(7-(3-(methylsulfonyl)phenyl)-4-morpholino-pyrido[3,2-d]pyrimidin-2-yl)phenyl)ureido)-N,N-dimethyl-benzamide;

4-(3-(2-fluoro-4-(7-(2-methoxypyrimidin-5-yl)-4-morpholino-quinazolin-2-yl)phenyl)ureido)-N,N-dimethyl-benzamide;

4-(3-(2-fluoro-4-(7-(2-fluoropyridin-3-yl)-4-morpholino-pyrido[3,2-d]pyrimidin-2-yl)phenyl)ureido)-N,N-dimethyl-benzamide;

4-(3-(4-(6-fluoro-7-(2-fluoropyridin-3-yl)-4-morpholino-quinazolin-2-yl)phenyl)ureido)-N,N-dimethyl-benzamide;

4-(3-(2-fluoro-4-(6-fluoro-7-(1-methyl-1H-pyrazol-4-yl)-4-morpholino-quinazolin-2-yl)phenyl)ureido dimethyl-benzamide)-N,N-dimethyl-benzamide;

4-(3-(2-fluoro-4-(6-fluoro-4-morpholino-7-(pyridin-3-yl)quinazolin-2-yl)phenyl)ureido)-N,N-dimethyl-benzamide;

4-(3-(4-(7-(2-aminopyrimidin-5-yl)-4-morpholino-quinazolin-2-yl)-2-fluorophenyl)ureido)-N,N-dimethyl-benzamide;

4-(3-(5-(7-(2-fluoropyridin-3-yl)-4-morpholino-pyrido[3,2-d]pyrimidin-2-yl)pyridin-2-yl)ureido)-N,N-dimethyl-benzamide;

4-(3-(5-(6-fluoro-7-(2-fluoropyridin-3-yl)-4-morpholino-quinazolin-2-yl)pyridin-2-yl)ureido)-N,N-dimethyl-benzamide;

4-(3-(5-(6-fluoro-7-(1-methyl-1H-pyrazol-4-yl)-4-morpholino-quinazolin-2-yl)pyridin-2-yl)ureido)-N,N-dimethyl-benzamide;

4-(3-(2-fluoro-4-(7-(furan-2-yl)-4-morpholino-quinazolin-2-yl)phenyl)ureido)-N,N-dimethyl-benzamide;

N,N-dimethyl-4-(3-(5-(7-(3-(methylsulfonyl)phenyl)-4-morpholino-pyrido[3,2-d]pyrimidin-2-yl)pyridin-2-yl)ureido)-benzamide;

4-(3-(2-fluoro-4-(7-(4-methylpyridin-3-yl)-4-morpholino-pyrido[3,2-d]pyrimidin-2-yl)phenyl)ureido)-N,N-dimethyl-benzamide;

4-(3-(2-fluoro-4-(7-(2-methoxypyrimidin-5-yl)-4-morpholino-pyrido[3,2-d]pyrimidin-2-yl)phenyl)ureido)-N,N-dimethyl-benzamide;

4-(3-(2-fluoro-4-(7-(3-(methylsulfonyl)phenyl)-4-morpholino-quinazolin-2-yl)phenyl)ureido)-N,N-dimethyl-benzamide;

4-(3-(5-(7-(2-methoxypyrimidin-5-yl)-4-morpholino-quinazolin-2-yl)pyridin-2-yl)ureido)-N,N-dimethyl-benzamide;

4-(3-(4-(7-(3,5-dimethylisoxazol-4-yl)-4-morpholino-pyrido[3,2-d]pyrimidin-2-yl)phenyl)ureido)-N,N-dimethyl-benzamide;

4-(3-(4-(7-(3,5-dimethylisoxazol-4-yl)-4-morpholino-quinazolin-2-yl)phenyl)ureido)-N,N-dimethyl-benzamide;

5-(3-(2-fluoro-4-(7-(5-methylfuran-2-yl)-4-morpholino-quinazolin-2-yl)phenyl)ureido)-N,N-dimethylpicolinamide;

5-(3-(2-fluoro-4-(4-morpholino-7-(pyrimidin-5-yl)quinazolin-2-yl)phenyl)ureido)-N,N-dimethylpicolinamide;

5-(3-(2-fluoro-4-(7-(1-methyl-1H-pyrazol-4-yl)-4-morpholino-pyrido[3,2-d]pyrimidin-2-yl)phenyl)ureido)-N,N-dimethylpicolinamide;

4-(3-(4-(4-(2,6-dimethylmorpholino)-7-(1-methyl-1H-pyrazol-4-yl)pyrido[3,2-d]pyrimidin-2-yl)phenyl)ureido)-N,N-dimethyl-benzamide;

4-(3-(4-(4-(2,6-dimethylmorpholino)-7-(1-methyl-1H-pyrazol-4-yl)pyrido[3,2-d]pyrimidin-2-yl)-2-fluorophenyl)ureido)-N,N-dimethyl-benzamide;

4-(3-(4-(7-(2-aminopyrimidin-5-yl)-4-morpholinopyrido[3,2-d]pyrimidin-2-yl)-2-fluorophenyl)ureido)-N,N-dimethyl-benzamide;

4-(3-(4-(4-(2,6-dimethylmorpholino)-7-(pyrimidin-5-yl)quinazolin-2-yl)phenyl)ureido)-N,N-dimethyl-benzamide;

N,N-dimethyl-5-(3-(5-(7-(5-methylfuran-2-yl)-4-morpholino-quinazolin-2-yl)pyridin-2-yl)ureido)picolinamide;

5-(3-(2-fluoro-4-(7-(3-(methylsulfonyl)phenyl)-4-morpholino-quinazolin-2-yl)phenyl)ureido)-N,N-dimethylpicolinamide;

4-(3-(4-(7-(3,5-dimethylisoxazol-4-yl)-4-morpholino-quinazolin-2-yl)-2-fluorophenyl)ureido)-N,N-dimethyl-benzamide;

4-(3-(4-(4-(2,6-dimethylmorpholino)-7-(pyrimidin-5-yl)quinazolin-2-yl)-2-fluorophenyl)ureido)-N,N-dimethyl-benzamide;

3-fluoro-N,N-dimethyl-4-(3-(4-(4-morpholino-7-(pyrimidin-5-yl)quinazolin-2-yl)phenyl)ureido)-benzamide;

3-fluoro-N,N-dimethyl-4-(3-(4-(7-(1-methyl-1H-pyrazol-4-yl)-4-morpholino-pyrido[3,2-d]pyrimidin-2-yl)phenyl)ureido)-benzamide;

4-(3-(4-(7-(3,5-dimethylisoxazol-4-yl)-4-morpholino-pyrido[3,2-d]pyrimidin-2-yl)-2-fluorophenyl)ureido)-N,N-dimethyl-benzamide;

3-fluoro-N,N-dimethyl-4-(3-(4-(7-(5-methylfuran-2-yl)-4-morpholino-quinazolin-2-yl)phenyl)ureido)-benzamide;

4-(3-(2-fluoro-4-(4-morpholino-7-(pyridin-4-yl)quinazolin-2-yl)phenyl)ureido)-N,N-dimethyl-benzamide;

N,N-dimethyl-4-(3-(4-(4-(2-methylmorpholino)-7-(pyrimidin-5-yl)quinazolin-2-yl)phenyl)ureido)-benzamide;

3-fluoro-4-(3-(2-fluoro-4-(4-morpholino-7-(pyrimidin-5-yl)quinazolin-2-yl)phenyl)ureido)-N,N-dimethyl-benzamide;

3-fluoro-N,N-dimethyl-4-(3-(5-(4-morpholino-7-(pyrimidin-5-yl)quinazolin-2-yl)pyridin-2-yl)ureido)-benzamide;

3-fluoro-4-(3-(2-fluoro-4-(7-(1-methyl-1H-pyrazol-4-yl)-4-morpholino-pyrido[3,2-d]pyrimidin-2-yl)phenyl)ureido)-N,N-dimethyl-benzamide;

N,N-dimethyl-4-(3-(4-(7-(5-methylfuran-2-yl)-4-(2-methylmorpholino)quinazolin-2-yl)phenyl)ureido)-benzamide;

4-(3-(4-(7-(3,5-dimethylisoxazol-4-yl)-6-fluoro-4-morpholino-quinazolin-2-yl)phenyl)ureido)-N,N-dimethyl-benzamide;

4-(3-(2-fluoro-4-(4-(2-methylmorpholino)-7-(pyrimidin-5-yl)quinazolin-2-yl)phenyl)ureido)-N,N-dimethyl-benzamide;

3-fluoro-4-(3-(4-(7-(2-fluoropyridin-3-yl)-4-morpholino-pyrido[3,2-d]pyrimidin-2-yl)phenyl)ureido)-N,N-dimethyl-benzamide;

3-fluoro-4-(3-(4-(7-(2-fluoropyridin-3-yl)-4-morpholino-quinazolin-2-yl)phenyl)ureido)-N,N-dimethyl-benzamide;

3-fluoro-4-(3-(4-(7-(2-methoxypyrimidin-5-yl)-4-morpholino-quinazolin-2-yl)phenyl)ureido)-N,N-dimethyl-benzamide;

N,N-dimethyl-4-(3-(4-(7-(1-methyl-1H-pyrazol-4-yl)-4-(2-methylmorpholino)pyrido[3,2-d]pyrimidin-2-yl)phenyl)ureido)-benzamide;

4-(3-(4-(6-fluoro-7-(furan-2-yl)-4-morpholino-quinazolin-2-yl)phenyl)ureido)-N,N-dimethyl-benzamide;

4-(3-(4-(7-(2-hydroxypyrimidin-5-yl)-4-morpholino-quinazolin-2-yl)phenyl)ureido)-N,N-dimethyl-benzamide;

4-(3-(2-fluoro-4-(7-(6-methoxypyridin-3-yl)-4-morpholino-quinazolin-2-yl)phenyl)ureido)-N,N-dimethyl-benzamide;

3-fluoro-N,N-dimethyl-4-(3-(4-(4-morpholino-7-(pyridin-3-yl)quinazolin-2-yl)phenyl)ureido)-benzamide;

3-fluoro-N,N-dimethyl-4-(3-(4-(4-morpholino-7-(pyridin-3-yl)pyrido[3,2-d]pyrimidin-2-yl)phenyl)ureido)-benzamide;

3-fluoro-N,N-dimethyl-4-(3-(4-(4-morpholino-7-(pyrimidin-5-yl)pyrido[3,2-d]pyrimidin-2-yl)phenyl)ureido)-benzamide;

N,N-dimethyl-4-(3-(4-(4-morpholino-7-(pyridin-2-yl)quinazolin-2-yl)phenyl)ureido)-benzamide;

4-(3-(2-fluoro-4-(4-morpholino-7-(pyridin-2-yl)quinazolin-2-yl)phenyl)ureido)-N,N-dimethyl-benzamide;

3-fluoro-4-(3-(4-(7-(2-methoxypyrimidin-5-yl)-4-morpholino-pyrido[3,2-d]pyrimidin-2-yl)phenyl)ureido)-N,N-dimethyl-benzamide;

1-(4-(7-(furan-2-yl)-4-morpholino-quinazolin-2-yl)phenyl)-3-(4-(4-methylpiperazine-1-carbonyl)phenyl)urea;

4-(3-(5-(7-(furan-2-yl)-4-morpholino-quinazolin-2-yl)pyridin-2-yl)ureido)-N,N-dimethyl-benzamide;

3-fluoro-4-(3-(4-(7-(furan-2-yl)-4-morpholino-quinazolin-2-yl)phenyl)ureido)-N,N-dimethyl-benzamide;

N,N-dimethyl-4-(3-(4-(7-(6-methylpyridin-3-yl)-4-morpholino-quinazolin-2-yl)phenyl)ureido)-benzamide;

N,N-dimethyl-4-(3-(4-(4-morpholino-7-(1,3,5-trimethyl-1H-pyrazol-4-yl)quinazolin-2-yl)phenyl)ureido)-benzamide;

4-(3-(4-(7-(2-methoxypyridin-3-yl)-4-morpholino-quinazolin-2-yl)phenyl)ureido)-N,N-dimethyl-benzamide;

4-(3-(4-(7-(5-fluoropyridin-3-yl)-4-morpholino-quinazolin-2-yl)phenyl)ureido)-N,N-dimethyl-benzamide;

N,N-dimethyl-4-(3-(4-(7-(2-methylpyridin-3-yl)-4-morpholino-quinazolin-2-yl)phenyl)ureido)-benzamide;

3-fluoro-N,N-dimethyl-4-(3-(4-(7-(6-methylpyridin-3-yl)-4-morpholino-quinazolin-2-yl)phenyl)ureido)-benzamide;

3-fluoro-N,N-dimethyl-4-(3-(4-(7-(2-methylpyridin-3-yl)-4-morpholino-quinazolin-2-yl)phenyl)ureido)-benzamide;

3-fluoro-N,N-dimethyl-4-(3-(4-(4-morpholino-7-(pyridin-2-yl)quinazolin-2-yl)phenyl)ureido)-benzamide;

4-(3-(4-(7-(4-methoxypyridin-3-yl)-4-morpholino-quinazolin-2-yl)phenyl)ureido)-N,N-dimethyl-benzamide;

3-fluoro-4-(3-(4-(7-(6-methoxypyridin-3-yl)-4-morpholino-quinazolin-2-yl)phenyl)ureido)-N,N-dimethyl-benzamide;
3-chloro-4-(3-(4-(7-(furan-2-yl)-4-morpholino-quinazolin-2-yl)phenyl)ureido)-N,N-dimethyl-benzamide;
3-fluoro-N,N-dimethyl-4-(3-(5-(7-(1-methyl-1H-pyrazol-4-yl)-4-morpholino-quinazolin-2-yl)pyridin-2-yl)ureido)-benzamide;
3-fluoro-4-(3-(4-(6-fluoro-4-morpholino-7-(pyridin-3-yl)quinazolin-2-yl)phenyl)ureido)-N,N-dimethyl-benzamide;
3-fluoro-4-(3-(4-(6-fluoro-4-morpholino-7-(pyrimidin-5-yl)quinazolin-2-yl)phenyl)ureido)-N,N-dimethyl-benzamide;
4-(3-(5-(6-fluoro-4-morpholino-7-(pyridin-3-yl)quinazolin-2-yl)pyridin-2-yl)ureido)-N,N-dimethyl-benzamide;
4-(3-(5-(6-fluoro-4-morpholino-7-(pyrimidin-5-yl)quinazolin-2-yl)pyridin-2-yl)ureido)-N,N-dimethyl-benzamide;
4-(3-(4-(7-(6-aminopyridin-3-yl)-4-morpholino-quinazolin-2-yl)phenyl)ureido)-N,N-dimethyl-benzamide;
4-(3-(4-(7-(6-aminopyridin-3-yl)-4-morpholino-quinazolin-2-yl)phenyl)ureido)-3-fluoro-N,N-dimethyl-benzamide;
N,N-dimethyl-4-(3-(4-(4-morpholino-quinazolin-2-yl)phenyl)ureido)-benzamide 4-(3-(4-(7-methoxy-4-morpholino-quinazolin-2-yl)phenyl)ureido)-N,N-dimethyl-benzamide;
4-(3-(4-(6,7-dimethoxy-4-morpholino-quinazolin-2-yl)phenyl)ureido)-N,N-dimethyl-benzamide;
4-(3-(2-fluoro-4-(7-methoxy-4-morpholino-quinazolin-2-yl)phenyl)ureido)-N,N-dimethyl-benzamide;
4-(3-(4-(7-(5-(hydroxymethyl)furan-2-yl)-4-morpholino-quinazolin-2-yl)phenyl)ureido)-N,N-dimethyl-benzamide;
(R)-1-(4-(3-(dimethylamino)pyrrolidine-1-carbonyl)phenyl)-3-(4-(7-(1-methyl-1H-pyrazol-4-yl)-4-morpholino-pyrido[3,2-d]pyrimidin-2-yl)phenyl)urea;
(S)-1-(4-(3-(dimethylamino)pyrrolidine-1-carbonyl)phenyl)-3-(4-(7-(1-methyl-1H-pyrazol-4-yl)-4-morpholino-pyrido[3,2-d]pyrimidin-2-yl)phenyl)urea;
1-(4-(4-(dimethylamino)piperidine-1-carbonyl)phenyl)-3-(4-(7-(1-methyl-1H-pyrazol-4-yl)-4-morpholino-pyrido[3,2-d]pyrimidin-2-yl)phenyl)urea;
(R)-1-(4-(3-(dimethylamino)pyrrolidine-1-carbonyl)phenyl)-3-(4-(4-morpholino-7-(pyrimidin-5-yl)quinazolin-2-yl)phenyl)urea;
(S)-1-(4-(3-(dimethylamino)pyrrolidine-1-carbonyl)phenyl)-3-(4-(4-morpholino-7-(pyrimidin-5-yl)quinazolin-2-yl)phenyl)urea;
1-(4-(3-hydroxypyrrolidine-1-carbonyl)phenyl)-3-(4-(4-morpholino-7-(pyrimidin-5-yl)quinazolin-2-yl)phenyl)urea;
4-(3-(4-(7-(5-(((dimethylamino)methyl)furan-2-yl)-4-morpholino-quinazolin-2-yl)phenyl)ureido)-N,N-dimethyl-benzamide;
1-(4-(4-(dimethylamino)piperidine-1-carbonyl)phenyl)-3-(4-(7-(5-methylfuran-2-yl)-4-morpholino-quinazolin-2-yl)phenyl)urea;
N-(2-(dimethylamino)ethyl)-4-(3-(4-(4-morpholino-7-(pyrimidin-5-yl)quinazolin-2-yl)phenyl)ureido)-benzamide;
1-(4-(4-(dimethylamino)piperidine-1-carbonyl)phenyl)-3-(4-(7-(4-methylpyridin-3-yl)-4-morpholino-quinazolin-2-yl)phenyl)urea;
(S)-1-(4-(3-aminopyrrolidine-1-carbonyl)phenyl)-3-(4-(4-morpholino-7-(pyrimidin-5-yl)quinazolin-2-yl)phenyl)urea;
(S)-1-(4-(3-(dimethylamino)pyrrolidine-1-carbonyl)phenyl)-3-(4-(7-(5-methylfuran-2-yl)-4-morpholino-quinazolin-2-yl)phenyl)urea;
(R)-1-(4-(3-(dimethylamino)pyrrolidine-1-carbonyl)phenyl)-3-(4-(7-(5-methylfuran-2-yl)-4-morpholino-quinazolin-2-yl)phenyl)urea;
(R)-1-(4-(3-aminopyrrolidine-1-carbonyl)phenyl)-3-(4-(4-morpholino-7-(pyrimidin-5-yl)quinazolin-2-yl)phenyl)urea;
(S)-1-(4-(3-(dimethylamino)pyrrolidine-1-carbonyl)phenyl)-3-(4-(6-fluoro-4-morpholino-7-(pyridin-3-yl)quinazolin-2-yl)phenyl)urea;
(S)-1-(4-(3-(dimethylamino)pyrrolidine-1-carbonyl)phenyl)-3-(4-(4-morpholino-7-(pyrimidin-5-yl)pyrido[3,2-d]pyrimidin-2-yl)phenyl)urea;
(R)-1-(4-(3-(dimethylamino)pyrrolidine-1-carbonyl)phenyl)-3-(4-(6-fluoro-4-morpholino-7-(pyridin-3-yl)quinazolin-2-yl)phenyl)urea;
N-(2-(dimethylamino)ethyl)-4-(3-(4-(7-(5-methylfuran-2-yl)-4-morpholino-quinazolin-2-yl)phenyl)ureido)-benzamide;
4-(3-(4-(7-(1-methyl-1H-pyrazol-4-yl)-4-morpholino-pyrido[3,2-d]pyrimidin-2-yl)phenyl)ureido)-benzamide;
4-(3-(2-fluoro-4-(7-(5-(hydroxymethyl)furan-2-yl)-4-morpholino-quinazolin-2-yl)phenyl)ureido)-N,N-dimethyl-benzamide;
1-(4-(3-hydroxypyrrolidine-1-carbonyl)phenyl)-3-(4-(7-(5-methylfuran-2-yl)-4-morpholino-quinazolin-2-yl)phenyl)urea;
(R)-1-(4-(3-(dimethylamino)pyrrolidine-1-carbonyl)phenyl)-3-(2-fluoro-4-(7-(1-methyl-1H-pyrazol-4-yl)-4-morpholino-pyrido[3,2-d]pyrimidin-2-yl)phenyl)urea;
4-(3-(4-(7-(5-(1-hydroxyethyl)furan-2-yl)-4-morpholino-quinazolin-2-yl)phenyl)ureido)-N,N-dimethyl-benzamide;
(S)-1-(4-(3-(dimethylamino)pyrrolidine-1-carbonyl)phenyl)-3-(2-fluoro-4-(4-morpholino-7-(pyrimidin-5-yl)quinazolin-2-yl)phenyl)urea;
(S)-1-(4-(3-aminopyrrolidine-1-carbonyl)phenyl)-3-(2-fluoro-4-(4-morpholino-7-(pyrimidin-5-yl)quinazolin-2-yl)phenyl)urea;
(R)-1-(4-(3-aminopyrrolidine-1-carbonyl)phenyl)-3-(2-fluoro-4-(4-morpholino-7-(pyrimidin-5-yl)quinazolin-2-yl)phenyl)urea;
(S)-1-(4-(3-(dimethylamino)pyrrolidine-1-carbonyl)phenyl)-3-(2-fluoro-4-(7-(1-methyl-1H-pyrazol-4-yl)-4-morpholino-pyrido[3,2-d]pyrimidin-2-yl)phenyl)urea;
1-(2-fluoro-4-(6-fluoro-4-morpholino-7-(pyridin-3-yl)quinazolin-2-yl)phenyl)-3-(4-(4-methylpiperazine-1-carbonyl)phenyl)urea;
1-(2-fluoro-4-(4-morpholino-7-(pyridin-4-yl)quinazolin-2-yl)phenyl)-3-(4-(4-methylpiperazine-1-carbonyl)phenyl)urea;
(S)-1-(4-(3-(dimethylamino)pyrrolidine-1-carbonyl)phenyl)-3-(2-fluoro-4-(7-(2-fluoropyridin-3-yl)-4-morpholino-pyrido[3,2-d]pyrimidin-2-yl)phenyl)urea;
4-(3-(2-fluoro-4-(7-(5-(1-hydroxyethyl)furan-2-yl)-4-morpholino-quinazolin-2-yl)phenyl)ureido)-N,N-dimethyl-benzamide;
4-(3-(2-fluoro-4-(4-morpholino-7-(pyrimidin-5-yl)quinazolin-2-yl)phenyl)ureido)-N-methyl-benzamide;
4-(3-(4-(7-(5-(1-hydroxyethyl)furan-2-yl)-4-morpholino-pyrido[3,2-d]pyrimidin-2-yl)phenyl)ureido)-N,N-dimethyl-benzamide;

N-(2-(dimethylamino)ethyl)-4-(3-(2-fluoro-4-(4-morpholino-7-(pyrimidin-5-yl)quinazolin-2-yl)phenyl)ureido)-benzamide;

4-(3-(2-fluoro-4-(7-(5-(hydroxymethyl)furan-2-yl)-4-morpholino-pyrido[3,2-d]pyrimidin-2-yl)phenyl)ureido)-N,N-dimethyl-benzamide;

3-fluoro-4-(3-(4-(7-(5-(hydroxymethyl)furan-2-yl)-4-morpholino-quinazolin-2-yl)phenyl)ureido)-N,N-dimethyl-benzamide;

(S)-1-(4-(3-(dimethylamino)pyrrolidine-1-carbonyl)phenyl)-3-(4-(7-(3,5-dimethylisoxazol-4-yl)-4-morpholino-quinazolin-2-yl)phenyl)urea;

(S)-1-(4-(3-(dimethylamino)pyrrolidine-1-carbonyl)phenyl)-3-(4-(7-(3,5-dimethylisoxazol-4-yl)-4-morpholino-quinazolin-2-yl)-2-fluorophenyl)urea;

4-(3-(4-(7-(5-(2-hydroxypropan-2-yl)furan-2-yl)-4-morpholino-quinazolin-2-yl)phenyl)ureido)-N,N-dimethyl-benzamide;

4-(3-(4-(7-(5-cyanofuran-2-yl)-4-morpholino-quinazolin-2-yl)phenyl)ureido)-N,N-dimethyl-benzamide;

4-(3-(4-(7-(5-acetylfuran-2-yl)-4-morpholino-quinazolin-2-yl)phenyl)ureido)-N,N-dimethyl-benzamide;

N-(2-(dimethylamino)ethyl)-5-(2-(4-(3-(4-(dimethylcarbamoyl)phenyl)ureido)phenyl)-4-morpholino-quinazolin-7-yl)furan-2-carboxamide;

4-(3-(4-(7-(2-(dimethylamino)pyrimidin-5-yl)-4-morpholino-quinazolin-2-yl)phenyl)ureido)-N,N-dimethyl-benzamide;

3-fluoro-4-(3-(4-(7-(5-(1-hydroxyethyl)furan-2-yl)-4-morpholino-quinazolin-2-yl)phenyl)ureido)-N,N-dimethyl-benzamide;

3-fluoro-4-(3-(4-(7-(5-(hydroxymethyl)furan-2-yl)-4-morpholino-quinazolin-2-yl)phenyl)ureido)-N,N-dimethyl-benzamide;

5-(2-(4-(3-(4-(dimethylcarbamoyl)phenyl)ureido)phenyl)-4-morpholino-quinazolin-7-yl)-N,N-dimethylfuran-2-carboxamide;

4-(3-(4-(7-(2-(dimethylamino)pyrimidin-5-yl)-4-morpholino-pyrido[3,2-d]pyrimidin-2-yl)phenyl)ureido)-N,N-dimethyl-benzamide;

4-(3-(4-(7-(2-(dimethylamino)pyrimidin-5-yl)-4-morpholino-quinazolin-2-yl)-2-fluorophenyl)ureido)-N,N-dimethyl-benzamide;

1-(4-(7-(furan-2-yl)-4-morpholino-quinazolin-2-yl)phenyl)-3-(4-(3-hydroxypyrrolidine-1-carbonyl)phenyl)urea;

4-(3-(4-(7-(furan-2-yl)-4-morpholino-quinazolin-2-yl)phenyl)ureido)-N-methyl-benzamide;

(S)-1-(4-(3-aminopyrrolidine-1-carbonyl)phenyl)-3-(4-(7-(furan-2-yl)-4-morpholino-quinazolin-2-yl)phenyl)urea;

N-(2-(dimethylamino)ethyl)-4-(3-(4-(7-(furan-2-yl)-4-morpholino-quinazolin-2-yl)phenyl)ureido)-benzamide;

N-(2-(dimethylamino)ethyl)-4-(3-(4-(7-(furan-2-yl)-4-morpholino-quinazolin-2-yl)phenyl)ureido)-N-methyl-benzamide;

4-(3-(3-fluoro-4-(4-morpholino-7-(pyrimidin-5-yl)quinazolin-2-yl)phenyl)ureido)-N,N-dimethyl-benzamide;

4-(3-(3-fluoro-4-(7-(1-methyl-1H-pyrazol-4-yl)-4-morpholino-pyrido[3,2-d]pyrimidin-2-yl)phenyl)ureido)-N,N-dimethyl-benzamide;

4-(3-(3-fluoro-4-(7-(5-methylfuran-2-yl)-4-morpholino-quinazolin-2-yl)phenyl)ureido)-N,N-dimethyl-benzamide;

2-fluoro-N,N-dimethyl-4-(3-(4-(4-morpholino-7-(pyrimidin-5-yl)quinazolin-2-yl)phenyl)ureido)-benzamide;

4-(3-(3-fluoro-4-(7-(2-fluoropyridin-3-yl)-4-morpholino-quinazolin-2-yl)phenyl)ureido)-N,N-dimethyl-benzamide;

4-(3-(3-fluoro-4-(7-(2-methoxypyrimidin-5-yl)-4-morpholino-quinazolin-2-yl)phenyl)ureido)-N,N-dimethyl-benzamide;

4-(3-(3-fluoro-4-(4-morpholino-7-(pyridin-3-yl)quinazolin-2-yl)phenyl)ureido)-N,N-dimethyl-benzamide;

4-(3-(3-fluoro-4-(7-(2-fluoropyridin-3-yl)-4-morpholino-pyrido[3,2-d]pyrimidin-2-yl)phenyl)ureido)-N,N-dimethyl-benzamide;

4-(3-(3-fluoro-4-(7-(3-(methylsulfonyl)phenyl)-4-morpholino-quinazolin-2-yl)phenyl)ureido)-N,N-dimethyl-benzamide;

4-(3-(4-(7-(3,5-dimethylisoxazol-4-yl)-4-morpholino-quinazolin-2-yl)phenyl)ureido)-2-fluoro-N,N-dimethyl-benzamide;

4-(3-(3-fluoro-4-(7-(furan-2-yl)-4-morpholino-quinazolin-2-yl)phenyl)ureido)-N,N-dimethyl-benzamide;

2-fluoro-4-(3-(4-(7-(2-fluoropyridin-3-yl)-4-morpholino-pyrido[3,2-d]pyrimidin-2-yl)phenyl)ureido)-N,N-dimethyl-benzamide;

4-(3-(3-fluoro-4-(7-(1-methyl-1H-pyrazol-4-yl)-4-morpholino-quinazolin-2-yl)phenyl)ureido)-N,N-dimethyl-benzamide;

4-(3-(3-fluoro-4-(4-morpholino-7-(pyrimidin-5-yl)pyrido[3,2-d]pyrimidin-2-yl)phenyl)ureido)-N,N-dimethyl-benzamide;

5-(3-(3-fluoro-4-(4-morpholino-7-(pyrimidin-5-yl)quinazolin-2-yl)phenyl)ureido)-N,N-dimethylpicolinamide;

4-(3-(4-(7-(3,5-dimethylisoxazol-4-yl)-4-morpholino-quinazolin-2-yl)-3-fluorophenyl)ureido)-N,N-dimethyl-benzamide;

2-fluoro-N,N-dimethyl-4-(3-(5-(7-(3-(methylsulfonyl)phenyl)-4-morpholino-quinazolin-2-yl)pyridin-2-yl)ureido)-benzamide;

4-(3-(3-fluoro-4-(4-(2-methylmorpholino)-7-(pyrimidin-5-yl)quinazolin-2-yl)phenyl)ureido)-N,N-dimethyl-benzamide;

2-fluoro-4-(3-(4-(7-(2-fluoropyridin-3-yl)-4-morpholino-quinazolin-2-yl)phenyl)ureido)-N,N-dimethyl-benzamide;

4-(3-(3-fluoro-4-(6-fluoro-4-morpholino-7-(pyrimidin-5-yl)quinazolin-2-yl)phenyl)ureido)-N,N-dimethyl-benzamide;

2-fluoro-4-(3-(4-(7-(2-methoxypyrimidin-5-yl)-4-morpholino-quinazolin-2-yl)phenyl)ureido)-N,N-dimethyl-benzamide;

4-(3-(3-fluoro-4-(7-(6-methoxypyridin-3-yl)-4-morpholino-quinazolin-2-yl)phenyl)ureido)-N,N-dimethyl-benzamide;

2-fluoro-4-(3-(4-(7-(6-methoxypyridin-3-yl)-4-morpholino-quinazolin-2-yl)phenyl)ureido)-N,N-dimethyl-benzamide;

2-fluoro-N,N-dimethyl-4-(3-(4-(4-morpholino-7-(pyridin-3-yl)quinazolin-2-yl)phenyl)ureido)-benzamide;

4-(3-(3-fluoro-4-(4-morpholino-7-(pyridin-3-yl)pyrido[3,2-d]pyrimidin-2-yl)phenyl)ureido)-N,N-dimethyl-benzamide;

2-fluoro-N,N-dimethyl-4-(3-(4-(4-morpholino-7-(pyrimidin-5-yl)pyrido[3,2-d]pyrimidin-2-yl)phenyl)ureido)-benzamide;

4-(3-(3-fluoro-4-(7-(2-methoxypyrimidin-5-yl)-4-morpholino-pyrido[3,2-d]pyrimidin-2-yl)phenyl)ureido)-N,N-dimethyl-benzamide;

2-fluoro-N,N-dimethyl-4-(3-(4-(4-morpholino-7-(pyridin-3-yl)pyrido[3,2-d]pyrimidin-2-yl)phenyl)ureido)-benzamide;

2-fluoro-4-(3-(4-(7-(furan-2-yl)-4-morpholino-quinazolin-2-yl)phenyl)ureido)-N,N-dimethyl-benzamide;

2-fluoro-N,N-dimethyl-4-(3-(4-(7-(5-methylfuran-2-yl)-4-morpholino-quinazolin-2-yl)phenyl)ureido)-benzamide;

2-fluoro-N,N-dimethyl-4-(3-(4-(4-morpholino-7-(pyridin-2-yl)quinazolin-2-yl)phenyl)ureido)-benzamide;

4-(3-(3-fluoro-4-(4-morpholino-7-(pyridin-2-yl)quinazolin-2-yl)phenyl)ureido)-N,N-dimethyl-benzamide;

4-(3-(3-fluoro-4-(4-morpholino-7-(1,3,5-trimethyl-1H-pyrazol-4-yl)quinazolin-2-yl)phenyl)ureido)-N,N-dimethyl-benzamide;

4-(3-(3-fluoro-4-(7-(2-methoxypyridin-3-yl)-4-morpholino-quinazolin-2-yl)phenyl)ureido)-N,N-dimethyl-benzamide;

4-(3-(3-fluoro-4-(7-(6-methylpyridin-3-yl)-4-morpholino-quinazolin-2-yl)phenyl)ureido)-N,N-dimethyl-benzamide;

4-(3-(3-fluoro-4-(7-(2-methylpyridin-3-yl)-4-morpholino-quinazolin-2-yl)phenyl)ureido)-N,N-dimethyl-benzamide;

2-fluoro-N,N-dimethyl-4-(3-(4-(7-(1-methyl-1H-pyrazol-4-yl)-4-morpholino-pyrido[3,2-d]pyrimidin-2-yl)phenyl)ureido)-benzamide;

4-(3-(3-fluoro-4-(7-(5-(hydroxymethyl)furan-2-yl)-4-morpholino-quinazolin-2-yl)phenyl)ureido)-N,N-dimethyl-benzamide;

4-(3-(3-fluoro-4-(7-(5-(1-hydroxyethyl)furan-2-yl)-4-morpholino-quinazolin-2-yl)phenyl)ureido)-N,N-dimethyl-benzamide;

4-(3-(3-fluoro-4-(7-(5-(2-hydroxypropan-2-yl)furan-2-yl)-4-morpholino-quinazolin-2-yl)phenyl)ureido)-N,N-dimethyl-benzamide;

4-(3-(4-(7-(2-(dimethylamino)pyrimidin-5-yl)-4-morpholino-quinazolin-2-yl)-3-fluorophenyl)ureido)-N,N-dimethyl-benzamide;

2-fluoro-4-(3-(4-(7-(5-(hydroxymethyl)furan-2-yl)-4-morpholino-quinazolin-2-yl)phenyl)ureido)-N,N-dimethyl-benzamide;

4-(3-(2,5-difluoro-4-(4-morpholino-7-(pyrimidin-5-yl)quinazolin-2-yl)phenyl)ureido)-N,N-dimethyl-benzamide;

4-(3-(2,3-difluoro-4-(4-morpholino-7-(pyrimidin-5-yl)quinazolin-2-yl)phenyl)ureido)-N,N-dimethyl-benzamide;

4-(3-(2,3-difluoro-4-(7-(5-methylfuran-2-yl)-4-morpholino-quinazolin-2-yl)phenyl)ureido)-N,N-dimethyl-benzamide;

-(3-(2,3-difluoro-4-(7-(furan-2-yl)-4-morpholino-quinazolin-2-yl)phenyl)ureido)-N,N-dimethyl-benzamide;

4-(3-(4-(7-(2-((2-hydroxyethyl)amino)pyridin-3-yl)-4-morpholino-quinazolin-2-yl)phenyl)ureido)-N,N-dimethyl-benzamide;

4-(3-(4-(7-((4-hydroxypiperidin-1-yl)methyl)-4-morpholino-quinazolin-2-yl)phenyl)ureido)-N,N-dimethyl-benzamide;

4-(3-(4-(7-(hydroxymethyl)-4-morpholino-quinazolin-2-yl)phenyl)ureido)-N,N-dimethyl-benzamide;

1-(4-(4-(dimethylamino)piperidine-1-carbonyl)phenyl)-3-(4-(7-(2-hydroxypropan-2-yl)-4-morpholino-quinazolin-2-yl)phenyl)urea;

4-(3-(4-(7-(4-(dimethylamino)piperidine-1-carbonyl)-4-morpholino-quinazolin-2-yl)phenyl)ureido)-N,N-dimethyl-benzamide;

(R)-1-(4-(3-(dimethylamino)pyrrolidine-1-carbonyl)phenyl)-3-(4-(7-(2-hydroxypropan-2-yl)-4-morpholino-quinazolin-2-yl)phenyl)urea;

(S)-1-(4-(3-(dimethylamino)pyrrolidine-1-carbonyl)phenyl)-3-(4-(7-(2-hydroxypropan-2-yl)-4-morpholino-quinazolin-2-yl)phenyl)urea;

4-(3-(2-fluoro-4-(7-(2-hydroxypropan-2-yl)-4-morpholino-quinazolin-2-yl)phenyl)ureido)-N,N-dimethyl-benzamide;

N-(4-(3-(4-(4-morpholino-7-(pyrimidin-5-yl)quinazolin-2-yl)phenyl)ureido)phenyl)-acetamide;

1-(4-(7-(2-fluoropyridin-3-yl)-4-morpholinoquinazolin-2-yl)phenyl)-3-(4-(2-oxopyrrolidin-1-yl)phenyl)urea;

N-(4-(3-(4-(7-(2-fluoropyridin-3-yl)-4-morpholinopyrido[3,2-d]pyrimidin-2-yl)phenyl)ureido)phenyl)acetamide;

N-(4-(3-(4-(7-(1-methyl-1H-pyrazol-4-yl)-4-morpholinopyrido[3,2-d]pyrimidin-2-yl)phenyl)ureido)phenyl)acetamide;

N,N-dimethyl-4-(3-(4-(4-morpholino-7-(1,3,5-trimethyl-1H-pyrazol-4-yl)pyrido[3,2-d]pyrimidin-2-yl)phenyl)ureido)-benzamide;

4-(3-(2-fluoro-4-(4-morpholino-7-(1,3,5-trimethyl-1H-pyrazol-4-yl)pyrido[3,2-d]pyrimidin-2-yl)phenyl)ureido)-N,N-dimethyl-benzamide;

N,N-dimethyl-4-(3-(4-(7-(2-methylpyridin-3-yl)-4-morpholinopyrido[3,2-d]pyrimidin-2-yl)phenyl)ureido)-benzamide;

4-(3-(2-fluoro-4-(7-(2-methylpyridin-3-yl)-4-morpholinopyrido[3,2-d]pyrimidin-2-yl)phenyl)ureido)-N,N-dimethyl-benzamide;

N,N-dimethyl-4-(3-(4-(7-(6-methylpyridin-3-yl)-4-morpholinopyrido[3,2-d]pyrimidin-2-yl)phenyl)ureido)-benzamide;

4-(3-(2-fluoro-4-(7-(6-methylpyridin-3-yl)-4-morpholinopyrido[3,2-d]pyrimidin-2-yl)phenyl)ureido)-N,N-dimethyl-benzamide;

N-(4-(3-(4-(7-(5-methylfuran-2-yl)-4-morpholinopyrido[3,2-d]pyrimidin-2-yl)phenyl)ureido)phenyl)acetamide;

N-(4-(3-(4-(7-(2-fluoropyridin-3-yl)-4-morpholinopyrido[3,2-d]pyrimidin-2-yl)phenyl)ureido)phenyl)acetamide;

N-(4-(3-(4-(4-morpholino-7-(pyridin-3-yl)pyrido[3,2-d]pyrimidin-2-yl)phenyl)ureido)phenyl)acetamide;

N-(4-(3-(4-(4-morpholino-7-(pyridin-4-yl)pyrido[3,2-d]pyrimidin-2-yl)phenyl)ureido)phenyl)acetamide;

N-(4-(3-(4-(4-morpholino-7-(pyridin-2-yl)pyrido[3,2-d]pyrimidin-2-yl)phenyl)ureido)phenyl)acetamide;

N-(4-(3-(4-(4-morpholino-7-(pyrimidin-5-yl)pyrido[3,2-d]pyrimidin-2-yl)phenyl)ureido)phenyl)acetamide;

N-(4-(3-(4-(4-morpholino-7-(pyridazin-4-yl)pyrido[3,2-d]pyrimidin-2-yl)phenyl)ureido)phenyl)acetamide;

N-(4-(3-(4-(7-(2-methoxypyrimidin-5-yl)-4-morpholinopyrido[3,2-d]pyrimidin-2-yl)phenyl)ureido)phenyl)acetamide;

N-(4-(3-(4-(7-(6-methoxypyridin-3-yl)-4-morpholinopyrido[3,2-d]pyrimidin-2-yl)phenyl)ureido)phenyl)acetamide;

N-(4-(3-(4-(7-(3-(methylsulfonyl)phenyl)-4-morpholinopyrido[3,2-d]pyrimidin-2-yl)phenyl)ureido)phenyl)acetamide;
N-(4-(3-(4-(7-(2-aminopyrimidin-5-yl)-4-morpholinopyrida[3,2-d]pyrimidin-2-yl)phenyl)ureido)phenyl)acetamide;
N-(4-(3-(4-(4-morpholino-7-(1,3,5-trimethyl-1H-pyrazol-4-yl)quinazolin-2-yl)phenyl)ureido)phenyl)acetamide;
N-(4-(3-(4-(7-(2-methylpyridin-3-yl)-4-morpholinopyrida[3,2-d]pyrimidin-2-yl)phenyl)ureido)phenyl)acetamide;
N-(4-(3-(4-(7-(6-methylpyridin-3-yl)-4-morpholinopyrida[3,2-d]pyrimidin-2-yl)phenyl)ureido)phenyl)acetamide;
N-(4-(3-(5-(7-(2-fluoropyridin-3-yl)-4-morpholinopyrida[3,2-d]pyrimidin-2-yl)pyridin-2-yl)ureido)phenyl)acetamide;
N-(4-(3-(5-(7-(1-methyl-1H-pyrazol-4-yl)-4-morpholinopyrido[3,2-d]pyrimidin-2-yl)pyridin-2-yl)ureido)phenyl)acetamide;
4-(3-(4-(7-(5-ethylfuran-2-yl)-4-morpholinoquinazolin-2-yl)phenyl)ureido)-N,N-dimethyl-benzamide;
4-(3-(4-(7-(5-(1,2-dihydroxyethyl)furan-2-yl)-4-morpholinoquinazolin-2-yl)phenyl)ureido)-N,N-dimethylbenzamide;
N-(4-(3-(4-(7-(5-ethylfuran-2-yl)-4-morpholinoquinazolin-2-yl)phenyl)ureido)phenyl)acetamide;
N-(4-(3-(4-(7-(5-(hydroxymethyl)furan-2-yl)-4-morpholinoquinazolin-2-yl)phenyl)ureido)phenyl)acetamide;
N-(4-(3-(4-(7-(5-(1-hydroxyethyl)furan-2-yl)-4-morpholinoquinazolin-2-yl)phenyl)ureido)phenyl)acetamide;
N-(4-(3-(4-(7-(5-(2-hydroxypropan-2-yl)furan-2-yl)-4-morpholinoquinazolin-2-yl)phenyl)ureido)phenyl)acetamide;
N-(4-(3-(4-(7-(furan-2-yl)-4-morpholinoquinazolin-2-yl)phenyl)ureido)phenyl)acetamide;
N-(4-(3-(4-(4-morpholino-7-(pyridin-3-yl)quinazolin-2-yl)phenyl)ureido)phenyl)acetamide;
N-(4-(3-(4-(4-morpholino-7-(pyridin-4-yl)quinazolin-2-yl)phenyl)ureido)phenyl)acetamide;
N-(4-(3-(4-(4-morpholino-7-(pyridin-2-yl)quinazolin-2-yl)phenyl)ureido)phenyl)acetamide;
N-(4-(3-(4-(4-morpholino-7-(pyridazin-4-yl)quinazolin-2-yl)phenyl)ureido)phenyl)acetamide;
N-(4-(3-(4-(7-(2-methoxypyrimidin-5-yl)-4-morpholinoquinazolin-2-yl)phenyl)ureido)phenyl)acetamide;
N-(4-(3-(4-(7-(6-methoxypyridin-3-yl)-4-morpholinoquinazolin-2-yl)phenyl)ureido)phenyl)acetamide;
N-(4-(3-(4-(7-(3-(methylsulfonyl)phenyl)-4-morpholinoquinazolin-2-yl)phenyl)ureido)phenyl)acetamide;
N-(4-(3-(4-(7-(2-aminopyrimidin-5-yl)-4-morpholinoquinazolin-2-yl)phenyl)ureido)phenyl)acetamide;
N-(4-(3-(4-(4-morpholino-7-(1,3,5-trimethyl-1H-pyrazol-4-yl)quinazolin-2-yl)phenyl)ureido)phenyl)acetamide;
N-(4-(3-(4-(7-(2-methylpyridin-3-yl)-4-morpholinoquinazolin-2-yl)phenyl)ureido)phenyl)acetamide;
N-(4-(3-(4-(7-(6-methylpyridin-3-yl)-4-morpholinoquinazolin-2-yl)phenyl)ureido)phenyl)acetamide;
N-(4-(3-(5-(7-(5-methylfuran-2-yl)-4-morpholinoquinazolin-2-yl)pyridin-2-yl)ureido)phenyl)acetamide;
N-(4-(3-(5-(7-(furan-2-yl)-4-morpholinoquinazolin-2-yl)pyridin-2-yl)ureido)phenyl)acetamide;
N-(4-(3-(5-(4-morpholino-7-(pyrimidin-5-yl)quinazolin-2-yl)pyridin-2-yl)ureido)phenyl)acetamide;
N-(4-(3-(5-(7-(1-methyl-1H-pyrazol-4-yl)-4-morpholinoquinazolin-2-yl)pyridin-2-yl)ureido)phenyl)acetamide;
N-(4-(3-(4-(6-fluoro-7-(5-methylfuran-2-yl)-4-morpholinoquinazolin-2-yl)phenyl)ureido)phenyl)acetamide;
N-(4-(3-(4-(6-fluoro-7-(furan-2-yl)-4-morpholinoquinazolin-2-yl)phenyl)ureido)phenyl)acetamide;
N-(4-(3-(4-(6-fluoro-4-morpholino-7-(pyridin-3-yl)quinazolin-2-yl)phenyl)ureido)phenyl)acetamide;
N-(4-(3-(4-(6-fluoro-4-morpholino-7-(pyrimidin-5-yl)quinazolin-2-yl)phenyl)ureido)phenyl)acetamide;
N-(3-fluoro-4-(3-(4-(7-(5-methylfuran-2-yl)-4-morpholinoquinazolin-2-yl)phenyl)ureido)phenyl)acetamide;
N-(4-(3-(4-(7-(5-ethylfuran-2-yl)-4-morpholinoquinazolin-2-yl)phenyl)ureido)-3-fluorophenyl)acetamide;
N-(3-fluoro-4-(3-(4-(7-(furan-2-yl)-4-morpholinoquinazolin-2-yl)phenyl)ureido)phenyl)acetamide;
N-(3-fluoro-4-(3-(4-(4-morpholino-7-(pyridin-3-yl)quinazolin-2-yl)phenyl)ureido)phenyl)acetamide;
N-(3-fluoro-4-(3-(4-(7-(2-fluoropyridin-3-yl)-4-morpholinoquinazolin-2-yl)phenyl)ureido)phenyl)acetamide;
N-(3-fluoro-4-(3-(4-(7-(2-methylpyridin-3-yl)-4-morpholinoquinazolin-2-yl)phenyl)ureido)phenyl)acetamide;
N-(3-fluoro-4-(3-(4-(7-(6-methylpyridin-3-yl)-4-morpholinoquinazolin-2-yl)phenyl)ureido)phenyl)acetamide;
N-(3-fluoro-4-(3-(4-(4-morpholino-7-(pyridin-2-yl)quinazolin-2-yl)phenyl)ureido)phenyl)acetamide;
N-(3-fluoro-4-(3-(4-(4-morpholino-7-(pyridin-4-yl)quinazolin-2-yl)phenyl)ureido)phenyl)acetamide;
N-(3-fluoro-4-(3-(4-(4-morpholino-7-(pyrimidin-5-yl)quinazolin-2-yl)phenyl)ureido)phenyl)acetamide;
N-(3-fluoro-4-(3-(4-(7-(2-methoxypyrimidin-5-yl)-4-morpholinoquinazolin-2-yl)phenyl)ureido)phenyl)acetamide;
N-(4-(3-(4-(7-(2-aminopyrimidin-5-yl)-4-morpholinoquinazolin-2-yl)phenyl)ureido)-3-fluorophenyl)acetamide;
N-(3-fluoro-4-(3-(4-(7-(6-methoxypyridin-3-yl)-4-morpholinoquinazolin-2-yl)phenyl)ureido)phenyl)acetamide;
N-(3-fluoro-4-(3-(4-(7-(1-methyl-1H-pyrazol-4-yl)-4-morpholinoquinazolin-2-yl)phenyl)ureido)phenyl)acetamide;
N-(3-fluoro-4-(3-(4-(4-morpholino-7-(1,3,5-trimethyl-1H-pyrazol-4-yl)quinazolin-2-yl)phenyl)ureido)phenyl)acetamide;
N-(3-fluoro-4-(3-(4-(7-(3-(methylsulfonyl)phenyl)-4-morpholinoquinazolin-2-yl)phenyl)ureido)phenyl)acetamide;
N-(3-fluoro-4-(3-(4-(7-(5-(hydroxymethyl)furan-2-yl)-4-morpholinoquinazolin-2-yl)phenyl)ureido)phenyl)acetamide;
N-(3-fluoro-4-(3-(4-(7-(5-(1-hydroxyethyl)furan-2-yl)-4-morpholinoquinazolin-2-yl)phenyl)ureido)phenyl)acetamide;
N-(3-fluoro-4-(3-(4-(7-(5-(2-hydroxypropan-2-yl)furan-2-yl)-4-morpholinoquinazolin-2-yl)phenyl)ureido)phenyl)acetamide;
N-(2-fluoro-4-(3-(4-(7-(5-methylfuran-2-yl)-4-morpholinoquinazolin-2-yl)phenyl)ureido)phenyl)acetamide;
N-(4-(3-(4-(7-(5-ethylfuran-2-yl)-4-morpholinoquinazolin-2-yl)phenyl)ureido)-2-fluorophenyl)acetamide;

N-(2-fluoro-4-(3-(4-(7-(furan-2-yl)-4-morpholino-quinazolin-2-yl)phenyl)ureido)phenyl)acetamide;
N-(2-fluoro-4-(3-(4-(4-morpholino-7-(pyridin-3-yl)quinazolin-2-yl)phenyl)ureido)phenyl)acetamide;
N-(2-fluoro-4-(3-(4-(7-(2-fluoropyridin-3-yl)-4-morpholinoquinazolin-2-yl)phenyl)ureido)phenyl)acetamide;
N-(2-fluoro-4-(3-(4-(7-(2-methylpyridin-3-yl)-4-morpholinoquinazolin-2-yl)phenyl)ureido)phenyl)acetamide;
N-(2-fluoro-4-(3-(4-(7-(6-methylpyridin-3-yl)-4-morpholinoquinazolin-2-yl)phenyl)ureido)phenyl)acetamide;
N-(2-fluoro-4-(3-(4-(4-morpholino-7-(pyridin-2-yl)quinazolin-2-yl)phenyl)ureido)phenyl)acetamide;
N-(2-fluoro-4-(3-(4-(4-morpholino-7-(pyridin-4-yl)quinazolin-2-yl)phenyl)ureido)phenyl)acetamide;
N-(2-fluoro-4-(3-(4-(4-morpholino-7-(pyrimidin-5-yl)quinazolin-2-yl)phenyl)ureido)phenyl)acetamide;
N-(2-fluoro-4-(3-(4-(7-(2-methoxypyrimidin-5-yl)-4-morpholinoquinazolin-2-yl)phenyl)ureido)phenyl)acetamide;
N-(4-(3-(4-(7-(2-aminopyrimidin-5-yl)-4-morpholinoquinazolin-2-yl)phenyl)ureido)-2-fluorophenyl)acetamide;
N-(2-fluoro-4-(3-(4-(7-(6-methoxypyridin-3-yl)-4-morpholinoquinazolin-2-yl)phenyl)ureido)phenyl)acetamide;
N-(2-fluoro-4-(3-(4-(7-(1-methyl-1H-pyrazol-4-yl)-4-morpholinoquinazolin-2-yl)phenyl)ureido)phenyl)acetamide;
N-(2-fluoro-4-(3-(4-(4-morpholino-7-(1,3,5-trimethyl-1H-pyrazol-4-yl)quinazolin-2-yl)phenyl)ureido)phenyl)acetamide;
N-(2-fluoro-4-(3-(4-(7-(3-(methylsulfonyl)phenyl)-4-morpholinoquinazolin-2-yl)phenyl)ureido)phenyl)acetamide;
N-(2-fluoro-4-(3-(4-(7-(5-(hydroxymethyl)furan-2-yl)-4-morpholinoquinazolin-2-yl)phenyl)ureido)phenyl)acetamide;
N-(2-fluoro-4-(3-(4-(7-(5-(1-hydroxyethyl)furan-2-yl)-4-morpholinoquinazolin-2-yl)phenyl)ureido)phenyl)acetamide;
N-(2-fluoro-4-(3-(4-(7-(5-(2-hydroxypropan-2-yl)furan-2-yl)-4-morpholinoquinazolin-2-yl)phenyl)ureido)phenyl)acetamide;
N-methyl-N-(4-(3-(4-(7-(5-methylfuran-2-yl)-4-morpholinoquinazolin-2-yl)phenyl)ureido)phenyl)acetamide;
N-(4-(3-(4-(7-(5-ethylfuran-2-yl)-4-morpholinoquinazolin-2-yl)phenyl)ureido)phenyl)-N-methylacetamide;
N-(4-(3-(4-(7-(furan-2-yl)-4-morpholinoquinazolin-2-yl)phenyl)ureido)phenyl)-N-methylacetamide;
N-(4-(3-(4-(7-(2-methoxypyrimidin-5-yl)-4-morpholinoquinazolin-2-yl)phenyl)ureido)phenyl)-N-methylacetamide;
N-methyl-N-(4-(3-(4-(4-morpholino-7-(pyrimidin-5-yl)quinazolin-2-yl)phenyl)ureido)phenyl)acetamide;
N-methyl-N-(4-(3-(4-(4-morpholino-7-(pyridin-3-yl)quinazolin-2-yl)phenyl)ureido)phenyl)acetamide;
N-(4-(3-(4-(7-(2-fluoropyridin-3-yl)-4-morpholino-quinazolin-2-yl)phenyl)ureido)phenyl)-N-methylacetamide;
N-methyl-N-(4-(3-(4-(4-morpholino-7-(pyridin-2-yl)quinazolin-2-yl)phenyl)ureido)phenyl)acetamide;
N-(3-fluoro-4-(3-(4-(6-fluoro-7-(5-methylfuran-2-yl)-4-morpholinoquinazolin-2-yl)phenyl)ureido)phenyl)acetamide;
N-(3-fluoro-4-(3-(4-(6-fluoro-7-(furan-2-yl)-4-morpholinoquinazolin-2-yl)phenyl)ureido)phenyl)acetamide;
N-(3-fluoro-4-(3-(4-(6-fluoro-4-morpholino-7-(pyrimidin-5-yl)quinazolin-2-yl)phenyl)ureido)phenyl)acetamide;
N-(3-fluoro-4-(3-(4-(6-fluoro-4-morpholino-7-(pyridin-3-yl)quinazolin-2-yl)phenyl)ureido)phenyl)acetamide;
N-(2-fluoro-4-(3-(4-(6-fluoro-7-(5-methylfuran-2-yl)-4-morpholinoquinazolin-2-yl)phenyl)ureido)phenyl)acetamide;
N-(2-fluoro-4-(3-(4-(6-fluoro-7-(furan-2-yl)-4-morpholinoquinazolin-2-yl)phenyl)ureido)phenyl)acetamide;
N-(2-fluoro-4-(3-(4-(6-fluoro-4-morpholino-7-(pyrimidin-5-yl)quinazolin-2-yl)phenyl)ureido)phenyl)acetamide;
N-(2-fluoro-4-(3-(4-(6-fluoro-4-morpholino-7-(pyridin-3-yl)quinazolin-2-yl)phenyl)ureido)phenyl)acetamide;
N-(4-(3-(4-(6-fluoro-7-(5-methylfuran-2-yl)-4-morpholinoquinazolin-2-yl)phenyl)ureido)phenyl)-N-methylacetamide;
N-(4-(3-(4-(6-fluoro-7-(furan-2-yl)-4-morpholinoquinazolin-2-yl)phenyl)ureido)phenyl)-N-methylacetamide;
N-(4-(3-(4-(6-fluoro-4-morpholino-7-(pyrimidin-5-yl)quinazolin-2-yl)phenyl)ureido)phenyl)-N-methylacetamide;
N-(4-(3-(4-(6-fluoro-4-morpholino-7-(pyridin-3-yl)quinazolin-2-yl)phenyl)ureido)phenyl)-N-methylacetamide;
N-(3-fluoro-4-(3-(4-(7-(5-methylfuran-2-yl)-4-morpholinopyrido[3,2-d]pyrimidin-2-yl)phenyl)ureido)phenyl)acetamide;
N-(3-fluoro-4-(3-(4-(7-(furan-2-yl)-4-morpholinopyrido[3,2-d]pyrimidin-2-yl)phenyl)ureido)phenyl)acetamide;
N-(3-fluoro-4-(3-(4-(4-morpholino-7-(pyrimidin-5-yl)pyrido[3,2-d]pyrimidin-2-yl)phenyl)ureido)phenyl)acetamide;
N-(3-fluoro-4-(3-(4-(7-(2-fluoropyridin-3-yl)-4-morpholinopyrido[3,2-d]pyrimidin-2-yl)phenyl)ureido)phenyl)acetamide;
N-(3-fluoro-4-(3-(4-(4-morpholino-7-(pyridin-3-yl)pyrido[3,2-d]pyrimidin-2-yl)phenyl)ureido)phenyl)acetamide;
N-(3-fluoro-4-(3-(4-(7-(1-methyl-1H-pyrazol-4-yl)-4-morpholinopyrido[3,2-d]pyrimidin-2-yl)phenyl)ureido)phenyl)acetamide;
N-(2-fluoro-4-(3-(4-(7-(5-methylfuran-2-yl)-4-morpholinopyrido[3,2-d]pyrimidin-2-yl)phenyl)ureido)phenyl)acetamide;
N-(2-fluoro-4-(3-(4-(7-(furan-2-yl)-4-morpholinopyrido[3,2-d]pyrimidin-2-yl)phenyl)ureido)phenyl)acetamide;
N-(2-fluoro-4-(3-(4-(4-morpholino-7-(pyrimidin-5-yl)pyrido[3,2-d]pyrimidin-2-yl)phenyl)ureido)phenyl)acetamide;
N-(2-fluoro-4-(3-(4-(7-(2-fluoropyridin-3-yl)-4-morpholinopyrido[3,2-d]pyrimidin-2-yl)phenyl)ureido)phenyl)acetamide;
N-(2-fluoro-4-(3-(4-(4-morpholino-7-(pyridin-3-yl)pyrido[3,2-d]pyrimidin-2-yl)phenyl)ureido)phenyl)acetamide;

N-(2-fluoro-4-(3-(4-(7-(1-methyl-1H-pyrazol-4-yl)-4-morpholinopyrido[3,2-d]pyrimidin-2-yl)phenyl)ureido)phenyl)acetamide;

N-methyl-N-(4-(3-(4-(7-(5-methylfuran-2-yl)-4-morpholinopyrido[3,2-d]pyrimidin-2-yl)phenyl)ureido)phenyl)acetamide;

N-(4-(3-(4-(7-(furan-2-yl)-4-morpholinopyrido[3,2-d]pyrimidin-2-yl)phenyl)ureido)phenyl)-N-methylacetamide;

N-methyl-N-(4-(3-(4-(4-morpholino-7-(pyrimidin-5-yl)pyrido[3,2-d]pyrimidin-2-yl)phenyl)ureido)phenyl)acetamide;

N-(4-(3-(4-(7-(2-fluoropyridin-3-yl)-4-morpholinopyrido[3,2-d]pyrimidin-2-yl)phenyl)ureido)phenyl)-N-methylacetamide;

N-methyl-N-(4-(3-(4-(4-morpholino-7-(pyridin-3-yl)pyrido[3,2-d]pyrimidin-2-yl)phenyl)ureido)phenyl)acetamide;

N-methyl-N-(4-(3-(4-(7-(1-methyl-1H-pyrazol-4-yl)-4-morpholinopyrido[3,2-d]pyrimidin-2-yl)phenyl)ureido)phenyl)acetamide;

N-(4-(3-(2-fluoro-4-(7-(5-methylfuran-2-yl)-4-morpholinoquinazolin-2-yl)phenyl)ureido)phenyl)acetamide;

N-(4-(3-(2-fluoro-4-(7-(furan-2-yl)-4-morpholinoquinazolin-2-yl)phenyl)ureido)phenyl)acetamide;

N-(4-(3-(2-fluoro-4-(7-(2-methoxypyrimidin-5-yl)-4-morpholinoquinazolin-2-yl)phenyl)ureido)phenyl)acetamide;

N-(4-(3-(2-fluoro-4-(4-morpholino-7-(pyrimidin-5-yl)quinazolin-2-yl)phenyl)ureido)phenyl)acetamide;

N-(4-(3-(2-fluoro-4-(4-morpholino-7-(pyridin-3-yl)quinazolin-2-yl)phenyl)ureido)phenyl)acetamide;

N-(4-(3-(2-fluoro-4-(7-(2-fluoropyridin-3-yl)-4-morpholinoquinazolin-2-yl)phenyl)ureido)phenyl)acetamide;

N-(4-(3-(2-fluoro-4-(4-morpholino-7-(pyridin-2-yl)quinazolin-2-yl)phenyl)ureido)phenyl)acetamide;

N-(4-(3-(3-fluoro-4-(7-(5-methylfuran-2-yl)-4-morpholinoquinazolin-2-yl)phenyl)ureido)phenyl)acetamide;

N-(4-(3-(3-fluoro-4-(7-(furan-2-yl)-4-morpholinoquinazolin-2-yl)phenyl)ureido)phenyl)acetamide;

N-(4-(3-(3-fluoro-4-(7-(2-methoxypyrimidin-5-yl)-4-morpholinoquinazolin-2-yl)phenyl)ureido)phenyl)acetamide;

N-(4-(3-(3-fluoro-4-(4-morpholino-7-(pyrimidin-5-yl)quinazolin-2-yl)phenyl)ureido)phenyl)acetamide;

N-(4-(3-(3-fluoro-4-(4-morpholino-7-(pyridin-3-yl)quinazolin-2-yl)phenyl)ureido)phenyl)acetamide;

N-(4-(3-(3-fluoro-4-(7-(2-fluoropyridin-3-yl)-4-morpholinoquinazolin-2-yl)phenyl)ureido)phenyl)acetamide;

N-(4-(3-(3-fluoro-4-(4-morpholino-7-(pyridin-2-yl)quinazolin-2-yl)phenyl)ureido)phenyl)acetamide;

N-(4-(3-(2-fluoro-4-(6-fluoro-7-(5-methylfuran-2-yl)-4-morpholinoquinazolin-2-yl)phenyl)ureido)phenyl)acetamide;

N-(4-(3-(2-fluoro-4-(6-fluoro-7-(furan-2-yl)-4-morpholinoquinazolin-2-yl)phenyl)ureido)phenyl)acetamide;

N-(4-(3-(2-fluoro-4-(6-fluoro-4-morpholino-7-(pyrimidin-5-yl)quinazolin-2-yl)phenyl)ureido)phenyl)acetamide;

N-(4-(3-(2-fluoro-4-(6-fluoro-4-morpholino-7-(pyridin-3-yl)quinazolin-2-yl)phenyl)ureido)phenyl)acetamide;

N-(4-(3-(3-fluoro-4-(6-fluoro-7-(5-methylfuran-2-yl)-4-morpholinoquinazolin-2-yl)phenyl)ureido)phenyl)acetamide;

N-(4-(3-(3-fluoro-4-(6-fluoro-7-(furan-2-yl)-4-morpholinoquinazolin-2-yl)phenyl)ureido)phenyl)acetamide;

N-(4-(3-(3-fluoro-4-(6-fluoro-4-morpholino-7-(pyrimidin-5-yl)quinazolin-2-yl)phenyl)ureido)phenyl)acetamide;

N-(4-(3-(3-fluoro-4-(6-fluoro-4-morpholino-7-(pyridin-3-yl)quinazolin-2-yl)phenyl)ureido)phenyl)acetamide;

N-(4-(3-(2-fluoro-4-(7-(5-methylfuran-2-yl)-4-morpholinopyrido[3,2-d]pyrimidin-2-yl)phenyl)ureido)phenyl)acetamide;

N-(4-(3-(2-fluoro-4-(7-(furan-2-yl)-4-morpholinopyrido[3,2-d]pyrimidin-2-yl)phenyl)ureido)phenyl)acetamide;

N-(4-(3-(2-fluoro-4-(4-morpholino-7-(pyrimidin-5-yl)pyrido[3,2-d]pyrimidin-2-yl)phenyl)ureido)phenyl)acetamide;

N-(4-(3-(2-fluoro-4-(7-(2-fluoropyridin-3-yl)-4-morpholinopyrido[3,2-d]pyrimidin-2-yl)phenyl)ureido)phenyl)acetamide;

N-(4-(3-(2-fluoro-4-(4-morpholino-7-(pyridin-3-yl)pyrido[3,2-d]pyrimidin-2-yl)phenyl)ureido)phenyl)acetamide;

N-(4-(3-(2-fluoro-4-(7-(1-methyl-1H-pyrazol-4-yl)-4-morpholinopyrido[3,2-d]pyrimidin-2-yl)phenyl)ureido)phenyl)acetamide;

N-(4-(3-(3-fluoro-4-(7-(5-methylfuran-2-yl)-4-morpholinopyrido[3,2-d]pyrimidin-2-yl)phenyl)ureido)phenyl)acetamide;

N-(4-(3-(3-fluoro-4-(7-(furan-2-yl)-4-morpholinopyrido[3,2-d]pyrimidin-2-yl)phenyl)ureido)phenyl)acetamide;

N-(4-(3-(3-fluoro-4-(4-morpholino-7-(pyrimidin-5-yl)pyrido[3,2-d]pyrimidin-2-yl)phenyl)ureido)phenyl)acetamide;

N-(4-(3-(3-fluoro-4-(7-(2-fluoropyridin-3-yl)-4-morpholinopyrido[3,2-d]pyrimidin-2-yl)phenyl)ureido)phenyl)acetamide;

N-(4-(3-(3-fluoro-4-(4-morpholino-7-(pyridin-3-yl)pyrido[3,2-d]pyrimidin-2-yl)phenyl)ureido)phenyl)acetamide; and N-(4-(3-(3-fluoro-4-(7-(1-methyl-1H-pyrazol-4-yl)-4-morpholinopyrido[3,2-d]pyrimidin-2-yl)phenyl)ureido)phenyl)acetamide, or a pharmaceutically acceptable salt or solvate thereof.

2. The method according to claim 1, wherein said co-regulation comprises inhibition of the PI3K/AKT/mTOR pathway.

3. A method for treating a condition treatable by inhibiting the PI3K/AKT/pathway, said method comprising administering a therapeutically effective amount of a compound to a patient in need thereof, wherein the compound is selected from the group consisting of N,N-Dimethyl-4-{3-[4-(4-morpholin-4-yl-7-pyrimidin-5-yl-quinazolin-2-yl)-phenyl]-ureido}-benzamide;

N,N-Dimethyl-4-(3-{4-[7-(5-methyl-furan-2-yl)-4-morpholin-4-yl-quinazolin-2-yl]-phenyl}-ureido)-benzamide;

4-(3-{5-[7-(3-Methanesulfonyl-phenyl)-4-morpholin-4-yl-quinazolin-2-yl]-pyridin-2-yl}-ureido)-N,N-dimethyl-benzamide;

1-[4-(6-Fluoro-4-morpholin-4-yl-7-pyridin-3-yl-quinazolin-2-yl)-phenyl]-3-[4-(4-methyl-piperazine-1-carbonyl)-phenyl]-urea;

4-(3-{4-[8-(3-Hydroxy-phenyl)-4-morpholin-4-yl-quinazolin-2-yl]-phenyl}-ureido)-N,N-dimethyl-benzamide;

4-(3-{4-[8-(6-Fluoro-pyridin-3-yl)-4-morpholin-4-yl-quinazolin-2-yl]-phenyl}-ureido)-N,N-dimethyl-benzamide;

2-{4-[3-(4-Dimethylcarbamoyl-phenyl)-ureido]-phenyl}-4-morpholin-4-yl-quinazoline-7-carboxylic acid (2-dimethylamino-ethyl)-amide;

4-(3-{2-Fluoro-4-[7-(5-methyl-furan-2-yl)-4-morpholin-4-yl-quinazolin-2-yl]-phenyl}-ureido)-N,N-dimethyl-benzamide;

N,N-Dimethyl-4-{3-[4-(4-morpholin-4-yl-7-pyrimidin-5-yl-pyrido[3,2-d]pyrimidin-2-yl)-phenyl]-ureido}-benzamide;

5-(2-(4-(3-(4-(dimethylcarbamoyl)phenyl)ureido)phenyl)-4-morpholino-quinazolin-7-yl)furan-2-carboxylic acid;

N,N-dimethyl-4-(3-(4-(7-(5-(4-methylpiperazine-1-carbonyl)furan-2-yl)-4-morpholino-quinazolin-2-yl)phenyl)ureido)-benzamide;

4-(3-(4-(7-(5-cyanofuran-2-yl)-4-morpholino-quinazolin-2-yl)-3-fluorophenyl)ureido)-N,N-dimethyl-benzamide;

4-(3-(4-(7-(5-acetylfuran-2-yl)-4-morpholino-quinazolin-2-yl)phenyl)ureido)-2-fluoro-N,N-dimethyl-benzamide;

4-(3-(2,3-difluoro-4-(7-(1-methyl-1H-pyrazol-4-yl)-4-morpholino-pyrido[3,2-d]pyrimidin-2-yl)phenyl)ureido)-N,N-dimethyl-benzamide;

4-(3-(2-fluoro-4-(7-(5-(1-hydroxyethyl)furan-2-yl)-4-morpholino-pyrido[3,2-d]pyrimidin-2-yl)phenyl)ureido)-N,N-dimethyl-benzamide;

4-(3-(4-(7-(2-hydroxypropan-2-yl)-4-morpholino-quinazolin-2-yl)phenyl)ureido)-N,N-dimethyl-benzamide;

N-(4-(3-(4-(7-(5-methylfuran-2-yl)-4-morpholino-quinazolin-2-yl)phenyl)ureido)-phenyl)-acetamide;

1-(4-(7-(5-methylfuran-2-yl)-4-morpholino-quinazolin-2-yl)phenyl)-3-(4-(2-oxopyrrolidin-1-yl)phenyl)urea;

4-(3-{4-[7-(3-Methanesulfonyl-phenyl)-4-morpholin-4-yl-quinazolin-2-yl]-phenyl}-ureido)-N,N-dimethyl-benzamide;

4-(3-{4-[7-(3-Methanesulfonyl-phenyl)-4-morpholin-4-yl-quinazolin-2-yl]-phenyl}-ureido)-N-methyl-benzamide;

4-(3-{4-[7-(2-Fluoro-pyridin-3-yl)-4-morpholin-4-yl-quinazolin-2-yl]-phenyl}-ureido)-N,N-dimethyl-benzamide;

N,N-Dimethyl-4-(3-{4-[7-(1-methyl-1H-pyrazol-4-yl)-4-morpholin-4-yl-quinazolin-2-yl]-phenyl}-ureido)-benzamide;

4-(3-{4-[7-(3-Methanesulfonylamino-phenyl)-4-morpholin-4-yl-quinazolin-2-yl]-phenyl}-ureido)-N,N-dimethyl-benzamide;

N,N-Dimethyl-4-{3-[4-(4-morpholin-4-yl-7-pyridin-3-yl-quinazolin-2-yl)-phenyl]-ureido}-benzamide;

4-(3-{4-[7-(3-Methanesulfonyl-phenyl)-4-morpholin-4-yl-quinazolin-2-yl]-phenyl}-ureido)-benzamide;

1-{4-[7-(2-Fluoro-pyridin-3-yl)-4-morpholin-4-yl-quinazolin-2-yl]-phenyl}-3-[4-(4-methyl-piperazine-1-carbonyl)-phenyl]-urea;

1-[4-(4-Methyl-piperazine-1-carbonyl)-phenyl]-3-{4-[7-(1-methyl-1H-pyrazol-4-yl)-4-morpholin-4-yl-quinazolin-2-yl]-phenyl}-urea;

5-(3-{4-[7-(2-Fluoro-pyridin-3-yl)-4-morpholin-4-yl-quinazolin-2-yl]-phenyl}-ureido)-pyridine-2-carboxylic acid dimethylamide;

4-{3-[4-(6-Fluoro-4-morpholin-4-yl-7-pyridin-3-yl-quinazolin-2-yl)-phenyl]-ureido}-N,N-dimethyl-benzamide;

4-{3-[4-(6-Fluoro-4-morpholin-4-yl-7-pyrimidin-5-yl-quinazolin-2-yl)-phenyl]-ureido}-N,N-dimethyl-benzamide;

5-(3-{4-[7-(3-Methanesulfonyl-phenyl)-4-morpholin-4-yl-quinazolin-2-yl]-phenyl}-ureido)-pyridine-2-carboxylic acid dimethylamide;

1-(4-(4-methylpiperazine-1-carbonyl)phenyl)-3-(4-(7-(3-(methylsulfonyl)phenyl)-4-morpholino-quinazolin-2-yl)phenyl)urea;

1-[4-(4-Methyl-piperazine-1-carbonyl)-phenyl]-3-[4-(4-morpholin-4-yl-7-pyridin-3-yl-quinazolin-2-yl)-phenyl]-urea;

4-(3-{4-[7-(5-Methanesulfonyl-pyridin-3-yl)-4-morpholin-4-yl-quinazolin-2-yl]-phenyl}-ureido)-N,N-dimethyl-benzamide;

4-(3-{4-[6-Fluoro-7-(1-methyl-1H-pyrazol-4-yl)-4-morpholin-4-yl-quinazolin-2-yl]-phenyl}-ureido)-N,N-dimethyl-benzamide;

4-(3-{4-[6-Fluoro-7-(3-methanesulfonyl-phenyl)-4-morpholin-4-yl-quinazolin-2-yl]-phenyl}-ureido)-N,N-dimethyl-benzamide;

1-[4-(4-Methyl-piperazine-1-carbonyl)-phenyl]-3-[4-(4-morpholin-4-yl-7-thiophen-3-yl-quinazolin-2-yl)-phenyl]-urea;

4-(3-{4-[6-Fluoro-7-(5-methanesulfonyl-pyridin-3-yl)-4-morpholin-4-yl-quinazolin-2-yl]-phenyl}-ureido)-N,N-dimethyl-benzamide;

4-(3-{4-[7-(3-Methanesulfonyl-phenyl)-4-morpholin-4-yl-pyrido[3,2-d]pyrimidin-2-yl]-phenyl}-ureido)-N,N-dimethyl-benzamide;

4-(3-{4-[8-(2-Fluoro-pyridin-3-yl)-4-morpholin-4-yl-quinazolin-2-yl]-phenyl}-ureido)-N,N-dimethyl-benzamide;

4-(3-{4-[7-(3-Hydroxy-phenyl)-4-morpholin-4-yl-quinazolin-2-yl]-phenyl}-ureido)-N,N-dimethyl-benzamide;

N,N-Dimethyl-4-(3-{4-[7-(1-methyl-1H-pyrazol-4-yl)-4-morpholin-4-yl-pyrido[3,2-d]pyrimidin-2-yl]-phenyl}-ureido)-benzamide;

N,N-Dimethyl-4-(3-{4-[7-(5-methyl-furan-2-yl)-4-morpholin-4-yl-pyrido[3,2-d]pyrimidin-2-yl]-phenyl}-ureido)-benzamide;

N-(2-Dimethylamino-ethyl)-N-methyl-4-{3-[4-(4-morpholin-4-yl-7-pyrimidin-5-yl-quinazolin-2-yl)-phenyl]-ureido}-benzamide;

4-(3-{4-[7-(3-Hydroxymethyl-phenyl)-4-morpholin-4-yl-quinazolin-2-yl]-phenyl}-ureido)-N,N-dimethyl-benzamide;

N,N-Dimethyl-4-{3-[4-(4-morpholin-4-yl-7-pyridin-3-yl-pyrido[3,2-d]pyrimidin-2-yl)-phenyl]-ureido}-benzamide;

4-(3-{4-[7-(3-Fluoro-phenyl)-4-morpholin-4-yl-quinazolin-2-yl]-phenyl}-ureido)-N,N-dimethyl-benzamide;

4-(3-{4-[7-(3-Methoxy-phenyl)-4-morpholin-4-yl-quinazolin-2-yl]-phenyl}-ureido)-N,N-dimethyl-benzamide;

4-(3-{4-[7-(3-Acetylamino-phenyl)-4-morpholin-4-yl-quinazolin-2-yl]-phenyl}-ureido)-N,N-dimethyl-benzamide;

4-(3-{4-[7-(3-Dimethylamino-phenyl)-4-morpholin-4-yl-quinazolin-2-yl]-phenyl}-ureido)-N,N-dimethyl-benzamide;

4-{3-[4-(7-Furan-2-yl-4-morpholin-4-yl-quinazolin-2-yl)-phenyl]-ureido}-N,N-dimethyl-benzamide;

N,N-Dimethyl-4-{3-[4-(4-morpholin-4-yl-7-thiophen-3-yl-quinazolin-2-yl)-phenyl]-ureido}-benzamide;
4-{3-[4-(7-Furan-3-yl-4-morpholin-4-yl-quinazolin-2-yl)-phenyl]-ureido}-N,N-dimethyl-benzamide;
4-(3-{5-[7-(2-Fluoro-pyridin-3-yl)-4-morpholin-4-yl-quinazolin-2-yl]-pyridin-2-yl}-ureido)-N,N-dimethyl-benzamide;
N,N-Dimethyl-4-(3-{5-[7-(1-methyl-1H-pyrazol-4-yl)-4-morpholin-4-yl-quinazolin-2-yl]-pyridin-2-yl}-ureido)-benzamide;
N-Methyl-4-(3-{4-[7-(5-methyl-furan-2-yl)-4-morpholin-4-yl-quinazolin-2-yl]-phenyl}-ureido)-benzamide;
N,N-Dimethyl-4-(3-{5-[7-(5-methyl-furan-2-yl)-4-morpholin-4-yl-quinazolin-2-yl]-pyridin-2-yl}-ureido)-benzamide;
N,N-Dimethyl-4-{3-[4-(4-morpholin-4-yl-7-pyridin-4-yl-quinazolin-2-yl)-phenyl]-ureido}-benzamide;
N,N-Dimethyl-4-{3-[4-(4-morpholin-4-yl-7-quinolin-3-yl-quinazolin-2-yl)-phenyl]-ureido}-benzamide;
4-(3-{4-[7-(6-Methoxy-pyridin-3-yl)-4-morpholin-4-yl-quinazolin-2-yl]-phenyl}-ureido)-N,N-dimethyl-benzamide;
N,N-Dimethyl-4-(3-{4-[7-(5-methyl-thiophen-2-yl)-4-morpholin-4-yl-quinazolin-2-yl]-phenyl}-ureido)-benzamide;
N,N-Dimethyl-4-(3-{4-[7-(4-methyl-pyridin-3-yl)-4-morpholin-4-yl-quinazolin-2-yl]-phenyl}-ureido)-benzamide;
N-(2-Dimethylamino-ethyl)-N-methyl-4-(3-{4-[7-(5-methyl-furan-2-yl)-4-morpholin-4-yl-quinazolin-2-yl]-phenyl}-ureido)-benzamide;
4-{3-[4-(7-Benzofuran-2-yl-4-morpholin-4-yl-quinazolin-2-yl)-phenyl]-ureido}-N,N-dimethyl-benzamide;
4-(3-{4-[7-(3-Fluoro-pyridin-4-yl)-4-morpholin-4-yl-quinazolin-2-yl]-phenyl}-ureido)-N,N-dimethyl-benzamide;
4-(3-{4-[7-(5-Acetylamino-pyridin-3-yl)-4-morpholin-4-yl-quinazolin-2-yl]-phenyl}-ureido)-N,N-dimethyl-benzamide;
1-[4-(4-Methyl-piperazine-1-carbonyl)-phenyl]-3-[4-(4-morpholin-4-yl-7-pyrimidin-5-yl-pyrido[3,2-d]pyrimidin-2-yl)-phenyl]-urea;
4-(3-{4-[7-(2-Fluoro-pyridin-4-yl)-4-morpholin-4-yl-quinazolin-2-yl]-phenyl}-ureido)-N,N-dimethyl-benzamide;
1-[4-(4-Methyl-piperazine-1-carbonyl)-phenyl]-3-[4-(4-morpholin-4-yl-7-pyridin-4-yl-quinazolin-2-yl)-phenyl]-urea;
1-{4-[7-(5-Methyl-furan-2-yl)-4-morpholin-4-yl-quinazolin-2-yl]-phenyl}-3-[4-(4-methyl-piperazine-1-carbonyl)-phenyl]-urea;
N,N-Dimethyl-4-(3-{4-[8-(5-methyl-furan-2-yl)-4-morpholin-4-yl-quinazolin-2-yl]-phenyl}-ureido)-benzamide;
N-(2-Dimethylamino-ethyl)-N-methyl-4-{3-[4-(4-morpholin-4-yl-7-pyridin-4-yl-quinazolin-2-yl)-phenyl]-ureido}-benzamide;
1-[4-(4-Methyl-piperazine-1-carbonyl)-phenyl]-3-{4-[7-(1-methyl-1H-pyrazol-4-yl)-4-morpholin-4-yl-pyrido[3,2-d]pyrimidin-2-yl]-phenyl}-urea;
N,N-Dimethyl-4-{3-[4-(4-morpholin-4-yl-7-thiophen-2-yl-quinazolin-2-yl)-phenyl]-ureido}-benzamide;
4-(3-{4-[7-(2-Methoxy-pyrimidin-5-yl)-4-morpholin-4-yl-quinazolin-2-yl]-phenyl}-ureido)-N,N-dimethyl-benzamide;
4-(3-{4-[7-(2-Amino-pyrimidin-5-yl)-4-morpholin-4-yl-quinazolin-2-yl]-phenyl}-ureido)-N,N-dimethyl-benzamide;
4-(3-(4-(7-(5-(2-(Dimethylamino)acetamido)pyridin-3-yl)-4-morpholino-quinazolin-2-yl)phenyl)ureido]-N,N-dimethyl-benzamide;
4-(3-{4-[7-(2-Fluoro-pyridin-3-yl)-4-morpholin-4-yl-pyrido[3,2-d]pyrimidin-2-yl]-phenyl}-ureido)-N,N-dimethyl-benzamide;
1-[4-(4-Methyl-piperazine-1-carbonyl)-phenyl]-3-[4-(4-morpholin-4-yl-7-pyrimidin-5-yl-quinazolin-2-yl)-phenyl]-urea;
N,N-Dimethyl-4-(3-{4-[7-(furan-2-yl)-4-morpholin-4-yl-quinazolin-2-yl]-phenyl}-ureido)-benzamide;
1-(4-(4-(dimethylamino)piperidine-1-carbonyl)phenyl)-3-(5-(7-(2-fluoropyridin-3-yl)-4-morpholino-quinazolin-2-yl)pyridin-2-yl)urea;
4-(3-(2-fluoro-4-(7-(1-methyl-1H-pyrazol-4-yl)-4-morpholino-pyrido[3,2-d]pyrimidin-2-yl)phenyl)ureido)-N,N-dimethyl-benzamide;
4-(3-(4-(7-(1-(2-(dimethylamino)ethyl)-1H-pyrazol-4-yl)-4-morpholino-quinazolin-2-yl)phenyl)ureido)-N,N-dimethyl-benzamide;
4-(3-(2-fluoro-4-(4-morpholino-7-(pyrimidin-5-yl)quinazolin-2-yl)phenyl)ureido)-N,N-dimethyl-benzamide;
N,N-dimethyl-4-(3-(5-(7-(1-methyl-1H-pyrazol-4-yl)-4-morpholino-pyrido[3,2-d]pyrimidin-2-yl)pyridin-2-yl)ureido)-benzamide;
N,N-dimethyl-4-(3-(4-(4-morpholino-7-(pyridazin-4-yl)quinazolin-2-yl)phenyl)ureido)-benzamide;
4-(3-(4-(6-fluoro-7-(5-methylfuran-2-yl)-4-morpholino-quinazolin-2-yl)phenyl)ureido)-N,N-dimethyl-benzamide;
N-methyl-4-(3-(4-(4-morpholino-7-(pyrimidin-5-yl)quinazolin-2-yl)phenyl)ureido)-benzamide;
N-methyl-4-(3-(4-(7-(1-methyl-1H-pyrazol-4-yl)-4-morpholino-pyrido[3,2-d]pyrimidin-2-yl)phenyl)ureido)-benzamide;
4-(3-(4-(7-(furan-2-yl)-4-morpholino-pyrido[3,2-d]pyrimidin-2-yl)phenyl)ureido)-N,N-dimethyl-benzamide;
4-(3-(2-fluoro-4-(7-(2-fluoropyridin-3-yl)-4-morpholino-quinazolin-2-yl)phenyl)ureido)-N,N-dimethyl-benzamide;
4-(3-(4-(7-(2-aminopyrimidin-5-yl)-4-morpholino-pyrido[3,2-d]pyrimidin-2-yl)phenyl)ureido)-N,N-dimethyl-benzamide;
N,N-dimethyl-4-(3-(4-(7-(4-methylpyridin-3-yl)-4-morpholino-pyrido[3,2-d]pyrimidin-2-yl)phenyl)ureido)-benzamide;
4-(3-(4-(7-(2-methoxypyrimidin-5-yl)-4-morpholino-pyrido[3,2-d]pyrimidin-2-yl)phenyl)ureido)-N,N-dimethyl-benzamide;
4-(3-(4-(7-(6-methoxypyridin-2-yl)-4-morpholino-quinazolin-2-yl)phenyl)ureido)-N,N-dimethyl-benzamide;
N,N-dimethyl-4-(3-(4-(4-morpholino-7-(pyridazin-4-yl)pyrido[3,2-d]pyrimidin-2-yl)phenyl)ureido)-benzamide;
4-(3-(2-fluoro-4-(7-(1-methyl-1H-pyrazol-4-yl)-4-morpholino-quinazolin-2-yl)phenyl)ureido)-N,N-dimethyl-benzamide;
4-(3-(2-fluoro-4-(4-morpholino-7-(pyridazin-4-yl)quinazolin-2-yl)phenyl)ureido)-N,N-dimethyl-benzamide;

4-(3-(2-fluoro-4-(6-fluoro-4-morpholino-7-(pyrimidin-5-yl)quinazolin-2-yl)phenyl)ureido)-N,N-dimethyl-benzamide;
4-(3-(2-fluoro-4-(7-(4-methylpyridin-3-yl)-4-morpholino-quinazolin-2-yl)phenyl)ureido)-N,N-dimethyl-benzamide;
4-(3-(2-fluoro-4-(4-morpholino-7-(pyrimidin-5-yl)pyrido[3,2-d]pyrimidin-2-yl)phenyl)ureido)-N,N-dimethyl-benzamide;
4-(3-(2-fluoro-4-(4-morpholino-7-(pyridin-3-yl)pyrido[3,2-d]pyrimidin-2-yl)phenyl)ureido)-N,N-dimethyl-benzamide;
4-(3-(2-fluoro-4-(4-morpholino-7-(pyridin-3-yl)quinazolin-2-yl)phenyl)ureido)-N,N-dimethyl-benzamide;
4-(3-(2-fluoro-4-(7-(3-(methylsulfonyl)phenyl)-4-morpholino-pyrido[3,2-d]pyrimidin-2-yl)phenyl)ureido)-N,N-dimethyl-benzamide;
4-(3-(2-fluoro-4-(7-(2-methoxypyrimidin-5-yl)-4-morpholino-quinazolin-2-yl)phenyl)ureido)-N,N-dimethyl-benzamide;
4-(3-(2-fluoro-4-(7-(2-fluoropyridin-3-yl)-4-morpholinopyrido[3,2-d]pyrimidin-2-yl)phenyl)ureido)-N,N-dimethyl-benzamide;
4-(3-(4-(6-fluoro-7-(2-fluoropyridin-3-yl)-4-morpholino-quinazolin-2-yl)phenyl)ureido)-N,N-dimethyl-benzamide;
4-(3-(2-fluoro-4-(6-fluoro-7-(1-methyl-1H-pyrazol-4-yl)-4-morpholino-quinazolin-2-yl)phenyl)ureido dimethyl-benzamide)-N,N-dimethyl-benzamide;
4-(3-(2-fluoro-4-(6-fluoro-4-morpholino-7-(pyridin-3-yl)quinazolin-2-yl)phenyl)ureido)-N,N-dimethyl-benzamide;
4-(3-(4-(7-(2-aminopyrimidin-5-yl)-4-morpholino-quinazolin-2-yl)-2-fluorophenyl)ureido)-N,N-dimethyl-benzamide;
4-(3-(5-(7-(2-fluoropyridin-3-yl)-4-morpholino-pyrido[3,2-d]pyrimidin-2-yl)pyridin-2-yl)ureido)-N,N-dimethyl-benzamide;
4-(3-(5-(6-fluoro-7-(2-fluoropyridin-3-yl)-4-morpholino-quinazolin-2-yl)pyridin-2-yl)ureido)-N,N-dimethyl-benzamide;
4-(3-(5-(6-fluoro-7-(1-methyl-1H-pyrazol-4-yl)-4-morpholino-quinazolin-2-yl)pyridin-2-yl)ureido)-N,N-dimethyl-benzamide;
4-(3-(2-fluoro-4-(7-(furan-2-yl)-4-morpholino-quinazolin-2-yl)phenyl)ureido)-N,N-dimethyl-benzamide;
N,N-dimethyl-4-(3-(5-(7-(3-(methylsulfonyl)phenyl)-4-morpholino-pyrido[3,2-d]pyrimidin-2-yl)pyridin-2-yl)ureido)-benzamide;
4-(3-(2-fluoro-4-(7-(4-methylpyridin-3-yl)-4-morpholino-pyrido[3,2-d]pyrimidin-2-yl)phenyl)ureido)-N,N-dimethyl-benzamide;
4-(3-(2-fluoro-4-(7-(2-methoxypyrimidin-5-yl)-4-morpholino-pyrido[3,2-d]pyrimidin-2-yl)phenyl)ureido)-N,N-dimethyl-benzamide;
4-(3-(2-fluoro-4-(7-(3-(methylsulfonyl)phenyl)-4-morpholino-quinazolin-2-yl)phenyl)ureido)-N,N-dimethyl-benzamide;
4-(3-(5-(7-(2-methoxypyrimidin-5-yl)-4-morpholino-quinazolin-2-yl)pyridin-2-yl)ureido)-N,N-dimethyl-benzamide;
4-(3-(4-(7-(3,5-dimethylisoxazol-4-yl)-4-morpholino-pyrido[3,2-d]pyrimidin-2-yl)phenyl)ureido)-N,N-dimethyl-benzamide;
4-(3-(4-(7-(3,5-dimethylisoxazol-4-yl)-4-morpholino-quinazolin-2-yl)phenyl)ureido)-N,N-dimethyl-benzamide;
5-(3-(2-fluoro-4-(7-(5-methylfuran-2-yl)-4-morpholino-quinazolin-2-yl)phenyl)ureido)-N,N-dimethylpicolinamide;
5-(3-(2-fluoro-4-(4-morpholino-7-(pyrimidin-5-yl)quinazolin-2-yl)phenyl)ureido)-N,N-dimethylpicolinamide;
5-(3-(2-fluoro-4-(7-(1-methyl-1H-pyrazol-4-yl)-4-morpholino-pyrido[3,2-d]pyrimidin-2-yl)phenyl)ureido)-N,N-dimethylpicolinamide;
4-(3-(4-(4-(2,6-dimethylmorpholino)-7-(1-methyl-1H-pyrazol-4-yl)pyrido[3,2-d]pyrimidin-2-yl)phenyl)ureido)-N,N-dimethyl-benzamide;
4-(3-(4-(4-(2,6-dimethylmorpholino)-7-(1-methyl-1H-pyrazol-4-yl)pyrido[3,2-d]pyrimidin-2-yl)-2-fluorophenyl)ureido)-N,N-dimethyl-benzamide;
4-(3-(4-(7-(2-aminopyrimidin-5-yl)-4-morpholinopyrido[3,2-d]pyrimidin-2-yl)-2-fluorophenyl)ureido)-N,N-dimethyl-benzamide;
4-(3-(4-(4-(2,6-dimethylmorpholino)-7-(pyrimidin-5-yl)quinazolin-2-yl)phenyl)ureido)-N,N-dimethyl-benzamide;
N,N-dimethyl-5-(3-(5-(7-(5-methylfuran-2-yl)-4-morpholino-quinazolin-2-yl)pyridin-2-yl)ureido)picolinamide;
5-(3-(2-fluoro-4-(7-(3-(methylsulfonyl)phenyl)-4-morpholino-quinazolin-2-yl)phenyl)ureido)-N,N-dimethylpicolinamide;
4-(3-(4-(7-(3,5-dimethylisoxazol-4-yl)-4-morpholino-quinazolin-2-yl)-2-fluorophenyl)ureido)-N,N-dimethyl-benzamide;
4-(3-(4-(4-(2,6-dimethylmorpholino)-7-(pyrimidin-5-yl)quinazolin-2-yl)-2-fluorophenyl)ureido)-N,N-dimethyl-benzamide;
3-fluoro-N,N-dimethyl-4-(3-(4-(4-morpholino-7-(pyrimidin-5-yl)quinazolin-2-yl)phenyl)ureido)-benzamide;
3-fluoro-N,N-dimethyl-4-(3-(4-(7-(1-methyl-1H-pyrazol-4-yl)-4-morpholino-pyrido[3,2-d]pyrimidin-2-yl)phenyl)ureido)-benzamide;
4-(3-(4-(7-(3,5-dimethylisoxazol-4-yl)-4-morpholino-pyrido[3,2-d]pyrimidin-2-yl)-2-fluorophenyl)ureido)-N,N-dimethyl-benzamide;
3-fluoro-N,N-dimethyl-4-(3-(4-(7-(5-methylfuran-2-yl)-4-morpholino-quinazolin-2-yl)phenyl)ureido)-benzamide;
4-(3-(2-fluoro-4-(4-morpholino-7-(pyridin-4-yl)quinazolin-2-yl)phenyl)ureido)-N,N-dimethyl-benzamide;
N,N-dimethyl-4-(3-(4-(4-(2-methylmorpholino)-7-(pyrimidin-5-yl)quinazolin-2-yl)phenyl)ureido)-benzamide;
3-fluoro-4-(3-(2-fluoro-4-(4-morpholino-7-(pyrimidin-5-yl)quinazolin-2-yl)phenyl)ureido)-N,N-dimethyl-benzamide;
3-fluoro-N,N-dimethyl-4-(3-(5-(4-morpholino-7-(pyrimidin-5-yl)quinazolin-2-yl)pyridin-2-yl)ureido)-benzamide;
3-fluoro-4-(3-(2-fluoro-4-(7-(1-methyl-1H-pyrazol-4-yl)-4-morpholino-pyrido[3,2-d]pyrimidin-2-yl)phenyl)ureido)-N,N-dimethyl-benzamide;
N,N-dimethyl-4-(3-(4-(7-(5-methylfuran-2-yl)-4-(2-methylmorpholino)quinazolin-2-yl)phenyl)ureido)-benzamide;
4-(3-(4-(7-(3,5-dimethylisoxazol-4-yl)-6-fluoro-4-morpholino-quinazolin-2-yl)phenyl)ureido)-N,N-dimethyl-benzamide;
4-(3-(2-fluoro-4-(4-(2-methylmorpholino)-7-(pyrimidin-5-yl)quinazolin-2-yl)phenyl)ureido)-N,N-dimethyl-benzamide;

3-fluoro-4-(3-(4-(7-(2-fluoropyridin-3-yl)-4-morpholino-pyrido[3,2-d]pyrimidin-2-yl)phenyl)ureido)-N,N-dimethyl-benzamide;
3-fluoro-4-(3-(4-(7-(2-fluoropyridin-3-yl)-4-morpholino-quinazolin-2-yl)phenyl)ureido)-N,N-dimethyl-benzamide;
3-fluoro-4-(3-(4-(7-(2-methoxypyrimidin-5-yl)-4-morpholino-quinazolin-2-yl)phenyl)ureido)-N,N-dimethyl-benzamide;
N,N-dimethyl-4-(3-(4-(7-(1-methyl-1H-pyrazol-4-yl)-4-(2-methylmorpholino)pyrido[3,2-d]pyrimidin-2-yl)phenyl)ureido)-benzamide;
4-(3-(4-(6-fluoro-7-(furan-2-yl)-4-morpholino-quinazolin-2-yl)phenyl)ureido)-N,N-dimethyl-benzamide;
4-(3-(4-(7-(2-hydroxypyrimidin-5-yl)-4-morpholino-quinazolin-2-yl)phenyl)ureido)-N,N-dimethyl-benzamide;
4-(3-(2-fluoro-4-(7-(6-methoxypyridin-3-yl)-4-morpholino-quinazolin-2-yl)phenyl)ureido)-N,N-dimethyl-benzamide;
3-fluoro-N,N-dimethyl-4-(3-(4-(4-morpholino-7-(pyridin-3-yl)quinazolin-2-yl)phenyl)ureido)-benzamide;
3-fluoro-N,N-dimethyl-4-(3-(4-(4-morpholino-7-(pyridin-3-yl)pyrido[3,2-d]pyrimidin-2-yl)phenyl)ureido)-benzamide;
3-fluoro-N,N-dimethyl-4-(3-(4-(4-morpholino-7-(pyrimidin-5-yl)pyrido[3,2-d]pyrimidin-2-yl)phenyl)ureido)-benzamide;
N,N-dimethyl-4-(3-(4-(4-morpholino-7-(pyridin-2-yl)quinazolin-2-yl)phenyl)ureido)-benzamide;
4-(3-(2-fluoro-4-(4-morpholino-7-(pyridin-2-yl)quinazolin-2-yl)phenyl)ureido)-N,N-dimethyl-benzamide;
3-fluoro-4-(3-(4-(7-(2-methoxypyrimidin-5-yl)-4-morpholino-pyrido[3,2-d]pyrimidin-2-yl)phenyl)ureido)-N,N-dimethyl-benzamide;
1-(4-(7-(furan-2-yl)-4-morpholino-quinazolin-2-yl)phenyl)-3-(4-(4-methylpiperazine-1-carbonyl)phenyl)urea;
4-(3-(5-(7-(furan-2-yl)-4-morpholino-quinazolin-2-yl)pyridin-2-yl)ureido)-N,N-dimethyl-benzamide;
3-fluoro-4-(3-(4-(7-(furan-2-yl)-4-morpholino-quinazolin-2-yl)phenyl)ureido)-N,N-dimethyl-benzamide;
N,N-dimethyl-4-(3-(4-(7-(6-methylpyridin-3-yl)-4-morpholino-quinazolin-2-yl)phenyl)ureido)-benzamide;
N,N-dimethyl-4-(3-(4-(4-morpholino-7-(1,3,5-trimethyl-1H-pyrazol-4-yl)quinazolin-2-yl)phenyl)ureido)-benzamide;
4-(3-(4-(7-(2-methoxypyridin-3-yl)-4-morpholino-quinazolin-2-yl)phenyl)ureido)-N,N-dimethyl-benzamide;
4-(3-(4-(7-(5-fluoropyridin-3-yl)-4-morpholino-quinazolin-2-yl)phenyl)ureido)-N,N-dimethyl-benzamide;
N,N-dimethyl-4-(3-(4-(7-(2-methylpyridin-3-yl)-4-morpholino-quinazolin-2-yl)phenyl)ureido)-benzamide;
3-fluoro-N,N-dimethyl-4-(3-(4-(7-(6-methylpyridin-3-yl)-4-morpholino-quinazolin-2-yl)phenyl)ureido)-benzamide;
3-fluoro-N,N-dimethyl-4-(3-(4-(7-(2-methylpyridin-3-yl)-4-morpholino-quinazolin-2-yl)phenyl)ureido)-benzamide;
3-fluoro-N,N-dimethyl-4-(3-(4-(4-morpholino-7-(pyridin-3-yl)quinazolin-2-yl)phenyl)ureido)-benzamide;
4-(3-(4-(7-(4-methoxypyridin-3-yl)-4-morpholino-quinazolin-2-yl)phenyl)ureido)-N,N-dimethyl-benzamide;
3-fluoro-4-(3-(4-(7-(6-methoxypyridin-3-yl)-4-morpholino-quinazolin-2-yl)phenyl)ureido)-N,N-dimethyl-benzamide;
3-chloro-4-(3-(4-(7-(furan-2-yl)-4-morpholino-quinazolin-2-yl)phenyl)ureido)-N,N-dimethyl-benzamide;
3-fluoro-N,N-dimethyl-4-(3-(5-(7-(1-methyl-1H-pyrazol-4-yl)-4-morpholino-quinazolin-2-yl)pyridin-2-yl)ureido)-benzamide;
3-fluoro-4-(3-(4-(6-fluoro-4-morpholino-7-(pyridin-3-yl)quinazolin-2-yl)phenyl)ureido)-N,N-dimethyl-benzamide;
3-fluoro-4-(3-(4-(6-fluoro-4-morpholino-7-(pyrimidin-5-yl)quinazolin-2-yl)phenyl)ureido)-N,N-dimethyl-benzamide;
4-(3-(5-(6-fluoro-4-morpholino-7-(pyridin-3-yl)quinazolin-2-yl)pyridin-2-yl)ureido)-N,N-dimethyl-benzamide;
4-(3-(5-(6-fluoro-4-morpholino-7-(pyrimidin-5-yl)quinazolin-2-yl)pyridin-2-yl)ureido)-N,N-dimethyl-benzamide;
4-(3-(4-(7-(6-aminopyridin-3-yl)-4-morpholino-quinazolin-2-yl)phenyl)ureido)-N,N-dimethyl-benzamide;
4-(3-(4-(7-(6-aminopyridin-3-yl)-4-morpholino-quinazolin-2-yl)phenyl)ureido)-3-fluoro-N,N-dimethyl-benzamide;
N,N-dimethyl-4-(3-(4-(4-morpholino-quinazolin-2-yl)phenyl)ureido)-benzamide
4-(3-(4-(7-methoxy-4-morpholino-quinazolin-2-yl)phenyl)ureido)-N,N-dimethyl-benzamide;
4-(3-(4-(6,7-dimethoxy-4-morpholino-quinazolin-2-yl)phenyl)ureido)-N,N-dimethyl-benzamide;
4-(3-(2-fluoro-4-(7-methoxy-4-morpholino-quinazolin-2-yl)phenyl)ureido)-N,N-dimethyl-benzamide;
4-(3-(4-(7-(5-(hydroxymethyl)furan-2-yl)-4-morpholino-quinazolin-2-yl)phenyl)ureido)-N,N-dimethyl-benzamide;
(R)-1-(4-(3-(dimethylamino)pyrrolidine-1-carbonyl)phenyl)-3-(4-(7-(1-methyl-1H-pyrazol-4-yl)-4-morpholino-pyrido[3,2-d]pyrimidin-2-yl)phenyl)urea;
(S)-1-(4-(3-(dimethylamino)pyrrolidine-1-carbonyl)phenyl)-3-(4-(7-(1-methyl-1H-pyrazol-4-yl)-4-morpholino-pyrido[3,2-d]pyrimidin-2-yl)phenyl)urea;
1-(4-(4-(dimethylamino)piperidine-1-carbonyl)phenyl)-3-(4-(7-(1-methyl-1H-pyrazol-4-yl)-4-morpholino-pyrido[3,2-d]pyrimidin-2-yl)phenyl)urea;
(R)-1-(4-(3-(dimethylamino)pyrrolidine-1-carbonyl)phenyl)-3-(4-(4-morpholino-7-(pyrimidin-5-yl)quinazolin-2-yl)phenyl)urea;
(S)-1-(4-(3-(dimethylamino)pyrrolidine-1-carbonyl)phenyl)-3-(4-(4-morpholino-7-(pyrimidin-5-yl)quinazolin-2-yl)phenyl)urea;
1-(4-(3-hydroxypyrrolidine-1-carbonyl)phenyl)-3-(4-(4-morpholino-7-(pyrimidin-5-yl)quinazolin-2-yl)phenyl)urea;
4-(3-(4-(7-(5-((dimethylamino)methyl)furan-2-yl)-4-morpholino-quinazolin-2-yl)phenyl)ureido)-N,N-dimethyl-benzamide;
1-(4-(4-(dimethylamino)piperidine-1-carbonyl)phenyl)-3-(4-(7-(5-methylfuran-2-yl)-4-morpholino-quinazolin-2-yl)phenyl)urea;
N-(2-(dimethylamino)ethyl)-4-(3-(4-(4-morpholino-7-(pyrimidin-5-yl)quinazolin-2-yl)phenyl)ureido)-benzamide;
1-(4-(4-(dimethylamino)piperidine-1-carbonyl)phenyl)-3-(4-(7-(4-methylpyridin-3-yl)-4-morpholino-quinazolin-2-yl)phenyl)urea;

(S)-1-(4-(3-aminopyrrolidine-1-carbonyl)phenyl)-3-(4-(4-morpholino-7-(pyrimidin-5-yl)quinazolin-2-yl)phenyl)urea;

(S)-1-(4-(3-(dimethylamino)pyrrolidine-1-carbonyl)phenyl)-3-(4-(7-(5-methylfuran-2-yl)-4-morpholino-quinazolin-2-yl)phenyl)urea;

(R)-1-(4-(3-(dimethylamino)pyrrolidine-1-carbonyl)phenyl)-3-(4-(7-(5-methylfuran-2-yl)-4-morpholino-quinazolin-2-yl)phenyl)urea;

(R)-1-(4-(3-aminopyrrolidine-1-carbonyl)phenyl)-3-(4-(4-morpholino-7-(pyrimidin-5-yl)quinazolin-2-yl)phenyl)urea;

(S)-1-(4-(3-(dimethylamino)pyrrolidine-1-carbonyl)phenyl)-3-(4-(6-fluoro-4-morpholino-7-(pyridin-3-yl)quinazolin-2-yl)phenyl)urea;

(S)-1-(4-(3-(dimethylamino)pyrrolidine-1-carbonyl)phenyl)-3-(4-(4-morpholino-7-(pyrimidin-5-yl)pyrido[3,2-d]pyrimidin-2-yl)phenyl)urea;

(R)-1-(4-(3-(dimethylamino)pyrrolidine-1-carbonyl)phenyl)-3-(4-(6-fluoro-4-morpholino-7-(pyridin-3-yl)quinazolin-2-yl)phenyl)urea;

N-(2-(dimethylamino)ethyl)-4-(3-(4-(7-(5-methylfuran-2-yl)-4-morpholino-quinazolin-2-yl)phenyl)ureido)-benzamide;

4-(3-(4-(7-(1-methyl-1H-pyrazol-4-yl)-4-morpholino-pyrido[3,2-d]pyrimidin-2-yl)phenyl)ureido)-benzamide;

4-(3-(2-fluoro-4-(7-(5-(hydroxymethyl)furan-2-yl)-4-morpholino-quinazolin-2-yl)phenyl)ureido)-N,N-dimethyl-benzamide;

1-(4-(3-hydroxypyrrolidine-1-carbonyl)phenyl)-3-(4-(7-(5-methylfuran-2-yl)-4-morpholino-quinazolin-2-yl)phenyl)urea;

(R)-1-(4-(3-(dimethylamino)pyrrolidine-1-carbonyl)phenyl)-3-(2-fluoro-4-(7-(1-methyl-1H-pyrazol-4-yl)-4-morpholino-pyrido[3,2-d]pyrimidin-2-yl)phenyl)urea;

4-(3-(4-(7-(5-(1-hydroxyethyl)furan-2-yl)-4-morpholino-quinazolin-2-yl)phenyl)ureido)-N,N-dimethyl-benzamide;

(S)-1-(4-(3-(dimethylamino)pyrrolidine-1-carbonyl)phenyl)-3-(2-fluoro-4-(4-morpholino-7-(pyrimidin-5-yl)quinazolin-2-yl)phenyl)urea;

(S)-1-(4-(3-aminopyrrolidine-1-carbonyl)phenyl)-3-(2-fluoro-4-(4-morpholino-7-(pyrimidin-5-yl)quinazolin-2-yl)phenyl)urea;

(R)-1-(4-(3-aminopyrrolidine-1-carbonyl)phenyl)-3-(2-fluoro-4-(4-morpholino-7-(pyrimidin-5-yl)quinazolin-2-yl)phenyl)urea;

(S)-1-(4-(3-(dimethylamino)pyrrolidine-1-carbonyl)phenyl)-3-(2-fluoro-4-(7-(1-methyl-1H-pyrazol-4-yl)-4-morpholino-pyrido[3,2-d]pyrimidin-2-yl)phenyl)urea;

1-(2-fluoro-4-(6-fluoro-4-morpholino-7-(pyridin-3-yl)quinazolin-2-yl)phenyl)-3-(4-(4-methylpiperazine-1-carbonyl)phenyl)urea;

1-(2-fluoro-4-(4-morpholino-7-(pyridin-4-yl)quinazolin-2-yl)phenyl)-3-(4-(4-methylpiperazine-1-carbonyl)phenyl)urea;

(S)-1-(4-(3-(dimethylamino)pyrrolidine-1-carbonyl)phenyl)-3-(2-fluoro-4-(7-(2-fluoropyridin-3-yl)-4-morpholino-pyrido[3,2-d]pyrimidin-2-yl)phenyl)urea;

4-(3-(2-fluoro-4-(7-(5-(1-hydroxyethyl)furan-2-yl)-4-morpholino-quinazolin-2-yl)phenyl)ureido)-N,N-dimethyl-benzamide;

4-(3-(2-fluoro-4-(4-morpholino-7-(pyrimidin-5-yl)quinazolin-2-yl)phenyl)ureido)-N-methyl-benzamide;

4-(3-(4-(7-(5-(1-hydroxyethyl)furan-2-yl)-4-morpholino-pyrido[3,2-d]pyrimidin-2-yl)phenyl)ureido)-N,N-dimethyl-benzamide;

N-(2-(dimethylamino)ethyl)-4-(3-(2-fluoro-4-(4-morpholino-7-(pyrimidin-5-yl)quinazolin-2-yl)phenyl)ureido)-benzamide;

4-(3-(2-fluoro-4-(7-(5-(hydroxymethyl)furan-2-yl)-4-morpholino-pyrido[3,2-d]pyrimidin-2-yl)phenyl)ureido)-N,N-dimethyl-benzamide;

3-fluoro-4-(3-(4-(7-(5-(hydroxymethyl)furan-2-yl)-4-morpholino-quinazolin-2-yl)phenyl)ureido)-N,N-dimethyl-benzamide;

(S)-1-(4-(3-(dimethylamino)pyrrolidine-1-carbonyl)phenyl)-3-(4-(7-(3,5-dimethylisoxazol-4-yl)-4-morpholino-quinazolin-2-yl)phenyl)urea;

(S)-1-(4-(3-(dimethylamino)pyrrolidine-1-carbonyl)phenyl)-3-(4-(7-(3,5-dimethylisoxazol-4-yl)-4-morpholino-quinazolin-2-yl)-2-fluorophenyl)urea;

4-(3-(4-(7-(5-(2-hydroxypropan-2-yl)furan-2-yl)-4-morpholino-quinazolin-2-yl)phenyl)ureido)-N,N-dimethyl-benzamide;

4-(3-(4-(7-(5-cyanofuran-2-yl)-4-morpholino-quinazolin-2-yl)phenyl)ureido)-N,N-dimethyl-benzamide;

4-(3-(4-(7-(5-acetylfuran-2-yl)-4-morpholino-quinazolin-2-yl)phenyl)ureido)-N,N-dimethyl-benzamide;

N-(2-(dimethylamino)ethyl)-5-(2-(4-(3-(4-(dimethylcarbamoyl)phenyl)ureido)phenyl)-4-morpholino-quinazolin-7-yl)furan-2-carboxamide;

4-(3-(4-(7-(2-(dimethylamino)pyrimidin-5-yl)-4-morpholino-quinazolin-2-yl)phenyl)ureido)-N,N-dimethyl-benzamide;

3-fluoro-4-(3-(4-(7-(5-(1-hydroxyethyl)furan-2-yl)-4-morpholino-quinazolin-2-yl)phenyl)ureido)-N,N-dimethyl-benzamide;

3-fluoro-4-(3-(4-(7-(5-(hydroxymethyl)furan-2-yl)-4-morpholino-quinazolin-2-yl)phenyl)ureido)-N,N-dimethyl-benzamide;

5-(2-(4-(3-(4-(dimethylcarbamoyl)phenyl)ureido)phenyl)-4-morpholino-quinazolin-7-yl)-N,N-dimethylfuran-2-carboxamide;

4-(3-(4-(7-(2-(dimethylamino)pyrimidin-5-yl)-4-morpholino-pyrido[3,2-d]pyrimidin-2-yl)phenyl)ureido)-N,N-dimethyl-benzamide;

4-(3-(4-(7-(2-(dimethylamino)pyrimidin-5-yl)-4-morpholino-quinazolin-2-yl)-2-fluorophenyl)ureido)-N,N-dimethyl-benzamide;

1-(4-(7-(furan-2-yl)-4-morpholino-quinazolin-2-yl)phenyl)-3-(4-(3-hydroxypyrrolidine-1-carbonyl)phenyl)urea;

4-(3-(4-(7-(furan-2-yl)-4-morpholino-quinazolin-2-yl)phenyl)ureido)-N-methyl-benzamide;

(S)-1-(4-(3-aminopyrrolidine-1-carbonyl)phenyl)-3-(4-(7-(furan-2-yl)-4-morpholino-quinazolin-2-yl)phenyl)urea;

N-(2-(dimethylamino)ethyl)-4-(3-(4-(7-(furan-2-yl)-4-morpholino-quinazolin-2-yl)phenyl)ureido)-benzamide;

N-(2-(dimethylamino)ethyl)-4-(3-(4-(7-(furan-2-yl)-4-morpholino-quinazolin-2-yl)phenyl)ureido)-N-methyl-benzamide;

4-(3-(3-fluoro-4-(4-morpholino-7-(pyrimidin-5-yl)quinazolin-2-yl)phenyl)ureido)-N,N-dimethyl-benzamide;

4-(3-(3-fluoro-4-(7-(1-methyl-1H-pyrazol-4-yl)-4-morpholino-pyrido[3,2-d]pyrimidin-2-yl)phenyl)ureido)-N,N-dimethyl-benzamide;

4-(3-(3-fluoro-4-(7-(5-methylfuran-2-yl)-4-morpholino-quinazolin-2-yl)phenyl)ureido)-N,N-dimethyl-benzamide;

2-fluoro-N,N-dimethyl-4-(3-(4-(4-morpholino-7-(pyrimidin-5-yl)quinazolin-2-yl)phenyl)ureido)-benzamide;

4-(3-(3-fluoro-4-(7-(2-fluoropyridin-3-yl)-4-morpholino-quinazolin-2-yl)phenyl)ureido)-N,N-dimethyl-benzamide;

4-(3-(3-fluoro-4-(7-(2-methoxypyrimidin-5-yl)-4-morpholino-quinazolin-2-yl)phenyl)ureido)-N,N-dimethyl-benzamide;

4-(3-(3-fluoro-4-(4-morpholino-7-(pyridin-3-yl)quinazolin-2-yl)phenyl)ureido)-N,N-dimethyl-benzamide;

4-(3-(3-fluoro-4-(7-(2-fluoropyridin-3-yl)-4-morpholino-pyrido[3,2-d]pyrimidin-2-yl)phenyl)ureido)-N,N-dimethyl-benzamide;

4-(3-(3-fluoro-4-(7-(3-(methylsulfonyl)phenyl)-4-morpholino-quinazolin-2-yl)phenyl)ureido)-N,N-dimethyl-benzamide;

4-(3-(4-(7-(3,5-dimethylisoxazol-4-yl)-4-morpholino-quinazolin-2-yl)phenyl)ureido)-2-fluoro-N,N-dimethyl-benzamide;

4-(3-(3-fluoro-4-(7-(furan-2-yl)-4-morpholino-quinazolin-2-yl)phenyl)ureido)-N,N-dimethyl-benzamide;

2-fluoro-4-(3-(4-(7-(2-fluoropyridin-3-yl)-4-morpholino-pyrido[3,2-d]pyrimidin-2-yl)phenyl)ureido)-N,N-dimethyl-benzamide;

4-(3-(3-fluoro-4-(7-(1-methyl-1H-pyrazol-4-yl)-4-morpholino-quinazolin-2-yl)phenyl)ureido)-N,N-dimethyl-benzamide;

4-(3-(3-fluoro-4-(4-morpholino-7-(pyrimidin-5-yl)pyrido[3,2-d]pyrimidin-2-yl)phenyl)ureido)-N,N-dimethyl-benzamide;

5-(3-(3-fluoro-4-(4-morpholino-7-(pyrimidin-5-yl)quinazolin-2-yl)phenyl)ureido)-N,N-dimethylpicolinamide;

4-(3-(4-(7-(3,5-dimethylisoxazol-4-yl)-4-morpholino-quinazolin-2-yl)-3-fluorophenyl)ureido)-N,N-dimethyl-benzamide;

2-fluoro-N,N-dimethyl-4-(3-(5-(7-(3-(methylsulfonyl)phenyl)-4-morpholino-quinazolin-2-yl)pyridin-2-yl)ureido)-benzamide;

4-(3-(3-fluoro-4-(4-(2-methylmorpholino)-7-(pyrimidin-5-yl)quinazolin-2-yl)phenyl)ureido)-N,N-dimethyl-benzamide;

2-fluoro-4-(3-(4-(7-(2-fluoropyridin-3-yl)-4-morpholino-quinazolin-2-yl)phenyl)ureido)-N,N-dimethyl-benzamide;

4-(3-(3-fluoro-4-(6-fluoro-4-morpholino-7-(pyrimidin-5-yl)quinazolin-2-yl)phenyl)ureido)-N,N-dimethyl-benzamide;

2-fluoro-4-(3-(4-(7-(2-methoxypyrimidin-5-yl)-4-morpholino-quinazolin-2-yl)phenyl)ureido)-N,N-dimethyl-benzamide;

4-(3-(3-fluoro-4-(7-(6-methoxypyridin-3-yl)-4-morpholino-quinazolin-2-yl)phenyl)ureido)-N,N-dimethyl-benzamide;

2-fluoro-4-(3-(4-(7-(6-methoxypyridin-3-yl)-4-morpholino-quinazolin-2-yl)phenyl)ureido)-N,N-dimethyl-benzamide;

2-fluoro-N,N-dimethyl-4-(3-(4-(4-morpholino-7-(pyridin-3-yl)quinazolin-2-yl)phenyl)ureido)-benzamide;

4-(3-(3-fluoro-4-(4-morpholino-7-(pyridin-3-yl)pyrido[3,2-d]pyrimidin-2-yl)phenyl)ureido)-N,N-dimethyl-benzamide;

2-fluoro-N,N-dimethyl-4-(3-(4-(4-morpholino-7-(pyrimidin-5-yl)pyrido[3,2-d]pyrimidin-2-yl)phenyl)ureido)-benzamide;

4-(3-(3-fluoro-4-(7-(2-methoxypyrimidin-5-yl)-4-morpholino-pyrido[3,2-d]pyrimidin-2-yl)phenyl)ureido)-N,N-dimethyl-benzamide;

2-fluoro-N,N-dimethyl-4-(3-(4-(4-morpholino-7-(pyridin-3-yl)pyrido[3,2-d]pyrimidin-2-yl)phenyl)ureido)-benzamide;

2-fluoro-4-(3-(4-(7-(furan-2-yl)-4-morpholino-quinazolin-2-yl)phenyl)ureido)-N,N-dimethyl-benzamide;

2-fluoro-N,N-dimethyl-4-(3-(4-(7-(5-methylfuran-2-yl)-4-morpholino-quinazolin-2-yl)phenyl)ureido)-benzamide;

2-fluoro-N,N-dimethyl-4-(3-(4-(4-morpholino-7-(pyridin-2-yl)quinazolin-2-yl)phenyl)ureido)-benzamide;

4-(3-(3-fluoro-4-(4-morpholino-7-(pyridin-2-yl)quinazolin-2-yl)phenyl)ureido)-N,N-dimethyl-benzamide;

4-(3-(3-fluoro-4-(4-morpholino-7-(1,3,5-trimethyl-1H-pyrazol-4-yl)quinazolin-2-yl)phenyl)ureido)-N,N-dimethyl-benzamide;

4-(3-(3-fluoro-4-(7-(2-methoxypyridin-3-yl)-4-morpholino-quinazolin-2-yl)phenyl)ureido)-N,N-dimethyl-benzamide;

4-(3-(3-fluoro-4-(7-(6-methylpyridin-3-yl)-4-morpholino-quinazolin-2-yl)phenyl)ureido)-N,N-dimethyl-benzamide;

4-(3-(3-fluoro-4-(7-(2-methylpyridin-3-yl)-4-morpholino-quinazolin-2-yl)phenyl)ureido)-N,N-dimethyl-benzamide;

2-fluoro-N,N-dimethyl-4-(3-(4-(7-(1-methyl-1H-pyrazol-4-yl)-4-morpholino-pyrido[3,2-d]pyrimidin-2-yl)phenyl)ureido)-benzamide;

4-(3-(3-fluoro-4-(7-(5-(hydroxymethyl)furan-2-yl)-4-morpholino-quinazolin-2-yl)phenyl)ureido)-N,N-dimethyl-benzamide;

4-(3-(3-fluoro-4-(7-(5-(1-hydroxyethyl)furan-2-yl)-4-morpholino-quinazolin-2-yl)phenyl)ureido)-N,N-dimethyl-benzamide;

4-(3-(3-fluoro-4-(7-(5-(2-hydroxypropan-2-yl)furan-2-yl)-4-morpholino-quinazolin-2-yl)phenyl)ureido)-N,N-dimethyl-benzamide;

4-(3-(4-(7-(2-(dimethylamino)pyrimidin-5-yl)-4-morpholino-quinazolin-2-yl)-3-fluorophenyl)ureido)-N,N-dimethyl-benzamide;

2-fluoro-4-(3-(4-(7-(5-(hydroxymethyl)furan-2-yl)-4-morpholino-quinazolin-2-yl)phenyl)ureido)-N,N-dimethyl-benzamide;

4-(3-(2,5-difluoro-4-(4-morpholino-7-(pyrimidin-5-yl)quinazolin-2-yl)phenyl)ureido)-N,N-dimethyl-benzamide;

4-(3-(2,3-difluoro-4-(4-morpholino-7-(pyrimidin-5-yl)quinazolin-2-yl)phenyl)ureido)-N,N-dimethyl-benzamide;

4-(3-(2,3-difluoro-4-(7-(5-methylfuran-2-yl)-4-morpholino-quinazolin-2-yl)phenyl)ureido)-N,N-dimethyl-benzamide;

-(3-(2,3-difluoro-4-(7-(furan-2-yl)-4-morpholino-quinazolin-2-yl)phenyl)ureido)-N,N-dimethyl-benzamide;

4-(3-(4-(7-(2-((2-hydroxyethyl)amino)pyridin-3-yl)-4-morpholino-quinazolin-2-yl)phenyl)ureido)-N,N-dimethyl-benzamide;

4-(3-(4-(7-((4-hydroxypiperidin-1-yl)methyl)-4-morpholino-quinazolin-2-yl)phenyl)ureido)-N,N-dimethyl-benzamide;

4-(3-(4-(7-(hydroxymethyl)-4-morpholino-quinazolin-2-yl)phenyl)ureido)-N,N-dimethyl-benzamide;

1-(4-(4-(dimethylamino)piperidine-1-carbonyl)phenyl)-3-(4-(7-(2-hydroxypropan-2-yl)-4-morpholino-quinazolin-2-yl)phenyl)urea;
4-(3-(4-(7-(4-(dimethylamino)piperidine-1-carbonyl)-4-morpholino-quinazolin-2-yl)phenyl)ureido)-N,N-dimethyl-benzamide;
(R)-1-(4-(3-(dimethylamino)pyrrolidine-1-carbonyl)phenyl)-3-(4-(7-(2-hydroxypropan-2-yl)-4-morpholino-quinazolin-2-yl)phenyl)urea;
(S)-1-(4-(3-(dimethylamino)pyrrolidine-1-carbonyl)phenyl)-3-(4-(7-(2-hydroxypropan-2-yl)-4-morpholino-quinazolin-2-yl)phenyl)urea;
4-(3-(2-fluoro-4-(7-(2-hydroxypropan-2-yl)-4-morpholino-quinazolin-2-yl)phenyl)ureido)-N,N-dimethyl-benzamide;
N-(4-(3-(4-(4-morpholino-7-(pyrimidin-5-yl)quinazolin-2-yl)phenyl)ureido)phenyl)-acetamide;
1-(4-(7-(2-fluoropyridin-3-yl)-4-morpholinoquinazolin-2-yl)phenyl)-3-(4-(2-oxopyrrolidin-1-yl)phenyl)urea;
N-(4-(3-(4-(7-(2-fluoropyridin-3-yl)-4-morpholinopyrido[3,2-d]pyrimidin-2-yl)phenyl)ureido)phenyl)acetamide;
N-(4-(3-(4-(7-(1-methyl-1H-pyrazol-4-yl)-4-morpholinopyrido[3,2-d]pyrimidin-2-yl)phenyl)ureido)phenyl)acetamide;
N,N-dimethyl-4-(3-(4-(4-morpholino-7-(1,3,5-trimethyl-1H-pyrazol-4-yl)pyrido[3,2-d]pyrimidin-2-yl)phenyl)ureido)-benzamide;
4-(3-(2-fluoro-4-(4-morpholino-7-(1,3,5-trimethyl-1H-pyrazol-4-yl)pyrido[3,2-d]pyrimidin-2-yl)phenyl)ureido)-N,N-dimethyl-benzamide;
N,N-dimethyl-4-(3-(4-(7-(2-methylpyridin-3-yl)-4-morpholinopyrido[3,2-d]pyrimidin-2-yl)phenyl)ureido)-benzamide;
4-(3-(2-fluoro-4-(7-(2-methylpyridin-3-yl)-4-morpholinopyrido[3,2-d]pyrimidin-2-yl)phenyl)ureido)-N,N-dimethyl-benzamide;
N,N-dimethyl-4-(3-(4-(7-(6-methylpyridin-3-yl)-4-morpholinopyrido[3,2-d]pyrimidin-2-yl)phenyl)ureido)-benzamide;
4-(3-(2-fluoro-4-(7-(6-methylpyridin-3-yl)-4-morpholinopyrido[3,2-d]pyrimidin-2-yl)phenyl)ureido)-N,N-dimethyl-benzamide;
N-(4-(3-(4-(7-(5-methylfuran-2-yl)-4-morpholinopyrido[3,2-d]pyrimidin-2-yl)phenyl)ureido)phenyl)acetamide;
N-(4-(3-(4-(7-(2-fluoropyridin-3-yl)-4-morpholinopyrido[3,2-d]pyrimidin-2-yl)phenyl)ureido)phenyl)acetamide;
N-(4-(3-(4-(4-morpholino-7-(pyridin-3-yl)pyrido[3,2-d]pyrimidin-2-yl)phenyl)ureido)phenyl)acetamide;
N-(4-(3-(4-(4-morpholino-7-(pyridin-4-yl)pyrido[3,2-d]pyrimidin-2-yl)phenyl)ureido)phenyl)acetamide;
N-(4-(3-(4-(4-morpholino-7-(pyridin-2-yl)pyrido[3,2-d]pyrimidin-2-yl)phenyl)ureido)phenyl)acetamide;
N-(4-(3-(4-(4-morpholino-7-(pyrimidin-5-yl)pyrido[3,2-d]pyrimidin-2-yl)phenyl)ureido)phenyl)acetamide;
N-(4-(3-(4-(4-morpholino-7-(pyridazin-4-yl)pyrido[3,2-d]pyrimidin-2-yl)phenyl)ureido)phenyl)acetamide;
N-(4-(3-(4-(7-(2-methoxypyrimidin-5-yl)-4-morpholinopyrido[3,2-d]pyrimidin-2-yl)phenyl)ureido)phenyl)acetamide;
N-(4-(3-(4-(7-(6-methoxypyridin-3-yl)-4-morpholinopyrido[3,2-d]pyrimidin-2-yl)phenyl)ureido)phenyl)acetamide;
N-(4-(3-(4-(7-(3-(methylsulfonyl)phenyl)-4-morpholinopyrido[3,2-d]pyrimidin-2-yl)phenyl)ureido)phenyl)acetamide;
N-(4-(3-(4-(7-(2-aminopyrimidin-5-yl)-4-morpholinopyrido[3,2-d]pyrimidin-2-yl)phenyl)ureido)phenyl)acetamide;
N-(4-(3-(4-(4-morpholino-7-(1,3,5-trimethyl-1H-pyrazol-4-yl)quinazolin-2-yl)phenyl)ureido)phenyl)acetamide;
N-(4-(3-(4-(7-(2-methylpyridin-3-yl)-4-morpholinopyrido[3,2-d]pyrimidin-2-yl)phenyl)ureido)phenyl)acetamide;
N-(4-(3-(4-(7-(6-methylpyridin-3-yl)-4-morpholinopyrido[3,2-d]pyrimidin-2-yl)phenyl)ureido)phenyl)acetamide;
N-(4-(3-(5-(7-(2-fluoropyridin-3-yl)-4-morpholinopyrido[3,2-d]pyrimidin-2-yl)pyridin-2-yl)ureido)phenyl)acetamide;
N-(4-(3-(5-(7-(1-methyl-1H-pyrazol-4-yl)-4-morpholinopyrido[3,2-d]pyrimidin-2-yl)pyridin-2-yl)ureido)phenyl)acetamide;
4-(3-(4-(7-(5-ethylfuran-2-yl)-4-morpholinoquinazolin-2-yl)phenyl)ureido)-N,N-dimethyl-benzamide;
4-(3-(4-(7-(5-(1,2-dihydroxyethyl)furan-2-yl)-4-morpholinoquinazolin-2-yl)phenyl)ureido)-N,N-dimethyl-benzamide;
N-(4-(3-(4-(7-(5-ethylfuran-2-yl)-4-morpholinoquinazolin-2-yl)phenyl)ureido)phenyl)acetamide;
N-(4-(3-(4-(7-(5-(hydroxymethyl)furan-2-yl)-4-morpholinoquinazolin-2-yl)phenyl)ureido)phenyl)acetamide;
N-(4-(3-(4-(7-(5-(1-hydroxyethyl)furan-2-yl)-4-morpholinoquinazolin-2-yl)phenyl)ureido)phenyl)acetamide;
N-(4-(3-(4-(7-(5-(2-hydroxypropan-2-yl)furan-2-yl)-4-morpholinoquinazolin-2-yl)phenyl)ureido)phenyl)acetamide;
N-(4-(3-(4-(7-(furan-2-yl)-4-morpholinoquinazolin-2-yl)phenyl)ureido)phenyl)acetamide;
N-(4-(3-(4-(4-morpholino-7-(pyridin-3-yl)quinazolin-2-yl)phenyl)ureido)phenyl)acetamide;
N-(4-(3-(4-(4-morpholino-7-(pyridin-4-yl)quinazolin-2-yl)phenyl)ureido)phenyl)acetamide;
N-(4-(3-(4-(4-morpholino-7-(pyridin-2-yl)quinazolin-2-yl)phenyl)ureido)phenyl)acetamide;
N-(4-(3-(4-(4-morpholino-7-(pyridazin-4-yl)quinazolin-2-yl)phenyl)ureido)phenyl)acetamide;
N-(4-(3-(4-(7-(2-methoxypyrimidin-5-yl)-4-morpholinoquinazolin-2-yl)phenyl)ureido)phenyl)acetamide;
N-(4-(3-(4-(7-(6-methoxypyridin-3-yl)-4-morpholinoquinazolin-2-yl)phenyl)ureido)phenyl)acetamide;
N-(4-(3-(4-(7-(3-(methylsulfonyl)phenyl)-4-morpholinoquinazolin-2-yl)phenyl)ureido)phenyl)acetamide;
N-(4-(3-(4-(7-(2-aminopyrimidin-5-yl)-4-morpholinoquinazolin-2-yl)phenyl)ureido)phenyl)acetamide;
N-(4-(3-(4-(4-morpholino-7-(1,3,5-trimethyl-1H-pyrazol-4-yl)quinazolin-2-yl)phenyl)ureido)phenyl)acetamide;
N-(4-(3-(4-(7-(2-methylpyridin-3-yl)-4-morpholinoquinazolin-2-yl)phenyl)ureido)phenyl)acetamide;
N-(4-(3-(4-(7-(6-methylpyridin-3-yl)-4-morpholinoquinazolin-2-yl)phenyl)ureido)phenyl)acetamide;
N-(4-(3-(5-(7-(5-methylfuran-2-yl)-4-morpholinoquinazolin-2-yl)pyridin-2-yl)ureido)phenyl)acetamide;
N-(4-(3-(5-(7-(furan-2-yl)-4-morpholinoquinazolin-2-yl)pyridin-2-yl)ureido)phenyl)acetamide;

N-(4-(3-(5-(4-morpholino-7-(pyrimidin-5-yl)quinazolin-2-yl)pyridin-2-yl)ureido)phenyl)acetamide;
N-(4-(3-(5-(7-(1-methyl-1H-pyrazol-4-yl)-4-morpholinoquinazolin-2-yl)pyridin-2-yl)ureido)phenyl)acetamide;
N-(4-(3-(4-(6-fluoro-7-(5-methylfuran-2-yl)-4-morpholinoquinazolin-2-yl)phenyl)ureido)phenyl)acetamide;
N-(4-(3-(4-(6-fluoro-7-(furan-2-yl)-4-morpholinoquinazolin-2-yl)phenyl)ureido)phenyl)acetamide;
N-(4-(3-(4-(6-fluoro-4-morpholino-7-(pyridin-3-yl)quinazolin-2-yl)phenyl)ureido)phenyl)acetamide;
N-(4-(3-(4-(6-fluoro-4-morpholino-7-(pyrimidin-5-yl)quinazolin-2-yl)phenyl)ureido)phenyl)acetamide;
N-(3-fluoro-4-(3-(4-(7-(5-methylfuran-2-yl)-4-morpholinoquinazolin-2-yl)phenyl)ureido)phenyl)acetamide;
N-(4-(3-(4-(7-(5-ethylfuran-2-yl)-4-morpholinoquinazolin-2-yl)phenyl)ureido)-3-fluorophenyl)acetamide;
N-(3-fluoro-4-(3-(4-(7-(furan-2-yl)-4-morpholinoquinazolin-2-yl)phenyl)ureido)phenyl)acetamide;
N-(3-fluoro-4-(3-(4-(4-morpholino-7-(pyridin-3-yl)quinazolin-2-yl)phenyl)ureido)phenyl)acetamide;
N-(3-fluoro-4-(3-(4-(7-(2-fluoropyridin-3-yl)-4-morpholinoquinazolin-2-yl)phenyl)ureido)phenyl)acetamide;
N-(3-fluoro-4-(3-(4-(7-(2-methylpyridin-3-yl)-4-morpholinoquinazolin-2-yl)phenyl)ureido)phenyl)acetamide;
N-(3-fluoro-4-(3-(4-(7-(6-methylpyridin-3-yl)-4-morpholinoquinazolin-2-yl)phenyl)ureido)phenyl)acetamide;
N-(3-fluoro-4-(3-(4-(4-morpholino-7-(pyridin-2-yl)quinazolin-2-yl)phenyl)ureido)phenyl)acetamide;
N-(3-fluoro-4-(3-(4-(4-morpholino-7-(pyridin-4-yl)quinazolin-2-yl)phenyl)ureido)phenyl)acetamide;
N-(3-fluoro-4-(3-(4-(4-morpholino-7-(pyrimidin-5-yl)quinazolin-2-yl)phenyl)ureido)phenyl)acetamide;
N-(3-fluoro-4-(3-(4-(7-(2-methoxypyrimidin-5-yl)-4-morpholinoquinazolin-2-yl)phenyl)ureido)phenyl)acetamide;
N-(4-(3-(4-(7-(2-aminopyrimidin-5-yl)-4-morpholinoquinazolin-2-yl)phenyl)ureido)-3-fluorophenyl)acetamide;
N-(3-fluoro-4-(3-(4-(7-(6-methoxypyridin-3-yl)-4-morpholinoquinazolin-2-yl)phenyl)ureido)phenyl)acetamide;
N-(3-fluoro-4-(3-(4-(7-(1-methyl-1H-pyrazol-4-yl)-4-morpholinoquinazolin-2-yl)phenyl)ureido)phenyl)acetamide;
N-(3-fluoro-4-(3-(4-(4-morpholino-7-(1,3,5-trimethyl-1H-pyrazol-4-yl)quinazolin-2-yl)phenyl)ureido)phenyl)acetamide;
N-(3-fluoro-4-(3-(4-(7-(3-(methylsulfonyl)phenyl)-4-morpholinoquinazolin-2-yl)phenyl)ureido)phenyl)acetamide;
N-(3-fluoro-4-(3-(4-(7-(5-(hydroxymethyl)furan-2-yl)-4-morpholinoquinazolin-2-yl)phenyl)ureido)phenyl)acetamide;
N-(3-fluoro-4-(3-(4-(7-(5-(1-hydroxyethyl)furan-2-yl)-4-morpholinoquinazolin-2-yl)phenyl)ureido)phenyl)acetamide;
N-(3-fluoro-4-(3-(4-(7-(5-(2-hydroxypropan-2-yl)furan-2-yl)-4-morpholinoquinazolin-2-yl)phenyl)ureido)phenyl)acetamide;
N-(2-fluoro-4-(3-(4-(7-(5-methylfuran-2-yl)-4-morpholinoquinazolin-2-yl)phenyl)ureido)phenyl)acetamide;
N-(4-(3-(4-(7-(5-ethylfuran-2-yl)-4-morpholinoquinazolin-2-yl)phenyl)ureido)-2-fluorophenyl)acetamide;
N-(2-fluoro-4-(3-(4-(7-(furan-2-yl)-4-morpholinoquinazolin-2-yl)phenyl)ureido)phenyl)acetamide;
N-(2-fluoro-4-(3-(4-(4-morpholino-7-(pyridin-3-yl)quinazolin-2-yl)phenyl)ureido)phenyl)acetamide;
N-(2-fluoro-4-(3-(4-(7-(2-fluoropyridin-3-yl)-4-morpholinoquinazolin-2-yl)phenyl)ureido)phenyl)acetamide;
N-(2-fluoro-4-(3-(4-(7-(2-methylpyridin-3-yl)-4-morpholinoquinazolin-2-yl)phenyl)ureido)phenyl)acetamide;
N-(2-fluoro-4-(3-(4-(7-(6-methylpyridin-3-yl)-4-morpholinoquinazolin-2-yl)phenyl)ureido)phenyl)acetamide;
N-(2-fluoro-4-(3-(4-(4-morpholino-7-(pyridin-2-yl)quinazolin-2-yl)phenyl)ureido)phenyl)acetamide;
N-(2-fluoro-4-(3-(4-(4-morpholino-7-(pyridin-4-yl)quinazolin-2-yl)phenyl)ureido)phenyl)acetamide;
N-(2-fluoro-4-(3-(4-(4-morpholino-7-(pyrimidin-5-yl)quinazolin-2-yl)phenyl)ureido)phenyl)acetamide;
N-(2-fluoro-4-(3-(4-(7-(2-methoxypyrimidin-5-yl)-4-morpholinoquinazolin-2-yl)phenyl)ureido)phenyl)acetamide;
N-(4-(3-(4-(7-(2-aminopyrimidin-5-yl)-4-morpholinoquinazolin-2-yl)phenyl)ureido)-2-fluorophenyl)acetamide;
N-(2-fluoro-4-(3-(4-(7-(6-methoxypyridin-3-yl)-4-morpholinoquinazolin-2-yl)phenyl)ureido)phenyl)acetamide;
N-(2-fluoro-4-(3-(4-(7-(1-methyl-1H-pyrazol-4-yl)-4-morpholinoquinazolin-2-yl)phenyl)ureido)phenyl)acetamide;
N-(2-fluoro-4-(3-(4-(4-morpholino-7-(1,3,5-trimethyl-1H-pyrazol-4-yl)quinazolin-2-yl)phenyl)ureido)phenyl)acetamide;
N-(2-fluoro-4-(3-(4-(7-(3-(methylsulfonyl)phenyl)-4-morpholinoquinazolin-2-yl)phenyl)ureido)phenyl)acetamide;
N-(2-fluoro-4-(3-(4-(7-(5-(hydroxymethyl)furan-2-yl)-4-morpholinoquinazolin-2-yl)phenyl)ureido)phenyl)acetamide;
N-(2-fluoro-4-(3-(4-(7-(5-(1-hydroxyethyl)furan-2-yl)-4-morpholinoquinazolin-2-yl)phenyl)ureido)phenyl)acetamide;
N-(2-fluoro-4-(3-(4-(7-(5-(2-hydroxypropan-2-yl)furan-2-yl)-4-morpholinoquinazolin-2-yl)phenyl)ureido)phenyl)acetamide;
N-methyl-N-(4-(3-(4-(7-(5-methylfuran-2-yl)-4-morpholinoquinazolin-2-yl)phenyl)ureido)phenyl)acetamide;
N-(4-(3-(4-(7-(5-ethylfuran-2-yl)-4-morpholinoquinazolin-2-yl)phenyl)ureido)phenyl)-N-methylacetamide;
N-(4-(3-(4-(7-(furan-2-yl)-4-morpholinoquinazolin-2-yl)phenyl)ureido)phenyl)-N-methylacetamide;
N-(4-(3-(4-(7-(2-methoxypyrimidin-5-yl)-4-morpholinoquinazolin-2-yl)phenyl)ureido)phenyl)-N-methylacetamide;
N-methyl-N-(4-(3-(4-(4-morpholino-7-(pyrimidin-5-yl)quinazolin-2-yl)phenyl)ureido)phenyl)acetamide;
N-methyl-N-(4-(3-(4-(4-morpholino-7-(pyridin-3-yl)quinazolin-2-yl)phenyl)ureido)phenyl)acetamide;
N-(4-(3-(4-(7-(2-fluoropyridin-3-yl)-4-morpholinoquinazolin-2-yl)phenyl)ureido)phenyl)-N-methylacetamide;
N-methyl-N-(4-(3-(4-(4-morpholino-7-(pyridin-2-yl)quinazolin-2-yl)phenyl)ureido)phenyl)acetamide;

N-(3-fluoro-4-(3-(4-(6-fluoro-7-(5-methylfuran-2-yl)-4-morpholinoquinazolin-2-yl)phenyl)ureido)phenyl)acetamide;

N-(3-fluoro-4-(3-(4-(6-fluoro-7-(furan-2-yl)-4-morpholinoquinazolin-2-yl)phenyl)ureido)phenyl)acetamide;

N-(3-fluoro-4-(3-(4-(6-fluoro-4-morpholino-7-(pyrimidin-5-yl)quinazolin-2-yl)phenyl)ureido)phenyl)acetamide;

N-(3-fluoro-4-(3-(4-(6-fluoro-4-morpholino-7-(pyridin-3-yl)quinazolin-2-yl)phenyl)ureido)phenyl)acetamide;

N-(2-fluoro-4-(3-(4-(6-fluoro-7-(5-methylfuran-2-yl)-4-morpholinoquinazolin-2-yl)phenyl)ureido)phenyl)acetamide;

N-(2-fluoro-4-(3-(4-(6-fluoro-7-(furan-2-yl)-4-morpholinoquinazolin-2-yl)phenyl)ureido)phenyl)acetamide;

N-(2-fluoro-4-(3-(4-(6-fluoro-4-morpholino-7-(pyrimidin-5-yl)quinazolin-2-yl)phenyl)ureido)phenyl)acetamide;

N-(2-fluoro-4-(3-(4-(6-fluoro-4-morpholino-7-(pyridin-3-yl)quinazolin-2-yl)phenyl)ureido)phenyl)acetamide;

N-(4-(3-(4-(6-fluoro-7-(5-methylfuran-2-yl)-4-morpholinoquinazolin-2-yl)phenyl)ureido)phenyl)-N-methylacetamide;

N-(4-(3-(4-(6-fluoro-7-(furan-2-yl)-4-morpholinoquinazolin-2-yl)phenyl)ureido)phenyl)-N-methylacetamide;

N-(4-(3-(4-(6-fluoro-4-morpholino-7-(pyrimidin-5-yl)quinazolin-2-yl)phenyl)ureido)phenyl)-N-methylacetamide;

N-(4-(3-(4-(6-fluoro-4-morpholino-7-(pyridin-3-yl)quinazolin-2-yl)phenyl)ureido)phenyl)-N-methylacetamide;

N-(3-fluoro-4-(3-(4-(7-(5-methylfuran-2-yl)-4-morpholinopyrido[3,2-d]pyrimidin-2-yl)phenyl)ureido)phenyl)acetamide;

N-(3-fluoro-4-(3-(4-(7-(furan-2-yl)-4-morpholinopyrido[3,2-d]pyrimidin-2-yl)phenyl)ureido)phenyl)acetamide;

N-(3-fluoro-4-(3-(4-(4-morpholino-7-(pyrimidin-5-yl)pyrido[3,2-d]pyrimidin-2-yl)phenyl)ureido)phenyl)acetamide;

N-(3-fluoro-4-(3-(4-(7-(2-fluoropyridin-3-yl)-4-morpholinopyrido[3,2-d]pyrimidin-2-yl)phenyl)ureido)phenyl)acetamide;

N-(3-fluoro-4-(3-(4-(4-morpholino-7-(pyridin-3-yl)pyrido[3,2-d]pyrimidin-2-yl)phenyl)ureido)phenyl)acetamide;

N-(3-fluoro-4-(3-(4-(7-(1-methyl-1H-pyrazol-4-yl)-4-morpholinopyrido[3,2-d]pyrimidin-2-yl)phenyl)ureido)phenyl)acetamide;

N-(2-fluoro-4-(3-(4-(7-(5-methylfuran-2-yl)-4-morpholinopyrido[3,2-d]pyrimidin-2-yl)phenyl)ureido)phenyl)acetamide;

N-(2-fluoro-4-(3-(4-(7-(furan-2-yl)-4-morpholinopyrido[3,2-d]pyrimidin-2-yl)phenyl)ureido)phenyl)acetamide;

N-(2-fluoro-4-(3-(4-(4-morpholino-7-(pyrimidin-5-yl)pyrido[3,2-d]pyrimidin-2-yl)phenyl)ureido)phenyl)acetamide;

N-(2-fluoro-4-(3-(4-(7-(2-fluoropyridin-3-yl)-4-morpholinopyrido[3,2-d]pyrimidin-2-yl)phenyl)ureido)phenyl)acetamide;

N-(2-fluoro-4-(3-(4-(4-morpholino-7-(pyridin-3-yl)pyrido[3,2-d]pyrimidin-2-yl)phenyl)ureido)phenyl)acetamide;

N-(2-fluoro-4-(3-(4-(7-(1-methyl-1H-pyrazol-4-yl)-4-morpholinopyrido[3,2-d]pyrimidin-2-yl)phenyl)ureido)phenyl)acetamide;

N-methyl-N-(4-(3-(4-(7-(5-methylfuran-2-yl)-4-morpholinopyrido[3,2-d]pyrimidin-2-yl)phenyl)ureido)phenyl)acetamide;

N-(4-(3-(4-(7-(furan-2-yl)-4-morpholinopyrido[3,2-d]pyrimidin-2-yl)phenyl)ureido)phenyl)-N-methylacetamide;

N-methyl-N-(4-(3-(4-(4-morpholino-7-(pyrimidin-5-yl)pyrido[3,2-d]pyrimidin-2-yl)phenyl)ureido)phenyl)acetamide;

N-methyl-N-(4-(3-(4-(7-(2-fluoropyridin-3-yl)-4-morpholinopyrido[3,2-d]pyrimidin-2-yl)phenyl)ureido)phenyl)-N-methylacetamide;

N-methyl-N-(4-(3-(4-(4-morpholino-7-(pyridin-3-yl)pyrido[3,2-d]pyrimidin-2-yl)phenyl)ureido)phenyl)acetamide;

N-methyl-N-(4-(3-(4-(7-(1-methyl-1H-pyrazol-4-yl)-4-morpholinopyrido[3,2-d]pyrimidin-2-yl)phenyl)ureido)phenyl)acetamide;

N-(4-(3-(2-fluoro-4-(7-(5-methylfuran-2-yl)-4-morpholinoquinazolin-2-yl)phenyl)ureido)phenyl)acetamide;

N-(4-(3-(2-fluoro-4-(7-(furan-2-yl)-4-morpholinoquinazolin-2-yl)phenyl)ureido)phenyl)acetamide;

N-(4-(3-(2-fluoro-4-(7-(2-methoxypyrimidin-5-yl)-4-morpholinoquinazolin-2-yl)phenyl)ureido)phenyl)acetamide;

N-(4-(3-(2-fluoro-4-(4-morpholino-7-(pyrimidin-5-yl)quinazolin-2-yl)phenyl)ureido)phenyl)acetamide;

N-(4-(3-(2-fluoro-4-(4-morpholino-7-(pyridin-3-yl)quinazolin-2-yl)phenyl)ureido)phenyl)acetamide;

N-(4-(3-(2-fluoro-4-(7-(2-fluoropyridin-3-yl)-4-morpholinoquinazolin-2-yl)phenyl)ureido)phenyl)acetamide;

N-(4-(3-(2-fluoro-4-(4-morpholino-7-(pyridin-2-yl)quinazolin-2-yl)phenyl)ureido)phenyl)acetamide;

N-(4-(3-(3-fluoro-4-(7-(5-methylfuran-2-yl)-4-morpholinoquinazolin-2-yl)phenyl)ureido)phenyl)acetamide;

N-(4-(3-(3-fluoro-4-(7-(furan-2-yl)-4-morpholinoquinazolin-2-yl)phenyl)ureido)phenyl)acetamide;

N-(4-(3-(3-fluoro-4-(7-(2-methoxypyrimidin-5-yl)-4-morpholinoquinazolin-2-yl)phenyl)ureido)phenyl)acetamide;

N-(4-(3-(3-fluoro-4-(4-morpholino-7-(pyrimidin-5-yl)quinazolin-2-yl)phenyl)ureido)phenyl)acetamide;

N-(4-(3-(3-fluoro-4-(4-morpholino-7-(pyridin-3-yl)quinazolin-2-yl)phenyl)ureido)phenyl)acetamide;

N-(4-(3-(3-fluoro-4-(7-(2-fluoropyridin-3-yl)-4-morpholinoquinazolin-2-yl)phenyl)ureido)phenyl)acetamide;

N-(4-(3-(3-fluoro-4-(4-morpholino-7-(pyridin-2-yl)quinazolin-2-yl)phenyl)ureido)phenyl)acetamide;

N-(4-(3-(2-fluoro-4-(6-fluoro-7-(5-methylfuran-2-yl)-4-morpholinoquinazolin-2-yl)phenyl)ureido)phenyl)acetamide;

N-(4-(3-(2-fluoro-4-(6-fluoro-7-(furan-2-yl)-4-morpholinoquinazolin-2-yl)phenyl)ureido)phenyl)acetamide;

N-(4-(3-(2-fluoro-4-(6-fluoro-4-morpholino-7-(pyrimidin-5-yl)quinazolin-2-yl)phenyl)ureido)phenyl)acetamide;

N-(4-(3-(2-fluoro-4-(6-fluoro-4-morpholino-7-(pyridin-3-yl)quinazolin-2-yl)phenyl)ureido)phenyl)acetamide;

N-(4-(3-(3-fluoro-4-(6-fluoro-7-(5-methylfuran-2-yl)-4-morpholinoquinazolin-2-yl)phenyl)ureido)phenyl)acetamide;

N-(4-(3-(3-fluoro-4-(6-fluoro-7-(furan-2-yl)-4-morpholinoquinazolin-2-yl)phenyl)ureido)phenyl)acetamide;
N-(4-(3-(3-fluoro-4-(6-fluoro-4-morpholino-7-(pyrimidin-5-yl)quinazolin-2-yl)phenyl)ureido)phenyl)acetamide;
N-(4-(3-(3-fluoro-4-(6-fluoro-4-morpholino-7-(pyridin-3-yl)quinazolin-2-yl)phenyl)ureido)phenyl)acetamide;
N-(4-(3-(2-fluoro-4-(7-(5-methylfuran-2-yl)-4-morpholinopyrido[3,2-d]pyrimidin-2-yl)phenyl)ureido)phenyl)acetamide;
N-(4-(3-(2-fluoro-4-(7-(furan-2-yl)-4-morpholinopyrido[3,2-d]pyrimidin-2-yl)phenyl)ureido)phenyl)acetamide;
N-(4-(3-(2-fluoro-4-(4-morpholino-7-(pyrimidin-5-yl)pyrido[3,2-d]pyrimidin-2-yl)phenyl)ureido)phenyl)acetamide;
N-(4-(3-(2-fluoro-4-(7-(2-fluoropyridin-3-yl)-4-morpholinopyrido[3,2-d]pyrimidin-2-yl)phenyl)ureido)phenyl)acetamide;
N-(4-(3-(2-fluoro-4-(4-morpholino-7-(pyridin-3-yl)pyrido[3,2-d]pyrimidin-2-yl)phenyl)ureido)phenyl)acetamide;
N-(4-(3-(2-fluoro-4-(7-(1-methyl-1H-pyrazol-4-yl)-4-morpholinopyrido[3,2-d]pyrimidin-2-yl)phenyl)ureido)phenyl)acetamide;
N-(4-(3-(3-fluoro-4-(7-(5-methylfuran-2-yl)-4-morpholinopyrido[3,2-d]pyrimidin-2-yl)phenyl)ureido)phenyl)acetamide;
N-(4-(3-(3-fluoro-4-(7-(furan-2-yl)-4-morpholinopyrido[3,2-d]pyrimidin-2-yl)phenyl)ureido)phenyl)acetamide;
N-(4-(3-(3-fluoro-4-(4-morpholino-7-(pyrimidin-5-yl)pyrido[3,2-d]pyrimidin-2-yl)phenyl)ureido)phenyl)acetamide;
N-(4-(3-(3-fluoro-4-(7-(2-fluoropyridin-3-yl)-4-morpholinopyrido[3,2-d]pyrimidin-2-yl)phenyl)ureido)phenyl)acetamide;
N-(4-(3-(3-fluoro-4-(4-morpholino-7-(pyridin-3-yl)pyrido[3,2-d]pyrimidin-2-yl)phenyl)ureido)phenyl)acetamide; and
N-(4-(3-(3-fluoro-4-(7-(1-methyl-1H-pyrazol-4-yl)-4-morpholinopyrido[3,2-d]pyrimidin-2-yl)phenyl)ureido)phenyl)acetamide, or a pharmaceutically acceptable salt or solvate thereof.

4. The method according to claim 3, wherein said condition is an inflammatory disorder.

5. The method according to claim 4, wherein said inflammatory disorder is selected from the group consisting of arthritis, pulmonary fibrosis, myocardial infarction, and peritonitis.

6. A method for treating a disease characterized by an abnormal cellular proliferation resulting from a dysregulated PI3K/AKT/mTOR pathway, said method comprising administering of a therapeutically effective amount of a compound to a patient in need thereof wherein the compound is selected from the group consisting of N,N-Dimethyl-4-{3-[4-(4-morpholin-4-yl-7-pyrimidin-5-yl-quinazolin-2-yl)-phenyl]-ureido}-benzamide;
N,N-Dimethyl-4-(3-{4-[7-(5-methyl-furan-2-yl)-4-morpholin-4-yl-quinazolin-2-yl]-phenyl}-ureido)-benzamide;
4-(3-{5-[7-(3-Methanesulfonyl-phenyl)-4-morpholin-4-yl-quinazolin-2-yl]-pyridin-2-yl}-ureido)-N,N-dimethyl-benzamide;
1-[4-(6-Fluoro-4-morpholin-4-yl-7-pyridin-3-yl-quinazolin-2-yl)-phenyl]-3-[4-(4-methyl-piperazine-1-carbonyl)-phenyl]-urea;
4-(3-{4-[8-(3-Hydroxy-phenyl)-4-morpholin-4-yl-quinazolin-2-yl]-phenyl}-ureido)-N,N-dimethyl-benzamide;
4-(3-{4-[8-(6-Fluoro-pyridin-3-yl)-4-morpholin-4-yl-quinazolin-2-yl]-phenyl}-ureido)-N,N-dimethyl-benzamide;
2-{4-[3-(4-Dimethylcarbamoyl-phenyl)-ureido]-phenyl}-4-morpholin-4-yl-quinazoline-7-carboxylic acid (2-dimethylamino-ethyl)-amide;
4-(3-{2-Fluoro-4-[7-(5-methyl-furan-2-yl)-4-morpholin-4-yl-quinazolin-2-yl]-phenyl}-ureido)-N,N-dimethyl-benzamide;
N,N-Dimethyl-4-{3-[4-(4-morpholin-4-yl-7-pyrimidin-5-yl-pyrido[3,2-d]pyrimidin-2-yl)-phenyl]-ureido}-benzamide;
5-(2-(4-(3-(4-(dimethylcarbamoyl)phenyl)ureido)phenyl)-4-morpholino-quinazolin-7-yl)furan-2-carboxylic acid;
N,N-dimethyl-4-(3-(4-(7-(5-(4-methylpiperazine-1-carbonyl)furan-2-yl)-4-morpholino-quinazolin-2-yl)phenyl)ureido)-benzamide;
4-(3-(4-(7-(5-cyanofuran-2-yl)-4-morpholino-quinazolin-2-yl)-3-fluorophenyl)ureido)-N,N-dimethyl-benzamide;
4-(3-(4-(7-(5-acetylfuran-2-yl)-4-morpholino-quinazolin-2-yl)phenyl)ureido)-2-fluoro-N,N-dimethyl-benzamide;
4-(3-(2,3-difluoro-4-(7-(1-methyl-1H-pyrazol-4-yl)-4-morpholino-pyrido[3,2-d]pyrimidin-2-yl)phenyl)ureido)-N,N-dimethyl-benzamide;
4-(3-(2-fluoro-4-(7-(5-(1-hydroxyethyl)furan-2-yl)-4-morpholino-pyrido[3,2-d]pyrimidin-2-yl)phenyl)ureido)-N,N-dimethyl-benzamide;
4-(3-(4-(7-(2-hydroxypropan-2-yl)-4-morpholino-quinazolin-2-yl)phenyl)ureido)-N,N-dimethyl-benzamide;
N-(4-(3-(4-(7-(5-methylfuran-2-yl)-4-morpholino-quinazolin-2-yl)phenyl)ureido)-phenyl)-acetamide;
1-(4-(7-(5-methylfuran-2-yl)-4-morpholino-quinazolin-2-yl)phenyl)-3-(4-(2-oxopyrrolidin-1-yl)phenyl)urea;
4-(3-{4-[7-(3-Methanesulfonyl-phenyl)-4-morpholin-4-yl-quinazolin-2-yl]-phenyl}-ureido)-N,N-dimethyl-benzamide;
4-(3-{4-[7-(3-Methanesulfonyl-phenyl)-4-morpholin-4-yl-quinazolin-2-yl]-phenyl}-ureido)-N-methyl-benzamide;
4-(3-{4-[7-(2-Fluoro-pyridin-3-yl)-4-morpholin-4-yl-quinazolin-2-yl]-phenyl}-ureido)-N,N-dimethyl-benzamide;
N,N-Dimethyl-4-(3-{4-[7-(1-methyl-1H-pyrazol-4-yl)-4-morpholin-4-yl-quinazolin-2-yl]-phenyl}-ureido)-benzamide;
4-(3-{4-[7-(3-Methanesulfonylamino-phenyl)-4-morpholin-4-yl-quinazolin-2-yl]-phenyl}-ureido)-N,N-dimethyl-benzamide;
N,N-Dimethyl-4-{3-[4-(4-morpholin-4-yl-7-pyridin-3-yl-quinazolin-2-yl)-phenyl]-ureido}-benzamide;
4-(3-{4-[7-(3-Methanesulfonyl-phenyl)-4-morpholin-4-yl-quinazolin-2-yl]-phenyl}-ureido)-benzamide;
1-{4-[7-(2-Fluoro-pyridin-3-yl)-4-morpholin-4-yl-quinazolin-2-yl]-phenyl}-3-[4-(4-methyl-piperazine-1-carbonyl)-phenyl]-urea;
1-[4-(4-Methyl-piperazine-1-carbonyl)-phenyl]-3-{4-[7-(1-methyl-1H-pyrazol-4-yl)-4-morpholin-4-yl-quinazolin-2-yl]-phenyl}-urea;

5-(3-{4-[7-(2-Fluoro-pyridin-3-yl)-4-morpholin-4-yl-quinazolin-2-yl]-phenyl}-ureido)-pyridine-2-carboxylic acid dimethylamide;
4-{3-[4-(6-Fluoro-4-morpholin-4-yl-7-pyridin-3-yl-quinazolin-2-yl)-phenyl]-ureido}-N,N-dimethyl-benzamide;
4-{3-[4-(6-Fluoro-4-morpholin-4-yl-7-pyrimidin-5-yl-quinazolin-2-yl)-phenyl]-ureido}-N,N-dimethyl-benzamide;
5-(3-{4-[7-(3-Methanesulfonyl-phenyl)-4-morpholin-4-yl-quinazolin-2-yl]-phenyl}-ureido)-pyridine-2-carboxylic acid dimethylamide;
1-(4-(4-methylpiperazine-1-carbonyl)phenyl)-3-(4-(7-(3-(methylsulfonyl)phenyl)-4-morpholino-quinazolin-2-yl)phenyl)urea;
1-[4-(4-Methyl-piperazine-1-carbonyl)-phenyl]-3-[4-(4-morpholin-4-yl-7-pyridin-3-yl-quinazolin-2-yl)-phenyl]-urea;
4-(3-{4-[7-(5-Methanesulfonyl-pyridin-3-yl)-4-morpholin-4-yl-quinazolin-2-yl]-phenyl}-ureido)-N,N-dimethyl-benzamide;
4-(3-{4-[6-Fluoro-7-(1-methyl-1H-pyrazol-4-yl)-4-morpholin-4-yl-quinazolin-2-yl]-phenyl}-ureido)-N,N-dimethyl-benzamide;
4-(3-{4-[6-Fluoro-7-(3-methanesulfonyl-phenyl)-4-morpholin-4-yl-quinazolin-2-yl]-phenyl}-ureido)-N,N-dimethyl-benzamide;
1-[4-(4-Methyl-piperazine-1-carbonyl)-phenyl]-3-[4-(4-morpholin-4-yl-7-thiophen-3-yl-quinazolin-2-yl)-phenyl]-urea;
4-(3-{4-[6-Fluoro-7-(5-methanesulfonyl-pyridin-3-yl)-4-morpholin-4-yl-quinazolin-2-yl]-phenyl}-ureido)-N,N-dimethyl-benzamide;
4-(3-{4-[7-(3-Methanesulfonyl-phenyl)-4-morpholin-4-yl-pyrido[3,2-d]pyrimidin-2-yl]-phenyl}-ureido)-N,N-dimethyl-benzamide;
4-(3-{4-[8-(2-Fluoro-pyridin-3-yl)-4-morpholin-4-yl-quinazolin-2-yl]-phenyl}-ureido)-N,N-dimethyl-benzamide;
4-(3-{4-[7-(3-Hydroxy-phenyl)-4-morpholin-4-yl-quinazolin-2-yl]-phenyl}-ureido)-N,N-dimethyl-benzamide;
N,N-Dimethyl-4-(3-{4-[7-(1-methyl-1H-pyrazol-4-yl)-4-morpholin-4-yl-pyrido[3,2-d]pyrimidin-2-yl]-phenyl}-ureido)-benzamide;
N,N-Dimethyl-4-(3-{4-[7-(5-methyl-furan-2-yl)-4-morpholin-4-yl-pyrido[3,2-d]pyrimidin-2-yl]-phenyl}-ureido)-benzamide;
N-(2-Dimethylamino-ethyl)-N-methyl-4-{3-[4-(4-morpholin-4-yl-7-pyrimidin-5-yl-quinazolin-2-yl)-phenyl]-ureido}-benzamide;
4-(3-{4-[7-(3-Hydroxymethyl-phenyl)-4-morpholin-4-yl-quinazolin-2-yl]-phenyl}-ureido)-N,N-dimethyl-benzamide;
N,N-Dimethyl-4-{3-[4-(4-morpholin-4-yl-7-pyridin-3-yl-pyrido[3,2-d]pyrimidin-2-yl)-phenyl]-ureido}-benzamide;
4-(3-{4-[7-(3-Fluoro-phenyl)-4-morpholin-4-yl-quinazolin-2-yl]-phenyl}-ureido)-N,N-dimethyl-benzamide;
4-(3-{4-[7-(3-Methoxy-phenyl)-4-morpholin-4-yl-quinazolin-2-yl]-phenyl}-ureido)-N,N-dimethyl-benzamide;
4-(3-{4-[7-(3-Acetylamino-phenyl)-4-morpholin-4-yl-quinazolin-2-yl]-phenyl}-ureido)-N,N-dimethyl-benzamide;
4-(3-{4-[7-(3-Dimethylamino-phenyl)-4-morpholin-4-yl-quinazolin-2-yl]-phenyl}-ureido)-N,N-dimethyl-benzamide;
4-{3-[4-(7-Furan-2-yl-4-morpholin-4-yl-quinazolin-2-yl)-phenyl]-ureido}-N,N-dimethyl-benzamide;
N,N-Dimethyl-4-{3-[4-(4-morpholin-4-yl-7-thiophen-3-yl-quinazolin-2-yl)-phenyl]-ureido}-benzamide;
4-{3-[4-(7-Furan-3-yl-4-morpholin-4-yl-quinazolin-2-yl)-phenyl]-ureido}-N,N-dimethyl-benzamide;
4-(3-{5-[7-(2-Fluoro-pyridin-3-yl)-4-morpholin-4-yl-quinazolin-2-yl]-pyridin-2-yl}-ureido)-N,N-dimethyl-benzamide;
N,N-Dimethyl-4-(3-{5-[7-(1-methyl-1H-pyrazol-4-yl)-4-morpholin-4-yl-quinazolin-2-yl]-pyridin-2-yl}-ureido)-benzamide;
N-Methyl-4-(3-{4-[7-(5-methyl-furan-2-yl)-4-morpholin-4-yl-quinazolin-2-yl]-phenyl}-ureido)-benzamide;
N,N-Dimethyl-4-(3-{5-[7-(5-methyl-furan-2-yl)-4-morpholin-4-yl-quinazolin-2-yl]-pyridin-2-yl}-ureido)-benzamide;
N,N-Dimethyl-4-{3-[4-(4-morpholin-4-yl-7-pyridin-4-yl-quinazolin-2-yl)-phenyl]-ureido}-benzamide;
N,N-Dimethyl-4-{3-[4-(4-morpholin-4-yl-7-quinolin-3-yl-quinazolin-2-yl)-phenyl]-ureido}-benzamide;
4-(3-{4-[7-(6-Methoxy-pyridin-3-yl)-4-morpholin-4-yl-quinazolin-2-yl]-phenyl}-ureido)-N,N-dimethyl-benzamide;
N,N-Dimethyl-4-(3-{4-[7-(5-methyl-thiophen-2-yl)-4-morpholin-4-yl-quinazolin-2-yl]-phenyl}-ureido)-benzamide;
N,N-Dimethyl-4-(3-{4-[7-(4-methyl-pyridin-3-yl)-4-morpholin-4-yl-quinazolin-2-yl]-phenyl}-ureido)-benzamide;
N-(2-Dimethylamino-ethyl)-N-methyl-4-(3-{4-[7-(5-methyl-furan-2-yl)-4-morpholin-4-yl-quinazolin-2-yl]-phenyl}-ureido)-benzamide;
4-{3-[4-(7-Benzofuran-2-yl-4-morpholin-4-yl-quinazolin-2-yl)-phenyl]-ureido}-N,N-dimethyl-benzamide;
4-(3-{4-[7-(3-Fluoro-pyridin-4-yl)-4-morpholin-4-yl-quinazolin-2-yl]-phenyl}-ureido)-N,N-dimethyl-benzamide;
4-(3-{4-[7-(5-Acetylamino-pyridin-3-yl)-4-morpholin-4-yl-quinazolin-2-yl]-phenyl}-ureido)-N,N-dimethyl-benzamide;
1-[4-(4-Methyl-piperazine-1-carbonyl)-phenyl]-3-[4-(4-morpholin-4-yl-7-pyrimidin-5-yl-pyrido[3,2-d]pyrimidin-2-yl)-phenyl]-urea;
4-(3-{4-[7-(2-Fluoro-pyridin-4-yl)-4-morpholin-4-yl-quinazolin-2-yl]-phenyl}-ureido)-N,N-dimethyl-benzamide;
1-[4-(4-Methyl-piperazine-1-carbonyl)-phenyl]-3-[4-(4-morpholin-4-yl-7-pyridin-4-yl-quinazolin-2-yl)-phenyl]-urea;
1-{4-[7-(5-Methyl-furan-2-yl)-4-morpholin-4-yl-quinazolin-2-yl]-phenyl}-3-[4-(4-methyl-piperazine-1-carbonyl)-phenyl]-urea;
N,N-Dimethyl-4-(3-{4-[8-(5-methyl-furan-2-yl)-4-morpholin-4-yl-quinazolin-2-yl]-phenyl}-ureido)-benzamide;
N-(2-Dimethylamino-ethyl)-N-methyl-4-{3-[4-(4-morpholin-4-yl-7-pyridin-4-yl-quinazolin-2-yl)-phenyl]-ureido}-benzamide;
1-[4-(4-Methyl-piperazine-1-carbonyl)-phenyl]-3-{4-[7-(1-methyl-1H-pyrazol-4-yl)-4-morpholin-4-yl-pyrido[3,2-d]pyrimidin-2-yl]-phenyl}-urea;
N,N-Dimethyl-4-{3-[4-(4-morpholin-4-yl-7-thiophen-2-yl-quinazolin-2-yl)-phenyl]-ureido}-benzamide;

4-(3-{4-[7-(2-Methoxy-pyrimidin-5-yl)-4-morpholin-4-yl-quinazolin-2-yl]-phenyl}-ureido)-N,N-dimethyl-benzamide;

4-(3-{4-[7-(2-Amino-pyrimidin-5-yl)-4-morpholin-4-yl-quinazolin-2-yl]-phenyl}-ureido)-N,N-dimethyl-benzamide;

4-(3-(4-(7-(5-(2-(Dimethylamino)acetamido)pyridin-3-yl)-4-morpholino-quinazolin-2-yl)phenyl)ureido}-N,N-dimethyl-benzamide;

4-(3-{4-[7-(2-Fluoro-pyridin-3-yl)-4-morpholin-4-yl-pyrido[3,2-d]pyrimidin-2-yl]-phenyl}-ureido)-N,N-dimethyl-benzamide;

1-[4-(4-Methyl-piperazine-1-carbonyl)-phenyl]-3-[4-(4-morpholin-4-yl-7-pyrimidin-5-yl-quinazolin-2-yl)-phenyl]-urea;

N,N-Dimethyl-4-(3-{4-[7-(furan-2-yl)-4-morpholin-4-yl-quinazolin-2-yl]-phenyl}-ureido)-benzamide;

1-(4-(4-(dimethylamino)piperidine-1-carbonyl)phenyl)-3-(5-(7-(2-fluoropyridin-3-yl)-4-morpholino-quinazolin-2-yl)pyridin-2-yl)urea;

4-(3-(2-fluoro-4-(7-(1-methyl-1H-pyrazol-4-yl)-4-morpholino-pyrido[3,2-d]pyrimidin-2-yl)phenyl)ureido)-N,N-dimethyl-benzamide;

4-(3-(4-(7-(1-(2-(dimethylamino)ethyl)-1H-pyrazol-4-yl)-4-morpholino-quinazolin-2-yl)phenyl)ureido)-N,N-dimethyl-benzamide;

4-(3-(2-fluoro-4-(4-morpholino-7-(pyrimidin-5-yl)quinazolin-2-yl)phenyl)ureido)-N,N-dimethyl-benzamide;

N,N-dimethyl-4-(3-(5-(7-(1-methyl-1H-pyrazol-4-yl)-4-morpholino-pyrido[3,2-d]pyrimidin-2-yl)pyridin-2-yl)ureido)-benzamide;

N,N-dimethyl-4-(3-(4-(4-morpholino-7-(pyridazin-4-yl)quinazolin-2-yl)phenyl)ureido)-benzamide;

4-(3-(4-(6-fluoro-7-(5-methylfuran-2-yl)-4-morpholino-quinazolin-2-yl)phenyl)ureido)-N,N-dimethyl-benzamide;

N-methyl-4-(3-(4-(4-morpholino-7-(pyrimidin-5-yl)quinazolin-2-yl)phenyl)ureido)-benzamide;

N-methyl-4-(3-(4-(7-(1-methyl-1H-pyrazol-4-yl)-4-morpholino-pyrido[3,2-d]pyrimidin-2-yl)phenyl)ureido)-benzamide;

4-(3-(4-(7-(furan-2-yl)-4-morpholino-pyrido[3,2-d]pyrimidin-2-yl)phenyl)ureido)-N,N-dimethyl-benzamide;

4-(3-(2-fluoro-4-(7-(2-fluoropyridin-3-yl)-4-morpholino-quinazolin-2-yl)phenyl)ureido)-N,N-dimethyl-benzamide;

4-(3-(4-(7-(2-aminopyrimidin-5-yl)-4-morpholino-pyrido[3,2-d]pyrimidin-2-yl)phenyl)ureido)-N,N-dimethyl-benzamide;

N,N-dimethyl-4-(3-(4-(7-(4-methylpyridin-3-yl)-4-morpholino-pyrido[3,2-d]pyrimidin-2-yl)phenyl)ureido)-benzamide;

4-(3-(4-(7-(2-methoxypyrimidin-5-yl)-4-morpholino-pyrido[3,2-d]pyrimidin-2-yl)phenyl)ureido)-N,N-dimethyl-benzamide;

4-(3-(4-(7-(6-methoxypyridin-2-yl)-4-morpholino-quinazolin-2-yl)phenyl)ureido)-N,N-dimethyl-benzamide;

N,N-dimethyl-4-(3-(4-(4-morpholino-7-(pyridazin-4-yl)pyrido[3,2-d]pyrimidin-2-yl)phenyl)ureido)-benzamide;

4-(3-(2-fluoro-4-(7-(1-methyl-1H-pyrazol-4-yl)-4-morpholino-quinazolin-2-yl)phenyl)ureido)-N,N-dimethyl-benzamide;

4-(3-(2-fluoro-4-(4-morpholino-7-(pyridazin-4-yl)quinazolin-2-yl)phenyl)ureido)-N,N-dimethyl-benzamide;

4-(3-(2-fluoro-4-(6-fluoro-4-morpholino-7-(pyrimidin-5-yl)quinazolin-2-yl)phenyl)ureido)-N,N-dimethyl-benzamide;

4-(3-(2-fluoro-4-(7-(4-methylpyridin-3-yl)-4-morpholino-quinazolin-2-yl)phenyl)ureido)-N,N-dimethyl-benzamide;

4-(3-(2-fluoro-4-(4-morpholino-7-(pyrimidin-5-yl)pyrido[3,2-d]pyrimidin-2-yl)phenyl)ureido)-N,N-dimethyl-benzamide;

4-(3-(2-fluoro-4-(4-morpholino-7-(pyridin-3-yl)pyrido[3,2-d]pyrimidin-2-yl)phenyl)ureido)-N,N-dimethyl-benzamide;

4-(3-(2-fluoro-4-(4-morpholino-7-(pyridin-3-yl)quinazolin-2-yl)phenyl)ureido)-N,N-dimethyl-benzamide;

4-(3-(2-fluoro-4-(7-(3-(methylsulfonyl)phenyl)-4-morpholino-pyrido[3,2-d]pyrimidin-2-yl)phenyl)ureido)-N,N-dimethyl-benzamide;

4-(3-(2-fluoro-4-(7-(2-methoxypyrimidin-5-yl)-4-morpholino-quinazolin-2-yl)phenyl)ureido)-N,N-dimethyl-benzamide;

4-(3-(2-fluoro-4-(7-(2-fluoropyridin-3-yl)-4-morpholino-pyrido[3,2-d]pyrimidin-2-yl)phenyl)ureido)-N,N-dimethyl-benzamide;

4-(3-(4-(6-fluoro-7-(2-fluoropyridin-3-yl)-4-morpholino-quinazolin-2-yl)phenyl)ureido)-N,N-dimethyl-benzamide;

4-(3-(2-fluoro-4-(6-fluoro-7-(1-methyl-1H-pyrazol-4-yl)-4-morpholino-quinazolin-2-yl)phenyl)ureido dimethyl-benzamide)-N,N-dimethyl-benzamide;

4-(3-(2-fluoro-4-(6-fluoro-4-morpholino-7-(pyridin-3-yl)quinazolin-2-yl)phenyl)ureido)-N,N-dimethyl-benzamide;

4-(3-(4-(7-(2-aminopyrimidin-5-yl)-4-morpholino-quinazolin-2-yl)-2-fluorophenyl)ureido)-N,N-dimethyl-benzamide;

4-(3-(5-(7-(2-fluoropyridin-3-yl)-4-morpholino-pyrido[3,2-d]pyrimidin-2-yl)pyridin-2-yl)ureido)-N,N-dimethyl-benzamide;

4-(3-(5-(6-fluoro-7-(2-fluoropyridin-3-yl)-4-morpholino-quinazolin-2-yl)pyridin-2-yl)ureido)-N,N-dimethyl-benzamide;

4-(3-(5-(6-fluoro-7-(1-methyl-1H-pyrazol-4-yl)-4-morpholino-quinazolin-2-yl)pyridin-2-yl)ureido)-N,N-dimethyl-benzamide;

4-(3-(2-fluoro-4-(7-(furan-2-yl)-4-morpholino-quinazolin-2-yl)phenyl)ureido)-N,N-dimethyl-benzamide;

N,N-dimethyl-4-(3-(5-(7-(3-(methylsulfonyl)phenyl)-4-morpholino-pyrido[3,2-d]pyrimidin-2-yl)pyridin-2-yl)ureido)-benzamide;

4-(3-(2-fluoro-4-(7-(4-methylpyridin-3-yl)-4-morpholino-pyrido[3,2-d]pyrimidin-2-yl)phenyl)ureido)-N,N-dimethyl-benzamide;

4-(3-(2-fluoro-4-(7-(2-methoxypyrimidin-5-yl)-4-morpholino-pyrido[3,2-d]pyrimidin-2-yl)phenyl)ureido)-N,N-dimethyl-benzamide;

4-(3-(2-fluoro-4-(7-(3-(methylsulfonyl)phenyl)-4-morpholino-quinazolin-2-yl)phenyl)ureido)-N,N-dimethyl-benzamide;

4-(3-(5-(7-(2-methoxypyrimidin-5-yl)-4-morpholino-quinazolin-2-yl)pyridin-2-yl)ureido)-N,N-dimethyl-benzamide;

4-(3-(4-(7-(3,5-dimethylisoxazol-4-yl)-4-morpholino-pyrido[3,2-d]pyrimidin-2-yl)phenyl)ureido)-N,N-dimethyl-benzamide;

4-(3-(4-(7-(3,5-dimethylisoxazol-4-yl)-4-morpholino-quinazolin-2-yl)phenyl)ureido)-N,N-dimethyl-benzamide;
5-(3-(2-fluoro-4-(7-(5-methylfuran-2-yl)-4-morpholino-quinazolin-2-yl)phenyl)ureido)-N,N-dimethylpicolinamide;
5-(3-(2-fluoro-4-(4-morpholino-7-(pyrimidin-5-yl)quinazolin-2-yl)phenyl)ureido)-N,N-dimethylpicolinamide;
5-(3-(2-fluoro-4-(7-(1-methyl-1H-pyrazol-4-yl)-4-morpholino-pyrido[3,2-d]pyrimidin-2-yl)phenyl)ureido)-N,N-dimethylpicolinamide;
4-(3-(4-(4-(2,6-dimethylmorpholino)-7-(1-methyl-1H-pyrazol-4-yl)pyrido[3,2-d]pyrimidin-2-yl)phenyl)ureido)-N,N-dimethyl-benzamide;
4-(3-(4-(4-(2,6-dimethylmorpholino)-7-(1-methyl-1H-pyrazol-4-yl)pyrido[3,2-d]pyrimidin-2-yl)-2-fluorophenyl)ureido)-N,N-dimethyl-benzamide;
4-(3-(4-(7-(2-aminopyrimidin-5-yl)-4-morpholinopyrido[3,2-d]pyrimidin-2-yl)-2-fluorophenyl)ureido)-N,N-dimethyl-benzamide;
4-(3-(4-(4-(2,6-dimethylmorpholino)-7-(pyrimidin-5-yl)quinazolin-2-yl)phenyl)ureido)-N,N-dimethyl-benzamide;
N,N-dimethyl-5-(3-(5-(7-(5-methylfuran-2-yl)-4-morpholino-quinazolin-2-yl)pyridin-2-yl)ureido)picolinamide;
5-(3-(2-fluoro-4-(7-(3-(methylsulfonyl)phenyl)-4-morpholino-quinazolin-2-yl)phenyl)ureido)-N,N-dimethylpicolinamide;
4-(3-(4-(7-(3,5-dimethylisoxazol-4-yl)-4-morpholino-quinazolin-2-yl)-2-fluorophenyl)ureido)-N,N-dimethyl-benzamide;
4-(3-(4-(4-(2,6-dimethylmorpholino)-7-(pyrimidin-5-yl)quinazolin-2-yl)-2-fluorophenyl)ureido)-N,N-dimethyl-benzamide;
3-fluoro-N,N-dimethyl-4-(3-(4-(4-morpholino-7-(pyrimidin-5-yl)quinazolin-2-yl)phenyl)ureido)-benzamide;
3-fluoro-N,N-dimethyl-4-(3-(4-(7-(1-methyl-1H-pyrazol-4-yl)-4-morpholino-pyrido[3,2-d]pyrimidin-2-yl)phenyl)ureido)-benzamide;
4-(3-(4-(7-(3,5-dimethylisoxazol-4-yl)-4-morpholino-pyrido[3,2-d]pyrimidin-2-yl)-2-fluorophenyl)ureido)-N,N-dimethyl-benzamide;
3-fluoro-N,N-dimethyl-4-(3-(4-(7-(5-methylfuran-2-yl)-4-morpholino-quinazolin-2-yl)phenyl)ureido)-benzamide;
4-(3-(2-fluoro-4-(4-morpholino-7-(pyridin-4-yl)quinazolin-2-yl)phenyl)ureido)-N,N-dimethyl-benzamide;
N,N-dimethyl-4-(3-(4-(4-(2-methylmorpholino)-7-(pyrimidin-5-yl)quinazolin-2-yl)phenyl)ureido)-benzamide;
3-fluoro-4-(3-(2-fluoro-4-(4-morpholino-7-(pyrimidin-5-yl)quinazolin-2-yl)phenyl)ureido)-N,N-dimethyl-benzamide;
3-fluoro-N,N-dimethyl-4-(3-(5-(4-morpholino-7-(pyrimidin-5-yl)pyridin-2-yl)ureido)-benzamide;
3-fluoro-4-(3-(2-fluoro-4-(7-(1-methyl-1H-pyrazol-4-yl)-4-morpholino-pyrido[3,2-d]pyrimidin-2-yl)phenyl)ureido)-N,N-dimethyl-benzamide;
N,N-dimethyl-4-(3-(4-(7-(5-methylfuran-2-yl)-4-(2-methylmorpholino)quinazolin-2-yl)phenyl)ureido)-benzamide;
4-(3-(4-(7-(3,5-dimethylisoxazol-4-yl)-6-fluoro-4-morpholino-quinazolin-2-yl)phenyl)ureido)-N,N-dimethyl-benzamide;
4-(3-(2-fluoro-4-(4-(2-methylmorpholino)-7-(pyrimidin-5-yl)quinazolin-2-yl)phenyl)ureido)-N,N-dimethyl-benzamide;
3-fluoro-4-(3-(4-(7-(2-fluoropyridin-3-yl)-4-morpholino-pyrido[3,2-d]pyrimidin-2-yl)phenyl)ureido)-N,N-dimethyl-benzamide;
3-fluoro-4-(3-(4-(7-(2-fluoropyridin-3-yl)-4-morpholino-quinazolin-2-yl)phenyl)ureido)-N,N-dimethyl-benzamide;
3-fluoro-4-(3-(4-(7-(2-methoxypyrimidin-5-yl)-4-morpholino-quinazolin-2-yl)phenyl)ureido)-N,N-dimethyl-benzamide;
N,N-dimethyl-4-(3-(4-(7-(1-methyl-1H-pyrazol-4-yl)-4-(2-methylmorpholino)pyrido[3,2-d]pyrimidin-2-yl)phenyl)ureido)-benzamide;
4-(3-(4-(6-fluoro-7-(furan-2-yl)-4-morpholino-quinazolin-2-yl)phenyl)ureido)-N,N-dimethyl-benzamide;
4-(3-(4-(7-(2-hydroxypyrimidin-5-yl)-4-morpholino-quinazolin-2-yl)phenyl)ureido)-N,N-dimethyl-benzamide;
4-(3-(2-fluoro-4-(7-(6-methoxypyridin-3-yl)-4-morpholino-quinazolin-2-yl)phenyl)ureido)-N,N-dimethyl-benzamide;
3-fluoro-N,N-dimethyl-4-(3-(4-(4-morpholino-7-(pyridin-3-yl)quinazolin-2-yl)phenyl)ureido)-benzamide;
3-fluoro-N,N-dimethyl-4-(3-(4-(4-morpholino-7-(pyridin-3-yl)pyrido[3,2-d]pyrimidin-2-yl)phenyl)ureido)-benzamide;
3-fluoro-N,N-dimethyl-4-(3-(4-(4-morpholino-7-(pyrimidin-5-yl)pyrido[3,2-d]pyrimidin-2-yl)phenyl)ureido)-benzamide;
N,N-dimethyl-4-(3-(4-(4-morpholino-7-(pyridin-2-yl)quinazolin-2-yl)phenyl)ureido)-benzamide;
4-(3-(2-fluoro-4-(4-morpholino-7-(pyridin-2-yl)quinazolin-2-yl)phenyl)ureido)-N,N-dimethyl-benzamide;
3-fluoro-4-(3-(4-(7-(2-methoxypyrimidin-5-yl)-4-morpholino-pyrido[3,2-d]pyrimidin-2-yl)phenyl)ureido)-N,N-dimethyl-benzamide;
1-(4-(7-(furan-2-yl)-4-morpholino-quinazolin-2-yl)phenyl)-3-(4-(4-methylpiperazine-1-carbonyl)phenyl)urea;
4-(3-(5-(7-(furan-2-yl)-4-morpholino-quinazolin-2-yl)pyridin-2-yl)ureido)-N,N-dimethyl-benzamide;
3-fluoro-4-(3-(4-(7-(furan-2-yl)-4-morpholino-quinazolin-2-yl)phenyl)ureido)-N,N-dimethyl-benzamide;
N,N-dimethyl-4-(3-(4-(7-(6-methylpyridin-3-yl)-4-morpholino-quinazolin-2-yl)phenyl)ureido)-benzamide;
N,N-dimethyl-4-(3-(4-(4-morpholino-7-(1,3,5-trimethyl-1H-pyrazol-4-yl)quinazolin-2-yl)phenyl)ureido)-benzamide;
4-(3-(4-(7-(2-methoxypyridin-3-yl)-4-morpholino-quinazolin-2-yl)phenyl)ureido)-N,N-dimethyl-benzamide;
4-(3-(4-(7-(5-fluoropyridin-3-yl)-4-morpholino-quinazolin-2-yl)phenyl)ureido)-N,N-dimethyl-benzamide;
N,N-dimethyl-4-(3-(4-(7-(2-methylpyridin-3-yl)-4-morpholino-quinazolin-2-yl)phenyl)ureido)-benzamide;
3-fluoro-N,N-dimethyl-4-(3-(4-(7-(6-methylpyridin-3-yl)-4-morpholino-quinazolin-2-yl)phenyl)ureido)-benzamide;
3-fluoro-N,N-dimethyl-4-(3-(4-(7-(2-methylpyridin-3-yl)-4-morpholino-quinazolin-2-yl)phenyl)ureido)-benzamide;
3-fluoro-N,N-dimethyl-4-(3-(4-(4-morpholino-7-(pyridin-2-yl)quinazolin-2-yl)phenyl)ureido)-benzamide;

4-(3-(4-(7-(4-methoxypyridin-3-yl)-4-morpholino-quinazolin-2-yl)phenyl)ureido)-N,N-dimethyl-benzamide;

3-fluoro-4-(3-(4-(7-(6-methoxypyridin-3-yl)-4-morpholino-quinazolin-2-yl)phenyl)ureido)-N,N-dimethyl-benzamide;

3-chloro-4-(3-(4-(7-(furan-2-yl)-4-morpholino-quinazolin-2-yl)phenyl)ureido)-N,N-dimethyl-benzamide;

3-fluoro-N,N-dimethyl-4-(3-(5-(7-(1-methyl-1H-pyrazol-4-yl)-4-morpholino-quinazolin-2-yl)pyridin-2-yl)ureido)-benzamide;

3-fluoro-4-(3-(4-(6-fluoro-4-morpholino-7-(pyridin-3-yl)quinazolin-2-yl)phenyl)ureido)-N,N-dimethyl-benzamide;

3-fluoro-4-(3-(4-(6-fluoro-4-morpholino-7-(pyrimidin-5-yl)quinazolin-2-yl)phenyl)ureido)-N,N-dimethyl-benzamide;

4-(3-(5-(6-fluoro-4-morpholino-7-(pyridin-3-yl)quinazolin-2-yl)pyridin-2-yl)ureido)-N,N-dimethyl-benzamide;

4-(3-(5-(6-fluoro-4-morpholino-7-(pyrimidin-5-yl)quinazolin-2-yl)pyridin-2-yl)ureido)-N,N-dimethyl-benzamide;

4-(3-(4-(7-(6-aminopyridin-3-yl)-4-morpholino-quinazolin-2-yl)phenyl)ureido)-N,N-dimethyl-benzamide;

4-(3-(4-(7-(6-aminopyridin-3-yl)-4-morpholino-quinazolin-2-yl)phenyl)ureido)-3-fluoro-N,N-dimethyl-benzamide;

N,N-dimethyl-4-(3-(4-(4-morpholino-quinazolin-2-yl)phenyl)ureido)-benzamide 4-(3-(4-(7-methoxy-4-morpholino-quinazolin-2-yl)phenyl)ureido)-N,N-dimethyl-benzamide;

4-(3-(4-(6,7-dimethoxy-4-morpholino-quinazolin-2-yl)phenyl)ureido)-N,N-dimethyl-benzamide;

4-(3-(2-fluoro-4-(7-methoxy-4-morpholino-quinazolin-2-yl)phenyl)ureido)-N,N-dimethyl-benzamide;

4-(3-(4-(7-(5-(hydroxymethyl)furan-2-yl)-4-morpholino-quinazolin-2-yl)phenyl)ureido)-N,N-dimethyl-benzamide;

(R)-1-(4-(3-(dimethylamino)pyrrolidine-1-carbonyl)phenyl)-3-(4-(7-(1-methyl-1H-pyrazol-4-yl)-4-morpholino-pyrido[3,2-d]pyrimidin-2-yl)phenyl)urea;

(S)-1-(4-(3-(dimethylamino)pyrrolidine-1-carbonyl)phenyl)-3-(4-(7-(1-methyl-1H-pyrazol-4-yl)-4-morpholino-pyrido[3,2-d]pyrimidin-2-yl)phenyl)urea;

1-(4-(4-(dimethylamino)piperidine-1-carbonyl)phenyl)-3-(4-(7-(1-methyl-1H-pyrazol-4-yl)-4-morpholino-pyrido[3,2-d]pyrimidin-2-yl)phenyl)urea;

(R)-1-(4-(3-(dimethylamino)pyrrolidine-1-carbonyl)phenyl)-3-(4-(4-morpholino-7-(pyrimidin-5-yl)quinazolin-2-yl)phenyl)urea;

(S)-1-(4-(3-(dimethylamino)pyrrolidine-1-carbonyl)phenyl)-3-(4-(4-morpholino-7-(pyrimidin-5-yl)quinazolin-2-yl)phenyl)urea;

1-(4-(3-hydroxypyrrolidine-1-carbonyl)phenyl)-3-(4-(4-morpholino-7-(pyrimidin-5-yl)quinazolin-2-yl)phenyl)urea;

4-(3-(4-(7-(5-(((dimethylamino)methyl)furan-2-yl)-4-morpholino-quinazolin-2-yl)phenyl)ureido)-N,N-dimethyl-benzamide;

1-(4-(4-(dimethylamino)piperidine-1-carbonyl)phenyl)-3-(4-(7-(5-methylfuran-2-yl)-4-morpholino-quinazolin-2-yl)phenyl)urea;

N-(2-(dimethylamino)ethyl)-4-(3-(4-(4-morpholino-7-(pyrimidin-5-yl)quinazolin-2-yl)phenyl)ureido)-benzamide;

1-(4-(4-(dimethylamino)piperidine-1-carbonyl)phenyl)-3-(4-(7-(4-methylpyridin-3-yl)-4-morpholino-quinazolin-2-yl)phenyl)urea;

(S)-1-(4-(3-aminopyrrolidine-1-carbonyl)phenyl)-3-(4-(4-morpholino-7-(pyrimidin-5-yl)quinazolin-2-yl)phenyl)urea;

(S)-1-(4-(3-(dimethylamino)pyrrolidine-1-carbonyl)phenyl)-3-(4-(7-(5-methylfuran-2-yl)-4-morpholino-quinazolin-2-yl)phenyl)urea;

(R)-1-(4-(3-(dimethylamino)pyrrolidine-1-carbonyl)phenyl)-3-(4-(7-(5-methylfuran-2-yl)-4-morpholino-quinazolin-2-yl)phenyl)urea;

(R)-1-(4-(3-aminopyrrolidine-1-carbonyl)phenyl)-3-(4-(4-morpholino-7-(pyrimidin-5-yl)quinazolin-2-yl)phenyl)urea;

(S)-1-(4-(3-(dimethylamino)pyrrolidine-1-carbonyl)phenyl)-3-(4-(6-fluoro-4-morpholino-7-(pyridin-3-yl)quinazolin-2-yl)phenyl)urea;

(S)-1-(4-(3-(dimethylamino)pyrrolidine-1-carbonyl)phenyl)-3-(4-(4-morpholino-7-(pyrimidin-5-yl)pyrido[3,2-d]pyrimidin-2-yl)phenyl)urea;

(R)-1-(4-(3-(dimethylamino)pyrrolidine-1-carbonyl)phenyl)-3-(4-(6-fluoro-4-morpholino-7-(pyridin-3-yl)quinazolin-2-yl)phenyl)urea;

N-(2-(dimethylamino)ethyl)-4-(3-(4-(7-(5-methylfuran-2-yl)-4-morpholino-quinazolin-2-yl)phenyl)ureido)-benzamide;

4-(3-(4-(7-(1-methyl-1H-pyrazol-4-yl)-4-morpholino-pyrido[3,2-d]pyrimidin-2-yl)phenyl)ureido)-benzamide;

4-(3-(2-fluoro-4-(7-(5-(hydroxymethyl)furan-2-yl)-4-morpholino-quinazolin-2-yl)phenyl)ureido)-N,N-dimethyl-benzamide;

1-(4-(3-hydroxypyrrolidine-1-carbonyl)phenyl)-3-(4-(7-(5-methylfuran-2-yl)-4-morpholino-quinazolin-2-yl)phenyl)urea;

(R)-1-(4-(3-(dimethylamino)pyrrolidine-1-carbonyl)phenyl)-3-(2-fluoro-4-(7-(1-methyl-1H-pyrazol-4-yl)-4-morpholino-pyrido[3,2-d]pyrimidin-2-yl)phenyl)urea;

4-(3-(4-(7-(5-(1-hydroxyethyl)furan-2-yl)-4-morpholino-quinazolin-2-yl)phenyl)ureido)-N,N-dimethyl-benzamide;

(S)-1-(4-(3-(dimethylamino)pyrrolidine-1-carbonyl)phenyl)-3-(2-fluoro-4-(4-morpholino-7-(pyrimidin-5-yl)quinazolin-2-yl)phenyl)urea;

(S)-1-(4-(3-aminopyrrolidine-1-carbonyl)phenyl)-3-(2-fluoro-4-(4-morpholino-7-(pyrimidin-5-yl)quinazolin-2-yl)phenyl)urea;

(R)-1-(4-(3-aminopyrrolidine-1-carbonyl)phenyl)-3-(2-fluoro-4-(4-morpholino-7-(pyrimidin-5-yl)quinazolin-2-yl)phenyl)urea;

(S)-1-(4-(3-(dimethylamino)pyrrolidine-1-carbonyl)phenyl)-3-(2-fluoro-4-(7-(1-methyl-1H-pyrazol-4-yl)-4-morpholino-pyrido[3,2-d]pyrimidin-2-yl)phenyl)urea;

1-(2-fluoro-4-(6-fluoro-4-morpholino-7-(pyridin-3-yl)quinazolin-2-yl)phenyl)-3-(4-(4-methylpiperazine-1-carbonyl)phenyl)urea;

1-(2-fluoro-4-(4-morpholino-7-(pyridin-4-yl)quinazolin-2-yl)phenyl)-3-(4-(4-methylpiperazine-1-carbonyl)phenyl)urea;

(S)-1-(4-(3-(dimethylamino)pyrrolidine-1-carbonyl)phenyl)-3-(2-fluoro-4-(7-(2-fluoropyridin-3-yl)-4-morpholino-pyrido[3,2-d]pyrimidin-2-yl)phenyl)urea;

4-(3-(2-fluoro-4-(7-(5-(1-hydroxyethyl)furan-2-yl)-4-morpholino-quinazolin-2-yl)phenyl)ureido)-N,N-dimethyl-benzamide;

4-(3-(2-fluoro-4-(4-morpholino-7-(pyrimidin-5-yl)quinazolin-2-yl)phenyl)ureido)-N-methyl-benzamide;

4-(3-(4-(7-(5-(1-hydroxyethyl)furan-2-yl)-4-morpholino-pyrido[3,2-d]pyrimidin-2-yl)phenyl)ureido)-N,N-dimethyl-benzamide;

N-(2-(dimethylamino)ethyl)-4-(3-(2-fluoro-4-(4-morpholino-7-(pyrimidin-5-yl)quinazolin-2-yl)phenyl)ureido)-benzamide;

4-(3-(2-fluoro-4-(7-(5-(hydroxymethyl)furan-2-yl)-4-morpholino-pyrido[3,2-d]pyrimidin-2-yl)phenyl)ureido)-N,N-dimethyl-benzamide;

3-fluoro-4-(3-(4-(7-(5-(hydroxymethyl)furan-2-yl)-4-morpholino-quinazolin-2-yl)phenyl)ureido)-N,N-dimethyl-benzamide;

(S)-1-(4-(3-(dimethylamino)pyrrolidine-1-carbonyl)phenyl)-3-(4-(7-(3,5-dimethylisoxazol-4-yl)-4-morpholino-quinazolin-2-yl)phenyl)urea;

(S)-1-(4-(3-(dimethylamino)pyrrolidine-1-carbonyl)phenyl)-3-(4-(7-(3,5-dimethylisoxazol-4-yl)-4-morpholino-quinazolin-2-yl)-2-fluorophenyl)urea;

4-(3-(4-(7-(5-(2-hydroxypropan-2-yl)furan-2-yl)-4-morpholino-quinazolin-2-yl)phenyl)ureido)-N,N-dimethyl-benzamide;

4-(3-(4-(7-(5-cyanofuran-2-yl)-4-morpholino-quinazolin-2-yl)phenyl)ureido)-N,N-dimethyl-benzamide;

4-(3-(4-(7-(5-acetylfuran-2-yl)-4-morpholino-quinazolin-2-yl)phenyl)ureido)-N,N-dimethyl-benzamide;

N-(2-(dimethylamino)ethyl)-5-(2-(4-(3-(4-(dimethylcarbamoyl)phenyl)ureido)phenyl)-4-morpholino-quinazolin-7-yl)furan-2-carboxamide;

4-(3-(4-(7-(2-(dimethylamino)pyrimidin-5-yl)-4-morpholino-quinazolin-2-yl)phenyl)ureido)-N,N-dimethyl-benzamide;

3-fluoro-4-(3-(4-(7-(5-(1-hydroxyethyl)furan-2-yl)-4-morpholino-quinazolin-2-yl)phenyl)ureido)-N,N-dimethyl-benzamide;

3-fluoro-4-(3-(4-(7-(5-(hydroxymethyl)furan-2-yl)-4-morpholino-quinazolin-2-yl)phenyl)ureido)-N,N-dimethyl-benzamide;

5-(2-(4-(3-(4-(dimethylcarbamoyl)phenyl)ureido)phenyl)-4-morpholino-quinazolin-7-yl)-N,N-dimethylfuran-2-carboxamide;

4-(3-(4-(7-(2-(dimethylamino)pyrimidin-5-yl)-4-morpholino-pyrido[3,2-d]pyrimidin-2-yl)phenyl)ureido)-N,N-dimethyl-benzamide;

4-(3-(4-(7-(2-(dimethylamino)pyrimidin-5-yl)-4-morpholino-quinazolin-2-yl)-2-fluorophenyl)ureido)-N,N-dimethyl-benzamide;

1-(4-(7-(furan-2-yl)-4-morpholino-quinazolin-2-yl)phenyl)-3-(4-(3-hydroxypyrrolidine-1-carbonyl)phenyl)urea;

4-(3-(4-(7-(furan-2-yl)-4-morpholino-quinazolin-2-yl)phenyl)ureido)-N-methyl-benzamide;

(S)-1-(4-(3-aminopyrrolidine-1-carbonyl)phenyl)-3-(4-(7-(furan-2-yl)-4-morpholino-quinazolin-2-yl)phenyl)urea;

N-(2-(dimethylamino)ethyl)-4-(3-(4-(7-(furan-2-yl)-4-morpholino-quinazolin-2-yl)phenyl)ureido)-benzamide;

N-(2-(dimethylamino)ethyl)-4-(3-(4-(7-(furan-2-yl)-4-morpholino-quinazolin-2-yl)phenyl)ureido)-N-methyl-benzamide;

4-(3-(3-fluoro-4-(4-morpholino-7-(pyrimidin-5-yl)quinazolin-2-yl)phenyl)ureido)-N,N-dimethyl-benzamide;

4-(3-(3-fluoro-4-(7-(1-methyl-1H-pyrazol-4-yl)-4-morpholino-pyrido[3,2-d]pyrimidin-2-yl)phenyl)ureido)-N,N-dimethyl-benzamide;

4-(3-(3-fluoro-4-(7-(5-methylfuran-2-yl)-4-morpholino-quinazolin-2-yl)phenyl)ureido)-N,N-dimethyl-benzamide;

2-fluoro-N,N-dimethyl-4-(3-(4-(4-morpholino-7-(pyrimidin-5-yl)quinazolin-2-yl)phenyl)ureido)-benzamide;

4-(3-(3-fluoro-4-(7-(2-fluoropyridin-3-yl)-4-morpholino-quinazolin-2-yl)phenyl)ureido)-N,N-dimethyl-benzamide;

4-(3-(3-fluoro-4-(7-(2-methoxypyrimidin-5-yl)-4-morpholino-quinazolin-2-yl)phenyl)ureido)-N,N-dimethyl-benzamide;

4-(3-(3-fluoro-4-(4-morpholino-7-(pyridin-3-yl)quinazolin-2-yl)phenyl)ureido)-N,N-dimethyl-benzamide;

4-(3-(3-fluoro-4-(7-(2-fluoropyridin-3-yl)-4-morpholino-pyrido[3,2-d]pyrimidin-2-yl)phenyl)ureido)-N,N-dimethyl-benzamide;

4-(3-(3-fluoro-4-(7-(3-(methylsulfonyl)phenyl)-4-morpholino-quinazolin-2-yl)phenyl)ureido)-N,N-dimethyl-benzamide;

4-(3-(4-(7-(3,5-dimethylisoxazol-4-yl)-4-morpholino-quinazolin-2-yl)phenyl)ureido)-2-fluoro-N,N-dimethyl-benzamide;

4-(3-(3-fluoro-4-(7-(furan-2-yl)-4-morpholino-quinazolin-2-yl)phenyl)ureido)-N,N-dimethyl-benzamide;

2-fluoro-4-(3-(4-(7-(2-fluoropyridin-3-yl)-4-morpholino-pyrido[3,2-d]pyrimidin-2-yl)phenyl)ureido)-N,N-dimethyl-benzamide;

4-(3-(3-fluoro-4-(7-(1-methyl-1H-pyrazol-4-yl)-4-morpholino-quinazolin-2-yl)phenyl)ureido)-N,N-dimethyl-benzamide;

4-(3-(3-fluoro-4-(4-morpholino-7-(pyrimidin-5-yl)pyrido[3,2-d]pyrimidin-2-yl)phenyl)ureido)-N,N-dimethyl-benzamide;

5-(3-(3-fluoro-4-(4-morpholino-7-(pyrimidin-5-yl)quinazolin-2-yl)phenyl)ureido)-N,N-dimethylpicolinamide;

4-(3-(4-(7-(3,5-dimethylisoxazol-4-yl)-4-morpholino-quinazolin-2-yl)-3-fluorophenyl)ureido)-N,N-dimethyl-benzamide;

2-fluoro-N,N-dimethyl-4-(3-(5-(7-(3-(methylsulfonyl)phenyl)-4-morpholino-quinazolin-2-yl)pyridin-2-yl)ureido)-benzamide;

4-(3-(3-fluoro-4-(4-(2-methylmorpholino)-7-(pyrimidin-5-yl)quinazolin-2-yl)phenyl)ureido)-N,N-dimethyl-benzamide;

2-fluoro-4-(3-(4-(7-(2-fluoropyridin-3-yl)-4-morpholino-quinazolin-2-yl)phenyl)ureido)-N,N-dimethyl-benzamide;

4-(3-(3-fluoro-4-(6-fluoro-4-morpholino-7-(pyrimidin-5-yl)quinazolin-2-yl)phenyl)ureido)-N,N-dimethyl-benzamide;

2-fluoro-4-(3-(4-(7-(2-methoxypyrimidin-5-yl)-4-morpholino-quinazolin-2-yl)phenyl)ureido)-N,N-dimethyl-benzamide;

4-(3-(3-fluoro-4-(7-(6-methoxypyridin-3-yl)-4-morpholino-quinazolin-2-yl)phenyl)ureido)-N,N-dimethyl-benzamide;

2-fluoro-4-(3-(4-(7-(6-methoxypyridin-3-yl)-4-morpholino-quinazolin-2-yl)phenyl)ureido)-N,N-dimethyl-benzamide;

2-fluoro-N,N-dimethyl-4-(3-(4-(4-morpholino-7-(pyridin-3-yl)quinazolin-2-yl)phenyl)ureido)-benzamide;

4-(3-(3-fluoro-4-(4-morpholino-7-(pyridin-3-yl)pyrido[3,2-d]pyrimidin-2-yl)phenyl)ureido)-N,N-dimethyl-benzamide;

2-fluoro-N,N-dimethyl-4-(3-(4-(4-morpholino-7-(pyrimidin-5-yl)pyrido[3,2-d]pyrimidin-2-yl)phenyl)ureido)-benzamide;

4-(3-(3-fluoro-4-(7-(2-methoxypyrimidin-5-yl)-4-morpholino-pyrido[3,2-d]pyrimidin-2-yl)phenyl)ureido)-N,N-dimethyl-benzamide;

2-fluoro-N,N-dimethyl-4-(3-(4-(4-morpholino-7-(pyridin-3-yl)pyrido[3,2-d]pyrimidin-2-yl)phenyl)ureido)-benzamide;

2-fluoro-4-(3-(4-(7-(furan-2-yl)-4-morpholino-quinazolin-2-yl)phenyl)ureido)-N,N-dimethyl-benzamide;

2-fluoro-N,N-dimethyl-4-(3-(4-(7-(5-methylfuran-2-yl)-4-morpholino-quinazolin-2-yl)phenyl)ureido)-benzamide;

2-fluoro-N,N-dimethyl-4-(3-(4-(4-morpholino-7-(pyridin-2-yl)quinazolin-2-yl)phenyl)ureido)-benzamide;

4-(3-(3-fluoro-4-(4-morpholino-7-(pyridin-2-yl)quinazolin-2-yl)phenyl)ureido)-N,N-dimethyl-benzamide;

4-(3-(3-fluoro-4-(4-morpholino-7-(1,3,5-trimethyl-1H-pyrazol-4-yl)quinazolin-2-yl)phenyl)ureido)-N,N-dimethyl-benzamide;

4-(3-(3-fluoro-4-(7-(2-methoxypyridin-3-yl)-4-morpholino-quinazolin-2-yl)phenyl)ureido)-N,N-dimethyl-benzamide;

4-(3-(3-fluoro-4-(7-(6-methylpyridin-3-yl)-4-morpholino-quinazolin-2-yl)phenyl)ureido)-N,N-dimethyl-benzamide;

4-(3-(3-fluoro-4-(7-(2-methylpyridin-3-yl)-4-morpholino-quinazolin-2-yl)phenyl)ureido)-N,N-dimethyl-benzamide;

2-fluoro-N,N-dimethyl-4-(3-(4-(7-(1-methyl-1H-pyrazol-4-yl)-4-morpholino-pyrido[3,2-d]pyrimidin-2-yl)phenyl)ureido)-benzamide;

4-(3-(3-fluoro-4-(7-(5-(hydroxymethyl)furan-2-yl)-4-morpholino-quinazolin-2-yl)phenyl)ureido)-N,N-dimethyl-benzamide;

4-(3-(3-fluoro-4-(7-(5-(1-hydroxyethyl)furan-2-yl)-4-morpholino-quinazolin-2-yl)phenyl)ureido)-N,N-dimethyl-benzamide;

4-(3-(3-fluoro-4-(7-(5-(2-hydroxypropan-2-yl)furan-2-yl)-4-morpholino-quinazolin-2-yl)phenyl)ureido)-N,N-dimethyl-benzamide;

4-(3-(4-(7-(2-(dimethylamino)pyrimidin-5-yl)-4-morpholino-quinazolin-2-yl)-3-fluorophenyl)ureido)-N,N-dimethyl-benzamide;

2-fluoro-4-(3-(4-(7-(5-(hydroxymethyl)furan-2-yl)-4-morpholino-quinazolin-2-yl)phenyl)ureido)-N,N-dimethyl-benzamide;

4-(3-(2,5-difluoro-4-(4-morpholino-7-(pyrimidin-5-yl)quinazolin-2-yl)phenyl)ureido)-N,N-dimethyl-benzamide;

4-(3-(2,3-difluoro-4-(4-morpholino-7-(pyrimidin-5-yl)quinazolin-2-yl)phenyl)ureido)-N,N-dimethyl-benzamide;

4-(3-(2,3-difluoro-4-(7-(5-methylfuran-2-yl)-4-morpholino-quinazolin-2-yl)phenyl)ureido)-N,N-dimethyl-benzamide;

-(3-(2,3-difluoro-4-(7-(furan-2-yl)-4-morpholino-quinazolin-2-yl)phenyl)ureido)-N,N-dimethyl-benzamide;

4-(3-(4-(7-(2-((2-hydroxyethyl)amino)pyridin-3-yl)-4-morpholino-quinazolin-2-yl)phenyl)ureido)-N,N-dimethyl-benzamide;

4-(3-(4-(7-((4-hydroxypiperidin-1-yl)methyl)-4-morpholino-quinazolin-2-yl)phenyl)ureido)-N,N-dimethyl-benzamide;

4-(3-(4-(7-(hydroxymethyl)-4-morpholino-quinazolin-2-yl)phenyl)ureido)-N,N-dimethyl-benzamide;

1-(4-(4-(dimethylamino)piperidine-1-carbonyl)phenyl)-3-(4-(7-(2-hydroxypropan-2-yl)-4-morpholino-quinazolin-2-yl)phenyl)urea;

4-(3-(4-(7-(4-(dimethylamino)piperidine-1-carbonyl)-4-morpholino-quinazolin-2-yl)phenyl)ureido)-N,N-dimethyl-benzamide;

(R)-1-(4-(3-(dimethylamino)pyrrolidine-1-carbonyl)phenyl)-3-(4-(7-(2-hydroxypropan-2-yl)-4-morpholino-quinazolin-2-yl)phenyl)urea;

(S)-1-(4-(3-(dimethylamino)pyrrolidine-1-carbonyl)phenyl)-3-(4-(7-(2-hydroxypropan-2-yl)-4-morpholino-quinazolin-2-yl)phenyl)urea;

4-(3-(2-fluoro-4-(7-(2-hydroxypropan-2-yl)-4-morpholino-quinazolin-2-yl)phenyl)ureido)-N,N-dimethyl-benzamide;

N-(4-(3-(4-(4-morpholino-7-(pyrimidin-5-yl)quinazolin-2-yl)phenyl)ureido)phenyl)-acetamide;

1-(4-(7-(2-fluoropyridin-3-yl)-4-morpholinoquinazolin-2-yl)phenyl)-3-(4-(2-oxopyrrolidin-1-yl)phenyl)urea;

N-(4-(3-(4-(7-(2-fluoropyridin-3-yl)-4-morpholinopyrido[3,2-d]pyrimidin-2-yl)phenyl)ureido)phenyl)acetamide;

N-(4-(3-(4-(7-(1-methyl-1H-pyrazol-4-yl)-4-morpholinopyrido[3,2-d]pyrimidin-2-yl)phenyl)ureido)phenyl)acetamide;

N,N-dimethyl-4-(3-(4-(4-morpholino-7-(1,3,5-trimethyl-1H-pyrazol-4-yl)pyrido[3,2-d]pyrimidin-2-yl)phenyl)ureido)-benzamide;

4-(3-(2-fluoro-4-(4-morpholino-7-(1,3,5-trimethyl-1H-pyrazol-4-yl)pyrido[3,2-d]pyrimidin-2-yl)phenyl)ureido)-N,N-dimethyl-benzamide;

N,N-dimethyl-4-(3-(4-(7-(2-methylpyridin-3-yl)-4-morpholinopyrido[3,2-d]pyrimidin-2-yl)phenyl)ureido)-benzamide;

4-(3-(2-fluoro-4-(7-(2-methylpyridin-3-yl)-4-morpholinopyrido[3,2-d]pyrimidin-2-yl)phenyl)ureido)-N,N-dimethyl-benzamide;

N,N-dimethyl-4-(3-(4-(7-(6-methylpyridin-3-yl)-4-morpholinopyrido[3,2-d]pyrimidin-2-yl)phenyl)ureido)-benzamide;

4-(3-(2-fluoro-4-(7-(6-methylpyridin-3-yl)-4-morpholinopyrido[3,2-d]pyrimidin-2-yl)phenyl)ureido)-N,N-dimethyl-benzamide;

N-(4-(3-(4-(7-(5-methylfuran-2-yl)-4-morpholinopyrido[3,2-d]pyrimidin-2-yl)phenyl)ureido)phenyl)acetamide;

N-(4-(3-(4-(7-(2-fluoropyridin-3-yl)-4-morpholinopyrido[3,2-d]pyrimidin-2-yl)phenyl)ureido)phenyl)acetamide;

N-(4-(3-(4-(4-morpholino-7-(pyridin-3-yl)pyrido[3,2-d]pyrimidin-2-yl)phenyl)ureido)phenyl)acetamide;

N-(4-(3-(4-(4-morpholino-7-(pyridin-4-yl)pyrido[3,2-d]pyrimidin-2-yl)phenyl)ureido)phenyl)acetamide;

N-(4-(3-(4-(4-morpholino-7-(pyridin-2-yl)pyrido[3,2-d]pyrimidin-2-yl)phenyl)ureido)phenyl)acetamide;

N-(4-(3-(4-(4-morpholino-7-(pyrimidin-5-yl)pyrido[3,2-d]pyrimidin-2-yl)phenyl)ureido)phenyl)acetamide;

N-(4-(3-(4-(4-morpholino-7-(pyridazin-4-yl)pyrido[3,2-d]pyrimidin-2-yl)phenyl)ureido)phenyl)acetamide;

N-(4-(3-(4-(7-(2-methoxypyrimidin-5-yl)-4-morpholinopyrido[3,2-d]pyrimidin-2-yl)phenyl)ureido)phenyl)acetamide;

N-(4-(3-(4-(7-(6-methoxypyridin-3-yl)-4-morpholinopyrido[3,2-d]pyrimidin-2-yl)phenyl)ureido)phenyl)acetamide;

N-(4-(3-(4-(7-(3-(methylsulfonyl)phenyl)-4-morpholinopyrido[3,2-d]pyrimidin-2-yl)phenyl)ureido)phenyl)acetamide;
N-(4-(3-(4-(7-(2-aminopyrimidin-5-yl)-4-morpholinopyrido[3,2-d]pyrimidin-2-yl)phenyl)ureido)phenyl)acetamide;
N-(4-(3-(4-(4-morpholino-7-(1,3,5-trimethyl-1H-pyrazol-4-yl)quinazolin-2-yl)phenyl)ureido)phenyl)acetamide;
N-(4-(3-(4-(7-(2-methylpyridin-3-yl)-4-morpholinopyrido[3,2-d]pyrimidin-2-yl)phenyl)ureido)phenyl)acetamide;
N-(4-(3-(4-(7-(6-methylpyridin-3-yl)-4-morpholinopyrido[3,2-d]pyrimidin-2-yl)phenyl)ureido)phenyl)acetamide;
N-(4-(3-(5-(7-(2-fluoropyridin-3-yl)-4-morpholinopyrido[3,2-d]pyrimidin-2-yl)pyridin-2-yl)ureido)phenyl)acetamide;
N-(4-(3-(5-(7-(1-methyl-1H-pyrazol-4-yl)-4-morpholinopyrido[3,2-d]pyrimidin-2-yl)pyridin-2-yl)ureido)phenyl)acetamide;
4-(3-(4-(7-(5-ethylfuran-2-yl)-4-morpholinoquinazolin-2-yl)phenyl)ureido)-N,N-dimethyl-benzamide;
4-(3-(4-(7-(5-(1,2-dihydroxyethyl)furan-2-yl)-4-morpholinoquinazolin-2-yl)phenyl)ureido)-N,N-dimethylbenzamide;
N-(4-(3-(4-(7-(5-ethylfuran-2-yl)-4-morpholinoquinazolin-2-yl)phenyl)ureido)phenyl)acetamide;
N-(4-(3-(4-(7-(5-(hydroxymethyl)furan-2-yl)-4-morpholinoquinazolin-2-yl)phenyl)ureido)phenyl)acetamide;
N-(4-(3-(4-(7-(5-(1-hydroxyethyl)furan-2-yl)-4-morpholinoquinazolin-2-yl)phenyl)ureido)phenyl)acetamide;
N-(4-(3-(4-(7-(5-(2-hydroxypropan-2-yl)furan-2-yl)-4-morpholinoquinazolin-2-yl)phenyl)ureido)phenyl)acetamide;
N-(4-(3-(4-(7-(furan-2-yl)-4-morpholinoquinazolin-2-yl)phenyl)ureido)phenyl)acetamide;
N-(4-(3-(4-(4-morpholino-7-(pyridin-3-yl)quinazolin-2-yl)phenyl)ureido)phenyl)acetamide;
N-(4-(3-(4-(4-morpholino-7-(pyridin-4-yl)quinazolin-2-yl)phenyl)ureido)phenyl)acetamide;
N-(4-(3-(4-(4-morpholino-7-(pyridin-2-yl)quinazolin-2-yl)phenyl)ureido)phenyl)acetamide;
N-(4-(3-(4-(4-morpholino-7-(pyridazin-4-yl)quinazolin-2-yl)phenyl)ureido)phenyl)acetamide;
N-(4-(3-(4-(7-(2-methoxypyrimidin-5-yl)-4-morpholinoquinazolin-2-yl)phenyl)ureido)phenyl)acetamide;
N-(4-(3-(4-(7-(6-methoxypyridin-3-yl)-4-morpholinoquinazolin-2-yl)phenyl)ureido)phenyl)acetamide;
N-(4-(3-(4-(7-(3-(methylsulfonyl)phenyl)-4-morpholinoquinazolin-2-yl)phenyl)ureido)phenyl)acetamide;
N-(4-(3-(4-(7-(2-aminopyrimidin-5-yl)-4-morpholinoquinazolin-2-yl)phenyl)ureido)phenyl)acetamide;
N-(4-(3-(4-(4-morpholino-7-(1,3,5-trimethyl-1H-pyrazol-4-yl)quinazolin-2-yl)phenyl)ureido)phenyl)acetamide;
N-(4-(3-(4-(7-(2-methylpyridin-3-yl)-4-morpholinoquinazolin-2-yl)phenyl)ureido)phenyl)acetamide;
N-(4-(3-(4-(7-(6-methylpyridin-3-yl)-4-morpholinoquinazolin-2-yl)phenyl)ureido)phenyl)acetamide;
N-(4-(3-(5-(7-(5-methylfuran-2-yl)-4-morpholinoquinazolin-2-yl)pyridin-2-yl)ureido)phenyl)acetamide;
N-(4-(3-(5-(7-(furan-2-yl)-4-morpholinoquinazolin-2-yl)pyridin-2-yl)ureido)phenyl)acetamide;
N-(4-(3-(5-(4-morpholino-7-(pyrimidin-5-yl)quinazolin-2-yl)pyridin-2-yl)ureido)phenyl)acetamide;
N-(4-(3-(5-(7-(1-methyl-1H-pyrazol-4-yl)-4-morpholinoquinazolin-2-yl)pyridin-2-yl)ureido)phenyl)acetamide;
N-(4-(3-(4-(6-fluoro-7-(5-methylfuran-2-yl)-4-morpholinoquinazolin-2-yl)phenyl)ureido)phenyl)acetamide;
N-(4-(3-(4-(6-fluoro-7-(furan-2-yl)-4-morpholinoquinazolin-2-yl)phenyl)ureido)phenyl)acetamide;
N-(4-(3-(4-(6-fluoro-4-morpholino-7-(pyridin-3-yl)quinazolin-2-yl)phenyl)ureido)phenyl)acetamide;
N-(4-(3-(4-(6-fluoro-4-morpholino-7-(pyrimidin-5-yl)quinazolin-2-yl)phenyl)ureido)phenyl)acetamide;
N-(3-fluoro-4-(3-(4-(7-(5-methylfuran-2-yl)-4-morpholinoquinazolin-2-yl)phenyl)ureido)phenyl)acetamide;
N-(4-(3-(4-(7-(5-ethylfuran-2-yl)-4-morpholinoquinazolin-2-yl)phenyl)ureido)-3-fluorophenyl)acetamide;
N-(3-fluoro-4-(3-(4-(7-(furan-2-yl)-4-morpholinoquinazolin-2-yl)phenyl)ureido)phenyl)acetamide;
N-(3-fluoro-4-(3-(4-(4-morpholino-7-(pyridin-3-yl)quinazolin-2-yl)phenyl)ureido)phenyl)acetamide;
N-(3-fluoro-4-(3-(4-(7-(2-fluoropyridin-3-yl)-4-morpholinoquinazolin-2-yl)phenyl)ureido)phenyl)acetamide;
N-(3-fluoro-4-(3-(4-(7-(2-methylpyridin-3-yl)-4-morpholinoquinazolin-2-yl)phenyl)ureido)phenyl)acetamide;
N-(3-fluoro-4-(3-(4-(7-(6-methylpyridin-3-yl)-4-morpholinoquinazolin-2-yl)phenyl)ureido)phenyl)acetamide;
N-(3-fluoro-4-(3-(4-(4-morpholino-7-(pyridin-2-yl)quinazolin-2-yl)phenyl)ureido)phenyl)acetamide;
N-(3-fluoro-4-(3-(4-(4-morpholino-7-(pyridin-4-yl)quinazolin-2-yl)phenyl)ureido)phenyl)acetamide;
N-(3-fluoro-4-(3-(4-(4-morpholino-7-(pyrimidin-5-yl)quinazolin-2-yl)phenyl)ureido)phenyl)acetamide;
N-(3-fluoro-4-(3-(4-(7-(2-methoxypyrimidin-5-yl)-4-morpholinoquinazolin-2-yl)phenyl)ureido)phenyl)acetamide;
N-(4-(3-(4-(7-(2-aminopyrimidin-5-yl)-4-morpholinoquinazolin-2-yl)phenyl)ureido)-3-fluorophenyl)acetamide;
N-(3-fluoro-4-(3-(4-(7-(6-methoxypyridin-3-yl)-4-morpholinoquinazolin-2-yl)phenyl)ureido)phenyl)acetamide;
N-(3-fluoro-4-(3-(4-(7-(1-methyl-1H-pyrazol-4-yl)-4-morpholinoquinazolin-2-yl)phenyl)ureido)phenyl)acetamide;
N-(3-fluoro-4-(3-(4-(4-morpholino-7-(1,3,5-trimethyl-1H-pyrazol-4-yl)quinazolin-2-yl)phenyl)ureido)phenyl)acetamide;
N-(3-fluoro-4-(3-(4-(7-(3-(methylsulfonyl)phenyl)-4-morpholinoquinazolin-2-yl)phenyl)ureido)phenyl)acetamide;
N-(3-fluoro-4-(3-(4-(7-(5-(hydroxymethyl)furan-2-yl)-4-morpholinoquinazolin-2-yl)phenyl)ureido)phenyl)acetamide;
N-(3-fluoro-4-(3-(4-(7-(5-(1-hydroxyethyl)furan-2-yl)-4-morpholinoquinazolin-2-yl)phenyl)ureido)phenyl)acetamide;
N-(3-fluoro-4-(3-(4-(7-(5-(2-hydroxypropan-2-yl)furan-2-yl)-4-morpholinoquinazolin-2-yl)phenyl)ureido)phenyl)acetamide;
N-(2-fluoro-4-(3-(4-(7-(5-methylfuran-2-yl)-4-morpholinoquinazolin-2-yl)phenyl)ureido)phenyl)acetamide;
N-(4-(3-(4-(7-(5-ethylfuran-2-yl)-4-morpholinoquinazolin-2-yl)phenyl)ureido)-2-fluorophenyl)acetamide;

N-(2-fluoro-4-(3-(4-(7-(furan-2-yl)-4-morpholino-quinazolin-2-yl)phenyl)ureido)phenyl)acetamide;
N-(2-fluoro-4-(3-(4-(4-morpholino-7-(pyridin-3-yl)quinazolin-2-yl)phenyl)ureido)phenyl)acetamide;
N-(2-fluoro-4-(3-(4-(7-(2-fluoropyridin-3-yl)-4-morpholinoquinazolin-2-yl)phenyl)ureido)phenyl)acetamide;
N-(2-fluoro-4-(3-(4-(7-(2-methylpyridin-3-yl)-4-morpholinoquinazolin-2-yl)phenyl)ureido)phenyl)acetamide;
N-(2-fluoro-4-(3-(4-(7-(6-methylpyridin-3-yl)-4-morpholinoquinazolin-2-yl)phenyl)ureido)phenyl)acetamide;
N-(2-fluoro-4-(3-(4-(4-morpholino-7-(pyridin-2-yl)quinazolin-2-yl)phenyl)ureido)phenyl)acetamide;
N-(2-fluoro-4-(3-(4-(4-morpholino-7-(pyridin-4-yl)quinazolin-2-yl)phenyl)ureido)phenyl)acetamide;
N-(2-fluoro-4-(3-(4-(4-morpholino-7-(pyrimidin-5-yl)quinazolin-2-yl)phenyl)ureido)phenyl)acetamide;
N-(2-fluoro-4-(3-(4-(7-(2-methoxypyrimidin-5-yl)-4-morpholinoquinazolin-2-yl)phenyl)ureido)phenyl)acetamide;
N-(4-(3-(4-(7-(2-aminopyrimidin-5-yl)-4-morpholinoquinazolin-2-yl)phenyl)ureido)-2-fluorophenyl)acetamide;
N-(2-fluoro-4-(3-(4-(7-(6-methoxypyridin-3-yl)-4-morpholinoquinazolin-2-yl)phenyl)ureido)phenyl)acetamide;
N-(2-fluoro-4-(3-(4-(7-(1-methyl-1H-pyrazol-4-yl)-4-morpholinoquinazolin-2-yl)phenyl)ureido)phenyl)acetamide;
N-(2-fluoro-4-(3-(4-(4-morpholino-7-(1,3,5-trimethyl-1H-pyrazol-4-yl)quinazolin-2-yl)phenyl)ureido)phenyl)acetamide;
N-(2-fluoro-4-(3-(4-(7-(3-(methylsulfonyl)phenyl)-4-morpholinoquinazolin-2-yl)phenyl)ureido)phenyl)acetamide;
N-(2-fluoro-4-(3-(4-(7-(5-(hydroxymethyl)furan-2-yl)-4-morpholinoquinazolin-2-yl)phenyl)ureido)phenyl)acetamide;
N-(2-fluoro-4-(3-(4-(7-(5-(1-hydroxyethyl)furan-2-yl)-4-morpholinoquinazolin-2-yl)phenyl)ureido)phenyl)acetamide;
N-(2-fluoro-4-(3-(4-(7-(5-(2-hydroxypropan-2-yl)furan-2-yl)-4-morpholinoquinazolin-2-yl)phenyl)ureido)phenyl)acetamide;
N-methyl-N-(4-(3-(4-(7-(5-methylfuran-2-yl)-4-morpholinoquinazolin-2-yl)phenyl)ureido)phenyl)acetamide;
N-(4-(3-(4-(7-(5-ethylfuran-2-yl)-4-morpholinoquinazolin-2-yl)phenyl)ureido)phenyl)-N-methylacetamide;
N-(4-(3-(4-(7-(furan-2-yl)-4-morpholinoquinazolin-2-yl)phenyl)ureido)phenyl)-N-methylacetamide;
N-(4-(3-(4-(7-(2-methoxypyrimidin-5-yl)-4-morpholinoquinazolin-2-yl)phenyl)ureido)phenyl)-N-methylacetamide;
N-methyl-N-(4-(3-(4-(4-morpholino-7-(pyrimidin-5-yl)quinazolin-2-yl)phenyl)ureido)phenyl)acetamide;
N-methyl-N-(4-(3-(4-(4-morpholino-7-(pyridin-3-yl)quinazolin-2-yl)phenyl)ureido)phenyl)acetamide;
N-(4-(3-(4-(7-(2-fluoropyridin-3-yl)-4-morpholino-quinazolin-2-yl)phenyl)ureido)phenyl)-N-methylacetamide;
N-methyl-N-(4-(3-(4-(4-morpholino-7-(pyridin-2-yl)quinazolin-2-yl)phenyl)ureido)phenyl)acetamide;
N-(3-fluoro-4-(3-(4-(6-fluoro-7-(5-methylfuran-2-yl)-4-morpholinoquinazolin-2-yl)phenyl)ureido)phenyl)acetamide;
N-(3-fluoro-4-(3-(4-(6-fluoro-7-(furan-2-yl)-4-morpholinoquinazolin-2-yl)phenyl)ureido)phenyl)acetamide;
N-(3-fluoro-4-(3-(4-(6-fluoro-4-morpholino-7-(pyrimidin-5-yl)quinazolin-2-yl)phenyl)ureido)phenyl)acetamide;
N-(3-fluoro-4-(3-(4-(6-fluoro-4-morpholino-7-(pyridin-3-yl)quinazolin-2-yl)phenyl)ureido)phenyl)acetamide;
N-(2-fluoro-4-(3-(4-(6-fluoro-7-(5-methylfuran-2-yl)-4-morpholinoquinazolin-2-yl)phenyl)ureido)phenyl)acetamide;
N-(2-fluoro-4-(3-(4-(6-fluoro-7-(furan-2-yl)-4-morpholinoquinazolin-2-yl)phenyl)ureido)phenyl)acetamide;
N-(2-fluoro-4-(3-(4-(6-fluoro-4-morpholino-7-(pyrimidin-5-yl)quinazolin-2-yl)phenyl)ureido)phenyl)acetamide;
N-(2-fluoro-4-(3-(4-(6-fluoro-4-morpholino-7-(pyridin-3-yl)quinazolin-2-yl)phenyl)ureido)phenyl)acetamide;
N-(4-(3-(4-(6-fluoro-7-(5-methylfuran-2-yl)-4-morpholinoquinazolin-2-yl)phenyl)ureido)phenyl)-N-methylacetamide;
N-(4-(3-(4-(6-fluoro-7-(furan-2-yl)-4-morpholinoquinazolin-2-yl)phenyl)ureido)phenyl)-N-methylacetamide;
N-(4-(3-(4-(6-fluoro-4-morpholino-7-(pyrimidin-5-yl)quinazolin-2-yl)phenyl)ureido)phenyl)-N-methylacetamide;
N-(4-(3-(4-(6-fluoro-4-morpholino-7-(pyridin-3-yl)quinazolin-2-yl)phenyl)ureido)phenyl)-N-methylacetamide;
N-(3-fluoro-4-(3-(4-(7-(5-methylfuran-2-yl)-4-morpholinopyrido[3,2-d]pyrimidin-2-yl)phenyl)ureido)phenyl)acetamide;
N-(3-fluoro-4-(3-(4-(7-(furan-2-yl)-4-morpholinopyrido[3,2-d]pyrimidin-2-yl)phenyl)ureido)phenyl)acetamide;
N-(3-fluoro-4-(3-(4-(4-morpholino-7-(pyrimidin-5-yl)pyrido[3,2-d]pyrimidin-2-yl)phenyl)ureido)phenyl)acetamide;
N-(3-fluoro-4-(3-(4-(7-(2-fluoropyridin-3-yl)-4-morpholinopyrido[3,2-d]pyrimidin-2-yl)phenyl)ureido)phenyl)acetamide;
N-(3-fluoro-4-(3-(4-(4-morpholino-7-(pyridin-3-yl)pyrido[3,2-d]pyrimidin-2-yl)phenyl)ureido)phenyl)acetamide;
N-(3-fluoro-4-(3-(4-(7-(1-methyl-1H-pyrazol-4-yl)-4-morpholinopyrido[3,2-d]pyrimidin-2-yl)ureido)phenyl)acetamide;
N-(2-fluoro-4-(3-(4-(7-(5-methylfuran-2-yl)-4-morpholinopyrido[3,2-d]pyrimidin-2-yl)phenyl)ureido)phenyl)acetamide;
N-(2-fluoro-4-(3-(4-(7-(furan-2-yl)-4-morpholinopyrido[3,2-d]pyrimidin-2-yl)phenyl)ureido)phenyl)acetamide;
N-(2-fluoro-4-(3-(4-(4-morpholino-7-(pyrimidin-5-yl)pyrido[3,2-d]pyrimidin-2-yl)phenyl)ureido)phenyl)acetamide;
N-(2-fluoro-4-(3-(4-(7-(2-fluoropyridin-3-yl)-4-morpholinopyrido[3,2-d]pyrimidin-2-yl)phenyl)ureido)phenyl)acetamide;
N-(2-fluoro-4-(3-(4-(4-morpholino-7-(pyridin-3-yl)pyrido[3,2-d]pyrimidin-2-yl)phenyl)ureido)phenyl)acetamide;

N-(2-fluoro-4-(3-(4-(7-(1-methyl-1H-pyrazol-4-yl)-4-morpholinopyrido[3,2-d]pyrimidin-2-yl)phenyl)ureido)phenyl)acetamide;

N-methyl-N-(4-(3-(4-(7-(5-methylfuran-2-yl)-4-morpholinopyrido[3,2-d]pyrimidin-2-yl)phenyl)ureido)phenyl)acetamide;

N-(4-(3-(4-(7-(furan-2-yl)-4-morpholinopyrido[3,2-d]pyrimidin-2-yl)phenyl)ureido)phenyl)-N-methylacetamide;

N-methyl-N-(4-(3-(4-(4-morpholino-7-(pyrimidin-5-yl)pyrido[3,2-d]pyrimidin-2-yl)phenyl)ureido)phenyl)acetamide;

N-(4-(3-(4-(7-(2-fluoropyridin-3-yl)-4-morpholinopyrido[3,2-d]pyrimidin-2-yl)phenyl)ureido)phenyl)-N-methylacetamide;

N-methyl-N-(4-(3-(4-(4-morpholino-7-(pyridin-3-yl)pyrido[3,2-d]pyrimidin-2-yl)phenyl)ureido)phenyl)acetamide;

N-methyl-N-(4-(3-(4-(7-(1-methyl-1H-pyrazol-4-yl)-4-morpholinopyrido[3,2-d]pyrimidin-2-yl)phenyl)ureido)phenyl)acetamide;

N-(4-(3-(2-fluoro-4-(7-(5-methylfuran-2-yl)-4-morpholinoquinazolin-2-yl)phenyl)ureido)phenyl)acetamide;

N-(4-(3-(2-fluoro-4-(7-(furan-2-yl)-4-morpholinoquinazolin-2-yl)phenyl)ureido)phenyl)acetamide;

N-(4-(3-(2-fluoro-4-(7-(2-methoxypyrimidin-5-yl)-4-morpholinoquinazolin-2-yl)phenyl)ureido)phenyl)acetamide;

N-(4-(3-(2-fluoro-4-(4-morpholino-7-(pyrimidin-5-yl)quinazolin-2-yl)phenyl)ureido)phenyl)acetamide;

N-(4-(3-(2-fluoro-4-(4-morpholino-7-(pyridin-3-yl)quinazolin-2-yl)phenyl)ureido)phenyl)acetamide;

N-(4-(3-(2-fluoro-4-(7-(2-fluoropyridin-3-yl)-4-morpholinoquinazolin-2-yl)phenyl)ureido)phenyl)acetamide;

N-(4-(3-(2-fluoro-4-(4-morpholino-7-(pyridin-2-yl)quinazolin-2-yl)phenyl)ureido)phenyl)acetamide;

N-(4-(3-(3-fluoro-4-(7-(5-methylfuran-2-yl)-4-morpholinoquinazolin-2-yl)phenyl)ureido)phenyl)acetamide;

N-(4-(3-(3-fluoro-4-(7-(furan-2-yl)-4-morpholinoquinazolin-2-yl)phenyl)ureido)phenyl)acetamide;

N-(4-(3-(3-fluoro-4-(7-(2-methoxypyrimidin-5-yl)-4-morpholinoquinazolin-2-yl)phenyl)ureido)phenyl)acetamide;

N-(4-(3-(3-fluoro-4-(4-morpholino-7-(pyrimidin-5-yl)quinazolin-2-yl)phenyl)ureido)phenyl)acetamide;

N-(4-(3-(3-fluoro-4-(4-morpholino-7-(pyridin-3-yl)quinazolin-2-yl)phenyl)ureido)phenyl)acetamide;

N-(4-(3-(3-fluoro-4-(7-(2-fluoropyridin-3-yl)-4-morpholinoquinazolin-2-yl)phenyl)ureido)phenyl)acetamide;

N-(4-(3-(3-fluoro-4-(4-morpholino-7-(pyridin-2-yl)quinazolin-2-yl)phenyl)ureido)phenyl)acetamide;

N-(4-(3-(2-fluoro-4-(6-fluoro-7-(5-methylfuran-2-yl)-4-morpholinoquinazolin-2-yl)phenyl)ureido)phenyl)acetamide;

N-(4-(3-(2-fluoro-4-(6-fluoro-7-(furan-2-yl)-4-morpholinoquinazolin-2-yl)phenyl)ureido)phenyl)acetamide;

N-(4-(3-(2-fluoro-4-(6-fluoro-4-morpholino-7-(pyrimidin-5-yl)quinazolin-2-yl)phenyl)ureido)phenyl)acetamide;

N-(4-(3-(2-fluoro-4-(6-fluoro-4-morpholino-7-(pyridin-3-yl)quinazolin-2-yl)phenyl)ureido)phenyl)acetamide;

N-(4-(3-(3-fluoro-4-(6-fluoro-7-(5-methylfuran-2-yl)-4-morpholinoquinazolin-2-yl)phenyl)ureido)phenyl)acetamide;

N-(4-(3-(3-fluoro-4-(6-fluoro-7-(furan-2-yl)-4-morpholinoquinazolin-2-yl)phenyl)ureido)phenyl)acetamide;

N-(4-(3-(3-fluoro-4-(6-fluoro-4-morpholino-7-(pyrimidin-5-yl)quinazolin-2-yl)phenyl)ureido)phenyl)acetamide;

N-(4-(3-(3-fluoro-4-(6-fluoro-4-morpholino-7-(pyridin-3-yl)quinazolin-2-yl)phenyl)ureido)phenyl)acetamide;

N-(4-(3-(2-fluoro-4-(7-(5-methylfuran-2-yl)-4-morpholinopyrido[3,2-d]pyrimidin-2-yl)phenyl)ureido)phenyl)acetamide;

N-(4-(3-(2-fluoro-4-(7-(furan-2-yl)-4-morpholinopyrido[3,2-d]pyrimidin-2-yl)phenyl)ureido)phenyl)acetamide;

N-(4-(3-(2-fluoro-4-(4-morpholino-7-(pyrimidin-5-yl)pyrido[3,2-d]pyrimidin-2-yl)phenyl)ureido)phenyl)acetamide;

N-(4-(3-(2-fluoro-4-(7-(2-fluoropyridin-3-yl)-4-morpholinopyrido[3,2-d]pyrimidin-2-yl)phenyl)ureido)phenyl)acetamide;

N-(4-(3-(2-fluoro-4-(4-morpholino-7-(pyridin-3-yl)pyrido[3,2-d]pyrimidin-2-yl)phenyl)ureido)phenyl)acetamide;

N-(4-(3-(2-fluoro-4-(7-(1-methyl-1H-pyrazol-4-yl)-4-morpholinopyrido[3,2-d]pyrimidin-2-yl)phenyl)ureido)phenyl)acetamide;

N-(4-(3-(3-fluoro-4-(7-(5-methylfuran-2-yl)-4-morpholinopyrido[3,2-d]pyrimidin-2-yl)phenyl)ureido)phenyl)acetamide;

N-(4-(3-(3-fluoro-4-(7-(furan-2-yl)-4-morpholinopyrido[3,2-d]pyrimidin-2-yl)phenyl)ureido)phenyl)acetamide;

N-(4-(3-(3-fluoro-4-(4-morpholino-7-(pyrimidin-5-yl)pyrido[3,2-d]pyrimidin-2-yl)phenyl)ureido)phenyl)acetamide;

N-(4-(3-(3-fluoro-4-(7-(2-fluoropyridin-3-yl)-4-morpholinopyrido[3,2-d]pyrimidin-2-yl)phenyl)ureido)phenyl)acetamide;

N-(4-(3-(3-fluoro-4-(4-morpholino-7-(pyridin-3-yl)pyrido[3,2-d]pyrimidin-2-yl)phenyl)ureido)phenyl)acetamide; and N-(4-(3-(3-fluoro-4-(7-(1-methyl-1H-pyrazol-4-yl)-4-morpholinopyrido[3,2-d]pyrimidin-2-yl)phenyl)ureido)phenyl)acetamide, or a pharmaceutically acceptable salt or solvate thereof.

7. The method according to claim 6, wherein said disease is cancer.

8. The method according to claim 7, wherein said cancer is of the prostate, head, neck, eye, mouth, throat, esophagus, bronchus, larynx, pharynx, chest, bone, lung, colon, rectum, stomach, bladder, uterus, cervix, breast, ovaries, vagina, testicles, skin, thyroid, blood, lymph nodes, kidney, liver, intestines, pancreas, brain, central nervous system, adrenal gland, or skin or a leukemia.

9. The method according to claim 8, wherein said cancer is cancer of the prostate.

10. The method according to claim 7, wherein said patient has at least one solid tumor.

11. A pharmaceutical composition comprising: a pharmaceutically acceptable carrier, and a compound selected from the group consisting of:

N,N-Dimethyl-4-{3-[4-(4-morpholin-4-yl-7-pyrimidin-5-yl-quinazolin-2-yl)-phenyl]-ureido}-benzamide;

N,N-Dimethyl-4-(3-{4-[7-(5-methyl-furan-2-yl)-4-morpholin-4-yl-quinazolin-2-yl]-phenyl}-ureido)-benzamide;

4-(3-{5-[7-(3-Methanesulfonyl-phenyl)-4-morpholin-4-yl-quinazolin-2-yl]-pyridin-2-yl}-ureido)-N,N-dimethyl-benzamide;
1-[4-(6-Fluoro-4-morpholin-4-yl-7-pyridin-3-yl-quinazolin-2-yl)-phenyl]-3-[4-(4-methyl-piperazine-1-carbonyl)-phenyl]-urea;
4-(3-{4-[8-(3-Hydroxy-phenyl)-4-morpholin-4-yl-quinazolin-2-yl]-phenyl}-ureido)-N,N-dimethyl-benzamide;
4-(3-{4-[8-(6-Fluoro-pyridin-3-yl)-4-morpholin-4-yl-quinazolin-2-yl]-phenyl}-ureido)-N,N-dimethyl-benzamide;
2-{4-[3-(4-Dimethylcarbamoyl-phenyl)-ureido]-phenyl}-4-morpholin-4-yl-quinazoline-7-carboxylic acid (2-dimethylamino-ethyl)-amide;
4-(3-{2-Fluoro-4-[7-(5-methyl-furan-2-yl)-4-morpholin-4-yl-quinazolin-2-yl]-phenyl}-ureido)-N,N-dimethyl-benzamide;
N,N-Dimethyl-4-{3-[4-(4-morpholin-4-yl-7-pyrimidin-5-yl-pyrido[3,2-d]pyrimidin-2-yl)-phenyl]-ureido}-benzamide;
5-(2-(4-(3-(4-(dimethylcarbamoyl)phenyl)ureido)phenyl)-4-morpholino-quinazolin-7-yl)furan-2-carboxylic acid;
N,N-dimethyl-4-(3-(4-(7-(5-(4-methylpiperazine-1-carbonyl)furan-2-yl)-4-morpholino-quinazolin-2-yl)phenyl)ureido)-benzamide;
4-(3-(4-(7-(5-cyanofuran-2-yl)-4-morpholino-quinazolin-2-yl)-3-fluorophenyl)ureido)-N,N-dimethyl-benzamide;
4-(3-(4-(7-(5-acetylfuran-2-yl)-4-morpholino-quinazolin-2-yl)phenyl)ureido)-2-fluoro-N,N-dimethyl-benzamide;
4-(3-(2,3-difluoro-4-(7-(1-methyl-1H-pyrazol-4-yl)-4-morpholino-pyrido[3,2-d]pyrimidin-2-yl)phenyl)ureido)-N,N-dimethyl-benzamide;
4-(3-(2-fluoro-4-(7-(5-(1-hydroxyethyl)furan-2-yl)-4-morpholino-pyrido[3,2-d]pyrimidin-2-yl)phenyl)ureido)-N,N-dimethyl-benzamide;
4-(3-(4-(7-(2-hydroxypropan-2-yl)-4-morpholino-quinazolin-2-yl)phenyl)ureido)-N,N-dimethyl-benzamide;
N-(4-(3-(4-(7-(5-methylfuran-2-yl)-4-morpholino-quinazolin-2-yl)phenyl)ureido)-phenyl)-acetamide;
1-(4-(7-(5-methylfuran-2-yl)-4-morpholino-quinazolin-2-yl)phenyl)-3-(4-(2-oxopyrrolidin-1-yl)phenyl)urea;
4-(3-{4-[7-(3-Methanesulfonyl-phenyl)-4-morpholin-4-yl-quinazolin-2-yl]-phenyl}-ureido)-N,N-dimethyl-benzamide;
4-(3-{4-[7-(3-Methanesulfonyl-phenyl)-4-morpholin-4-yl-quinazolin-2-yl]-phenyl}-ureido)-N-methyl-benzamide;
4-(3-{4-[7-(2-Fluoro-pyridin-3-yl)-4-morpholin-4-yl-quinazolin-2-yl]-phenyl}-ureido)-N,N-dimethyl-benzamide;
N,N-Dimethyl-4-(3-{4-[7-(1-methyl-1H-pyrazol-4-yl)-4-morpholin-4-yl-quinazolin-2-yl]-phenyl}-ureido)-benzamide;
4-(3-{4-[7-(3-Methanesulfonylamino-phenyl)-4-morpholin-4-yl-quinazolin-2-yl]-phenyl}-ureido)-N,N-dimethyl-benzamide;
N,N-Dimethyl-4-{3-[4-(4-morpholin-4-yl-7-pyridin-3-yl-quinazolin-2-yl)-phenyl]-ureido}-benzamide;
4-(3-{4-[7-(3-Methanesulfonyl-phenyl)-4-morpholin-4-yl-quinazolin-2-yl]-phenyl}-ureido)-benzamide;
1-{4-[7-(2-Fluoro-pyridin-3-yl)-4-morpholin-4-yl-quinazolin-2-yl]-phenyl}-3-[4-(4-methyl-piperazine-1-carbonyl)-phenyl]-urea;
1-[4-(4-Methyl-piperazine-1-carbonyl)-phenyl]-3-{4-[7-(1-methyl-1H-pyrazol-4-yl)-4-morpholin-4-yl-quinazolin-2-yl]-phenyl}-urea;
5-(3-{4-[7-(2-Fluoro-pyridin-3-yl)-4-morpholin-4-yl-quinazolin-2-yl]-phenyl}-ureido)-pyridine-2-carboxylic acid dimethylamide;
4-{3-[4-(6-Fluoro-4-morpholin-4-yl-7-pyridin-3-yl-quinazolin-2-yl)-phenyl]-ureido}-N,N-dimethyl-benzamide;
4-{3-[4-(6-Fluoro-4-morpholin-4-yl-7-pyrimidin-5-yl-quinazolin-2-yl)-phenyl]-ureido}-N,N-dimethyl-benzamide;
5-(3-{4-[7-(3-Methanesulfonyl-phenyl)-4-morpholin-4-yl-quinazolin-2-yl]-phenyl}-ureido)-pyridine-2-carboxylic acid dimethylamide;
1-(4-(4-methylpiperazine-1-carbonyl)phenyl)-3-(4-(7-(3-(methylsulfonyl)phenyl)-4-morpholino-quinazolin-2-yl)phenyl)urea;
1-[4-(4-Methyl-piperazine-1-carbonyl)-phenyl]-3-[4-(4-morpholin-4-yl-7-pyridin-3-yl-quinazolin-2-yl)-phenyl]-urea;
4-(3-{4-[7-(5-Methanesulfonyl-pyridin-3-yl)-4-morpholin-4-yl-quinazolin-2-yl]-phenyl}-ureido)-N,N-dimethyl-benzamide;
4-(3-{4-[6-Fluoro-7-(1-methyl-1H-pyrazol-4-yl)-4-morpholin-4-yl-quinazolin-2-yl]-phenyl}-ureido)-N,N-dimethyl-benzamide;
4-(3-{4-[6-Fluoro-7-(3-methanesulfonyl-phenyl)-4-morpholin-4-yl-quinazolin-2-yl]-phenyl}-ureido)-N,N-dimethyl-benzamide;
1-[4-(4-Methyl-piperazine-1-carbonyl)-phenyl]-3-[4-(4-morpholin-4-yl-7-thiophen-3-yl-quinazolin-2-yl)-phenyl]-urea;
4-(3-{4-[6-Fluoro-7-(5-methanesulfonyl-pyridin-3-yl)-4-morpholin-4-yl-quinazolin-2-yl]-phenyl}-ureido)-N,N-dimethyl-benzamide;
4-(3-{4-[7-(3-Methanesulfonyl-phenyl)-4-morpholin-4-yl-pyrido[3,2-d]pyrimidin-2-yl]-phenyl}-ureido)-N,N-dimethyl-benzamide;
4-(3-{4-[8-(2-Fluoro-pyridin-3-yl)-4-morpholin-4-yl-quinazolin-2-yl]-phenyl}-ureido)-N,N-dimethyl-benzamide;
4-(3-{4-[7-(3-Hydroxy-phenyl)-4-morpholin-4-yl-quinazolin-2-yl]-phenyl}-ureido)-N,N-dimethyl-benzamide;
N,N-Dimethyl-4-(3-{4-[7-(1-methyl-1H-pyrazol-4-yl)-4-morpholin-4-yl-pyrido[3,2-d]pyrimidin-2-yl]-phenyl}-ureido)-benzamide;
N,N-Dimethyl-4-(3-{4-[7-(5-methyl-furan-2-yl)-4-morpholin-4-yl-pyrido[3,2-d]pyrimidin-2-yl]-phenyl}-ureido)-benzamide;
N-(2-Dimethylamino-ethyl)-N-methyl-4-{3-[4-(4-morpholin-4-yl-7-pyrimidin-5-yl-quinazolin-2-yl)-phenyl]-ureido}-benzamide;
4-(3-{4-[7-(3-Hydroxymethyl-phenyl)-4-morpholin-4-yl-quinazolin-2-yl]-phenyl}-ureido)-N,N-dimethyl-benzamide;
N,N-Dimethyl-4-{3-[4-(4-morpholin-4-yl-7-pyridin-3-yl-pyrido[3,2-d]pyrimidin-2-yl)-phenyl]-ureido}-benzamide;
4-(3-{4-[7-(3-Fluoro-phenyl)-4-morpholin-4-yl-quinazolin-2-yl]-phenyl}-ureido)-N,N-dimethyl-benzamide;

4-(3-{4-[7-(3-Methoxy-phenyl)-4-morpholin-4-yl-quinazolin-2-yl]-phenyl}-ureido)-N,N-dimethyl-benzamide;

4-(3-{4-[7-(3-Acetylamino-phenyl)-4-morpholin-4-yl-quinazolin-2-yl]-phenyl}-ureido)-N,N-dimethyl-benzamide;

4-(3-{4-[7-(3-Dimethylamino-phenyl)-4-morpholin-4-yl-quinazolin-2-yl]-phenyl}-ureido)-N,N-dimethyl-benzamide;

4-{3-[4-(7-Furan-2-yl-4-morpholin-4-yl-quinazolin-2-yl)-phenyl]-ureido}-N,N-dimethyl-benzamide;

N,N-Dimethyl-4-{3-[4-(4-morpholin-4-yl-7-thiophen-3-yl-quinazolin-2-yl)-phenyl]-ureido}-benzamide;

4-{3-[4-(7-Furan-3-yl-4-morpholin-4-yl-quinazolin-2-yl)-phenyl]-ureido}-N,N-dimethyl-benzamide;

4-(3-{5-[7-(2-Fluoro-pyridin-3-yl)-4-morpholin-4-yl-quinazolin-2-yl]-pyridin-2-yl}-ureido)-N,N-dimethyl-benzamide;

N,N-Dimethyl-4-(3-{5-[7-(1-methyl-1H-pyrazol-4-yl)-4-morpholin-4-yl-quinazolin-2-yl]-pyridin-2-yl}-ureido)-benzamide;

N-Methyl-4-(3-{4-[7-(5-methyl-furan-2-yl)-4-morpholin-4-yl-quinazolin-2-yl]-phenyl}-ureido)-benzamide;

N,N-Dimethyl-4-(3-{5-[7-(5-methyl-furan-2-yl)-4-morpholin-4-yl-quinazolin-2-yl]-pyridin-2-yl}-ureido)-benzamide;

N,N-Dimethyl-4-{3-[4-(4-morpholin-4-yl-7-pyridin-4-yl-quinazolin-2-yl)-phenyl]-ureido}-benzamide;

N,N-Dimethyl-4-{3-[4-(4-morpholin-4-yl-7-quinolin-3-yl-quinazolin-2-yl)-phenyl]-ureido}-benzamide;

4-(3-{4-[7-(6-Methoxy-pyridin-3-yl)-4-morpholin-4-yl-quinazolin-2-yl]-phenyl}-ureido)-N,N-dimethyl-benzamide;

N,N-Dimethyl-4-(3-{4-[7-(5-methyl-thiophen-2-yl)-4-morpholin-4-yl-quinazolin-2-yl]-phenyl}-ureido)-benzamide;

N,N-Dimethyl-4-(3-{4-[7-(4-methyl-pyridin-3-yl)-4-morpholin-4-yl-quinazolin-2-yl]-phenyl}-ureido)-benzamide;

N-(2-Dimethylamino-ethyl)-N-methyl-4-(3-{4-[7-(5-methyl-furan-2-yl)-4-morpholin-4-yl-quinazolin-2-yl]-phenyl}-ureido)-benzamide;

4-{3-[4-(7-Benzofuran-2-yl-4-morpholin-4-yl-quinazolin-2-yl)-phenyl]-ureido}-N,N-dimethyl-benzamide;

4-(3-{4-[7-(3-Fluoro-pyridin-4-yl)-4-morpholin-4-yl-quinazolin-2-yl]-phenyl}-ureido)-N,N-dimethyl-benzamide;

4-(3-{4-[7-(5-Acetylamino-pyridin-3-yl)-4-morpholin-4-yl-quinazolin-2-yl]-phenyl}-ureido)-N,N-dimethyl-benzamide;

1-[4-(4-Methyl-piperazine-1-carbonyl)-phenyl]-3-[4-(4-morpholin-4-yl-7-pyrimidin-5-yl-pyrido[3,2-d]pyrimidin-2-yl)-phenyl]-urea;

4-(3-{4-[7-(2-Fluoro-pyridin-4-yl)-4-morpholin-4-yl-quinazolin-2-yl]-phenyl}-ureido)-N,N-dimethyl-benzamide;

1-[4-(4-Methyl-piperazine-1-carbonyl)-phenyl]-3-[4-(4-morpholin-4-yl-7-pyridin-4-yl-quinazolin-2-yl)-phenyl]-urea;

1-{4-[7-(5-Methyl-furan-2-yl)-4-morpholin-4-yl-quinazolin-2-yl]-phenyl}-3-[4-(4-methyl-piperazine-1-carbonyl)-phenyl]-urea;

N,N-Dimethyl-4-(3-{4-[8-(5-methyl-furan-2-yl)-4-morpholin-4-yl-quinazolin-2-yl]-phenyl}-ureido)-benzamide;

N-(2-Dimethylamino-ethyl)-N-methyl-4-{3-[4-(4-morpholin-4-yl-7-pyridin-4-yl-quinazolin-2-yl)-phenyl]-ureido}-benzamide;

1-[4-(4-Methyl-piperazine-1-carbonyl)-phenyl]-3-{4-[7-(1-methyl-1H-pyrazol-4-yl)-4-morpholin-4-yl-pyrido[3,2-d]pyrimidin-2-yl]-phenyl}-urea;

N,N-Dimethyl-4-{3-[4-(4-morpholin-4-yl-7-thiophen-2-yl-quinazolin-2-yl)-phenyl]-ureido}-benzamide;

4-(3-{4-[7-(2-Methoxy-pyrimidin-5-yl)-4-morpholin-4-yl-quinazolin-2-yl]-phenyl}-ureido)-N,N-dimethyl-benzamide;

4-(3-{4-[7-(2-Amino-pyrimidin-5-yl)-4-morpholin-4-yl-quinazolin-2-yl]-phenyl}-ureido)-N,N-dimethyl-benzamide;

4-(3-(4-(7-(5-(2-(Dimethylamino)acetamido)pyridin-3-yl)-4-morpholino-quinazolin-2-yl)phenyl)ureido}-N,N-dimethyl-benzamide;

4-(3-{4-[7-(2-Fluoro-pyridin-3-yl)-4-morpholin-4-yl-pyrido[3,2-d]pyrimidin-2-yl]-phenyl}-ureido)-N,N-dimethyl-benzamide;

1-[4-(4-Methyl-piperazine-1-carbonyl)-phenyl]-3-[4-(4-morpholin-4-yl-7-pyrimidin-5-yl-quinazolin-2-yl)-phenyl]-urea;

N,N-Dimethyl-4-(3-{4-[7-(furan-2-yl)-4-morpholin-4-yl-quinazolin-2-yl]-phenyl}-ureido)-benzamide;

1-(4-(4-(dimethylamino)piperidine-1-carbonyl)phenyl)-3-(5-(7-(2-fluoropyridin-3-yl)-4-morpholino-quinazolin-2-yl)pyridin-2-yl)urea;

4-(3-(2-fluoro-4-(7-(1-methyl-1H-pyrazol-4-yl)-4-morpholino-pyrido[3,2-d]pyrimidin-2-yl)phenyl)ureido)-N,N-dimethyl-benzamide;

4-(3-(4-(7-(1-(2-(dimethylamino)ethyl)-1H-pyrazol-4-yl)-4-morpholino-quinazolin-2-yl)phenyl)ureido)-N,N-dimethyl-benzamide;

4-(3-(2-fluoro-4-(4-morpholino-7-(pyrimidin-5-yl)quinazolin-2-yl)phenyl)ureido)-N,N-dimethyl-benzamide;

N,N-dimethyl-4-(3-(5-(7-(1-methyl-1H-pyrazol-4-yl)-4-morpholino-pyrido[3,2-d]pyrimidin-2-yl)pyridin-2-yl)ureido)-benzamide;

N,N-dimethyl-4-(3-(4-(4-morpholino-7-(pyridazin-4-yl)quinazolin-2-yl)phenyl)ureido)-benzamide;

4-(3-(4-(6-fluoro-7-(5-methylfuran-2-yl)-4-morpholino-quinazolin-2-yl)phenyl)ureido)-N,N-dimethyl-benzamide;

N-methyl-4-(3-(4-(4-morpholino-7-(pyrimidin-5-yl)quinazolin-2-yl)phenyl)ureido)-benzamide;

N-methyl-4-(3-(4-(7-(1-methyl-1H-pyrazol-4-yl)-4-morpholino-pyrido[3,2-d]pyrimidin-2-yl)phenyl)ureido)-benzamide;

4-(3-(4-(7-(furan-2-yl)-4-morpholino-pyrido[3,2-d]pyrimidin-2-yl)phenyl)ureido)-N,N-dimethyl-benzamide;

4-(3-(2-fluoro-4-(7-(2-fluoropyridin-3-yl)-4-morpholino-quinazolin-2-yl)phenyl)ureido)-N,N-dimethyl-benzamide;

4-(3-(4-(7-(2-aminopyrimidin-5-yl)-4-morpholino-pyrido[3,2-d]pyrimidin-2-yl)phenyl)ureido)-N,N-dimethyl-benzamide;

N,N-dimethyl-4-(3-(4-(7-(4-methylpyridin-3-yl)-4-morpholino-pyrido[3,2-d]pyrimidin-2-yl)phenyl)ureido)-benzamide;

4-(3-(4-(7-(2-methoxypyrimidin-5-yl)-4-morpholino-pyrido[3,2-d]pyrimidin-2-yl)phenyl)ureido)-N,N-dimethyl-benzamide;

4-(3-(4-(7-(6-methoxypyridin-2-yl)-4-morpholino-quinazolin-2-yl)phenyl)ureido)-N,N-dimethyl-benzamide;

N,N-dimethyl-4-(3-(4-(4-morpholino-7-(pyridazin-4-yl)pyrido[3,2-d]pyrimidin-2-yl)phenyl)ureido)-benzamide;

4-(3-(2-fluoro-4-(7-(1-methyl-1H-pyrazol-4-yl)-4-morpholino-quinazolin-2-yl)phenyl)ureido)-N,N-dimethyl-benzamide;

4-(3-(2-fluoro-4-(4-morpholino-7-(pyridazin-4-yl)quinazolin-2-yl)phenyl)ureido)-N,N-dimethyl-benzamide;

4-(3-(2-fluoro-4-(6-fluoro-4-morpholino-7-(pyrimidin-5-yl)quinazolin-2-yl)phenyl)ureido)-N,N-dimethyl-benzamide;

4-(3-(2-fluoro-4-(7-(4-methylpyridin-3-yl)-4-morpholino-quinazolin-2-yl)phenyl)ureido)-N,N-dimethyl-benzamide;

4-(3-(2-fluoro-4-(4-morpholino-7-(pyrimidin-5-yl)pyrido[3,2-d]pyrimidin-2-yl)phenyl)ureido)-N,N-dimethyl-benzamide;

4-(3-(2-fluoro-4-(4-morpholino-7-(pyridin-3-yl)pyrido[3,2-d]pyrimidin-2-yl)phenyl)ureido)-N,N-dimethyl-benzamide;

4-(3-(2-fluoro-4-(4-morpholino-7-(pyridin-3-yl)quinazolin-2-yl)phenyl)ureido)-N,N-dimethyl-benzamide;

4-(3-(2-fluoro-4-(7-(3-(methylsulfonyl)phenyl)-4-morpholino-pyrido[3,2-d]pyrimidin-2-yl)phenyl)ureido)-N,N-dimethyl-benzamide;

4-(3-(2-fluoro-4-(7-(2-methoxypyrimidin-5-yl)-4-morpholino-quinazolin-2-yl)phenyl)ureido)-N,N-dimethyl-benzamide;

4-(3-(2-fluoro-4-(7-(2-fluoropyridin-3-yl)-4-morpholino-pyrido[3,2-d]pyrimidin-2-yl)phenyl)ureido)-N,N-dimethyl-benzamide;

4-(3-(4-(6-fluoro-7-(2-fluoropyridin-3-yl)-4-morpholino-quinazolin-2-yl)phenyl)ureido)-N,N-dimethyl-benzamide;

4-(3-(2-fluoro-4-(6-fluoro-7-(1-methyl-1H-pyrazol-4-yl)-4-morpholino-quinazolin-2-yl)phenyl)ureido dimethyl-benzamide)-N,N-dimethyl-benzamide;

4-(3-(2-fluoro-4-(6-fluoro-4-morpholino-7-(pyridin-3-yl)quinazolin-2-yl)phenyl)ureido)-N,N-dimethyl-benzamide;

4-(3-(4-(7-(2-aminopyrimidin-5-yl)-4-morpholino-quinazolin-2-yl)-2-fluorophenyl)ureido)-N,N-dimethyl-benzamide;

4-(3-(5-(7-(2-fluoropyridin-3-yl)-4-morpholino-pyrido[3,2-d]pyrimidin-2-yl)pyridin-2-yl)ureido)-N,N-dimethyl-benzamide;

4-(3-(5-(6-fluoro-7-(2-fluoropyridin-3-yl)-4-morpholino-quinazolin-2-yl)pyridin-2-yl)ureido)-N,N-dimethyl-benzamide;

4-(3-(5-(6-fluoro-7-(1-methyl-1H-pyrazol-4-yl)-4-morpholino-quinazolin-2-yl)pyridin-2-yl)ureido)-N,N-dimethyl-benzamide;

4-(3-(2-fluoro-4-(7-(furan-2-yl)-4-morpholino-quinazolin-2-yl)phenyl)ureido)-N,N-dimethyl-benzamide;

N,N-dimethyl-4-(3-(5-(7-(3-(methylsulfonyl)phenyl)-4-morpholino-pyrido[3,2-d]pyrimidin-2-yl)pyridin-2-yl)ureido)-benzamide;

4-(3-(2-fluoro-4-(7-(4-methylpyridin-3-yl)-4-morpholino-pyrido[3,2-d]pyrimidin-2-yl)phenyl)ureido)-N,N-dimethyl-benzamide;

4-(3-(2-fluoro-4-(7-(2-methoxypyrimidin-5-yl)-4-morpholino-pyrido[3,2-d]pyrimidin-2-yl)phenyl)ureido)-N,N-dimethyl-benzamide;

4-(3-(2-fluoro-4-(7-(3-(methylsulfonyl)phenyl)-4-morpholino-quinazolin-2-yl)phenyl)ureido)-N,N-dimethyl-benzamide;

4-(3-(5-(7-(2-methoxypyrimidin-5-yl)-4-morpholino-quinazolin-2-yl)pyridin-2-yl)ureido)-N,N-dimethyl-benzamide;

4-(3-(4-(7-(3,5-dimethylisoxazol-4-yl)-4-morpholino-pyrido[3,2-d]pyrimidin-2-yl)phenyl)ureido)-N,N-dimethyl-benzamide;

4-(3-(4-(7-(3,5-dimethylisoxazol-4-yl)-4-morpholino-quinazolin-2-yl)phenyl)ureido)-N,N-dimethyl-benzamide;

5-(3-(2-fluoro-4-(7-(5-methylfuran-2-yl)-4-morpholino-quinazolin-2-yl)phenyl)ureido)-N,N-dimethylpicolinamide;

5-(3-(2-fluoro-4-(4-morpholino-7-(pyrimidin-5-yl)quinazolin-2-yl)phenyl)ureido)-N,N-dimethylpicolinamide;

5-(3-(2-fluoro-4-(7-(1-methyl-1H-pyrazol-4-yl)-4-morpholino-pyrido[3,2-d]pyrimidin-2-yl)phenyl)ureido)-N,N-dimethylpicolinamide;

4-(3-(4-(4-(2,6-dimethylmorpholino)-7-(1-methyl-1H-pyrazol-4-yl)pyrido[3,2-d]pyrimidin-2-yl)phenyl)ureido)-N,N-dimethyl-benzamide;

4-(3-(4-(4-(2,6-dimethylmorpholino)-7-(1-methyl-1H-pyrazol-4-yl)pyrido[3,2-d]pyrimidin-2-yl)-2-fluorophenyl)ureido)-N,N-dimethyl-benzamide;

4-(3-(4-(7-(2-aminopyrimidin-5-yl)-4-morpholinopyrido[3,2-d]pyrimidin-2-yl)-2-fluorophenyl)ureido)-N,N-dimethyl-benzamide;

4-(3-(4-(4-(2,6-dimethylmorpholino)-7-(pyrimidin-5-yl)quinazolin-2-yl)phenyl)ureido)-N,N-dimethyl-benzamide;

N,N-dimethyl-5-(3-(5-(7-(5-methylfuran-2-yl)-4-morpholino-quinazolin-2-yl)pyridin-2-yl)ureido)picolinamide;

5-(3-(2-fluoro-4-(7-(3-(methylsulfonyl)phenyl)-4-morpholino-quinazolin-2-yl)phenyl)ureido)-N,N-dimethylpicolinamide;

4-(3-(4-(7-(3,5-dimethylisoxazol-4-yl)-4-morpholino-quinazolin-2-yl)-2-fluorophenyl)ureido)-N,N-dimethyl-benzamide;

4-(3-(4-(4-(2,6-dimethylmorpholino)-7-(pyrimidin-5-yl)quinazolin-2-yl)-2-fluorophenyl)ureido)-N,N-dimethyl-benzamide;

3-fluoro-N,N-dimethyl-4-(3-(4-(4-morpholino-7-(pyrimidin-5-yl)quinazolin-2-yl)phenyl)ureido)-benzamide;

3-fluoro-N,N-dimethyl-4-(3-(4-(7-(1-methyl-1H-pyrazol-4-yl)-4-morpholino-pyrido[3,2-d]pyrimidin-2-yl)phenyl)ureido)-benzamide;

4-(3-(4-(7-(3,5-dimethylisoxazol-4-yl)-4-morpholino-pyrido[3,2-d]pyrimidin-2-yl)-2-fluorophenyl)ureido)-N,N-dimethyl-benzamide;

3-fluoro-N,N-dimethyl-4-(3-(4-(7-(5-methylfuran-2-yl)-4-morpholino-quinazolin-2-yl)phenyl)ureido)-benzamide;

4-(3-(2-fluoro-4-(4-morpholino-7-(pyridin-4-yl)quinazolin-2-yl)phenyl)ureido)-N,N-dimethyl-benzamide;

N,N-dimethyl-4-(3-(4-(4-(2-methylmorpholino)-7-(pyrimidin-5-yl)quinazolin-2-yl)phenyl)ureido)-benzamide;

3-fluoro-4-(3-(2-fluoro-4-(4-morpholino-7-(pyrimidin-5-yl)quinazolin-2-yl)phenyl)ureido)-N,N-dimethyl-benzamide;

3-fluoro-N,N-dimethyl-4-(3-(5-(4-morpholino-7-(pyrimidin-5-yl)quinazolin-2-yl)pyridin-2-yl)ureido)-benzamide;

3-fluoro-4-(3-(2-fluoro-4-(7-(1-methyl-1H-pyrazol-4-yl)-4-morpholino-pyrido[3,2-d]pyrimidin-2-yl)phenyl)ureido)-N,N-dimethyl-benzamide;

N,N-dimethyl-4-(3-(4-(7-(5-methylfuran-2-yl)-4-(2-methylmorpholino)quinazolin-2-yl)phenyl)ureido)-benzamide;
4-(3-(4-(7-(3,5-dimethylisoxazol-4-yl)-6-fluoro-4-morpholino-quinazolin-2-yl)phenyl)ureido)-N,N-dimethyl-benzamide;
4-(3-(2-fluoro-4-(4-(2-methylmorpholino)-7-(pyrimidin-5-yl)quinazolin-2-yl)phenyl)ureido)-N,N-dimethyl-benzamide;
3-fluoro-4-(3-(4-(7-(2-fluoropyridin-3-yl)-4-morpholino-pyrido[3,2-d]pyrimidin-2-yl)phenyl)ureido)-N,N-dimethyl-benzamide;
3-fluoro-4-(3-(4-(7-(2-fluoropyridin-3-yl)-4-morpholino-quinazolin-2-yl)phenyl)ureido)-N,N-dimethyl-benzamide;
3-fluoro-4-(3-(4-(7-(2-methoxypyrimidin-5-yl)-4-morpholino-quinazolin-2-yl)phenyl)ureido)-N,N-dimethyl-benzamide;
N,N-dimethyl-4-(3-(4-(7-(1-methyl-1H-pyrazol-4-yl)-4-(2-methylmorpholino)pyrido[3,2-d]pyrimidin-2-yl)phenyl)ureido)-benzamide;
4-(3-(4-(6-fluoro-7-(furan-2-yl)-4-morpholino-quinazolin-2-yl)phenyl)ureido)-N,N-dimethyl-benzamide;
4-(3-(4-(7-(2-hydroxypyrimidin-5-yl)-4-morpholino-quinazolin-2-yl)phenyl)ureido)-N,N-dimethyl-benzamide;
4-(3-(2-fluoro-4-(7-(6-methoxypyridin-3-yl)-4-morpholino-quinazolin-2-yl)phenyl)ureido)-N,N-dimethyl-benzamide;
3-fluoro-N,N-dimethyl-4-(3-(4-(4-morpholino-7-(pyridin-3-yl)quinazolin-2-yl)phenyl)ureido)-benzamide;
3-fluoro-N,N-dimethyl-4-(3-(4-(4-morpholino-7-(pyridin-3-yl)pyrido[3,2-d]pyrimidin-2-yl)phenyl)ureido)-benzamide;
3-fluoro-N,N-dimethyl-4-(3-(4-(4-morpholino-7-(pyrimidin-5-yl)pyrido[3,2-d]pyrimidin-2-yl)phenyl)ureido)-benzamide;
N,N-dimethyl-4-(3-(4-(4-morpholino-7-(pyridin-2-yl)quinazolin-2-yl)phenyl)ureido)-benzamide;
4-(3-(2-fluoro-4-(4-morpholino-7-(pyridin-2-yl)quinazolin-2-yl)phenyl)ureido)-N,N-dimethyl-benzamide;
3-fluoro-4-(3-(4-(7-(2-methoxypyrimidin-5-yl)-4-morpholino-pyrido[3,2-d]pyrimidin-2-yl)phenyl)ureido)-N,N-dimethyl-benzamide;
1-(4-(7-(furan-2-yl)-4-morpholino-quinazolin-2-yl)phenyl)-3-(4-(4-methylpiperazine-1-carbonyl)phenyl)urea;
4-(3-(5-(7-(furan-2-yl)-4-morpholino-quinazolin-2-yl)pyridin-2-yl)ureido)-N,N-dimethyl-benzamide;
3-fluoro-4-(3-(4-(7-(furan-2-yl)-4-morpholino-quinazolin-2-yl)phenyl)ureido)-N,N-dimethyl-benzamide;
N,N-dimethyl-4-(3-(4-(7-(6-methylpyridin-3-yl)-4-morpholino-quinazolin-2-yl)phenyl)ureido)-benzamide;
N,N-dimethyl-4-(3-(4-(4-morpholino-7-(1,3,5-trimethyl-1H-pyrazol-4-yl)quinazolin-2-yl)phenyl)ureido)-benzamide;
4-(3-(4-(7-(2-methoxypyridin-3-yl)-4-morpholino-quinazolin-2-yl)phenyl)ureido)-N,N-dimethyl-benzamide;
4-(3-(4-(7-(5-fluoropyridin-3-yl)-4-morpholino-quinazolin-2-yl)phenyl)ureido)-N,N-dimethyl-benzamide;
N,N-dimethyl-4-(3-(4-(7-(2-methylpyridin-3-yl)-4-morpholino-quinazolin-2-yl)phenyl)ureido)-benzamide;
3-fluoro-N,N-dimethyl-4-(3-(4-(7-(6-methylpyridin-3-yl)-4-morpholino-quinazolin-2-yl)phenyl)ureido)-benzamide;
3-fluoro-N,N-dimethyl-4-(3-(4-(7-(2-methylpyridin-3-yl)-4-morpholino-quinazolin-2-yl)phenyl)ureido)-benzamide;
3-fluoro-N,N-dimethyl-4-(3-(4-(4-morpholino-7-(pyridin-2-yl)quinazolin-2-yl)phenyl)ureido)-benzamide;
4-(3-(4-(7-(4-methoxypyridin-3-yl)-4-morpholino-quinazolin-2-yl)phenyl)ureido)-N,N-dimethyl-benzamide;
3-fluoro-4-(3-(4-(7-(6-methoxypyridin-3-yl)-4-morpholino-quinazolin-2-yl)phenyl)ureido)-N,N-dimethyl-benzamide;
3-chloro-4-(3-(4-(7-(furan-2-yl)-4-morpholino-quinazolin-2-yl)phenyl)ureido)-N,N-dimethyl-benzamide;
3-fluoro-N,N-dimethyl-4-(3-(5-(7-(1-methyl-1H-pyrazol-4-yl)-4-morpholino-quinazolin-2-yl)pyridin-2-yl)ureido)-benzamide;
3-fluoro-4-(3-(4-(6-fluoro-4-morpholino-7-(pyridin-3-yl)quinazolin-2-yl)phenyl)ureido)-N,N-dimethyl-benzamide;
3-fluoro-4-(3-(4-(6-fluoro-4-morpholino-7-(pyrimidin-5-yl)quinazolin-2-yl)phenyl)ureido)-N,N-dimethyl-benzamide;
4-(3-(5-(6-fluoro-4-morpholino-7-(pyridin-3-yl)quinazolin-2-yl)pyridin-2-yl)ureido)-N,N-dimethyl-benzamide;
4-(3-(5-(6-fluoro-4-morpholino-7-(pyrimidin-5-yl)quinazolin-2-yl)pyridin-2-yl)ureido)-N,N-dimethyl-benzamide;
4-(3-(4-(7-(6-aminopyridin-3-yl)-4-morpholino-quinazolin-2-yl)phenyl)ureido)-N,N-dimethyl-benzamide;
4-(3-(4-(7-(6-aminopyridin-3-yl)-4-morpholino-quinazolin-2-yl)phenyl)ureido)-3-fluoro-N,N-dimethyl-benzamide;
N,N-dimethyl-4-(3-(4-(4-morpholino-quinazolin-2-yl)phenyl)ureido)-benzamide 4-(3-(4-(7-methoxy-4-morpholino-quinazolin-2-yl)phenyl)ureido)-N,N-dimethyl-benzamide;
4-(3-(4-(6,7-dimethoxy-4-morpholino-quinazolin-2-yl)phenyl)ureido)-N,N-dimethyl-benzamide;
4-(3-(2-fluoro-4-(7-methoxy-4-morpholino-quinazolin-2-yl)phenyl)ureido)-N,N-dimethyl-benzamide;
4-(3-(4-(7-(5-(hydroxymethyl)furan-2-yl)-4-morpholino-quinazolin-2-yl)phenyl)ureido)-N,N-dimethyl-benzamide;
(R)-1-(4-(3-(dimethylamino)pyrrolidine-1-carbonyl)phenyl)-3-(4-(7-(1-methyl-1H-pyrazol-4-yl)-4-morpholino-pyrido[3,2-d]pyrimidin-2-yl)phenyl)urea;
(S)-1-(4-(3-(dimethylamino)pyrrolidine-1-carbonyl)phenyl)-3-(4-(7-(1-methyl-1H-pyrazol-4-yl)-4-morpholino-pyrido[3,2-d]pyrimidin-2-yl)phenyl)urea;
1-(4-(4-(dimethylamino)piperidine-1-carbonyl)phenyl)-3-(4-(7-(1-methyl-1H-pyrazol-4-yl)-4-morpholino-pyrido[3,2-d]pyrimidin-2-yl)phenyl)urea;
(R)-1-(4-(3-(dimethylamino)pyrrolidine-1-carbonyl)phenyl)-3-(4-(4-morpholino-7-(pyrimidin-5-yl)quinazolin-2-yl)phenyl)urea;
(S)-1-(4-(3-(dimethylamino)pyrrolidine-1-carbonyl)phenyl)-3-(4-(4-morpholino-7-(pyrimidin-5-yl)quinazolin-2-yl)phenyl)urea;
1-(4-(3-hydroxypyrrolidine-1-carbonyl)phenyl)-3-(4-(4-morpholino-7-(pyrimidin-5-yl)quinazolin-2-yl)phenyl)urea;
4-(3-(4-(7-(5-((dimethylamino)methyl)furan-2-yl)-4-morpholino-quinazolin-2-yl)phenyl)ureido)-N,N-dimethyl-benzamide;

1-(4-(4-(dimethylamino)piperidine-1-carbonyl)phenyl)-3-(4-(7-(5-methylfuran-2-yl)-4-morpholino-quinazolin-2-yl)phenyl)urea;
N-(2-(dimethylamino)ethyl)-4-(3-(4-(4-morpholino-7-(pyrimidin-5-yl)quinazolin-2-yl)phenyl)ureido)-benzamide;
1-(4-(4-(dimethylamino)piperidine-1-carbonyl)phenyl)-3-(4-(7-(4-methylpyridin-3-yl)-4-morpholino-quinazolin-2-yl)phenyl)urea;
(S)-1-(4-(3-aminopyrrolidine-1-carbonyl)phenyl)-3-(4-(4-morpholino-7-(pyrimidin-5-yl)quinazolin-2-yl)phenyl)urea;
(S)-1-(4-(3-(dimethylamino)pyrrolidine-1-carbonyl)phenyl)-3-(4-(7-(5-methylfuran-2-yl)-4-morpholino-quinazolin-2-yl)phenyl)urea;
(R)-1-(4-(3-(dimethylamino)pyrrolidine-1-carbonyl)phenyl)-3-(4-(7-(5-methylfuran-2-yl)-4-morpholino-quinazolin-2-yl)phenyl)urea;
(R)-1-(4-(3-aminopyrrolidine-1-carbonyl)phenyl)-3-(4-(4-morpholino-7-(pyrimidin-5-yl)quinazolin-2-yl)phenyl)urea;
(S)-1-(4-(3-(dimethylamino)pyrrolidine-1-carbonyl)phenyl)-3-(4-(6-fluoro-4-morpholino-7-(pyridin-3-yl)quinazolin-2-yl)phenyl)urea;
(S)-1-(4-(3-(dimethylamino)pyrrolidine-1-carbonyl)phenyl)-3-(4-(4-morpholino-7-(pyrimidin-5-yl)pyrido[3,2-d]pyrimidin-2-yl)phenyl)urea;
(R)-1-(4-(3-(dimethylamino)pyrrolidine-1-carbonyl)phenyl)-3-(4-(6-fluoro-4-morpholino-7-(pyridin-3-yl)quinazolin-2-yl)phenyl)urea;
N-(2-(dimethylamino)ethyl)-4-(3-(4-(7-(5-methylfuran-2-yl)-4-morpholino-quinazolin-2-yl)phenyl)ureido)-benzamide;
4-(3-(4-(7-(1-methyl-1H-pyrazol-4-yl)-4-morpholino-pyrido[3,2-d]pyrimidin-2-yl)phenyl)ureido)-benzamide;
4-(3-(2-fluoro-4-(7-(5-(hydroxymethyl)furan-2-yl)-4-morpholino-quinazolin-2-yl)phenyl)ureido)-N,N-dimethyl-benzamide;
1-(4-(3-hydroxypyrrolidine-1-carbonyl)phenyl)-3-(4-(7-(5-methylfuran-2-yl)-4-morpholino-quinazolin-2-yl)phenyl)urea;
(R)-1-(4-(3-(dimethylamino)pyrrolidine-1-carbonyl)phenyl)-3-(2-fluoro-4-(7-(1-methyl-1H-pyrazol-4-yl)-4-morpholino-pyrido[3,2-d]pyrimidin-2-yl)phenyl)urea;
4-(3-(4-(7-(5-(1-hydroxyethyl)furan-2-yl)-4-morpholino-quinazolin-2-yl)phenyl)ureido)-N,N-dimethyl-benzamide;
(S)-1-(4-(3-(dimethylamino)pyrrolidine-1-carbonyl)phenyl)-3-(2-fluoro-4-(4-morpholino-7-(pyrimidin-5-yl)quinazolin-2-yl)phenyl)urea;
(S)-1-(4-(3-aminopyrrolidine-1-carbonyl)phenyl)-3-(2-fluoro-4-(4-morpholino-7-(pyrimidin-5-yl)quinazolin-2-yl)phenyl)urea;
(R)-1-(4-(3-aminopyrrolidine-1-carbonyl)phenyl)-3-(2-fluoro-4-(4-morpholino-7-(pyrimidin-5-yl)quinazolin-2-yl)phenyl)urea;
(S)-1-(4-(3-(dimethylamino)pyrrolidine-1-carbonyl)phenyl)-3-(2-fluoro-4-(7-(1-methyl-1H-pyrazol-4-yl)-4-morpholino-pyrido[3,2-d]pyrimidin-2-yl)phenyl)urea;
1-(2-fluoro-4-(6-fluoro-4-morpholino-7-(pyridin-3-yl)quinazolin-2-yl)phenyl)-3-(4-(4-methylpiperazine-1-carbonyl)phenyl)urea;
1-(2-fluoro-4-(4-morpholino-7-(pyridin-4-yl)quinazolin-2-yl)phenyl)-3-(4-(4-methylpiperazine-1-carbonyl)phenyl)urea;
(S)-1-(4-(3-(dimethylamino)pyrrolidine-1-carbonyl)phenyl)-3-(2-fluoro-4-(7-(2-fluoropyridin-3-yl)-4-morpholino-pyrido[3,2-d]pyrimidin-2-yl)phenyl)urea;
4-(3-(2-fluoro-4-(7-(5-(1-hydroxyethyl)furan-2-yl)-4-morpholino-quinazolin-2-yl)phenyl)ureido)-N,N-dimethyl-benzamide;
4-(3-(2-fluoro-4-(4-morpholino-7-(pyrimidin-5-yl)quinazolin-2-yl)phenyl)ureido)-N-methyl-benzamide;
4-(3-(4-(7-(5-(1-hydroxyethyl)furan-2-yl)-4-morpholino-pyrido[3,2-d]pyrimidin-2-yl)phenyl)ureido)-N,N-dimethyl-benzamide;
N-(2-(dimethylamino)ethyl)-4-(3-(2-fluoro-4-(4-morpholino-7-(pyrimidin-5-yl)quinazolin-2-yl)phenyl)ureido)-benzamide;
4-(3-(2-fluoro-4-(7-(5-(hydroxymethyl)furan-2-yl)-4-morpholino-pyrido[3,2-d]pyrimidin-2-yl)phenyl)ureido)-N,N-dimethyl-benzamide;
3-fluoro-4-(3-(4-(7-(5-(hydroxymethyl)furan-2-yl)-4-morpholino-quinazolin-2-yl)phenyl)ureido)-N,N-dimethyl-benzamide;
(S)-1-(4-(3-(dimethylamino)pyrrolidine-1-carbonyl)phenyl)-3-(4-(7-(3,5-dimethylisoxazol-4-yl)-4-morpholino-quinazolin-2-yl)phenyl)urea;
(S)-1-(4-(3-(dimethylamino)pyrrolidine-1-carbonyl)phenyl)-3-(4-(7-(3,5-dimethylisoxazol-4-yl)-4-morpholino-quinazolin-2-yl)-2-fluorophenyl)urea;
4-(3-(4-(7-(5-(2-hydroxypropan-2-yl)furan-2-yl)-4-morpholino-quinazolin-2-yl)phenyl)ureido)-N,N-dimethyl-benzamide;
4-(3-(4-(7-(5-cyanofuran-2-yl)-4-morpholino-quinazolin-2-yl)phenyl)ureido)-N,N-dimethyl-benzamide;
4-(3-(4-(7-(5-acetylfuran-2-yl)-4-morpholino-quinazolin-2-yl)phenyl)ureido)-N,N-dimethyl-benzamide;
N-(2-(dimethylamino)ethyl)-5-(2-(4-(3-(4-(dimethylcarbamoyl)phenyl)ureido)phenyl)-4-morpholino-quinazolin-7-yl)furan-2-carboxamide;
4-(3-(4-(7-(2-(dimethylamino)pyrimidin-5-yl)-4-morpholino-quinazolin-2-yl)phenyl)ureido)-N,N-dimethyl-benzamide;
3-fluoro-4-(3-(4-(7-(5-(1-hydroxyethyl)furan-2-yl)-4-morpholino-quinazolin-2-yl)phenyl)ureido)-N,N-dimethyl-benzamide;
3-fluoro-4-(3-(4-(7-(5-(hydroxymethyl)furan-2-yl)-4-morpholino-quinazolin-2-yl)phenyl)ureido)-N,N-dimethyl-benzamide;
5-(2-(4-(3-(4-(dimethylcarbamoyl)phenyl)ureido)phenyl)-4-morpholino-quinazolin-7-yl)-N,N-dimethylfuran-2-carboxamide;
4-(3-(4-(7-(2-(dimethylamino)pyrimidin-5-yl)-4-morpholino-pyrido[3,2-d]pyrimidin-2-yl)phenyl)ureido)-N,N-dimethyl-benzamide;
4-(3-(4-(7-(2-(dimethylamino)pyrimidin-5-yl)-4-morpholino-quinazolin-2-yl)-2-fluorophenyl)ureido)-N,N-dimethyl-benzamide;
1-(4-(7-(furan-2-yl)-4-morpholino-quinazolin-2-yl)phenyl)-3-(4-(3-hydroxypyrrolidine-1-carbonyl)phenyl)urea;
4-(3-(4-(7-(furan-2-yl)-4-morpholino-quinazolin-2-yl)phenyl)ureido)-N-methyl-benzamide;
(S)-1-(4-(3-aminopyrrolidine-1-carbonyl)phenyl)-3-(4-(7-(furan-2-yl)-4-morpholino-quinazolin-2-yl)phenyl)urea;
N-(2-(dimethylamino)ethyl)-4-(3-(4-(7-(furan-2-yl)-4-morpholino-quinazolin-2-yl)phenyl)ureido)-benzamide;

N-(2-(dimethylamino)ethyl)-4-(3-(4-(7-(furan-2-yl)-4-morpholino-quinazolin-2-yl)phenyl)ureido)-N-methyl-benzamide;
4-(3-(3-fluoro-4-(4-morpholino-7-(pyrimidin-5-yl)quinazolin-2-yl)phenyl)ureido)-N,N-dimethyl-benzamide;
4-(3-(3-fluoro-4-(7-(1-methyl-1H-pyrazol-4-yl)-4-morpholino-pyrido[3,2-d]pyrimidin-2-yl)phenyl)ureido)-N,N-dimethyl-benzamide;
4-(3-(3-fluoro-4-(7-(5-methylfuran-2-yl)-4-morpholino-quinazolin-2-yl)phenyl)ureido)-N,N-dimethyl-benzamide;
2-fluoro-N,N-dimethyl-4-(3-(4-(4-morpholino-7-(pyrimidin-5-yl)quinazolin-2-yl)phenyl)ureido)-benzamide;
4-(3-(3-fluoro-4-(7-(2-fluoropyridin-3-yl)-4-morpholino-quinazolin-2-yl)phenyl)ureido)-N,N-dimethyl-benzamide;
4-(3-(3-fluoro-4-(7-(2-methoxypyrimidin-5-yl)-4-morpholino-quinazolin-2-yl)phenyl)ureido)-N,N-dimethyl-benzamide;
4-(3-(3-fluoro-4-(4-morpholino-7-(pyridin-3-yl)quinazolin-2-yl)phenyl)ureido)-N,N-dimethyl-benzamide;
4-(3-(3-fluoro-4-(7-(2-fluoropyridin-3-yl)-4-morpholino-pyrido[3,2-d]pyrimidin-2-yl)phenyl)ureido)-N,N-dimethyl-benzamide;
4-(3-(3-fluoro-4-(7-(3-(methylsulfonyl)phenyl)-4-morpholino-quinazolin-2-yl)phenyl)ureido)-N,N-dimethyl-benzamide;
4-(3-(4-(7-(3,5-dimethylisoxazol-4-yl)-4-morpholino-quinazolin-2-yl)phenyl)ureido)-2-fluoro-N,N-dimethyl-benzamide;
4-(3-(3-fluoro-4-(7-(furan-2-yl)-4-morpholino-quinazolin-2-yl)phenyl)ureido)-N,N-dimethyl-benzamide;
2-fluoro-4-(3-(4-(7-(2-fluoropyridin-3-yl)-4-morpholino-pyrido[3,2-d]pyrimidin-2-yl)phenyl)ureido)-N,N-dimethyl-benzamide;
4-(3-(3-fluoro-4-(7-(1-methyl-1H-pyrazol-4-yl)-4-morpholino-quinazolin-2-yl)phenyl)ureido)-N,N-dimethyl-benzamide;
4-(3-(3-fluoro-4-(4-morpholino-7-(pyrimidin-5-yl)pyrido[3,2-d]pyrimidin-2-yl)phenyl)ureido)-N,N-dimethyl-benzamide;
5-(3-(3-fluoro-4-(4-morpholino-7-(pyrimidin-5-yl)quinazolin-2-yl)phenyl)ureido)-N,N-dimethylpicolinamide;
4-(3-(4-(7-(3,5-dimethylisoxazol-4-yl)-4-morpholino-quinazolin-2-yl)-3-fluorophenyl)ureido)-N,N-dimethyl-benzamide;
2-fluoro-N,N-dimethyl-4-(3-(5-(7-(3-(methylsulfonyl)phenyl)-4-morpholino-quinazolin-2-yl)pyridin-2-yl)ureido)-benzamide;
4-(3-(3-fluoro-4-(4-(2-methylmorpholino)-7-(pyrimidin-5-yl)quinazolin-2-yl)phenyl)ureido)-N,N-dimethyl-benzamide;
2-fluoro-4-(3-(4-(7-(2-fluoropyridin-3-yl)-4-morpholino-quinazolin-2-yl)phenyl)ureido)-N,N-dimethyl-benzamide;
4-(3-(3-fluoro-4-(6-fluoro-4-morpholino-7-(pyrimidin-5-yl)quinazolin-2-yl)phenyl)ureido)-N,N-dimethyl-benzamide;
2-fluoro-4-(3-(4-(7-(2-methoxypyrimidin-5-yl)-4-morpholino-quinazolin-2-yl)phenyl)ureido)-N,N-dimethyl-benzamide;
4-(3-(3-fluoro-4-(7-(6-methoxypyridin-3-yl)-4-morpholino-quinazolin-2-yl)phenyl)ureido)-N,N-dimethyl-benzamide;
2-fluoro-4-(3-(4-(7-(6-methoxypyridin-3-yl)-4-morpholino-quinazolin-2-yl)phenyl)ureido)-N,N-dimethyl-benzamide;
2-fluoro-N,N-dimethyl-4-(3-(4-(4-morpholino-7-(pyridin-3-yl)quinazolin-2-yl)phenyl)ureido)-benzamide;
4-(3-(3-fluoro-4-(4-morpholino-7-(pyridin-3-yl)pyrido[3,2-d]pyrimidin-2-yl)phenyl)ureido)-N,N-dimethyl-benzamide;
2-fluoro-N,N-dimethyl-4-(3-(4-(4-morpholino-7-(pyrimidin-5-yl)pyrido[3,2-d]pyrimidin-2-yl)phenyl)ureido)-benzamide;
4-(3-(3-fluoro-4-(7-(2-methoxypyrimidin-5-yl)-4-morpholino-pyrido[3,2-d]pyrimidin-2-yl)phenyl)ureido)-N,N-dimethyl-benzamide;
2-fluoro-N,N-dimethyl-4-(3-(4-(4-morpholino-7-(pyridin-3-yl)pyrido[3,2-d]pyrimidin-2-yl)phenyl)ureido)-benzamide;
2-fluoro-4-(3-(4-(7-(furan-2-yl)-4-morpholino-quinazolin-2-yl)phenyl)ureido)-N,N-dimethyl-benzamide;
2-fluoro-N,N-dimethyl-4-(3-(4-(7-(5-methylfuran-2-yl)-4-morpholino-quinazolin-2-yl)phenyl)ureido)-benzamide;
2-fluoro-N,N-dimethyl-4-(3-(4-(4-morpholino-7-(pyridin-2-yl)quinazolin-2-yl)phenyl)ureido)-benzamide;
4-(3-(3-fluoro-4-(4-morpholino-7-(pyridin-2-yl)quinazolin-2-yl)phenyl)ureido)-N,N-dimethyl-benzamide;
4-(3-(3-fluoro-4-(4-morpholino-7-(1,3,5-trimethyl-1H-pyrazol-4-yl)quinazolin-2-yl)phenyl)ureido)-N,N-dimethyl-benzamide;
4-(3-(3-fluoro-4-(7-(2-methoxypyridin-3-yl)-4-morpholino-quinazolin-2-yl)phenyl)ureido)-N,N-dimethyl-benzamide;
4-(3-(3-fluoro-4-(7-(6-methylpyridin-3-yl)-4-morpholino-quinazolin-2-yl)phenyl)ureido)-N,N-dimethyl-benzamide;
4-(3-(3-fluoro-4-(7-(2-methylpyridin-3-yl)-4-morpholino-quinazolin-2-yl)phenyl)ureido)-N,N-dimethyl-benzamide;
2-fluoro-N,N-dimethyl-4-(3-(4-(7-(1-methyl-1H-pyrazol-4-yl)-4-morpholino-pyrido[3,2-d]pyrimidin-2-yl)phenyl)ureido)-benzamide;
4-(3-(3-fluoro-4-(7-(5-(hydroxymethyl)furan-2-yl)-4-morpholino-quinazolin-2-yl)phenyl)ureido)-N,N-dimethyl-benzamide;
4-(3-(3-fluoro-4-(7-(5-(1-hydroxyethyl)furan-2-yl)-4-morpholino-quinazolin-2-yl)phenyl)ureido)-N,N-dimethyl-benzamide;
4-(3-(3-fluoro-4-(7-(5-(2-hydroxypropan-2-yl)furan-2-yl)-4-morpholino-quinazolin-2-yl)phenyl)ureido)-N,N-dimethyl-benzamide;
4-(3-(4-(7-(2-(dimethylamino)pyrimidin-5-yl)-4-morpholino-quinazolin-2-yl)-3-fluorophenyl)ureido)-N,N-dimethyl-benzamide;
2-fluoro-4-(3-(4-(7-(5-(hydroxymethyl)furan-2-yl)-4-morpholino-quinazolin-2-yl)phenyl)ureido)-N,N-dimethyl-benzamide;
4-(3-(2,5-difluoro-4-(4-morpholino-7-(pyrimidin-5-yl)quinazolin-2-yl)phenyl)ureido)-N,N-dimethyl-benzamide;
4-(3-(2,3-difluoro-4-(4-morpholino-7-(pyrimidin-5-yl)quinazolin-2-yl)phenyl)ureido)-N,N-dimethyl-benzamide;
4-(3-(2,3-difluoro-4-(7-(5-methylfuran-2-yl)-4-morpholino-quinazolin-2-yl)phenyl)ureido)-N,N-dimethyl-benzamide;

-(3-(2,3-difluoro-4-(7-(furan-2-yl)-4-morpholino-quinazolin-2-yl)phenyl)ureido)-N,N-dimethyl-benzamide;
4-(3-(4-(7-(2-((2-hydroxyethyl)amino)pyridin-3-yl)-4-morpholino-quinazolin-2-yl)phenyl)ureido)-N,N-dimethyl-benzamide;
4-(3-(4-(7-((4-hydroxypiperidin-1-yl)methyl)-4-morpholino-quinazolin-2-yl)phenyl)ureido)-N,N-dimethyl-benzamide;
4-(3-(4-(7-(hydroxymethyl)-4-morpholino-quinazolin-2-yl)phenyl)ureido)-N,N-dimethyl-benzamide;
1-(4-(4-(dimethylamino)piperidine-1-carbonyl)phenyl)-3-(4-(7-(2-hydroxypropan-2-yl)-4-morpholino-quinazolin-2-yl)phenyl)urea;
4-(3-(4-(7-(4-(dimethylamino)piperidine-1-carbonyl)-4-morpholino-quinazolin-2-yl)phenyl)ureido)-N,N-dimethyl-benzamide;
(R)-1-(4-(3-(dimethylamino)pyrrolidine-1-carbonyl)phenyl)-3-(4-(7-(2-hydroxypropan-2-yl)-4-morpholino-quinazolin-2-yl)phenyl)urea;
(S)-1-(4-(3-(dimethylamino)pyrrolidine-1-carbonyl)phenyl)-3-(4-(7-(2-hydroxypropan-2-yl)-4-morpholino-quinazolin-2-yl)phenyl)urea;
4-(3-(2-fluoro-4-(7-(2-hydroxypropan-2-yl)-4-morpholino-quinazolin-2-yl)phenyl)ureido)-N,N-dimethyl-benzamide;
N-(4-(3-(4-(4-morpholino-7-(pyrimidin-5-yl)quinazolin-2-yl)phenyl)ureido)phenyl)-acetamide;
1-(4-(7-(2-fluoropyridin-3-yl)-4-morpholinoquinazolin-2-yl)phenyl)-3-(4-(2-oxopyrrolidin-1-yl)phenyl)urea;
N-(4-(3-(4-(7-(2-fluoropyridin-3-yl)-4-morpholinopyrido[3,2-d]pyrimidin-2-yl)phenyl)ureido)phenyl)acetamide;
N-(4-(3-(4-(7-(1-methyl-1H-pyrazol-4-yl)-4-morpholinopyrido[3,2-d]pyrimidin-2-yl)phenyl)ureido)phenyl)acetamide;
N,N-dimethyl-4-(3-(4-(4-morpholino-7-(1,3,5-trimethyl-1H-pyrazol-4-yl)pyrido[3,2-d]pyrimidin-2-yl)phenyl)ureido)-benzamide;
4-(3-(2-fluoro-4-(4-morpholino-7-(1,3,5-trimethyl-1H-pyrazol-4-yl)pyrido[3,2-d]pyrimidin-2-yl)phenyl)ureido)-N,N-dimethyl-benzamide;
N,N-dimethyl-4-(3-(4-(7-(2-methylpyridin-3-yl)-4-morpholinopyrido[3,2-d]pyrimidin-2-yl)phenyl)ureido)-benzamide;
4-(3-(2-fluoro-4-(7-(2-methylpyridin-3-yl)-4-morpholinopyrido[3,2-d]pyrimidin-2-yl)phenyl)ureido)-N,N-dimethyl-benzamide;
N,N-dimethyl-4-(3-(4-(7-(6-methylpyridin-3-yl)-4-morpholinopyrido[3,2-d]pyrimidin-2-yl)phenyl)ureido)-benzamide;
4-(3-(2-fluoro-4-(7-(6-methylpyridin-3-yl)-4-morpholinopyrido[3,2-d]pyrimidin-2-yl)phenyl)ureido)-N,N-dimethyl-benzamide;
N-(4-(3-(4-(7-(5-methylfuran-2-yl)-4-morpholinopyrido[3,2-d]pyrimidin-2-yl)phenyl)ureido)phenyl)acetamide;
N-(4-(3-(4-(7-(2-fluoropyridin-3-yl)-4-morpholinopyrido[3,2-d]pyrimidin-2-yl)phenyl)ureido)phenyl)acetamide;
N-(4-(3-(4-(4-morpholino-7-(pyridin-3-yl)pyrido[3,2-d]pyrimidin-2-yl)phenyl)ureido)phenyl)acetamide;
N-(4-(3-(4-(4-morpholino-7-(pyridin-4-yl)pyrido[3,2-d]pyrimidin-2-yl)phenyl)ureido)phenyl)acetamide;
N-(4-(3-(4-(4-morpholino-7-(pyridin-2-yl)pyrido[3,2-d]pyrimidin-2-yl)phenyl)ureido)phenyl)acetamide;
N-(4-(3-(4-(4-morpholino-7-(pyrimidin-5-yl)pyrido[3,2-d]pyrimidin-2-yl)phenyl)ureido)phenyl)acetamide;
N-(4-(3-(4-(4-morpholino-7-(pyridazin-4-yl)pyrido[3,2-d]pyrimidin-2-yl)phenyl)ureido)phenyl)acetamide;
N-(4-(3-(4-(7-(2-methoxypyrimidin-5-yl)-4-morpholinopyrido[3,2-d]pyrimidin-2-yl)phenyl)ureido)phenyl)acetamide;
N-(4-(3-(4-(7-(6-methoxypyridin-3-yl)-4-morpholinopyrido[3,2-d]pyrimidin-2-yl)phenyl)ureido)phenyl)acetamide;
N-(4-(3-(4-(7-(3-(methylsulfonyl)phenyl)-4-morpholinopyrido[3,2-d]pyrimidin-2-yl)phenyl)ureido)phenyl)acetamide;
N-(4-(3-(4-(7-(2-aminopyrimidin-5-yl)-4-morpholinopyrido[3,2-d]pyrimidin-2-yl)phenyl)ureido)phenyl)acetamide;
N-(4-(3-(4-(4-morpholino-7-(1,3,5-trimethyl-1H-pyrazol-4-yl)quinazolin-2-yl)phenyl)ureido)phenyl)acetamide;
N-(4-(3-(4-(7-(2-methylpyridin-3-yl)-4-morpholinopyrido[3,2-d]pyrimidin-2-yl)phenyl)ureido)phenyl)acetamide;
N-(4-(3-(4-(7-(6-methylpyridin-3-yl)-4-morpholinopyrido[3,2-d]pyrimidin-2-yl)phenyl)ureido)phenyl)acetamide;
N-(4-(3-(5-(7-(2-fluoropyridin-3-yl)-4-morpholinopyrido[3,2-d]pyrimidin-2-yl)pyridin-2-yl)ureido)phenyl)acetamide;
N-(4-(3-(5-(7-(1-methyl-1H-pyrazol-4-yl)-4-morpholinopyrido[3,2-d]pyrimidin-2-yl)pyridin-2-yl)ureido)phenyl)acetamide;
4-(3-(4-(7-(5-ethylfuran-2-yl)-4-morpholinoquinazolin-2-yl)phenyl)ureido)-N,N-dimethyl-benzamide;
4-(3-(4-(7-(5-(1,2-dihydroxyethyl)furan-2-yl)-4-morpholinoquinazolin-2-yl)phenyl)ureido)-N,N-dimethyl-benzamide;
N-(4-(3-(4-(7-(5-ethylfuran-2-yl)-4-morpholinoquinazolin-2-yl)phenyl)ureido)phenyl)acetamide;
N-(4-(3-(4-(7-(5-(hydroxymethyl)furan-2-yl)-4-morpholinoquinazolin-2-yl)phenyl)ureido)phenyl)acetamide;
N-(4-(3-(4-(7-(5-(1-hydroxyethyl)furan-2-yl)-4-morpholinoquinazolin-2-yl)phenyl)ureido)phenyl)acetamide;
N-(4-(3-(4-(7-(5-(2-hydroxypropan-2-yl)furan-2-yl)-4-morpholinoquinazolin-2-yl)phenyl)ureido)phenyl)acetamide;
N-(4-(3-(4-(7-(furan-2-yl)-4-morpholinoquinazolin-2-yl)phenyl)ureido)phenyl)acetamide;
N-(4-(3-(4-(4-morpholino-7-(pyridin-3-yl)quinazolin-2-yl)phenyl)ureido)phenyl)acetamide;
N-(4-(3-(4-(4-morpholino-7-(pyridin-4-yl)quinazolin-2-yl)phenyl)ureido)phenyl)acetamide;
N-(4-(3-(4-(4-morpholino-7-(pyridin-2-yl)quinazolin-2-yl)phenyl)ureido)phenyl)acetamide;
N-(4-(3-(4-(4-morpholino-7-(pyridazin-4-yl)quinazolin-2-yl)phenyl)ureido)phenyl)acetamide;
N-(4-(3-(4-(7-(2-methoxypyrimidin-5-yl)-4-morpholino-quinazolin-2-yl)phenyl)ureido)phenyl)acetamide;
N-(4-(3-(4-(7-(6-methoxypyridin-3-yl)-4-morpholino-quinazolin-2-yl)phenyl)ureido)phenyl)acetamide;
N-(4-(3-(4-(7-(3-(methylsulfonyl)phenyl)-4-morpholino-quinazolin-2-yl)phenyl)ureido)phenyl)acetamide;
N-(4-(3-(4-(7-(2-aminopyrimidin-5-yl)-4-morpholino-quinazolin-2-yl)phenyl)ureido)phenyl)acetamide;

N-(4-(3-(4-(4-morpholino-7-(1,3,5-trimethyl-1H-pyrazol-4-yl)quinazolin-2-yl)phenyl)ureido)phenyl)acetamide;
N-(4-(3-(4-(7-(2-methylpyridin-3-yl)-4-morpholinoquinazolin-2-yl)phenyl)ureido)phenyl)acetamide;
N-(4-(3-(4-(7-(6-methylpyridin-3-yl)-4-morpholinoquinazolin-2-yl)phenyl)ureido)phenyl)acetamide;
N-(4-(3-(5-(7-(5-methylfuran-2-yl)-4-morpholinoquinazolin-2-yl)pyridin-2-yl)ureido)phenyl)acetamide;
N-(4-(3-(5-(7-(furan-2-yl)-4-morpholinoquinazolin-2-yl)pyridin-2-yl)ureido)phenyl)acetamide;
N-(4-(3-(5-(4-morpholino-7-(pyrimidin-5-yl)quinazolin-2-yl)pyridin-2-yl)ureido)phenyl)acetamide;
N-(4-(3-(5-(7-(1-methyl-1H-pyrazol-4-yl)-4-morpholinoquinazolin-2-yl)pyridin-2-yl)ureido)phenyl)acetamide;
N-(4-(3-(4-(6-fluoro-7-(5-methylfuran-2-yl)-4-morpholinoquinazolin-2-yl)phenyl)ureido)phenyl)acetamide;
N-(4-(3-(4-(6-fluoro-7-(furan-2-yl)-4-morpholinoquinazolin-2-yl)phenyl)ureido)phenyl)acetamide;
N-(4-(3-(4-(6-fluoro-4-morpholino-7-(pyridin-3-yl)quinazolin-2-yl)phenyl)ureido)phenyl)acetamide;
N-(4-(3-(4-(6-fluoro-4-morpholino-7-(pyrimidin-5-yl)quinazolin-2-yl)phenyl)ureido)phenyl)acetamide;
N-(3-fluoro-4-(3-(4-(7-(5-methylfuran-2-yl)-4-morpholinoquinazolin-2-yl)phenyl)ureido)phenyl)acetamide;
N-(4-(3-(4-(7-(5-ethylfuran-2-yl)-4-morpholinoquinazolin-2-yl)phenyl)ureido)-3-fluorophenyl)acetamide;
N-(3-fluoro-4-(3-(4-(7-(furan-2-yl)-4-morpholinoquinazolin-2-yl)phenyl)ureido)phenyl)acetamide;
N-(3-fluoro-4-(3-(4-(4-morpholino-7-(pyridin-3-yl)quinazolin-2-yl)phenyl)ureido)phenyl)acetamide;
N-(3-fluoro-4-(3-(4-(7-(2-fluoropyridin-3-yl)-4-morpholinoquinazolin-2-yl)phenyl)ureido)phenyl)acetamide;
N-(3-fluoro-4-(3-(4-(7-(2-methylpyridin-3-yl)-4-morpholinoquinazolin-2-yl)phenyl)ureido)phenyl)acetamide;
N-(3-fluoro-4-(3-(4-(7-(6-methylpyridin-3-yl)-4-morpholinoquinazolin-2-yl)phenyl)ureido)phenyl)acetamide;
N-(3-fluoro-4-(3-(4-(4-morpholino-7-(pyridin-2-yl)quinazolin-2-yl)phenyl)ureido)phenyl)acetamide;
N-(3-fluoro-4-(3-(4-(4-morpholino-7-(pyridin-4-yl)quinazolin-2-yl)phenyl)ureido)phenyl)acetamide;
N-(3-fluoro-4-(3-(4-(4-morpholino-7-(pyrimidin-5-yl)quinazolin-2-yl)phenyl)ureido)phenyl)acetamide;
N-(3-fluoro-4-(3-(4-(7-(2-methoxypyrimidin-5-yl)-4-morpholinoquinazolin-2-yl)phenyl)ureido)phenyl)acetamide;
N-(4-(3-(4-(7-(2-aminopyrimidin-5-yl)-4-morpholinoquinazolin-2-yl)phenyl)ureido)-3-fluorophenyl)acetamide;
N-(3-fluoro-4-(3-(4-(7-(6-methoxypyridin-3-yl)-4-morpholinoquinazolin-2-yl)phenyl)ureido)phenyl)acetamide;
N-(3-fluoro-4-(3-(4-(7-(1-methyl-1H-pyrazol-4-yl)-4-morpholinoquinazolin-2-yl)phenyl)ureido)phenyl)acetamide;
N-(3-fluoro-4-(3-(4-(4-morpholino-7-(1,3,5-trimethyl-1H-pyrazol-4-yl)quinazolin-2-yl)phenyl)ureido)phenyl)acetamide;
N-(3-fluoro-4-(3-(4-(7-(3-(methylsulfonyl)phenyl)-4-morpholinoquinazolin-2-yl)phenyl)ureido)phenyl)acetamide;
N-(3-fluoro-4-(3-(4-(7-(5-(hydroxymethyl)furan-2-yl)-4-morpholinoquinazolin-2-yl)phenyl)ureido)phenyl)acetamide;
N-(3-fluoro-4-(3-(4-(7-(5-(1-hydroxyethyl)furan-2-yl)-4-morpholinoquinazolin-2-yl)phenyl)ureido)phenyl)acetamide;
N-(3-fluoro-4-(3-(4-(7-(5-(2-hydroxypropan-2-yl)furan-2-yl)-4-morpholinoquinazolin-2-yl)phenyl)ureido)phenyl)acetamide;
N-(2-fluoro-4-(3-(4-(7-(5-methylfuran-2-yl)-4-morpholinoquinazolin-2-yl)phenyl)ureido)phenyl)acetamide;
N-(4-(3-(4-(7-(5-ethylfuran-2-yl)-4-morpholinoquinazolin-2-yl)phenyl)ureido)-2-fluorophenyl)acetamide;
N-(2-fluoro-4-(3-(4-(7-(furan-2-yl)-4-morpholinoquinazolin-2-yl)phenyl)ureido)phenyl)acetamide;
N-(2-fluoro-4-(3-(4-(4-morpholino-7-(pyridin-3-yl)quinazolin-2-yl)phenyl)ureido)phenyl)acetamide;
N-(2-fluoro-4-(3-(4-(7-(2-fluoropyridin-3-yl)-4-morpholinoquinazolin-2-yl)phenyl)ureido)phenyl)acetamide;
N-(2-fluoro-4-(3-(4-(7-(2-methylpyridin-3-yl)-4-morpholinoquinazolin-2-yl)phenyl)ureido)phenyl)acetamide;
N-(2-fluoro-4-(3-(4-(7-(6-methylpyridin-3-yl)-4-morpholinoquinazolin-2-yl)phenyl)ureido)phenyl)acetamide;
N-(2-fluoro-4-(3-(4-(4-morpholino-7-(pyridin-2-yl)quinazolin-2-yl)phenyl)ureido)phenyl)acetamide;
N-(2-fluoro-4-(3-(4-(4-morpholino-7-(pyridin-4-yl)quinazolin-2-yl)phenyl)ureido)phenyl)acetamide;
N-(2-fluoro-4-(3-(4-(4-morpholino-7-(pyrimidin-5-yl)quinazolin-2-yl)phenyl)ureido)phenyl)acetamide;
N-(2-fluoro-4-(3-(4-(7-(2-methoxypyrimidin-5-yl)-4-morpholinoquinazolin-2-yl)phenyl)ureido)phenyl)acetamide;
N-(4-(3-(4-(7-(2-aminopyrimidin-5-yl)-4-morpholinoquinazolin-2-yl)phenyl)ureido)-2-fluorophenyl)acetamide;
N-(2-fluoro-4-(3-(4-(7-(6-methoxypyridin-3-yl)-4-morpholinoquinazolin-2-yl)phenyl)ureido)phenyl)acetamide;
N-(2-fluoro-4-(3-(4-(7-(1-methyl-1H-pyrazol-4-yl)-4-morpholinoquinazolin-2-yl)phenyl)ureido)phenyl)acetamide;
N-(2-fluoro-4-(3-(4-(4-morpholino-7-(1,3,5-trimethyl-1H-pyrazol-4-yl)quinazolin-2-yl)phenyl)ureido)phenyl)acetamide;
N-(2-fluoro-4-(3-(4-(7-(3-(methylsulfonyl)phenyl)-4-morpholinoquinazolin-2-yl)phenyl)ureido)phenyl)acetamide;
N-(2-fluoro-4-(3-(4-(7-(5-(hydroxymethyl)furan-2-yl)-4-morpholinoquinazolin-2-yl)phenyl)ureido)phenyl)acetamide;
N-(2-fluoro-4-(3-(4-(7-(5-(1-hydroxyethyl)furan-2-yl)-4-morpholinoquinazolin-2-yl)phenyl)ureido)phenyl)acetamide;
N-(2-fluoro-4-(3-(4-(7-(5-(2-hydroxypropan-2-yl)furan-2-yl)-4-morpholinoquinazolin-2-yl)phenyl)ureido)phenyl)acetamide;
N-methyl-N-(4-(3-(4-(7-(5-methylfuran-2-yl)-4-morpholinoquinazolin-2-yl)phenyl)ureido)phenyl)acetamide;
N-(4-(3-(4-(7-(5-ethylfuran-2-yl)-4-morpholinoquinazolin-2-yl)phenyl)ureido)phenyl)-N-methylacetamide;
N-(4-(3-(4-(7-(furan-2-yl)-4-morpholinoquinazolin-2-yl)phenyl)ureido)phenyl)-N-methylacetamide;
N-(4-(3-(4-(7-(2-methoxypyrimidin-5-yl)-4-morpholinoquinazolin-2-yl)phenyl)ureido)phenyl)-N-methylacetamide;

N-methyl-N-(4-(3-(4-(4-morpholino-7-(pyrimidin-5-yl)quinazolin-2-yl)phenyl)ureido)phenyl)acetamide;
N-methyl-N-(4-(3-(4-(4-morpholino-7-(pyridin-3-yl)quinazolin-2-yl)phenyl)ureido)phenyl)acetamide;
N-(4-(3-(4-(7-(2-fluoropyridin-3-yl)-4-morpholinoquinazolin-2-yl)phenyl)ureido)phenyl)-N-methylacetamide;
N-methyl-N-(4-(3-(4-(4-morpholino-7-(pyridin-2-yl)quinazolin-2-yl)phenyl)ureido)phenyl)acetamide;
N-(3-fluoro-4-(3-(4-(6-fluoro-7-(5-methylfuran-2-yl)-4-morpholinoquinazolin-2-yl)phenyl)ureido)phenyl)acetamide;
N-(3-fluoro-4-(3-(4-(6-fluoro-7-(furan-2-yl)-4-morpholinoquinazolin-2-yl)phenyl)ureido)phenyl)acetamide;
N-(3-fluoro-4-(3-(4-(6-fluoro-4-morpholino-7-(pyrimidin-5-yl)quinazolin-2-yl)phenyl)ureido)phenyl)acetamide;
N-(3-fluoro-4-(3-(4-(6-fluoro-4-morpholino-7-(pyridin-3-yl)quinazolin-2-yl)phenyl)ureido)phenyl)acetamide;
N-(2-fluoro-4-(3-(4-(6-fluoro-7-(5-methylfuran-2-yl)-4-morpholinoquinazolin-2-yl)phenyl)ureido)phenyl)acetamide;
N-(2-fluoro-4-(3-(4-(6-fluoro-7-(furan-2-yl)-4-morpholinoquinazolin-2-yl)phenyl)ureido)phenyl)acetamide;
N-(2-fluoro-4-(3-(4-(6-fluoro-4-morpholino-7-(pyrimidin-5-yl)quinazolin-2-yl)phenyl)ureido)phenyl)acetamide;
N-(2-fluoro-4-(3-(4-(6-fluoro-4-morpholino-7-(pyridin-3-yl)quinazolin-2-yl)phenyl)ureido)phenyl)acetamide;
N-(4-(3-(4-(6-fluoro-7-(5-methylfuran-2-yl)-4-morpholinoquinazolin-2-yl)phenyl)ureido)phenyl)-N-methylacetamide;
N-(4-(3-(4-(6-fluoro-7-(furan-2-yl)-4-morpholinoquinazolin-2-yl)phenyl)ureido)phenyl)-N-methylacetamide;
N-(4-(3-(4-(6-fluoro-4-morpholino-7-(pyrimidin-5-yl)quinazolin-2-yl)phenyl)ureido)phenyl)-N-methylacetamide;
N-(4-(3-(4-(6-fluoro-4-morpholino-7-(pyridin-3-yl)quinazolin-2-yl)phenyl)ureido)phenyl)-N-methylacetamide;
N-(3-fluoro-4-(3-(4-(7-(5-methylfuran-2-yl)-4-morpholinopyrido[3,2-d]pyrimidin-2-yl)phenyl)ureido)phenyl)acetamide;
N-(3-fluoro-4-(3-(4-(7-(furan-2-yl)-4-morpholinopyrido[3,2-d]pyrimidin-2-yl)phenyl)ureido)phenyl)acetamide;
N-(3-fluoro-4-(3-(4-(4-morpholino-7-(pyrimidin-5-yl)pyrido[3,2-d]pyrimidin-2-yl)phenyl)ureido)phenyl)acetamide;
N-(3-fluoro-4-(3-(4-(7-(2-fluoropyridin-3-yl)-4-morpholinopyrido[3,2-d]pyrimidin-2-yl)phenyl)ureido)phenyl)acetamide;
N-(3-fluoro-4-(3-(4-(4-morpholino-7-(pyridin-3-yl)pyrido[3,2-d]pyrimidin-2-yl)phenyl)ureido)phenyl)acetamide;
N-(3-fluoro-4-(3-(4-(7-(1-methyl-1H-pyrazol-4-yl)-4-morpholinopyrido[3,2-d]pyrimidin-2-yl)phenyl)ureido)phenyl)acetamide;
N-(2-fluoro-4-(3-(4-(7-(5-methylfuran-2-yl)-4-morpholinopyrido[3,2-d]pyrimidin-2-yl)phenyl)ureido)phenyl)acetamide;
N-(2-fluoro-4-(3-(4-(7-(furan-2-yl)-4-morpholinopyrido[3,2-d]pyrimidin-2-yl)phenyl)ureido)phenyl)acetamide;
N-(2-fluoro-4-(3-(4-(4-morpholino-7-(pyrimidin-5-yl)pyrido[3,2-d]pyrimidin-2-yl)phenyl)ureido)phenyl)acetamide;
N-(2-fluoro-4-(3-(4-(7-(2-fluoropyridin-3-yl)-4-morpholinopyrido[3,2-d]pyrimidin-2-yl)phenyl)ureido)phenyl)acetamide;
N-(2-fluoro-4-(3-(4-(4-morpholino-7-(pyridin-3-yl)pyrido[3,2-d]pyrimidin-2-yl)phenyl)ureido)phenyl)acetamide;
N-(2-fluoro-4-(3-(4-(7-(1-methyl-1H-pyrazol-4-yl)-4-morpholinopyrido[3,2-d]pyrimidin-2-yl)phenyl)ureido)phenyl)acetamide;
N-methyl-N-(4-(3-(4-(7-(5-methylfuran-2-yl)-4-morpholinopyrido[3,2-d]pyrimidin-2-yl)phenyl)ureido)phenyl)acetamide;
N-(4-(3-(4-(7-(furan-2-yl)-4-morpholinopyrido[3,2-d]pyrimidin-2-yl)phenyl)ureido)phenyl)-N-methylacetamide;
N-methyl-N-(4-(3-(4-(4-morpholino-7-(pyrimidin-5-yl)pyrido[3,2-d]pyrimidin-2-yl)phenyl)ureido)phenyl)acetamide;
N-(4-(3-(4-(7-(2-fluoropyridin-3-yl)-4-morpholinopyrido[3,2-d]pyrimidin-2-yl)phenyl)ureido)phenyl)-N-methylacetamide;
N-methyl-N-(4-(3-(4-(4-morpholino-7-(pyridin-3-yl)pyrido[3,2-d]pyrimidin-2-yl)phenyl)ureido)phenyl)acetamide;
N-methyl-N-(4-(3-(4-(7-(1-methyl-1H-pyrazol-4-yl)-4-morpholinopyrido[3,2-d]pyrimidin-2-yl)phenyl)ureido)phenyl)acetamide;
N-(4-(3-(2-fluoro-4-(7-(5-methylfuran-2-yl)-4-morpholinoquinazolin-2-yl)phenyl)ureido)phenyl)acetamide;
N-(4-(3-(2-fluoro-4-(7-(furan-2-yl)-4-morpholinoquinazolin-2-yl)phenyl)ureido)phenyl)acetamide;
N-(4-(3-(2-fluoro-4-(7-(2-methoxypyrimidin-5-yl)-4-morpholinoquinazolin-2-yl)phenyl)ureido)phenyl)acetamide;
N-(4-(3-(2-fluoro-4-(4-morpholino-7-(pyrimidin-5-yl)quinazolin-2-yl)phenyl)ureido)phenyl)acetamide;
N-(4-(3-(2-fluoro-4-(4-morpholino-7-(pyridin-3-yl)quinazolin-2-yl)phenyl)ureido)phenyl)acetamide;
N-(4-(3-(2-fluoro-4-(7-(2-fluoropyridin-3-yl)-4-morpholinoquinazolin-2-yl)phenyl)ureido)phenyl)acetamide;
N-(4-(3-(2-fluoro-4-(4-morpholino-7-(pyridin-2-yl)quinazolin-2-yl)phenyl)ureido)phenyl)acetamide;
N-(4-(3-(3-fluoro-4-(7-(5-methylfuran-2-yl)-4-morpholinoquinazolin-2-yl)phenyl)ureido)phenyl)acetamide;
N-(4-(3-(3-fluoro-4-(7-(furan-2-yl)-4-morpholinoquinazolin-2-yl)phenyl)ureido)phenyl)acetamide;
N-(4-(3-(3-fluoro-4-(7-(2-methoxypyrimidin-5-yl)-4-morpholinoquinazolin-2-yl)phenyl)ureido)phenyl)acetamide;
N-(4-(3-(3-fluoro-4-(4-morpholino-7-(pyrimidin-5-yl)quinazolin-2-yl)phenyl)ureido)phenyl)acetamide;
N-(4-(3-(3-fluoro-4-(4-morpholino-7-(pyridin-3-yl)quinazolin-2-yl)phenyl)ureido)phenyl)acetamide;
N-(4-(3-(3-fluoro-4-(7-(2-fluoropyridin-3-yl)-4-morpholinoquinazolin-2-yl)phenyl)ureido)phenyl)acetamide;
N-(4-(3-(3-fluoro-4-(4-morpholino-7-(pyridin-2-yl)quinazolin-2-yl)phenyl)ureido)phenyl)acetamide;
N-(4-(3-(2-fluoro-4-(6-fluoro-7-(5-methylfuran-2-yl)-4-morpholinoquinazolin-2-yl)phenyl)ureido)phenyl)acetamide;
N-(4-(3-(2-fluoro-4-(6-fluoro-7-(furan-2-yl)-4-morpholinoquinazolin-2-yl)phenyl)ureido)phenyl)acetamide;

N-(4-(3-(2-fluoro-4-(6-fluoro-4-morpholino-7-(pyrimidin-5-yl)quinazolin-2-yl)phenyl)ureido)phenyl)acetamide;

N-(4-(3-(2-fluoro-4-(6-fluoro-4-morpholino-7-(pyridin-3-yl)quinazolin-2-yl)phenyl)ureido)phenyl)acetamide;

N-(4-(3-(3-fluoro-4-(6-fluoro-7-(5-methylfuran-2-yl)-4-morpholinoquinazolin-2-yl)phenyl)ureido)phenyl)acetamide;

N-(4-(3-(3-fluoro-4-(6-fluoro-7-(furan-2-yl)-4-morpholinoquinazolin-2-yl)phenyl)ureido)phenyl)acetamide;

N-(4-(3-(3-fluoro-4-(6-fluoro-4-morpholino-7-(pyrimidin-5-yl)quinazolin-2-yl)phenyl)ureido)phenyl)acetamide;

N-(4-(3-(3-fluoro-4-(6-fluoro-4-morpholino-7-(pyridin-3-yl)quinazolin-2-yl)phenyl)ureido)phenyl)acetamide;

N-(4-(3-(2-fluoro-4-(7-(5-methylfuran-2-yl)-4-morpholinopyrido[3,2-d]pyrimidin-2-yl)phenyl)ureido)phenyl)acetamide;

N-(4-(3-(2-fluoro-4-(7-(furan-2-yl)-4-morpholinopyrido[3,2-d]pyrimidin-2-yl)phenyl)ureido)phenyl)acetamide;

N-(4-(3-(2-fluoro-4-(4-morpholino-7-(pyrimidin-5-yl)pyrido[3,2-d]pyrimidin-2-yl)phenyl)ureido)phenyl)acetamide;

N-(4-(3-(2-fluoro-4-(7-(2-fluoropyridin-3-yl)-4-morpholinopyrido[3,2-d]pyrimidin-2-yl)phenyl)ureido)phenyl)acetamide;

N-(4-(3-(2-fluoro-4-(4-morpholino-7-(pyridin-3-yl)pyrido[3,2-d]pyrimidin-2-yl)phenyl)ureido)phenyl)acetamide;

N-(4-(3-(2-fluoro-4-(7-(1-methyl-1H-pyrazol-4-yl)-4-morpholinopyrido[3,2-d]pyrimidin-2-yl)phenyl)ureido)phenyl)acetamide;

N-(4-(3-(3-fluoro-4-(7-(5-methylfuran-2-yl)-4-morpholinopyrido[3,2-d]pyrimidin-2-yl)phenyl)ureido)phenyl)acetamide;

N-(4-(3-(3-fluoro-4-(7-(furan-2-yl)-4-morpholinopyrido[3,2-d]pyrimidin-2-yl)phenyl)ureido)phenyl)acetamide;

N-(4-(3-(3-fluoro-4-(4-morpholino-7-(pyrimidin-5-yl)pyrido[3,2-d]pyrimidin-2-yl)phenyl)ureido)phenyl)acetamide;

N-(4-(3-(3-fluoro-4-(7-(2-fluoropyridin-3-yl)-4-morpholinopyrido[3,2-d]pyrimidin-2-yl)phenyl)ureido)phenyl)acetamide;

N-(4-(3-(3-fluoro-4-(4-morpholino-7-(pyridin-3-yl)pyrido[3,2-d]pyrimidin-2-yl)phenyl)ureido)phenyl)acetamide; and N-(4-(3-(3-fluoro-4-(7-(1-methyl-1H-pyrazol-4-yl)-4-morpholinopyrido[3,2-d]pyrimidin-2-yl)phenyl)ureido)phenyl)acetamide, or a pharmaceutically acceptable salt or solvate thereof.

12. The pharmaceutical composition of claim 11, wherein the compound is present in a therapeutically effective amount.

\* \* \* \* \*